(12) United States Patent
Ibrahim et al.

(10) Patent No.: US 9,617,267 B2
(45) Date of Patent: Apr. 11, 2017

(54) COMPOUNDS AND METHODS FOR KINASE MODULATION, AND INDICATIONS THEREFOR

(71) Applicant: Plexxikon Inc., Berkeley, CA (US)

(72) Inventors: Prabha N. Ibrahim, Mountain View, CA (US); Wayne Spevak, Berkeley, CA (US); Hanna Cho, Oakland, CA (US); Songyuan Shi, Fremont, CA (US); Chao Zhang, Moraga, CA (US); Ying Zhang, Fremont, CA (US)

(73) Assignee: Plexxikon Inc., Berkeley, CA (US)

( * ) Notice: Subject to any disclaimer, the term of this patent is extended or adjusted under 35 U.S.C. 154(b) by 3 days.

(21) Appl. No.: 14/216,980

(22) Filed: Mar. 17, 2014

(65) Prior Publication Data
US 2014/0288070 A1  Sep. 25, 2014

Related U.S. Application Data

(62) Division of application No. 12/949,741, filed on Nov. 18, 2010, now Pat. No. 8,673,928.

(60) Provisional application No. 61/262,510, filed on Nov. 18, 2009, provisional application No. 61/383,310, filed on Sep. 15, 2010.

(51) Int. Cl.
| | |
|---|---|
| *C07D 487/04* | (2006.01) |
| *A61K 31/519* | (2006.01) |
| *C07D 401/04* | (2006.01) |
| *C07D 403/04* | (2006.01) |
| *A61K 31/437* | (2006.01) |
| *A61K 31/5377* | (2006.01) |
| *C07D 471/04* | (2006.01) |

(52) U.S. Cl.
CPC .......... *C07D 487/04* (2013.01); *A61K 31/437* (2013.01); *A61K 31/519* (2013.01); *A61K 31/5377* (2013.01); *C07D 401/04* (2013.01); *C07D 403/04* (2013.01); *C07D 471/04* (2013.01)

(58) Field of Classification Search
CPC ............................ C07D 487/04; A61K 31/519
USPC ........................................ 544/280; 514/265.1
See application file for complete search history.

(56) References Cited

U.S. PATENT DOCUMENTS

| | | | |
|---|---|---|---|
| 5,958,930 A | 9/1999 | Gangjee | |
| 7,202,266 B2 | 4/2007 | Arnold et al. | |
| 7,348,338 B2 | 3/2008 | Arnold et al. | |
| 7,476,746 B2 | 1/2009 | Artis et al. | |
| 7,491,831 B2 | 2/2009 | Artis et al. | |
| 7,498,342 B2 | 3/2009 | Ibrahim et al. | |
| 7,504,509 B2 | 3/2009 | Ibrahim et al. | |
| 7,517,970 B2 | 4/2009 | West et al. | |
| 7,531,568 B2 | 5/2009 | Lin et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,723,374 B2 | 5/2010 | Artis et al. | |
| 7,846,941 B2 | 12/2010 | Ibrahim et al. | |
| 7,863,288 B2 | 1/2011 | Ibrahim et al. | |
| 7,872,018 B2 | 1/2011 | Ibrahim et al. | |

(Continued)

FOREIGN PATENT DOCUMENTS

| | | |
|---|---|---|
| WO | WO-2004/056830 | 7/2004 |
| WO | WO-2005/062795 | 7/2005 |

(Continued)

OTHER PUBLICATIONS

U.S. Appl. No. 14/602,119, filed Jan. 21, 2015, Ibrahim et al.

(Continued)

*Primary Examiner* — Susanna Moore
(74) *Attorney, Agent, or Firm* — Sheppard Mullin Richter & Hampton LLP

(57) ABSTRACT

Compounds of formula (I):

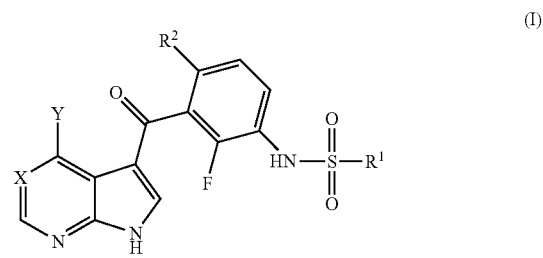

and salts thereof, formulations thereof, conjugates thereof, derivatives thereof, forms thereof and uses thereof are described. In certain aspects and embodiments, the described compounds of formula (I) or salts thereof, formulations thereof, conjugates thereof, derivatives thereof, forms thereof are active on at least one Raf protein kinase. In certain aspects and embodiments, the described compounds are active in inhibiting proliferation of a Ras mutant cell line. Also described are methods of use thereof to treat diseases and conditions, including diseases and conditions associated with activity of B-Raf V600E mutant protein kinase, including melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. Also described are methods of use thereof to treat diseases and conditions, including diseases and conditions associated with activity of c-Raf-1 protein kinase, including acute pain, chronic pain or polycystic kidney disease.

6 Claims, No Drawings

(56) References Cited

U.S. PATENT DOCUMENTS

| | | |
|---|---|---|
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Ibrahim et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,642,606 B2 | 2/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 2004/0077595 A1 | 4/2004 | Cheng et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0167338 A1 | 7/2008 | Spevak et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2009/0076046 A1 | 3/2009 | Zhang et al. |
| 2009/0286783 A1 | 11/2009 | Ibrahim et al. |
| 2010/0190777 A1 | 7/2010 | Wu et al. |
| 2010/0310659 A1 | 12/2010 | Desai et al. |
| 2011/0092538 A1 | 4/2011 | Spevak et al. |
| 2011/0112127 A1 | 5/2011 | Zhang et al. |
| 2011/0152258 A1 | 6/2011 | Ibrahim et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0037617 A1 | 2/2014 | Bollag et al. |
| 2014/0038948 A1 | 2/2014 | Wu et al. |
| 2014/0045840 A1 | 2/2014 | Zhang et al. |
| 2014/0094611 A1 | 4/2014 | Ibrahim et al. |
| 2014/0128373 A1 | 5/2014 | Ibrahim et al. |
| 2014/0128390 A1 | 5/2014 | Lin et al. |
| 2014/0213554 A1 | 7/2014 | Wu et al. |
| 2014/0243365 A1 | 8/2014 | Zhang et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0080372 A1 | 3/2015 | Ibrahim et al. |
| 2015/0133400 A1 | 5/2015 | Zhang et al. |
| 2015/0166547 A1 | 6/2015 | Ibrahim et al. |
| 2015/0183793 A1 | 7/2015 | Zhang et al. |

FOREIGN PATENT DOCUMENTS

| | | |
|---|---|---|
| WO | WO 2007/002325 | 1/2007 |
| WO | WO 2007/002433 | 1/2007 |
| WO | WO-2007/013896 | 2/2007 |
| WO | WO-2008/064255 | 5/2008 |
| WO | WO-2008/079906 | 7/2008 |
| WO | WO-2008/080015 | 7/2008 |
| WO | WO-2008/082730 | 7/2008 |
| WO | WO-2009/012283 | 1/2009 |
| WO | WO-2009/143024 | 11/2009 |
| WO | WO 2010/104973 | 9/2010 |
| WO | WO-2010/111527 | 9/2010 |
| WO | WO-2010/129467 | 11/2010 |
| WO | WO 2010/129567 | 11/2010 |
| WO | WO-2011/061080 | 5/2011 |
| WO | WO-2011/062939 | 5/2011 |

OTHER PUBLICATIONS

U.S. Appl. No. 14/637,303, filed Mar. 3, 2015, Lin et al.
U.S. Appl. No. 14/733,830, filed Jun. 8, 2015, Zhang et al.
U.S. Appl. No. 14/798,167, filed Jul. 13, 2015, Ibrahim et al.
Extended European Search Report for EP Application 10832209.0 dated Apr. 17, 2013.
Bagshawe, Antibody-Directed Enzyme Prodrug Therapy: A Review, Drug Dev. Res., 34:220-230, (1995).
Balak et. al., Novel D761Y and Common Secondary T790M Mutations in Epidermal Growth Factor Receptor 13 Mutant Lung Adenocarcinomas with Acquired Resistance to Kinase Inhibitors, Clin Cancer Res. 12:6494-501 (2006).
Beaucage and Iyer, Advances in the Synthesis of Oligonucleotides by the Phosphoramidite Approach, Tetrahedron 48:2223-2311 (1992).
Bertolini et al., A new rational hypothesis for the pharmacophore of the active metabolite of leflunomide, a potent immunosuppressive drug, Med. Chem., 40:2011-2016 (1997).
Crump, Inhibition of Raf Kinase in the Treatment of Acute Myeloid Leukemia, Pharm Des, 8(25):2243-8 (2002).
Hood et al., Tumor Regression by Targeted Gene Delivery to the Neovasculature, Science 296:2404 (2002).
International Search Report and Written Opinion dated Jan. 25, 2011 in application PCT/US2010/057293.
Jaiswal et al., Combined Targeting of BRAF and CRAF or BRAF and PI3K Effector Pathways is Required for Efficacy in NRAS Mutant Tumors, PLoS One, 4(5):e5717 (2009).
Kunnimalaiyaan et al., The Raf-1 pathway: a molecular target for treatment of select neuroendocrine tumors? Anticancer Drugs, 17(2):139-42 (2006).
McDermott et al., Identification of genotype-correlated sensitivity to selective kinase inhibitors by using high-throughput tumor cell line profiling; PNAS, 104(50): 19936-19941 (2007).
Niihori et al., Germline KRAS and BRAF mutations in cardio-facio-cutaneous syndrome; Nat Genet. 38(3):294-6 (2006).
Remington: The Science and Practice of Pharmacy; Remington's Pharmaceutical Sciences, 19th ed., Mack Publishing Co., Easton, PA, vol. 2, p. 1454-1457 (1995).
Shan et al., Prodrug Strategies Based on Intramolecular Cyclization Reactions; J Pharm Sci 86(7):765-767 (1997).
U.S. Appl. No. 14/839,668, filed Aug. 28, 2015, Ibrahim.
U.S. Appl. No. 14/846,545, filed Sep. 4, 2015, Zhang et al.
U.S. Appl. No. 14/850,912, filed Sep. 10, 2015, Shi et al.
U.S. Appl. No. 15/048,851, filed Feb. 19, 2016, Wu, et al.
U.S. Appl. No. 15/093,660, filed Apr. 7, 2016, Lin, et al.
U.S. Appl. No. 15/147,781, filed May 5, 2016, Bollag, et al.
U.S. Appl. No. 15/147,692, filed May 5, 2016, Ibrahim, et al.
U.S. Appl. No. 15/147,709, filed May 5, 2016, Ibrahim, et al.
U.S. Appl. No. 15/160,729, filed May 20, 2016, Ibrahim, et al.
U.S. Appl. No. 15/241,773, filed Aug. 19, 2016, Desai et al.
U.S. Appl. No. 15/288,558, filed Oct. 7, 2016, Zhang et al.
U.S. Appl. No. 15/260,042, filed Sep. 8, 2016, Wu et al.
U.S. Appl. No. 15/221,474, filed Jul. 27, 2016, Holladay et al.
U.S. Appl. No. 15/269,054, filed Sep. 19, 2016, Ibrahim et al.

COMPOUNDS AND METHODS FOR KINASE MODULATION, AND INDICATIONS THEREFOR

CROSS-REFERENCE TO RELATED APPLICATIONS

This application is a divisional application of U.S. application Ser. No. 12/949,741, filed Nov. 18, 2010, which claims the benefit under 35 U.S. C. §119(e) of U.S. Application No. 61/262,510, filed Nov. 18, 2009, and 61/383,310, filed Sep. 15, 2010, each of which are hereby incorporated by reference in their entirety.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. In some embodiments, compounds are of Formula I, Formula II, Formula III and Formula IIIa as described below. In certain embodiments, the compounds inhibit one or more Raf protein kinases, including one or more of A-Raf, B-Raf, and c-Raf-1, and any mutations thereof. In certain embodiments, the compounds inhibit c-Raf-1 protein kinase. In certain embodiments, the compounds inhibit c-Raf-1 protein kinase selectively to other Raf protein kinases. In certain embodiments, the compounds inhibit a B-Raf V600X mutant protein kinase (where X is an amino acid other than valine, e.g., alanine, arginine, aspartic acid, glycine, lysine or methionine). In certain embodiments, the compounds inhibit a B-Raf V600E mutant protein kinase. In certain embodiments, the compounds inhibit a B-Raf V600E mutant protein kinase selectively relative to other Raf protein kinases, including B-Raf protein kinase. In certain embodiments, the compounds inhibit each of c-Raf-1, B-Raf, B-Raf V600X, and B-Raf V600E protein kinase.

Also contemplated in accordance with the present invention are methods for the use of the compounds in treating diseases and conditions associated with regulation of the activity of one or more Raf protein kinases, including one or more of A-Raf, B-Raf, and c-Raf-1, and any mutations thereof. Thus, the use of compounds for therapeutic methods involving modulation of protein kinases are provided. In certain embodiments, the compounds inhibit the activity on one or more Raf kinases, including A-Raf, B-Raf and/or c-Raf-1, including any mutations thereof. In certain embodiments, the compounds are used for therapeutic methods involving modulation of one or more Raf protein kinases, including treatment of a variety of indications, including, but not limited to, melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain and polycystic kidney disease. In certain embodiments, the compounds are used for therapeutic methods involving modulation of B-Raf V600E mutant protein kinase, including treatment of a variety of indications, including, but not limited to, melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In certain embodiments, the compounds are used for therapeutic methods involving modulation of c-Raf-1 protein kinase, including treatment of a variety of indications, including, but not limited to, acute pain, chronic pain and polycystic kidney disease.

In a first aspect, compounds having the structure according to the following Formula I are provided:

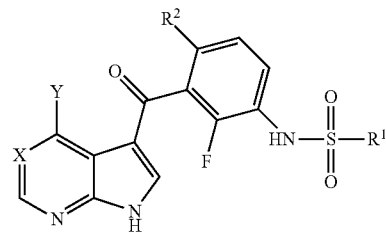

Formula I or a pharmaceutically acceptable salt thereof,
wherein:
X is —N= or —C($R^5$)=;
Y is selected from the group consisting of fluoro, chloro, bromo, iodo, lower alkyl, lower alkoxy, haloalkyl, CN, —OH, fluoro substituted alkyl, cycloalkyl, —O$R^8$, and —N($R^3$)—$R^4$;
$R^1$ is selected from the group consisting of lower alkyl, haloalkyl, haloalkoxy, fluoro substituted lower alkyl, cycloalkyl optionally substituted with one or more $R^7$, heterocycloalkyl, mono-alkylamino, di-alkylamino, cycloalkylamino, heterocycloalkylamino, aryl optionally substituted with one or more $R^6$ (e.g., $R^1$ is 2-fluoro-substituted phenyl, 3-fluoro-substituted phenyl, 2,5-difluoro-substituted phenyl or 4-lower alkyl-substituted phenyl, wherein lower alkyl is optionally substituted with one or more fluorine), and heteroaryl optionally substituted with one or more $R^7$;
$R^2$ is hydrogen, fluoro, chloro or lower alkyl optionally substituted with one or more fluorine;
$R^3$ is hydrogen and $R^4$ is selected from the group consisting of hydrogen, —O$R^8$, lower alkyl optionally substituted with one or more $R^{11}$, cycloalkyl optionally substituted with one or more $R^{12}$, cycloalkylalkyl optionally substituted with one or more $R^{12}$, heterocycloalkyl optionally substituted with one or more $R^{13}$, heterocycloalkylalkyl optionally substituted with one or more $R^{13}$, aryl optionally substituted with one or more $R^{14}$, arylalkyl optionally substituted with one or more $R^{14}$, and heteroaryl optionally substituted with one or more $R^{15}$;
or $R^3$ and $R^4$ are both lower alkyl;
or $R^3$ and $R^4$ combine with the nitrogen to which they are attached to form cycloalkylamino or $R^3$ and
$R^4$ combine with the nitrogen atom to which they are attached to form a 3-7 membered ring having 0-1 additional heteroatom selected from O or N;
$R^5$ is selected from the group consisting of hydrogen, fluoro, chloro, —CN, lower alkyl optionally substituted with one or more $R^{16}$, and lower alkoxy optionally substituted with one or more $R^{17}$;
each $R^6$, when present, is independently selected from the group consisting of fluoro, chloro, —CN, —NO$_2$, lower alkyl, fluoro substituted lower alkyl, lower alkoxy, fluoro substituted lower alkoxy, —C(O)—O—$R^{18}$, —N(H)—C(O)—$R^{19}$, and heteroaryl optionally substituted with one or more lower alkyl; or two $R^6$ on adjacent carbons combine to form a fused heterocycloalkyl optionally substituted with one or more lower alkyl;

each $R^7$, when present, is independently selected from the group consisting of lower alkyl, fluoro substituted lower alkyl, lower alkoxy, —C(O)—O—$R^{20}$, and heteroaryl optionally substituted with one or more lower alkyl;

$R^8$ is hydrogen, lower alkyl optionally substituted with one or more fluorine, or, when $R^8$ is a $C_{2-6}$ alkyl, said alkyl may optionally be substituted with one or more $R^{21}$; cycloalkyl optionally substituted with one or more $R^{21}$, or heterocycloalkyl optionally substituted with one or more $R^{21}$;

each $R^{11}$, when present, is independently selected from the group consisting of fluoro, —OH, lower alkoxy, fluoro substituted lower alkoxy, —$NH_2$, mono-alkylamino, di-alkylamino, cycloalkylamino, heterocycloalkylamino, cycloalkyl optionally substituted with one or more $R^{12}$, heterocycloalkyl optionally substituted with one or more $R^{13}$, aryl optionally substituted with one or more $R^{14}$, and heteroaryl optionally substituted with one or more $R^{15}$;

each $R^{12}$, when present, is independently selected from the group consisting of fluoro, lower alkyl, fluoro substituted lower alkyl, —OH, lower alkoxy, fluoro substituted lower alkoxy, —$NH_2$, mono-alkylamino, di-alkylamino, cycloalkylamino, heterocycloalkylamino, —N(H)—C(O)—$R^{22}$, —N(H)—S(O)$_2$—$R^{23}$, C(O)—$R^{24}$, and S(O)$_2$—$R^{25}$;

each $R^{13}$, when present, is independently selected from the group consisting of fluoro, —OH, lower alkoxy, fluoro substituted lower alkoxy, —$NH_2$, mono-alkylamino, di-alkylamino, cycloalkylamino, heterocycloalkylamino, —N(H)—C(O)—$R^{26}$, —N(H)—S(O)$_2$—$R^{27}$, C(O)—$R^{28}$, S(O)$_2$—$R^{29}$, and lower alkyl optionally substituted with one or more $R^{30}$;

each $R^{14}$ and $R^{15}$, when present, are independently selected from the group consisting of fluoro, chloro, —OH, —$NH_2$, —CN, —$NO_2$, —N(H)—C(O)—$R^{31}$, —N(H)—S(O)$_2$—$R^{32}$, C(O)—$R^{33}$, S(O)$_2$—$R^{34}$, lower alkyl, fluoro substituted lower alkyl, lower alkoxy, fluoro substituted lower alkoxy, mono-alkylamino, di-alkylamino, cycloalkylamino, heterocycloalkylamino, aryl optionally substituted with one or more $R^{35}$, and heteroaryl optionally substituted with one or more $R^{36}$;

each $R^{16}$, when present, is independently fluoro, —OH, lower alkoxy, —$NH_2$, mono-alkylamino, di-alkylamino, cycloalkylamino, or heterocycloalkylamino;

each $R^{17}$, when present, is independently fluoro, —OH, lower alkoxy, —$NH_2$, mono-alkylamino, di-alkylamino, cycloalkylamino, or heterocycloalkylamino;

each $R^{18}$ and $R^{20}$, when present, are independently hydrogen, lower alkyl or fluoro substituted lower alkyl;

each $R^{19}$, $R^{22}$, $R^{23}$, $R^{26}$, $R^{27}$, $R^{31}$ and $R^{32}$, when present, are independently lower alkyl or fluoro substituted lower alkyl;

each $R^{21}$, when present, is fluoro, —OH, lower alkoxy, —$NH_2$, mono-alkylamino, di-alkylamino, cycloalkylamino, or heterocycloalkylamino;

each $R^{24}$, $R^{25}$, $R^{28}$, $R^{29}$, $R^{33}$, and $R^{34}$, when present, are independently lower alkyl, fluoro substituted lower alkyl, —OH, lower alkoxy, fluor substituted lower alkoxy, —$NH_2$, mono-alkylamino, di-alkylamino, cycloalkylamino, or heterocycloalkylamino;

each $R^{30}$, when present, is independently fluoro, aryl optionally substituted with one or more $R^{35}$ or heteroaryl optionally substituted with one or more $R^{36}$; and each $R^{35}$ and $R^{36}$, when present, are independently selected from the group consisting of fluoro, chloro, —OH, —$NH_2$, —CN, —$NO_2$, lower alkyl, fluoro substituted lower alkyl, lower alkoxy, fluoro substituted lower alkoxy, mono-alkylamino, di-alkylamino, cycloalkylamino, and heterocycloalkylamino.

In some embodiments of compounds of Formula I:

X is —N═ or —C($R^5$)═; wherein $R^5$ is selected from the group consisting of hydrogen, fluoro, chloro, —CN, lower alkyl and lower alkoxy, wherein the lower alkyl or lower alkoxy is optionally substituted with from one to three groups selected from fluoro, —OH, lower alkoxy, —$NH_2$, mono-alkylamino, di-alkylamino, cycloalkylamino, or heterocycloalkylamino.

Y is selected from the group consisting of fluoro, chloro, bromo, iodo, lower alkyl, lower alkoxy, haloalkyl (e.g., fluoro substituted alkyl), CN, —OH, cycloalkyl, —$OR^8$, and —N($R^3$)—$R^4$;

$R^1$ is selected from the group consisting of lower alkyl, fluoro substituted lower alkyl, cycloalkyl, mono-alkylamino, di-alkylamino, cycloalkylamino, heterocycloalkylamino, phenyl optionally substituted with from one to three $R^6$ (e.g., $R^1$ is 2-fluoro-substituted phenyl, 3-fluoro-substituted phenyl, 2,5-difluoro-substituted phenyl or 4-lower alkyl-substituted phenyl, wherein lower alkyl is optionally substituted with from one to three fluorine atoms), and heteroaryl optionally substituted with one to three $R^7$;

$R^2$ is hydrogen, fluoro, chloro, or lower alkyl optionally substituted with one or more fluorine;

$R^3$ is hydrogen and $R^4$ is selected from the group consisting of (i) hydrogen, —$OR^8$ and lower alkyl optionally substituted with from one to three $R^{11}$; (ii) cycloalkyl or cycloalkylalkyl, each of which is optionally substituted with from one to three $R^{12}$; (iii) heterocycloalkyl or heterocycloalkylalkyl, each of which is optionally substituted with from one to three $R^{13}$; (iv) aryl or arylalkyl, each of which is optionally substituted with from one to three $R^{14}$ optionally, wherein the two adjacent $R^{14}$ groups on the aryl ring are taken together to form a 5 or 6-membered hetero aromatic ring having from 1-4 heteroatoms selected from O or N; and (v) heteroaryl or heteroarylalkyl, each of which is optionally substituted with from one to three $R^{15}$;

or $R^3$ and $R^4$ are both lower alkyl;

or $R^3$ and $R^4$ combine with the nitrogen atom to which they are attached to form a three to seven membered ring having 0-1 additional heteroatom selected from O, N or S, wherein the nitrogen and sulfur atoms are optionally oxidized;

each $R^6$, when present, is independently selected from the group consisting of fluoro, chloro, —CN, —$NO_2$, lower alkyl, fluoro substituted lower alkyl, lower alkoxy, fluoro substituted lower alkoxy, —C(O)—O—$R^{18}$, —N(H)—C(O)—$R^{19}$, and heteroaryl optionally substituted with one or more lower alkyl; or two $R^6$ on adjacent carbons combine to form a fused heterocycloalkyl optionally substituted with one or more lower alkyl;

each $R^7$, when present, is independently selected from the group consisting of lower alkyl, fluoro substituted lower alkyl, lower alkoxy, —C(O)—O—R$^{20}$, and heteroaryl optionally substituted with one or more lower alkyl;

R$^{11}$, when present, is selected from the group consisting of cycloalkyl, —OH, lower alkoxy, mono-alkylamino, di-alkylamino, cycloalkylamino, and heterocycloalkylamino;

each R$^{14}$ and R$^{15}$, when present, are independently selected from the group consisting of fluoro, chloro, —CN, —NO$_2$, lower alkyl, fluoro substituted lower alkyl, lower alkoxy, and fluoro substituted lower alkoxy;

each R$^{18}$, when present, is independently hydrogen or lower alkyl;

each R$^{19}$, when present, is independently lower alkyl; and each R$^{20}$, when present, is independently hydrogen or lower alkyl.

In some embodiments of compounds of Formula I, Y is fluoro, chloro, bromo, or iodo, preferably fluoro; R$^1$ is lower alkyl or cycloalkyl, preferably lower alkyl, preferably n-propyl, i-propyl, sec-butyl, i-butyl, and the like. In some embodiments, R$^1$ is lower alkyl or cycloalkyl (e.g., cyclopropyl), preferably lower alkyl, preferably n-propyl, i-propyl, sec-butyl, i-butyl, and the like. In some embodiments of compounds of Formula I, Y is fluoro, chloro, bromo, or iodo, preferably fluoro; R$^1$ is lower alkyl or cycloalkyl, preferably lower alkyl, preferably n-propyl, i-propyl, sec-butyl, i-butyl, and the like; and R$^2$ is hydrogen. In some embodiments of compounds of Formula I, Y is fluoro, chloro, bromo, or iodo, preferably fluoro; R$^1$ is lower alkyl or cycloalkyl, preferably lower alkyl, preferably n-propyl, i-propyl, sec-butyl, i-butyl, and the like; and R$^2$ is fluoro. All the other variables are as defined in any of the above embodiments or as described hereinafter.

In some embodiments, X is selected from the group consisting of —N═, —CH═, —C(CH$_3$)═, —C(OCH$_3$)═, —C(F)═, —C(CN)═, —C(CH$_2$OH)═ and —C(Cl)═. In certain instances, X is —N═, —CH═, —C(CH$_3$)═, —C(F)═ or —C(CN)═. In a preferred embodiment, X is —N═. All the other variables are as defined in any of the above embodiments or as described hereinafter.

In some embodiments of compounds of Formula I, Y is lower alkyl, fluoro substituted alkyl, or cycloalkyl; R$^1$ is lower alkyl or cycloalkyl, preferably lower alkyl, preferably n-propyl, i-propyl, sec-butyl, i-butyl, and the like. In some embodiments, R$^1$ is lower alkyl or cycloalkyl, preferably lower alkyl, preferably n-propyl, i-propyl, sec-butyl, i-butyl, and the like; and R$^2$ is hydrogen. In some embodiments of compounds of Formula I, Y is lower alkyl, fluoro substituted alkyl, or cycloalkyl; R$^1$ is lower alkyl or cycloalkyl, preferably lower alkyl, preferably n-propyl, i-propyl, sec-butyl, i-butyl, and the like; and R$^2$ is fluoro. All the other variables are as defined in any of the above embodiments or as described hereinafter.

In some embodiments of compounds of Formula I, Y is —OR$^8$; R$^1$ is lower alkyl or cycloalkyl, preferably lower alkyl, preferably n-propyl, i-propyl, sec-butyl, i-butyl, and the like. In some embodiments, R$^1$ is lower alkyl or cycloalkyl, preferably lower alkyl, preferably n-propyl, i-propyl, sec-butyl, i-butyl, and the like, and R$^8$ is hydrogen, lower alkyl optionally substituted with one or more fluorine, or cycloalkyl optionally substituted with one or more fluorine. In some embodiments, R$^1$ is lower alkyl or cycloalkyl, preferably lower alkyl, preferably n-propyl, i-propyl, sec-butyl, i-butyl, and the like, and R$^8$ is hydrogen, lower alkyl optionally substituted with one or more fluorine, or cycloalkyl optionally substituted with one or more fluorine; and R$^2$ is hydrogen. In some embodiments, R$^1$ is lower alkyl or cycloalkyl, preferably lower alkyl, preferably n-propyl, i-propyl, sec-butyl, i-butyl, and the like, and R$^8$ is hydrogen or lower alkyl; and R$^2$ is fluoro. All the other variables are as defined in any of the above embodiments, or as described hereinafter.

In some embodiments of compounds of Formula I, Y is —N(R$^3$)—R$^4$; R$^1$ is lower alkyl or cycloalkyl, preferably lower alkyl, preferably n-propyl, i-propyl, sec-butyl, i-butyl, and the like. In some embodiments of compounds of Formula I, Y—N(R$^3$)—R$^4$; R$^1$ is lower alkyl or cycloalkyl, preferably lower alkyl, preferably n-propyl, i-propyl, sec-butyl, i-butyl, and the like; and R$^2$ is hydrogen. In some embodiments of compounds of Formula I, Y—N(R$^3$)—R$^4$; R$^1$ is lower alkyl or cycloalkyl, preferably lower alkyl, preferably n-propyl, i-propyl, sec-butyl, i-butyl, and the like; and R$^2$ is fluoro. In some embodiments, R$^1$ is lower alkyl or cycloalkyl, preferably lower alkyl, preferably n-propyl, i-propyl, sec-butyl, i-butyl, and the like, R$^3$ is hydrogen and R$^4$ is selected from the group consisting of hydrogen, —OH, lower alkyl optionally substituted with R$^{11}$, cycloalkyl, heterocycloalkyl optionally substituted with lower alkyl, phenyl optionally substituted with one or more R$^{14}$, and 5-6 membered heteroaryl optionally substituted with one or more lower alkyl, or R$^3$ and R$^4$ are both lower alkyl, or R$^3$ and R$^4$ combine with the nitrogen to which they are attached to form a three to seven membered ring having 0-1 additional heteroatom selected from O, N or S, wherein the nitrogen and sulfur atoms are optionally oxidized, wherein R$^{11}$ and R$^{14}$ are as defined for Formula I, preferably wherein R$^{11}$ is selected from the group consisting of cycloalkyl, —OH, lower alkoxy, mono-alkylamino, di-alkylamino, cycloalkylamino, heterocycloalkylamino and R$^{14}$ is selected from the group consisting of fluoro, chloro, —CN, —NO$_2$, lower alkyl, fluoro substituted lower alkyl, lower alkoxy, and fluoro substituted lower alkoxy. All the other variables are as defined in any of the above embodiments or as described hereinafter.

In some embodiments of compounds of Formula I, Y is fluoro, chloro, bromo, or iodo, preferably fluoro; R$^1$ is mono-alkylamino, di-alkylamino, cycloalkylamino, or heterocycloalkylamino, preferably di-alkylamino or cycloalkylamino. In some embodiments of compounds of Formula I, Y is fluoro, chloro, bromo, or iodo, preferably fluoro; R$^1$ is mono-alkylamino, di-alkylamino, cycloalkylamino, or heterocycloalkylamino, preferably di-alkylamino or cycloalkylamino; and R$^2$ is hydrogen. In some embodiments of compounds of Formula I, Y is fluoro, chloro, bromo, or iodo, preferably fluoro; R$^1$ is mono-alkylamino, di-alkylamino, cycloalkylamino, or heterocycloalkylamino, preferably di-alkylamino or cycloalkylamino; and R$^2$ is fluoro. In some embodiments, R$^1$ is mono-alkylamino, di-alkylamino, cycloalkylamino, or heterocycloalkylamino, preferably di-alkylamino or cycloalkylamino. All the other variables are as defined in any of the above embodiments or as described hereinafter.

In some embodiments of compounds of Formula I, Y is lower alkyl, fluoro substituted alkyl, or cycloalkyl; R$^1$ is mono-alkylamino, di-alkylamino, cycloalkylamino, or heterocycloalkylamino, preferably di-alkylamino or cycloalkylamino. In some embodiments of compounds of Formula I, Y is lower alkyl, fluoro substituted alkyl, or cycloalkyl; R$^1$ is mono-alkylamino, di-alkylamino, cycloalkylamino, or heterocycloalkylamino, preferably di-alkylamino or cycloalkylamino; and R$^2$ is hydrogen. In some embodiments, R$^1$ is mono-alkylamino, di-alkylamino, cycloalkylamino, or heterocycloalkylamino, preferably di-alkylamino or cycloalkylamino; and $R^2$ is fluoro. All the other variables are as defined in any of the above embodiments or as described hereinafter.

In some embodiments of compounds of Formula I, Y is —$OR^8$; $R^1$ is mono-alkylamino, di-alkylamino, cycloalkylamino, or heterocycloalkylamino, preferably di-alkylamino or cycloalkylamino. In some embodiments of compounds of Formula I, Y is —$OR^8$; $R^1$ is mono-alkylamino, di-alkylamino, cycloalkylamino, or heterocycloalkylamino, preferably di-alkylamino or cycloalkylamino; and $R^2$ is hydrogen. In some embodiments of compounds of Formula I, Y is —$OR^8$; $R^1$ is mono-alkylamino, di-alkylamino, cycloalkylamino, or heterocycloalkylamino, preferably di-alkylamino or cycloalkylamino; and $R^2$ is fluoro. In some embodiments, $R^1$ is mono-alkylamino, di-alkylamino, cycloalkylamino, or heterocycloalkylamino, preferably di-alkylamino or cycloalkylamino, and $R^8$ is hydrogen or lower alkyl. All the other variables are as defined in any of the above embodiments or as described hereinafter.

In some embodiments of compounds of Formula I, Y is —$N(R^3)$—$R^4$; $R^1$ is mono-alkylamino, di-alkylamino, cycloalkylamino, or heterocycloalkylamino, preferably di-alkylamino or cycloalkylamino. In some embodiments of compounds of Formula I, Y is —$N(R^3)$—$R^4$; $R^1$ is mono-alkylamino, di-alkylamino, cycloalkylamino, or heterocycloalkylamino, preferably di-alkylamino or cycloalkylamino; and $R^2$ is hydrogen. In some embodiments of compounds of Formula I, Y is —$N(R^3)$—$R^4$; $R^1$ is mono-alkylamino, di-alkylamino, cycloalkylamino, or heterocycloalkylamino, preferably di-alkylamino or cycloalkylamino; and $R^2$ is fluoro. In some embodiments, $R^1$ is mono-alkylamino, di-alkylamino, cycloalkylamino, or heterocycloalkylamino, preferably di-alkylamino or cycloalkylamino, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino, wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{14}$ is selected from the group consisting of fluoro, chloro, —CN, —$NO_2$, lower alkyl, fluoro substituted lower alkyl, lower alkoxy, and fluoro substituted lower alkoxy. All the other variables are as defined in any of the above embodiments or as described hereinafter.

In some embodiments of compounds of Formula I, Y is fluoro, chloro, bromo, or iodo, preferably fluoro; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments of compounds of Formula I, Y is fluoro, chloro, bromo, or iodo, preferably fluoro; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is hydrogen. In some embodiments of compounds of Formula I, Y is fluoro, chloro, bromo, or iodo, preferably fluoro; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy. All the other variables are as defined in any of the above embodiments or as described hereinafter.

In some embodiments of compounds of Formula I, Y is lower alkyl, fluoro substituted alkyl, or cycloalkyl; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments of compounds of Formula I, Y is lower alkyl, fluoro substituted alkyl, or cycloalkyl; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is hydrogen. In some embodiments of compounds of Formula I, Y is lower alkyl, fluoro substituted alkyl, or cycloalkyl; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy. All the other variables are as defined in any of the above embodiments or as described hereinafter.

In some embodiments of compounds of Formula I, Y is —$OR^8$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments of compounds of Formula I, Y is —$OR^8$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is hydrogen. In some embodiments of compounds of Formula I, Y is —$OR^8$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy, and $R^8$ is hydrogen or lower alkyl. All the other variables are as defined in any of the above embodiments or as described hereinafter.

In some embodiments of compounds of Formula I, Y is —$N(R^3)$—$R^4$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments of compounds of Formula I, Y is —N($R^3$)—$R^4$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is hydrogen. In some embodiments, $R^1$ is phenyl mono-substituted with fluoro, lower alkyl, or —$CF_3$, or di-substituted with two fluoro, two lower alkyl, or one fluoro and one lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{13}$ is selected from the group consisting of fluoro, chloro, —CN, —$NO_2$, lower alkyl, fluoro substituted lower alkyl, lower alkoxy, and fluoro substituted lower alkoxy. In some embodiments, $R^1$ is phenyl mono-substituted with fluoro, lower alkyl, or —$CF_3$, or di-substituted with two fluoro, two lower alkyl, or one fluoro and one lower alkoxy, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino, wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{14}$ is selected from the group consisting of fluoro, chloro, —CN, —$NO_2$, lower alkyl, fluoro substituted lower alkyl, lower alkoxy, and fluoro substituted lower alkoxy. All the other variables are as defined in any of the above embodiments or as described hereinafter.

In some embodiments of compounds of Formula I, Y is fluoro, chloro, bromo, or iodo, preferably fluoro; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula I, Y is fluoro, chloro, bromo, or iodo, preferably fluoro; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula I, Y is fluoro, chloro, bromo, or iodo, preferably fluoro; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy. All the other variables are as defined in any of the above embodiments or as described hereinafter.

In some embodiments of compounds of Formula I, Y is lower alkyl, fluoro substituted alkyl, or cycloalkyl; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula I, Y is lower alkyl, fluoro substituted alkyl, or cycloalkyl; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula I, Y is lower alkyl, fluoro substituted alkyl, or cycloalkyl; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy. All the other variables are as defined in any of the above embodiments or as described hereinafter.

In some embodiments of compounds of Formula I, Y is —$OR^8$; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula I, Y is —$OR^8$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula I, Y is —$OR^8$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy, and $R^8$ is hydrogen or lower alkyl. All the other variables are as defined in any of the above embodiments or as described hereinafter.

In some embodiments of compounds of Formula I, Y is —N($R^3$)—$R^4$; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula I, Y is —N($R^3$)—$R^4$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula I, Y is —N($R^3$)—$R^4$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino, wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{14}$ is selected from the group consisting of fluoro, chloro, —CN, —NO$_2$, lower alkyl, fluoro substituted lower alkyl, lower alkoxy, and fluoro substituted lower alkoxy. All the other variables are as defined in any of the above embodiments or as described hereinafter.

In a second aspect, compounds having the structure according to the following Formula II are provided:

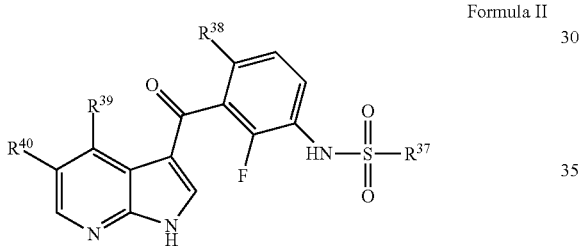

Formula II or a pharmaceutically acceptable salt thereof,
wherein:
$R^{37}$ is selected from the group consisting of lower alkyl, fluoro substituted lower alkyl, cycloalkyl, mono-alkylamino, di-alkylamino, cycloalkylamino, heterocycloalkylamino, phenyl optionally substituted with one or more $R^{41}$ (e.g., $R^{37}$ is 2-fluoro-substituted phenyl, 3-fluoro-substituted phenyl, 2,5-difluoro-substituted phenyl or 4-lower alkyl-substituted phenyl, wherein lower alkyl is optionally substituted with one or more fluorine), and heteroaryl optionally substituted with one or more $R^{42}$;
$R^{38}$ is hydrogen, fluoro, chloro, or lower alkyl optionally substituted with one or more fluorine;
$R^{39}$ and $R^{40}$ are independently selected from the group consisting of fluoro, chloro, —CN, —OH, —NH$_2$, lower alkyl optionally substituted with one or more $R^{43}$, lower alkenyl optionally substituted with C(O)—O—$R^{44}$, lower alkynyl optionally substituted with lower alkyl optionally substituted with one or more fluorine, or, on a non-alkynyl carbon thereof, $R^{45}$, lower alkoxy optionally substituted with $R^{46}$, mono-alkylamino, di-alkylamino, cycloalkylamino, and heterocycloalkylamino;
each $R^{41}$, when present, is independently selected from the group consisting of fluoro, chloro, —CN, —NO$_2$, lower alkyl, fluoro substituted lower alkyl, lower alkoxy, fluoro substituted lower alkoxy, —C(O)—O—$R^{47}$, —N(H)—C(O)—$R^{48}$, and heteroaryl optionally substituted with one or more lower alkyl; or two $R^{41}$ on adjacent carbons combine to form a fused heterocycloalkyl optionally substituted with one or more lower alkyl;
each $R^{42}$, when present, is independently selected from the group consisting of lower alkyl, fluoro substituted lower alkyl, lower alkoxy, fluoro substituted lower alkoxy, —C(O)—O—$R^{49}$, and heteroaryl optionally substituted with one or more lower alkyl;
each $R^{43}$, when present, is independently selected from the group consisting of fluoro, —OH, lower alkoxy, mono-alkylamino, di-alkylamino, cycloalkylamino, and heterocycloalkylamino;
each $R^{44}$, when present, is independently hydrogen or lower alkyl optionally substituted with one or more fluorine;
each $R^{45}$, when present, is independently selected from the group consisting of —OH, lower alkoxy, mono-alkylamino, di-alkylamino, cycloalkylamino, and heterocycloalkylamino;
each $R^{46}$, when present, is independently selected from the group consisting of —OH, lower alkoxy, mono-alkylamino, di-alkylamino, cycloalkylamino, and heterocycloalkylamino;
each $R^{47}$, when present, is independently hydrogen or lower alkyl optionally substituted with one or more fluorine;
each $R^{48}$, when present, is independently lower alkyl optionally substituted with one or more fluorine; and
each $R^{49}$, when present, is independently hydrogen or lower alkyl optionally substituted with one or more fluorine.

In some embodiments of compounds of Formula II, $R^{37}$ is lower alkyl or cycloalkyl, preferably lower alkyl, preferably n-propyl, i-propyl, sec-butyl, i-butyl, and the like. In some embodiments, $R^{37}$ is lower alkyl or cycloalkyl, preferably lower alkyl, preferably n-propyl, i-propyl, sec-butyl, i-butyl, and the like, $R^{39}$ is fluoro, chloro, —CN, lower alkyl, or lower alkoxy, and $R^{40}$ is fluoro, chloro, —CN, lower alkyl, or lower alkoxy. In some embodiments, $R^{37}$ is lower alkyl, fluoro substituted lower alkyl or phenyl, optionally substituted with from 1-3$R^{41}$ groups. In other embodiments, $R^{37}$ is lower alkyl, fluoro substituted lower alkyl or phenyl substituted with from 1-3 groups selected from fluoro, chloro, —CN, —NO$_2$, lower alkyl, fluoro substituted lower alkyl, lower alkoxy, fluoro substituted lower alkoxy, —C(O)—O—$R^{47}$ or —N(H)—C(O)—$R^{48}$. In yet other embodiments, $R^{37}$ is lower alkyl or phenyl substituted with from 1-2 groups selected from fluoro, chloro, —CN, —NO$_2$, lower alkyl, fluoro substituted lower alkyl, lower alkoxy or fluoro substituted lower alkoxy. In some embodiments, $R^{37}$ is lower alkyl or phenyl optionally substituted with 1-2 members selected from CF$_3$ or halogen. In other embodiments, $R^{37}$ is propyl. In yet other embodiments, $R^{37}$ is 2-trifluoromethylphenyl, 3-trifluoromethylphenyl, 4-trifluoromethylphenyl, 2-fluorophenyl, 3-fluorophenyl, 4-fluorophenyl or 2,5-difluoro-substituted phenyl. All the other variables are as defined in any of the embodiments of the compounds of Formula II described herein.

In some embodiments of compounds of Formula II, $R^{37}$ is mono-alkylamino, di-alkylamino, cycloalkylamino, or heterocycloalkylamino, preferably di-alkylamino or cycloalkylamino. In some embodiments, $R^{37}$ is mono-alkylamino, di-alkylamino, cycloalkylamino, or heterocycloalkylamino, preferably di-alkylamino or cycloalkylamino, $R^{39}$ is fluoro, chloro, —CN, lower alkyl, or lower alkoxy, and $R^{40}$ is fluoro, chloro, —CN, lower alkyl, or lower alkoxy. In some embodiments, $R^{37}$ is mono-alkylamino, di-alkylamino, cycloalkylamino, or heterocycloalkylamino, preferably di-alkylamino or cycloalkylamino, $R^{39}$ is fluoro, chloro, —CN, lower alkyl, or lower alkoxy, and $R^{40}$ is fluoro, chloro, —CN, lower alkyl, or lower alkoxy; and $R^{38}$ is hydrogen. In some embodiments, $R^{37}$ is mono-alkylamino, di-alkylamino, cycloalkylamino, or heterocycloalkylamino, preferably di-alkylamino or cycloalkylamino, $R^{39}$ is fluoro, chloro, —CN, lower alkyl, or lower alkoxy, and $R^{40}$ is fluoro, chloro, —CN, lower alkyl, or lower alkoxy; and $R^{38}$ is fluoro. All the other variables are as defined in any of the embodiments of the compounds of Formula II described herein.

In some embodiments of compounds of Formula II, $R^{37}$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments, $R^{37}$ is phenyl optionally substituted with 1 or 2 substituents independently selected from the group consisting of fluoro, lower alkyl, fluoro substituted lower alkyl, lower alkoxy, and fluoro substituted lower alkoxy, $R^{39}$ is fluoro, chloro, —CN, lower alkyl, or lower alkoxy, and $R^{40}$ is fluoro, chloro, —CN, lower alkyl, or lower alkoxy. In some embodiments, $R^{37}$ is phenyl mono-substituted with fluoro, lower alkyl, or —CF$_3$, or di-substituted with two fluoro, two lower alkyl, or one fluoro and one lower alkoxy. In some embodiments, $R^{37}$ is phenyl mono-substituted with fluoro, lower alkyl, or —CF$_3$, or di-substituted with two fluoro, two lower alkyl, or one fluoro and one lower alkoxy, $R^{39}$ is fluoro, chloro, —CN, lower alkyl, or lower alkoxy, and $R^{40}$ is fluoro, chloro, —CN, lower alkyl, or lower alkoxy. In some embodiments, $R^{37}$ is phenyl mono-substituted with fluoro, lower alkyl, or —CF$_3$, or di-substituted with two fluoro, two lower alkyl, or one fluoro and one lower alkoxy, $R^{39}$ is fluoro, chloro, —CN, lower alkyl, or lower alkoxy, and $R^{40}$ is fluoro, chloro, —CN, lower alkyl, or lower alkoxy; and $R^{38}$ is hydrogen. In some embodiments, $R^{37}$ is phenyl mono-substituted with fluoro, lower alkyl, or —CF$_3$, or di-substituted with two fluoro, two lower alkyl, or one fluoro and one lower alkoxy, $R^{39}$ is fluoro, chloro, —CN, lower alkyl, or lower alkoxy, and $R^{40}$ is fluoro, chloro, —CN, lower alkyl, or lower alkoxy; and $R^{38}$ is fluoro. In some embodiments, $R^{37}$ is 4-trifluoromethylphenyl, 2-fluorophenyl, 3-fluorophenyl or 2,5-difluoro-substituted phenyl. All the other variables are as defined in any of the embodiments of the compounds of Formula II described herein.

In some embodiments of compounds of Formula II, $R^{37}$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments, $R^{37}$ is 5-6 membered heteroaryl optionally substituted with 1 or 2 substituents independently selected from the group consisting of lower alkyl and lower alkoxy, preferably pyrdinyl mono- or di-substituted with methoxy, $R^{39}$ is fluoro, chloro, —CN, lower alkyl, or lower alkoxy, and $R^{40}$ is fluoro, chloro, —CN, lower alkyl, or lower alkoxy. In some embodiments, $R^{37}$ is 5-6 membered heteroaryl optionally substituted with 1 or 2 substituents independently selected from the group consisting of lower alkyl and lower alkoxy, preferably pyrdinyl mono- or di-substituted with methoxy, $R^{39}$ is fluoro, chloro, —CN, lower alkyl, or lower alkoxy, and $R^{40}$ is fluoro, chloro, —CN, lower alkyl, or lower alkoxy; and $R^{38}$ is hydrogen. In some embodiments, $R^{37}$ is 5-6 membered heteroaryl optionally substituted with 1 or 2 substituents independently selected from the group consisting of lower alkyl and lower alkoxy, preferably pyrdinyl mono- or di-substituted with methoxy, $R^{39}$ is fluoro, chloro, —CN, lower alkyl, or lower alkoxy, and $R^{40}$ is fluoro, chloro, —CN, lower alkyl, or lower alkoxy; and $R^{38}$ is fluoro.

In some embodiments of compounds of Formula II, $R^{38}$ is H, —F or fluoro substituted lower alkyl. In certain instances, $R^{38}$ is H, F or CF$_3$. In another instances, $R^{38}$ is F. In other embodiments, $R^{39}$ is fluoro, chloro, —CN, —OH, —NH$_2$, lower alkoxy, lower alkyl optionally substituted with one or more $R^{43}$, cycloalkylamino, cycloalkylalkyl-NH—, heterocycloalkylamino and heterocycloalkylalkyl-NH—. In some embodiments, $R^{39}$ is fluoro, chloro, —CN, —OH, —NH$_2$, lower alkyl optionally substituted with fluoro, lower alkoxy, cycloalkylamino, cycloalkylalkyl-NH—, heterocycloalkylamino and heterocycloalkylalkyl-NH—. In a further embodiments, $R^{39}$ is fluoro, chloro, —CN, —OH, —NH$_2$, CH$_3$, CH$_3$O—, CF$_3$, cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopentylamino, cyclohexylamino, cyclopropylmethylamino, cyclobutylmethylamino, cyclopentylmethylamino, cyclohexylmethylamino, 2-tetrahydrofuranylamino, 3-tetrahydrofuranylamino or 4-tetrahydropyranylamino. All the other variables are as defined in any of the embodiments of the compounds of Formula II described herein.

In some embodiments of compounds of Formula II, $R^{40}$ is H, lower alkyl optionally substituted with one or more $R^{43}$, halogen, lower alkoxy or CN. In some embodiments, $R^{43}$ is fluoro, —OH, lower alkoxy, mono-alkylamino, di-alkylamino, cyclopropylamino, cyclobutylamino, cyclopentylamino, cyclohexylamino, cycloheptylamino, 2-tetrahydrofuranylamino, 3-tetrahydrofuranylamino, 2-tetrahydropyranylamino, 3-tetrahydropyranylamino or 4-tetrahydropyranylamino. All the other variables are as defined in any of the embodiments of the compounds of Formula II described herein.

In a third aspect, compounds having the structure according to the following Formula III are provided:

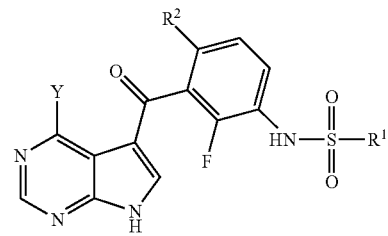

Formula III or a pharmaceutically acceptable salt thereof,
  wherein Y, $R^1$ and $R^2$ in Formula III are as defined in any of the embodiments of the compounds of Formula II described herein. In some embodiments:
  Y is selected from the group consisting of fluoro, chloro, bromo, iodo, lower alkyl, lower alkoxy, haloalkyl, CN, —OH, fluoro substituted alkyl, cycloalkyl, —OR$^8$, and —N(R$^3$)—R$^4$;
  $R^1$ is selected from the group consisting of lower alkyl, fluoro substituted lower alkyl, cycloalkyl, mono-alkylamino, di-alkylamino, cycloalkylamino, heterocycloalkylamino, phenyl optionally substituted with one or more R$^6$ (e.g., $R^1$ is 2-fluoro-substituted phenyl, 3-fluoro-substituted phenyl, 2,5-difluoro-substituted phenyl or 4-lower alkyl-substituted phenyl, wherein lower alkyl is optionally substituted with one or more fluorine), and heteroaryl optionally substituted with one or more $R^7$;

$R^2$ is hydrogen, fluoro, chloro, or lower alkyl optionally substituted with one or more fluorine;

$R^3$ is hydrogen and $R^4$ is selected from the group consisting of hydrogen, —$OR^8$, lower alkyl optionally substituted with one or more $R^{11}$, cycloalkyl optionally substituted with one or more $R^{12}$, heterocycloalkyl optionally substituted with one or more $R^{13}$, aryl optionally substituted with one or more $R^{14}$, and heteroaryl optionally substituted with one or more $R^{15}$;

or $R^3$ and $R^4$ are both lower alkyl;

or $R^3$ and $R^4$ combine with the nitrogen to which they are attached to form cycloalkylamino;

each $R^6$, when present, is independently selected from the group consisting of fluoro, chloro, —CN, —$NO_2$, lower alkyl, fluoro substituted lower alkyl, lower alkoxy, fluoro substituted lower alkoxy, —C(O)—O—$R^{18}$, —N(H)—C(O)—$R^{19}$, and heteroaryl optionally substituted with one or more lower alkyl; or two $R^6$ on adjacent carbons combine to form a fused heterocycloalkyl optionally substituted with one or more lower alkyl;

each $R^7$, when present, is independently selected from the group consisting of lower alkyl, fluoro substituted lower alkyl, lower alkoxy, —C(O)—O—$R^{20}$, and heteroaryl optionally substituted with one or more lower alkyl;

$R^8$ is hydrogen, lower alkyl optionally substituted with one or more fluorine, or, when $R^8$ is a $C_{2-6}$ alkyl, said alkyl may optionally be substituted with one or more $R^{21}$; cycloalkyl optionally substituted with one or more $R^{21}$, or heterocycloalkyl optionally substituted with one or more $R^{21}$;

each $R^{11}$, when present, is independently selected from the group consisting of fluoro, —OH, lower alkoxy, fluoro substituted lower alkoxy, —$NH_2$, mono-alkylamino, di-alkylamino, cycloalkylamino, heterocycloalkylamino, cycloalkyl optionally substituted with one or more $R^{12}$, heterocycloalkyl optionally substituted with one or more $R^{13}$, aryl optionally substituted with one or more $R^{14}$, and heteroaryl optionally substituted with one or more $R^{15}$;

each $R^{12}$, when present, is independently selected from the group consisting of fluoro, lower alkyl, fluoro substituted lower alkyl, —OH, lower alkoxy, fluoro substituted lower alkoxy, —$NH_2$, mono-alkylamino, di-alkylamino, cycloalkylamino, heterocycloalkylamino, —N(H)—C(O)—$R^{22}$, —N(H)—S(O)$_2$—$R^{23}$, C(O)—$R^{24}$, and S(O)$_2$—$R^{25}$;

each $R^{13}$, when present, is independently selected from the group consisting of fluoro, —OH, lower alkoxy, fluoro substituted lower alkoxy, —$NH_2$, mono-alkylamino, di-alkylamino, cycloalkylamino, heterocycloalkylamino, —N(H)—C(O)—$R^{26}$, —N(H)—S(O)$_2$—$R^{27}$, C(O)—$R^{28}$, S(O)$_2$—$R^{29}$, and lower alkyl optionally substituted with one or more $R^{30}$;

each $R^{14}$ and $R^{15}$, when present, are independently selected from the group consisting of fluoro, chloro, —OH, —$NH_2$, —CN, —$NO_2$, —N(H)—C(O)—$R^{31}$, —N(H)—S(O)$_2$—$R^{32}$, C(O)—$R^{33}$, S(O)$_2$—$R^{34}$, lower alkyl, fluoro substituted lower alkyl, lower alkoxy, fluoro substituted lower alkoxy, mono-alkylamino, di-alkylamino, cycloalkylamino, heterocycloalkylamino, aryl optionally substituted with one or more $R^{35}$, and heteroaryl optionally substituted with one or more $R^{36}$;

each $R^{17}$, when present, is independently fluoro, —OH, lower alkoxy, —$NH_2$, mono-alkylamino, di-alkylamino, cycloalkylamino, or heterocycloalkylamino;

each $R^{18}$ and $R^{20}$, when present, are independently hydrogen, lower alkyl or fluoro substituted lower alkyl;

each $R^{19}$, $R^{22}$, $R^{23}$, $R^{26}$, $R^{27}$, $R^{31}$ and $R^{32}$, when present, are independently lower alkyl, fluoro substituted lower alkyl, mono-alkylamino, di-alkylamino, cycloalkylamino, or heterocycloalkylamino;

each $R^{21}$, when present, is fluoro, —OH, lower alkoxy, —$NH_2$, mono-alkylamino, di-alkylamino, cycloalkylamino, or heterocycloalkylamino;

each $R^{24}$, $R^{25}$, $R^{28}$, $R^{29}$, $R^{33}$, and $R^{34}$, when present, are independently lower alkyl, fluoro substituted lower alkyl, —OH, lower alkoxy, fluor substituted lower alkoxy, —$NH_2$, mono-alkylamino, di-alkylamino, cycloalkylamino, or heterocycloalkylamino;

each $R^{30}$, when present, is independently fluoro, aryl optionally substituted with one or more $R^{35}$ or heteroaryl optionally substituted with one or more $R^{36}$; and each $R^{35}$ and $R^{36}$, when present, are independently selected from the group consisting of fluoro, chloro, —OH, —$NH_2$, —CN, —$NO_2$, lower alkyl, fluoro substituted lower alkyl, lower alkoxy, fluoro substituted lower alkoxy, mono-alkylamino, di-alkylamino, cycloalkylamino, and heterocycloalkylamino.

In some embodiments of compounds of Formula III, Y is fluoro, chloro, bromo, or iodo, preferably fluoro; $R^1$ is lower alkyl or cycloalkyl, preferably lower alkyl, preferably n-propyl, i-propyl, sec-butyl, i-butyl, and the like. In some embodiments of compounds of Formula III, Y is fluoro, chloro, bromo, or iodo, preferably fluoro; $R^1$ is lower alkyl or cycloalkyl, preferably lower alkyl, preferably n-propyl, i-propyl, sec-butyl, i-butyl, and the like; and $R^2$ is hydrogen. In some embodiments of compounds of Formula III, Y is fluoro, chloro, bromo, or iodo, preferably fluoro; $R^1$ is lower alkyl or cycloalkyl, preferably lower alkyl, preferably n-propyl, i-propyl, sec-butyl, i-butyl, and the like; and $R^2$ is fluoro. In some embodiments, $R^1$ is lower alkyl or cycloalkyl, preferably lower alkyl, preferably n-propyl, i-propyl, sec-butyl, i-butyl, and the like. All the other variables are as defined in any of the embodiments of the compounds of Formulas I, II and III described herein.

In some embodiments of compounds of Formula III, Y is lower alkyl, fluoro substituted alkyl, or cycloalkyl; $R^1$ is lower alkyl or cycloalkyl, preferably lower alkyl, preferably n-propyl, i-propyl, sec-butyl, i-butyl, and the like. In some embodiments of compounds of Formula III, Y is lower alkyl, fluoro substituted alkyl, or cycloalkyl; $R^1$ is lower alkyl or cycloalkyl, preferably lower alkyl, preferably n-propyl, i-propyl, sec-butyl, i-butyl, and the like; and $R^2$ is hydrogen. In some embodiments of compounds of Formula III, Y is lower alkyl, fluoro substituted alkyl, or cycloalkyl; $R^1$ is lower alkyl or cycloalkyl, preferably lower alkyl, preferably n-propyl, i-propyl, sec-butyl, i-butyl, and the like; and $R^2$ is fluoro. In some embodiments, $R^1$ is lower alkyl or cycloalkyl, preferably lower alkyl, preferably n-propyl, i-propyl, sec-butyl, i-butyl, and the like. All the other variables are as defined in any of the embodiments of the compounds of Formulas I, II and III described herein.

In some embodiments of compounds of Formula III, Y is —$OR^8$; $R^1$ is lower alkyl or cycloalkyl, preferably lower alkyl, preferably n-propyl, i-propyl, sec-butyl, i-butyl, and the like. In some embodiments of compounds of Formula III, Y is —OR$^8$; R$^1$ is lower alkyl or cycloalkyl, preferably lower alkyl, preferably n-propyl, i-propyl, sec-butyl, i-butyl, and the like; and R$^2$ is hydrogen. In some embodiments of compounds of Formula III, Y is —OR$^8$; R$^1$ is lower alkyl or cycloalkyl, preferably lower alkyl, preferably n-propyl, i-propyl, sec-butyl, i-butyl, and the like; and R$^2$ is fluoro. In some embodiments, R$^1$ is lower alkyl or cycloalkyl, preferably lower alkyl, preferably n-propyl, i-propyl, sec-butyl, i-butyl, and the like, and R$^8$ is hydrogen or lower alkyl. All the other variables are as defined in any of the embodiments of the compounds of Formulas I, II and III described herein.

In some embodiments of compounds of Formula III, Y—N(R$^3$)—R$^4$; R$^1$ is lower alkyl or cycloalkyl, preferably lower alkyl, preferably n-propyl, i-propyl, sec-butyl, i-butyl, and the like. In some embodiments of compounds of Formula III, Y—N(R$^3$)—R$^4$; R$^1$ is lower alkyl or cycloalkyl, preferably lower alkyl, preferably n-propyl, i-propyl, sec-butyl, i-butyl, and the like; and R$^2$ is hydrogen. In some embodiments of compounds of Formula III, Y—N(R$^3$)—R$^4$; R$^1$ is lower alkyl or cycloalkyl, preferably lower alkyl, preferably n-propyl, i-propyl, sec-butyl, i-butyl, and the like; and R$^2$ is fluoro. In some embodiments, R$^1$ is lower alkyl or cycloalkyl, preferably lower alkyl, preferably n-propyl, i-propyl, sec-butyl, i-butyl, and the like, R$^3$ is hydrogen and R$^4$ is selected from the group consisting of hydrogen, —OH, lower alkyl optionally substituted with R$^{11}$, cycloalkyl, heterocycloalkyl optionally substituted with lower alkyl, phenyl optionally substituted with one or more R$^{14}$, and 5-6 membered heteroaryl optionally substituted with one or more lower alkyl, or R$^3$ and R$^4$ are both lower alkyl, or R$^3$ and R$^4$ combine with the nitrogen to which they are attached to form cycloalkylamino, wherein R$^{11}$ and R$^{14}$ are as defined for Formula I, preferably wherein R$^{11}$ is selected from the group consisting of cycloalkyl, —OH, lower alkoxy, mono-alkylamino, di-alkylamino, cycloalkylamino, and heterocloalkylamino, and R$^{14}$ is selected from the group consisting of fluoro, chloro, —CN, —NO$_2$, lower alkyl, fluoro substituted lower alkyl, lower alkoxy, and fluoro substituted lower alkoxy. All the other variables are as defined in any of the embodiments of the compounds of Formulas I, II and III described herein.

In some embodiments of compounds of Formula III, Y is fluoro, chloro, bromo, or iodo, preferably fluoro; R$^1$ is mono-alkylamino, di-alkylamino, cycloalkylamino, or heterocycloalkylamino, preferably di-alkylamino or cycloalkylamino. In some embodiments of compounds of Formula III, Y is fluoro, chloro, bromo, or iodo, preferably fluoro; R$^1$ is mono-alkylamino, di-alkylamino, cycloalkylamino, or heterocycloalkylamino, preferably di-alkylamino or cycloalkylamino; and R$^2$ is hydrogen. In some embodiments of compounds of Formula III, Y is fluoro, chloro, bromo, or iodo, preferably fluoro; R$^1$ is mono-alkylamino, di-alkylamino, cycloalkylamino, or heterocycloalkylamino, preferably di-alkylamino or cycloalkylamino; and R$^2$ is fluoro. In some embodiments, R$^1$ is mono-alkylamino, di-alkylamino, cycloalkylamino, or heterocycloalkylamino, preferably di-alkylamino or cycloalkylamino. All the other variables are as defined in any of the embodiments of the compounds of Formulas I, II and III described herein.

In some embodiments of compounds of Formula III, Y is lower alkyl, fluoro substituted alkyl, or cycloalkyl; R$^1$ is mono-alkylamino, di-alkylamino, cycloalkylamino, or heterocycloalkylamino, preferably di-alkylamino or cycloalkylamino. In some embodiments of compounds of Formula III, Y is lower alkyl, fluoro substituted alkyl, or cycloalkyl; R$^1$ is mono-alkylamino, di-alkylamino, cycloalkylamino, or heterocycloalkylamino, preferably di-alkylamino or cycloalkylamino; and R$^2$ is hydrogen. In some embodiments of compounds of Formula III, Y is lower alkyl, fluoro substituted alkyl, or cycloalkyl; R$^1$ is mono-alkylamino, di-alkylamino, cycloalkylamino, or heterocycloalkylamino, preferably di-alkylamino or cycloalkylamino; and R$^2$ is fluoro. In some embodiments, R$^1$ is mono-alkylamino, di-alkylamino, or cycloalkylamino, preferably di-alkylamino, cycloalkylamino, or heterocycloalkylamino. All the other variables are as defined in any of the embodiments of the compounds of Formulas I, II and III described herein.

In some embodiments of compounds of Formula III, Y is —OR$^8$; R$^1$ is mono-alkylamino, di-alkylamino, cycloalkylamino, or heterocycloalkylamino, preferably di-alkylamino or cycloalkylamino. In some embodiments of compounds of Formula III, Y is —OR$^8$; R$^1$ is mono-alkylamino, di-alkylamino, cycloalkylamino, or heterocycloalkylamino, preferably di-alkylamino or cycloalkylamino; and R$^2$ is hydrogen. In some embodiments of compounds of Formula III, Y is —OR$^8$; R$^1$ is mono-alkylamino, di-alkylamino, cycloalkylamino, or heterocycloalkylamino, preferably di-alkylamino or cycloalkylamino; and R$^2$ is fluoro. In some embodiments, R$^1$ is mono-alkylamino, di-alkylamino, cycloalkylamino, or heterocycloalkylamino, preferably di-alkylamino or cycloalkylamino, and R$^8$ is hydrogen or lower alkyl. All the other variables are as defined in any of the embodiments of the compounds of Formulas I, II and III described herein.

In some embodiments of compounds of Formula III, Y is —N(R$^3$)—R$^4$; R$^1$ is mono-alkylamino, di-alkylamino, cycloalkylamino, or heterocycloalkylamino, preferably di-alkylamino or cycloalkylamino. In some embodiments of compounds of Formula III, Y is —N(R$^3$)—R$^4$; R$^1$ is mono-alkylamino, di-alkylamino, cycloalkylamino, or heterocycloalkylamino, preferably di-alkylamino or cycloalkylamino; and R$^2$ is hydrogen. In some embodiments of compounds of Formula III, Y is —N(R$^3$)—R$^4$; R$^1$ is mono-alkylamino, di-alkylamino, cycloalkylamino, or heterocycloalkylamino, preferably di-alkylamino or cycloalkylamino; and R$^2$ is fluoro. In some embodiments, R$^1$ is mono-alkylamino, di-alkylamino, cycloalkylamino, or heterocycloalkylamino, preferably di-alkylamino or cycloalkylamino, R$^3$ is hydrogen and R$^4$ is selected from the group consisting of hydrogen, —OH, lower alkyl optionally substituted with R$^{11}$, cycloalkyl, heterocycloalkyl optionally substituted with lower alkyl, phenyl optionally substituted with one or more R$^{14}$, and 5-6 membered heteroaryl optionally substituted with one or more lower alkyl, or R$^3$ and R$^4$ are both lower alkyl, or R$^3$ and R$^4$ combine with the nitrogen to which they are attached to form cycloalkylamino, wherein R$^{11}$ and R$^{14}$ are as defined for Formula I, preferably wherein R$^{11}$ is selected from the group consisting of cycloalkyl, —OH, lower alkoxy, mono-alkylamino, di-alkylamino, cycloalkylamino, and heterocycloalkylamino, and R$^{14}$ is selected from the group consisting of fluoro, chloro, —CN, —NO$_2$, lower alkyl, fluoro substituted lower alkyl, lower alkoxy, and fluoro substituted lower alkoxy. All the other variables are as defined in any of the embodiments of the compounds of Formulas I, II and III described herein.

In some embodiments of compounds of Formula III, Y is fluoro, chloro, bromo, or iodo, preferably fluoro; R$^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments of compounds of Formula III, Y is fluoro, chloro, bromo, or iodo, preferably fluoro; R$^1$ is phenyl optionally substituted with 1 or 2 substituents independently selected from the group consisting of fluoro, lower alkyl, fluoro substituted lower alkyl, lower alkoxy, and fluoro substituted lower alkyl; and $R^2$ is hydrogen. In some embodiments of compounds of Formula III, Y is fluoro, chloro, bromo, or iodo, preferably fluoro; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy. All the other variables are as defined in any of the embodiments of the compounds of Formulas I, II and III described herein.

In some embodiments of compounds of Formula III, Y is lower alkyl, fluoro substituted alkyl, or cycloalkyl; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments of compounds of Formula III, Y is lower alkyl, fluoro substituted alkyl, or cycloalkyl; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is hydrogen. In some embodiments of compounds of Formula III, Y is lower alkyl, fluoro substituted alkyl, or cycloalkyl; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy. All the other variables are as defined in any of the embodiments of the compounds of Formulas I, II and III described herein.

In some embodiments of compounds of Formula III, Y is —$OR^8$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments of compounds of Formula III, Y is —$OR^8$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments, $R^1$ is phenyl mono-substituted with fluoro, lower alkyl, or —$CF_3$, or di-substituted with two fluoro, two lower alkyl, or one fluoro and one lower alkoxy; and $R^2$ is hydrogen. In some embodiments, $R^1$ is phenyl mono-substituted with fluoro, lower alkyl, or —$CF_3$, or di-substituted with two fluoro, two lower alkyl, or one fluoro and one lower alkoxy; and $R^2$ is fluoro. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy, and $R^8$ is hydrogen or lower alkyl. All the other variables are as defined in any of the embodiments of the compounds of Formulas I, II and III described herein.

In some embodiments of compounds of Formula III, Y is —$N(R^3)$—$R^4$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy. In some embodiments of compounds of Formula III, Y is —$N(R^3)$—$R^4$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is hydrogen. In some embodiments of compounds of Formula III, Y is —$N(R^3)$—$R^4$; $R^1$ is phenyl optionally substituted with 1 or 2 substituents independently selected from the group consisting of fluoro, lower alkyl, fluoro substituted lower alkyl, lower alkoxy, and fluoro substituted lower alkoxy; and $R^2$ is fluoro. In some embodiments, $R^1$ is phenyl mono-substituted with fluoro, lower alkyl, or —$CF_3$, or di-substituted with two fluoro, two lower alkyl, or one fluoro and one lower alkoxy. In some embodiments, $R^1$ is phenyl optionally substituted with 1 or 2 substituents independently selected from the group consisting of fluoro, lower alkyl, fluoro substituted lower alkyl, lower alkoxy, and fluoro substituted lower alkoxy, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{13}$ is selected from the group consisting of fluoro, chloro, —CN, —$NO_2$, lower alkyl, fluoro substituted lower alkyl, lower alkoxy, and fluoro substituted lower alkoxy. In some embodiments, $R^1$ is phenyl mono-substituted with fluoro, lower alkyl, or —$CF_3$, or di-substituted with two fluoro, two lower alkyl, or one fluoro and one lower alkoxy, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino, wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{14}$ is selected from the group consisting of fluoro, chloro, —CN, —$NO_2$, lower alkyl, fluoro substituted lower alkyl, lower alkoxy, and fluoro substituted lower alkoxy. All the other variables are as defined in any of the embodiments of the compounds of Formulas I, II and III described herein.

In some embodiments of compounds of Formula III, Y is fluoro, chloro, bromo, or iodo, preferably fluoro; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula III, Y is fluoro, chloro, bromo, or iodo, preferably fluoro; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula III, Y is fluoro, chloro, bromo, or iodo, preferably fluoro; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy. All the other variables are as defined in any of the embodiments of the compounds of Formulas I, II and III described herein.

In some embodiments of compounds of Formula III, Y is lower alkyl, fluoro substituted alkyl, or cycloalkyl; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula III, Y is lower alkyl, fluoro substituted alkyl, or cycloalkyl; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula III, Y is lower alkyl, fluoro substituted alkyl, or cycloalkyl; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy. All the other variables are as defined in any of the embodiments of the compounds of Formulas I, II and III described herein.

In some embodiments of compounds of Formula III, Y is —$OR^8$; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula III, Y is —$OR^8$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula III, Y is —$OR^8$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy, and $R^8$ is hydrogen or lower alkyl. All the other variables are as defined in any of the embodiments of the compounds of Formulas I, II and III described herein.

In some embodiments of compounds of Formula III, Y is —$N(R^3)$—$R^4$; $R^1$ is 5-6 membered heteroaryl optionally substituted with 1 or 2 substituents independently selected from the group consisting of lower alkyl and lower alkoxy, preferably pyrdinyl mono- or di-substituted with methoxy. In some embodiments of compounds of Formula III, Y is —$N(R^3)$—$R^4$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is hydrogen. In some embodiments of compounds of Formula III, Y is —$N(R^3)$—$R^4$; $R^1$ is 5-6 membered heteroaryl optionally substituted with 1 or 2 substituents independently selected from the group consisting of lower alkyl and lower alkoxy, preferably pyrdinyl mono- or di-substituted with methoxy; and $R^2$ is fluoro. In some embodiments, $R^1$ is 5-6 membered heteroaryl optionally substituted with 1 or 2 substituents independently selected from the group consisting of lower alkyl and lower alkoxy, preferably pyrdinyl mono- or di-substituted with methoxy, $R^3$ is hydrogen and $R^4$ is selected from the group consisting of hydrogen, —OH, lower alkyl optionally substituted with $R^{11}$, cycloalkyl, heterocycloalkyl optionally substituted with lower alkyl, phenyl optionally substituted with one or more $R^{14}$, and 5-6 membered heteroaryl optionally substituted with one or more lower alkyl, or $R^3$ and $R^4$ are both lower alkyl, or $R^3$ and $R^4$ combine with the nitrogen to which they are attached to form cycloalkylamino, wherein $R^{11}$ and $R^{14}$ are as defined for Formula I, preferably wherein $R^{11}$ is selected from the group consisting of cycloalkyl, —OH, lower alkoxy, mono-alkylamino, di-alkylamino, cycloalkylamino, and heterocycloalkylamino, and $R^{14}$ is selected from the group consisting of fluoro, chloro, —CN, —$NO_2$, lower alkyl, fluoro substituted lower alkyl, lower alkoxy, and fluoro substituted lower alkoxy. All the other variables are as defined in any of the embodiments of the compounds of Formulas I, II and III described herein.

In some embodiments of compounds of Formulas I, II and III, Y is fluoro, chloro, bromo, iodo, lower alkyl, lower alkoxy, haloalkyl, CN, —OH, cycloalkyl, —$OR^8$ or —NH($R^4$). In a preferred embodiment, Y is $CH_3$, ethyl, methoxy, ethyoxy, isobutyl, CN, OH, F, Cl, Br, I, $NH_2$, butyoxy, 2-methylpropoxy, 4-tetrahydropyranyloxy, 2-tetrahyrofuranyloxy, 3-tetrahyrofuranyloxy, alkoxyamino or HO—NH—.

In another aspects, the invention provides a compound having sub formula IIIa:

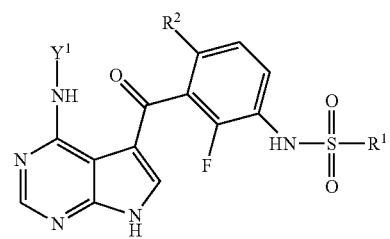

IIIa wherein $Y^1$ is lower alkyl optionally substituted with from one to three $R^{11}$, cycloalkyl, cycloalkylalkyl, aryl, arylalkyl, heterocycloalkyl, heterocycloalkylalkyl, heteroaryl or heteroarylalkyl, wherein: the cycloalkyl and cycloalkylalkyl are each optionally substituted with from one to three $R^{12}$; the heterocycloalkyl and heterocycloalkylalkyl are each optionally substituted with from one to three $R^{13}$; the aryl and arylalkyl are each optionally substituted with from one to three $R^{14}$ optionally, wherein the two adjacent $R^{14}$ groups on the aryl ring are taken together to form a 5 or 6-membered hetero aromatic ring having from 1-4 heteroatoms selected from O or N; and the heteroaryl and heteroarylalkyl are each optionally substituted with from one to three $R^{15}$. The other variables $R^1$ and $R^2$ are as defined in any of the embodiments of compounds of Formulas I, II and III described herein.

In some embodiments of the compounds of Formula IIIa, $Y^1$ is selected from lower alkyl, halogen substituted lower alkyl, 2-hydroxyethyl, cyclopropylamino, cyclobutyl, cyclopropylmethyl, cyclobutylmethyl, cyclopentyl, cyclopentylmethyl, cyclohexylmethyl, cyclohexyl, 2-oxetanyl, 2-oxetanylmethyl, 3-oxetanyl, 3-oxetanylmethyl, 2-tetrahydrofuranyl, 3-tetrahydrofuranyl, 2-tetrahydropyranyl, 3-tetrahydropyranyl, 4-tetrahydropyranyl, 2-tetrahydrofuranylmethyl, 3-tetrahydrofuranylmethyl, 2-tetrahydropyranylmethyl, 3-tetrahydropyranylmethyl, 4-tetrahydropyranylmethyl, 1-methyl-2-aziridinyl, 1-methyl-2-aziridinylmethyl, 1-methyl-2-azetidinyl, 1-methyl-2-azetidinylmethyl, 1-methyl-3-azetidinyl, 1-methyl-3-azetidinylmethyl, 1-methyl-2-pyrrolidinyl, 1-methyl-2-pyrrolidinylmethyl, 1-methyl-3-pyrrolidinyl, 1-methyl-3-pyrrolidinylmethyl, 1-methyl-2-piperidinyl, 1-methyl-2-piperidinylmethyl, 1-methyl-3-piperidinyl, 1-methyl-3-piperidinylmethyl, 1-methyl-4-piperidinyl, 1-methyl-4-piperidinylmethyl, 1-methylsulfonyl-2-piperidinyl, 1-methylsulfonyl-2-piperidinylmethyl, 1-methylsulfonyl-3-piperidinyl, 1-methylsulfonyl-3-piperidinylmethyl, 1-methylsulfonyl-4-piperidinyl, 1-methylsulfonyl-4-piperidinylmethyl, 1,1-dioxo-4-thianyl, 1,1-dioxo-4-thianylmethyl, phenyl, 2-fluorophenyl, 3-fluorophenyl, 4-fluorophenyl, 2-benzyl, 2-fluorobenzyl, 3-fluorobenzyl, 4-fluorobenzyl, 2-pyridyl, 2-pyridylmethyl, 3-pyridyl, 3-pyridylmethyl, 4-pyridyl, 4-pyridylmethyl, 2-chlorophenyl, 3-chlorophenyl, 4-chlorophenyl, 2-dimethylaminophenyl, 3-dimethylaminophenyl, 4-dimethylaminophenyl, 2-dimethylaminobenzyl, 2-dimethylaminobenzyl, 3-dimethylaminobenzyl, 4-dimethylaminobenzyl, 2-hydroxyphenyl, 3-hydroxyphenyl, 4-hydroxyphenyl, 2-hydroxybenzyl, 3-hydroxybenzyl, 4-hydroxybenzyl, 2-carboxyphenyl, 3-carboxyphenyl, 4-carboxyphenyl, 2-carboxybenzyl, 3-carboxybenzyl, 4-carboxybenzyl, 2-methoxycarbonylphenyl, 3-methoxycarbonylphenyl, 4-methoxycarbonylphenyl, 2-methoxycarbonylbenzyl, 3-methoxycarbonylbenzyl, 4-methoxycarbonylbenzyl, 1-alkyl-4-pyrazolyl, 1-alkyl-4-pyrazolylmethyl, 3-pyridazinyl, pyridazinylmethyl, 4-pyridazinyl, 4-pyridazinylmethyl, triazolyl, triazolymethyl, tetrazolyl, tetrazolylmethyl, 2,1,3-benzoxadiazolyl, 2,1,3-benzoxadiazol-5-yl, 2,1,3-benzoxadiazolyl-methyl, 2,1,3-benzoxadiazol-5-ylmethyl, 2,1,3-benzothiadiazolyl, 2,1,3-benzothiadiazol-5-yl, 2,1,3-benzothiadiazolyl-methyl, 2,1,3-benzothiadiazol-5-ylmethyl, 1H-1,2,4-triazol-5-yl, 1H-1,2,4-triazol-5-methyl, 2-oxobenzimidazol-4-yl, 2-oxobenzimidazol-4-methyl, 2-oxobenzimidazol-5-yl, 2-oxobenzimidazol-5-methyl, 1,1-dioxo-thiolan-3-yl, 1,1-dioxothiolan-3-methyl, 3-(2-methyl-1,2,3,4-tetrazol-5-yl)phenyl, 3-(2-methyl-1,2,3,4-tetrazol-5-yl)benzyl, 3-(5-methyl-1,2,3,4-tetrazol-1-yl)phenyl, 3-(1,2,4-triazol-5-yl)phenyl, 3-(1,2,4-triazol-5-yl)benzyl, 3-3-methyl-4H-1,2,4-triazol-5-methyl or 2-(3-methyl-4H-1,2,4-triazol-5-yl)ethyl. In certain instances, $Y^1$ is cyclopropylmethyl. The other variables $R^1$ and $R^2$ are as defined in any of the embodiments of compounds of Formulas I, II, III and IIIa described herein.

In some embodiments of the compounds of Formula IIIa, $R^2$ is H or F. The other variables $R^1$ and $Y^1$ are as defined in any of the embodiments of compounds of Formulas I, II, III and IIIa described herein.

In some embodiments of the compounds of Formulas I, II, III and IIIa, $R^1$ is lower alkyl, cycloalkyl optionally substituted with 1-2 groups selected from halogen or lower alkyl, heterocycloalkyl, heteroaryl optionally substituted with lower alkyl or lower alkoxy, phenyl optionally substituted with 1-2 substitutents selected from lower alkyl, halogen, lower alkoxy, haloalkyl, haloalkoxy or CN. In some embodiments, $R^1$ is methyl, propyl, isobutyl, 2-methylpropyl, $CF_3$, $CF_3CH_2$—, $CHF_2CH_2$—, 4-trifluorophenyl, 2-trifluorophenyl, 3-trifluorophenyl, 3,5-dimethylphenyl, 4-propylphenyl, 3-fluoro-4-methoxyphenyl, 2-cyanophenyl, 3-cyanophenyl, 4-cyanophenyl, 4-fluoro-3-methoxyphenyl, 2,5-difluorophenyl, 2,6-difluorophenyl, 2,4-difluorophenyl, 2-pyridyl, 3-pyridyl, 5-methoxy-2-pyridyl, 3-methoxy-2-pyridyl, 4-methoxy-2-pyridyl, 6-methyl-2-pyridyl, 5-methyl-2-pyridyl, 4-methyl-2-pyridyl, 3-methyl-2-pyridyl, dialkylamino, 1-pyrrolidinyl, 1-piperidinyl, 4-morpholinyl, cycloprpyl, cyclobutyl, cyclopentyl, cyclohexyl, 4,4-difluorocyclohexyl, 1-methyl-4-pyrazolyl, 1-ethyl-4-pyrazolyl, 1-methyl-3-pyrazolyl, 1-ethyl-3-pyrazolyl, 6-methyl-3-pyridyl, 5-methyl-3-pyridyl, 4-methyl-3-pyridyl or 2-methyl-3-pyridyl. In a further embodiment, $R^1$ is 2-fluorophenyl, 3-fluorophenyl, 2,5-difluorophenyl or 4-lower alkyl-substituted phenyl, wherein lower alkyl is optionally substituted with one or more fluorine. All the other variables are as defined in any of the embodiments of compounds of Formulas I, II, III and IIIa described herein.

In a particular group of embodiments of compounds of Formulas I, II, III and IIIa, Y is —$NR^3R^4$, wherein $R^3$ and $R^4$ combine with the nitrogen atom to which they are attached to form a three to seven membered ring having 0-1 additional ring heteroatom selected from O, N or S, wherein the nitrogen or sulfur atom is optionally oxidized. In certain instances, Y is 1-aziridinyl, 1-azetidinyl, 1-pyrrolidinyl, 1-piperidinyl, 1-morpholinyl or 1-azepanyl. All the other variables are as defined in any of the embodiments of compounds of Formulas I, II, III and IIIa described herein.

In various aspects and embodiments, provided are the compounds shown in Table I below, and/or pharmaceutically acceptable salts of the compounds shown in Table I.

TABLE I

| Comp # | Structure | Name | MS |
|---|---|---|---|
| P-1001 | 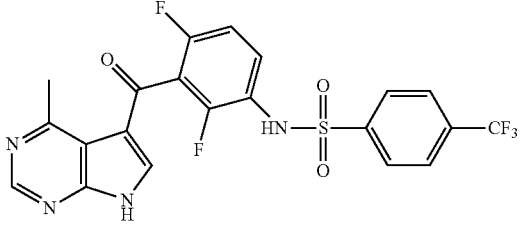 [SMILES: Cc1ncnc2[nH]cc(C(=O)c3c(F)ccc(NS(=O)(=O)c4ccc(C(F)(F)F)cc4)c3F)c12] | N-[2,4-Difluoro-3-(4-methyl-7H-pyrrolo[2,3-d]pyrimidine-5-carbonyl)-phenyl]-4-trifluoromethyl-benzenesulfonamide | 496.9 |

TABLE I-continued

| Comp # | Name | MS |
|---|---|---|
| P-1002 | Propane-1-sulfonic acid [3-(4-ethoxy-7H-pyrrolo[2,3-d]pyrimidine-5-carbonyl)-2,4-difluoro-phenyl]-amide | 424.9 |
| P-1003 | 2-Methyl-propane-1-sulfonic acid [2,4-difluoro-3-(4-methyl-7H-pyrrolo[2,3-d]pyrimidine-5-carbonyl)-phenyl]-amide | 409.3 |
| P-1004 | 2-Methyl-propane-1-sulfonic acid [2,4-difluoro-3-(4-methoxy-7H-pyrrolo[2,3-d]pyrimidine-5-carbonyl)-phenyl]-amide | 425.1 |
| P-1005 | N-[2,4-Difluoro-3-(4-methoxy-7H-pyrrolo[2,3-d]pyrimidine-5-carbonyl)-phenyl]-4-propyl-benzenesulfonamide | 486.95 |
| P-1006 | N-[3-(4-Ethoxy-7H-pyrrolo[2,3-d]pyrimidine-5-carbonyl)-2,4-difluoro-phenyl]-4-trifluoromethyl-benzenesulfonamide | 526.95 |
| P-1007 | N-[2,4-Difluoro-3-(4-methyl-7H-pyrrolo[2,3-d]pyrimidine-5-carbonyl)-phenyl]-4-propyl-benzenesulfonamide | 470.95 |

TABLE I-continued

| Comp # | Structure | Name | MS |
|---|---|---|---|
| P-1008 | 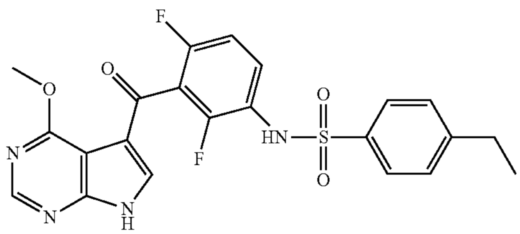 [SMILES: CCc1ccc(S(=O)(=O)Nc2ccc(F)c(C(=O)c3c[nH]c4ncnc(OC)c34)c2F)cc1] | N-[2,4-Difluoro-3-(4-methoxy-7H-pyrrolo[2,3-d]pyrimidine-5-carbonyl)-phenyl]-4-ethyl-benzenesulfonamide | 473.0 |
| P-1009 | 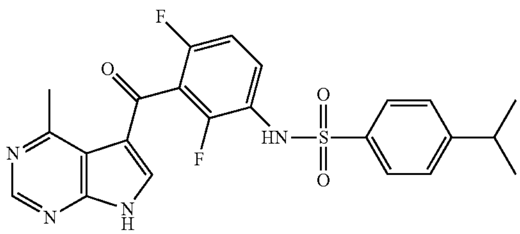 [SMILES: Cc1ncnc2[nH]cc(C(=O)c3c(F)ccc(NS(=O)(=O)c4ccc(C(C)C)cc4)c3F)c12] | N-[2,4-Difluoro-3-(4-methyl-7H-pyrrolo[2,3-d]pyrimidine-5-carbonyl)-phenyl]-4-isopropyl-benzenesulfonamide | 471.3 |
| P-1010 | 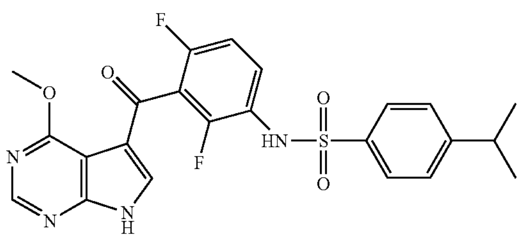 [SMILES: COc1ncnc2[nH]cc(C(=O)c3c(F)ccc(NS(=O)(=O)c4ccc(C(C)C)cc4)c3F)c12] | N-[2,4-Difluoro-3-(4-methoxy-7H-pyrrolo[2,3-d]pyrimidine-5-carbonyl)-phenyl]-4-isopropyl-benzenesulfonamide | 486.8 |
| P-1011 | 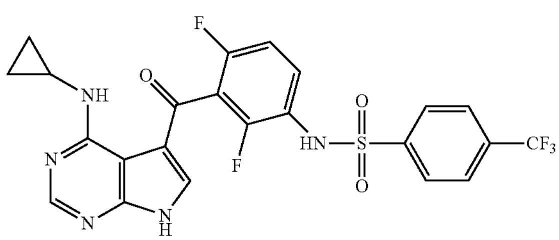 [SMILES: O=C(c1c(F)ccc(NS(=O)(=O)c2ccc(C(F)(F)F)cc2)c1F)c1c[nH]c2ncnc(NC3CC3)c12] | N-[3-(4-Cyclopropylamino-7H-pyrrolo[2,3-d]pyrimidine-5-carbonyl)-2,4-difluoro-phenyl]-4-trifluoromethyl-benzenesulfonamide | 537.8 |
| P-1012 | 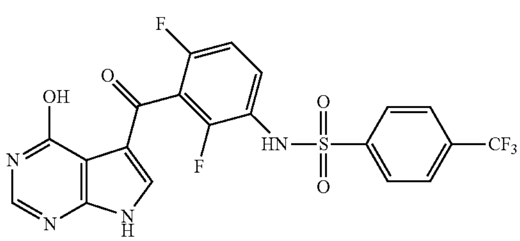 [SMILES: O=C(c1c(F)ccc(NS(=O)(=O)c2ccc(C(F)(F)F)cc2)c1F)c1c[nH]c2ncnc(O)c12] | N-[2,4-Difluoro-3-(4-hydroxy-7H-pyrrolo[2,3-d]pyrimidine-5-carbonyl)-phenyl]-4-trifluoromethyl-benzenesulfonamide | 499.0 |
| P-1013 | 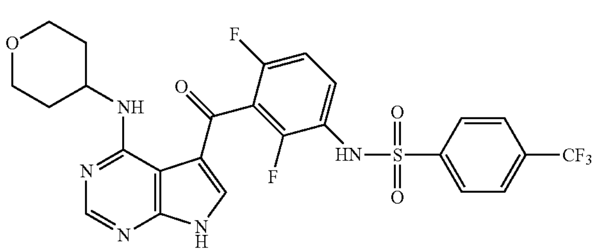 | N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide | 581.8; 582.0 |

TABLE I-continued

| Comp # | Name | MS |
|---|---|---|
| P-1014 | Propane-1-sulfonic acid [2,4-difluoro-3-(4-isobutyl-7H-pyrrolo[2,3-d]pyrimidine-5-carbonyl)-phenyl]-amide | 436.7 |
| P-1015 | N-[2,4-Difluoro-3-(4-isobutyl-7H-pyrrolo[2,3-d]pyrimidine-5-carbonyl)-phenyl]-4-trifluoromethyl-benzenesulfonamide | 538.6 |
| P-1016 | N-[3-(4-Chloro-7H-pyrrolo[2,3-d]pyrimidine-5-carbonyl)-2,4-difluoro-phenyl]-4-trifluoromethyl-benzenesulfonamide | 516.9 |
| P-1017 | N-[2,4-Difluoro-3-(4-morpholin-4-yl-7H-pyrrolo[2,3-d]pyrimidine-5-carbonyl)-phenyl]-4-trifluoromethyl-benzenesulfonamide | 567.8 |
| P-1018 | 6-Methoxy-pyridine-3-sulfonic acid [2,4-difluoro-3-(4-methoxy-7H-pyrrolo[2,3-d]pyrimidine-5-carbonyl)-phenyl]-amide | 476.0 |
| P-1019 | N-[2,4-Difluoro-3-(4-methyl-7H-pyrrolo[2,3-d]pyrimidine-5-carbonyl)-phenyl]-4-ethyl-benzenesulfonamide | 457.2 |

TABLE I-continued

| Comp # | Structure | Name | MS |
|---|---|---|---|
| P-1020 | 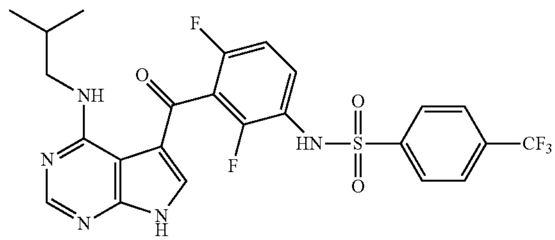 | N-[2,4-Difluoro-3-(4-isobutylamino-7H-pyrrolo[2,3-d]pyrimidine-5-carbonyl)-phenyl]-4-trifluoromethyl-benzenesulfonamide | 554.4; 554.0 |
| P-1021 | 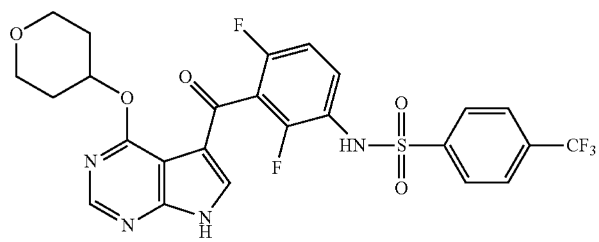 [SMILES: O=C(c1c(F)ccc(NS(=O)(=O)c2ccc(C(F)(F)F)cc2)c1F)c1c[nH]c2ncnc(OC3CCOCC3)c12] | N-{2,4-Difluoro-3-[4-(tetrahydro-pyran-4-yloxy)-7H-pyrrolo[2,3-d]pyrimidine-5-carbonyl]-phenyl}-4-trifluoromethyl-benzenesulfonamide | 581.2 |
| P-1022 | 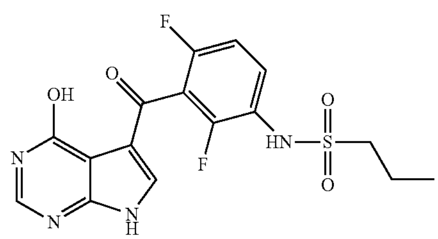 [SMILES: CCCS(=O)(=O)Nc1ccc(F)c(C(=O)c2c[nH]c3ncnc(O)c23)c1F] | Propane-1-sulfonic acid [2,4-difluoro-3-(4-hydroxy-7H-pyrrolo[2,3-d]pyrimidine-5-carbonyl)-phenyl]-amide | 397.0 |
| P-1023 | 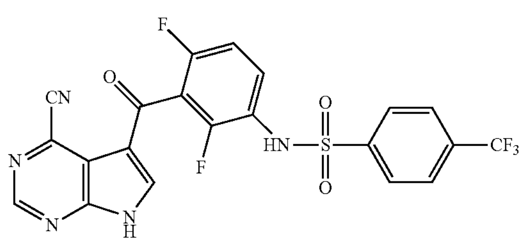 | N-[3-(4-Cyano-7H-pyrrolo[2,3-d]pyrimidine-5-carbonyl)-2,4-difluoro-phenyl]-4-trifluoromethyl-benzenesulfonamide | 508.1 |
| P-1024 | 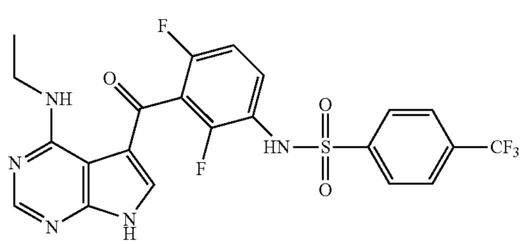 | N-[3-(4-Ethylamino-7H-pyrrolo[2,3-d]pyrimidine-5-carbonyl)-2,4-difluoro-phenyl]-4-trifluoromethyl-benzenesulfonamide | 525.95 |
| P-1025 | 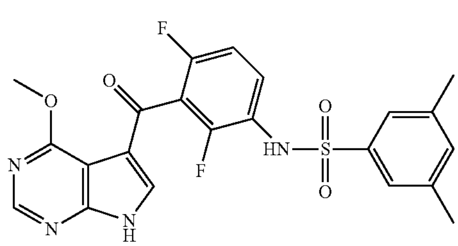 [SMILES: COc1ncnc2[nH]cc(C(=O)c3c(F)ccc(NS(=O)(=O)c4cc(C)cc(C)c4)c3F)c12] | N-[2,4-Difluoro-3-(4-methoxy-7H-pyrrolo[2,3-d]pyrimidine-5-carbonyl)-phenyl]-3,5-dimethyl-benzenesulfonamide | 473.0 |

TABLE I-continued

| Comp # | Structure | Name | MS |
|---|---|---|---|
| P-1026 | 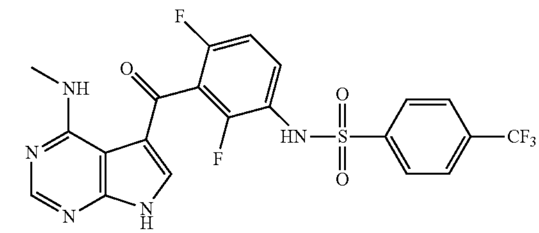 [SMILES: CNc1ncnc2[nH]cc(C(=O)c3c(F)ccc(NS(=O)(=O)c4ccc(C(F)(F)F)cc4)c3F)c12] | N-[2,4-Difluoro-3-(4-methylamino-7H-pyrrolo[2,3-d]pyrimidine-5-carbonyl)-phenyl]-4-trifluoromethyl-benzenesulfonamide | 512.0 |
| P-1027 | 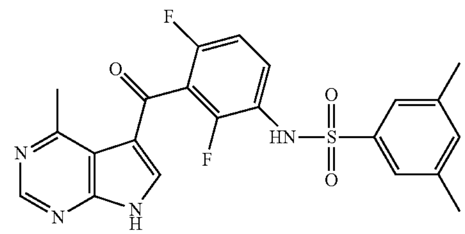 [SMILES: Cc1cc(C)cc(S(=O)(=O)Nc2ccc(F)c(C(=O)c3c[nH]c4ncnc(C)c34)c2F)c1] | N-[2,4-Difluoro-3-(4-methyl-7H-pyrrolo[2,3-d]pyrimidine-5-carbonyl)-phenyl]-3,5-dimethyl-benzenesulfonamide | 456.95 |
| P-1028 | 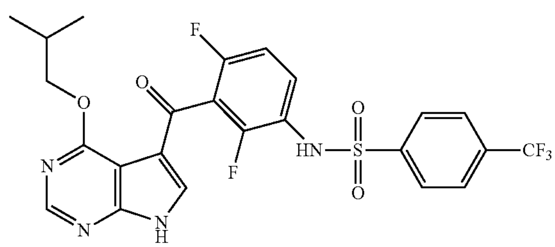 [SMILES: CC(C)COc1ncnc2[nH]cc(C(=O)c3c(F)ccc(NS(=O)(=O)c4ccc(C(F)(F)F)cc4)c3F)c12] | N-[2,4-Difluoro-3-(4-isobutoxy-7H-pyrrolo[2,3-d]pyrimidine-5-carbonyl)-phenyl]-4-trifluoromethyl-benzenesulfonamide | 553.2 |
| P-1029 | 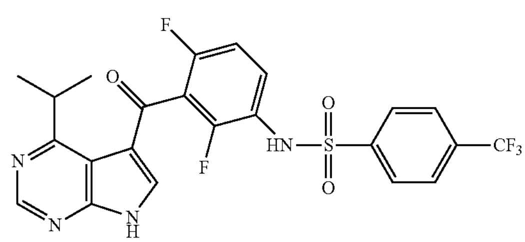 [SMILES: CC(C)c1ncnc2[nH]cc(C(=O)c3c(F)ccc(NS(=O)(=O)c4ccc(C(F)(F)F)cc4)c3F)c12] | N-[2,4-Difluoro-3-(4-isopropyl-7H-pyrrolo[2,3-d]pyrimidine-5-carbonyl)-phenyl]-4-trifluoromethyl-benzenesulfonamide | 525.2 |
| P-1030 | 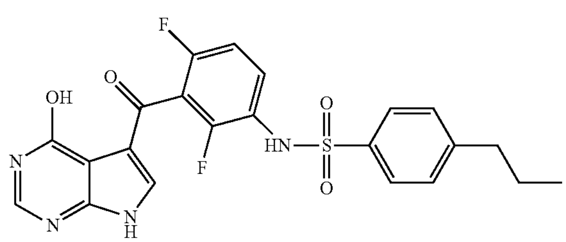 [SMILES: CCCc1ccc(S(=O)(=O)Nc2ccc(F)c(C(=O)c3c[nH]c4ncnc(O)c34)c2F)cc1] | N-[2,4-Difluoro-3-(4-hydroxy-7H-pyrrolo[2,3-d]pyrimidine-5-carbonyl)-phenyl]-4-propyl-benzenesulfonamide | 472.9 |
| P-1031 | 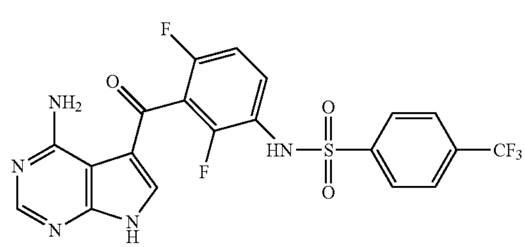 | N-[3-(4-Amino-7H-pyrrolo[2,3-d]pyrimidine-5-carbonyl)-2,4-difluoro-phenyl]-4-trifluoromethyl-benzenesulfonamide | 497.9 |

TABLE I-continued

| Comp # | Structure | Name | MS |
|---|---|---|---|
| P-1032 | 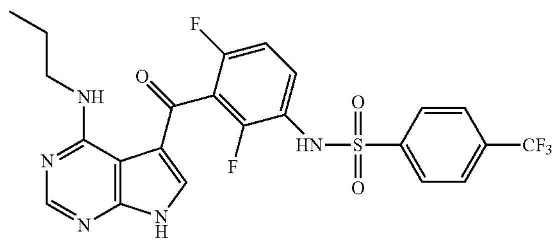 [SMILES: CCCNc1ncnc2[nH]cc(C(=O)c3c(F)ccc(NS(=O)(=O)c4ccc(C(F)(F)F)cc4)c3F)c12] | N-[2,4-Difluoro-3-(4-propylamino-7H-pyrrolo[2,3-d]pyrimidine-5-carbonyl)-phenyl]-4-trifluoromethyl-benzenesulfonamide | 539.95 |
| P-1033 | 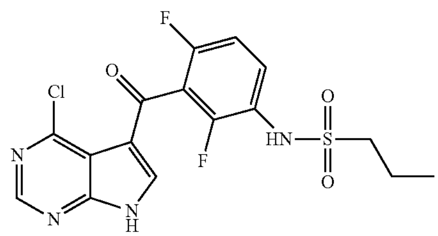 [SMILES: CCCS(=O)(=O)Nc1ccc(F)c(C(=O)c2c[nH]c3ncnc(Cl)c23)c1F] | Propane-1-sulfonic acid [3-(4-chloro-7H-pyrrolo[2,3-d]pyrimidine-5-carbonyl)-2,4-difluoro-phenyl]-amide | 414.8 |
| P-1034 | 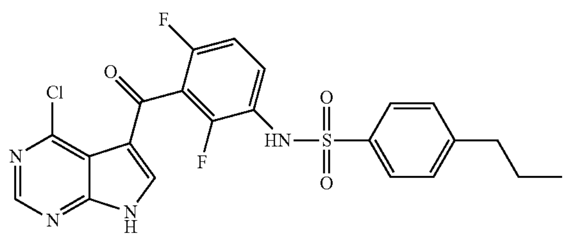 [SMILES: CCCc1ccc(S(=O)(=O)Nc2ccc(F)c(C(=O)c3c[nH]c4ncnc(Cl)c34)c2F)cc1] | N-[3-(4-Chloro-7H-pyrrolo[2,3-d]pyrimidine-5-carbonyl)-2,4-difluoro-phenyl]-5-propyl-benzenesulfonamide | 490.9 |
| P-1035 | 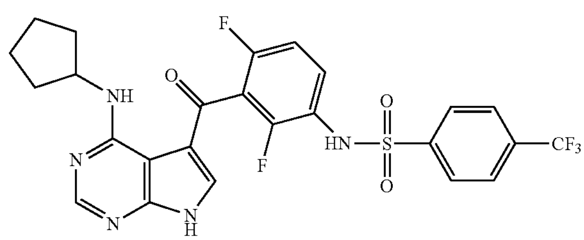 [SMILES: O=C(c1c(F)ccc(NS(=O)(=O)c2ccc(C(F)(F)F)cc2)c1F)c1c[nH]c2ncnc(NC3CCCC3)c12] | N-[3-(4-Cyclopentylamino-7H-pyrrolo[2,3-d]pyrimidine-5-carbonyl)-2,4-difluoro-phenyl]-4-trifluoromethyl-benzenesulfonamide | 566.3 |
| P-1036 | 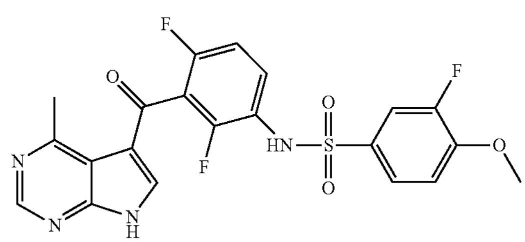 [SMILES: COc1ccc(S(=O)(=O)Nc2ccc(F)c(C(=O)c3c[nH]c4ncnc(C)c34)c2F)cc1F] | N-[2,4-Difluoro-3-(4-methyl-7H-pyrrolo[2,3-d]pyrimidine-5-carbonyl)-phenyl]-3-fluoro-4-methoxy-benzenesulfonamide | 477.0 |
| P-1037 | 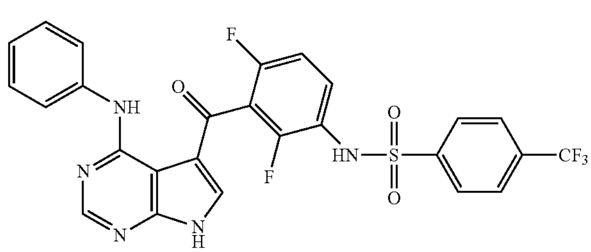 [SMILES: O=C(c1c(F)ccc(NS(=O)(=O)c2ccc(C(F)(F)F)cc2)c1F)c1c[nH]c2ncnc(Nc3ccccc3)c12] | N-[2,4-Difluoro-3-(4-phenylamino-7H-pyrrolo[2,3-d]pyrimidine-5-carbonyl)-phenyl]-4-trifluoromethyl-benzenesulfonamide | 573.9 |

TABLE I-continued

| Comp # | Structure | Name | MS |
|---|---|---|---|
| P-1038 | 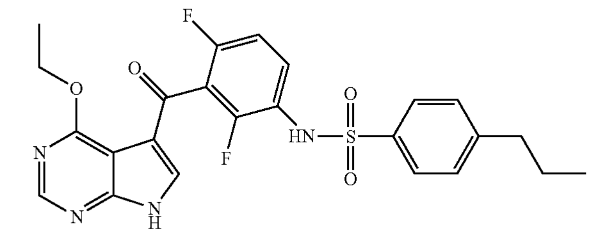 [SMILES: CCCc1ccc(S(=O)(=O)Nc2ccc(F)c(C(=O)c3c[nH]c4ncnc(OCC)c34)c2F)cc1] | N-[3-(4-Ethoxy-7H-pyrrolo[2,3-d]pyrimidine-5-carbonyl)-2,4-difluoro-phenyl]-4-propyl-benzenesulfonamide | 501.0 |
| P-1039 | 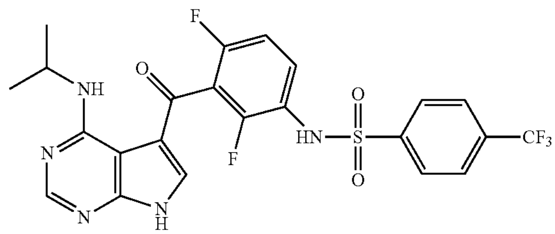 [SMILES: CC(C)Nc1ncnc2[nH]cc(C(=O)c3c(F)ccc(NS(=O)(=O)c4ccc(C(F)(F)F)cc4)c3F)c12] | N-[2,4-Difluoro-3-(4-isopropylamino-7H-pyrrolo[2,3-d]pyrimidine-5-carbonyl)-phenyl]-4-trifluoromethyl-benzenesulfonamide | 540.0 |
| P-1040 | 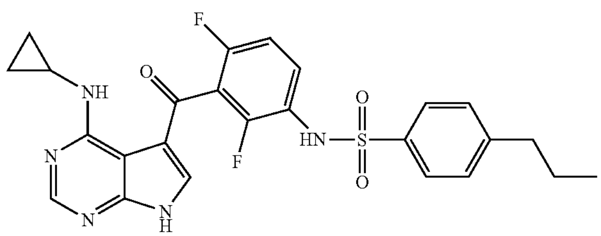 [SMILES: CCCc1ccc(S(=O)(=O)Nc2ccc(F)c(C(=O)c3c[nH]c4ncnc(NC5CC5)c34)c2F)cc1] | N-[3-(4-Cyclopropylamino-7H-pyrrolo[2,3-d]pyrimidine-5-carbonyl)-2,4-difluoro-phenyl]-4-propyl-benzenesulfonamide | 512.0 |
| P-1041 | 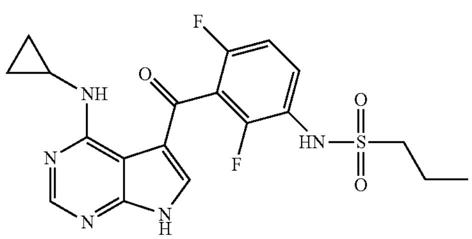 [SMILES: CCCS(=O)(=O)Nc1ccc(F)c(C(=O)c2c[nH]c3ncnc(NC4CC4)c23)c1F] | Propane-1-sulfonic acid [3-(4-cyclopropylamino-7H-pyrrolo[2,3-d]pyrimidine-5-carbonyl)-2,4-difluoro-phenyl]-amide | 435.95 |
| P-1042 | 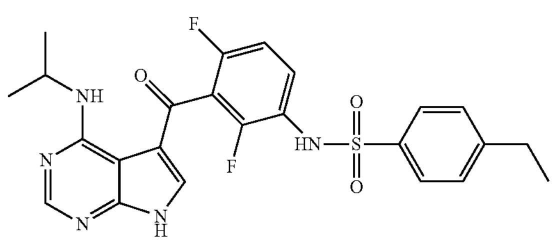 [SMILES: CCc1ccc(S(=O)(=O)Nc2ccc(F)c(C(=O)c3c[nH]c4ncnc(NC(C)C)c34)c2F)cc1] | N-[2,4-Difluoro-3-(4-isopropylamino-7H-pyrrolo[2,3-d]pyrimidine-5-carbonyl)-phenyl]-4-ethyl-benzenesulfonamide | 500.27 |
| P-1043 | 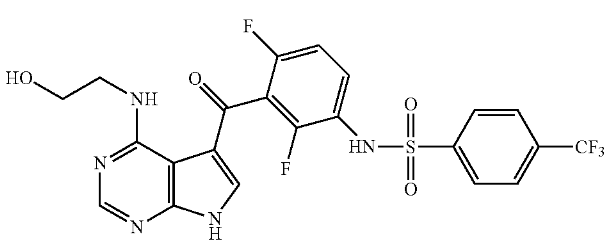 [SMILES: O=C(c1c(F)ccc(NS(=O)(=O)c2ccc(C(F)(F)F)cc2)c1F)c1c[nH]c2ncnc(NCCO)c12] | N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide | 541.95 |

TABLE I-continued

| Comp # | Name | MS |
|---|---|---|
| P-1044 | N-[2,4-Difluoro-3-(4-isopropylamino-7H-pyrrolo[2,3-d]pyrimidine-5-carbonyl)-phenyl]-4-isopropyl-benzenesulfonamide | 514.0 |
| P-1045 | N-[2,4-Difluoro-3-(4-isopropylamino-7H-pyrrolo[2,3-d]pyrimidine-5-carbonyl)-phenyl]-3,5-dimethyl-benzenesulfonamide | 500.05 |
| P-1046 | N-[2,4-Difluoro-3-[4-(tetrahydro-pyran-4-ylamino)-7H-pyrrolo[2,3-d]pyrimidine-5-carbonyl]-phenyl}-4-propyl-benzenesulfonamide | 556.0 |
| P-1047 | Propane-1-sulfonic acid {2,4-difluoro-3-[4-(tetrahydro-pyran-4-ylamino)-7H-pyrrolo[2,3-d]pyrimidine-5-carbonyl]-phenyl}-amide | 479.95 |
| P-1048 | Propane-1-sulfonic acid [2,4-difluoro-3-(4-phenylamino-7H-pyrrolo[2,3-d]pyrimidine-5-carbonyl)-phenyl]-amide | 473.95 |
| P-1049 | N-[3-(4-Dimethylamino-7H-pyrrolo[2,3-d]pyrimidine-5-carbonyl)-2,4-difluoro-phenyl]-4-trifluoromethyl-benzenesulfonamide | 525.95 |

TABLE I-continued

| Comp # | Structure | Name | MS |
|---|---|---|---|
| P-1050 | 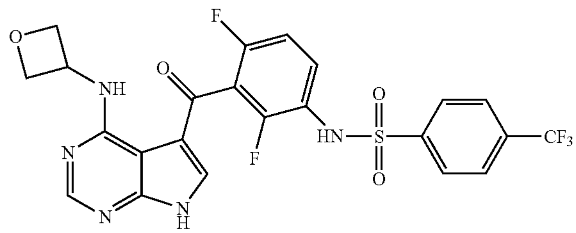 [SMILES: O=C(c1c(F)ccc(NS(=O)(=O)c2ccc(C(F)(F)F)cc2)c1F)c1c[nH]c2ncnc(NC3COC3)c12] | N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide | 554.0 |
| P-1051 | 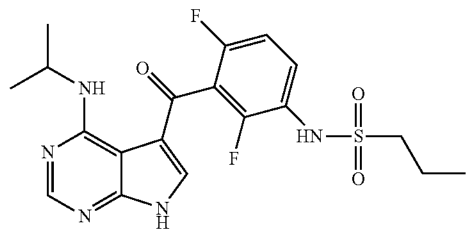 [SMILES: CCCS(=O)(=O)Nc1ccc(F)c(C(=O)c2c[nH]c3ncnc(NC(C)C)c23)c1F] | Propane-1-sulfonic acid [2,4-difluoro-3-(4-isopropylamino-7H-pyrrolo[2,3-d]pyrimidine-5-carbonyl)-phenyl]-amide | 437.95 |
| P-1052 | 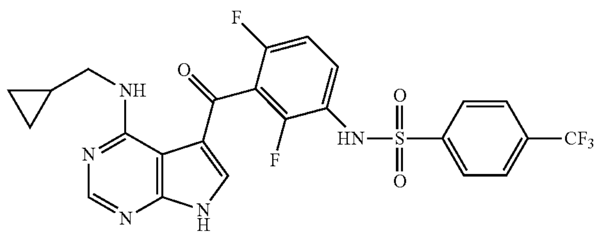 [SMILES: O=C(c1c(F)ccc(NS(=O)(=O)c2ccc(C(F)(F)F)cc2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide | 552.2 |
| P-1053 | 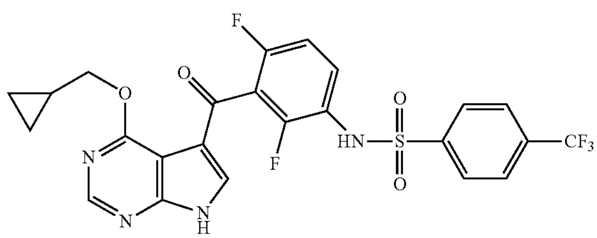 [SMILES: O=C(c1c(F)ccc(NS(=O)(=O)c2ccc(C(F)(F)F)cc2)c1F)c1c[nH]c2ncnc(OCC3CC3)c12] | N-[3-(4-Cyclopropylmethoxy-7H-pyrrolo[2,3-d]pyrimidine-5-carbonyl)-2,4-difluoro-phenyl]-4-trifluoromethyl-benzenesulfonamide | 553.2 |
| P-1054 | 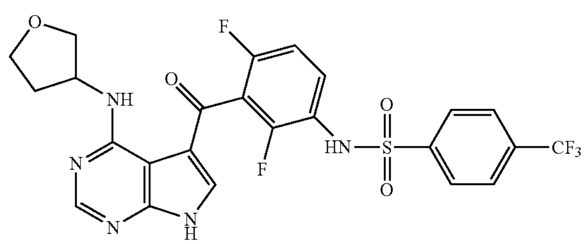 [SMILES: O=C(c1c(F)ccc(NS(=O)(=O)c2ccc(C(F)(F)F)cc2)c1F)c1c[nH]c2ncnc(NC3CCOC3)c12] | N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide | 568.0 |
| P-1055 | 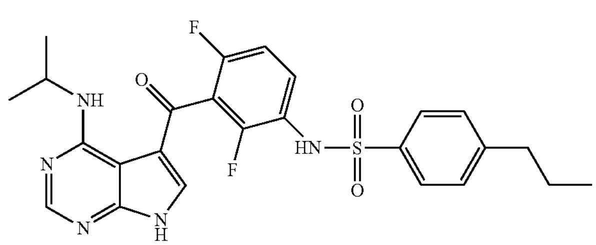 [SMILES: CCCc1ccc(S(=O)(=O)Nc2ccc(F)c(C(=O)c3c[nH]c4ncnc(NC(C)C)c34)c2F)cc1] | N-[2,4-Difluoro-3-(4-isopropylamino-7H-pyrrolo[2,3-d]pyrimidine-5-carbonyl)-phenyl]-4-propyl-benzenesulfonamide | 514.0 |

TABLE I-continued

| Comp # | Structure | Name | MS |
|---|---|---|---|
| P-1056 | 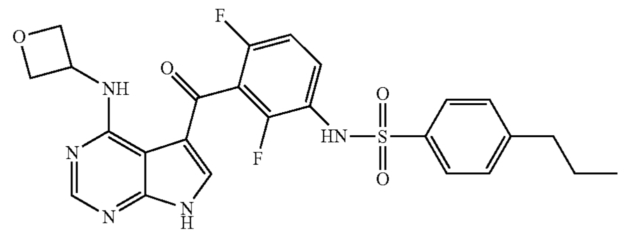 [SMILES: CCCc1ccc(S(=O)(=O)Nc2ccc(F)c(C(=O)c3c[nH]c4ncnc(NC5COC5)c34)c2F)cc1] | N-{2,4-Difluoro-3-[4-(oxetan-3-ylamino)-7H-pyrrolo[2,3-d]pyrimidine-5-carbonyl]-phenyl}-4-propyl-benzenesulfonamide | 528.0 |
| P-1057 | 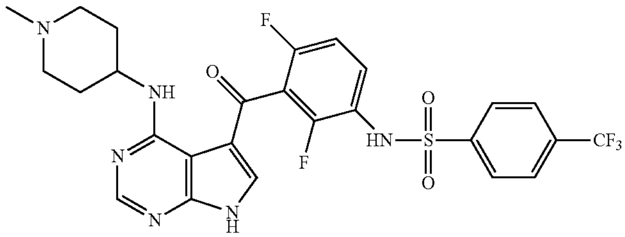 [SMILES: CN1CCC(Nc2ncnc3[nH]cc(C(=O)c4c(F)ccc(NS(=O)(=O)c5ccc(C(F)(F)F)cc5)c4F)c23)CC1] | N-{2,4-Difluoro-3-[4-(1-methyl-piperidin-4-ylamino)-7H-pyrrolo[2,3-d]pyrimidine-5-carbonyl]-phenyl}-4-trifluoromethyl-benzenesulfonamide | 595.0 |
| P-1058 | 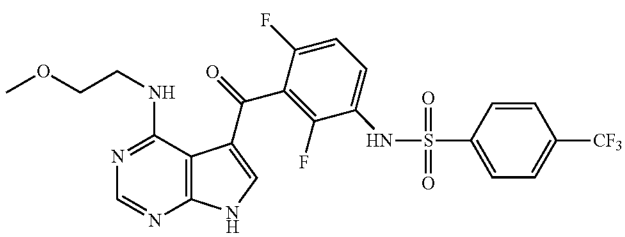 [SMILES: COCCNc1ncnc2[nH]cc(C(=O)c3c(F)ccc(NS(=O)(=O)c4ccc(C(F)(F)F)cc4)c3F)c12] | N-{2,4-Difluoro-3-[4-(2-methoxy-ethylamino)-7H-pyrrolo[2,3-d]pyrimidine-5-carbonyl]-phenyl}-4-trifluoromethyl-benzenesulfonamide | 556.3 |
| P-1059 | 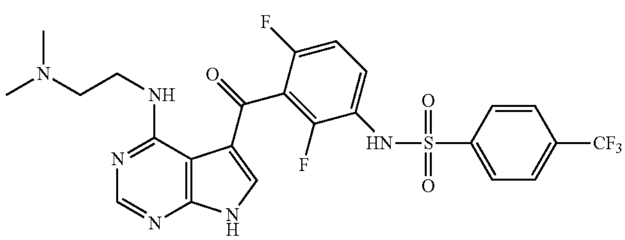 [SMILES: CN(C)CCNc1ncnc2[nH]cc(C(=O)c3c(F)ccc(NS(=O)(=O)c4ccc(C(F)(F)F)cc4)c3F)c12] | N-{3-[4-(2-Dimethylamino-ethylamino)-7H-pyrrolo[2,3-d]pyrimidine-5-carbonyl]-2,4-difluoro-phenyl}-4-trifluoromethyl-benzenesulfonamide | 569.5 |
| P-1060 | 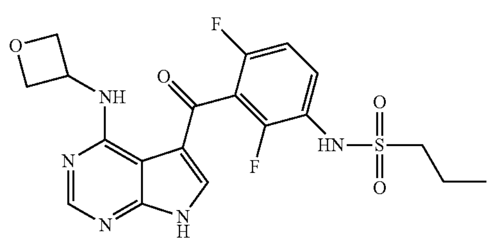 [SMILES: CCCS(=O)(=O)Nc1ccc(F)c(C(=O)c2c[nH]c3ncnc(NC4COC4)c23)c1F] | Propane-1-sulfonic acid {2,4-difluoro-3-[4-(oxetan-3-ylamino)-7H-pyrrolo[2,3-d]pyrimidine-5-carbonyl]-phenyl}-amide | 451.95 |
| P-1061 | 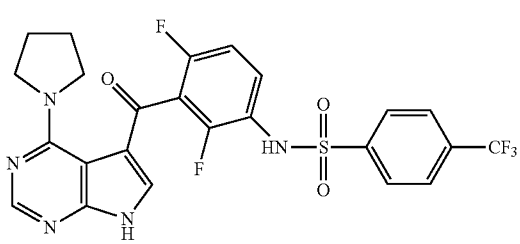 [SMILES: O=C(c1c(F)ccc(NS(=O)(=O)c2ccc(C(F)(F)F)cc2)c1F)c1c[nH]c2ncnc(N3CCCC3)c12] | N-[2,4-Difluoro-3-(4-pyrrolidin-1-yl-7H-pyrrolo[2,3-d]pyrimidine-5-carbonyl)-phenyl]-4-trifluoromethyl-benzenesulfonamide | 552.5 |

TABLE I-continued

| Comp # | Structure | Name | MS |
|---|---|---|---|
| P-1062 | 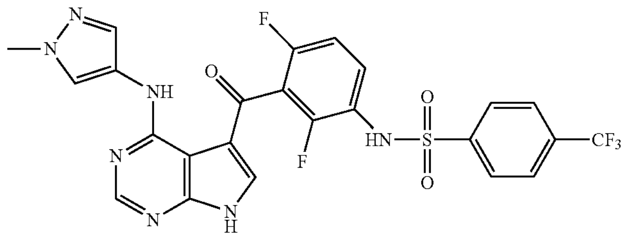 [SMILES: Cn1cc(Nc2ncnc3[nH]cc(C(=O)c4c(F)ccc(NS(=O)(=O)c5ccc(C(F)(F)F)cc5)c4F)c23)cn1] | N-{2,4-Difluoro-3-[4-(1-methyl-1H-pyrazol-4-ylamino)-7H-pyrrolo[2,3-d]pyrimidine-5-carbonyl]-phenyl}-4-trifluoromethyl-benzenesulfonamide | 578.1 |
| P-1063 | 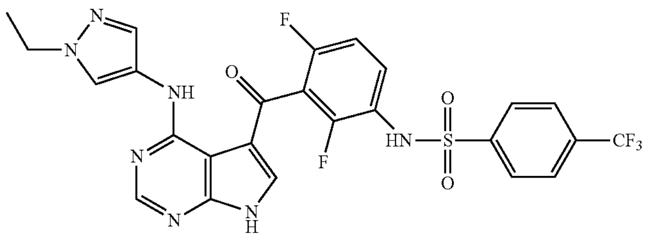 [SMILES: CCn1cc(Nc2ncnc3[nH]cc(C(=O)c4c(F)ccc(NS(=O)(=O)c5ccc(C(F)(F)F)cc5)c4F)c23)cn1] | N-{3-[4-(1-Ethyl-1H-pyrazol-4-ylamino)-7H-pyrrolo[2,3-d]pyrimidine-5-carbonyl]-2,4-difluoro-phenyl}-4-trifluoromethyl-benzenesulfonamide | 592.5 |
| P-1064 | 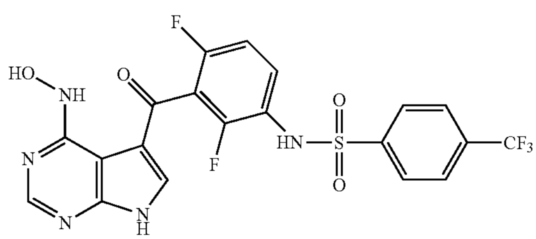 [SMILES: O=C(c1c(F)ccc(NS(=O)(=O)c2ccc(C(F)(F)F)cc2)c1F)c1c[nH]c2ncnc(NO)c12] | N-[2,4-Difluoro-3-(4-hydroxyamino-7H-pyrrolo[2,3-d]pyrimidine-5-carbonyl)-phenyl]-4-trifluoromethyl-benzenesulfonamide | 513.9 |
| P-1065 | 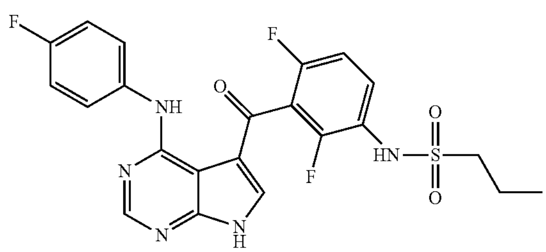 [SMILES: CCCS(=O)(=O)Nc1ccc(F)c(C(=O)c2c[nH]c3ncnc(Nc4ccc(F)cc4)c23)c1F] | Propane-1-sulfonic acid {2,4-difluoro-3-[4-(4-fluoro-phenylamino)-7H-pyrrolo[2,3-d]pyrimidine-5-carbonyl]-phenyl}-amide | 490.0 |
| P-1067 | 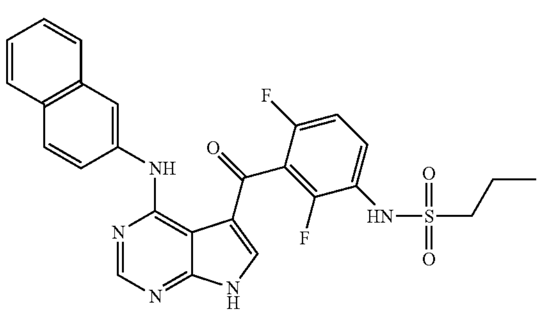 [SMILES: CCCS(=O)(=O)Nc1ccc(F)c(C(=O)c2c[nH]c3ncnc(Nc4ccc5ccccc5c4)c23)c1F] | Propane-1-sulfonic acid {2,4-difluoro-3-[4-(napthalen-2-ylamino)-7H-pyrrolo[2,3-d]pyrimidine-5-carbonyl]-phenyl}-amide | 522.25 |
| P-1068 | 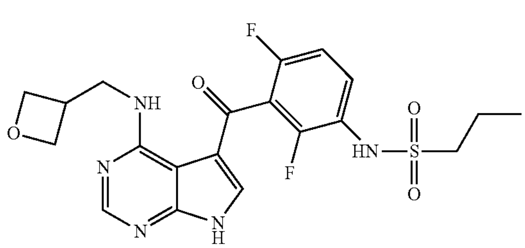 [SMILES: CCCS(=O)(=O)Nc1ccc(F)c(C(=O)c2c[nH]c3ncnc(NCC4COC4)c23)c1F] | Propane-1-sulfonic acid (2,4-difluoro-3-{4-[(oxetan-3-ylmethyl)-amino]-7H-pyrrolo[2,3-d]pyrimidine-5-carbonyl}-phenyl)-amide | 513.9 |

TABLE I-continued

| Comp # | Name | MS |
|---|---|---|
| P-1069 | N-{2,4-Difluoro-3-[4-(4-fluoro-phenylamino)-7H-pyrrolo[2,3-d]pyrimidine-5-carbonyl-phenyl}-2,5-difluoro-benzenesulfonamide | 559.9 |
| P-1070 | N-[2,4-Difluoro-3-(4-hydroxy-7H-pyrrolo[2,3-d]pyrimidine-5-carbonyl)-phenyl]-2-fluoro-benzenesulfonamide | 448.9 |
| P-1071 | N-[3-(4-Chloro-7H-pyrrolo[2,3-d]pyrimidine-5-carbonyl)-2,4-difluoro-phenyl]-2-fluoro-benzenesulfonamide | 466.9/ 468.9 |
| P-1072 | Propane-1-sulfonic acid {2,4-difluoro-3-[4-(naphthalen-1-ylamino)-7H-pyrrolo[2,3-d]pyrimidine-5-carbonyl]-phenyl}-amide | 522.0 |
| P-1073 | N-[2,4-Difluoro-3-(4-isopropylamino-7H-pyrrolo[2,3-d]pyrimidine-5-carbonyl)-phenyl]-2-fluoro-benzenesulfonamide | 490.0 |
| P-1074 | Propane-1-sulfonic acid [3-(4-benzylamino-7H-pyrrolo[2,3-d]pyrimidine-5-carbonyl)-2,4-difluoro-phenyl]-amide | 486.5 |

TABLE I-continued

| Comp # | Structure | Name | MS |
|---|---|---|---|
| P-1075 | 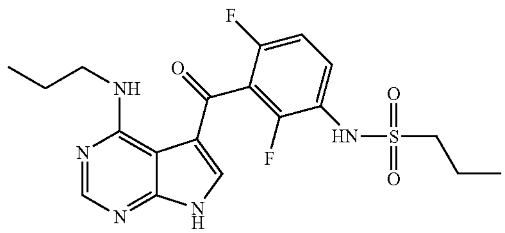 [SMILES: CCCNc1ncnc2[nH]cc(C(=O)c3c(F)ccc(NS(=O)(=O)CCC)c3F)c12] | Propane-1-sulfonic acid [2,4-difluoro-3-(4-propylamino-7H-pyrrolo[2,3-d]pyrimidine-5-carbonyl)-phenyl]-amide | 438.0 |
| P-1076 | 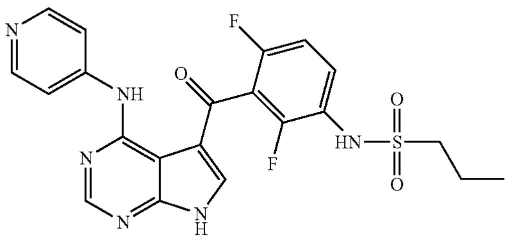 [SMILES: CCCS(=O)(=O)Nc1ccc(F)c(C(=O)c2c[nH]c3ncnc(Nc4ccncc4)c23)c1F] | Propane-1-sulfonic acid {2,4-difluoro-3-[4-(pyridin-4-ylamino)-7H-pyrrolo[2,3-d]pyrimidine-5-carbonyl]-phenyl}-amide | 473.0 |
| P-1077 | 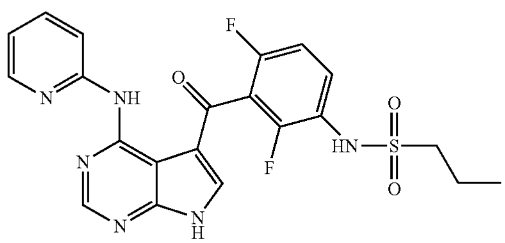 [SMILES: CCCS(=O)(=O)Nc1ccc(F)c(C(=O)c2c[nH]c3ncnc(Nc4ccccn4)c23)c1F] | Propane-1-sulfonic acid {2,4-difluoro-3-[4-(pyridin-2-ylamino)-7H-pyrrolo[2,3-d]pyrimidine-5-carbonyl]-phenyl}-amide | 473.0 |
| P-1078 | 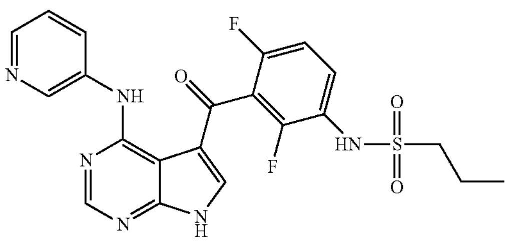 [SMILES: CCCS(=O)(=O)Nc1ccc(F)c(C(=O)c2c[nH]c3ncnc(Nc4cccnc4)c23)c1F] | Propane-1-sulfonic acid {2,4-difluoro-3-[4-(pyridin-3-ylamino)-7H-pyrrolo[2,3-d]pyrimidine-5-carbonyl]-phenyl}-amide | 473.0 |
| P-1079 | 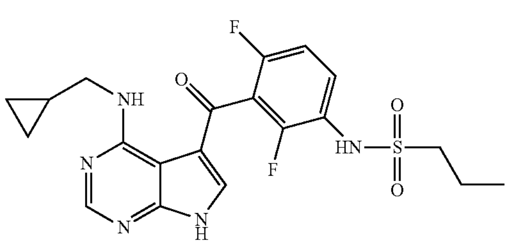 [SMILES: CCCS(=O)(=O)Nc1ccc(F)c(C(=O)c2c[nH]c3ncnc(NCC4CC4)c23)c1F] | Propane-1-sulfonic acid {3-[4-(cyclopropylmethyl-amino)-7H-pyrrolo[2,3-d]pyrimidine-5-carbonyl]-2,4-difluoro-phenyl}-amide | 450.0 |
| P-1080 | 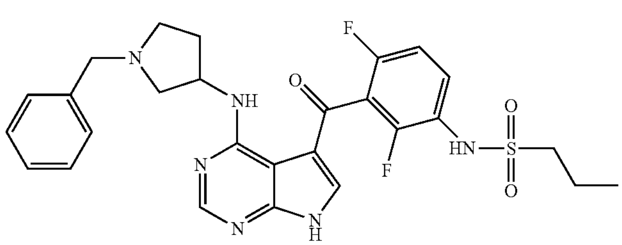 [SMILES: CCCS(=O)(=O)Nc1ccc(F)c(C(=O)c2c[nH]c3ncnc(NC4CCN(Cc5ccccc5)C4)c23)c1F] | Propane-1-sulfonic acid {3-[4-(1-benzyl-pyrrolidin-3-ylamino)-7H-pyrrolo[2,3-d]pyrimidine-5-carbonyl]-2,4-difluoro-phenyl}-amide | 555.5 |

TABLE I-continued

| Comp # | Structure | Name | MS |
|---|---|---|---|
| P-1081 | 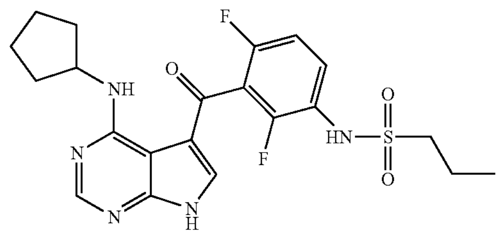 [SMILES: CCCS(=O)(=O)Nc1ccc(F)c(C(=O)c2c[nH]c3ncnc(NC4CCCC4)c23)c1F] | Propane-1-sulfonic acid [3-(4-cyclopentylamino-7H-pyrrolo[2,3-d]pyrimidine-5-carbonyl)-2,4-difluoro-phenyl]-amide | 464.0 |
| P-1082 | 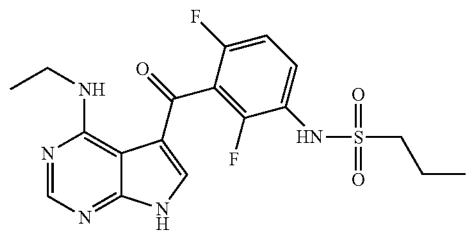 [SMILES: CCCS(=O)(=O)Nc1ccc(F)c(C(=O)c2c[nH]c3ncnc(NCC)c23)c1F] | Propane-1-sulfonic acid [3-(4-ethylamino-7H-pyrrolo[2,3-d]pyrimidine-5-carbonyl)-2,4-difluoro-phenyl]-amide | 424.0 |
| P-1083 | 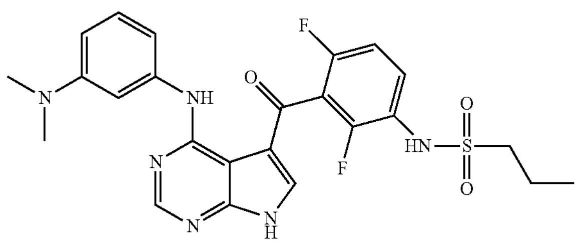 | Propane-1-sulfonic acid {3-[4-(3-dimethylamino-phenylamino)-7H-pyrrolo[2,3-d]pyrimidine-5-carbonyl]-2,4-difluoro-phenyl}-amide | 515.5 |
| P-1084 | 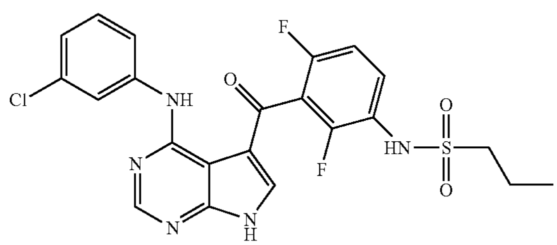 [SMILES: CCCS(=O)(=O)Nc1ccc(F)c(C(=O)c2c[nH]c3ncnc(Nc4cccc(Cl)c4)c23)c1F] | Propane-1-sulfonic acid {3-[4-(3-chloro-phenylamino)-7H-pyrrolo[2,3-d]pyrimidine-5-carbonyl]-2,4-difluoro-phenyl}-amide | 506.0 |
| P-1085 | 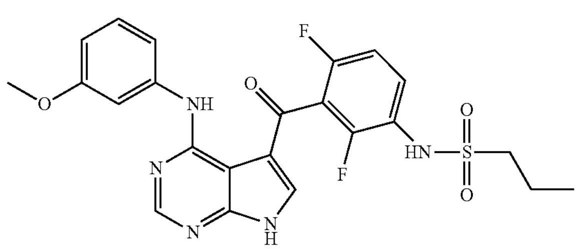 [SMILES: CCCS(=O)(=O)Nc1ccc(F)c(C(=O)c2c[nH]c3ncnc(Nc4cccc(OC)c4)c23)c1F] | Propane-1-sulfonic acid {2,4-difluoro-3-[4-(3-methoxy-phenylamino)-7H-pyrrolo[2,3-d]pyrimidine-5-carbonyl]-phenyl}-amide | 502.5 |
| P-1086 | 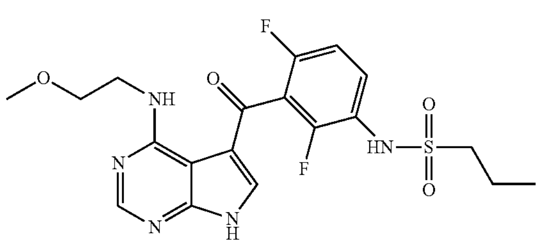 [SMILES: CCCS(=O)(=O)Nc1ccc(F)c(C(=O)c2c[nH]c3ncnc(NCCOC)c23)c1F] | Propane-1-sulfonic acid {2,4-difluoro-3-[4-(2-methoxy-ethylamino)-7H-pyrrolo[2,3-d]pyrimidine-5-carbonyl]-phenyl}-amide | 454.0 |

TABLE I-continued

| Comp # | Structure | Name | MS |
|---|---|---|---|
| P-1087 | 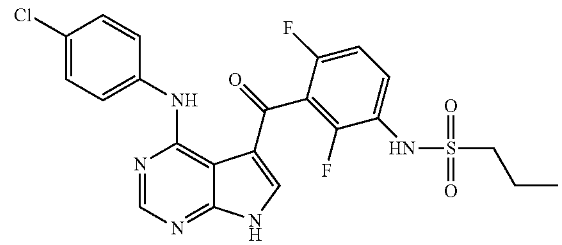 [SMILES: CCCS(=O)(=O)Nc1ccc(F)c(C(=O)c2c[nH]c3ncnc(Nc4ccc(Cl)cc4)c23)c1F] | Propane-1-sulfonic acid {3-[4-(4-chloro-phenylamino)-7H-pyrrolo[2,3-d]pyrimidine-5-carbonyl]-2,4-difluoro-phenyl}-amide | 506.0 |
| P-1088 | 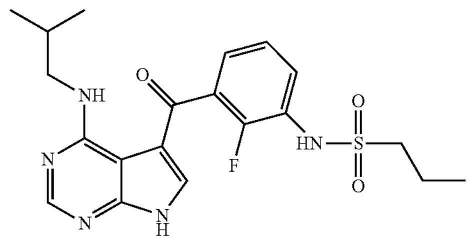 [SMILES: CCCS(=O)(=O)Nc1cccc(C(=O)c2c[nH]c3ncnc(NCC(C)C)c23)c1F] | Propane-1-sulfonic acid [2,4-difluoro-3-(4-isobutylamino-7H-pyrrolo[2,3-d]pyrimidine-5-carbonyl)-phenyl]-amide | 452.0 |
| P-1089 | 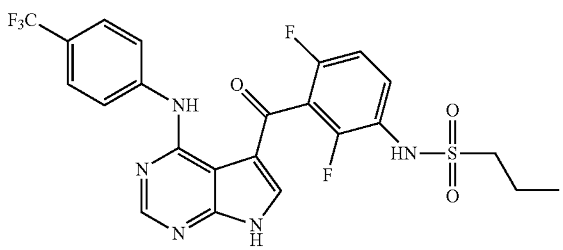 [SMILES: CCCS(=O)(=O)Nc1ccc(F)c(C(=O)c2c[nH]c3ncnc(Nc4ccc(C(F)(F)F)cc4)c23)c1F] | Propane-1-sulfonic acid {2,4-difluoro-3-[4-(4-trifluoromethyl-phenylamino)-7H-pyrrolo[2,3-d]pyrimidine-5-carbonyl]-phenyl}-amide | 540.5 |
| P-1090 | 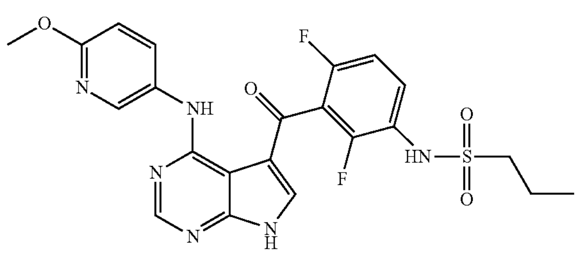 [SMILES: CCCS(=O)(=O)Nc1ccc(F)c(C(=O)c2c[nH]c3ncnc(Nc4ccc(OC)nc4)c23)c1F] | Propane-1-sulfonic acid {2,4-difluoro-3-[4-(6-methoxy-pyridin-3-ylamino)-7H-pyrrolo[2,3-d]pyrimidine-5-carbonyl]-phenyl}-amide | 503.0 |
| P-1091 | 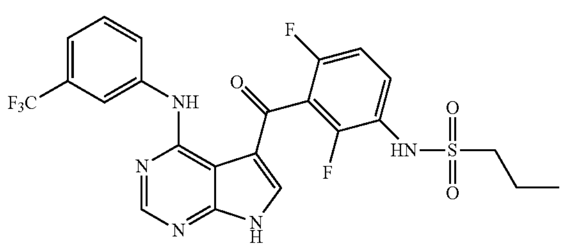 [SMILES: CCCS(=O)(=O)Nc1ccc(F)c(C(=O)c2c[nH]c3ncnc(Nc4cccc(C(F)(F)F)c4)c23)c1F] | Propane-1-sulfonic acid {2,4-difluoro-3-[4-(3-trifluoromethyl-phenylamino)-7H-pyrrolo[2,3-d]pyrimidine-5-carbonyl]-phenyl}-amide | 540.5 |
| P-1092 | 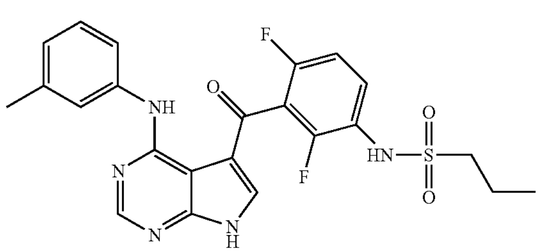 [SMILES: CCCS(=O)(=O)Nc1ccc(F)c(C(=O)c2c[nH]c3ncnc(Nc4cccc(C)c4)c23)c1F] | Propane-1-sulfonic acid [2,4-difluoro-3-(4-m-tolylamino-7H-pyrrolo[2,3-d]pyrimidine-5-carbonyl)-phenyl]-amide | 486.5 |

TABLE I-continued

| Comp # | Structure | Name | MS |
|---|---|---|---|
| P-1093 | 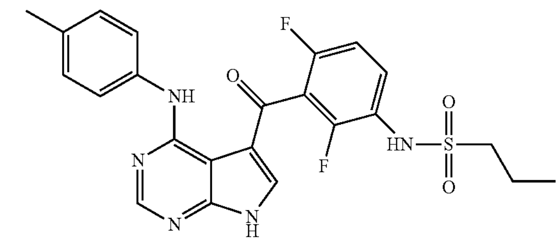 [SMILES: CCCS(=O)(=O)Nc1ccc(F)c(C(=O)c2c[nH]c3ncnc(Nc4ccc(C)cc4)c23)c1F] | Propane-1-sulfonic acid [2,4-difluoro-3-(4-p-tolylamino-7H-pyrrolo[2,3-d]pyrimidine-5-carbonyl)-phenyl]-amide | 486.5 |
| P-1094 | 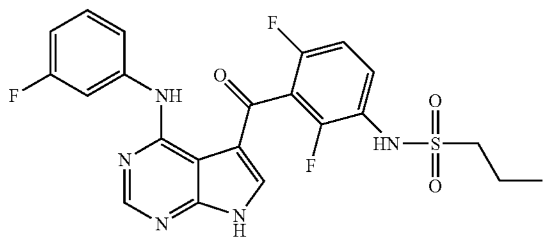 [SMILES: CCCS(=O)(=O)Nc1ccc(F)c(C(=O)c2c[nH]c3ncnc(Nc4cccc(F)c4)c23)c1F] | Propane-1-sulfonic acid {2,4-difluoro-3-[4-(3-fluoro-phenylamino)-7H-pyrrolo[2,3-d]pyrimidine-5-carbonyl]-phenyl}-amide | 490.5 |
| P-1095 | 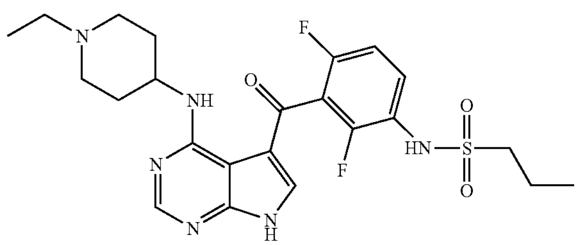 [SMILES: CCCS(=O)(=O)Nc1ccc(F)c(C(=O)c2c[nH]c3ncnc(NC4CCN(CC)CC4)c23)c1F] | Propane-1-sulfonic acid {3-[4-(1-ethyl-piperidin-4-ylamino)-7H-pyrrolo[2,3-d]pyrimidine-5-carbonyl]-2,4-difluoro-phenyl}-amide | 507.5 |
| P-1096 | 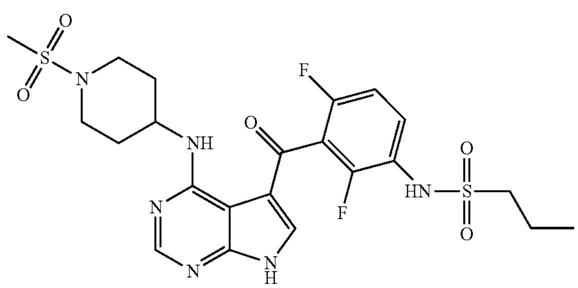 [SMILES: CCCS(=O)(=O)Nc1ccc(F)c(C(=O)c2c[nH]c3ncnc(NC4CCN(S(C)(=O)=O)CC4)c23)c1F] | Propane-1-sulfonic acid {2,4-difluoro-3-[4-(1-methanesulfonyl-piperidin-4-ylamino)-7H-pyrrolo[2,3-d]pyrimidine-5-carbonyl]-phenyl}-amide | 557.5 |
| P-1097 | 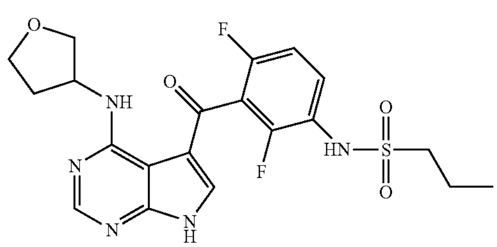 [SMILES: CCCS(=O)(=O)Nc1ccc(F)c(C(=O)c2c[nH]c3ncnc(NC4CCOC4)c23)c1F] | Propane-1-sulfonic acid {2,4-difluoro-3-[4-(tetrahydro-furan-3-ylamino)-7H-pyrrolo[2,3-d]pyrimidine-5-carbonyl]-phenyl}-amide | 466.5 |
| P-1098 | 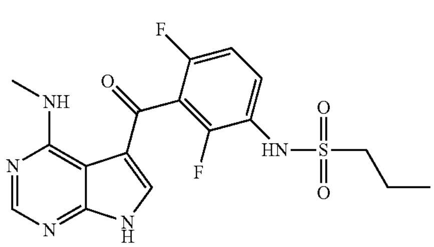 [SMILES: CCCS(=O)(=O)Nc1ccc(F)c(C(=O)c2c[nH]c3ncnc(NC)c23)c1F] | Propane-1-sulfonic acid [2,4-difluoro-3-(4-methylamino-7H-pyrrolo[2,3-d]pyrimidine-5-carbonyl)-phenyl]-amide | 410.0 |

TABLE I-continued

| Comp # | Structure | Name | MS |
|---|---|---|---|
| P-1099 | 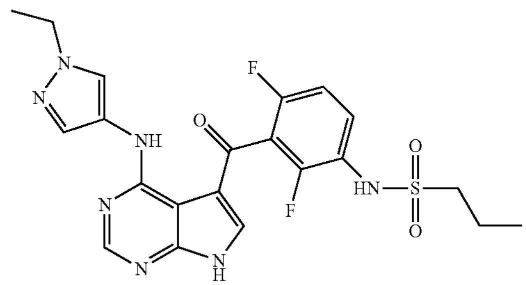 [SMILES: CCCS(=O)(=O)Nc1ccc(F)c(C(=O)c2c[nH]c3ncnc(Nc4cnn(CC)c4)c23)c1F] | Propane-1-sulfonic acid {3-[4-(1-ethyl-1H-pyrazol-4-ylamino)-7H-pyrrolo[2,3-d]pyrimidine-5-carbonyl]-2,4-difluoro-phenyl}-amide | 490.5 |
| P-1100 | 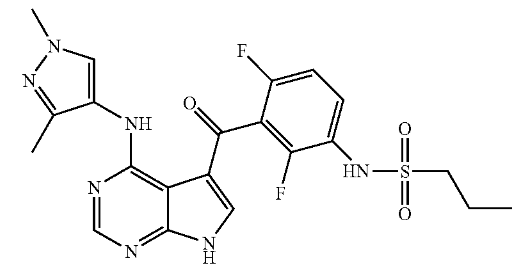 [SMILES: CCCS(=O)(=O)Nc1ccc(F)c(C(=O)c2c[nH]c3ncnc(Nc4cn(C)nc4C)c23)c1F] | Propane-1-sulfonic acid {3-[4-(1,3-dimethyl-1H-pyrazol-4-ylamino)-7H-pyrrolo[2,3-d]pyrimidine-5-carbonyl]-2,4-difluoro-phenyl}-amide | 490.5 |
| P-1101 | 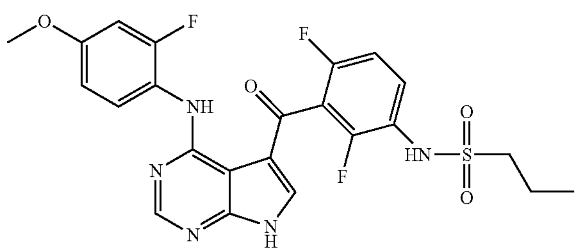 | Propane-1-sulfonic acid {2,4-difluoro-3-[4-(2-fluoro-4-methoxy-phenylamino)-7H-pyrrolo[2,3-d]pyrimidine-5-carbonyl]-phenyl}-amide | 520.5 |
| P-1102 | 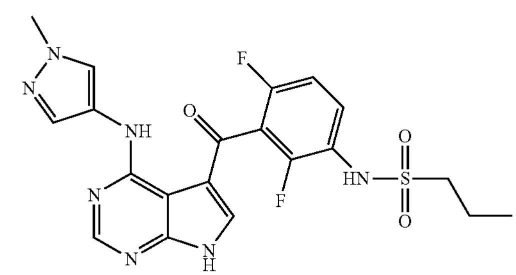 [SMILES: CCCS(=O)(=O)Nc1ccc(F)c(C(=O)c2c[nH]c3ncnc(Nc4cnn(C)c4)c23)c1F] | Propane-1-sulfonic acid {2,4-difluoro-3-[4-(1-methyl-1H-pyrazol-4-ylamino)-7H-pyrrolo[2,3-d]pyrimidine-5-carbonyl]-phenyl}-amide | 476.0 |
| P-1103 | 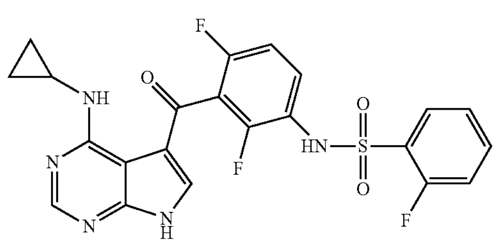 [SMILES: O=C(c1c(F)ccc(NS(=O)(=O)c2ccccc2F)c1F)c1c[nH]c2ncnc(NC3CC3)c12] | N-[3-(4-Cyclopropylamino-7H-pyrrolo[2,3-d]pyrimidine-5-carbonyl)-2,4-difluoro-phenyl]-2-fluoro-benzenesulfonamide | 488.0 |
| P-1104 | 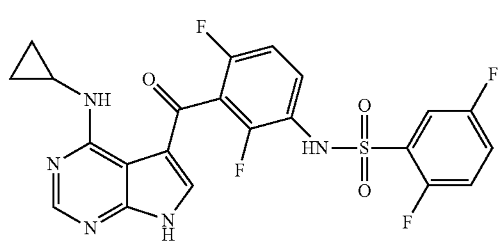 [SMILES: O=C(c1c(F)ccc(NS(=O)(=O)c2cc(F)ccc2F)c1F)c1c[nH]c2ncnc(NC3CC3)c12] | N-[3-(4-Cyclopropylamino-7H-pyrrolo[2,3-d]pyrimidine-5-carbonyl)-2,4-difluoro-phenyl]-2,5-difluoro-benzenesulfonamide | 506.0 |

TABLE I-continued

| Comp # | Structure | Name | MS |
|---|---|---|---|
| P-1105 | 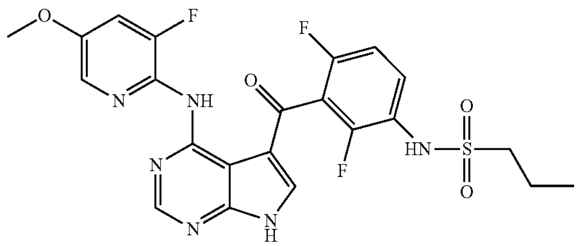 [SMILES: CCCS(=O)(=O)Nc1ccc(F)c(C(=O)c2c[nH]c3ncnc(Nc4ncc(OC)cc4F)c23)c1F] | Propane-1-sulfonic acid {2,4-difluoro-3-[4-(3-fluoro-5-methoxy-pyridin-2-ylamino)-7H-pyrrolo[2,3-d]pyrimidine-5-carbonyl]-phenyl}-amide | 521.0 |
| P-1106 | 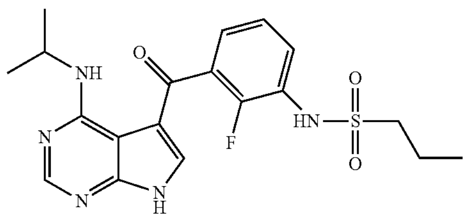 [SMILES: CCCS(=O)(=O)Nc1cccc(C(=O)c2c[nH]c3ncnc(NC(C)C)c23)c1F] | Propane-1-sulfonic acid [2-fluoro-3-(4-isopropylamino-7H-pyrrolo[2,3-d]pyrimidine-5-carbonyl)-phenyl]-amide | 420.0 |
| P-1107 | 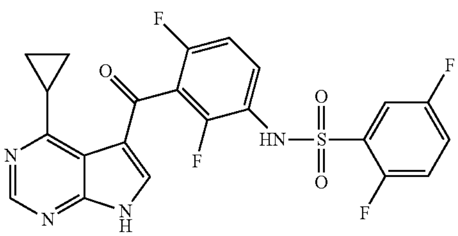 [SMILES: O=C(c1c(F)ccc(NS(=O)(=O)c2cc(F)ccc2F)c1F)c1c[nH]c2ncnc(C3CC3)c12] | N-[3-(4-Cyclopropyl-7H-pyrrolo[2,3-d]pyrimidine-5-carbonyl)-2,4-difluoro-phenyl]-2,5-difluoro-benzenesulfonamide | 491.4 |
| P-1108 | 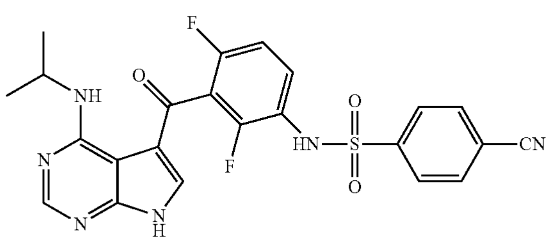 [SMILES: CC(C)Nc1ncnc2[nH]cc(C(=O)c3c(F)ccc(NS(=O)(=O)c4ccc(C#N)cc4)c3F)c12] | 4-Cyano-N-[2,5-difluoro-3-(4-isopropylamino-7H-pyrrolo[2,3-d]pyrimidine-5-carbonyl)-phenyl]-benzenesulfonamide | 497.5 |
| P-1109 | 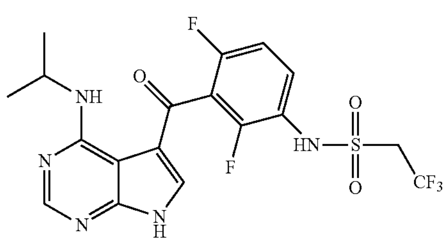 [SMILES: CC(C)Nc1ncnc2[nH]cc(C(=O)c3c(F)ccc(NS(=O)(=O)CC(F)(F)F)c3F)c12] | 2,2,2-Trifluoro-ethanesulfonic acid [2,4-difluoro-3-(4-isopropylamino-7H-pyrrolo[2,3-d]pyrimidine-5-carbonyl)-phenyl]-amide | 478.0 |
| P-1110 | 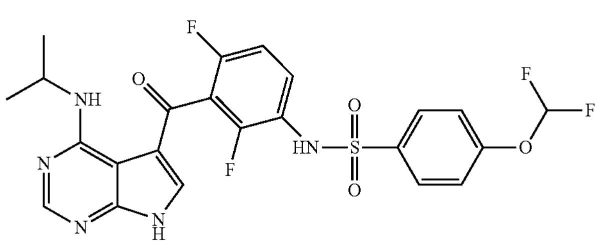 [SMILES: CC(C)Nc1ncnc2[nH]cc(C(=O)c3c(F)ccc(NS(=O)(=O)c4ccc(OC(F)F)cc4)c3F)c12] | N-[2,4-Difluoro-3-(4-isopropylamino-7H-pyrrolo[2,3-d]pyrimidine-5-carbonyl)-phenyl]-4-difluoromethoxy-benzenesulfonamide | 538.5 |

TABLE I-continued

| Comp # | Structure | Name | MS |
|---|---|---|---|
| P-1111 | 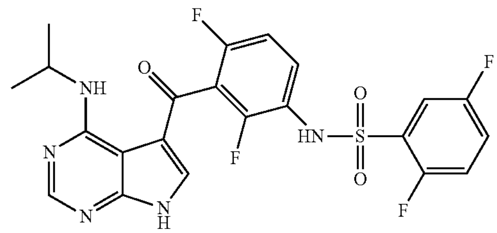 [SMILES: CC(C)Nc1ncnc2[nH]cc(C(=O)c3c(F)ccc(NS(=O)(=O)c4cc(F)ccc4F)c3F)c12] | N-[2,4-Difluoro-3-(4-isopropylamino-7H-pyrrolo[2,3-d]pyrimidine-5-carbonyl)-phenyl]-2,5-difluoro-benzenesulfonamide | 508.0 |
| P-1112 | 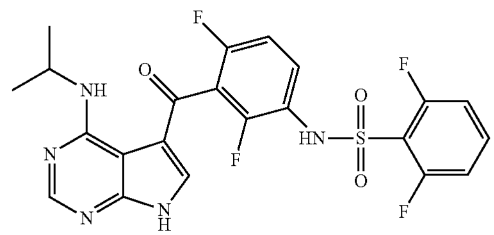 [SMILES: CC(C)Nc1ncnc2[nH]cc(C(=O)c3c(F)ccc(NS(=O)(=O)c4c(F)cccc4F)c3F)c12] | N-[2,4-Difluoro-3-(4-isopropylamino-7H-pyrrolo[2,3-d]pyrimidine-5-carbonyl)-phenyl]-2,6-difluoro-benzenesulfonamide | 508.0 |
| P-1113 | 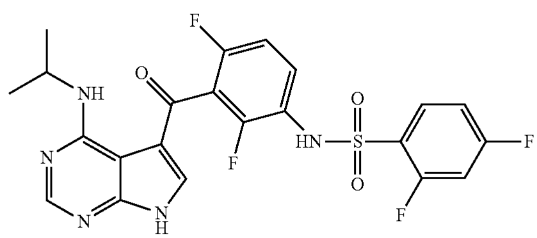 [SMILES: CC(C)Nc1ncnc2[nH]cc(C(=O)c3c(F)ccc(NS(=O)(=O)c4ccc(F)cc4F)c3F)c12] | N-[2,4-Difluoro-3-(4-isopropylamino-7H-pyrrolo[2,3-d]pyrimidine-5-carbonyl)-phenyl]-2,4-difluoro-benzenesulfonamide | 508.0 |
| P-1114 | 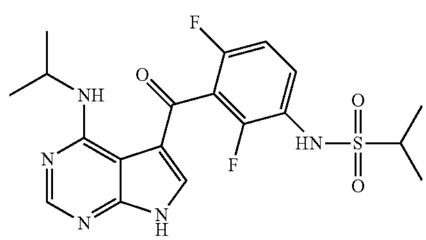 [SMILES: CC(C)Nc1ncnc2[nH]cc(C(=O)c3c(F)ccc(NS(=O)(=O)C(C)C)c3F)c12] | Propane-2-sulfonic acid [2,4-difluoro-3-(4-isopropylamino-7H-pyrrolo[2,3-d]pyrimidine-5-carbonyl)-phenyl]-amide | 438.0 |
| P-1115 | 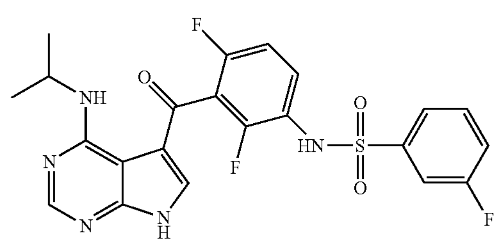 [SMILES: CC(C)Nc1ncnc2[nH]cc(C(=O)c3c(F)ccc(NS(=O)(=O)c4cccc(F)c4)c3F)c12] | N-[2,4-Difluoro-3-(4-isopropylamino-7H-pyrrolo[2,3-d]pyrimidine-5-carbonyl)-phenyl]-3-fluoro-benzenesulfonamide | 490.5 |
| P-1116 | 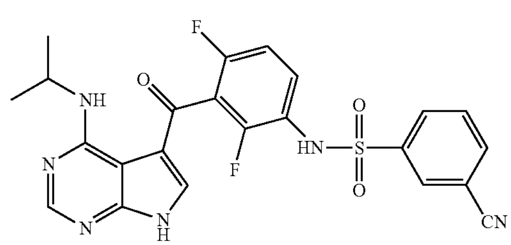 [SMILES: CC(C)Nc1ncnc2[nH]cc(C(=O)c3c(F)ccc(NS(=O)(=O)c4cccc(C#N)c4)c3F)c12] | 3-Cyano-N-[2,4-difluoro-3-(4-isopropylamino-7H-pyrrolo[2,3-d]pyrimidine-5-carbonyl)-phenyl]-benzenesulfonamide | 497.5 |

TABLE I-continued

| Comp # | Structure | Name | MS |
|---|---|---|---|
| P-1117 | 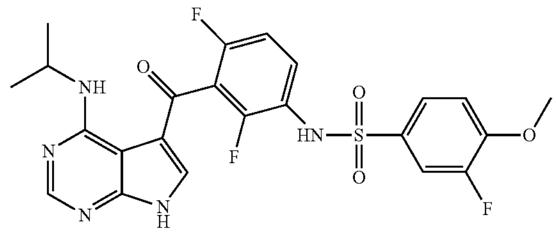 [SMILES: COc1ccc(S(=O)(=O)Nc2ccc(F)c(C(=O)c3c[nH]c4ncnc(NC(C)C)c34)c2F)cc1F] | N-[2,4-Difluoro-3-(4-isopropylamino-7H-pyrrolo[2,3-d]pyrimidine-5-carbonyl)-phenyl]-3-fluoro-4-methoxy-benzenesulfonamide | 520.5 |
| P-1118 | 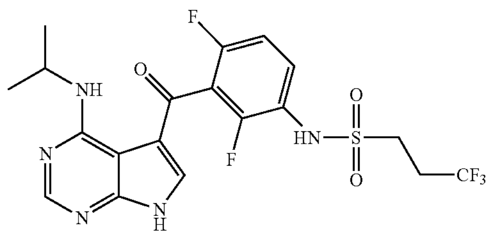 [SMILES: CC(C)Nc1ncnc2[nH]cc(C(=O)c3c(F)ccc(NS(=O)(=O)CCC(F)(F)F)c3F)c12] | 3,3,3-Trifluoro-propane-1-sulfonic acid [2,4-difluoro-3-(4-isopropylamino-7H-pyrrolo[2,3-d]pyrimidine-5-carbonyl)-phenyl]-amide | 492.0 |
| P-1119 | 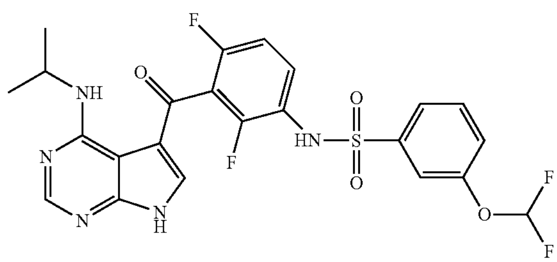 [SMILES: CC(C)Nc1ncnc2[nH]cc(C(=O)c3c(F)ccc(NS(=O)(=O)c4cccc(OC(F)F)c4)c3F)c12] | N-[2,4-Difluoro-3-(4-isopropylamino-7H-pyrrolo[2,3-d]pyrimidine-5-carbonyl)-phenyl]-3-difluoromethoxy-benzenesulfonamide | 538.5 |
| P-1120 | 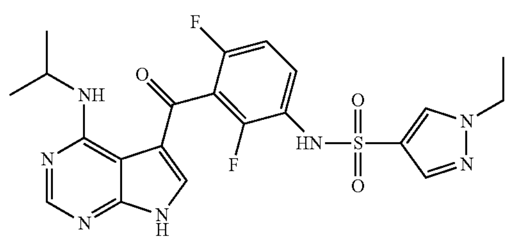 [SMILES: CCn1cc(S(=O)(=O)Nc2ccc(F)c(C(=O)c3c[nH]c4ncnc(NC(C)C)c34)c2F)cn1] | 1-Ethyl-1H-pyrazole-4-sulfonic acid [2,4-difluoro-3-(4-isopropylamino-7H-pyrrolo[2,3-d]pyrimidine-5-carbonyl)-phenyl]-amide | 490.5 |
| P-1121 | 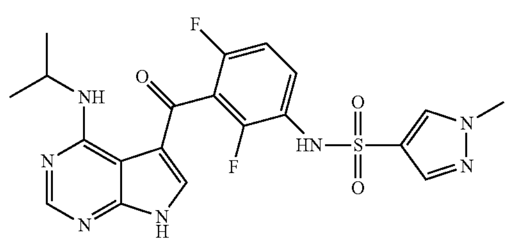 [SMILES: CC(C)Nc1ncnc2[nH]cc(C(=O)c3c(F)ccc(NS(=O)(=O)c4cnn(C)c4)c3F)c12] | 1-Methyl-1H-pyrazole-4-sulfonic acid [2,4-difluoro-3-(4-isopropylamino-7H-pyrrolo[2,3-d]pyrimidine-5-carbonyl)-phenyl]-amide | 476.0 |
| P-1122 | 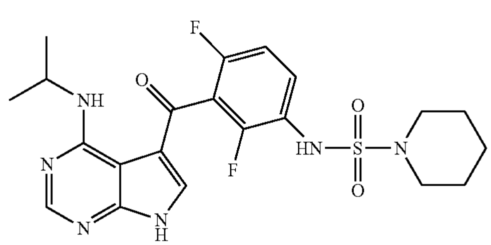 [SMILES: CC(C)Nc1ncnc2[nH]cc(C(=O)c3c(F)ccc(NS(=O)(=O)N4CCCCC4)c3F)c12] | Piperidine-1-sulfonic acid [2,4-difluoro-3-(4-isopropylamino-7H-pyrrolo[2,3-d]pyrimidine-5-carbonyl)-phenyl]-amide | 479.0 |

TABLE I-continued

| Comp # | Structure | Name | MS |
|---|---|---|---|
| P-1123 | 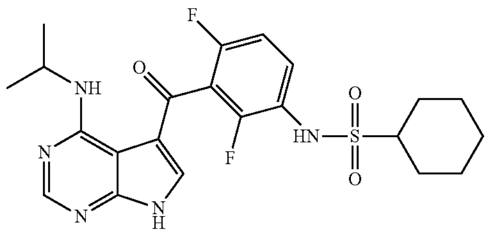 | Cyclohexanesulfonic acid [2,4-difluoro-3-(4-isopropylamino-7H-pyrrolo[2,3-d]pyrimidine-5-carbonyl)-phenyl]-amide | 478.0 |
| P-1124 | 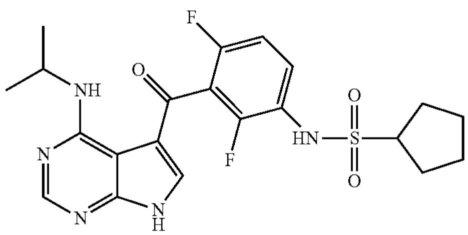 [SMILES: CC(C)Nc1ncnc2[nH]cc(C(=O)c3c(F)ccc(NS(=O)(=O)C4CCCC4)c3F)c12] | Cyclopentanesulfonic acid [2,4-difluoro-3-(4-isopropylamino-7H-pyrrolo[2,3-d]pyrimidine-5-carbonyl)-phenyl]-amide | 464.0 |
| P-1125 | 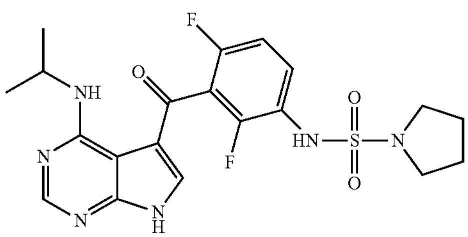 [SMILES: CC(C)Nc1ncnc2[nH]cc(C(=O)c3c(F)ccc(NS(=O)(=O)N4CCCC4)c3F)c12] | Pyrrolidine-1-sulfonic acid [2,4-difluoro-3-(4-isopropylamino-7H-pyrrolo[2,3-d]pyrimidine-5-carbonyl)-phenyl]-amide | 465.0 |
| P-1126 | 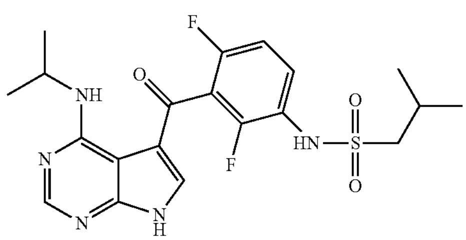 [SMILES: CC(C)CS(=O)(=O)Nc1ccc(F)c(C(=O)c2c[nH]c3ncnc(NC(C)C)c23)c1F] | 2-Methyl-propane-1-sulfonic acid [2,4-difluoro-3-(4-isopropylamino-7H-pyrrolo[2,3-d]pyrimidine-5-carbonyl)-phenyl]-amide | 452.0 |
| P-1127 | 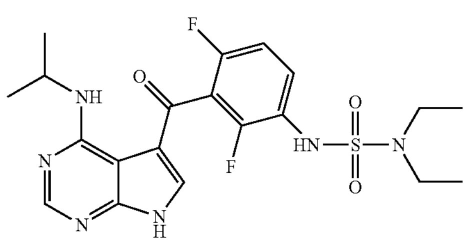 [SMILES: CCN(CC)S(=O)(=O)Nc1ccc(F)c(C(=O)c2c[nH]c3ncnc(NC(C)C)c23)c1F] | Diethylamine-1-sulfonic acid [2,4-difluoro-3-(4-isopropylamino-7H-pyrrolo[2,3-d]pyrimidine-5-carbonyl)-phenyl]-amide | 467.5 |
| P-1128 | 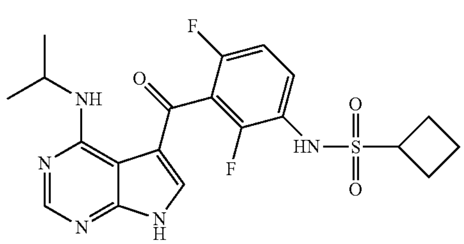 [SMILES: CC(C)Nc1ncnc2[nH]cc(C(=O)c3c(F)ccc(NS(=O)(=O)C4CCC4)c3F)c12] | Cyclobutanesulfonic acid [2,4-difluoro-3-(4-isopropylamino-7H-pyrrolo[2,3-d]pyrimidine-5-carbonyl)-phenyl]-amide | 450.0 |

TABLE I-continued

| Comp # | Structure | Name | MS |
|---|---|---|---|
| P-1129 | 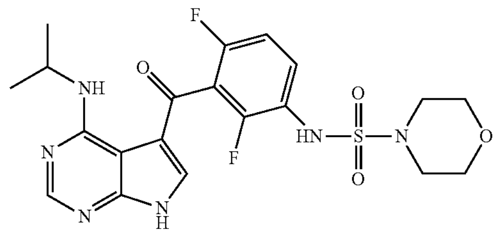 [SMILES: CC(C)Nc1ncnc2[nH]cc(C(=O)c3c(F)ccc(NS(=O)(=O)N4CCOCC4)c3F)c12] | Morpholine-4-sulfonic acid [2,4-difluoro-3-(4-isopropylamino-7H-pyrrolo[2,3-d]pyrimidine-5-carbonyl)-phenyl]-amide | 481.0 |
| P-1130 | 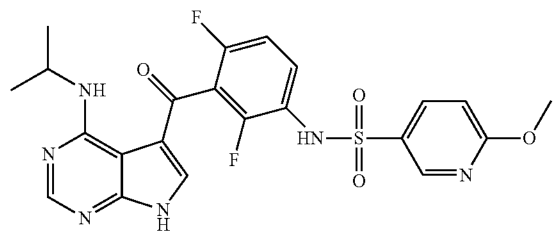 [SMILES: COc1ccc(S(=O)(=O)Nc2ccc(F)c(C(=O)c3c[nH]c4ncnc(NC(C)C)c34)c2F)cn1] | 6-Methoxy-pyridine-3-sulfonic acid [2,4-difluoro-3-(4-isopropylamino-7H-pyrrolo[2,3-d]pyrimidine-5-carbonyl)-phenyl]-amide | 503.0 |
| P-1131 | 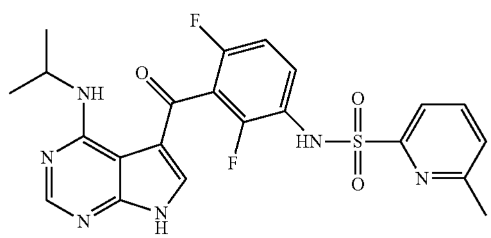 [SMILES: Cc1cccc(S(=O)(=O)Nc2ccc(F)c(C(=O)c3c[nH]c4ncnc(NC(C)C)c34)c2F)n1] | 6-Methyl-pyridine-2-sulfonic acid [2,4-difluoro-3-(4-isopropylamino-7H-pyrrolo[2,3-d]pyrimidine-5-carbonyl)-phenyl]-amide | 487.5 |
| P-1132 | 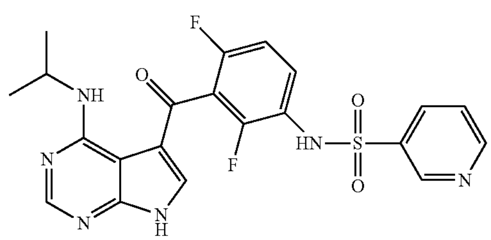 [SMILES: CC(C)Nc1ncnc2[nH]cc(C(=O)c3c(F)ccc(NS(=O)(=O)c4cccnc4)c3F)c12] | Pyridine-3-sulfonic acid [2,4-difluoro-3-(4-isopropylamino-7H-pyrrolo[2,3-d]pyrimidine-5-carbonyl)-phenyl]-amide | 473.0 |
| P-1133 | 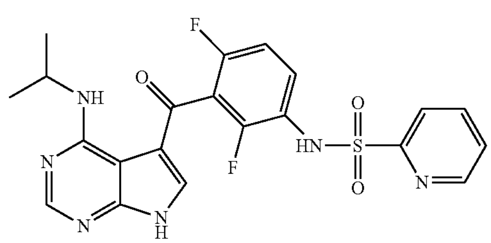 [SMILES: CC(C)Nc1ncnc2[nH]cc(C(=O)c3c(F)ccc(NS(=O)(=O)c4ccccn4)c3F)c12] | Pyridine-2-sulfonic acid [2,4-difluoro-3-(4-isopropylamino-7H-pyrrolo[2,3-d]pyrimidine-5-carbonyl)-phenyl]-amide | 473.0 |
| P-1134 | 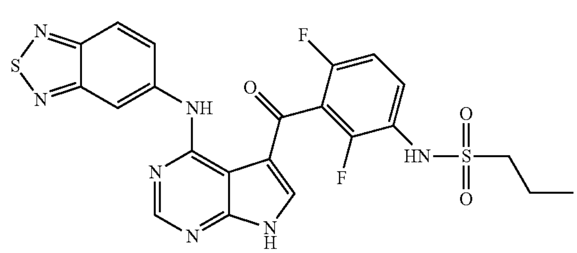 [SMILES: CCCS(=O)(=O)Nc1ccc(F)c(C(=O)c2c[nH]c3ncnc(Nc4ccc5nsnc5c4)c23)c1F] | Propane-1-sulfonic acid {3-[4-(benzo[1,2,5]thiadiazol-5-ylamino)-7H-pyrrolo[2,3-d]pyrimidine-5-carbonyl]-2,4-difluoro-phenyl}-amide | 530.0 |

TABLE I-continued

| Comp # | Structure | Name | MS |
|---|---|---|---|
| P-1135 | 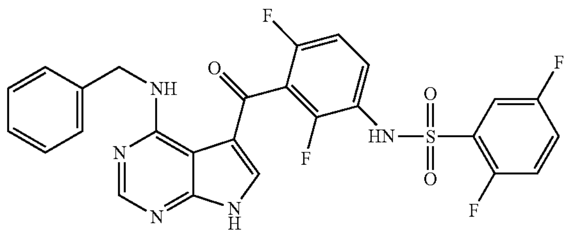 [SMILES: O=C(c1c(F)ccc(NS(=O)(=O)c2cc(F)ccc2F)c1F)c1c[nH]c2ncnc(NCc3ccccc3)c12] | N-[3-(4-Benzylamino-7H-pyrrolo[2,3-d]pyrimidine-5-carbonyl)-2,4-difluoro-phenyl]-2,5-difluoro-benzenesulfonamide | 556.0 |
| P-1136 | 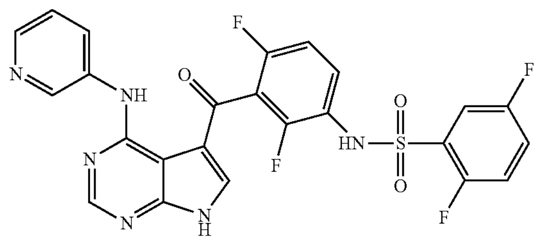 [SMILES: O=C(c1c(F)ccc(NS(=O)(=O)c2cc(F)ccc2F)c1F)c1c[nH]c2ncnc(Nc3cccnc3)c12] | N-{2,4-Difluoro-3-[4-(pyridin-3-ylamino)-7H-pyrrolo[2,3-d]pyrimidine-5-carbonyl]-phenyl}-2,5-difluoro-benzenesulfonamide | 543.5 |
| P-1137 | 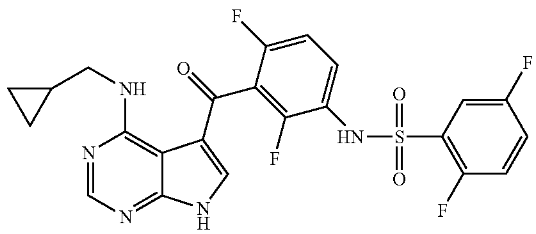 | N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide | 520.5 |
| P-1138 | 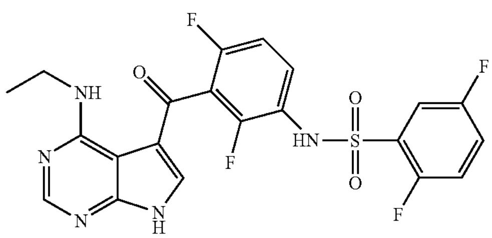 [SMILES: CCNc1ncnc2[nH]cc(C(=O)c3c(F)ccc(NS(=O)(=O)c4cc(F)ccc4F)c3F)c12] | N-[3-(4-Ethylamino-7H-pyrrolo[2,3-d]pyrimidine-5-carbonyl)-2,4-difluoro-phenyl]-2,5-difluoro-benzenesulfonamide | 494.0 |
| P-1139 | 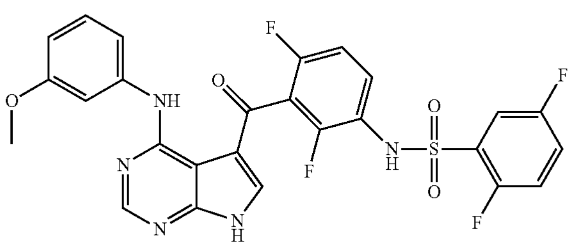 [SMILES: COc1cccc(Nc2ncnc3[nH]cc(C(=O)c4c(F)ccc(NS(=O)(=O)c5cc(F)ccc5F)c4F)c23)c1] | N-{2,4-Difluoro-3-[4-(3-methoxy-phenylamino)-7H-pyrrolo[2,3-d]pyrimidine-5-carbonyl]-phenyl}-2,5-difluoro-benzenesulfonamide | 572.0 |
| P-1140 | 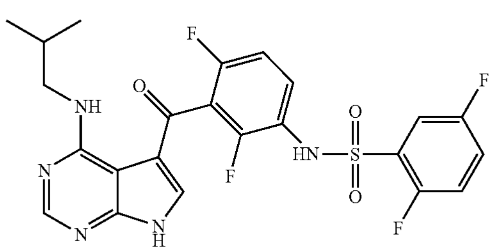 [SMILES: CC(C)CNc1ncnc2[nH]cc(C(=O)c3c(F)ccc(NS(=O)(=O)c4cc(F)ccc4F)c3F)c12] | N-[2,4-Difluoro-3-(4-isobutylamino-7H-pyrrolo[2,3-d]pyrimidine-5-carbonyl)-phenyl]-2,5-difluoro-benzenesulfonamide | 522.0 |

TABLE I-continued

| Comp # | Structure | Name | MS |
|---|---|---|---|
| P-1141 | 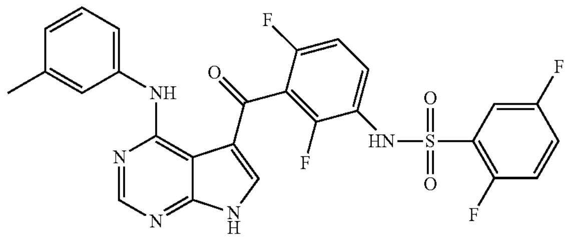 [SMILES: Cc1cccc(Nc2ncnc3[nH]cc(C(=O)c4c(F)ccc(NS(=O)(=O)c5cc(F)ccc5F)c4F)c23)c1] | N-[2,4-Difluoro-3-(4-m-tolylamino-7H-pyrrolo[2,3-d]pyrimidine-5-carbonyl)-phenyl]-2,5-difluoro-benzenesulfonamide | 556.0 |
| P-1142 | 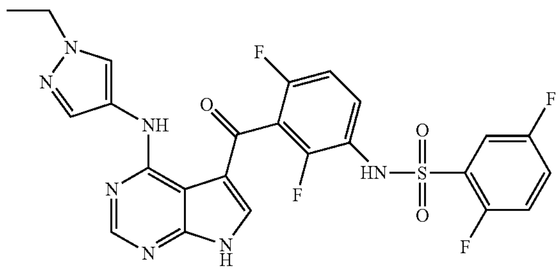 [SMILES: CCn1cc(Nc2ncnc3[nH]cc(C(=O)c4c(F)ccc(NS(=O)(=O)c5cc(F)ccc5F)c4F)c23)cn1] | N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide | 560.0 |
| P-1143 | 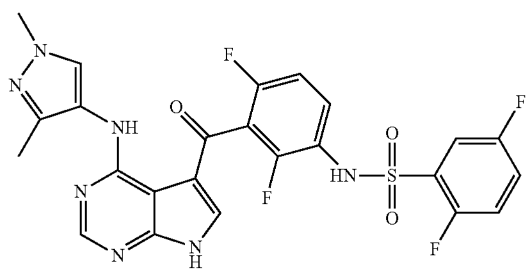 [SMILES: Cc1nn(C)cc1Nc1ncnc2[nH]cc(C(=O)c3c(F)ccc(NS(=O)(=O)c4cc(F)ccc4F)c3F)c12] | N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide | 560.0 |
| P-1144 | 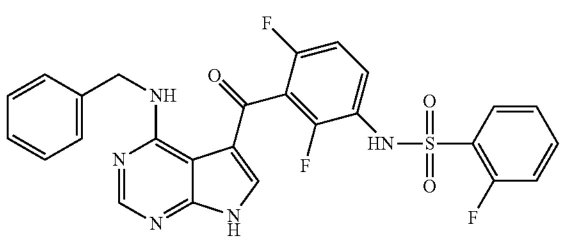 [SMILES: O=C(c1c(F)ccc(NS(=O)(=O)c2ccccc2F)c1F)c1c[nH]c2ncnc(NCc3ccccc3)c12] | N-[3-(4-Benzylamino-7H-pyrrolo[2,3-d]pyrimidine-5-carbonyl)-2,4-difluoro-phenyl]-2-fluoro-benzenesulfonamide | 538.5 |
| P-1145 | 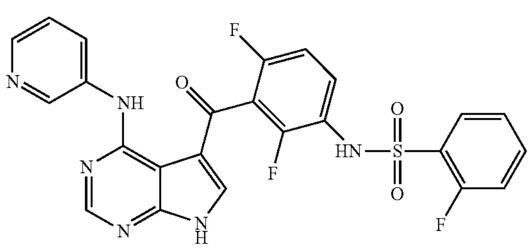 [SMILES: O=C(c1c(F)ccc(NS(=O)(=O)c2ccccc2F)c1F)c1c[nH]c2ncnc(Nc3cccnc3)c12] | N-{2,4-Difluoro-3-[4-(pyridin-3-ylamino)-7H-pyrrolo[2,3-d]pyrimidine-5-carbonyl]-phenyl}-2-fluoro-benzenesulfonamide | 525.5 |
| P-1146 | 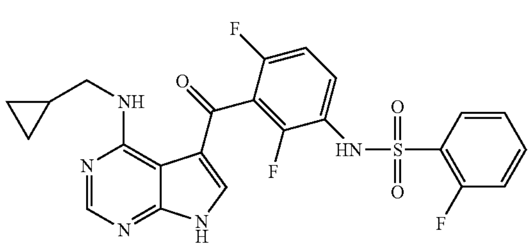 | N-{3-[4-(Cyclopropylmethyl-amino)-7H-pyrrolo[2,3-d]pyrimidine-5-carbonyl]-2,4-difluoro-phenyl}-2-fluoro-benzenesulfonamide | 502.0 |

TABLE I-continued

| Comp # | Structure | Name | MS |
|---|---|---|---|
| P-1147 | 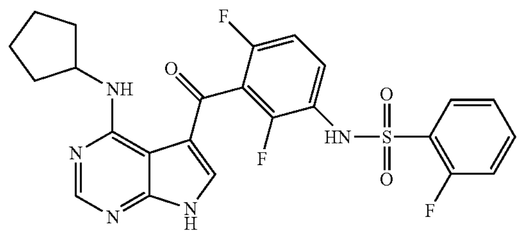 [SMILES: O=C(c1c(F)ccc(NS(=O)(=O)c2ccccc2F)c1F)c1c[nH]c2ncnc(NC3CCCC3)c12] | N-[3-(4-Cyclopentylamino-7H-pyrrolo[2,3-d]pyrimidine-5-carbonyl)-2,4-difluoro-phenyl]-2-fluoro-benzenesulfonamide | 516.5 |
| P-1148 | 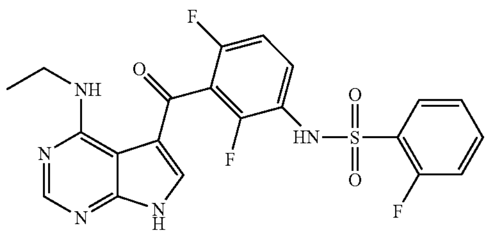 [SMILES: CCNc1ncnc2[nH]cc(C(=O)c3c(F)ccc(NS(=O)(=O)c4ccccc4F)c3F)c12] | N-[3-(4-Ethylamino-7H-pyrrolo[2,3-d]pyrimidine-5-carbonyl)-2,4-difluoro-phenyl]-2-fluoro-benzenesulfonamide | 476.0 |
| P-1149 | 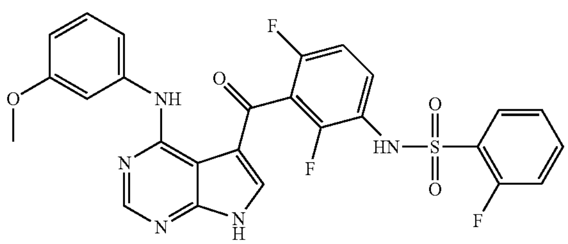 [SMILES: COc1cccc(Nc2ncnc3[nH]cc(C(=O)c4c(F)ccc(NS(=O)(=O)c5ccccc5F)c4F)c23)c1] | N-{2,4-Difluoro-3-[4-(3-methoxy-phenylamino)-7H-pyrrolo[2,3-d]pyrimidine-5-carbonyl]-phenyl}-2-fluoro-benzenesulfonamide | 554.0 |
| P-1150 | 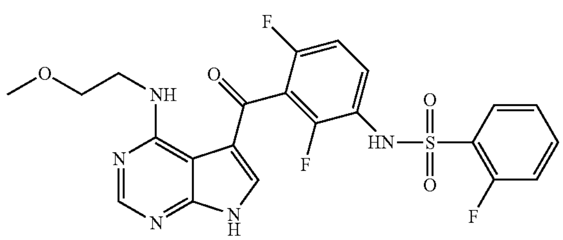 [SMILES: COCCNc1ncnc2[nH]cc(C(=O)c3c(F)ccc(NS(=O)(=O)c4ccccc4F)c3F)c12] | N-{2,4-Difluoro-3-[4-(2-methoxy-ethylamino)-7H-pyrrolo[2,3-d]pyrimidine-5-carbonyl]-phenyl}-2-fluoro-benzenesulfonamide | 506.0 |
| P-1151 | 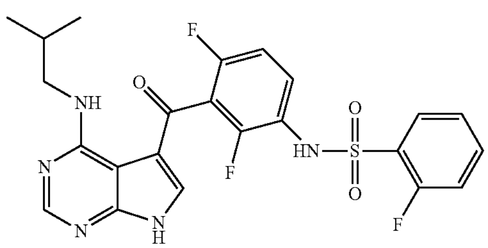 [SMILES: CC(C)CNc1ncnc2[nH]cc(C(=O)c3c(F)ccc(NS(=O)(=O)c4ccccc4F)c3F)c12] | N-[2,4-Difluoro-3-(4-isobutylamino-7H-pyrrolo[2,3-d]pyrimidine-5-carbonyl)-phenyl]-2-fluoro-benzenesulfonamide | 504.0 |
| P-1152 | 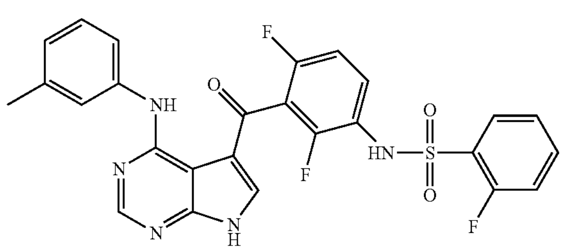 [SMILES: Cc1cccc(Nc2ncnc3[nH]cc(C(=O)c4c(F)ccc(NS(=O)(=O)c5ccccc5F)c4F)c23)c1] | N-[2,4-Difluoro-3-(4-m-tolylamino-7H-pyrrolo[2,3-d]pyrimidine-5-carbonyl)-phenyl]-2-fluoro-benzenesulfonamide | 538.5 |

TABLE I-continued

| Comp # | Structure | Name | MS |
|---|---|---|---|
| P-1153 | 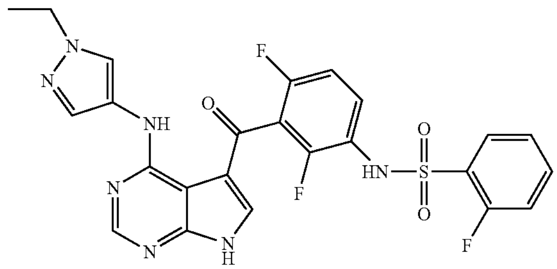 [SMILES: CCn1cc(Nc2ncnc3[nH]cc(C(=O)c4c(F)ccc(NS(=O)(=O)c5ccccc5F)c4F)c23)cn1] | N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide | 542.0 |
| P-1154 | 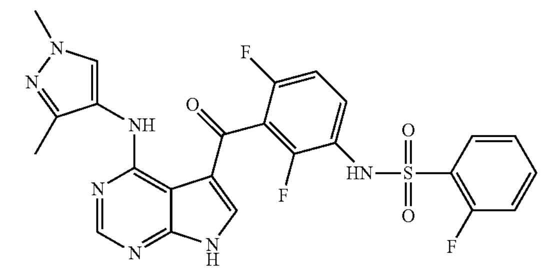 [SMILES: Cc1nn(C)cc1Nc1ncnc2[nH]cc(C(=O)c3c(F)ccc(NS(=O)(=O)c4ccccc4F)c3F)c12] | N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide | 542.0 |
| P-1155 | 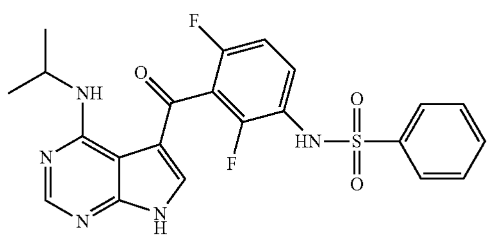 [SMILES: CC(C)Nc1ncnc2[nH]cc(C(=O)c3c(F)ccc(NS(=O)(=O)c4ccccc4)c3F)c12] | N-[2,4-Difluoro-3-(4-isopropylamino-7H-pyrrolo[2,3-d]pyrimidine-5-carbonyl)-phenyl]-benzenesulfonamide | 472.5 |
| P-1156 | 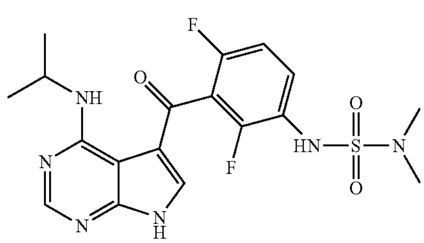 [SMILES: CC(C)Nc1ncnc2[nH]cc(C(=O)c3c(F)ccc(NS(=O)(=O)N(C)C)c3F)c12] | Dimethylamino-1-sulfonic acid [2,4-difluoro-3-(4-isopropylamino-7H-pyrrolo[2,3-d]pyrimidine-5-carbonyl)-phenyl]-amide | 439.0 |
| P-1157 | 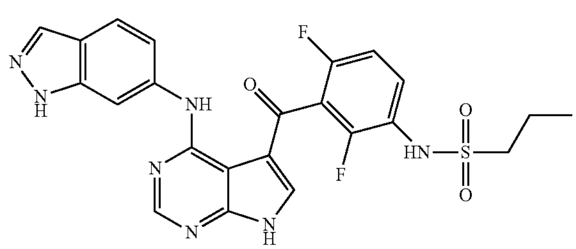 [SMILES: CCCS(=O)(=O)Nc1ccc(F)c(C(=O)c2c[nH]c3ncnc(Nc4ccc5cn[nH]c5c4)c23)c1F] | Propane-1-sulfonic acid {2,4-difluoro-3-[4-(1H-indazol-6-ylamino)-7H-pyrrolo[2,3-d]pyrimidine-5-carbonyl]-phenyl}-amide | 512.0 |
| P-1158 | 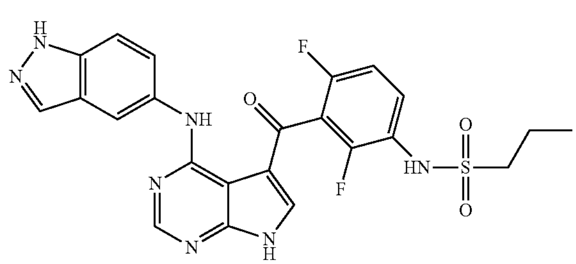 [SMILES: CCCS(=O)(=O)Nc1ccc(F)c(C(=O)c2c[nH]c3ncnc(Nc4ccc5[nH]ncc5c4)c23)c1F] | Propane-1-sulfonic acid {2,4-difluoro-3-[4-(1H-indazol-5-ylamino)-7H-pyrrolo[2,3-d]pyrimidine-5-carbonyl]-phenyl}-amide | 512.0 |

TABLE I-continued

| Comp # | Name | MS |
|---|---|---|
| P-1159 | Propane-1-sulfonic acid {2,4-difluoro-3-[4-(4-hydroxy-phenylamino)-7H-pyrrolo[2,3-d]pyrimidine-5-carbonyl]-phenyl}-amide | 489.1 |
| P-1160 | Propane-1-sulfonic acid (2,4-difluoro-3-{4-[(5-methyl-1H-pyrazol-3-ylmethyl)-amino]-7H-pyrrolo[2,3-d]pyrimidine-5-carbonyl}-phenyl)-amide | 488.0 [M − H⁺]⁻ |
| P-1161 | 3-({5-[2,6-Difluoro-3-(propane-1-sulfonylamino)-benzoyl]-7H-pyrrolo[2,3-d]pyrimidin-4-ylamino}-methyl)-benzoic acid | 530.0 |
| P-1162 | 4-{5-[2,6-Difluoro-3-(propane-1-sulfonylamino)-benzoyl]-7H-pyrrolo[2,3-d]pyrimidin-4-ylamino}-benzoic acid methyl ester | 530.0 |
| P-1163 | 4-{5-[2,6-Difluoro-3-(propane-1-sulfonylamino)-benzoyl]-7H-pyrrolo[2,3-d]pyrimidin-4-ylamino}-benzoic acid | 516.0 |
| P-1164 | Propane-1-sulfonic acid {2,4-difluoro-3-[4-(3-[1,2,4]triazol-1-yl-phenylamino)-7H-pyrrolo[2,3-d]pyrimidine-5-carbonyl]-phenyl}-amide | 539.5 |

TABLE I-continued

| Comp # | Structure | Name | MS |
|---|---|---|---|
| P-1165 | 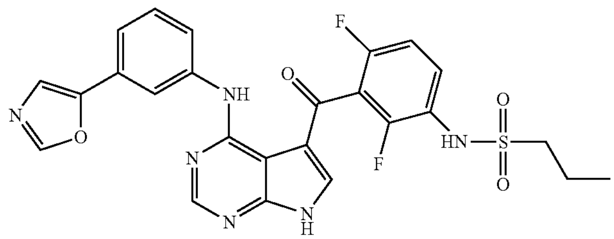 [SMILES: CCCS(=O)(=O)Nc1ccc(F)c(C(=O)c2c[nH]c3ncnc(Nc4cccc(-c5cnco5)c4)c23)c1F] | Propane-1-sulfonic acid {2,4-difluoro-3-[4-(3-oxazol-5-yl-phenylamino)-7H-pyrrolo[2,3-d]pyrimidine-5-carbonyl]-phenyl}-amide | 539.5 |
| P-1166 | 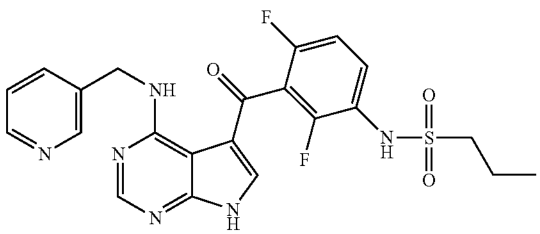 [SMILES: CCCS(=O)(=O)Nc1ccc(F)c(C(=O)c2c[nH]c3ncnc(NCc4cccnc4)c23)c1F] | Propane-1-sulfonic acid (2,4-difluoro-3-{4-[(pyridin-3-ylmethyl)-amino]-7H-pyrrolo[2,3-d]pyrimidine-5-carbonyl}-phenyl)-amide | 487.5 |
| P-1167 | 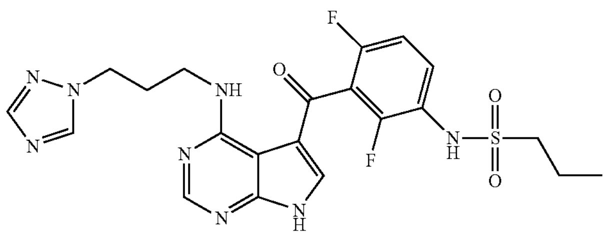 [SMILES: CCCS(=O)(=O)Nc1ccc(F)c(C(=O)c2c[nH]c3ncnc(NCCCn4cncn4)c23)c1F] | Propane-1-sulfonic acid {2,4-difluoro-3-[4-(3-[1,2,4]triazol-1-yl-propylamino)-7H-pyrrolo[2,3-d]pyrimidine-5-carbonyl]-phenyl}-amide | 505.0 |
| P-1168 | 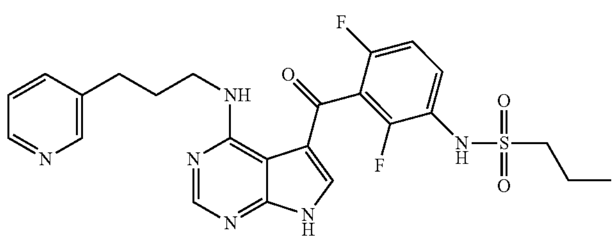 [SMILES: CCCS(=O)(=O)Nc1ccc(F)c(C(=O)c2c[nH]c3ncnc(NCCCc4cccnc4)c23)c1F] | Propane-1-sulfonic acid {2,4-difluoro-3-[4-(3-pyridin-3-yl-propylamino)-7H-pyrrolo[2,3-d]pyrimidine-5-carbonyl]-phenyl}-amide | 515.5 |
| P-1169 | 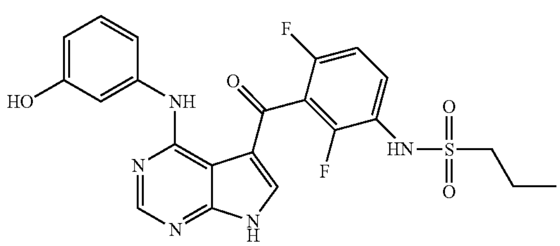 [SMILES: CCCS(=O)(=O)Nc1ccc(F)c(C(=O)c2c[nH]c3ncnc(Nc4cccc(O)c4)c23)c1F] | Propane-1-sulfonic acid {2,4-difluoro-3-[4-(3-hydroxy-phenylamino)-7H-pyrrolo[2,3-d]pyrimidine-5-carbonyl]-phenyl}-amide | 488.0 |
| P-1170 | 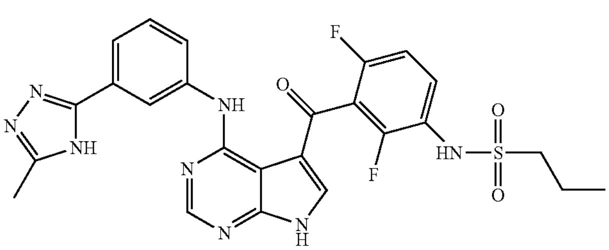 [SMILES: CCCS(=O)(=O)Nc1ccc(F)c(C(=O)c2c[nH]c3ncnc(Nc4cccc(-c5nnc(C)[nH]5)c4)c23)c1F] | Propane-1-sulfonic acid (2,4-difluoro-3-{4-[3-(5-methyl-4H-[1,2,4]triazol-3-yl)-phenylamino]-7H-pyrrolo[2,3-d]pyrimidine-5-carbonyl}-phenyl)-amide | 553.5 |

TABLE I-continued

| Comp # | Structure | Name | MS |
|---|---|---|---|
| P-1171 | 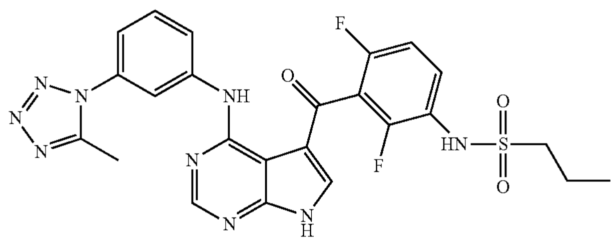 [SMILES: CCCS(=O)(=O)Nc1ccc(F)c(C(=O)c2c[nH]c3ncnc(Nc4cccc(-n5nnnc5C)c4)c23)c1F] | Propane-1-sulfonic acid (2,4-difluoro-3-{4-[3-(5-methyl-tetrazol-1-yl)-phenylamino]-7H-pyrrolo[2,3-d]pyrimidine-5-carbonyl}-phenyl)-amide | 554.0 |
| P-1172 | 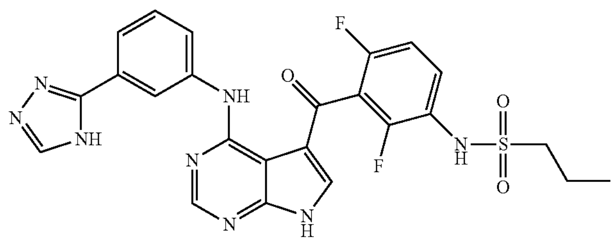 [SMILES: CCCS(=O)(=O)Nc1ccc(F)c(C(=O)c2c[nH]c3ncnc(Nc4cccc(-c5nnc[nH]5)c4)c23)c1F] | Propane-1-sulfonic acid (2,4-difluoro-3-{4-[3-(4H-[1,2,4]triazol-3-yl)-phenylamino]-7H-pyrrolo[2,3-d]pyrimidine-5-carbonyl}-phenyl)-amide | 539.5 |
| P-1173 | 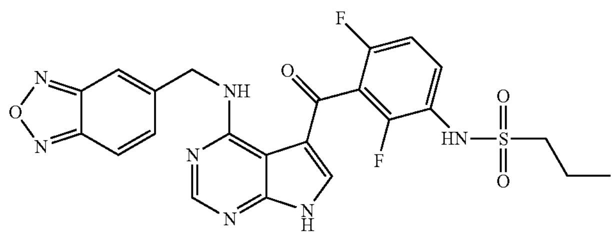 [SMILES: CCCS(=O)(=O)Nc1ccc(F)c(C(=O)c2c[nH]c3ncnc(NCc4ccc5nonc5c4)c23)c1F] | Propane-1-sulfonic acid (3-{4-[(benzo[1,2,5]oxadiazol-5-ylmethyl)-amino]-7H-pyrrolo[2,3-d]pyrimidine-5-carbonyl}-2,4-difluoro-phenyl)-amide | 528.0 |
| P-1174 | 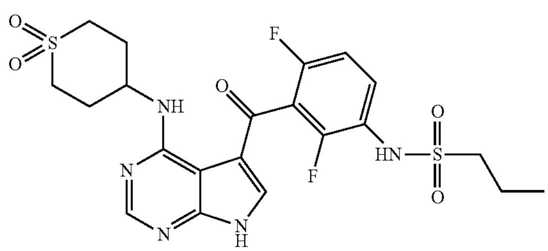 [SMILES: CCCS(=O)(=O)Nc1ccc(F)c(C(=O)c2c[nH]c3ncnc(NC4CCS(=O)(=O)CC4)c23)c1F] | Propane-1-sulfonic acid {3-[4-(1,1-dioxo-hexahydro-1lambda*6*-thiopyran-4-ylamino)-7H-pyrrolo[2,3-d]pyrimidine-5-carbonyl]-2,4-difluoro-phenyl}-amide | 528.0 |
| P-1175 | 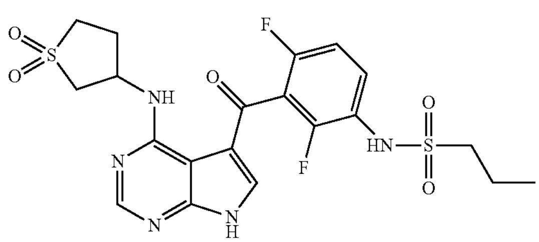 [SMILES: CCCS(=O)(=O)Nc1ccc(F)c(C(=O)c2c[nH]c3ncnc(NC4CCS(=O)(=O)C4)c23)c1F] | Propane-1-sulfonic acid {3-[4-(1,1-dioxo-tetrahydro-1lambda*6*-thiophen-3-ylamino)-7H-pyrrolo[2,3-d]pyrimidine-5-carbonyl]-2,4-difluoro-phenyl}-amide | 514.5 |
| P-1176 | 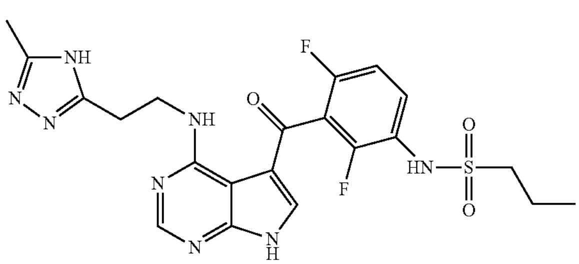 [SMILES: CCCS(=O)(=O)Nc1ccc(F)c(C(=O)c2c[nH]c3ncnc(NCCc4nnc(C)[nH]4)c23)c1F] | Propane-1-sulfonic acid (2,4-difluoro-3-{4-[2-(5-methyl-4H-[1,2,4]triazol-3-yl)-ethylamino]-7H-pyrrolo[2,3-d]pyrimidine-5-carbonyl}-phenyl)-amide | 505.0 |

| Comp # | Structure | Name | MS |
|---|---|---|---|
| P-1177 | 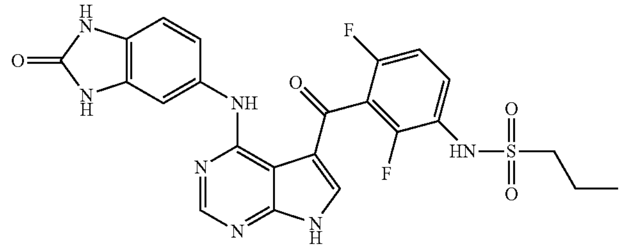 [SMILES: CCCS(=O)(=O)Nc1ccc(F)c(C(=O)c2c[nH]c3ncnc(Nc4ccc5[nH]c(=O)[nH]c5c4)c23)c1F] | Propane-1-sulfonic acid {2,4-difluoro-3-[4-(2-oxo-2,3-dihydro-1H-benzoimidazol-5-ylamino)-7H-pyrrolo[2,3-d]pyrimidine-5-carbonyl]-phenyl}-amide | 528.0 |
| P-1178 | 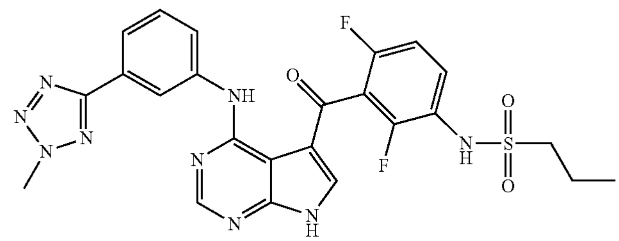 [SMILES: CCCS(=O)(=O)Nc1ccc(F)c(C(=O)c2c[nH]c3ncnc(Nc4cccc(-c5nnn(C)n5)c4)c23)c1F] | Propane-1-sulfonic acid (2,4-difluoro-3-{4-[3-(2-methyl-2H-tetrazol-5-yl)-phenylamino]-7H-pyrrolo[2,3-d]pyrimidine-5-carbonyl}-phenyl)-amide | 554.0 |
| P-1179 | 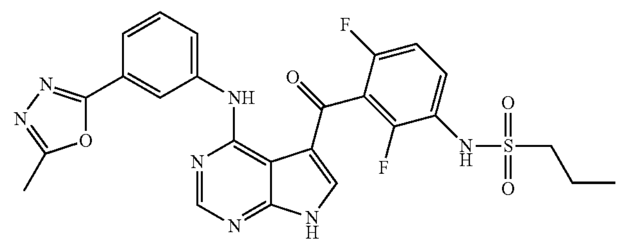 [SMILES: CCCS(=O)(=O)Nc1ccc(F)c(C(=O)c2c[nH]c3ncnc(Nc4cccc(-c5nnc(C)o5)c4)c23)c1F] | Propane-1-sulfonic acid (2,4-difluoro-3-{4-[3-(5-methyl-[1,3,4]oxadiazol-2-yl)-phenylamino]-7H-pyrrolo[2,3-d]pyrimidine-5-carbonyl}-phenyl)-amide | 554.0 |
| P-1180 | 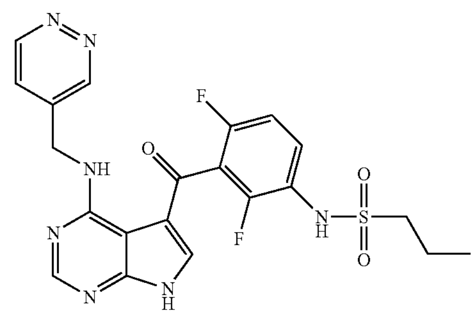 [SMILES: CCCS(=O)(=O)Nc1ccc(F)c(C(=O)c2c[nH]c3ncnc(NCc4ccnnc4)c23)c1F] | Propane-1-sulfonic acid (2,4-difluoro-3-{4-[(pyridazin-4-ylmethyl)-amino]-7H-pyrrolo[2,3-d]pyrimidine-5-carbonyl}-phenyl)-amide | 488.0 |
| P-1181 | 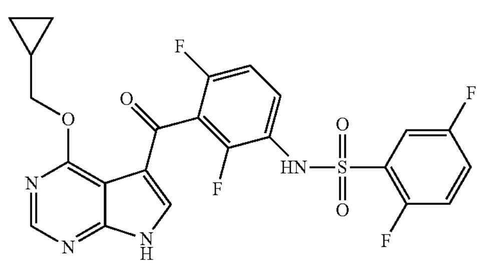 [SMILES: O=C(c1c(F)ccc(NS(=O)(=O)c2cc(F)ccc2F)c1F)c1c[nH]c2ncnc(OCC3CC3)c12] | N-[3-(4-Cyclopropylmethoxy-7H-pyrrolo[2,3-d]pyrimidine-5-carbonyl)-2,4-difluoro-phenyl]-2,5-difluoro-benzenesulfonamide | 521.0 |
| P-1182 | 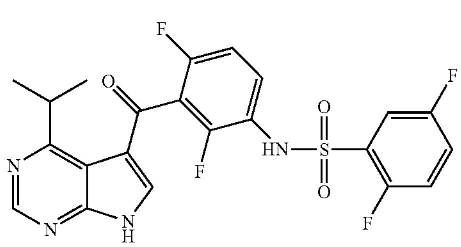 [SMILES: CC(C)c1ncnc2[nH]cc(C(=O)c3c(F)ccc(NS(=O)(=O)c4cc(F)ccc4F)c3F)c12] | N-[2,4-Difluoro-3-(4-isopropyl-7H-pyrrolo[2,3-d]pyrimidine-5-carbonyl)-phenyl]-2,5-difluoro-benzenesulfonamide | 493.0 |

TABLE I-continued

| Comp # | Structure | Name | MS |
|---|---|---|---|
| P-1183 | 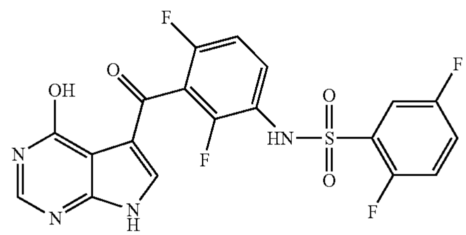 [SMILES: O=C(c1c(F)ccc(NS(=O)(=O)c2cc(F)ccc2F)c1F)c1c[nH]c2ncnc(O)c12] | N-[2,4-Difluoro-3-(4-hydroxy-7H-pyrrolo[2,3-d]pyrimidine-5-carbonyl)-phenyl]-2,5-difluoro-benzenesulfonamide | 466.9 |
| P-1184 | 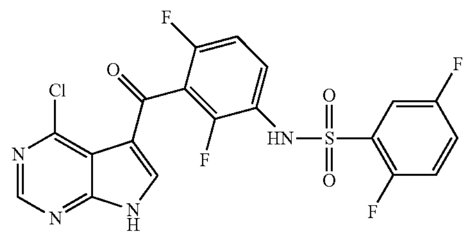 [SMILES: O=C(c1c(F)ccc(NS(=O)(=O)c2cc(F)ccc2F)c1F)c1c[nH]c2ncnc(Cl)c12] | N-[3-(4-Chloro-7H-pyrrolo[2,3-d]pyrimidine-5-carbonyl)-2,4-difluoro-phenyl]-2,5-difluoro-benzenesulfonamide | |
| P-1185 | 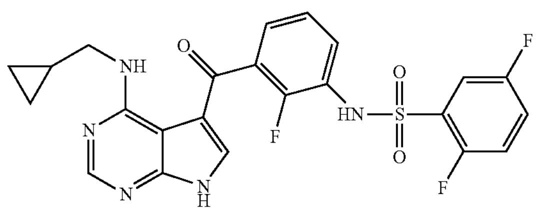 [SMILES: O=C(c1cccc(NS(=O)(=O)c2cc(F)ccc2F)c1F)c1c[nH]c2ncnc(NCC3CC3)c12] | N-{3-[4-(Cyclopropylmethyl-amino)-7H-pyrrolo[2,3-d]pyrimidine-5-carbonyl]-2-fluoro-phenyl}-2,5-difluoro-benzenesulfonamide | 502.0 |
| P-1186 | 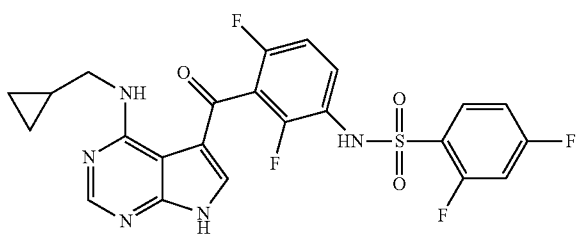 [SMILES: O=C(c1c(F)ccc(NS(=O)(=O)c2ccc(F)cc2F)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-2,4-difluoro-benzenesulfonamide | 520.5 |
| P-1187 | 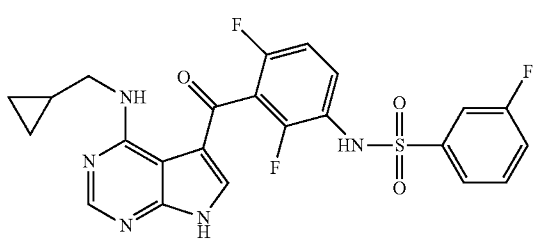 [SMILES: O=C(c1c(F)ccc(NS(=O)(=O)c2cccc(F)c2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-3-fluoro-benzenesulfonamide | 502.0 |
| P-1188 | 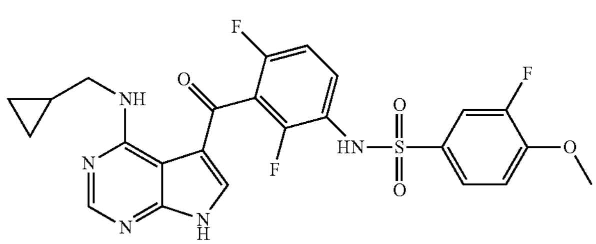 [SMILES: COc1ccc(S(=O)(=O)Nc2ccc(F)c(C(=O)c3c[nH]c4ncnc(NCC5CC5)c34)c2F)cc1F] | N-{3-[4-(Cyclopropylmethyl-amino)-7H-pyrrolo[2,3-d]pyrimidine-5-carbonyl]-2,4-difluoro-phenyl}-3-fluoro-4-methoxy-benzenesulfonamide | |

TABLE I-continued

| Comp # | Structure | Name | MS |
|---|---|---|---|
| P-1189 | 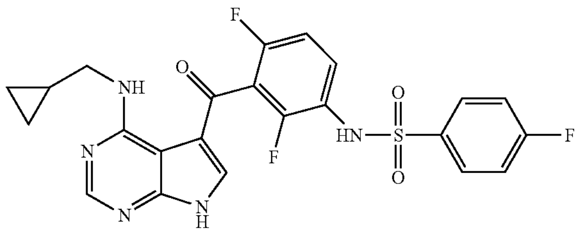 [SMILES: O=C(c1c(F)ccc(NS(=O)(=O)c2ccc(F)cc2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-4-fluoro-benzenesulfonamide | 502.0 |
| P-1190 | 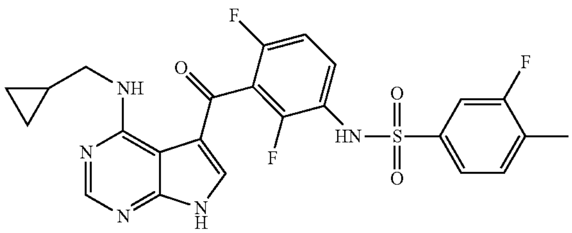 [SMILES: Cc1ccc(S(=O)(=O)Nc2ccc(F)c(C(=O)c3c[nH]c4ncnc(NCC5CC5)c34)c2F)cc1F] | N-{3-[4-(Cyclopropylmethyl-amino)-7H-pyrrolo[2,3-d]pyrimidine-5-carbonyl]-2,4-difluoro-phenyl}-3-benzenesulfonamide | 516.5 |
| P-1191 | 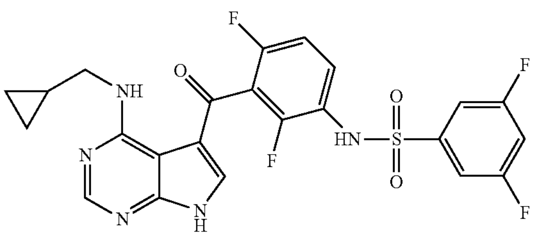 [SMILES: O=C(c1c(F)ccc(NS(=O)(=O)c2cc(F)cc(F)c2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-3,5-difluoro-benzenesulfonamide | 520.5 |
| P-1192 | 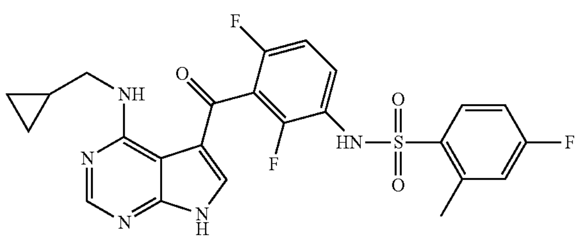 [SMILES: Cc1cc(F)ccc1S(=O)(=O)Nc1ccc(F)c(C(=O)c2c[nH]c3ncnc(NCC4CC4)c23)c1F] | N-{3-[4-(Cyclopropylmethyl-amino)-7H-pyrrolo[2,3-d]pyrimidine-5-carbonyl]-2,4-difluoro-2-phenyl}-4-benzenesulfonamide | 516.5 |
| P-1193 | 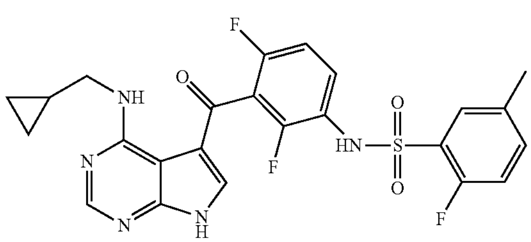 [SMILES: Cc1ccc(F)c(S(=O)(=O)Nc2ccc(F)c(C(=O)c3c[nH]c4ncnc(NCC5CC5)c34)c2F)c1] | N-{3-[4-(Cyclopropylmethyl-amino)-7H-pyrrolo[2,3-d]pyrimidine-5-carbonyl]-2,4-difluoro-phenyl}-2-fluoro-5-methyl-benzenesulfonamide | 516.5 |
| P-1194 | 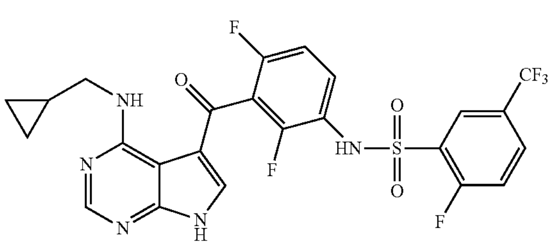 [SMILES: O=C(c1c(F)ccc(NS(=O)(=O)c2cc(C(F)(F)F)ccc2F)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-2-fluoro-5-trifluoromethyl-benzenesulfonamide | 570.5 |

TABLE I-continued

| Comp # | Structure | Name | MS |
|---|---|---|---|
| P-1195 | 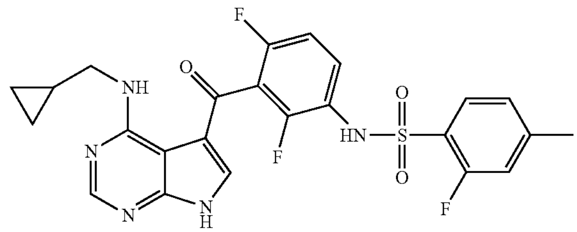 [SMILES: Cc1ccc(S(=O)(=O)Nc2ccc(F)c(C(=O)c3c[nH]c4ncnc(NCC5CC5)c34)c2F)c(F)c1] | N-{3-[4-(Cyclopropylmethyl-amino)-7H-pyrrolo[2,3-d]pyrimidine-5-carbonyl]-2,4-difluoro-phenyl}-2-fluoro-4-methyl-benzenesulfonamide | 516.5 |
| P-1196 | 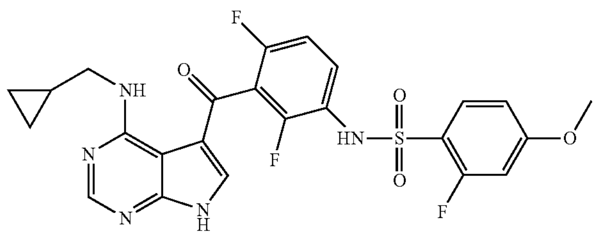 [SMILES: COc1ccc(S(=O)(=O)Nc2ccc(F)c(C(=O)c3c[nH]c4ncnc(NCC5CC5)c34)c2F)c(F)c1] | N-{3-[4-(Cyclopropylmethyl-amino)-7H-pyrrolo[2,3-d]pyrimidine-5-carbonyl]-2,4-difluoro-phenyl}-2-fluoro-4-methoxy-benzenesulfonamide | 532.0 |
| P-1197 | 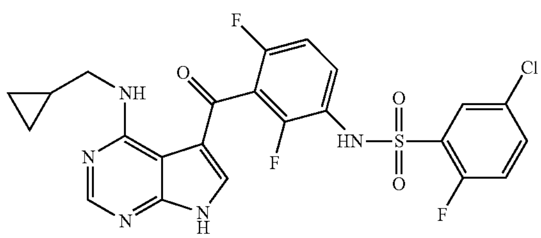 [SMILES: O=C(c1c(F)ccc(NS(=O)(=O)c2cc(Cl)ccc2F)c1F)c1c[nH]c2ncnc(NCC3CC3)c12] | 5-Chloro-N-{3-[4-(cyclopropylmethyl-amino)-7H-pyrrolo[2,3-d]pyrimidine-5-carbonyl]-2,4-difluoro-phenyl}-2-fluoro-benzenesulfonamide | |
| P-1198 | 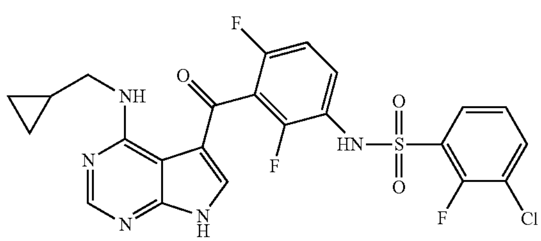 [SMILES: O=C(c1c(F)ccc(NS(=O)(=O)c2cccc(Cl)c2F)c1F)c1c[nH]c2ncnc(NCC3CC3)c12] | 3-Chloro-N-{3-[4-(cyclopropylmethyl-amino)-7H-pyrrolo[2,3-d]pyrimidine-5-carbonyl]-2,4-difluoro-phenyl}-2-fluoro-benzenesulfonamide | 536.0 |
| P-1199 | 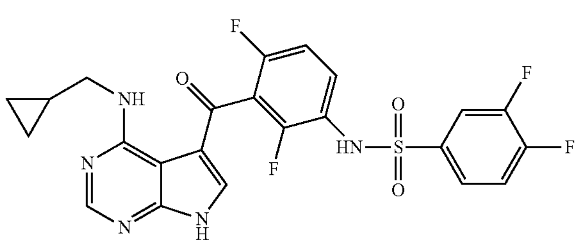 [SMILES: O=C(c1c(F)ccc(NS(=O)(=O)c2ccc(F)c(F)c2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-3,4-difluoro-benzenesulfonamide | 520.5 |
| P-1200 | 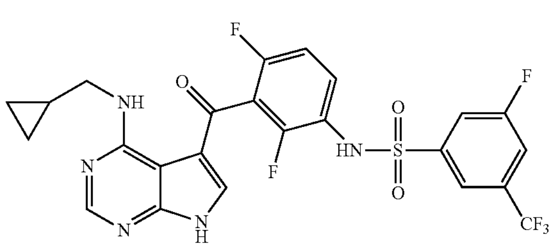 [SMILES: O=C(c1c(F)ccc(NS(=O)(=O)c2cc(F)cc(C(F)(F)F)c2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-3-fluoro-5-trifluoromethyl-benzenesulfonamide | 570.5 |

TABLE I-continued

| Comp # | Structure | Name | MS |
|---|---|---|---|
| P-1201 | 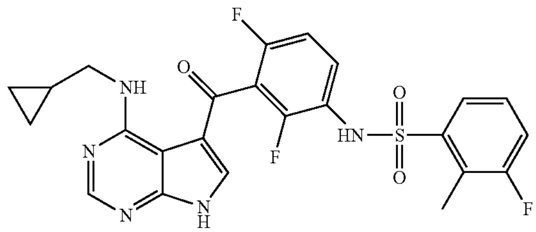 [SMILES: Cc1c(F)cccc1S(=O)(=O)Nc1ccc(F)c(C(=O)c2c[nH]c3ncnc(NCC4CC4)c23)c1F] | N-{3-[4-(Cyclopropylmethyl-amino)-7H-pyrrolo[2,3-d]pyrimidine-5-carbonyl]-2,4-difluoro-phenyl}-3-fluoro-2-methyl-benzenesulfonamide | 516.5 |
| P-1202 | 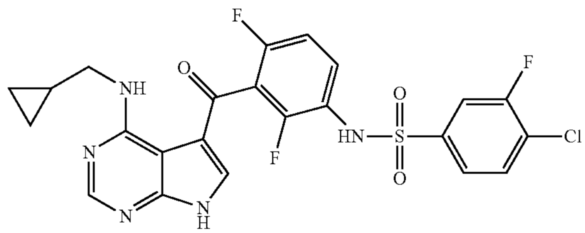 [SMILES: O=C(c1c(F)ccc(NS(=O)(=O)c2ccc(Cl)c(F)c2)c1F)c1c[nH]c2ncnc(NCC3CC3)c12] | 4-Chloro-N-{3-[4-(cyclopropylmethyl-amino)-7H-pyrrolo[2,3-d]pyrimidine-5-carbonyl]-2,4-difluoro-phenyl}-3-fluoro-benzenesulfonamide | 536.0 |
| P-1203 | 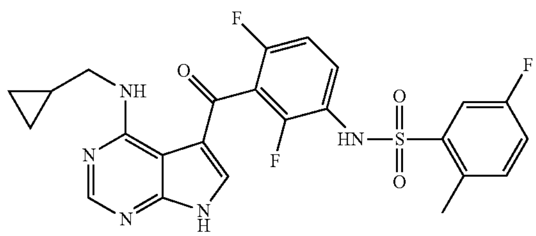 [SMILES: Cc1ccc(F)cc1S(=O)(=O)Nc1ccc(F)c(C(=O)c2c[nH]c3ncnc(NCC4CC4)c23)c1F] | N-{3-[4-(Cyclopropylmethyl-amino)-7H-pyrrolo[2,3-d]pyrimidine-5-carbonyl]-2,4-difluoro-phenyl}-5-fluoro-2-methyl-benzenesulfonamide | 516.5 |
| P-1204 | 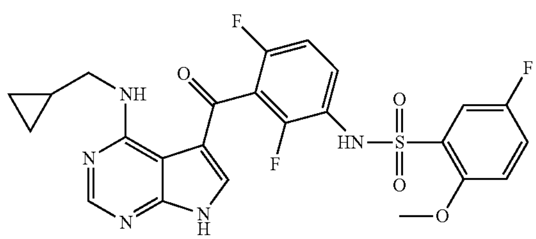 [SMILES: COc1ccc(F)cc1S(=O)(=O)Nc1ccc(F)c(C(=O)c2c[nH]c3ncnc(NCC4CC4)c23)c1F] | N-{3-[4-(Cyclopropylmethyl-amino)-7H-pyrrolo[2,3-d]pyrimidine-5-carbonyl]-2,4-difluoro-phenyl}-5-fluoro-2-methoxy-benzenesulfonamide | 532.0 |
| P-1205 | 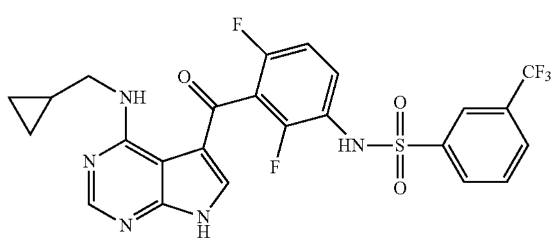 [SMILES: O=C(c1c(F)ccc(NS(=O)(=O)c2cccc(C(F)(F)F)c2)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-3-trifluoromethyl-benzenesulfonamide | 552.5 |
| P-1206 | 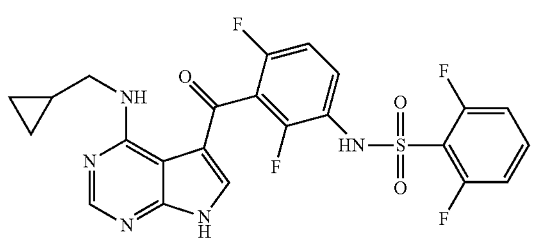 [SMILES: O=C(c1c(F)ccc(NS(=O)(=O)c2c(F)cccc2F)c1F)c1c[nH]c2ncnc(NCC3CC3)c12] | N-{3-[4-(Cyclopropylmethyl-amino)-7H-pyrrolo[2,3-d]pyrimidine-5-carbonyl]-2,4-difluoro-phenyl}-2,6-difluoro-benzenesulfonamide | 520.5 |

TABLE I-continued

| Comp # | Name | MS |
|---|---|---|
| P-1207 | N-{3-[4-(Cyclopropylmethyl-amino)-7H-pyrrolo[2,3-d]pyrimidine-5-carbonyl]-2,4-difluoro-phenyl}-benzenesulfonamide | 484.5 |
| P-1208 | Pyridine-2-sulfonic acid {3-[4-(cyclopropylmethyl-amino)-7H-pyrrolo[2,3-d]pyrimidine-5-carbonyl]-2,4-difluoro-phenyl}-amide | 485.5 |
| P-1209 | 4-Methyl-pyridine-2-sulfonic acid {3-[4-(cyclopropylmethyl-amino)-7H-pyrrolo[2,3-d]pyrimidine-5-carbonyl]-2,4-difluoro-phenyl}-amide | |
| P-1210 | 6-Fluoro-pyridine-2-sulfonic acid {3-[4-(cyclopropylmethyl-amino)-7H-pyrrolo[2,3-d]pyrimidine-5-carbonyl]-2,4-difluoro-phenyl}-amide | |
| P-1211 | Pyridine-3-sulfonic acid {3-[4-(cyclopropylmethyl-amino)-7H-pyrrolo[2,3-d]pyrimidine-5-carbonyl]-2,4-difluoro-phenyl}-amide | |
| P-1212 | 4-Chloro-pyridine-3-sulfonic acid {3-[4-(cyclopropylmethyl-amino)-7H-pyrrolo[2,3-d]pyrimidine-5-carbonyl]-2,4-difluoro-phenyl}-amide | |

TABLE I-continued

| Comp # | Structure | Name | MS |
|---|---|---|---|
| P-1213 | 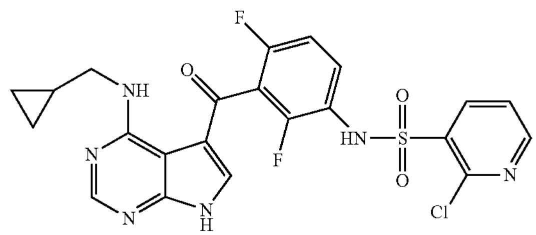 [SMILES: O=C(c1c(F)ccc(NS(=O)(=O)c2cccnc2Cl)c1F)c1c[nH]c2ncnc(NCC3CC3)c12] | 2-Chloro-pyridine-3-sulfonic acid {3-[4-(cyclopropylmethyl-amino)-7H-pyrrolo[2,3-d]pyrimidine-5-carbonyl]-2,4-difluoro-phenyl}-amide | 519.0 |
| P-1214 | 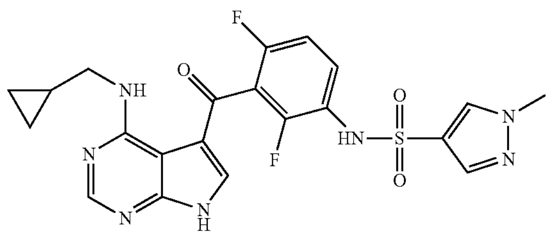 [SMILES: Cn1cc(S(=O)(=O)Nc2ccc(F)c(C(=O)c3c[nH]c4ncnc(NCC5CC5)c34)c2F)cn1] | 1-Methyl-1H-pyrazole-4-sulfonic acid {3-[4-(cyclopropylmethyl-amino)-7H-pyrrolo[2,3-d]pyrimidine-5-carbonyl]-2,4-difluoro-phenyl}-amide | 488.5 |
| P-1215 | 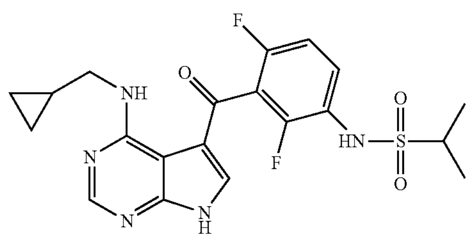 [SMILES: CC(C)S(=O)(=O)Nc1ccc(F)c(C(=O)c2c[nH]c3ncnc(NCC4CC4)c23)c1F] | N,N-Dimethylamino-sulfonic acid {3-[4-(cyclopropylmethyl-amino)-7H-pyrrolo[2,3-d]pyrimidine-5-carbonyl]-2,4-difluoro-phenyl}-amide | 451.0 |
| P-1216 | 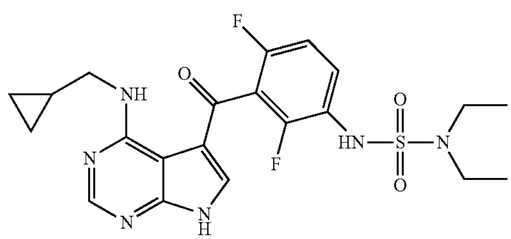 [SMILES: CCN(CC)S(=O)(=O)Nc1ccc(F)c(C(=O)c2c[nH]c3ncnc(NCC4CC4)c23)c1F] | N,N-Diethylamino-sulfonic acid {3-[4-(cyclopropylmethyl-amino)-7H-pyrrolo[2,3-d]pyrimidine-5-carbonyl]-2,4-difluoro-phenyl}-amide | 479.0 |
| P-1217 | 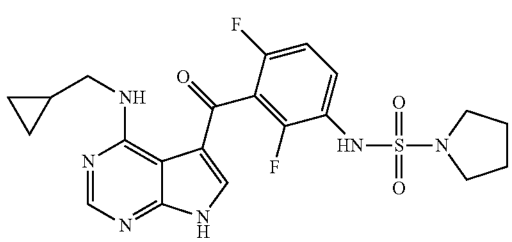 [SMILES: O=C(c1c(F)ccc(NS(=O)(=O)N2CCCC2)c1F)c1c[nH]c2ncnc(NCC3CC3)c12] | Pyrrolidine-1-sulfonic acid {3-[4-(cyclopropylmethyl-amino)-7H-pyrrolo[2,3-d]pyrimidine-5-carbonyl]-2,4-difluoro-phenyl}-amide | |
| P-1218 | 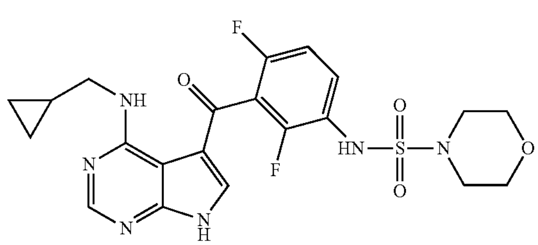 [SMILES: O=C(c1c(F)ccc(NS(=O)(=O)N2CCOCC2)c1F)c1c[nH]c2ncnc(NCC3CC3)c12] | Morpholine-4-sulfonic acid {3-[4-(cyclopropylmethyl-amino)-7H-pyrrolo[2,3-d]pyrimidine-5-carbonyl]-2,4-difluoro-phenyl}-amide | 493.5 |

| Comp # | Structure | Name | MS |
|---|---|---|---|
| P-1219 | 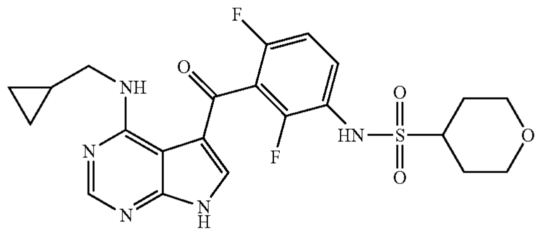 [SMILES: O=C(c1c(F)ccc(NS(=O)(=O)C2CCOCC2)c1F)c1c[nH]c2ncnc(NCC3CC3)c12] | Tetrahydro-pyran-4-sulfonic acid {3-[4-(cyclopropylmethyl-amino)-7H-pyrrolo[2,3-d]pyrimidine-5-carbonyl]-2,4-difluoro-phenyl}-amide | |
| P-1220 | 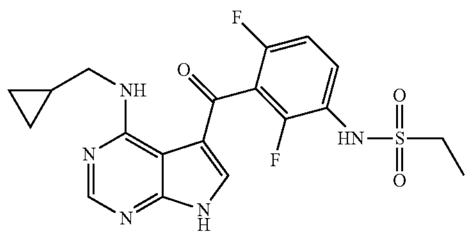 [SMILES: CCS(=O)(=O)Nc1ccc(F)c(C(=O)c2c[nH]c3ncnc(NCC4CC4)c23)c1F] | Ethanesulfonic acid {3-[4-(cyclopropylmethyl-amino)-7H-pyrrolo[2,3-d]pyrimidine-5-carbonyl]-2,4-difluoro-phenyl}-amide | |
| P-1221 | 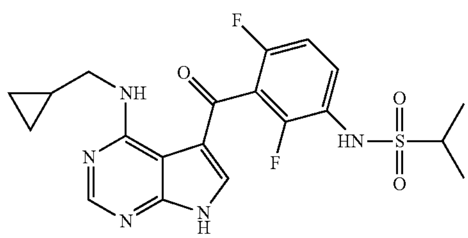 [SMILES: CC(C)S(=O)(=O)Nc1ccc(F)c(C(=O)c2c[nH]c3ncnc(NCC4CC4)c23)c1F] | Propane-2-sulfonic acid {3-[4-(cyclopropylmethyl-amino)-7H-pyrrolo[2,3-d]pyrimidine-5-carbonyl]-2,4-difluoro-phenyl}-amide | 450.0 |
| P-1222 | 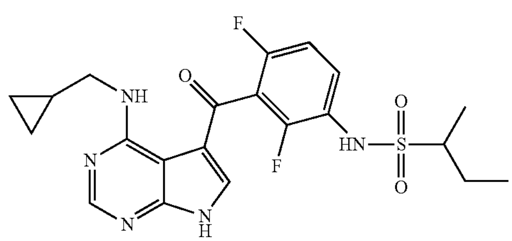 [SMILES: CCC(C)S(=O)(=O)Nc1ccc(F)c(C(=O)c2c[nH]c3ncnc(NCC4CC4)c23)c1F] | Butane-2-sulfonic acid {3-[4-(cyclopropylmethyl-amino)-7H-pyrrolo[2,3-d]pyrimidine-5-carbonyl]-2,4-difluoro-phenyl}-amide | |
| P-1223 | 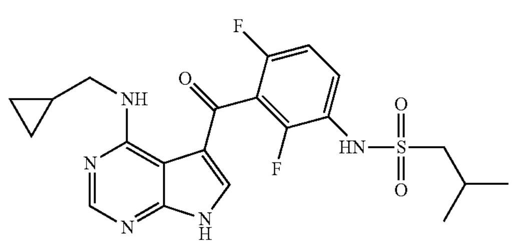 [SMILES: CC(C)CS(=O)(=O)Nc1ccc(F)c(C(=O)c2c[nH]c3ncnc(NCC4CC4)c23)c1F] | 2-Methyl-propane-1-sulfonic acid {3-[4-(cyclopropylmethyl-amino)-7H-pyrrolo[2,3-d]pyrimidine-5-carbonyl]-2,4-difluoro-phenyl}-amide | 464.0 |
| P-1224 | 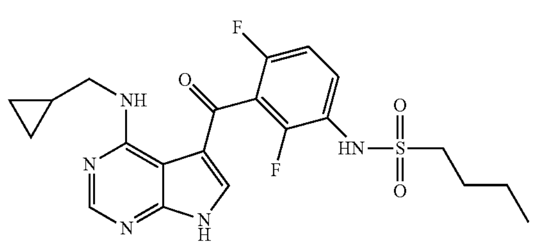 [SMILES: CCCCS(=O)(=O)Nc1ccc(F)c(C(=O)c2c[nH]c3ncnc(NCC4CC4)c23)c1F] | Butane-1-sulfonic acid {3-[4-(cyclopropylmethyl-amino)-7H-pyrrolo[2,3-d]pyrimidine-5-carbonyl]-2,4-difluoro-phenyl}-amide | 464.0 |

TABLE I-continued

| Comp # | Name | MS |
|---|---|---|
| P-1225 | Pentane-2-sulfonic acid {3-[4-(cyclopropylmethyl-amino)-7H-pyrrolo[2,3-d]pyrimidine-5-carbonyl]-2,4-difluoro-phenyl}-amide | 478.0 |
| P-1226 | N-{3-[4-(Cyclopropylmethyl-amino)-7H-pyrrolo[2,3-d]pyrimidine-5-carbonyl]-2,4-difluoro-phenyl}-C,C,C-trifluoro-methanesulfonamide | |
| P-1227 | 2,2,2-Trifluoro-ethanesulfonic acid {3-[4-(cyclopropylmethyl-amino)-7H-pyrrolo[2,3-d]pyrimidine-5-carbonyl]-2,4-difluoro-phenyl}-amide | 490.0 |
| P-1228 | 3,3,3-Trifluoro-propane-1-sulfonic acid {3-[4-(cyclopropylmethyl-amino)-7H-pyrrolo[2,3-d]pyrimidine-5-carbonyl]-2,4-difluoro-phenyl}-amide | 504.0 |
| P-1229 | Cyclohexanesulfonic acid {3-[4-(cyclopropylmethyl-amino)-7H-pyrrolo[2,3-d]pyrimidine-5-carbonyl]-2,4-difluoro-phenyl}-amide | 490.5 |
| P-1230 | Cyclopentanesulfonic acid {3-[4-(cyclopropylmethyl-amino)-7H-pyrrolo[2,3-d]pyrimidine-5-carbonyl]-2,4-difluoro-phenyl}-amide | 476.0 |

| Comp # | Structure | Name | MS |
|---|---|---|---|
| P-1231 | 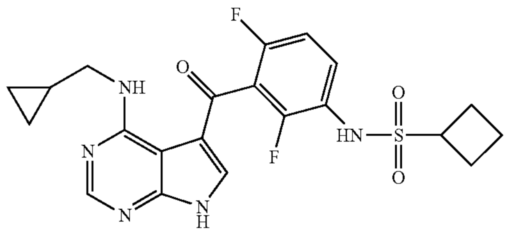 [SMILES: O=C(c1c(F)ccc(NS(=O)(=O)C2CCC2)c1F)c1c[nH]c2ncnc(NCC3CC3)c12] | Cyclobutanesulfonic acid {3-[4-(cyclopropylmethyl-amino)-7H-pyrrolo[2,3-d]pyrimidine-5-carbonyl]-2,4-difluoro-phenyl}-amide | 462.5 |
| P-1232 | 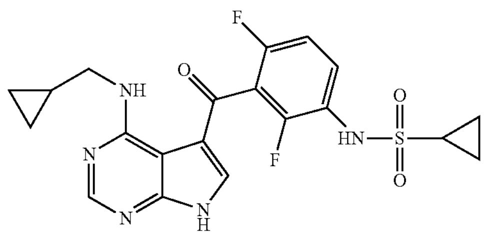 [SMILES: O=C(c1c(F)ccc(NS(=O)(=O)C2CC2)c1F)c1c[nH]c2ncnc(NCC3CC3)c12] | Cyclopropylsulfonic acid {3-[4-(cyclopropylmethyl-amino)-7H-pyrrolo[2,3-d]pyrimidine-5-carbonyl]-2,4-difluoro-phenyl}-amide | 448.0 |
| P-1233 | 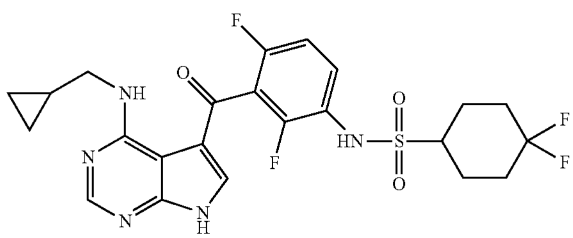 [SMILES: O=C(c1c(F)ccc(NS(=O)(=O)C2CCC(F)(F)CC2)c1F)c1c[nH]c2ncnc(NCC3CC3)c12] | 4,4-Difluoro-cyclohexanesulfonic acid {3-[4-(cyclopropylmethyl-amino)-7H-pyrrolo[2,3-d]pyrimidine-5-carbonyl]-2,4-difluoro-phenyl}-amide | |
| P-1234 | 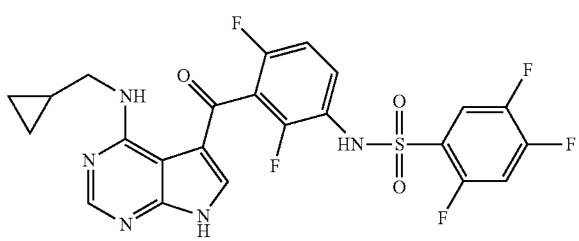 [SMILES: O=C(c1c(F)ccc(NS(=O)(=O)c2cc(F)c(F)cc2F)c1F)c1c[nH]c2ncnc(NCC3CC3)c12] | N-[3-[4-(cyclopropylmethylamino)-7H-pyrrolo[2,3-d]pyrimidine-5-carbonyl]-2,4-difluoro-phenyl]-2,4,5-trifluoro-benzenesulfonamide | 538.5 |
| P-1235 | 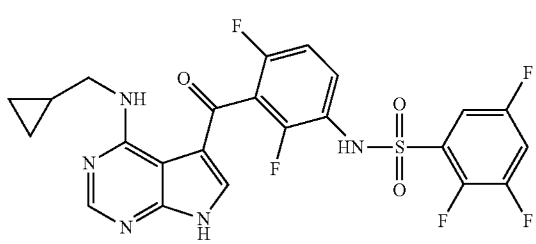 [SMILES: O=C(c1c(F)ccc(NS(=O)(=O)c2cc(F)cc(F)c2F)c1F)c1c[nH]c2ncnc(NCC3CC3)c12] | N-[3-[4-(cyclopropylmethylamino)-7H-pyrrolo[2,3-d]pyrimidine-5-carbonyl]-2,4-difluoro-phenyl]-2,3,5-trifluoro-benzenesulfonamide | 538.5 |
| P-1236 | 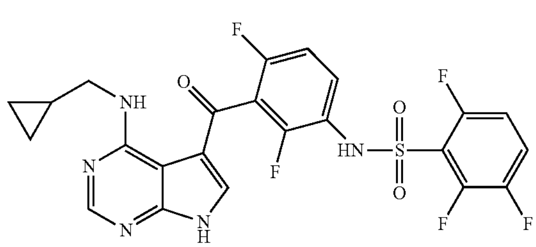 [SMILES: O=C(c1c(F)ccc(NS(=O)(=O)c2c(F)ccc(F)c2F)c1F)c1c[nH]c2ncnc(NCC3CC3)c12] | N-[3-[4-(cyclopropylmethylamino)-7H-pyrrolo[2,3-d]pyrimidine-5-carbonyl]-2,4-difluoro-phenyl]-2,3,6-trifluoro-benzenesulfonamide | 538.5 |

TABLE I-continued

| Comp # | Structure | Name | MS |
|---|---|---|---|
| P-1237 | 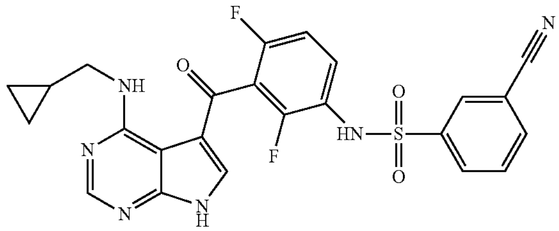 [SMILES: N#Cc1cccc(S(=O)(=O)Nc2ccc(F)c(C(=O)c3c[nH]c4ncnc(NCC5CC5)c34)c2F)c1] | 3-cyano-N-[3-[4-(cyclopropylmethylamino)-7H-pyrrolo[2,3-d]pyrimidine-5-carbonyl]-2,4-difluoro-phenyl]benzenesulfonamide | 509.0 |
| P-1238 | 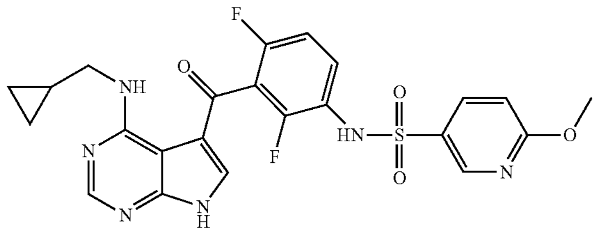 [SMILES: COc1ccc(S(=O)(=O)Nc2ccc(F)c(C(=O)c3c[nH]c4ncnc(NCC5CC5)c34)c2F)cn1] | N-[3-[4-(cyclopropylmethylamino)-7H-pyrrolo[2,3-d]pyrimidine-5-carbonyl]-2,4-difluoro-phenyl]-6-methoxy-pyridine-3-sulfonamide | |
| P-1239 | 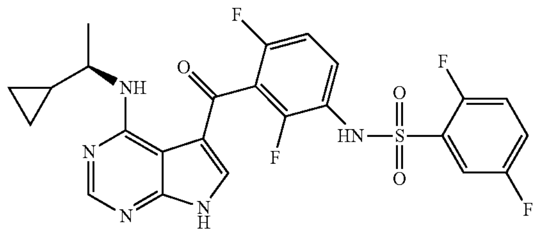 [SMILES: C[C@@H](Nc1ncnc2[nH]cc(C(=O)c3c(F)ccc(NS(=O)(=O)c4cc(F)ccc4F)c3F)c12)C1CC1] | N-[3-[4-[[(1R)-1-cyclopropylethyl]amino]-7H-pyrrolo[2,3-d]pyrimidine-5-carbonyl]-2,4-difluoro-phenyl]-2,5-difluoro-benzenesulfonamide | 534.5 |
| P-1240 | 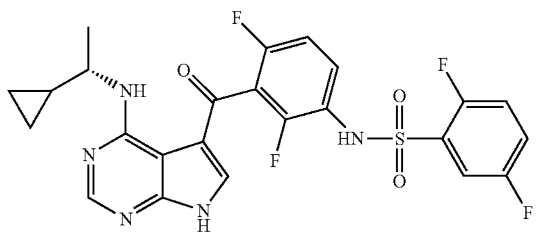 [SMILES: C[C@H](Nc1ncnc2[nH]cc(C(=O)c3c(F)ccc(NS(=O)(=O)c4cc(F)ccc4F)c3F)c12)C1CC1] | N-[3-[4-[[(1S)-1-cyclopropylethyl]amino]-7H-pyrrolo[2,3-d]pyrimidine-5-carbonyl]-2,4-difluoro-phenyl]-2,5-difluoro-benzenesulfonamide | 534.5 |
| P-1241 | 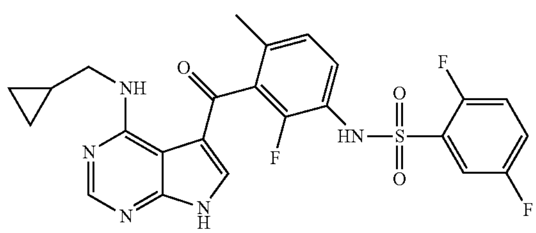 [SMILES: Cc1ccc(NS(=O)(=O)c2cc(F)ccc2F)c(F)c1C(=O)c1c[nH]c2ncnc(NCC3CC3)c12] | N-[3-[4-(cyclopropylmethylamino)-7H-pyrrolo[2,3-d]pyrimidine-5-carbonyl]-2-fluoro-4-methyl-phenyl]-2,5-difluoro-benzenesulfonamide | |

In various aspects and embodiments, provided are the compounds shown in Table II below, and/or pharmaceutically acceptable salts of the compounds shown in Table II.

| | | | |
|---|---|---|---|
| P-2001 | | Propane-1-sulfonic acid [3-(4-chloro-5-methyl-1H-pyrrolo[2,3-b]pyridine-3-carbonyl)-2,4-difluoro-phenyl]-amide | 427.9/ 429.9 |

| | | | |
|---|---|---|---|
| P-2002 | 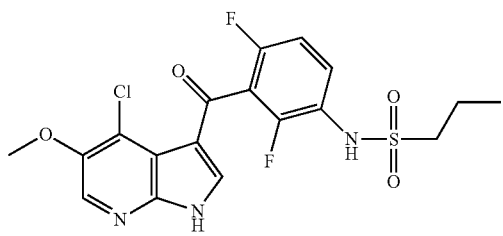 [SMILES: CCCS(=O)(=O)Nc1ccc(F)c(C(=O)c2c[nH]c3ncc(OC)c(Cl)c23)c1F] | Propane-1-sulfonic acid [3-(4-chloro-5-methoxy-1H-pyrrolo[2,3-b]pyridine-3-carbonyl)-2,4-difluoro-phenyl]-amide | 443.9/ 446.1 |
| P-2003 | 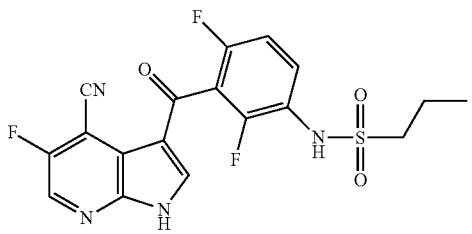 [SMILES: CCCS(=O)(=O)Nc1ccc(F)c(C(=O)c2c[nH]c3ncc(F)c(C#N)c23)c1F] | Propane-1-sulfonic acid [3-(4-cyano-5-fluoro-1H-pyrrolo[2,3-b]pyridine-3-carbonyl)-2,4-difluoro-phenyl]-amide | 421.4 |
| P-2004 | 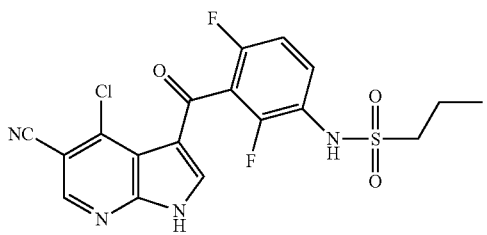 [SMILES: CCCS(=O)(=O)Nc1ccc(F)c(C(=O)c2c[nH]c3ncc(C#N)c(Cl)c23)c1F] | Propane-1-sulfonic acid [3-(4-chloro-5-cyano-1H-pyrrolo[2,3-b]pyridine-3-carbonyl)-2,4-difluoro-phenyl]-amide | 439.1 |
| P-2005 | 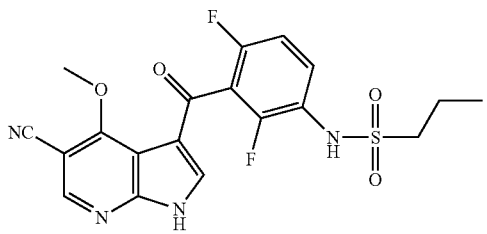 [SMILES: CCCS(=O)(=O)Nc1ccc(F)c(C(=O)c2c[nH]c3ncc(C#N)c(OC)c23)c1F] | Propane-1-sulfonic acid [3-[5-cyano-4-methoxy-1H-pyrrolo[2,3-b]pyridine-3-carbonyl)-2,4-difluoro-phenyl]-amide | 435.1 |
| P-2006 | 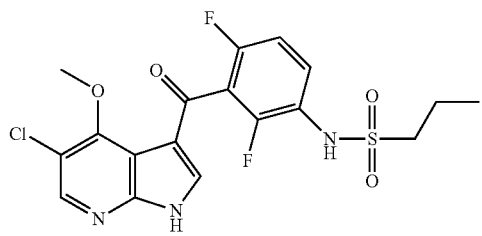 [SMILES: CCCS(=O)(=O)Nc1ccc(F)c(C(=O)c2c[nH]c3ncc(Cl)c(OC)c23)c1F] | Propane-1-sulfonic acid [3-[5-chloro-4-methoxy-1H-pyrrolo[2,3-b]pyridine-3-carbonyl)-2,4-difluoro-phenyl]-amide | 444.1 |
| P-2007 | 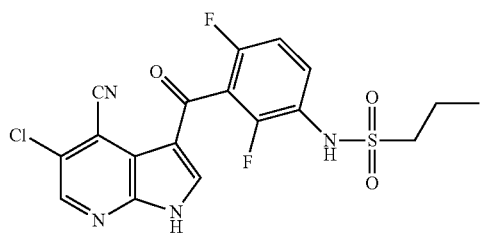 [SMILES: CCCS(=O)(=O)Nc1ccc(F)c(C(=O)c2c[nH]c3ncc(Cl)c(C#N)c23)c1F] | Propane-1-sulfonic acid [3-(5-chloro-4-cyano-1H-pyrrolo[2,3-b]pyridine-3-carbonyl)-2,4-difluoro-phenyl]-amide | 437.4/ 439.5 |

| | | | |
|---|---|---|---|
| P-2008 | 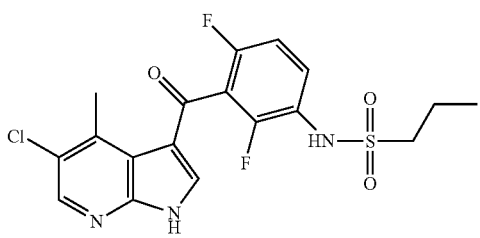 [SMILES: CCCS(=O)(=O)Nc1ccc(F)c(C(=O)c2c[nH]c3ncc(Cl)c(C)c23)c1F] | Propane-1-sulfonic acid [3-(5-chloro-4-methyl-1H-pyrrolo[2,3-b]pyridine-3-carbonyl)-2,4-difluoro-phenyl]-amide | 428.1/ 430.1 |
| P-2009 | 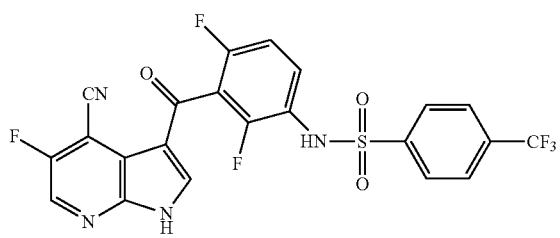 [SMILES: N#Cc1c(F)cnc2[nH]cc(C(=O)c3c(F)ccc(NS(=O)(=O)c4ccc(C(F)(F)F)cc4)c3F)c12] | N-[3-(4-Cyano-5-fluoro-1H-pyrrolo[2,3-b]pyridine-3-carbonyl)-2,4-difluoro-phenyl]-4-trifluoromethyl-benzenesulfonamide | 523.3 |
| P-2010 | 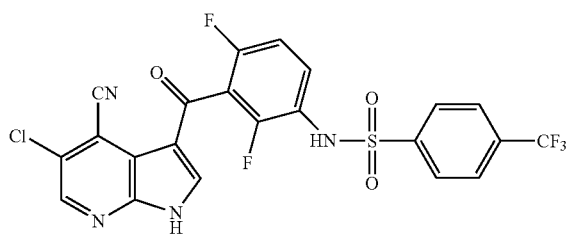 [SMILES: N#Cc1c(Cl)cnc2[nH]cc(C(=O)c3c(F)ccc(NS(=O)(=O)c4ccc(C(F)(F)F)cc4)c3F)c12] | N-[3-(5-Chloro-4-cyano-1H-pyrrolo[2,3-b]pyridine-3-carbonyl)-2,4-difluoro-phenyl]-4-trifluoromethyl-benzenesulfonamide | 539.3/ 541.3 |
| P-2011 | 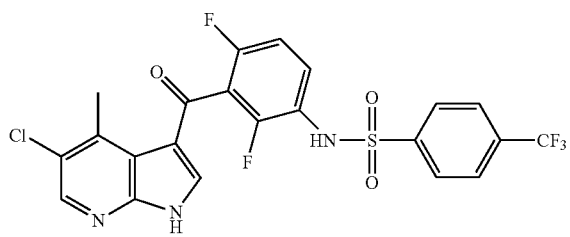 [SMILES: Cc1c(Cl)cnc2[nH]cc(C(=O)c3c(F)ccc(NS(=O)(=O)c4ccc(C(F)(F)F)cc4)c3F)c12] | N-[3-(5-Chloro-4-methyl-1H-pyrrolo[2,3-b]pyridine-3-carbonyl)-2,4-difluoro-phenyl]-4-trifluoromethyl-benzenesulfonamide | 530.0/ 532.4 |
| P-2012 | 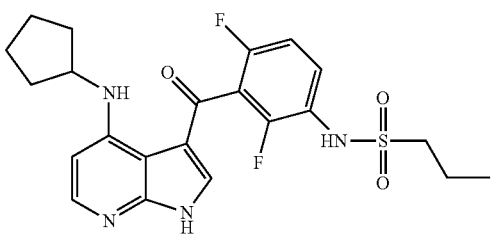 [SMILES: CCCS(=O)(=O)Nc1ccc(F)c(C(=O)c2c[nH]c3nccc(NC4CCCC4)c23)c1F] | Propane-1-sulfonic acid [3-(4-cyclopentylamino-1H-pyrrolo[2,3-b]pyridine-3-carbonyl)-2,4-difluoro-phenyl]-amide | 463.8 |
| P-2013 | 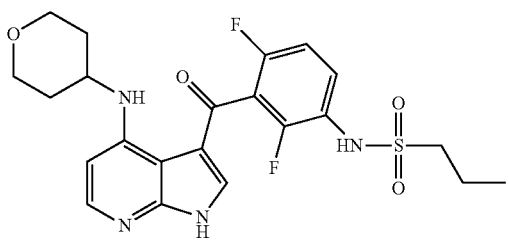 [SMILES: CCCS(=O)(=O)Nc1ccc(F)c(C(=O)c2c[nH]c3nccc(NC4CCOCC4)c23)c1F] | Propane-1-sulfonic acid {2,4-difluoro-3-[4-(tetrahydro-pyran-4-ylamino)-1H-pyrrolo[2,3-b]pyridine-3-carbonyl]-phenyl}-amide | 479.1 |

-continued

| | | | |
|---|---|---|---|
| P-2014 | | N-{2,4-Difluoro-3-[4-(tetrahydro-pyran-4-ylamino)-1H-pyrrolo[2,3-b]pyridine-3-carbonyl]-phenyl}-4-trifluoromethyl-benzenesulfonamide | 581.4 |
| P-2015 | | Propane-1-sulfonic acid [2,4-difluoro-3-(4-trifluoromethyl-1H-pyrrolo[2,3-b]pyridine-3-carbonyl)-phenyl]-amide | 447.9 |
| P-2016 | | N-[2,4-Difluoro-3-(4-trifluoromethyl-1H-pyrrolo[2,3-b]pyridine-3-carbonyl)-phenyl]-4-trifluoromethyl-benzenesulfonamide | 549.9 |
| P-2017 | | N-[2,4-Difluoro-3-(4-trifluoromethyl-1H-pyrrolo[2,3-b]pyridine-3-carbonyl)-phenyl]-benzenesulfonamide | 481.9 |
| P-2018 | | N-{3-[4-(Cyclopropylmethyl-amino)-1H-pyrrolo[2,3-b]pyridine-3-carbonyl]-2,4-difluoro-phenyl}-2,5-difluoro-benzenesulfonamide | 519.1 |
| P-2019 | | N-{3-[4-(Cyclopropylmethyl-amino)-5-fluoro-1H-pyrrolo[2,3-b]pyridine-3-carbonyl]-2,4-difluoro-phenyl}-2,5-difluoro-benzenesulfonamide | 535.1 |

| | | | |
|---|---|---|---|
| P-2020 | 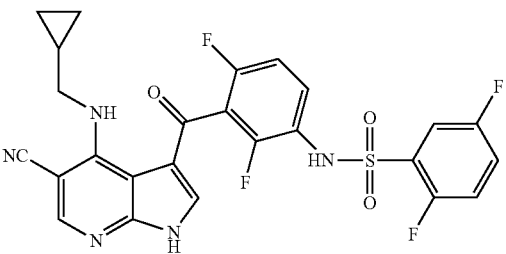 [SMILES: N#Cc1cnc2[nH]cc(C(=O)c3c(F)ccc(NS(=O)(=O)c4cc(F)ccc4F)c3F)c2c1NCC1CC1] | N-{3-[5-Cyano-4-(cyclopropylmethyl-amino)-1H-pyrrolo[2,3-b]pyridine-3-carbonyl]-2,4-difluoro-phenyl}-2,5-difluoro-benzenesulfonamide | 544.0 |
| P-2021 | 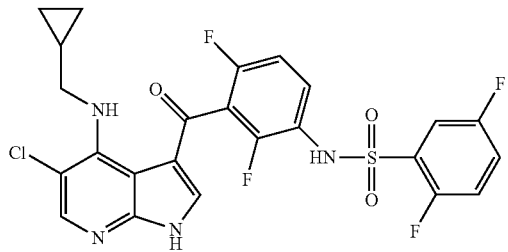 [SMILES: O=C(c1c(F)ccc(NS(=O)(=O)c2cc(F)ccc2F)c1F)c1c[nH]c2ncc(Cl)c(NCC3CC3)c12] | N-{3-[5-Chloro-4-(cyclopropylmethyl-amino)-1H-pyrrolo[2,3-b]pyridine-3-carbonyl]-2,4-difluoro-phenyl}-2,5-difluoro-benzenesulfonamide | |
| P-2022 | 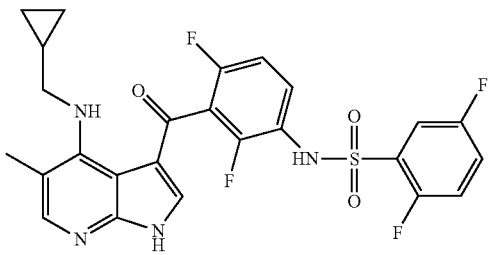 [SMILES: Cc1cnc2[nH]cc(C(=O)c3c(F)ccc(NS(=O)(=O)c4cc(F)ccc4F)c3F)c2c1NCC1CC1] | N-{3-[4-(Cyclopropylmethyl-amino)-5-methyl-1H-pyrrolo[2,3-b]pyridine-3-carbonyl]-2,4-difluoro-phenyl}-2,5-difluoro-benzenesulfonamide | |
| P-2023 | 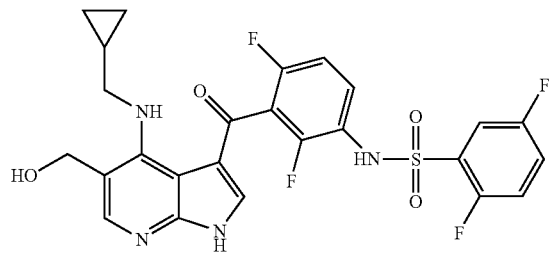 [SMILES: O=C(c1c(F)ccc(NS(=O)(=O)c2cc(F)ccc2F)c1F)c1c[nH]c2ncc(CO)c(NCC3CC3)c12] | N-{3-[4-(Cyclopropylmethyl-amino)-5-hydroxymethyl-1H-pyrrolo[2,3-b]pyridine-3-carbonyl]-2,4-difluoro-phenyl}-2,5-difluoro-benzenesulfonamide | |
| P-2024 | 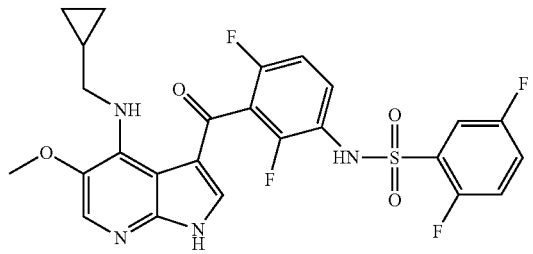 [SMILES: COc1cnc2[nH]cc(C(=O)c3c(F)ccc(NS(=O)(=O)c4cc(F)ccc4F)c3F)c2c1NCC1CC1] | N-{3-[4-(Cyclopropylmethyl-amino)-5-methoxy-1H-pyrrolo[2,3-b]pyridine-3-carbonyl]-2,4-difluoro-phenyl}-2,5-difluoro-benzenesulfonamide | |
| P-2025 | 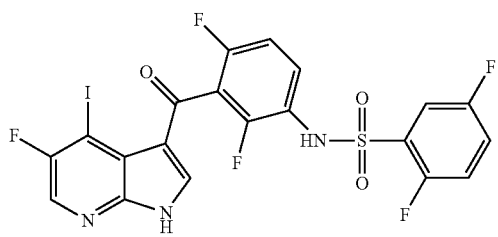 [SMILES: O=C(c1c(F)ccc(NS(=O)(=O)c2cc(F)ccc2F)c1F)c1c[nH]c2ncc(F)c(I)c12] | N-[2,4-Difluoro-3-(5-fluoro-4-iodo-1H-pyrrolo[2,3-b]pyridine-3-carbonyl)-phenyl]-2,5-difluoro-benzenesulfonamide | 593.8 |

-continued

| | | | |
|---|---|---|---|
| P-2026 | 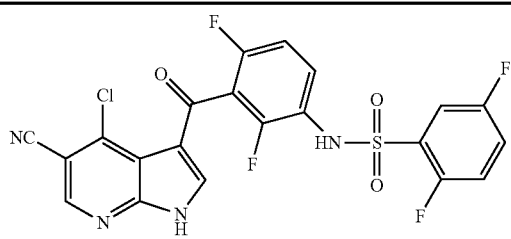 | N-[3-(4-Chloro-5-cyano-1H-pyrrolo[2,3-b]pyridine-3-carbonyl)-2,4-difluoro-phenyl]-2,5-difluoro-benzenesulfonamide | 508.9/ 510.9 |
| P-2027 | 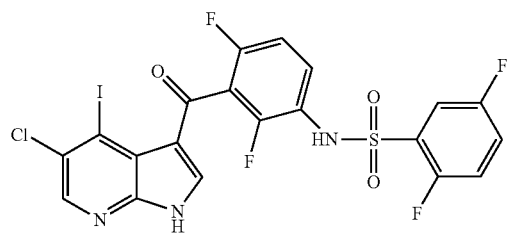 [SMILES: O=C(c1c(F)ccc(NS(=O)(=O)c2cc(F)ccc2F)c1F)c1c[nH]c2ncc(Cl)c(I)c12] | N-[3-(5-Chloro-4-iodo-1H-pyrrolo[2,3-b]pyridine-3-carbonyl)-2,4-difluoro-phenyl]-2,5-difluoro-benzenesulfonamide | |
| P-2028 | 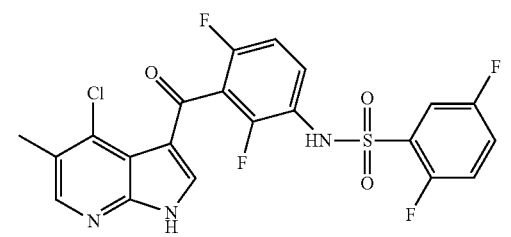 [SMILES: Cc1cnc2[nH]cc(C(=O)c3c(F)ccc(NS(=O)(=O)c4cc(F)ccc4F)c3F)c2c1Cl] | N-[3-(4-Chloro-5-methyl-1H-pyrrolo[2,3-b]pyridine-3-carbonyl)-2,4-difluoro-phenyl]-2,5-difluoro-benzenesulfonamide | |
| P-2029 | 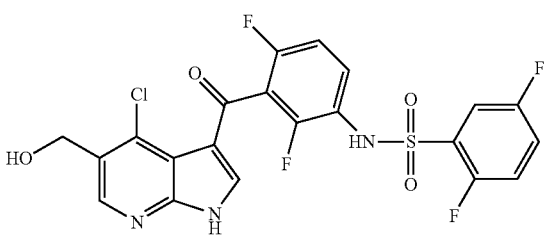 [SMILES: O=C(c1c(F)ccc(NS(=O)(=O)c2cc(F)ccc2F)c1F)c1c[nH]c2ncc(CO)c(Cl)c12] | N-[3-(4-Chloro-5-hydroxymethyl-1H-pyrrolo[2,3-b]pyridine-3-carbonyl)-2,4-difluoro-phenyl]-2,5-difluoro-benzenesulfonamide | |
| P-2030 | 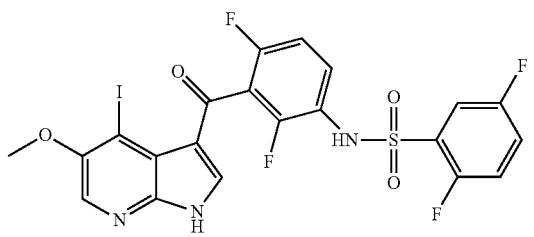 [SMILES: COc1cnc2[nH]cc(C(=O)c3c(F)ccc(NS(=O)(=O)c4cc(F)ccc4F)c3F)c2c1I] | N-[2,4-Difluoro-3-(4-iodo-5-methoxy-1H-pyrrolo[2,3-b]pyridine-3-carbonyl)-phenyl]-2,5-difluoro-benzenesulfonamide | |

In one embodiment of compounds contemplated herein, the compound is selected from the group consisting of:
N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011),
N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013),
N-[2,4-Difluoro-3-(4-morpholin-4-yl-7H-pyrrolo[2,3-d]pyrimidine-5-carbonyl)-phenyl]-4-trifluoromethyl-benzenesulfonamide (P-1017),
N-[2,4-Difluoro-3-(4-isobutylamino-7H-pyrrolo[2,3-d]pyrimidine-5-carbonyl)-phenyl]-4-trifluoromethyl-benzenesulfonamide (P-1020),
N-[3-(4-Ethylamino-7H-pyrrolo[2,3-d]pyrimidine-5-carbonyl)-2,4-difluoro-phenyl]-4-trifluoromethyl-benzenesulfonamide (P-1024),
N-[2,4-Difluoro-3-(4-methylamino-7H-pyrrolo[2,3-d]pyrimidine-5-carbonyl)-phenyl]-4-trifluoromethyl-benzenesulfonamide (P-1026),
N-[3-(4-Amino-7H-pyrrolo[2,3-d]pyrimidine-5-carbonyl)-2,4-difluoro-phenyl]-4-trifluoromethyl-benzene sulfonamide (P-1031),
N-[2,4-Difluoro-3-(4-propylamino-7H-pyrrolo[2,3-d]pyrimidine-5-carbonyl)-phenyl]-4-trifluoromethyl-benzenesulfonamide (P-1032),
N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035),
N-[2,4-Difluoro-3-(4-phenylamino-7H-pyrrolo[2,3-d]pyrimidine-5-carbonyl)-phenyl]-4-trifluoromethyl-benzene sulfonamide (P-1037), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), N-[3-(4-Cyclopropylamino-7H-pyrrolo[2,3-d]pyrimidine-5-carbonyl)-2,4-difluoro-phenyl]-4-propyl-benzenesulfonamide (P-1040), Propane-1-sulfonic acid [3-(4-cyclopropylamino-7H-pyrrolo[2,3-d]pyrimidine-5-carbonyl)-2,4-difluoro-phenyl]-amide (P-1041), N-[2,4-Difluoro-3-(4-isopropylamino-7H-pyrrolo[2,3-d]pyrimidine-5-carbonyl)-phenyl]-4-ethyl-benzenesulfonamide (P-1042), N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide (P-1043), N-[2,4-Difluoro-3-(4-isopropylamino-7H-pyrrolo[2,3-d]pyrimidine-5-carbonyl)-phenyl]-4-isopropyl-benzenesulfonamide (P-1044), N-[2,4-Difluoro-3-(4-isopropylamino-7H-pyrrolo[2,3-d]pyrimidine-5-carbonyl)-phenyl]-3,5-dimethyl-benzenesulfonamide (P-1045), N-{2,4-Difluoro-3-[4-(tetrahydro-pyran-4-ylamino)-7H-pyrrolo[2,3-d]pyrimidine-5-carbonyl]-phenyl}-4-propyl-benzenesulfonamide (P-1046), Propane-1-sulfonic acid {2,4-difluoro-3-[4-(tetrahydro-pyran-4-ylamino)-7H-pyrrolo[2,3-d]pyrimidine-5-carbonyl]-phenyl}-amide (P-1047), Propane-1-sulfonic acid [2,4-difluoro-3-(4-phenylamino-7H-pyrrolo[2,3-d]pyrimidine-5-carbonyl)-phenyl]-amide (P-1048), N-[3-(4-Dimethylamino-7H-pyrrolo[2,3-d]pyrimidine-5-carbonyl)-2,4-difluoro-phenyl]-4-trifluoromethyl-benzenesulfonamide (P-1049), N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050), Propane-1-sulfonic acid [2,4-difluoro-3-(4-isopropylamino-7H-pyrrolo[2,3-d]pyrimidine-5-carbonyl)-phenyl]-amide (P-1051), N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052), N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide (P-1054), N-[2,4-Difluoro-3-(4-isopropylamino-7H-pyrrolo[2,3-d]pyrimidine-5-carbonyl)-phenyl]-4-propyl-benzenesulfonamide (P-1055), N-{2,4-Difluoro-3-[4-(oxetan-3-ylamino)-7H-pyrrolo[2,3-d]pyrimidine-5-carbonyl]-phenyl}-4-propyl-benzenesulfonamide (P-1056), N-{2,4-Difluoro-3-[4-(1-methyl-piperidin-4-ylamino)-7H-pyrrolo[2,3-d]pyrimidine-5-carbonyl]-phenyl}4-trifluoromethyl-benzenesulfonamide (P-1057), N-{2,4-Difluoro-3-[4-(2-methoxy-ethylamino)-7H-pyrrolo[2,3-d]pyrimidine-5-carbonyl]-phenyl}-4-trifluoromethyl-benzenesulfonamide (P-1058), N-{3-[4-(2-Dimethylamino-ethylamino)-7H-pyrrolo[2,3-d]pyrimidine-5-carbonyl]-2,4-difluoro-phenyl}-4-trifluoromethyl-benzenesulfonamide (P-1059), Propane-1-sulfonic acid {2,4-difluoro-3-[4-(oxetan-3-ylamino)-7H-pyrrolo[2,3-d]pyrimidine-5-carbonyl]-phenyl}-amide (P-1060), N-[2,4-Difluoro-3-(4-pyrrolidin-1-yl-7H-pyrrolo[2,3-d]pyrimidine-5-carbonyl)-phenyl]-4-trifluoromethyl-benzenesulfonamide (P-1061), N-{2,4-Difluoro-3-[4-(1-methyl-1H-pyrazol-4-ylamino)-7H-pyrrolo[2,3-d]pyrimidine-5-carbonyl]-phenyl}-4-trifluoromethyl-benzenesulfonamide (P-1062), N-{3-[4-(1-Ethyl-1H-pyrazol-4-ylamino)-7H-pyrrolo[2,3-d]pyrimidine-5-carbonyl]-2,4-difluoro-phenyl}-4-trifluoromethyl-benzenesulfonamide (P-1063), N-[2,4-Difluoro-3-(4-hydroxyamino-7H-pyrrolo[2,3-d]pyrimidine-5-carbonyl)-phenyl]-4-trifluoromethyl-benzenesulfonamide (P-1064), Propane-1-sulfonic acid {2,4-difluoro-3-[4-(4-fluoro-phenylamino)-7H-pyrrolo[2,3-d]pyrimidine-5-carbonyl]-phenyl}-amide (P-1065), Propane-1-sulfonic acid [2,4-difluoro-3-(4-hydrazino-7H-pyrrolo[2,3-d]pyrimidine-5-carbonyl)-phenyl]-amide (P-1066), Propane-1-sulfonic acid {2,4-difluoro-3-[4-(naphthalen-2-ylamino)-7H-pyrrolo[2,3-d]pyrimidine-5-carbonyl]-phenyl}-amide (P-1067), Propane-1-sulfonic acid (2,4-difluoro-3-{4-[(oxetan-3-ylmethyl)-amino]-7H-pyrrolo[2,3-d]pyrimidine-5-carbonyl}-phenyl)-amide (P-1068), N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069), Propane-1-sulfonic acid {2,4-difluoro-3-[4-(naphthalen-1-ylamino)-7H-pyrrolo[2,3-d]pyrimidine-5-carbonyl]-phenyl}-amide (P-1072), N-[2,4-Difluoro-3-(4-isopropylamino-7H-pyrrolo[2,3-d]pyrimidine-5-carbonyl)-phenyl]-2-fluoro-benzene sulfonamide (P-1073), Propane-1-sulfonic acid [3-(4-b enzylamino-7H-pyrrolo[2,3-d]pyrimidine-5-carbonyl)-2,4-difluoro-phenyl]-amide (P-1074), Propane-1-sulfonic acid [2,4-difluoro-3-(4-propylamino-7H-pyrrolo[2,3-d]pyrimidine-5-carbonyl)-phenyl]-amide (P-1075), Propane-1-sulfonic acid {2,4-difluoro-3-[4-(pyridin-4-ylamino)-7H-pyrrolo[2,3-d]pyrimidine-5-carbonyl]-phenyl}-amide (P-1076), Propane-1-sulfonic acid {2,4-difluoro-3-[4-(pyridin-2-ylamino)-7H-pyrrolo[2,3-d]pyrimidine-5-carbonyl]-phenyl}-amide (P-1077), Propane-1-sulfonic acid {2,4-difluoro-3-[4-(pyridin-3-ylamino)-7H-pyrrolo[2,3-d]pyrimidine-5-carbonyl]-phenyl}-amide (P-1078), Propane-1-sulfonic acid {3-[4-(cyclopropylmethyl-amino)-7H-pyrrolo[2,3-d]pyrimidine-5-carbonyl]-2,4-difluoro-phenyl}-amide (P-1079), Propane-1-sulfonic acid {3-[4-(1-benzyl-pyrrolidin-3-ylamino)-7H-pyrrolo[2,3-d]pyrimidine-5-carbonyl]-2,4-difluoro-phenyl}-amide (P-1080), Propane-1-sulfonic acid [3-(4-cyclopentylamino-7H-pyrrolo[2,3-d]pyrimidine-5-carbonyl)-2,4-difluoro-phenyl]-amide (P-1081), Propane-1-sulfonic acid [3-(4-ethylamino-7H-pyrrolo[2,3-d]pyrimidine-5-carbonyl)-2,4-difluoro-phenyl]-amide (P-1082), Propane-1-sulfonic acid {3-[4-(3-dimethylamino-phenylamino)-7H-pyrrolo[2,3-d]pyrimidine-5-carbonyl]-2,4-difluoro-phenyl}-amide (P-1083), Propane-1-sulfonic acid {3-[4-(3-chloro-phenylamino)-7H-pyrrolo[2,3-d]pyrimidine-5-carbonyl]-2,4-difluoro-phenyl}-amide (P-1084), Propane-1-sulfonic acid {2,4-difluoro-3-[4-(3-methoxy-phenylamino)-7H-pyrrolo[2,3-d]pyrimidine-5-carbonyl]-phenyl}-amide (P-1085), Propane-1-sulfonic acid {2,4-difluoro-3-[4-(2-methoxy-ethylamino)-7H-pyrrolo[2,3-d]pyrimidine-5-carbonyl]-phenyl}-amide (P-1086), Propane-1-sulfonic acid {3-[4-(4-chloro-phenylamino)-7H-pyrrolo[2,3-d]pyrimidine-5-carbonyl]-2,4-difluoro-phenyl}-amide (P-1087), Propane-1-sulfonic acid [2,4-difluoro-3-(4-isobutylamino-7H-pyrrolo[2,3-d]pyrimidine-5-carbonyl)-phenyl]-amide (P-1088), Propane-1-sulfonic acid {2,4-difluoro-3-[4-(4-trifluoromethyl-phenylamino)-7H-pyrrolo[2,3-d]pyrimidine-5-carbonyl]-phenyl}-amide (P-1089), Propane-1-sulfonic acid {2,4-difluoro-3-[4-(6-methoxy-pyridin-3-ylamino)-7H-pyrrolo[2,3-d]pyrimidine-5-carbonyl]-phenyl}-amide (P-1090), Propane-1-sulfonic acid {2,4-difluoro-3-[4-(3-trifluoromethyl-phenylamino)-7H-pyrrolo[2,3-d]pyrimidine-5-carbonyl]-phenyl}-amide (P-1091), Propane-1-sulfonic acid [2,4-difluoro-3-(4-m-tolylamino-7H-pyrrolo[2,3-d]pyrimidine-5-carbonyl)-phenyl]-amide (P-1092), Propane-1-sulfonic acid [2,4-difluoro-3-(4-p-tolylamino-7H-pyrrolo[2,3-d]pyrimidine-5-carbonyl)-phenyl]-amide (P-1093), Propane-1-sulfonic acid {2,4-difluoro-3-[4-(3-fluoro-phenylamino)-7H-pyrrolo[2,3-d]pyrimidine-5-carbonyl]-phenyl}-amide (P-1094), Propane-1-sulfonic acid {3-[4-(1-ethyl-piperidin-4-ylamino)-7H-pyrrolo[2,3-d]pyrimidine-5-carbonyl]-2,4-difluoro-phenyl}-amide (P-1095), Propane-1-sulfonic acid {2,4-difluoro-3-[4-(1-methanesulfonyl-piperidin-4-ylamino)-7H-pyrrolo[2,3-d]pyrimidine-5-carbonyl]-phenyl}-amide (P-1096), Propane-1-sulfonic acid {2,4-difluoro-3-[4-(tetrahydro-furan-3-ylamino)-7H-pyrrolo[2,3-d]pyrimidine-5-carbonyl]-phenyl}-amide (P-1097), Propane-1-sulfonic acid [2,4-difluoro-3-(4-methylamino-7H-pyrrolo[2,3-d]pyrimidine-5-carbonyl)-phenyl]-amide (P-1098), Propane-1-sulfonic acid {3-[4-(1-ethyl-1H-pyrazol-4-ylamino)-7H-pyrrolo[2,3-d]pyrimidine-5-carbonyl]-2,4-difluoro-phenyl}-amide (P-1099), Propane-1-sulfonic acid {3-[4-(1,3-dimethyl-1H-pyrazol-4-ylamino)-7H-pyrrolo[2,3-d]pyrimidine-5-carbonyl]-2,4-difluoro-phenyl}-amide (P-1100), Propane-1-sulfonic acid {2,4-difluoro-3-[4-(2-fluoro-4-methoxy-phenylamino)-7H-pyrrolo[2,3-d]pyrimidine-5-carbonyl]-phenyl}-amide (P-1101), Propane-1-sulfonic acid {2,4-difluoro-3-[4-(1-methyl-1H-pyrazol-4-ylamino)-7H-pyrrolo[2,3-d]pyrimidine-5-carbonyl]-phenyl}-amide (P-1102), N-[3-(4-Cyclopropylamino-7H-pyrrolo[2,3-d]pyrimidine-5-carbonyl)-2,4-difluoro-phenyl]-2-fluoro-benzenesulfonamide (P-1103), N-[3-(4-Cyclopropylamino-7H-pyrrolo[2,3-d]pyrimidine-5-carbonyl)-2,4-difluoro-phenyl]-2,5-difluoro-benzenesulfonamide (P-1104), Propane-1-sulfonic acid {2,4-difluoro-3-[4-(3-fluoro-5-methoxy-pyridin-2-ylamino)-7H-pyrrolo[2,3-d]pyrimidine-5-carbonyl]-phenyl}-amide (P-1105), Propane-1-sulfonic acid [2-fluoro-3-(4-isopropylamino-7H-pyrrolo[2,3-d]pyrimidine-5-carbonyl)-phenyl]-amide (P-1106), 4-Cyano-N-[2,4-difluoro-3-(4-isopropylamino-7H-pyrrolo[2,3-d]pyrimidine-5-carbonyl)-phenyl]-benzenesulfonamide (P-1108), 2,2,2-Trifluoro-ethanesulfonic acid [2,4-difluoro-3-(4-isopropylamino-7H-pyrrolo[2,3-d]pyrimidine-5-carbonyl)-phenyl]-amide (P-1109), N-[2,4-Difluoro-3-(4-isopropylamino-7H-pyrrolo[2,3-d]pyrimidine-5-carbonyl)-phenyl]-4-difluoromethoxy-benzenesulfonamide (P-1110), N-[2,4-Difluoro-3-(4-isopropylamino-7H-pyrrolo[2,3-d]pyrimidine-5-carbonyl)-phenyl]-2,5-difluoro-benzenesulfonamide (P-1111), N-[2,4-Difluoro-3-(4-isopropylamino-7H-pyrrolo[2,3-d]pyrimidine-5-carbonyl)-phenyl]-2,6-difluoro-benzenesulfonamide (P-1112), N-[2,4-Difluoro-3-(4-isopropylamino-7H-pyrrolo[2,3-d]pyrimidine-5-carbonyl)-phenyl]-2,4-difluoro-benzenesulfonamide (P-1113), Propane-2-sulfonic acid [2,4-difluoro-3-(4-isopropylamino-7H-pyrrolo[2,3-d]pyrimidine-5-carbonyl)-phenyl]-amide (P-1114), N-[2,4-Difluoro-3-(4-isopropylamino-7H-pyrrolo[2,3-d]pyrimidine-5-carbonyl)-phenyl]-3-fluoro-benzenesulfonamide (P-1115), 3-Cyano-N-[2,4-difluoro-3-(4-isopropylamino-7H-pyrrolo[2,3-d]pyrimidine-5-carbonyl)-phenyl]-benzenesulfonamide (P-1116), N-[2,4-Difluoro-3-(4-isopropylamino-7H-pyrrolo[2,3-d]pyrimidine-5-carbonyl)-phenyl]-3-fluoro-4-methoxy-benzenesulfonamide (P-1117), 3,3,3-Trifluoro-propane-1-sulfonic acid [2,4-difluoro-3-(4-isopropylamino-7H-pyrrolo[2,3-d]pyrimidine-5-carbonyl)-phenyl]-amide (P-1118), N-[2,4-Difluoro-3-(4-isopropylamino-7H-pyrrolo[2,3-d]pyrimidine-5-carbonyl)-phenyl]-3-difluoromethoxy-benzenesulfonamide (P-1119), 1-Ethyl-1H-pyrazole-4-sulfonic acid [2,4-difluoro-3-(4-isopropylamino-7H-pyrrolo[2,3-d]pyrimidine-5-carbonyl)-phenyl]-amide (P-1120), 1-Methyl-1H-pyrazole-4-sulfonic acid [2,4-difluoro-3-(4-isopropylamino-7H-pyrrolo[2,3-d]pyrimidine-5-carbonyl)-phenyl]-amide (P-1121), Piperidine-1-sulfonic acid [2,4-difluoro-3-(4-isopropylamino-7H-pyrrolo[2,3-d]pyrimidine-5-carbonyl)-phenyl]-amide (P-1122), Cyclohexanesulfonic acid [2,4-difluoro-3-(4-isopropylamino-7H-pyrrolo[2,3-d]pyrimidine-5-carbonyl)-phenyl]-amide (P-1123), Cyclopentanesulfonic acid [2,4-difluoro-3-(4-isopropylamino-7H-pyrrolo[2,3-d]pyrimidine-5-carbonyl)-phenyl]-amide (P-1124), Pyrrolidine-1-sulfonic acid [2,4-difluoro-3-(4-isopropylamino-7H-pyrrolo[2,3-d]pyrimidine-5-carbonyl)-phenyl]-amide (P-1125), 2-Methyl-propane-1-sulfonic acid [2,4-difluoro-3-(4-isopropylamino-7H-pyrrolo[2,3-d]pyrimidine-5-carbonyl)-phenyl]-amide (P-1126), Diethylamine-1-sulfonic acid [2,4-difluoro-3-(4-isopropylamino-7H-pyrrolo[2,3-d]pyrimidine-5-carbonyl)-phenyl]-amide (P-1127), Cyclobutanesulfonic acid [2,4-difluoro-3-(4-isopropylamino-7H-pyrrolo[2,3-d]pyrimidine-5-carbonyl)-phenyl]-amide (P-1128), Morpholine-4-sulfonic acid [2,4-difluoro-3-(4-isopropylamino-7H-pyrrolo[2,3-d]pyrimidine-5-carbonyl)-phenyl]-amide (P-1129), 6-Methoxy-pyridine-3-sulfonic acid [2,4-difluoro-3-(4-isopropylamino-7H-pyrrolo[2,3-d]pyrimidine-5-carbonyl)-phenyl]-amide (P-1130), 6-Methyl-pyridine-2-sulfonic acid [2,4-difluoro-3-(4-isopropylamino-7H-pyrrolo[2,3-d]pyrimidine-5-carbonyl)-phenyl]-amide (P-1131), Pyridine-3-sulfonic acid [2,4-difluoro-3-(4-isopropylamino-7H-pyrrolo[2,3-d]pyrimidine-5-carbonyl)-phenyl]-amide (P-1132), Pyridine-2-sulfonic acid [2,4-difluoro-3-(4-isopropylamino-7H-pyrrolo[2,3-d]pyrimidine-5-carbonyl)-phenyl]-amide (P-1133), Propane-1-sulfonic acid {3-[4-(benzo[1,2,5]thiadiazol-5-ylamino)-7H-pyrrolo[2,3-d]pyrimidine-5-carbonyl]-2,4-difluoro-phenyl}-amide (P-1134), N-[3-(4-Benzylamino-7H-pyrrolo[2,3-d]pyrimidine-5-carbonyl)-2,4-difluoro-phenyl]-2,5-difluoro-benzenesulfonamide (P-1135), N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136), N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137), N-[3-(4-Ethylamino-7H-pyrrolo[2,3-d]pyrimidine-5-carbonyl)-2,4-difluoro-phenyl]-2,5-difluoro-benzenesulfonamide (P-1138), N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139), N-[2,4-Difluoro-3-(4-isobutylamino-7H-pyrrolo[2,3-d]pyrimidine-5-carbonyl)-phenyl]-2,5-difluoro-benzenesulfonamide (P-1140), N-[2,4-Difluoro-3-(4-m-tolylamino-7H-pyrrolo[2,3-d]pyrimidine-5-carbonyl)-phenyl]-2,5-difluoro-benzenesulfonamide (P-1141), N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142), N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1143), N-[3-(4-Benzylamino-7H-pyrrolo[2,3-d]pyrimidine-5-carbonyl)-2,4-difluoro-phenyl]-2-fluoro-benzenesulfonamide (P-1144), N-{2,4-Difluoro-3-[4-(pyridin-3-ylamino)-7H-pyrrolo[2,3-d]pyrimidine-5-carbonyl]-phenyl}-2-fluoro-benzenesulfonamide (P-1145), N-{3-[4-(Cyclopropylmethyl-amino)-7H-pyrrolo[2,3-d]pyrimidine-5-carbonyl]-2,4-difluoro-phenyl}-2-fluoro-benzenesulfonamide (P-1146), N-[3-(4-Cyclopentylamino-7H-pyrrolo[2,3-d]pyrimidine-5-carbonyl)-2,4-difluoro-phenyl]-2-fluoro-benzenesulfonamide (P-1147), N-[3-(4-Ethylamino-7H-pyrrolo[2,3-d]pyrimidine-5-carbonyl)-2,4-difluoro-phenyl]-2-fluoro-benzenesulfonamide (P-1148), N-{2,4-Difluoro-3-[4-(3-methoxy-phenylamino)-7H-pyrrolo[2,3-d]pyrimidine-5-carbonyl]-phenyl}-2-fluoro-benzenesulfonamide (P-1149), N-{2,4-Difluoro-3-[4-(2-methoxy-ethylamino)-7H-pyrrolo[2,3-d]pyrimidine-5-carbonyl]-phenyl}-2-fluoro-benzenesulfonamide (P-1150), N-[2,4-Difluoro-3-(4-isobutylamino-7H-pyrrolo[2,3-d]pyrimidine-5-carbonyl)-phenyl]-2-fluoro-benzenesulfonamide (P-1151), N-[2,4-Difluoro-3-(4-m-tolylamino-7H-pyrrolo[2,3-d]pyrimidine-5-carbonyl)-phenyl]-2-fluoro-benzenesulfonamide (P-1152), N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide (P-1153), N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide (P-1154), N-[2,4-Difluoro-3-(4-isopropylamino-7H-pyrrolo[2,3-d]pyrimidine-5-carbonyl)-phenyl]-benzenesulfonamide (P-1155), Dimethylamine-1-sulfonic acid [2,4-difluoro-3-(4-isopropylamino-7H-pyrrolo[2,3-d]pyrimidine-5-carbonyl)-phenyl]-amide (P-1156), Propane-1-sulfonic acid {2,4-difluoro-3-[4-(1H-indazol-6-ylamino)-7H-pyrrolo[2,3-d]pyrimidine-5-carbonyl]-phenyl}-amide (P-1157), Propane-1-sulfonic acid {2,4-difluoro-3-[4-(1H-indazol-5-ylamino)-7H-pyrrolo[2,3-d]pyrimidine-5-carbonyl]-phenyl}-amide (P-1158), Propane-1-sulfonic acid {2,4-difluoro-3-[4-(4-hydroxy-phenylamino)-7H-pyrrolo[2,3-d]pyrimidine-5-carbonyl]-phenyl}-amide (P-1159), Propane-1-sulfonic acid (2,4-difluoro-3-{4-[(5-methyl-1H-pyrazol-3-ylmethyl)-amino]-7H-pyrrolo[2,3-d]pyrimidine-5-carbonyl}-phenyl)-amide (P-1160), 3-({5-[2,6-Difluoro-3-(propane-1-sulfonylamino)-benzoyl]-7H-pyrrolo[2,3-d]pyrimidin-4-ylamino}-methyl)-benzoic acid (P-1161), 4-{5-[2,6-Difluoro-3-(propane-1-sulfonylamino)-benzoyl]-7H-pyrrolo[2,3-d]pyrimidin-4-ylamino}-benzoic acid methyl ester (P-1162), 4-{5-[2,6-Difluoro-3-(propane-1-sulfonylamino)-benzoyl]-7H-pyrrolo[2,3-d]pyrimidin-4-ylamino}-benzoic acid (P-1163), Propane-1-sulfonic acid {2,4-difluoro-3-[4-(3-[1,2,4]triazol-1-yl-phenylamino)-7H-pyrrolo[2,3-d]pyrimidine-5-carbonyl]-phenyl}-amide (P-1164), Propane-1-sulfonic acid {2,4-difluoro-3-[4-(3-oxazol-5-yl-phenylamino)-7H-pyrrolo[2,3-d]pyrimidine-5-carbonyl]-phenyl}-amide (P-1165), Propane-1-sulfonic acid (2,4-difluoro-3-{4-[(pyridin-3-ylmethyl)-amino]-7H-pyrrolo[2,3-d]pyrimidine-5-carbonyl}-phenyl)-amide (P-1166), Propane-1-sulfonic acid {2,4-difluoro-3-[4-(3-[1,2,4]triazol-1-yl-propylamino)-7H-pyrrolo[2,3-d]pyrimidine-5-carbonyl]-phenyl}-amide (P-1167), Propane-1-sulfonic acid {2,4-difluoro-3-[4-(3-pyridin-3-yl-propylamino)-7H-pyrrolo[2,3-d]pyrimidine-5-carbonyl]-phenyl}-amide (P-1168), Propane-1-sulfonic acid {2,4-difluoro-3-[4-(3-hydroxy-phenylamino)-7H-pyrrolo[2,3-d]pyrimidine-5-carbonyl]-phenyl}-amide (P-1169), Propane-1-sulfonic acid (2,4-difluoro-3-{4-[3-(5-methyl-4H-[1,2,4]triazol-3-yl)-phenylamino]-7H-pyrrolo[2,3-d]pyrimidine-5-carbonyl}-phenyl)-amide (P-1170), Propane-1-sulfonic acid (2,4-difluoro-3-{4-[3-(5-methyl-tetrazol-1-yl)-phenylamino]-7H-pyrrolo[2,3-d]pyrimidine-5-carbonyl}-phenyl)-amide (P-1171), Propane-1-sulfonic acid (2,4-difluoro-3-{4-[3-(4H-[1,2,4]triazol-3-yl)-phenylamino]-7H-pyrrolo[2,3-d]pyrimidine-5-carbonyl}-phenyl)-amide (P-1172), Propane-1-sulfonic acid (3-{4-[(benzo[1,2,5]oxadiazol-5-ylmethyl)-amino]-7H-pyrrolo[2,3-d]pyrimidine-5-carbonyl}-2,4-difluoro-phenyl)-amide (P-1173), Propane-1-sulfonic acid {3-[4-(1,1-dioxo-hexahydro-1 lambda*6*-thiopyran-4-ylamino)-7H-pyrrolo[2,3-d]pyrimidine-5-carbonyl]-2,4-difluoro-phenyl}-amide (P-1174), Propane-1-sulfonic acid {3-[4-(1,1-dioxo-tetrahydro-1 lambda*6*-thiophen-3-ylamino)-7H-pyrrolo[2,3-d]pyrimidine-5-carbonyl]-2,4-difluoro-phenyl}-amide (P-1175), Propane-1-sulfonic acid (2,4-difluoro-3-{4-[2-(5-methyl-4H-[1,2,4]triazol-3-yl)-ethylamino]-7H-pyrrolo[2,3-d]pyrimidine-5-carbonyl}-phenyl)-amide (P-1176), Propane-1-sulfonic acid {2,4-difluoro-3-[4-(2-oxo-2,3-dihydro-1H-benzoimidazol-5-ylamino)-7H-pyrrolo[2,3-d]pyrimidine-5-carbonyl]-phenyl}-amide (P-1177), Propane-1-sulfonic acid (2,4-difluoro-3-{4-[3-(2-methyl-2H-tetrazol-5-yl)-phenylamino]-7H-pyrrolo[2,3-d]pyrimidine-5-carbonyl}-phenyl)-amide (P-1178), Propane-1-sulfonic acid (2,4-difluoro-3-{4-[3-(5-methyl-[1,3,4]oxadiazol-2-yl)-phenylamino]-7H-pyrrolo[2,3-d]pyrimidine-5-carbonyl}-phenyl)-amide (P-1179), Propane-1-sulfonic acid (2,4-difluoro-3-{4-[(pyridazin-4-ylmethyl)-amino]-7H-pyrrolo[2,3-d]pyrimidine-5-carbonyl}-phenyl)-amide (P-1180), N-{3-[4-(Cyclopropylmethyl-amino)-7H-pyrrolo[2,3-d]pyrimidine-5-carbonyl]-2-fluoro-phenyl}-2,5-difluoro-benzenesulfonamide (P-1185), N-{3-[4-(Cyclopropylmethyl-amino)-7H-pyrrolo[2,3-d]pyrimidine-5-carbonyl]-2,4-difluoro-phenyl}-2,4-difluoro-benzenesulfonamide (P-1186), N-{3-[4-(Cyclopropylmethyl-amino)-7H-pyrrolo[2,3-d]pyrimidine-5-carbonyl]-2,4-difluoro-phenyl}-3-fluoro-benzenesulfonamide (P-1187), N-{3-[4-(Cyclopropylmethyl-amino)-7H-pyrrolo[2,3-d]pyrimidine-5-carbonyl]-2,4-difluoro-phenyl}-3-fluoro-4-methoxy-benzenesulfonamide (P-1188), N-{3-[4-(Cyclopropylmethyl-amino)-7H-pyrrolo[2,3-d]pyrimidine-5-carbonyl]-2,4-difluoro-phenyl}-4-fluoro-benzenesulfonamide (P-1189), N-{3-[4-(Cyclopropylmethyl-amino)-7H-pyrrolo[2,3-d]pyrimidine-5-carbonyl]-2,4-difluoro-phenyl}-3-fluoro-4-methyl-benzenesulfonamide (P-1190), N-{3-[4-(Cyclopropylmethyl-amino)-7H-pyrrolo[2,3-d]pyrimidine-5-carbonyl]-2,4-difluoro-phenyl}-3,5-difluoro-benzenesulfonamide (P-1191), N-{3-[4-(Cyclopropylmethyl-amino)-7H-pyrrolo[2,3-d]pyrimidine-5-carbonyl]-2,4-difluoro-phenyl}-4-fluoro-2-methyl-benzenesulfonamide (P-1192), N-{3-[4-(Cyclopropylmethyl-amino)-7H-pyrrolo[2,3-d]pyrimidine-5-carbonyl]-2,4-difluoro-phenyl}-2-fluoro-5-methyl-benzenesulfonamide (P-1193), N-{3-[4-(Cyclopropylmethyl-amino)-7H-pyrrolo[2,3-d]pyrimidine-5-carbonyl]-2,4-difluoro-phenyl}-2-fluoro-5-trifluoromethyl-benzenesulfonamide (P-1194), N-{3-[4-(Cyclopropylmethyl-amino)-7H-pyrrolo[2,3-d]pyrimidine-5-carbonyl]-2,4-difluoro-phenyl}-2-fluoro-4-methyl-benzenesulfonamide (P-1195), N-{3-[4-(Cyclopropylmethyl-amino)-7H-pyrrolo[2,3-d]pyrimidine-5-carbonyl]-2,4-difluoro-phenyl}-2-fluoro-4-methoxy-benzenesulfonamide (P-1196), 5-Chloro-N-{3-[4-(cyclopropylmethyl-amino)-7H-pyrrolo[2,3-d]pyrimidine-5-carbonyl]-2,4-difluoro-phenyl}-2-fluoro-benzenesulfonamide (P-1197), 3-Chloro-N-{3-[4-(cyclopropylmethyl-amino)-7H-pyrrolo[2,3-d]pyrimidine-5-carbonyl]-2,4-difluoro-phenyl}-2-fluoro-benzenesulfonamide (P-1198), N-{3-[4-(Cyclopropylmethyl-amino)-7H-pyrrolo[2,3-d]pyrimidine-5-carbonyl]-2,4-difluoro-phenyl}-3,4-difluoro-benzenesulfonamide (P-1199), N-{3-[4-(Cyclopropylmethyl-amino)-7H-pyrrolo[2,3-d]pyrimidine-5-carbonyl]-2,4-difluoro-phenyl}-3-fluoro-5-trifluoromethyl-benzenesulfonamide (P-1200), N-{3-[4-(Cyclopropylmethyl-amino)-7H-pyrrolo[2,3-d]pyrimidine-5-carbonyl]-2,4-difluoro-phenyl}-3-fluoro-2-methyl-benzenesulfonamide (P-1201), 4-Chloro-N-{3-[4-(cyclopropylmethyl-amino)-7H-pyrrolo[2,3-d]pyrimidine-5-carbonyl]-2,4-difluoro-phenyl}-3-fluoro-benzenesulfonamide (P-1202), N-{3-[4-(Cyclopropylmethyl-amino)-7H-pyrrolo[2,3-d]pyrimidine-5-carbonyl]-2,4-difluoro-phenyl}-5-fluoro-2-methyl-benzenesulfonamide (P-1203), N-{3-[4-(Cyclopropylmethyl-amino)-7H-pyrrolo[2,3-d]pyrimidine-5-carbonyl]-2,4-difluoro-phenyl}-5-fluoro-2-methoxy-benzenesulfonamide (P-1204), N-{3-[4-(Cyclopropylmethyl-amino)-7H-pyrrolo[2,3-d]pyrimidine-5-carbonyl]-2,4-difluoro-phenyl}-3-trifluoromethyl-benzenesulfonamide (P-1205), N-{3-[4-(Cyclopropylmethyl-amino)-7H-pyrrolo[2,3-d]pyrimidine-5-carbonyl]-2,4-difluoro-phenyl}-2,6-difluoro-benzenesulfonamide (P-1206), N-{3-[4-(Cyclopropylmethyl-amino)-7H-pyrrolo[2,3-d]pyrimidine-5-carbonyl]-2,4-difluoro-phenyl}-benzenesulfonamide (P-1207), Pyridine-2-sulfonic acid {3-[4-(cyclopropylmethyl-amino)-7H-pyrrolo[2,3-d]pyrimidine-5-carbonyl]-2,4-difluoro-phenyl}-amide (P-1208), 4-Methyl-pyridine-2-sulfonic acid {3-[4-(cyclopropylmethyl-amino)-7H-pyrrolo[2,3-d]pyrimidine-5-carbonyl]-2,4-difluoro-phenyl}-amide (P-1209), 6-Fluoro-pyridine-2-sulfonic acid {3-[4-(cyclopropylmethyl-amino)-7H-pyrrolo[2,3-d]pyrimidine-5-carbonyl]-2,4-difluoro-phenyl}-amide (P-1210), Pyridine-3-sulfonic acid {3-[4-(cyclopropylmethyl-amino)-7H-pyrrolo[2,3-d]pyrimidine-5-carbonyl]-2,4-difluoro-phenyl}-amide (P-1211), 4-Chloro-pyridine-3-sulfonic acid {3-[4-(cyclopropylmethyl-amino)-7H-pyrrolo[2,3-d]pyrimidine-5-carbonyl]-2,4-difluoro-phenyl}-amide (P-1212), 2-Chloro-pyridine-3-sulfonic acid {3-[4-(cyclopropylmethyl-amino)-7H-pyrrolo[2,3-d]pyrimidine-5-carbonyl]-2,4-difluoro-phenyl}-amide (P-1213), 1-Methyl-1H-pyrazole-4-sulfonic acid {3-[4-(cyclopropylmethyl-amino)-7H-pyrrolo[2,3-d]pyrimidine-5-carbonyl]-2,4-difluoro-phenyl}-amide (P-1214), N,N-Dimethylamino-sulfonic acid {3-[4-(cyclopropylmethyl-amino)-7H-pyrrolo[2,3-d]pyrimidine-5-carbonyl]-2,4-difluoro-phenyl}-amide (P-1215), N,N-Diethylamino-sulfonic acid {3-[4-(cyclopropylmethyl-amino)-7H-pyrrolo[2,3-d]pyrimidine-5-carbonyl]-2,4-difluoro-phenyl}-amide (P-1216), Pyrrolidine-1-sulfonic acid {3-[4-(cyclopropylmethyl-amino)-7H-pyrrolo[2,3-d]pyrimidine-5-carbonyl]-2,4-difluoro-phenyl}-amide (P-1217), Morpholine-4-sulfonic acid {3-[4-(cyclopropylmethyl-amino)-7H-pyrrolo[2,3-d]pyrimidine-5-carbonyl]-2,4-difluoro-phenyl}-amide (P-1218), Tetrahydro-pyran-4-sulfonic acid {3-[4-(cyclopropylmethyl-amino)-7H-pyrrolo[2,3-d]pyrimidine-5-carbonyl]-2,4-difluoro-phenyl}-amide (P-1219), Ethanesulfonic acid {3-[4-(cyclopropylmethyl-amino)-7H-pyrrolo[2,3-d]pyrimidine-5-carbonyl]-2,4-difluoro-phenyl}-amide (P-1220), Propane-2-sulfonic acid {3-[4-(cyclopropylmethyl-amino)-7H-pyrrolo[2,3-d]pyrimidine-5-carbonyl]-2,4-difluoro-phenyl}-amide (P-1221), Butane-2-sulfonic acid {3-[4-(cyclopropylmethyl-amino)-7H-pyrrolo[2,3-d]pyrimidine-5-carbonyl]-2,4-difluoro-phenyl}-amide (P-1222), 2-Methyl-propane-1-sulfonic acid {3-[4-(cyclopropylmethyl-amino)-7H-pyrrolo[2,3-d]pyrimidine-5-carbonyl]-2,4-difluoro-phenyl}-amide (P-1223), Butane-1-sulfonic acid {3-[4-(cyclopropylmethyl-amino)-7H-pyrrolo[2,3-d]pyrimidine-5-carbonyl]-2,4-difluoro-phenyl}-amide (P-1224), Pentane-2-sulfonic acid {3-[4-(cyclopropylmethyl-amino)-7H-pyrrolo[2,3-d]pyrimidine-5-carbonyl]-2,4-difluoro-phenyl}-amide (P-1225), N-{3-[4-(Cyclopropylmethyl-amino)-7H-pyrrolo[2,3-d]pyrimidine-5-carbonyl]-2,4-difluoro-phenyl}-C,C,C-trifluoro-methanesulfonamide (P-1226), 2,2,2-Trifluoro-ethanesulfonic acid {3-[4-(cyclopropylmethyl-amino)-7H-pyrrolo[2,3-d]pyrimidine-5-carbonyl]-2,4-difluoro-phenyl}-amide (P-1227), 3,3,3-Trifluoro-propane-1-sulfonic acid {3-[4-(cyclopropylmethyl-amino)-7H-pyrrolo[2,3-d]pyrimidine-5-carbonyl]-2,4-difluoro-phenyl}-amide (P-1228), Cyclohexanesulfonic acid {3-[4-(cyclopropylmethyl-amino)-7H-pyrrolo[2,3-d]pyrimidine-5-carbonyl]2,4-difluoro-phenyl}-amide (P-1229), Cyclopentanesulfonic acid {3-[4-(cyclopropylmethyl-amino)-7H-pyrrolo[2,3-d]pyrimidine-5-carbonyl]-2,4-difluoro-phenyl}-amide (P-1230), Cyclobutanesulfonic acid {3-[4-(cyclopropylmethyl-amino)-7H-pyrrolo[2,3-d]pyrimidine-5-carbonyl]-2,4-difluoro-phenyl}-amide (P-1231), Cyclopropanesulfonic acid {3-[4-(cyclopropylmethyl-amino)-7H-pyrrolo[2,3-d]pyrimidine-5-carbonyl]-2,4-difluoro-phenyl}-amide (P-1232), 4,4-Difluoro-cyclohexanesulfonic acid {3-[4-(cyclopropylmethyl-amino)-7H-pyrrolo[2,3-d]pyrimidine-5-carbonyl]-2,4-difluoro-phenyl}-amide (P-1233), 3,3-Difluoro-cyclopentanesulfonic acid {3-[4-(cyclopropylmethyl-amino)-7H-pyrrolo[2,3-d]pyrimidine-5-carbonyl]-2,4-difluoro-phenyl}-amide (P-1234), 3-Fluoro-cyclopentanesulfonic acid {3-[4-(cyclopropylmethyl-amino)-7H-pyrrolo[2,3-d]pyrimidine-5-carbonyl]-2,4-difluoro-phenyl}-amide (P-1235), Propane-1-sulfonic acid [3-(4-cyclopentylamino-1H-pyrrolo[2,3-b]pyridine-3-carbonyl)-2,4-difluoro-phenyl]-amide (P-2012), Propane-1-sulfonic acid {2,4-difluoro-3-[4-(tetrahydro-pyran-4-ylamino)-1H-pyrrolo[2,3-b]pyridine-3-carbonyl]-phenyl}-amide (P-2013), N-{2,4-Difluoro-3-[4-(tetrahydro-pyran-4-ylamino)-1H-pyrrolo[2,3-b]pyridine-3-carbonyl]-phenyl}-4-trifluoromethyl-benzenesulfonamide (P-2014), N-{3-[4-(Cyclopropylmethyl-amino)-1H-pyrrolo[2,3-b]pyridine-3-carbonyl]-2,4-difluoro-phenyl}-2,5-difluoro-benzenesulfonamide (P-2018), N-{3-[4-(Cyclopropylmethyl-amino)-5-fluoro-1H-pyrrolo[2,3-b]pyridine-3-carbonyl]-2,4-difluoro-phenyl}-2,5-difluoro-benzene sulfonamide (P-2019), N-{3-[5-Cyano-4-(cyclopropylmethyl-amino)-1H-pyrrolo[2,3-b]pyridine-3-carbonyl]-2,4-difluoro-phenyl}-2,5-difluoro-benzene sulfonamide (P-2020), N-{3-[5-Chloro-4-(cyclopropylmethyl-amino)-1H-pyrrolo[2,3-b]pyridine-3-carbonyl]-2,4-difluoro-phenyl}-2,5-difluoro-benzene sulfonamide (P-2021), N-{3-[4-(Cyclopropylmethyl-amino)-5-methyl-1H-pyrrolo[2,3-b]pyridine-3-carbonyl]-2,4-difluoro-phenyl}-2,5-difluoro-benzene sulfonamide (P-2022), N-{3-[4-(Cyclopropylmethyl-amino)-5-hydroxymethyl-1H-pyrrolo[2,3-b]pyridine-3-carbonyl]-2,4-difluoro-phenyl}-2,5-difluoro-benzene sulfonamide (P-2023), N-{3-[4-(Cyclopropylmethyl-amino)-5-methoxy-1H-pyrrolo[2,3-b]pyridine-3-carbonyl]-2,4-difluoro-phenyl}-2,5-difluoro-benzenesulfonamide (P-2024), and any pharmaceutically acceptable salt thereof.

In one embodiment of compounds contemplated herein, the compound is selected from the group consisting of:

N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011), N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013), N-[2,4-Difluoro-3-(4-isobutylamino-7H-pyrrolo[2,3-d]pyrimidine-5-carbonyl)-phenyl]-4-trifluoromethyl-benzenesulfonamide (P-1020), N-[3-(4-Ethylamino-7H-pyrrolo[2,3-d]pyrimidine-5-carbonyl)-2,4-difluoro-phenyl]-4-trifluoromethyl-benzenesulfonamide (P-1024), N-[2,4-Difluoro-3-(4-methylamino-7H-pyrrolo[2,3-d]pyrimidine-5-carbonyl)-phenyl]-4-trifluoromethyl-benzenesulfonamide (P-1026), N-[3-(4-Amino-7H-pyrrolo[2,3-d]pyrimidine-5-carbonyl)-2,4-difluoro-phenyl]-4-trifluoromethyl-benzenesulfonamide (P-1031), N-[2,4-Difluoro-3-(4-propylamino-7H-pyrrolo[2,3-d]pyrimidine-5-carbonyl)-phenyl]-4-trifluoromethyl-benzenesulfonamide (P-1032), N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035), N-[2,4-Difluoro-3-(4-phenylamino-7H-pyrrolo[2,3-d]pyrimidine-5-carbonyl)-phenyl]-4-trifluoromethyl-benzenesulfonamide (P-1037), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), N-[3-(4-Cyclopropylamino-7H-pyrrolo[2,3-d]pyrimidine-5-carbonyl)-2,4-difluoro-phenyl]-4-propyl-benzenesulfonamide (P-1040), Propane-1-sulfonic acid [3-(4-cyclopropylamino-7H-pyrrolo[2,3-d]pyrimidine-5-carbonyl)-2,4-difluoro-phenyl]-amide (P-1041), N-[2,4-Difluoro-3-(4-isopropylamino-7H-pyrrolo[2,3-d]pyrimidine-5-carbonyl)-phenyl]-4-ethyl-benzenesulfonamide (P-1042), N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide (P-1043), N-[2,4-Difluoro-3-(4-isopropylamino-7H-pyrrolo[2,3-d]pyrimidine-5-carbonyl)-phenyl]-4-isopropyl-benzenesulfonamide (P-1044), N-{2,4-Difluoro-3-[4-(tetrahydro-pyran-4-ylamino)-7H-pyrrolo[2,3-d]pyrimidine-5-carbonyl]-phenyl}-4-propyl-benzenesulfonamide (P-1046), N-[3-(4-Dimethylamino-7H-pyrrolo[2,3-d]pyrimidine-5-carbonyl)-2,4-difluoro-phenyl]-4-trifluoromethyl-benzenesulfonamide (P-1049), N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050), N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052), N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide (P-1054), N-[2,4-Difluoro-3-(4-isopropylamino-7H-pyrrolo[2,3-d]pyrimidine-5-carbonyl)-phenyl]-4-propyl-benzenesulfonamide (P-1055), N-{2,4-Difluoro-3-[4-(oxetan-3-ylamino)-7H-pyrrolo[2,3-d]pyrimidine-5-carbonyl]-phenyl}-4-propyl-benzenesulfonamide (P-1056), N-{2,4-Difluoro-3-[4-(1-methyl-piperidin-4-ylamino)-7H-pyrrolo[2,3-d]pyrimidine-5-carbonyl]-phenyl}-4-trifluoromethyl-benzenesulfonamide (P-1057), N-{2,4-Difluoro-3-[4-(2-methoxy-ethylamino)-7H-pyrrolo[2,3-d]pyrimidine-5-carbonyl]-phenyl}-4-trifluoromethyl-benzenesulfonamide (P-1058), N-{3-[4-(2-Dimethylamino-ethylamino)-7H-pyrrolo[2,3-d]pyrimidine-5-carbonyl]-2,4-difluoro-phenyl}-4-trifluoromethyl-benzenesulfonamide (P-1059), Propane-1-sulfonic acid {2,4-difluoro-3-[4-(oxetan-3-ylamino)-7H-pyrrolo[2,3-d]pyrimidine-5-carbonyl]-phenyl}-amide (P-1060), N-{2,4-Difluoro-3-[4-(tetrahydro-pyran-4-ylamino)-1H-pyrrolo[2,3-b]pyridine-3-carbonyl]-phenyl}-4-trifluoromethyl-benzenesulfonamide (P-2014), and any pharmaceutically acceptable salt thereof.

In one embodiment of compounds contemplated herein, the compound is selected from the group consisting of:

N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011), N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013), N-[2,4-Difluoro-3-(4-isobutylamino-7H-pyrrolo[2,3-d]pyrimidine-5-carbonyl)-phenyl]-4-trifluoromethyl-benzenesulfonamide (P-1020), N-[3-(4-Ethylamino-7H-pyrrolo[2,3-d]pyrimidine-5-carbonyl)-2,4-difluoro-phenyl]-4-trifluoromethyl-benzenesulfonamide (P-1024), N-[2,4-Difluoro-3-(4-methylamino-7H-pyrrolo[2,3-d]pyrimidine-5-carbonyl)-phenyl]-4-trifluoromethyl-benzenesulfonamide (P-1026), N-[3-(4-Amino-7H-pyrrolo[2,3-d]pyrimidine-5-carbonyl)-2,4-difluoro-phenyl]-4-trifluoromethyl-benzene sulfonamide (P-1031), N-[2,4-Difluoro-3-(4-propylamino-7H-pyrrolo[2,3-d]pyrimidine-5-carbonyl)-phenyl]-4-trifluoromethyl-benzenesulfonamide (P-1032), N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035), N-[2,4-Difluoro-3-(4-phenylamino-7H-pyrrolo[2,3-d]pyrimidine-5-carbonyl)-phenyl]-4-trifluoromethyl-benzene sulfonamide (P-1037), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide (P-1043), N-[2,4-Difluoro-3-(4-isopropylamino-7H-pyrrolo[2,3-d]pyrimidine-5-carbonyl)-phenyl]-4-isopropyl-benzenesulfonamide (P-1044), N-{2,4-Difluoro-3-[4-(tetrahydro-pyran-4-ylamino)-7H-pyrrolo[2,3-d]pyrimidine-5-carbonyl]-phenyl}-4-propyl-benzenesulfonamide (P-1046), N-[3-(4-Dimethylamino-7H-pyrrolo[2,3-d]pyrimidine-5-carbonyl)-2,4-difluoro-phenyl]-4-trifluoromethyl-benzenesulfonamide (P-1049), N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050), N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052), N-{2,4-Difluoro-3-[4-(oxetan-3-ylamino)-7H-pyrrolo[2,3-d]pyrimidine-5-carbonyl]-phenyl}-4-propyl-benzenesulfonamide (P-1056), N-{2,4-Difluoro-3-[4-(1-methyl-1H-pyrazol-4-ylamino)-7H-pyrrolo[2,3-d]pyrimidine-5-carbonyl]-phenyl}-4-trifluoromethyl-benzenesulfonamide (P-1062), N-{3-[4-(1-Ethyl-1H-pyrazol-4-ylamino)-7H-pyrrolo[2,3-d]pyrimidine-5-carbonyl]-2,4-difluoro-phenyl}-4-trifluoromethyl-benzenesulfonamide (P-1063), 4-Cyano-N-[2,4-difluoro-3-(4-isopropylamino-7H-pyrrolo[2,3-d]pyrimidine-5-carbonyl)-phenyl]-benzenesulfonamide (P-1108), N-[2,4-Difluoro-3-(4-isopropylamino-7H-pyrrolo[2,3-d]pyrimidine-5-carbonyl)-phenyl]-4-difluoromethoxy-benzenesulfonamide (P-1110), N-[2,4-Difluoro-3-(4-isopropylamino-7H-pyrrolo[2,3-d]pyrimidine-5-carbonyl)-phenyl]-3-difluoromethoxy-benzenesulfonamide (P-1119), 1-Methyl-1H-pyrazole-4-sulfonic acid [2,4-difluoro-3-(4-isopropylamino-7H-pyrrolo[2,3-d]pyrimidine-5-carbonyl)-phenyl]-amide (P-1121), and any pharmaceutically acceptable salt thereof.

In one embodiment of compounds contemplated herein, the compound is selected from the group consisting of:

Propane-1-sulfonic acid [3-(4-cyclopropylamino-7H-pyrrolo[2,3-d]pyrimidine-5-carbonyl)-2,4-difluoro-phenyl]-amide (P-1041), Propane-1-sulfonic acid {2,4-difluoro-3-[4-(oxetan-3-ylamino)-7H-pyrrolo[2,3-d]pyrimidine-5-carbonyl]-phenyl}-amide (P-1060), Propane-1-sulfonic acid {2,4-difluoro-3-[4-(4-fluoro-phenylamino)-7H-pyrrolo[2,3-d]pyrimidine-5-carbonyl]-phenyl}-amide (P-1065), N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069), Propane-1-sulfonic acid {2,4-difluoro-3-[4-(naphthalen-1-ylamino)-7H-pyrrolo[2,3-d]pyrimidine-5-carbonyl]-phenyl}-amide (P-1072), N-[2,4-Difluoro-3-(4-isopropylamino-7H-pyrrolo[2,3-d]pyrimidine-5-carbonyl)-phenyl]-2-fluoro-benzenesulfonamide (P-1073), Propane-1-sulfonic acid [3-(4-benzylamino-7H-pyrrolo[2,3-d]pyrimidine-5-carbonyl)-2,4-difluoro-phenyl]-amide (P-1074), Propane-1-sulfonic acid [2,4-difluoro-3-(4-propylamino-7H-pyrrolo[2,3-d]pyrimidine-5-carbonyl)-phenyl]-amide (P-1075), Propane-1-sulfonic acid {2,4-difluoro-3-[4-(pyridin-2-ylamino)-7H-pyrrolo[2,3-d]pyrimidine-5-carbonyl]-phenyl}-amide (P-1077), Propane-1-sulfonic acid {2,4-difluoro-3-[4-(pyridin-3-ylamino)-7H-pyrrolo[2,3-d]pyrimidine-5-carbonyl]-phenyl}-amide (P-1078), Propane-1-sulfonic acid {3-[4-(cyclopropylmethyl-amino)-7H-pyrrolo[2,3-d]pyrimidine-5-carbonyl]-2,4-difluoro-phenyl}-amide (P-1079), Propane-1-sulfonic acid [3-(4-cyclopentylamino-7H-pyrrolo[2,3-d]pyrimidine-5-carbonyl)-2,4-difluoro-phenyl]-amide (P-1081), Propane-1-sulfonic acid [3-(4-ethylamino-7H-pyrrolo[2,3-d]pyrimidine-5-carbonyl)-2,4-difluoro-phenyl]-amide (P-1082),
Propane-1-sulfonic acid {3-[4-(3-dimethylamino-phenylamino)-7H-pyrrolo[2,3-d]pyrimidine-5-carbonyl]-2,4-difluoro-phenyl}-amide (P-1083),
Propane-1-sulfonic acid {3-[4-(3-chloro-phenylamino)-7H-pyrrolo[2,3-d]pyrimidine-5-carbonyl]-2,4-difluoro-phenyl}-amide (P-1084),
Propane-1-sulfonic acid {2,4-difluoro-3-[4-(3-methoxy-phenylamino)-7H-pyrrolo[2,3-d]pyrimidine-5-carbonyl]-phenyl}-amide (P-1085),
Propane-1-sulfonic acid {2,4-difluoro-3-[4-(2-methoxy-ethylamino)-7H-pyrrolo[2,3-d]pyrimidine-5-carbonyl]-phenyl}-amide (P-1086),
Propane-1-sulfonic acid {3-[4-(4-chloro-phenylamino)-7H-pyrrolo[2,3-d]pyrimidine-5-carbonyl]-2,4-difluoro-phenyl}-amide (P-1087),
Propane-1-sulfonic acid [2,4-difluoro-3-(4-isobutylamino-7H-pyrrolo[2,3-d]pyrimidine-5-carbonyl)-phenyl]-amide (P-1088),
Propane-1-sulfonic acid {2,4-difluoro-3-[4-(4-trifluoromethyl-phenylamino)-7H-pyrrolo[2,3-d]pyrimidine-5-carbonyl]-phenyl}-amide (P-1089),
Propane-1-sulfonic acid {2,4-difluoro-3-[4-(6-methoxy-pyridin-3-ylamino)-7H-pyrrolo[2,3-d]pyrimidine-5-carbonyl]-phenyl}-amide (P-1090),
Propane-1-sulfonic acid {2,4-difluoro-3-[4-(3-trifluoromethyl-phenylamino)-7H-pyrrolo[2,3-d]pyrimidine-5-carbonyl]-phenyl}-amide (P-1091),
Propane-1-sulfonic acid [2,4-difluoro-3-(4-m-tolylamino-7H-pyrrolo[2,3-d]pyrimidine-5-carbonyl)-phenyl]-amide (P-1092),
Propane-1-sulfonic acid [2,4-difluoro-3-(4-p-tolylamino-7H-pyrrolo[2,3-d]pyrimidine-5-carbonyl)-phenyl]-amide (P-1093),
Propane-1-sulfonic acid {2,4-difluoro-3-[4-(3-fluoro-phenylamino)-7H-pyrrolo[2,3-d]pyrimidine-5-carbonyl]-phenyl}-amide (P-1094),
Propane-1-sulfonic acid {3-[4-(1-ethyl-piperidin-4-ylamino)-7H-pyrrolo[2,3-d]pyrimidine-5-carbonyl]-2,4-difluoro-phenyl}-amide (P-1095),
Propane-1-sulfonic acid {2,4-difluoro-3-[4-(1-methanesulfonyl-piperidin-4-ylamino)-7H-pyrrolo[2,3-d]pyrimidine-5-carbonyl]-phenyl}-amide (P-1096),
Propane-1-sulfonic acid {3-[4-(1-ethyl-1H-pyrazol-4-ylamino)-7H-pyrrolo[2,3-d]pyrimidine-5-carbonyl]2,4-difluoro-phenyl}-amide (P-1099),
Propane-1-sulfonic acid {3-[4-(1,3-dimethyl-1H-pyrazol-4-ylamino)-7H-pyrrolo[2,3-d]pyrimidine-5-carbonyl]-2,4-difluoro-phenyl}-amide (P-1100),
Propane-1-sulfonic acid {2,4-difluoro-3-[4-(2-fluoro-4-methoxy-phenylamino)-7H-pyrrolo[2,3-d]pyrimidine-5-carbonyl]-phenyl}-amide (P-1101),
Propane-1-sulfonic acid {2,4-difluoro-3-[4-(1-methyl-1H-pyrazol-4-ylamino)-7H-pyrrolo[2,3-d]pyrimidine-5-carbonyl]-phenyl}-amide (P-1102),
N-[3-(4-Cyclopropylamino-7H-pyrrolo[2,3-d]pyrimidine-5-carbonyl)-2,4-difluoro-phenyl]-2-fluoro-benzenesulfonamide (P-1103),
N-[3-(4-Cyclopropylamino-7H-pyrrolo[2,3-d]pyrimidine-5-carbonyl)-2,4-difluoro-phenyl]-2,5-difluoro-benzenesulfonamide (P-1104),
Propane-1-sulfonic acid {2,4-difluoro-3-[4-(3-fluoro-5-methoxy-pyridin-2-ylamino)-7H-pyrrolo[2,3-d]pyrimidine-5-carbonyl]-phenyl}-amide (P-1105),
N-[3-(4-Cyclopropyl-7H-pyrrolo[2,3-d]pyrimidine-5-carbonyl)-2,4-difluoro-phenyl]-2,5-difluoro-benzenesulfonamide (P-1107),
N-[2,4-Difluoro-3-(4-isopropylamino-7H-pyrrolo[2,3-d]pyrimidine-5-carbonyl)-phenyl]-2,5-difluoro-benzenesulfonamide (P-1111),
N-[2,4-Difluoro-3-(4-isopropylamino-7H-pyrrolo[2,3-d]pyrimidine-5-carbonyl)-phenyl]-3-fluoro-benzenesulfonamide (P-1115),
Piperidine-1-sulfonic acid [2,4-difluoro-3-(4-isopropylamino-7H-pyrrolo[2,3-d]pyrimidine-5-carbonyl)-phenyl]-amide (P-1122),
2-Methyl-propane-1-sulfonic acid [2,4-difluoro-3-(4-isopropylamino-7H-pyrrolo[2,3-d]pyrimidine-5-carbonyl)-phenyl]-amide (P-1126),
Pyridine-3-sulfonic acid [2,4-difluoro-3-(4-isopropylamino-7H-pyrrolo[2,3-d]pyrimidine-5-carbonyl)-phenyl]-amide (P-1132),
Propane-1-sulfonic acid {3-[4-(benzo[1,2,5]thiadiazol-5-ylamino)-7H-pyrrolo[2,3-d]pyrimidine-5-carbonyl]-2,4-difluoro-phenyl}-amide (P-1134),
N-[3-(4-Benzylamino-7H-pyrrolo[2,3-d]pyrimidine-5-carbonyl)-2,4-difluoro-phenyl]-2,5-difluoro-benzenesulfonamide (P-1135),
N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136),
N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137),
N-[3-(4-Ethylamino-7H-pyrrolo[2,3-d]pyrimidine-5-carbonyl)-2,4-difluoro-phenyl]-2,5-difluoro-benzenesulfonamide (P-1138),
N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139),
N-[2,4-Difluoro-3-(4-isobutylamino-7H-pyrrolo[2,3-d]pyrimidine-5-carbonyl)-phenyl]-2,5-difluoro-benzenesulfonamide (P-1140),
N-[2,4-Difluoro-3-(4-m-tolylamino-7H-pyrrolo[2,3-d]pyrimidine-5-carbonyl)-phenyl]-2,5-difluoro-benzenesulfonamide (P-1141),
N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142),
N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1143),
N-[3-(4-Benzylamino-7H-pyrrolo[2,3-d]pyrimidine-5-carbonyl)-2,4-difluoro-phenyl]-2-fluoro-benzenesulfonamide (P-1144),
N-{2,4-Difluoro-3-[4-(pyridin-3-ylamino)-7H-pyrrolo[2,3-d]pyrimidine-5-carbonyl]-phenyl}-2-fluoro-benzenesulfonamide (P-1145),
N-{3-[4-(Cyclopropylmethyl-amino)-7H-pyrrolo[2,3-d]pyrimidine-5-carbonyl]-2,4-difluoro-phenyl}-2-fluoro-benzenesulfonamide (P-1146),
N-[3-(4-Cyclopentylamino-7H-pyrrolo[2,3-d]pyrimidine-5-carbonyl)-2,4-difluoro-phenyl]-2-fluoro-benzenesulfonamide (P-1147),
N-[3-(4-Ethylamino-7H-pyrrolo[2,3-d]pyrimidine-5-carbonyl)-2,4-difluoro-phenyl]-2-fluoro-benzenesulfonamide (P-1148),
N-{2,4-Difluoro-3-[4-(3-methoxy-phenylamino)-7H-pyrrolo[2,3-d]pyrimidine-5-carbonyl]-phenyl}-2-fluoro-benzenesulfonamide (P-1149), N-{2,4-Difluoro-3-[4-(2-methoxy-ethylamino)-7H-pyrrolo[2,3-d]pyrimidine-5-carbonyl]-phenyl}-2-fluoro-benzenesulfonamide (P-1150), N-[2,4-Difluoro-3-(4-isobutylamino-7H-pyrrolo[2,3-d]pyrimidine-5-carbonyl)-phenyl]-2-fluoro-benzenesulfonamide (P-1151), N-[2,4-Difluoro-3-(4-m-tolylamino-7H-pyrrolo[2,3-d]pyrimidine-5-carbonyl)-phenyl]-2-fluoro-benzenesulfonamide (P-1152), N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide (P-1153), N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide (P-1154), Propane-1-sulfonic acid {2,4-difluoro-3-[4-(1H-indazol-6-ylamino)-7H-pyrrolo[2,3-d]pyrimidine-5-carbonyl]-phenyl}-amide (P-1157), Propane-1-sulfonic acid {2,4-difluoro-3-[4-(1H-indazol-5-ylamino)-7H-pyrrolo[2,3-d]pyrimidine-5-carbonyl]-phenyl}-amide (P-1158), Propane-1-sulfonic acid {2,4-difluoro-3-[4-(4-hydroxy-phenylamino)-7H-pyrrolo[2,3-d]pyrimidine-5-carbonyl]-phenyl}-amide (P-1159), 4-{5-[2,6-Difluoro-3-(propane-1-sulfonylamino)-benzoyl]-7H-pyrrolo[2,3-d]pyrimidin-4-ylamino}-benzoic acid methyl ester (P-1162), Propane-1-sulfonic acid (2,4-difluoro-3-{4-[3-(5-methyl-tetrazol-1-yl)-phenylamino]-7H-pyrrolo[2,3-d]pyrimidine-5-carbonyl}-phenyl)-amide (P-1171), Propane-1-sulfonic acid {2,4-difluoro-3-[4-(2-oxo-2,3-dihydro-1H-benzoimidazol-5-ylamino)-7H-pyrrolo[2,3-d]pyrimidine-5-carbonyl]-phenyl}-amide (P-1177), Propane-1-sulfonic acid (2,4-difluoro-3-{4-[3-(5-methyl-[1,3,4]oxadiazol-2-yl)-phenylamino]-7H-pyrrolo[2,3-d]pyrimidine-5-carbonyl}-phenyl)-amide (P-1179), and any pharmaceutically acceptable salt thereof.

In one embodiment of compounds contemplated herein, the compound is selected from the group consisting of:

N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069), N-[2,4-Difluoro-3-(4-isopropylamino-7H-pyrrolo[2,3-d]pyrimidine-5-carbonyl)-phenyl]-2-fluoro-benzenesulfonamide (P-1073), N-[3-(4-Cyclopropylamino-7H-pyrrolo[2,3-d]pyrimidine-5-carbonyl)-2,4-difluoro-phenyl]-2-fluoro-benzenesulfonamide (P-1103), N-[3-(4-Cyclopropylamino-7H-pyrrolo[2,3-d]pyrimidine-5-carbonyl)-2,4-difluoro-phenyl]-2,5-difluoro-benzenesulfonamide (P-1104), N-[3-(4-Cyclopropyl-7H-pyrrolo[2,3-d]pyrimidine-5-carbonyl)-2,4-difluoro-phenyl]-2,5-difluoro-benzenesulfonamide (P-1107), N-[2,4-Difluoro-3-(4-isopropylamino-7H-pyrrolo[2,3-d]pyrimidine-5-carbonyl)-phenyl]-2,5-difluoro-benzenesulfonamide (P-1111), N-[3-(4-Benzylamino-7H-pyrrolo[2,3-d]pyrimidine-5-carbonyl)-2,4-difluoro-phenyl]-2,5-difluoro-benzenesulfonamide (P-1135), N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136), N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137), N-[3-(4-Ethylamino-7H-pyrrolo[2,3-d]pyrimidine-5-carbonyl)-2,4-difluoro-phenyl]-2,5-difluoro-benzenesulfonamide (P-1138), N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139), N-[2,4-Difluoro-3-(4-isobutylamino-7H-pyrrolo[2,3-d]pyrimidine-5-carbonyl)-phenyl]-2,5-difluoro-benzenesulfonamide (P-1140), N-[2,4-Difluoro-3-(4-m-tolylamino-7H-pyrrolo[2,3-d]pyrimidine-5-carbonyl)-phenyl]-2,5-difluoro-benzenesulfonamide (P-1141), N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142), N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1143), N-[3-(4-Benzylamino-7H-pyrrolo[2,3-d]pyrimidine-5-carbonyl)-2,4-difluoro-phenyl]-2-fluoro-benzenesulfonamide (P-1144), N-{2,4-Difluoro-3-[4-(pyridin-3-ylamino)-7H-pyrrolo[2,3-d]pyrimidine-5-carbonyl]-phenyl}-2-fluoro-benzenesulfonamide (P-1145), N-{3-[4-(Cyclopropylmethyl-amino)-7H-pyrrolo[2,3-d]pyrimidine-5-carbonyl]-2,4-difluoro-phenyl}-2-fluoro-benzenesulfonamide (P-1146), N-[3-(4-Cyclopentylamino-7H-pyrrolo[2,3-d]pyrimidine-5-carbonyl)-2,4-difluoro-phenyl]-2-fluoro-benzenesulfonamide (P-1147), N-[3-(4-Ethylamino-7H-pyrrolo[2,3-d]pyrimidine-5-carbonyl)-2,4-difluoro-phenyl]-2-fluoro-benzenesulfonamide (P-1148), N-{2,4-Difluoro-3-[4-(3-methoxy-phenylamino)-7H-pyrrolo[2,3-d]pyrimidine-5-carbonyl]-phenyl}-2-fluoro-benzenesulfonamide (P-1149), N-{2,4-Difluoro-3-[4-(2-methoxy-ethylamino)-7H-pyrrolo[2,3-d]pyrimidine-5-carbonyl]-phenyl}-2-fluoro-benzenesulfonamide (P-1150), N-[2,4-Difluoro-3-(4-isobutylamino-7H-pyrrolo[2,3-d]pyrimidine-5-carbonyl)-phenyl]-2-fluoro-benzenesulfonamide (P-1151), N-[2,4-Difluoro-3-(4-m-tolylamino-7H-pyrrolo[2,3-d]pyrimidine-5-carbonyl)-phenyl]-2-fluoro-benzenesulfonamide (P-1152), N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide (P-1153), N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide (P-1154), and any pharmaceutically acceptable salt thereof.

In one embodiment of compounds contemplated herein, the compound is selected from the group consisting of:

N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069), N-[3-(4-Cyclopropylamino-7H-pyrrolo[2,3-d]pyrimidine-5-carbonyl)-2,4-difluoro-phenyl]-2,5-difluoro-benzenesulfonamide (P-1104), N-[3-(4-Cyclopropyl-7H-pyrrolo[2,3-d]pyrimidine-5-carbonyl)-2,4-difluoro-phenyl]-2,5-difluoro-benzenesulfonamide (P-1107), N-[2,4-Difluoro-3-(4-isopropylamino-7H-pyrrolo[2,3-d]pyrimidine-5-carbonyl)-phenyl]-2,5-difluoro-benzenesulfonamide (P-1111), N-[3-(4-Benzylamino-7H-pyrrolo[2,3-d]pyrimidine-5-carbonyl)-2,4-difluoro-phenyl]-2,5-difluoro-benzenesulfonamide (P-1135), N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136), N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137), N-[3-(4-Ethylamino-7H-pyrrolo[2,3-d]pyrimidine-5-carbonyl)-2,4-difluoro-phenyl]-2,5-difluoro-benzenesulfonamide (P-1138), N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139), N-[2,4-Difluoro-3-(4-isobutylamino-7H-pyrrolo[2,3-d]pyrimidine-5-carbonyl)-phenyl]-2,5-difluoro-benzenesulfonamide (P-1140), N-[2,4-Difluoro-3-(4-m-tolylamino-7H-pyrrolo[2,3-d]pyrimidine-5-carbonyl)-phenyl]-2,5-difluoro-benzenesulfonamide (P-1141), N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142), N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzene sulfonamide (P-1143), and any salt, prodrug, tautomer, or stereoisomer thereof.

In one embodiment of compounds contemplated herein, the compound is selected from the group consisting of:

Propane-1-sulfonic acid [3-(4-chloro-5-methyl-1H-pyrrolo[2,3-b]pyridine-3-carbonyl)-2,4-difluoro-phenyl]-amide (P-2001), Propane-1-sulfonic acid [3-(4-chloro-5-methoxy-1H-pyrrolo[2,3-b]pyridine-3-carbonyl)-2,4-difluoro-phenyl]-amide (P-2002), Propane-1-sulfonic acid [3-(4-cyano-5-fluoro-1H-pyrrolo[2,3-b]pyridine-3-carbonyl)-2,4-difluoro-phenyl]-amide (P-2003), Propane-1-sulfonic acid [3-(4-chloro-5-cyano-1H-pyrrolo[2,3-b]pyridine-3-carbonyl)-2,4-difluoro-phenyl]-amide (P-2004), Propane-1-sulfonic acid [3-(5-cyano-4-methoxy-1H-pyrrolo[2,3-b]pyridine-3-carbonyl)-2,4-difluoro-phenyl]-amide (P-2005), Propane-1-sulfonic acid [3-(5-chloro-4-methoxy-1H-pyrrolo[2,3-b]pyridine-3-carbonyl)-2,4-difluoro-phenyl-]amide (P-2006), Propane-1-sulfonic acid [3-(5-chloro-4-cyano-1H-pyrrolo[2,3-b]pyridine-3-carbonyl)-2,4-difluoro-phenyl-]amide (P-2007), Propane-1-sulfonic acid [3-(5-chloro-4-methyl-1H-pyrrolo[2,3-b]pyridine-3-carbonyl)-2,4-difluoro-phenyl-]amide (P-2008), N-[3-(4-Cyano-5-fluoro-1H-pyrrolo[2,3-b]pyridine-3-carbonyl)-2,4-difluoro-phenyl]-4-trifluoromethyl-benzene sulfonamide (P-2009), N-[3-(5-Chloro-4-cyano-1H-pyrrolo[2,3-b]pyridine-3-carbonyl)-2,4-difluoro-phenyl]-4-trifluoromethyl-benzenesulfonamide (P-2010), N-[3-(5-Chloro-4-methyl-1H-pyrrolo[2,3-b]pyridine-3-carbonyl)-2,4-difluoro-phenyl]-4-trifluoromethyl-benzene sulfonamide (P-2011), N-[2,4-Difluoro-3-(5-fluoro-4-iodo-1H-pyrrolo[2,3-b]pyridine-3-carbonyl)-phenyl]-2,5-difluoro-benzene sulfonamide (P-2025), N-[3-(4-Chloro-5-cyano-1H-pyrrolo[2,3-b]pyridine-3-carbonyl)-2,4-difluoro-phenyl]-2,5-difluoro-benzene sulfonamide (P-2026), N-[3-(5-Chloro-4-iodo-1H-pyrrolo[2,3-b]pyridine-3-carbonyl)-2,4-difluoro-phenyl]-2,5-difluoro-benzene sulfonamide (P-2027), N-[3-(4-Chloro-5-methyl-1H-pyrrolo[2,3-b]pyridine-3-carbonyl)-2,4-difluoro-phenyl]-2,5-difluoro-benzenesulfonamide (P-2028), N-[3-(4-Chloro-5-hydroxymethyl-1H-pyrrolo[2,3-b]pyridine-3-carbonyl)-2,4-difluoro-phenyl]-2,5-difluoro-benzenesulfonamide (P-2029), N-[2,4-Difluoro-3-(4-iodo-5-methoxy-1H-pyrrolo[2,3-b]pyridine-3-carbonyl)-phenyl]-2,5-difluoro-benzenesulfonamide (P-2030), and any pharmaceutically acceptable salt thereof.

In a fourth aspect, compounds are provided, wherein the compound is selected from the group consisting of:

N-[2,4-Difluoro-3-(4-methyl-7H-pyrrolo[2,3-d]pyrimidine-5-carbonyl)-phenyl]-4-trifluoromethyl-benzenesulfonamide (P-1001), Propane-1-sulfonic acid [3-(4-ethoxy-7H-pyrrolo[2,3-d]pyrimidine-5-carbonyl)-2,4-difluoro-phenyl]-amide (P-1002), 2-Methyl-propane-1-sulfonic acid [2,4-difluoro-3-(4-methyl-7H-pyrrolo[2,3-d]pyrimidine-5-carbonyl)-phenyl]-amide (P-1003), 2-Methyl-propane-1-sulfonic acid [2,4-difluoro-3-(4-methoxy-7H-pyrrolo[2,3-d]pyrimidine-5-carbonyl)-phenyl]-amide (P-1004), N-[2,4-Difluoro-3-(4-methoxy-7H-pyrrolo[2,3-d]pyrimidine-5-carbonyl)-phenyl]-4-propyl-benzenesulfonamide (P-1005), N-[3-(4-Ethoxy-7H-pyrrolo[2,3-d]pyrimidine-5-carbonyl)-2,4-difluoro-phenyl]-4-trifluoromethyl-benzenesulfonamide (P-1006), N-[2,4-Difluoro-3-(4-methyl-7H-pyrrolo[2,3-d]pyrimidine-5-carbonyl)-phenyl]-4-propyl-benzenesulfonamide (P-1007), N-[2,4-Difluoro-3-(4-methoxy-7H-pyrrolo[2,3-d]pyrimidine-5-carbonyl)-phenyl]-4-ethyl-benzenesulfonamide (P-1008), N-[2,4-Difluoro-3-(4-methyl-7H-pyrrolo[2,3-d]pyrimidine-5-carbonyl)-phenyl]-4-isopropyl-benzenesulfonamide (P-1009), N-[2,4-Difluoro-3-(4-methoxy-7H-pyrrolo[2,3-d]pyrimidine-5-carbonyl)-phenyl]-4-isopropyl-benzenesulfonamide (P-1010), N-[2,4-Difluoro-3-(4-hydroxy-7H-pyrrolo[2,3-d]pyrimidine-5-carbonyl)-phenyl]-4-trifluoromethyl-benzenesulfonamide (P-1012), Propane-1-sulfonic acid [2,4-difluoro-3-(4-isobutyl-7H-pyrrolo[2,3-d]pyrimidine-5-carbonyl)-phenyl]-amide (P-1014), N-[2,4-Difluoro-3-(4-isobutyl-7H-pyrrolo[2,3-d]pyrimidine-5-carbonyl)-phenyl]-4-trifluoromethyl-benzenesulfonamide (P-1015), N-[3-(4-Chloro-7H-pyrrolo[2,3-d]pyrimidine-5-carbonyl)-2,4-difluoro-phenyl]-4-trifluoromethyl-benzenesulfonamide (P-1016), 6-Methoxy-pyridine-3-sulfonic acid [2,4-difluoro-3-(4-methoxy-7H-pyrrolo[2,3-d]pyrimidine-5-carbonyl)-phenyl]-amide (P-1018), N-[2,4-Difluoro-3-(4-methyl-7H-pyrrolo[2,3-d]pyrimidine-5-carbonyl)-phenyl]-4-ethyl-benzenesulfonamide (P-1019), N-{2,4-Difluoro-3-[4-(tetrahydro-pyran-4-yloxy)-7H-pyrrolo[2,3-d]pyrimidine-5-carbonyl]-phenyl}-4-trifluoromethyl-benzenesulfonamide (P-1021), Propane-1-sulfonic acid [2,4-difluoro-3-(4-hydroxy-7H-pyrrolo[2,3-d]pyrimidine-5-carbonyl)-phenyl]-amide (P-1022), N-[3-(4-Cyano-7H-pyrrolo[2,3-d]pyrimidine-5-carbonyl)-2,4-difluoro-phenyl]-4-trifluoromethyl-benzenesulfonamide (P-1023), N-[2,4-Difluoro-3-(4-methoxy-7H-pyrrolo[2,3-d]pyrimidine-5-carbonyl)-phenyl]-3,5-dimethyl-benzenesulfonamide (P-1025), N-[2,4-Difluoro-3-(4-methyl-7H-pyrrolo[2,3-d]pyrimidine-5-carbonyl)-phenyl]-3,5-dimethyl-benzenesulfonamide (P-1027), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), N-[2,4-Difluoro-3-(4-isopropyl-7H-pyrrolo[2,3-d]pyrimidine-5-carbonyl)-phenyl]-4-trifluoromethyl-benzenesulfonamide (P-1029), N-[2,4-Difluoro-3-(4-hydroxy-7H-pyrrolo[2,3-d]pyrimidine-5-carbonyl)-phenyl]-4-propyl-benzenesulfonamide (P-1030), Propane-1-sulfonic acid [3-(4-chloro-7H-pyrrolo[2,3-d]pyrimidine-5-carbonyl)-2,4-difluoro-phenyl]-amide (P-1033), N-[3-(4-Chloro-7H-pyrrolo[2,3-d]pyrimidine-5-carbonyl)-2,4-difluoro-phenyl]-4-propyl-benzenesulfonamide (P-1034), N-[2,4-Difluoro-3-(4-methyl-7H-pyrrolo[2,3-d]pyrimidine-5-carbonyl)-phenyl]-3-fluoro-4-methoxy-benzenesulfonamide (P-1036), N-[3-(4-Ethoxy-7H-pyrrolo[2,3-d]pyrimidine-5-carbonyl)-2,4-difluoro-phenyl]-4-propyl-benzenesulfonamide (P-1038), N-[3-(4-Cyclopropylmethoxy-7H-pyrrolo[2,3-d]pyrimidine-5-carbonyl)-2,4-difluoro-phenyl]-4-trifluoromethyl-benzenesulfonamide (P-1053), N-[2,4-Difluoro-3-(4-hydroxy-7H-pyrrolo[2,3-d]pyrimidine-5-carbonyl)-phenyl]-2-fluoro-benzenesulfonamide (P-1070), N-[3-(4-Chloro-7H-pyrrolo[2,3-d]pyrimidine-5-carbonyl)-2,4-difluoro-phenyl]-2-fluoro-benzenesulfonamide (P-1071), N-[3-(4-Cyclopropyl-7H-pyrrolo[2,3-d]pyrimidine-5-carbonyl)-2,4-difluoro-phenyl]-2,5-difluoro-benzenesulfonamide (P-1107), N-[3-(4-Cyclopropylmethoxy-7H-pyrrolo[2,3-d]pyrimidine-5-carbonyl)-2,4-difluoro-phenyl]-2,5-difluoro-benzenesulfonamide (P-1181), N-[2,4-Difluoro-3-(4-isopropyl-7H-pyrrolo[2,3-d]pyrimidine-5-carbonyl)-phenyl]-2,5-difluoro-benzenesulfonamide (P-1182), N-[2,4-Difluoro-3-(4-hydroxy-7H-pyrrolo[2,3-d]pyrimidine-5-carbonyl)-phenyl]-2,5-difluoro-benzenesulfonamide (P-1183), N-[3-(4-Chloro-7H-pyrrolo[2,3-d]pyrimidine-5-carbonyl)-2,4-difluoro-phenyl]-2,5-difluoro-benzenesulfonamide (P-1184), Propane-1-sulfonic acid [2,4-difluoro-3-(4-trifluoromethyl-1H-pyrrolo[2,3-b]pyridine-3-carbonyl)-phenyl]-amide (P-2015), N-[2,4-Difluoro-3-(4-trifluoromethyl-1H-pyrrolo[2,3-b]pyridine-3-carbonyl)-phenyl]-4-trifluoromethyl-benzenesulfonamide (P-2016), N-[2,4-Difluoro-3-(4-trifluoromethyl-1H-pyrrolo[2,3-b]pyridine-3-carbonyl)-phenyl]-benzenesulfonamide (P-2017), and any pharmaceutically acceptable salt thereof.

In one embodiment of the fourth aspect the compound is selected from the group consisting of:

N-[2,4-Difluoro-3-(4-methyl-7H-pyrrolo[2,3-d]pyrimidine-5-carbonyl)-phenyl]-4-trifluoromethyl-benzenesulfonamide (P-1001), N-[2,4-Difluoro-3-(4-methoxy-7H-pyrrolo[2,3-d]pyrimidine-5-carbonyl)-phenyl]-4-propyl-benzenesulfonamide (P-1005), N-[3-(4-Ethoxy-7H-pyrrolo[2,3-d]pyrimidine-5-carbonyl)-2,4-difluoro-phenyl]-4-trifluoromethyl-benzenesulfonamide (P-1006), N-[2,4-Difluoro-3-(4-methyl-7H-pyrrolo[2,3-d]pyrimidine-5-carbonyl)-phenyl]-4-propyl-benzenesulfonamide (P-1007), N-[2,4-Difluoro-3-(4-hydroxy-7H-pyrrolo[2,3-d]pyrimidine-5-carbonyl)-phenyl]-4-trifluoromethyl-benzenesulfonamide (P-1012), Propane-1-sulfonic acid [2,4-difluoro-3-(4-isobutyl-7H-pyrrolo[2,3-d]pyrimidine-5-carbonyl)-phenyl]amide (P-1014), N-[2,4-Difluoro-3-(4-isobutyl-7H-pyrrolo[2,3-d]pyrimidine-5-carbonyl)-phenyl]-4-trifluoromethyl-benzenesulfonamide (P-1015), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), N-[2,4-Difluoro-3-(4-isopropyl-7H-pyrrolo[2,3-d]pyrimidine-5-carbonyl)-phenyl]-4-trifluoromethyl-benzenesulfonamide (P-1029), N-[3-(4-Chloro-7H-pyrrolo[2,3-d]pyrimidine-5-carbonyl)-2,4-difluoro-phenyl]-4-propyl-benzenesulfonamide (P-1034), N-[3-(4-Ethoxy-7H-pyrrolo[2,3-d]pyrimidine-5-carbonyl)-2,4-difluoro-phenyl]-4-propyl-benzenesulfonamide (P-1038), N-[3-(4-Cyclopropylmethoxy-7H-pyrrolo[2,3-d]pyrimidine-5-carbonyl)-2,4-difluoro-phenyl]-4-trifluoromethyl-benzenesulfonamide (P-1053), N-[2,4-Difluoro-3-(4-trifluoromethyl-1H-pyrrolo[2,3-b]pyridine-3-carbonyl)-phenyl]-4-trifluoromethyl-benzene sulfonamide (P-2016), and any pharmaceutically acceptable salt thereof.

In one embodiment of the fourth aspect the compound is selected from the group consisting of:

N-[2,4-Difluoro-3-(4-methyl-7H-pyrrolo[2,3-d]pyrimidine-5-carbonyl)-phenyl]-4-trifluoromethyl-benzenesulfonamide (P-1001), N-[2,4-Difluoro-3-(4-methoxy-7H-pyrrolo[2,3-d]pyrimidine-5-carbonyl)-phenyl]-4-propyl-benzenesulfonamide (P-1005), N-[3-(4-Ethoxy-7H-pyrrolo[2,3-d]pyrimidine-5-carbonyl)-2,4-difluoro-phenyl]-4-trifluoromethyl-benzenesulfonamide (P-1006), N-[2,4-Difluoro-3-(4-methyl-7H-pyrrolo[2,3-d]pyrimidine-5-carbonyl)-phenyl]-4-propyl-benzenesulfonamide (P-1007), N-[2,4-Difluoro-3-(4-hydroxy-7H-pyrrolo[2,3-d]pyrimidine-5-carbonyl)-phenyl]-4-trifluoromethyl-benzenesulfonamide (P-1012), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), and any pharmaceutically acceptable salt thereof.

In one embodiment of the fourth aspect the compound is selected from the group consisting of:
N-[2,4-Difluoro-3-(4-methyl-7H-pyrrolo[2,3-d]pyrimidine-5-carbonyl)-phenyl]-4-isopropyl-benzenesulfonamide (P-1009),
N-[2,4-Difluoro-3-(4-isobutyl-7H-pyrrolo[2,3-d]pyrimidine-5-carbonyl)-phenyl]-4-trifluoromethyl-benzenesulfonamide (P-1015),
N-[3-(4-Chloro-7H-pyrrolo[2,3-d]pyrimidine-5-carbonyl)-2,4-difluoro-phenyl]-4-trifluoromethyl-benzenesulfonamide (P-1016),
N-{2,4-Difluoro-3-[4-(tetrahydro-pyran-4-yloxy)-7H-pyrrolo[2,3-d]pyrimidine-5-carbonyl]-phenyl}-4-trifluoromethyl-benzenesulfonamide (P-1021),
N-[2,4-Difluoro-3-(4-isopropyl-7H-pyrrolo[2,3-d]pyrimidine-5-carbonyl)-phenyl]-4-trifluoromethyl-benzenesulfonamide (P-1029),
Propane-1-sulfonic acid [3-(4-chloro-7H-pyrrolo[2,3-d]pyrimidine-5-carbonyl)-2,4-difluoro-phenyl]-amide (P-1033),
N-[3-(4-Ethoxy-7H-pyrrolo[2,3-d]pyrimidine-5-carbonyl)-2,4-difluoro-phenyl]-4-propyl-benzenesulfonamide (P-1038), and
any pharmaceutically acceptable salt thereof.

In one embodiment of the fourth aspect the compound is selected from the group consisting of:
Propane-1-sulfonic acid [2,4-difluoro-3-(4-hydroxy-7H-pyrrolo[2,3-d]pyrimidine-5-carbonyl)-phenyl]-amide (P-1022),
N-[2,4-Difluoro-3-(4-hydroxy-7H-pyrrolo[2,3-d]pyrimidine-5-carbonyl)-phenyl]-2-fluoro-benzenesulfonamide (P-1070),
N-[3-(4-Chloro-7H-pyrrolo[2,3-d]pyrimidine-5-carbonyl)-2,4-difluoro-phenyl]-2-fluoro-benzenesulfonamide (P-1071),
N-[3-(4-Cyclopropyl-7H-pyrrolo[2,3-d]pyrimidine-5-carbonyl)-2,4-difluoro-phenyl]-2,5-difluoro-benzenesulfonamide (P-1107),
N-[3-(4-Cyclopropylmethoxy-7H-pyrrolo[2,3-d]pyrimidine-5-carbonyl)-2,4-difluoro-phenyl]-2,5-difluoro-benzenesulfonamide (P-1181),
N-[2,4-Difluoro-3-(4-isopropyl-7H-pyrrolo[2,3-d]pyrimidine-5-carbonyl)-phenyl]-2,5-difluoro-benzenesulfonamide (P-1182), and
any pharmaceutically acceptable salt thereof.

In one embodiment of any of the above aspects and embodiments, the compound includes any prodrug thereof.

In one embodiment of any of the above aspects and embodiments, the compound includes any tautomer thereof.

In one embodiment of any of the above aspects and embodiments, the compound includes any stereoisomer thereof.

In one embodiment of any of the above aspects and embodiments, the compound includes any pharmaceutically acceptable formulation thereof.

In one embodiment of any of the above aspects and embodiments, the compound includes any conjugate thereof.

In one embodiment of any of the above aspects and embodiments, the compound includes any derivative thereof.

In one embodiment of any of the above aspects and embodiments, the compound includes any form thereof.

In reference to compounds described herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds as described herein, i.e. compounds of the invention, it is understood (unless indicated otherwise) that a compound as described herein includes compounds of Formula I including all sub-embodiments thereof, compounds of Formula II including all sub-embodiments thereof, and compounds as listed in the third aspect above, including all sub-embodiments thereof.

In a fifth aspect, methods are provided for treating any Raf protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a sixth aspect, methods are provided for treating any B-Raf protein kinase mediated disease or condition, including any B-Raf mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a seventh aspect, methods are provided for treating any B-Raf V600E mutant protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In an eighth aspect, methods are provided for treating any c-Raf-1 protein kinase mediated disease or condition, including any c-Raf-1 mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a ninth aspect, a compound as described herein is a Raf kinase inhibitor and has an $IC_{50}$ of less than 500 nM, less than 100 nM, less than 50 nM, less than 20 nM, less than 10 nM, less than 5 nM, or less than 1 nM as determined in a generally accepted Raf kinase activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to B-Raf, c-Raf-1, or B-Raf V600E mutant. In some embodiments, a compound as described herein will selectively inhibit one or more Raf kinases relative to one or more other non-Raf kinases. In some embodiments, a compound as described herein will selectively inhibit one Raf kinase relative to one or more other Raf kinases. In some embodiments, the compound as described herein will selectively inhibit a mutation of the Raf kinase relative to the wild type kinase, for example B-Raf V600E mutant relative to wild type B-Raf.

In a tenth aspect, a compound as described herein is a B-Raf V600E inhibitor and has an $IC_{50}$ of less than 500 nM, less than 100 nM, less than 50 nM, less than 20 nM, less than 10 nM, less than 5 nM, or less than 1 nM as determined in a generally accepted B-Raf V600E mutant kinase activity assay. In some embodiments, the compound is selective relative to other protein kinases, such that the ratio of $IC_{50}$ for another kinase assessed comparably, divided by the $IC_{50}$ for B-Raf V600E mutant kinase is >10, also >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the compound is also selective relative to one or more other Raf kinases such that the ratio of $IC_{50}$ for another Raf kinase assessed comparably, divided by the $IC_{50}$ for B-Raf V600E mutant kinase is >10, also >20, also >30, also >40, also >50, also >60, also >70, also >80, also >90, also >100.

In an eleventh aspect, a compound as described herein is a c-Raf-1 inhibitor and has an $IC_{50}$ of less than 500 nM, less than 100 nM, less than 50 nM, less than 20 nM, less than 10 nM, less than 5 nM, or less than 1 nM as determined in a generally accepted c-Raf-1 kinase activity assay. In some embodiments, the compound is selective relative to other protein kinases, such that the ratio of $IC_{50}$ for another kinase assessed comparably, divided by the $IC_{50}$ for c-Raf-1 kinase is >10, also >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the compound is also selective relative to one or more other Raf kinases such that the ratio of $IC_{50}$ for another Raf kinase assessed comparably, divided by the $IC_{50}$ for c-Raf-1 kinase is >10, also >20, also >30, also >40, also >50, also >60, also >70, also >80, also >90, also >100. In some embodiments, a c-Raf-1 inhibitor is selective relative to at least B-Raf and B-Raf V600E. In one embodiment, the c-Raf-1 inhibitor is a compound selected from the group consisting of:

N-[2,4-Difluoro-3-(4-methyl-7H-pyrrolo[2,3-d]pyrimidine-5-carbonyl)-phenyl]-4-isopropyl-benzenesulfonamide (P-1009), N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011), N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013), N-[2,4-Difluoro-3-(4-isobutyl-7H-pyrrolo[2,3-d]pyrimidine-5-carbonyl)-phenyl]-4-trifluoromethyl-benzenesulfonamide (P-1015), N-[3-(4-Chloro-7H-pyrrolo[2,3-d]pyrimidine-5-carbonyl)-2,4-difluoro-phenyl]-4-trifluoromethyl-benzenesulfonamide (P-1016), N-[2,4-Difluoro-3-(4-isobutylamino-7H-pyrrolo[2,3-d]pyrimidine-5-carbonyl)-phenyl]-4-trifluoromethyl-benzenesulfonamide (P-1020), N-{2,4-Difluoro-3-[4-(tetrahydro-pyran-4-yloxy)-7H-pyrrolo[2,3-d]pyrimidine-5-carbonyl]-phenyl}-4-trifluoromethyl-benzenesulfonamide (P-1021), N-[3-(4-Ethylamino-7H-pyrrolo[2,3-d]pyrimidine-5-carbonyl)-2,4-difluoro-phenyl]-4-trifluoromethyl-benzenesulfonamide (P-1024), N-[2,4-Difluoro-3-(4-methylamino-7H-pyrrolo[2,3-d]pyrimidine-5-carbonyl)-phenyl]-4-trifluoromethyl-benzenesulfonamide (P-1026), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), N-[2,4-Difluoro-3-(4-isopropyl-7H-pyrrolo[2,3-d]pyrimidine-5-carbonyl)-phenyl]-4-trifluoromethyl-benzenesulfonamide (P-1029), N-[3-(4-Amino-7H-pyrrolo[2,3-d]pyrimidine-5-carbonyl)-2,4-difluoro-phenyl]-4-trifluoromethyl-benzene sulfonamide (P-1031), N-[2,4-Difluoro-3-(4-propylamino-7H-pyrrolo[2,3-d]pyrimidine-5-carbonyl)-phenyl]-4-trifluoromethyl-benzenesulfonamide (P-1032), N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035), N-[2,4-Difluoro-3-(4-phenylamino-7H-pyrrolo[2,3-d]pyrimidine-5-carbonyl)-phenyl]-4-trifluoromethyl-benzene sulfonamide (P-1037), N-[3-(4-Ethoxy-7H-pyrrolo[2,3-d]pyrimidine-5-carbonyl)-2,4-difluoro-phenyl]-4-propyl-benzenesulfonamide (P-1038), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide (P-1043), N-[2,4-Difluoro-3-(4-isopropylamino-7H-pyrrolo[2,3-d]pyrimidine-5-carbonyl)-phenyl]-4-isopropyl-benzenesulfonamide (P-1044), N-{2,4-Difluoro-3-[4-(tetrahydro-pyran-4-ylamino)-7H-pyrrolo[2,3-d]pyrimidine-5-carbonyl]-phenyl}-4-propyl-benzenesulfonamide (P-1046), Propane-1-sulfonic acid {2,4-difluoro-3-[4-(tetrahydro-pyran-4-ylamino)-7H-pyrrolo[2,3-d]pyrimidine-5-carbonyl]-phenyl}-amide (P-1047), Propane-1-sulfonic acid [2,4-difluoro-3-(4-phenylamino-7H-pyrrolo[2,3-d]pyrimidine-5-carbonyl)-phenyl]-amide (P-1048), N-[3-(4-Dimethylamino-7H-pyrrolo[2,3-d]pyrimidine-5-carbonyl)-2,4-difluoro-phenyl]-4-trifluoromethyl-benzenesulfonamide (P-1049), N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050), N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052), N-{2,4-Difluoro-3-[4-(oxetan-3-ylamino)-7H-pyrrolo[2,3-d]pyrimidine-5-carbonyl]-phenyl}-4-propyl-benzenesulfonamide (P-1056), N-{2,4-Difluoro-3-[4-(1-methyl-1H-pyrazol-4-ylamino)-7H-pyrrolo[2,3-d]pyrimidine-5-carbonyl]-phenyl}-4-trifluoromethyl-benzenesulfonamide (P-1062), N-{3-[4-(1-Ethyl-1H-pyrazol-4-ylamino)-7H-pyrrolo[2,3-d]pyrimidine-5-carbonyl]-2,4-difluoro-phenyl}-4-trifluoromethyl-benzenesulfonamide (P-1063), 4-Cyano-N-[2,4-difluoro-3-(4-isopropylamino-7H-pyrrolo[2,3-d]pyrimidine-5-carbonyl)-phenyl]-benzenesulfonamide (P-1108), N-[2,4-Difluoro-3-(4-isopropylamino-7H-pyrrolo[2,3-d]pyrimidine-5-carbonyl)-phenyl]-4-difluoromethoxy-benzenesulfonamide (P-1110), N-[2,4-Difluoro-3-(4-isopropylamino-7H-pyrrolo[2,3-d]pyrimidine-5-carbonyl)-phenyl]-3-difluoromethoxy-benzenesulfonamide (P-1119), 1-Methyl-1H-pyrazole-4-sulfonic acid [2,4-difluoro-3-(4-isopropylamino-7H-pyrrolo[2,3-d]pyrimidine-5-carbonyl)-phenyl]-amide (P-1121), N-[3-(4-Cyano-5-fluoro-1H-pyrrolo[2,3-b]pyridine-3-carbonyl)-2,4-difluoro-phenyl]-4-trifluoromethyl-benzenesulfonamide (P-2009), N-[3-(5-Chloro-4-cyano-1H-pyrrolo[2,3-b]pyridine-3-carbonyl)-2,4-difluoro-phenyl]-4-trifluoromethyl-benzenesulfonamide (P-2010), N-[2,4-Difluoro-3-(4-trifluoromethyl-1H-pyrrolo[2,3-b]pyridine-3-carbonyl)-phenyl]-benzenesulfonamide (P-2017), and any pharmaceutically acceptable salt thereof.

In one embodiment, the c-Raf-1 inhibitor is a compound selected from the group consisting of:

N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011), N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013), N-[2,4-Difluoro-3-(4-isobutyl-7H-pyrrolo[2,3-d]pyrimidine-5-carbonyl)-phenyl]-4-trifluoromethyl-benzenesulfonamide (P-1015), N-[2,4-Difluoro-3-(4-isobutylamino-7H-pyrrolo[2,3-d]pyrimidine-5-carbonyl)-phenyl]-4-trifluoromethyl-benzenesulfonamide (P-1020), N-[3-(4-Ethylamino-7H-pyrrolo[2,3-d]pyrimidine-5-carbonyl)-2,4-difluoro-phenyl]-4-trifluoromethyl-benzenesulfonamide (P-1024), N-[2,4-Difluoro-3-(4-methylamino-7H-pyrrolo[2,3-d]pyrimidine-5-carbonyl)-phenyl]-4-trifluoromethyl-benzenesulfonamide (P-1026), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), N-[2,4-Difluoro-3-(4-isopropyl-7H-pyrrolo[2,3-d]pyrimidine-5-carbonyl)-phenyl]-4-trifluoromethyl-benzenesulfonamide (P-1029), N-[3-(4-Amino-7H-pyrrolo[2,3-d]pyrimidine-5-carbonyl)-2,4-difluoro-phenyl]-4-trifluoromethyl-benzenesulfonamide (P-1031), N-[2,4-Difluoro-3-(4-propylamino-7H-pyrrolo[2,3-d]pyrimidine-5-carbonyl)-phenyl]-4-trifluoromethyl-benzenesulfonamide (P-1032), N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035), N-[2,4-Difluoro-3-(4-phenylamino-7H-pyrrolo[2,3-d]pyrimidine-5-carbonyl)-phenyl]-4-trifluoromethyl-benzenesulfonamide (P-1037), N-[3-(4-Ethoxy-7H-pyrrolo[2,3-d]pyrimidine-5-carbonyl)-2,4-difluoro-phenyl]-4-propyl-benzenesulfonamide (P-1038), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide (P-1043), N-[2,4-Difluoro-3-(4-isopropylamino-7H-pyrrolo[2,3-d]pyrimidine-5-carbonyl)-phenyl]-4-isopropyl-benzenesulfonamide (P-1044), N-{2,4-Difluoro-3-[4-(tetrahydro-pyran-4-ylamino)-7H-pyrrolo[2,3-d]pyrimidine-5-carbonyl]-phenyl}-4-propyl-benzenesulfonamide (P-1046), N-[3-(4-Dimethylamino-7H-pyrrolo[2,3-d]pyrimidine-5-carbonyl)-2,4-difluoro-phenyl]-4-trifluoromethyl-benzenesulfonamide (P-1049), N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050), N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052), N-{2,4-Difluoro-3-[4-(oxetan-3-ylamino)-7H-pyrrolo[2,3-d]pyrimidine-5-carbonyl]-phenyl}-4-propyl-benzenesulfonamide (P-1056), N-[3-(5-Chloro-4-cyano-1H-pyrrolo[2,3-b]pyridine-3-carbonyl)-2,4-difluoro-phenyl]-4-trifluoromethyl-benzenesulfonamide (P-2010), and any pharmaceutically acceptable salt thereof.

In one embodiment, the c-Raf-1 inhibitor is a compound selected from the group consisting of:

N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011), N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013), N-[2,4-Difluoro-3-(4-isobutylamino-7H-pyrrolo[2,3-d]pyrimidine-5-carbonyl)-phenyl]-4-trifluoromethyl-benzenesulfonamide (P-1020), N-[3-(4-Ethylamino-7H-pyrrolo[2,3-d]pyrimidine-5-carbonyl)-2,4-difluoro-phenyl]-4-trifluoromethyl-benzenesulfonamide (P-1024), N-[2,4-Difluoro-3-(4-methylamino-7H-pyrrolo[2,3-d]pyrimidine-5-carbonyl)-phenyl]-4-trifluoromethyl-benzenesulfonamide (P-1026), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), N-[3-(4-Amino-7H-pyrrolo[2,3-d]pyrimidine-5-carbonyl)-2,4-difluoro-phenyl]-4-trifluoromethyl-benzenesulfonamide (P-1031), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), and any pharmaceutically acceptable salt thereof.

In a twelfth aspect, a compound as described herein is a pan Raf inhibitor, i.e. inhibits each of B-Raf V600E mutant kinase, B-Raf kinase and c-Raf-1 kinase, with an $IC_{50}$ of less than 100 nM, less than 50 nM, less than 20 nM, less than 10 nM, less than 5 nM, or less than 1 nM as determined in each of a generally accepted B-Raf V600E mutant kinase activity assay, B-Raf kinase activity assay, and c-Raf-1 kinase activity assay. In some embodiments, the compounds are effectively equipotent on each of B-Raf V600E, B-Raf and c-Raf-1, i.e. the ratio of $IC_{50}$ for any of B-Raf V600E, B-Raf and c-Raf-1 divided by the $IC_{50}$ for any other of B-Raf V600E, B-Raf and c-Raf-1 (e.g. B-Raf $IC_{50}$ divided by B-Raf V600E $IC_{50}$) is in the range of 10 to 0.1, also 5 to 0.2. In some embodiments, the compound is selective relative to other protein kinases, such that the ratio of $IC_{50}$ for another kinase assessed comparably, divided by the $IC_{50}$ for any of B-Raf V600E, B-Raf and c-Raf-1 is >10, also >20, also >30, also >40, also >50, also >60, also >70, also >80, also >90, also >100, wherein the other protein kinase includes, but is not limited to CSK, Insulin receptor kinase, AMPK, PDGFR or VEGFR. In one embodiment, the pan Raf inhibitor is a compound selected from the group consisting of:

Propane-1-sulfonic acid [2,4-difluoro-3-(4-hydroxy-7H-pyrrolo[2,3-d]pyrimidine-5-carbonyl)-phenyl]-amide (P-1022),
N-[2,4-Difluoro-3-(4-propylamino-7H-pyrrolo[2,3-d]pyrimidine-5-carbonyl)-phenyl]-4-trifluoromethyl-benzenesulfonamide (P-1032),
N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035),
N-[2,4-Difluoro-3-(4-isopropylamino-7H-pyrrolo[2,3-d]pyrimidine-5-carbonyl)-phenyl]-4-trifluoromethyl-benzenesulfonamide (P-1039),
Propane-1-sulfonic acid [3-(4-cyclopropylamino-7H-pyrrolo[2,3-d]pyrimidine-5-carbonyl)-2,4-difluoro-phenyl]-amide (P-1041),
N-[2,4-Difluoro-3-(4-isopropylamino-7H-pyrrolo[2,3-d]pyrimidine-5-carbonyl)-phenyl]-4-ethyl-benzenesulfonamide (P-1042),
Propane-1-sulfonic acid {2,4-difluoro-3-[4-(tetrahydro-pyran-4-ylamino)-7H-pyrrolo[2,3-d]pyrimidine-5-carbonyl]-phenyl}-amide (P-1047),
Propane-1-sulfonic acid [2,4-difluoro-3-(4-phenylamino-7H-pyrrolo[2,3-d]pyrimidine-5-carbonyl)-phenyl]-amide (P-1048),
N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050),
Propane-1-sulfonic acid [2,4-difluoro-3-(4-isopropylamino-7H-pyrrolo[2,3-d]pyrimidine-5-carbonyl)-phenyl]-amide (P-1051),
N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052),
N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide (P-1054),
Propane-1-sulfonic acid {2,4-difluoro-3-[4-(oxetan-3-ylamino)-7H-pyrrolo[2,3-d]pyrimidine-5-carbonyl]-phenyl}-amide (P-1060),
N-{2,4-Difluoro-3-[4-(1-methyl-1H-pyrazol-4-ylamino)-7H-pyrrolo[2,3-d]pyrimidine-5-carbonyl]-phenyl}-4-trifluoromethyl-benzenesulfonamide (P-1062),
Propane-1-sulfonic acid {2,4-difluoro-3-[4-(4-fluoro-phenylamino)-7H-pyrrolo[2,3-d]pyrimidine-5-carbonyl]-phenyl}-amide (P-1065),
N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069),
Propane-1-sulfonic acid {2,4-difluoro-3-[4-(naphthalen-1-ylamino)-7H-pyrrolo[2,3-d]pyrimidine-5-carbonyl]-phenyl}-amide (P-1072),
N-[2,4-Difluoro-3-(4-isopropylamino-7H-pyrrolo[2,3-d]pyrimidine-5-carbonyl)-phenyl]-2-fluoro-benzenesulfonamide (P-1073),
Propane-1-sulfonic acid [3-(4-benzylamino-7H-pyrrolo[2,3-d]pyrimidine-5-carbonyl)-2,4-difluoro-phenyl]-amide (P-1074),
Propane-1-sulfonic acid [2,4-difluoro-3-(4-propylamino-7H-pyrrolo[2,3-d]pyrimidine-5-carbonyl)-phenyl]-amide (P-1075),
Propane-1-sulfonic acid {2,4-difluoro-3-[4-(pyridin-2-ylamino)-7H-pyrrolo[2,3-d]pyrimidine-5-carbonyl]-phenyl}-amide (P-1077),
Propane-1-sulfonic acid {2,4-difluoro-3-[4-(pyridin-3-ylamino)-7H-pyrrolo[2,3-d]pyrimidine-5-carbonyl]-phenyl}-amide (P-1078),
Propane-1-sulfonic acid {3-[4-(cyclopropylmethyl-amino)-7H-pyrrolo[2,3-d]pyrimidine-5-carbonyl]-2,4-difluoro-phenyl}-amide (P-1079),
Propane-1-sulfonic acid [3-(4-cyclopentylamino-7H-pyrrolo[2,3-d]pyrimidine-5-carbonyl)-2,4-difluoro-phenyl]-amide (P-1081),
Propane-1-sulfonic acid [3-(4-ethylamino-7H-pyrrolo[2,3-d]pyrimidine-5-carbonyl)-2,4-difluoro-phenyl]-amide (P-1082),
Propane-1-sulfonic acid {3-[4-(3-dimethylamino-phenylamino)-7H-pyrrolo[2,3-d]pyrimidine-5-carbonyl]-2,4-difluoro-phenyl}-amide (P-1083),
Propane-1-sulfonic acid {3-[4-(3-chloro-phenylamino)-7H-pyrrolo[2,3-d]pyrimidine-5-carbonyl]-2,4-difluoro-phenyl}-amide (P-1084),
Propane-1-sulfonic acid {2,4-difluoro-3-[4-(3-methoxy-phenylamino)-7H-pyrrolo[2,3-d]pyrimidine-5-carbonyl]-phenyl}-amide (P-1085),
Propane-1-sulfonic acid {2,4-difluoro-3-[4-(2-methoxy-ethylamino)-7H-pyrrolo[2,3-d]pyrimidine-5-carbonyl]-phenyl}-amide (P-1086),
Propane-1-sulfonic acid {3-[4-(4-chloro-phenylamino)-7H-pyrrolo[2,3-d]pyrimidine-5-carbonyl]-2,4-difluoro-phenyl}-amide (P-1087),
Propane-1-sulfonic acid [2,4-difluoro-3-(4-isobutylamino-7H-pyrrolo[2,3-d]pyrimidine-5-carbonyl)-phenyl]-amide (P-1088),
Propane-1-sulfonic acid {2,4-difluoro-3-[4-(4-trifluoromethyl-phenylamino)-7H-pyrrolo[2,3-d]pyrimidine-5-carbonyl]-phenyl}-amide (P-1089),
Propane-1-sulfonic acid {2,4-difluoro-3-[4-(6-methoxy-pyridin-3-ylamino)-7H-pyrrolo[2,3-d]pyrimidine-5-carbonyl]-phenyl}-amide (P-1090),
Propane-1-sulfonic acid {2,4-difluoro-3-[4-(3-trifluoromethyl-phenylamino)-7H-pyrrolo[2,3-d]pyrimidine-5-carbonyl]-phenyl}-amide (P-1091),
Propane-1-sulfonic acid [2,4-difluoro-3-(4-m-tolylamino-7H-pyrrolo[2,3-d]pyrimidine-5-carbonyl)-phenyl]-amide (P-1092),
Propane-1-sulfonic acid [2,4-difluoro-3-(4-p-tolylamino-7H-pyrrolo[2,3-d]pyrimidine-5-carbonyl)-phenyl]-amide (P-1093),
Propane-1-sulfonic acid {2,4-difluoro-3-[4-(3-fluoro-phenylamino)-7H-pyrrolo[2,3-d]pyrimidine-5-carbonyl]-phenyl}-amide (P-1094),
Propane-1-sulfonic acid {3-[4-(1-ethyl-piperidin-4-ylamino)-7H-pyrrolo[2,3-d]pyrimidine-5-carbonyl]-2,4-difluoro-phenyl}-amide (P-1095),
Propane-1-sulfonic acid {2,4-difluoro-3-[4-(1-methanesulfonyl-piperidin-4-ylamino)-7H-pyrrolo[2,3-d]pyrimidine-5-carbonyl]-phenyl}-amide (P-1096),
Propane-1-sulfonic acid {3-[4-(1-ethyl-1H-pyrazol-4-ylamino)-7H-pyrrolo[2,3-d]pyrimidine-5-carbonyl]-2,4-difluoro-phenyl}-amide (P-1099),
Propane-1-sulfonic acid {3-[4-(1,3-dimethyl-1H-pyrazol-4-ylamino)-7H-pyrrolo[2,3-d]pyrimidine-5-carbonyl]-2,4-difluoro-phenyl}-amide (P-1100),
Propane-1-sulfonic acid {2,4-difluoro-3-[4-(2-fluoro-4-methoxy-phenylamino)-7H-pyrrolo[2,3-d]pyrimidine-5-carbonyl]-phenyl}-amide (P-1101),
Propane-1-sulfonic acid {2,4-difluoro-3-[4-(1-methyl-1H-pyrazol-4-ylamino)-7H-pyrrolo[2,3-d]pyrimidine-5-carbonyl]-phenyl}-amide (P-1102),
N-[3-(4-Cyclopropylamino-7H-pyrrolo[2,3-d]pyrimidine-5-carbonyl)-2,4-difluoro-phenyl]-2-fluoro-benzenesulfonamide (P-1103), N-[3-(4-Cyclopropylamino-7H-pyrrolo[2,3-d]pyrimidine-5-carbonyl)-2,4-difluoro-phenyl]-2,5-difluoro-benzenesulfonamide (P-1104), Propane-1-sulfonic acid {2,4-difluoro-3-[4-(3-fluoro-5-methoxy-pyridin-2-ylamino)-7H-pyrrolo[2,3-d]pyrimidine-5-carbonyl]-phenyl}-amide (P-1105), N-[3-(4-Cyclopropyl-7H-pyrrolo[2,3-d]pyrimidine-5-carbonyl)-2,4-difluoro-phenyl]-2,5-difluoro-benzenesulfonamide (P-1107), N-[2,4-Difluoro-3-(4-isopropylamino-7H-pyrrolo[2,3-d]pyrimidine-5-carbonyl)-phenyl]-2,5-difluoro-benzenesulfonamide (P-1111), N-[2,4-Difluoro-3-(4-isopropylamino-7H-pyrrolo[2,3-d]pyrimidine-5-carbonyl)-phenyl]-3-fluoro-benzenesulfonamide (P-1115), Piperidine-1-sulfonic acid [2,4-difluoro-3-(4-isopropylamino-7H-pyrrolo[2,3-d]pyrimidine-5-carbonyl)-phenyl]-amide (P-1122), 2-Methyl-propane-1-sulfonic acid [2,4-difluoro-3-(4-isopropylamino-7H-pyrrolo[2,3-d]pyrimidine-5-carbonyl)-phenyl]-amide (P-1126), Pyridine-3-sulfonic acid [2,4-difluoro-3-(4-isopropylamino-7H-pyrrolo[2,3-d]pyrimidine-5-carbonyl)-phenyl]-amide (P-1132), Propane-1-sulfonic acid {3-[4-(benzo[1,2,5]thiadiazol-5-ylamino)-7H-pyrrolo[2,3-d]pyrimidine-5-carbonyl]-2,4-difluoro-phenyl}-amide (P-1134), N-[3-(4-Benzylamino-7H-pyrrolo[2,3-d]pyrimidine-5-carbonyl)-2,4-difluoro-phenyl]-2,5-difluoro-benzenesulfonamide (P-1135), N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136), N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137), N-[3-(4-Ethylamino-7H-pyrrolo[2,3-d]pyrimidine-5-carbonyl)-2,4-difluoro-phenyl]-2,5-difluoro-benzenesulfonamide (P-1138), N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139), N-[2,4-Difluoro-3-(4-isobutylamino-7H-pyrrolo[2,3-d]pyrimidine-5-carbonyl)-phenyl]-2,5-difluoro-benzenesulfonamide (P-1140), N-[2,4-Difluoro-3-(4-m-tolylamino-7H-pyrrolo[2,3-d]pyrimidine-5-carbonyl)-phenyl]-2,5-difluoro-benzenesulfonamide (P-1141), N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142), N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1143), N-[3-(4-Benzylamino-7H-pyrrolo[2,3-d]pyrimidine-5-carbonyl)-2,4-difluoro-phenyl]-2-fluoro-benzenesulfonamide (P-1144), N-{2,4-Difluoro-3-[4-(pyridin-3-ylamino)-7H-pyrrolo[2,3-d]pyrimidine-5-carbonyl]-phenyl}-2-fluoro-benzenesulfonamide (P-1145), N-{3-[4-(Cyclopropylmethyl-amino)-7H-pyrrolo[2,3-d]pyrimidine-5-carbonyl]-2,4-difluoro-phenyl}-2-fluoro-benzenesulfonamide (P-1146), N-[3-(4-Cyclopentylamino-7H-pyrrolo[2,3-d]pyrimidine-5-carbonyl)-2,4-difluoro-phenyl]-2-fluoro-benzenesulfonamide (P-1147), N-[3-(4-Ethylamino-7H-pyrrolo[2,3-d]pyrimidine-5-carbonyl)-2,4-difluoro-phenyl]-2-fluoro-benzenesulfonamide (P-1148), N-{2,4-Difluoro-3-[4-(3-methoxy-phenylamino)-7H-pyrrolo[2,3-d]pyrimidine-5-carbonyl]-phenyl}-2-fluoro-benzenesulfonamide (P-1149), N-{2,4-Difluoro-3-[4-(2-methoxy-ethylamino)-7H-pyrrolo[2,3-d]pyrimidine-5-carbonyl]-phenyl}-2-fluoro-benzenesulfonamide (P-1150), N-[2,4-Difluoro-3-(4-isobutylamino-7H-pyrrolo[2,3-d]pyrimidine-5-carbonyl)-phenyl]-2-fluoro-benzenesulfonamide (P-1151), N-[2,4-Difluoro-3-(4-m-tolylamino-7H-pyrrolo[2,3-d]pyrimidine-5-carbonyl)-phenyl]-2-fluoro-benzenesulfonamide (P-1152), N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide (P-1153), N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide (P-1154), Propane-1-sulfonic acid {2,4-difluoro-3-[4-(1H-indazol-6-ylamino)-7H-pyrrolo[2,3-d]pyrimidine-5-carbonyl]-phenyl}-amide (P-1157), Propane-1-sulfonic acid {2,4-difluoro-3-[4-(1H-indazol-5-ylamino)-7H-pyrrolo[2,3-d]pyrimidine-5-carbonyl]-phenyl}-amide (P-1158), Propane-1-sulfonic acid {2,4-difluoro-3-[4-(4-hydroxy-phenylamino)-7H-pyrrolo[2,3-d]pyrimidine-5-carbonyl]-phenyl}-amide (P-1159), 4-{5-[2,6-Difluoro-3-(propane-1-sulfonylamino)-benzoyl]-7H-pyrrolo[2,3-d]pyrimidin-4-ylamino}-benzoic acid methyl ester (P-1162), Propane-1-sulfonic acid (2,4-difluoro-3-{4-[3-(5-methyl-tetrazol-1-yl)-phenylamino]-7H-pyrrolo[2,3-d]pyrimidine-5-carbonyl}-phenyl)-amide (P-1171), Propane-1-sulfonic acid {2,4-difluoro-3-[4-(2-oxo-2,3-dihydro-1H-benzoimidazol-5-ylamino)-7H-pyrrolo[2,3-d]pyrimidine-5-carbonyl]-phenyl}-amide (P-1177), Propane-1-sulfonic acid (2,4-difluoro-3-{4-[3-(5-methyl-[1,3,4]oxadiazol-2-yl)-phenylamino]-7H-pyrrolo[2,3-d]pyrimidine-5-carbonyl}-phenyl)-amide (P-1179), N-[3-(4-Cyclopropylmethoxy-7H-pyrrolo[2,3-d]pyrimidine-5-carbonyl)-2,4-difluoro-phenyl]-2,5-difluoro-benzenesulfonamide (P-1181), N-[2,4-Difluoro-3-(4-isopropyl-7H-pyrrolo[2,3-d]pyrimidine-5-carbonyl)-phenyl]-2,5-difluoro-benzenesulfonamide (P-1182), Propane-1-sulfonic acid [3-(4-chloro-5-methyl-1H-pyrrolo[2,3-b]pyridine-3-carbonyl)-2,4-difluoro-phenyl]-amide (P-2001), Propane-1-sulfonic acid [3-(4-chloro-5-methoxy-1H-pyrrolo[2,3-b]pyridine-3-carbonyl)-2,4-difluoro-phenyl-]-amide (P-2002), Propane-1-sulfonic acid [3-(4-cyano-5-fluoro-1H-pyrrolo[2,3-b]pyridine-3-carbonyl)-2,4-difluoro-phenyl]-amide (P-2003), Propane-1-sulfonic acid [3-(4-chloro-5-cyano-1H-pyrrolo[2,3-b]pyridine-3-carbonyl)-2,4-difluoro-phenyl]-amide (P-2004), Propane-1-sulfonic acid [3-(5-cyano-4-methoxy-1H-pyrrolo[2,3-b]pyridine-3-carbonyl)-2,4-difluoro-phenyl]-amide (P-2005), Propane-1-sulfonic acid [3-(5-chloro-4-methoxy-1H-pyrrolo[2,3-b]pyridine-3-carbonyl)-2,4-difluoro-phenyl]-amide (P-2006), Propane-1-sulfonic acid [3-(5-chloro-4-cyano-1H-pyrrolo[2,3-b]pyridine-3-carbonyl)-2,4-difluoro-phenyl]-amide (P-2007),
Propane-1-sulfonic acid [3-(5-chloro-4-methyl-1H-pyrrolo[2,3-b]pyridine-3-carbonyl)-2,4-difluoro-phenyl]-amide (P-2008),
N-[3-(4-Cyano-5-fluoro-1H-pyrrolo[2,3-b]pyridine-3-carbonyl)-2,4-difluoro-phenyl]-4-trifluoromethyl-benzenesulfonamide (P-2009),
N-[3-(5-Chloro-4-cyano-1H-pyrrolo[2,3-b]pyridine-3-carbonyl)-2,4-difluoro-phenyl]-4-trifluoromethyl-benzenesulfonamide (P-2010),
Propane-1-sulfonic acid {2,4-difluoro-3-[4-(tetrahydro-pyran-4-ylamino)-1H-pyrrolo[2,3-b]pyridine-3-carbonyl]-phenyl}-amide (P-2013), and
any pharmaceutically acceptable salt thereof.

In one embodiment, the pan Raf inhibitor is a compound selected from the group consisting of:
Propane-1-sulfonic acid [3-(4-cyclopropylamino-7H-pyrrolo[2,3-d]pyrimidine-5-carbonyl)-2,4-difluoro-phenyl]-amide (P-1041),
N-[2,4-Difluoro-3-(4-isopropylamino-7H-pyrrolo[2,3-d]pyrimidine-5-carbonyl)-phenyl]-4-ethyl-benzenesulfonamide (P-1042),
Propane-1-sulfonic acid [2,4-difluoro-3-(4-isopropylamino-7H-pyrrolo[2,3-d]pyrimidine-5-carbonyl)-phenyl]-amide (P-1051),
N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide (P-1054),
Propane-1-sulfonic acid {2,4-difluoro-3-[4-(oxetan-3-ylamino)-7H-pyrrolo[2,3-d]pyrimidine-5-carbonyl]phenyl}-amide (P-1060),
Propane-1-sulfonic acid [3-(4-chloro-5-methyl-1H-pyrrolo[2,3-b]pyridine-3-carbonyl)-2,4-difluoro-phenyl]-amide (P-2001),
Propane-1-sulfonic acid [3-(4-chloro-5-methoxy-1H-pyrrolo[2,3-b]pyridine-3-carbonyl)-2,4-difluoro-phenyl]-amide (P-2002),
Propane-1-sulfonic acid [3-(4-cyano-5-fluoro-1H-pyrrolo[2,3-b]pyridine-3-carbonyl)-2,4-difluoro-phenyl]-amide (P-2003),
Propane-1-sulfonic acid [3-(4-chloro-5-cyano-1H-pyrrolo[2,3-b]pyridine-3-carbonyl)-2,4-difluoro-phenyl]-amide (P-2004),
Propane-1-sulfonic acid [3-(5-cyano-4-methoxy-1H-pyrrolo[2,3-b]pyridine-3-carbonyl)-2,4-difluoro-phenyl]-amide (P-2005),
Propane-1-sulfonic acid [3-(5-chloro-4-methoxy-1H-pyrrolo[2,3-b]pyridine-3-carbonyl)-2,4-difluoro-phenyl]-amide (P-2006),
Propane-1-sulfonic acid [3-(5-chloro-4-cyano-1H-pyrrolo[2,3-b]pyridine-3-carbonyl)-2,4-difluoro-phenyl]-amide (P-2007),
Propane-1-sulfonic acid [3-(5-chloro-4-methyl-1H-pyrrolo[2,3-b]pyridine-3-carbonyl)-2,4-difluoro-phenyl]-amide (P-2008), and
any pharmaceutically acceptable salt thereof.

In one embodiment, the pan Raf inhibitor is a compound selected from the group consisting of:
N-[2,4-Difluoro-3-(4-propylamino-7H-pyrrolo[2,3-d]pyrimidine-5-carbonyl)-phenyl]-4-trifluoromethyl-benzenesulfonamide (P-1032),
N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035),
N-[2,4-Difluoro-3-(4-isopropylamino-7H-pyrrolo[2,3-d]pyrimidine-5-carbonyl)-phenyl]-4-trifluoromethyl-benzenesulfonamide (P-1039),
Propane-1-sulfonic acid [3-(4-cyclopropylamino-7H-pyrrolo[2,3-d]pyrimidine-5-carbonyl)-2,4-difluoro-phenyl]-amide (P-1041),
N-[2,4-Difluoro-3-(4-isopropylamino-7H-pyrrolo[2,3-d]pyrimidine-5-carbonyl)-phenyl]-4-ethyl-benzenesulfonamide (P-1042),
N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050),
N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052),
N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide (P-1054),
Propane-1-sulfonic acid {2,4-difluoro-3-[4-(oxetan-3-ylamino)-7H-pyrrolo[2,3-d]pyrimidine-5-carbonyl]-phenyl}-amide (P-1060),
N-[3-(5-Chloro-4-cyano-1H-pyrrolo[2,3-b]pyridine-3-carbonyl)-2,4-difluoro-phenyl]-4-trifluoromethyl-benzenesulfonamide (P-2010), and
any pharmaceutically acceptable salt thereof.

In one embodiment, the pan Raf inhibitor is a compound selected from the group consisting of:
Propane-1-sulfonic acid [3-(4-cyclopropylamino-7H-pyrrolo[2,3-d]pyrimidine-5-carbonyl)-2,4-difluoro-phenyl]-amide (P-1041),
Propane-1-sulfonic acid [3-(4-chloro-5-methyl-1H-pyrrolo[2,3-b]pyridine-3-carbonyl)-2,4-difluoro-phenyl]-amide (P-2001),
Propane-1-sulfonic acid [3-(4-chloro-5-methoxy-1H-pyrrolo[2,3-b]pyridine-3-carbonyl)-2,4-difluoro-phenyl]-amide (P-2002),
Propane-1-sulfonic acid [3-(4-cyano-5-fluoro-1H-pyrrolo[2,3-b]pyridine-3-carbonyl)-2,4-difluoro-phenyl]-amide (P-2003),
Propane-1-sulfonic acid [3-(5-cyano-4-methoxy-1H-pyrrolo[2,3-b]pyridine-3-carbonyl)-2,4-difluoro-phenyl]-amide (P-2005),
Propane-1-sulfonic acid [3-(5-chloro-4-cyano-1H-pyrrolo[2,3-b]pyridine-3-carbonyl)-2,4-difluoro-phenyl]-amide (P-2007),
Propane-1-sulfonic acid [3-(5-chloro-4-methyl-1H-pyrrolo[2,3-b]pyridine-3-carbonyl)-2,4-difluoro-phenyl]-amide (P-2008), and
any pharmaceutically acceptable salt thereof.

In one embodiment, the pan Raf inhibitor is a compound selected from the group consisting of:
N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069),
N-[3-(4-Cyclopropylamino-7H-pyrrolo[2,3-d]pyrimidine-5-carbonyl)-2,4-difluoro-phenyl]-2,5-difluoro-benzenesulfonamide (P-1104),
N-[3-(4-Cyclopropyl-7H-pyrrolo[2,3-d]pyrimidine-5-carbonyl)-2,4-difluoro-phenyl]-2,5-difluoro-benzenesulfonamide (P-1107),
N-[2,4-Difluoro-3-(4-isopropylamino-7H-pyrrolo[2,3-d]pyrimidine-5-carbonyl)-phenyl]-2,5-difluoro-benzenesulfonamide (P-1111),
N-[3-(4-Benzylamino-7H-pyrrolo[2,3-d]pyrimidine-5-carbonyl)-2,4-difluoro-phenyl]-2,5-difluoro-benzenesulfonamide (P-1135), N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136),
N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137),
N-[3-(4-Ethylamino-7H-pyrrolo[2,3-d]pyrimidine-5-carbonyl)-2,4-difluoro-phenyl]-2,5-difluoro-benzenesulfonamide (P-1138),
N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139),
N-[2,4-Difluoro-3-(4-isobutylamino-7H-pyrrolo[2,3-d]pyrimidine-5-carbonyl)-phenyl]-2,5-difluoro-benzenesulfonamide (P-1140),
N-[2,4-Difluoro-3-(4-m-tolylamino-7H-pyrrolo[2,3-d]pyrimidine-5-carbonyl)-phenyl]-2,5-difluoro-benzenesulfonamide (P-1141),
N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142),
N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1143),
N-[3-(4-Cyclopropylmethoxy-7H-pyrrolo[2,3-d]pyrimidine-5-carbonyl)-2,4-difluoro-phenyl]-2,5-difluoro-benzenesulfonamide (P-1181),
N-[2,4-Difluoro-3-(4-isopropyl-7H-pyrrolo[2,3-d]pyrimidine-5-carbonyl)-phenyl]-2,5-difluoro-benzenesulfonamide (P-1182), and
any pharmaceutically acceptable salt thereof.

In one embodiment, the pan Raf inhibitor is a compound selected from the group consisting of:
N-[2,4-Difluoro-3-(4-hydroxy-7H-pyrrolo[2,3-d]pyrimidine-5-carbonyl)-phenyl]-2-fluoro-benzenesulfonamide (P-1070),
N-[3-(4-Chloro-7H-pyrrolo[2,3-d]pyrimidine-5-carbonyl)-2,4-difluoro-phenyl]-2-fluoro-benzenesulfonamide (P-1071),
N-[2,4-Difluoro-3-(4-isopropylamino-7H-pyrrolo[2,3-d]pyrimidine-5-carbonyl)-phenyl]-2-fluoro-benzenesulfonamide (P-1073),
N-[3-(4-Cyclopropylamino-7H-pyrrolo[2,3-d]pyrimidine-5-carbonyl)-2,4-difluoro-phenyl]-2-fluoro-benzenesulfonamide (P-1103),
N-[3-(4-Benzylamino-7H-pyrrolo[2,3-d]pyrimidine-5-carbonyl)-2,4-difluoro-phenyl]-2-fluoro-benzenesulfonamide (P-1144),
N-{2,4-Difluoro-3-[4-(pyridin-3-ylamino)-7H-pyrrolo[2,3-d]pyrimidine-5-carbonyl]-phenyl}-2-fluoro-benzenesulfonamide (P-1145),
N-{3-[4-(Cyclopropylmethyl-amino)-7H-pyrrolo[2,3-d]pyrimidine-5-carbonyl]-2,4-difluoro-phenyl}-2-fluoro-benzenesulfonamide (P-1146),
N-[3-(4-Cyclopentylamino-7H-pyrrolo[2,3-d]pyrimidine-5-carbonyl)-2,4-difluoro-phenyl]-2-fluoro-benzenesulfonamide (P-1147),
N-[3-(4-Ethylamino-7H-pyrrolo[2,3-d]pyrimidine-5-carbonyl)-2,4-difluoro-phenyl]-2-fluoro-benzenesulfonamide (P-1148),
N-{2,4-Difluoro-3-[4-(3-methoxy-phenylamino)-7H-pyrrolo[2,3-d]pyrimidine-5-carbonyl]-phenyl}-2-fluoro-benzenesulfonamide (P-1149),
N-{2,4-Difluoro-3-[4-(2-methoxy-ethylamino)-7H-pyrrolo[2,3-d]pyrimidine-5-carbonyl]-phenyl}-2-fluoro-benzenesulfonamide (P-1150),
N-[2,4-Difluoro-3-(4-isobutylamino-7H-pyrrolo[2,3-d]pyrimidine-5-carbonyl)-phenyl]-2-fluoro-benzenesulfonamide (P-1151),
N-[2,4-Difluoro-3-(4-m-tolylamino-7H-pyrrolo[2,3-d]pyrimidine-5-carbonyl)-phenyl]-2-fluoro-benzenesulfonamide (P-1152),
N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide (P-1153),
N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide (P-1154), and
any pharmaceutically acceptable salt thereof.

In a thirteenth aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In a fourteenth aspect, the invention provides methods for treating a disease or condition mediated by one or more Raf kinases (including A-Raf, B-Raf, and c-Raf-1 kinases), including mutations thereof, in a subject in need thereof by administering to the subject an effective amount of a composition including any one or more compound(s) as described herein. In one embodiment, the invention provides methods for treating a disease or condition mediated by one or more Raf kinases, including mutations thereof, by administering to the subject an effective amount of a composition including any one or more compound(s) as described herein in combination with one or more other suitable therapies for treating the disease.

In a fifteenth aspect, the invention provides methods for treating a disease or condition mediated by A-Raf kinase, including any mutations thereof, in a subject in need thereof by administering to the subject an effective amount of a composition including any one or more compound(s) as described herein. In one embodiment, the invention provides methods for treating a disease or condition mediated by A-Raf kinase, including any mutations thereof, by administering to the subject an effective amount of a composition including any one or more compound(s) as described herein in combination with one or more other suitable therapies for treating the disease.

In a sixteenth aspect, the invention provides methods for treating a disease or condition mediated by B-Raf kinase, including any mutations thereof, in a subject in need thereof by administering to the subject an effective amount of a composition including any one or more compound(s) as described herein. In one embodiment, the invention provides methods for treating a disease or condition mediated by B-Raf kinase, including any mutations thereof, by administering to the subject an effective amount of a composition including any one or more compound(s) as described herein in combination with one or more other suitable therapies for treating the disease.

In a seventeenth aspect, the invention provides methods for treating a disease or condition mediated by B-Raf V600E mutant kinase, in a subject in need thereof by administering to the subject an effective amount of a composition including any one or more compound(s) as described herein. In one embodiment, the invention provides methods for treating a disease or condition mediated by B-Raf V600E mutant kinase, by administering to the subject an effective amount of a composition including any one or more compound(s) as described herein in combination with one or more other suitable therapies for treating the disease. In one embodiment, the invention provides methods for treating a cancer mediated by B-Raf V600E mutant by administering to the subject an effective amount of a composition including any one or more compound(s) as described herein. In one embodiment, the invention provides methods for treating a cancer mediated by B-Raf V600E mutant by administering to the subject an effective amount of a composition including any one or more compound(s) as described herein in combination with one or more suitable anticancer therapies, such as one or more chemotherapeutic drugs.

In an eighteenth aspect, the invention provides methods for treating a disease or condition mediated by c-Raf-1 kinase, including any mutations thereof, in a subject in need thereof by administering to the subject an effective amount of a composition including any one or more compound(s) as described herein. In one embodiment, the invention provides methods for treating a disease or condition mediated by c-Raf-1 kinase, including any mutations thereof, by administering to the subject an effective amount of a composition including any one or more compound(s) as described herein in combination with one or more other suitable therapies for treating the disease.

In a nineteenth aspect, the invention provides a method of treating a cancer in a subject in need thereof by administering to the subject an effective amount of a composition including any one or more compound(s) as described herein. In one embodiment, the invention provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, y-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a twentieth aspect, the invention provides a pharmaceutical composition including a compound and another drug/agent, wherein the compound used in the combination includes those as described herein, for example, as defined in the claims and described in Formula I, Formula II, Formula III, Formula IIIa, Table I, or Table II. The invention further provides a method for treating a Raf protein kinase mediated disease or condition in a subject in need thereof, said method comprising administering to said subject an effective amount of a compound and another drug or a pharmaceutically acceptable salt thereof, wherein the compound used in the combination includes those as described herein, for example, as defined in the claims and described in Formula I, Formula II, Formula III, Formula IIIa, Table I, or Table II. In some embodiments, the invention provides a composition for, or a method of, treating a cancer in a subject in need thereof by administering to the subject an effective amount of a composition including any one or more compound(s) as described herein in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib). Preferably, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a twenty-first aspect, the invention provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug. The compound can be alone or can be part of a composition. In one embodiment, the invention provides a method of treating a disease or condition in a subject, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In a twenty-second aspect, the invention provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit includes written instructions for use and/or other indication that the compound or composition is suitable or approved for administration to a mammal, e.g., a human, for a Raf protein kinase-mediated disease or condition; and the compound or composition is packaged in unit dose or single dose form, e.g., single dose pills, capsules, or the like.

In aspects and embodiments involving treatment of a disease or condition with any one or more compound(s) as described herein, the invention provides methods for treating an A-Raf-mediated, B-Raf-mediated and/or c-Raf-1-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal A-Raf, B-Raf, and/or c-Raf-1 activity (e.g. kinase activity). In some embodiments, invention methods may involve administering to the subject suffering from or at risk of an A-Raf-mediated, B-Raf-mediated and/or c-Raf-1-mediated disease or condition an effective amount of any one or more Raf inhibitor(s) as described herein. In one embodiment, the A-Raf-mediated, B-Raf-mediated, and/or c-Raf-1-mediated disease is selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori, Hepatitis* and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In aspects and embodiments involving treatment of a disease or condition with any one or more compound(s) as described herein, the invention provides methods for treating a c-Raf-1-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal c-Raf-1 activity (e.g. kinase activity). In some embodiments, invention methods may involve administering to the subject suffering from or at risk of a c-Raf-1-mediated disease or condition an effective amount of any one or more c-Raf-1 inhibitor(s) as described herein. In one embodiment, the c-Raf-1-mediated disease is selected from the group consisting of polycystic kidney disease, acute pain, and chronic pain.

In aspects and embodiments involving treatment of a disease or condition with any one or more compound(s) as described herein, the invention provides methods for treating a B-Raf V600E mutant-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal B-Raf V600E mutant activity (e.g. kinase activity). In some embodiments, invention methods may involve administering to the subject suffering from or at risk of a B-Raf V600E mutant-mediated disease or condition an effective amount of any one or more B-Raf V600E inhibitor(s) as described herein. In one embodiment, B-Raf V600E mutant-mediated disease is a cancer, preferably a cancer selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma.

In aspects and embodiments involving treatment of a disease or condition with any one or more compound(s) as described herein, the invention provides methods for treating a cancer in a subject in need thereof (e.g. a mammal such as a human, other primates, sports animals, animals of commercial interest such as cattle, farm animals such as horses, or pets such as dogs and cats). In some embodiments, invention methods may involve administering to the subject suffering from or at risk of a cancer an effective amount of any one or more pan Raf inhibitor(s) as described herein, wherein the cancer is selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

In a twenty-third aspect, any one or more compound(s) as described herein can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, *Hepatitis* and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, pain, and polycystic kidney disease. In a preferred embodiment, the disease or condition is selected from the group consisting of melanoma, glioma, glioblastoma multiforme, pilocytic astrocytoma colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In a twenty-fourth aspect, any one or more c-Raf-1 inhibitor(s) as described herein can be used in the preparation of a medicament for the treatment of a c-Raf-1-mediated disease or condition selected from the group consisting of acute pain, chronic pain, and polycystic kidney disease.

In a twenty-fifth aspect, any one or more B-Raf V600E inhibitor(s) as described herein can be used in the preparation of a medicament for the treatment of a B-Raf-V600E-mediated disease or condition selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma.

In a twenty-sixth aspect, any one or more pan Raf inhibitor(s) as described herein can be used in the preparation of a medicament for the treatment of a cancer selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

In various aspects and embodiments, a compound as disclosed herein (including any compounds of Formula I, Formula II, Formula III, Formula IIIa, Table I, Table II, or any other compounds specifically disclosed herein) is a pan Raf inhibitor. In various aspects and embodiments, a compound as disclosed herein (including any compounds of Formula I, Formula II, Formula III, Formula IIIa, Table I, Table II, or any other compounds specifically disclosed herein) is a Ras activity inhibitor. In some embodiments, a compound as disclosed herein (including any compounds of Formula I, Formula II, Formula III, Formula IIIa, Table I, Table II, or any other compounds specifically disclosed herein) is both a pan Raf inhibitor and a Ras activity inhibitor. In certain embodiments, a compound as disclosed herein (including any compounds of Formula I, Formula II, Formula III, Formula Ma, Table I, Table II or any other compounds specifically disclosed herein) is a pan Raf inhibitor having an $IC_{50}$ of less than 500 nM in activity assays for each of B-Raf, c-Raf-1 and B-Raf V600E protein kinases and is a Ras activity inhibitor that inhibits proliferation of a mutant Ras cell line with an $IC_{50}$ of less than 1 μM.

In another aspect, the invention provides an intermediate compound of Formulas IVa and IVb:

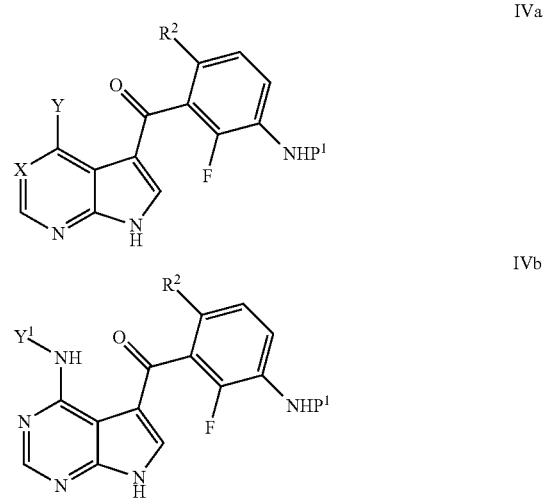

wherein $P^1$ is independently H or an amino protecting group. In one embodiment, $P^1$ is H. In another embodiment, $P^1$ is t-butoxycarbonyl or benzyloxycarbonyl. In another embodiment, X is —N=, —CH=, —C(CH₃)=, —C(OCH₃)=, —C(F)=, —C(CN)=, —C(CH₂OH)= or C(Cl)=. In certain instances, X is CH=. In other instances, X is —N=. The other substituents X, Y, $Y^1$ and $R^2$ are as defined in any of the embodiments for compounds of Formulas I, II, III and Ma described herein.

In another aspect, the invention provides a method for preparing a compound of Formula I

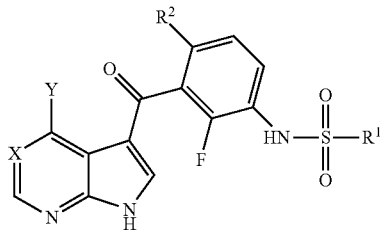
I

The method includes contacting a compound of Formula IVc:

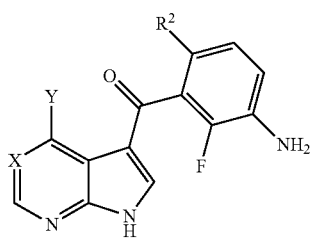
IVc with a compound of Formula V:

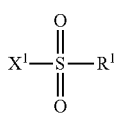
V under conditions sufficient to form the compound of Formula I, wherein $X^1$ is a halogen, such as Cl, Br or I, the other variables $R^1$, $R^2$, X and Y are as defined in any of the embodiments for compounds of Formulas I, II, III and IIIa described herein and in the Examples below. In some embodiments, X is —N═, —CH═, —C(CH$_3$)═, —C(OCH$_3$)═, —C(F)═, —C(CN)═, —C(CH$_2$OH)═ or C(Cl)═. In a preferred embodiment, $R^1$ is 2-fluorophenyl, 3-fluorophenyl, 2,5-difluorophenyl or 4-lower alkyl-substituted phenyl, wherein lower alkyl is optionally substituted with one or more fluorine.

In some embodiments, the invention provides a method for preparing a compound of Formula II:

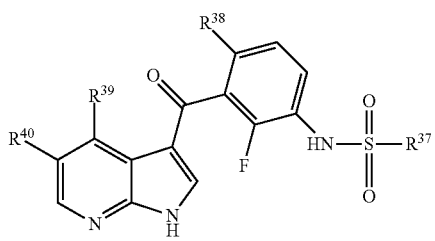
II

The method includes contacting a compound of Formula IVd:

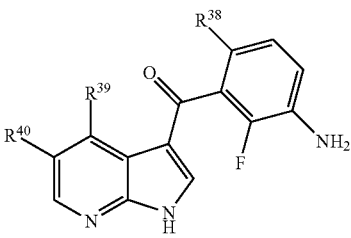
IVd with a compound of Formula Va:

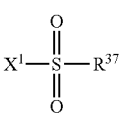
Va under conditions suitable to form the compound of Formula I, wherein $X^1$ is a halogen, such as Cl, Br or I, the other variables $R^{37}$, $R^{38}$, $R^{39}$ and $R^{40}$ are as defined in any of the embodiments for compounds of Formulas II described herein and in the Examples below. In a preferred embodiment, $R^{37}$ is 2-fluorophenyl, 3-fluorophenyl, 2,5-difluorophenyl or 4-lower alkyl-substituted phenyl, wherein lower alkyl is optionally substituted with one or more fluorine.

In some embodiments, the invention provides a method for preparing a compound of Formula IIIa:

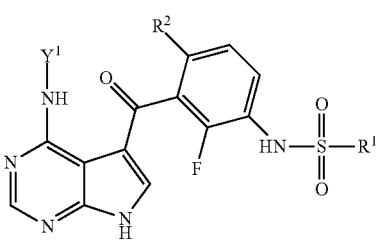
IIIa

The method includes contacting a compound of Formula IVe:

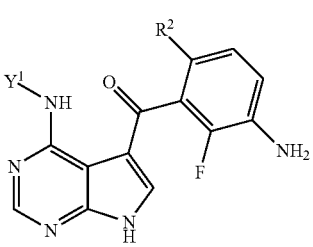
IVe with a compound of Formula V:

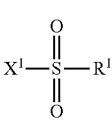
V under conditions sufficient to form the compound of Formula I, wherein $X^1$ is a halogen, such as Cl, Br or I, the other variables $Y^1$, $R^1$ and $R^2$ are as defined in any of the embodiments above for compounds of Formulas I and IIIa and in the Examples below. In a preferred embodiment, $R^1$ is 2-fluorophenyl, 3-fluorophenyl, 2,5-difluorophenyl or 4-lower alkyl-substituted phenyl, wherein lower alkyl is optionally substituted with one or more fluorine.

Additional aspects and embodiments will be apparent from the following Detailed Description of the Invention and from the claims.

DETAILED DESCRIPTION OF THE INVENTION

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" refer to all halogens, that is, chloro (Cl), fluoro (F), bromo (Br), or iodo (I).

"Haloalkyl or Halogen substituted lower alkyl" includes alkyl substituted by one to seven halogen atoms. Haloalkyl includes monohaloalkyl and polyhaloalkyl. For example, the term "haloalkyl" is meant to include trifluoromethyl, $CF_3CH_2$—, $CF_2HCH_2$—, 2,2,2-trifluoroethyl, 4-chlorobutyl, 3-bromopropyl, and the like.

"Haloalkoxy" refers to a —OR radical where R is haloalkyl group as defined above, e.g., trifluoromethoxy, 2,2,2-trifluoroethoxy, difluoromethoxy, and the like.

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A lower alkyl may be independently substituted as described herein, unless indicated otherwise, with one or more, preferably 1, 2, 3, 4 or 5, also 1, 2, or 3 substituents, wherein the substituents are as indicated. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that any such substitutions, or substitution of lower alkyl on another moiety, are chemically feasible and attached at any available atom to provide a stable compound.

"Alkylene" by itself or as part of another substituent means a linear or branched saturated divalent hydrocarbon radical derived from an alkane having the number of carbon atoms indicated in the prefix. For example, $(C_1-C_6)$alkylene is meant to include methylene, ethylene, propylene, 2-methylpropylene, pentylene, hexylene, and the like. Typically, an alkyl (or alkylene) group will have from 1 to 24 carbon atoms, with those groups having 10, 8, 6, 4 or fewer carbon atoms being preferred in the present invention. When a prefix is not included to indicate the number of carbon atoms in an alkyl or alkylene portion, the radical or portion thereof will have 8 or fewer main chain carbon atoms or 6 or fewer main chain carbon atoms or 4 or fewer main chain carbon atoms.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, wherein the substituents are as indicated. For example "lower alkenyl optionally substituted with C(O)—O—$R^{28}$" denotes a lower alkenyl group that may be substituted with a carboxylic acid moiety, i.e. C(O)—O—$R^{28}$ is substituted on the alkenyl group, where the carbon of C(O)—O—$R^{28}$ is bound to a carbon of the alkenyl group. It is understood that any such substitutions, or substitution of lower alkenyl on another moiety, are chemically feasible and attached at any available atom to provide a stable compound.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, wherein the substituents are as indicated. For example "lower alkynyl optionally substituted with $R^9$" denotes a lower alkynyl group that may be substituted with a substituent $R^9$. It is understood that any such substitutions, or substitution of lower alkynyl on another moiety, are chemically feasible and attached at any available atom to provide a stable compound.

"Cycloalkyl" refers to saturated or unsaturated, non-aromatic monocyclic carbon ring systems of 3-10, also 3-8, more preferably 3-6, ring members per ring, such as cyclopropyl, cyclopentyl, cyclohexyl, cycloheptyl, and the like. A "substituted cycloalkyl" is a cycloalkyl that is independently substituted, unless indicated otherwise, with one or more, preferably 1, 2, 3, 4 or 5, also 1, 2, or 3 substituents, wherein the substituents are as indicated. It is understood that substitutions on cycloalkyl, or substitution of cycloalkyl on another moiety, are chemically feasible and attached at any available atom to provide a stable compound.

"Cycloalkylalkyl" refers to a -(alkylene)-R radical, where R is cycloalkyl as defined above, e.g., cyclopropylmethyl, cyclobutylethyl, cyclobutylmethyl, and the like.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, dihydroindolyl, imidazolidinyl, pyrazolidinyl, butyrolactam radical, valerolactam radical, imidazolidinone radical, hydantoin, dioxolane radical, phthalimide radical, 1,4-dioxane radical, thiomorpholinyl, thiomorpholinyl-S-oxide, thiomorpholinyl-S,S-oxide, piperazinyl, pyranyl, 3-pyrrolinyl, thiopyranyl, pyrone radical, tetrahydrothiophenyl, quinuclidinyl, and the like. A "substituted heterocycloalkyl" is a heterocycloalkyl that is independently substituted, unless indicated otherwise, with one or more, preferably 1, 2, 3, 4 or 5, also 1, 2, or 3 substituents, wherein the substituents are as indicated. It is understood that substitutions on heterocycloalkyl, or substitution of heterocycloalkyl on another moiety, are chemically feasible and attached at any available atom to provide a stable compound. "Heteroycloalkylalkyl" refers to a -(alkylene)-R radical, where R is heterocycloalkyl as defined herein.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. A "substituted aryl" is an aryl that is independently substituted, unless indicated otherwise, with one or more, preferably 1, 2, 3, 4 or 5, also 1, 2, or 3 substituents, wherein the substituents are as indicated. It is understood that substitutions on aryl, or substitution of aryl on another moiety, are chemically feasible and attached at any available atom to provide a stable compound.

"Aralkyl" refers to a -(alkylene)-R radical, where R is aryl as defined above e.g., benzyl, phenethyl, and the like.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, quinoaxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A "substituted heteroaryl" is a heteroaryl that is independently substituted, unless indicated otherwise, with one or more, preferably 1, 2, 3, 4 or 5, also 1, 2, or 3 substituents, wherein the substituents are as indicated. It is understood that substitutions on heteroaryl, or substitution of heteroaryl on another moiety, are chemically feasible and attached at any available atom to provide a stable compound.

"Heteroarylalkyl" refers to a radical -(alkylene)-R, where R is a heteroaryl group as defined herein. Examples of heteroarylalkyl include 2-pyridylmethyl, 2-thiazolylethyl, 4H, 1,2,4-triazolylethyl, and the like.

"Lower alkoxy" denotes the group —$OR^a$, where $R^a$ is lower alkyl. "Substituted lower alkoxy" denotes lower alkoxy in which $R^a$ is lower alkyl substituted with one or more substituents as indicated herein. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy, or substitution of alkoxy on another moiety, are chemically feasible and attached at any available atom to provide a stable compound.

"Lower alkylthio" denotes the group —$SR^b$, where $R^b$ is lower alkyl. "Substituted lower alkylthio" denotes lower alkylthio in which $R^b$ is lower alkyl substituted with one or more substituents as indicated herein. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio, or substitution of alkylthio on another moiety, are chemically feasible and attached at any available atom to provide a stable compound.

As used herein, "one or more substituents" specifically contemplates, inter alia, from one to seven, more preferably from one to five, even more preferably from one to three substituents on a particular group so as to satisfy the valence thereof. For example, the number of substituents can be 1, 2, 3, 4, 5, 6 or 7.

"Mono-alkylamino" denotes the group —$NHR^c$ where $R^c$ is lower alkyl. "Di-alkylamino" denotes the group —$NR^cR^d$, where $R^c$ and $R^d$ are independently lower alkyl. "Cycloalkylamino" denotes the group —$NR^eR^f$, where $R^e$ and $R^f$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

As used herein "Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), CURRENT PROTOCOLS IN NUCLEIC ACID CHEMISTRY, John Wiley and Sons, New York, Volume 1, 2000).

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "Raf protein kinase mediated disease or condition" refers to a disease or condition in which the biological function of a Raf protein kinase (also referred to as Raf kinase, or Raf), including any of A-Raf protein kinase, B-Raf protein kinase or c-Raf-1 protein kinase, or any mutation thereof, affects the development, course, and/or symptoms of the disease or condition, and/or in which modulation of Raf alters the development, course, and/or symptoms of the disease or condition. The Raf mediated disease or condition includes a disease or condition for which Raf modulation provides a therapeutic benefit, e.g. wherein treatment with Raf inhibitor(s), including one or more compound(s) described herein, provides a therapeutic benefit to the subject suffering from or at risk of the disease or condition.

As used herein, the term "A-Raf protein kinase mediated disease or condition," and the like refer to a disease or condition in which the biological function of an A-Raf protein kinase (also referred to as A-Raf kinase, or A-Raf), including any mutations thereof, affects the development, course, and/or symptoms of the disease or condition, and/or in which modulation of A-Raf alters the development, course, and/or symptoms of the disease or condition. The A-Raf mediated disease or condition includes a disease or condition for which A-Raf inhibition provides a therapeutic benefit, e.g. wherein treatment with a compound that inhibits A-Raf, including one or more compound(s) described herein, provides a therapeutic benefit to the subject suffering from or at risk of the disease or condition.

As used herein, the term "B-Raf protein kinase mediated disease or condition," and the like refer to a disease or condition in which the biological function of a B-Raf protein kinase (also referred to as B-Raf kinase, or B-Raf), including any mutations thereof, affects the development, course, and/or symptoms of the disease or condition, and/or in which modulation of B-Raf alters the development, course, and/or symptoms of the disease or condition. The B-Raf mediated disease or condition includes a disease or condition for which B-Raf inhibition provides a therapeutic benefit, e.g. wherein treatment with a compound that inhibits B-Raf, including one or more compound(s) described herein, provides a therapeutic benefit to the subject suffering from or at risk of the disease or condition.

As used herein, the term "B-Raf V600E mutant protein kinase mediated disease or condition," and the like refer to a disease or condition in which the biological function of B-Raf V600E mutant protein kinase (also referred to as B-Raf V600E kinase, or B-Raf V600E) affects the development, course, and/or symptoms of the disease or condition, and/or in which modulation of B-Raf V600E alters the development, course, and/or symptoms of the disease or condition. The B-Raf V600E mediated disease or condition includes a disease or condition for which B-Raf V600E inhibition provides a therapeutic benefit, e.g. wherein treatment with compound that inhibits B-Raf V600E, including one or more compound(s) described herein, provides a therapeutic benefit to the subject suffering from or at risk of the disease or condition.

As used herein, the term "c-Raf-1 protein kinase mediated disease or condition," and the like refer to a disease or condition in which the biological function of a c-Raf-1 protein kinase (also referred to as c-Raf-1 kinase, or c-Raf-1), including any mutations thereof, affects the development, course, and/or symptoms of the disease or condition, and/or in which modulation of c-Raf-1 alters the development, course, and/or symptoms of the disease or condition. The c-Raf-1 mediated disease or condition includes a disease or condition for which c-Raf-1 inhibition provides a therapeutic benefit, e.g. wherein treatment with compound that inhibits c-Raf-1, including one or more compound(s) described herein, provides a therapeutic benefit to the subject suffering from or at risk of the disease or condition.

As used herein, the term "Raf inhibitor" refers to a compound that inhibits at least one of A-Raf, B-Raf, c-Raf-1, or any mutations thereof, i.e. a compound having an $IC_{50}$ of less than 500 nM, less than 100 nM, less than 50 nM, less than 20 nM, less than 10 nM, less than 5 nM, or less than 1 nM as determined in a generally accepted Raf kinase activity assay. Such compounds are preferably, but not necessarily, selective with respect to other protein kinases, i.e. when compared to another protein kinase, the $IC_{50}$ for the other kinase divided by the $IC_{50}$ for the Raf kinase is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR.

As used herein, the term "c-Raf-1 inhibitor" refers to a compound that inhibits c-Raf-1 protein kinase, i.e. a compound having an $IC_{50}$ of less than 500 nM, less than 100 nM, less than 50 nM, less than 20 nM, less than 10 nM, less than 5 nM, or less than 1 nM as determined in a generally accepted c-Raf-1 kinase activity assay. Such compounds are effective in treating a disease or condition that is c-Raf-1 mediated. Such compounds are preferably, but not necessarily, selective with respect to other protein kinases, i.e. when compared to another protein kinase, the $IC_{50}$ for the other kinase divided by the $IC_{50}$ for c-Raf-1 kinase is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. Such compounds are preferably, but not necessarily, also selective with respect to other Raf protein kinases, i.e. when compared to another Raf protein kinase, the $IC_{50}$ for the other Raf kinase divided by the $IC_{50}$ for c-Raf-1 kinase is >10, also >20, also >30, also >40, also >50, also >60, also >70, also >80, also >90, also >100. Preferably such compounds are at least selective relative to B-Raf and B-Raf V600E. While it is understood that a c-Raf-1 inhibitor may be used to treat any c-Raf-1 mediated disease or condition, the inhibition of c-Raf-1, preferably selective inhibition of c-Raf-1, provides beneficial effects in treating acute pain, chronic pain, and polycystic kidney disease.

As used herein, the term "B-Raf V600E inhibitor" refers to a compound that inhibits B-Raf V600E mutant protein kinase, i.e. a compound having an $IC_{50}$ of less than 500 nM, less than 100 nM, less than 50 nM, less than 20 nM, less than 10 nM, less than 5 nM, or less than 1 nM as determined in a generally accepted B-Raf V600E kinase activity assay. Such compounds are effective in treating a disease or condition that is B-Raf V600E mediated. Such compounds are preferably, but not necessarily, selective with respect to other protein kinases, i.e. when compared to another protein kinase, the $IC_{50}$ for the other kinase divided by the $IC_{50}$ for B-Raf V600E kinase is >10, also >20, also >30, also >40, also >50, also >60, also >70, also >80, also >90, also >100.

Preferably, the compounds are selective relative to other protein kinases including, but not limited to, CSK, Insulin receptor kinase, AMPK, PDGFR or VEGFR. Such compounds are preferably, but not necessarily, also selective with respect to other Raf protein kinases, i.e. when compared to another Raf protein kinase, the $IC_{50}$ for the other Raf kinase divided by the $IC_{50}$ for B-Raf V600E kinase is >10, also >20, also >30, also >40, also >50, also >60, also >70, also >80, also >90, also >100. While it is understood that a B-Raf V600E inhibitor may be used to treat any B-Raf V600E mediated disease or condition, the inhibition of B-Raf V600E provides beneficial effects in treating melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma.

As used herein, the term "pan Raf inhibitor" refers to a compound that inhibits at least each of B-Raf, c-Raf-1 and B-Raf V600E protein kinases, i.e. a compound having an $IC_{50}$ of less than 100 nM, less than 50 nM, less than 20 nM, less than 10 nM, less than 5 nM, or less than 1 nM as determined in a generally accepted B-Raf kinase activity assay, and having an $IC_{50}$ of less than 500 nM, less than 100 nM, less than 50 nM, less than 20 nM, less than 10 nM, less than 5 nM, or less than 1 nM as determined in a comparable generally accepted c-Raf-1 kinase activity assay, and having an $IC_{50}$ of less than 500 nM, less than 100 nM, less than 50 nM, less than 20 nM, less than 10 nM, less than 5 nM, or less than 1 nM as determined in a comparable generally accepted B-Raf V600E kinase activity assay. The pan Raf inhibitor may be, but is not necessarily, approximately equipotent on each of B-Raf, c-Raf-1 and B-Raf V600E. Compounds are considered approximately equipotent on each of B-Raf V600E, B-Raf and c-Raf-1 if the ratio of $IC_{50}$ for any of B-Raf V600E, B-Raf and c-Raf-1 divided by the $IC_{50}$ for any other of B-Raf V600E, B-Raf and c-Raf-1 (e.g. B-Raf $IC_{50}$ divided by B-Raf V600E $IC_{50}$) is in the range of 10 to 0.1, also 5 to 0.2. Such compounds are preferably, but not necessarily, selective with respect to other protein kinases, i.e. when compared to another protein kinase, the $IC_{50}$ for the other kinase divided by the $IC_{50}$ for any of B-Raf, c-Raf-1 or B-Raf V600E is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a pan Raf inhibitor may be used to treat any B-Raf, c-Raf-1 or B-Raf V600E kinase mediated disease or condition, the inhibition of each of B-Raf, c-Raf-1 and B-Raf V600E provides beneficial effects in treating cancers, in particular cancers having a Ras pathway mutation, including, but not limited to, melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. Such compounds are also beneficial in treating B-Raf V600E mediated cancers that become resistant to B-Raf V600E selective inhibitors.

As used herein, the term "Ras activity inhibitor" refers to a compound that inhibits proliferation of a mutant Ras cell line; i.e., a compound that inhibits proliferation of a mutant Ras cell line with an $IC_{50}$ of less than 1 µM, 100 nM, less than 50 nM, less than 20 nM, less than 10 nM, less than 5 nM, or less than 1 nM. In some embodiments, a Ras activity inhibitor inhibits proliferation of a mutant Ras cell line with an $IC_{50}$ of less than 1 µM. In some embodiments, a Ras activity inhibitor inhibits proliferation of a mutant Ras cell line with an $IC_{50}$ of less than 100 nM. In some embodiments, a Ras activity inhibitor inhibits proliferation of a mutant Ras cell line with an $IC_{50}$ of less than 50 nM. In some embodiments, a Ras activity inhibitor inhibits proliferation of a mutant Ras cell line with an $IC_{50}$ of less than 20 nM. In some embodiments, a Ras activity inhibitor inhibits proliferation of a mutant Ras cell line with an $IC_{50}$ of less than 10 nM. In some embodiments, a Ras activity inhibitor inhibits proliferation of a mutant Ras cell line with an $IC_{50}$ of less than 5 nM. In some embodiments, a Ras activity inhibitor inhibits proliferation of a mutant Ras cell line with an $IC_{50}$ of less than 1 nM. In some embodiments the mutant Ras cell line is a N-Ras mutant cell line, a K-Ras mutant cell line, or a H-Ras mutant cell line. In various embodiments a Ras activity inhibitor inhibits proliferation of a mutant N-Ras cell line with an $IC_{50}$ of less than 1 µM, 100 nM, less than 50 nM, less than 20 nM, less than 10 nM, less than 5 nM, or less than 1 nM. In some embodiments, a Ras activity inhibitor inhibits proliferation of a N-Ras mutant cell line with an $IC_{50}$ of less than 1 µM. In some embodiments, a Ras activity inhibitor inhibits proliferation of a N-Ras mutant cell line with an $IC_{50}$ of less than 100 nM. In some embodiments, a Ras activity inhibitor inhibits proliferation of a N-Ras mutant cell line with an $IC_{50}$ of less than 50 nM. In some embodiments, a Ras activity inhibitor inhibits proliferation of a N-Ras mutant cell line with an $IC_{50}$ of less than 20 nM. In some embodiments, a Ras activity inhibitor inhibits proliferation of a N-Ras mutant cell line with an $IC_{50}$ of less than 10 nM. In some embodiments, a Ras activity inhibitor inhibits proliferation of a N-Ras mutant cell line with an $IC_{50}$ of less than 5 nM. In some embodiments, a Ras activity inhibitor inhibits proliferation of a N-Ras mutant cell line with an $IC_{50}$ of less than 1 nM. In certain embodiments, the N-Ras mutant cell line is one or more cell lines selected from the group consisting of M244, M202, M207, SK-MEL-2, IPC-298, S'117, M296, SK-MEL-30, SK-MEL-173, and HL-60. In some embodiments, the N-Ras mutant cell line is one or more cell lines selected from the group consisting of M244, M202, M207, SK-MEL-2, SK-MEL-173, and IPC298. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 1 µM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 100 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 50 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 20 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 10 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 5 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 1 nM. In some embodiments, a Ras activity inhibitor inhibits proliferation of IPC298 cells with an $IC_{50}$ of less than 1 µM. In some embodiments, a Ras activity inhibitor inhibits proliferation of IPC298 cells with an $IC_{50}$ of less than 100 nM. In some embodiments, a Ras activity inhibitor inhibits proliferation of IPC298 cells with an $IC_{50}$ of less than 50 nM. In some embodiments, a Ras activity inhibitor inhibits proliferation of IPC298 cells with an $IC_{50}$ of less than 20 nM. In some embodiments, a Ras activity inhibitor inhibits proliferation of IPC298 cells with an $IC_{50}$ of less than 10 nM. In some embodiments, a Ras activity inhibitor inhibits proliferation of IPC298 cells with an $IC_{50}$ of less than 5 nM. In some embodiments, a Ras activity inhibitor inhibits proliferation of IPC298 cells with an $IC_{50}$ of less than 1 nM.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of a combination of two or more components, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present invention, including the dissolution, absorption and distribution of the compound on administration to a subject. As such, certain solid forms of compounds of the invention, such as amorphous complexes of compounds of the invention, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity (i.e. increasing or decreasing the activity), especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference as it relates to such kinase targets, as well as the following:

A-Raf:

Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf:

Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat. Genet. 2006, 38(3):294-6).

Many cancers associated with dysregulation of the RAS-RAF-ERK pathway, such as cancers having B-Raf V600E mutations or NRAS mutations, may be treated with Raf kinase inhibitors, such as the Pan Raf kinase inhibitors as described herein. The ability of these compounds to inhibit multiple Raf kinase targets, including c-Raf-1, B-Raf, and B-Raf V600E, provides additional benefits for inhibiting activating mutations in this pathway, with such cancers less likely to develop resistance to such inhibitors as they are targeting several points in the pathway. Pan Raf kinase inhibitors as described herein may be useful in treating a variety of cancers, including, but not limited to, melanoma, glioma, glioblastoma mulitforme, pilocytic astrocytoma, carcinoma (e.g. gastrointestinal, liver, biliary tract, bile duct (cholangiocarcinoma), colorectal, lung, brain, bladder, gallbladder, breast, pancreatic, thyroid, kidney, ovarian, adrenocortical, prostate), gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. See McDermott et al., PNAS, 2007, 104(50): 19936-19941; and Jaiswal et al., PLoS One, 2009, 4(5):e5717.

c-Raf-1:

Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). c-Raf-1 inhibitors may also be useful for the treatment of acute myeloid leukemia and myelodysplastic syndromes (Crump, Curr Pharm Des 2002, 8(25):2243-8). c-Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

Raf inhibitors (A-Raf and/or B-Raf and/or c-Raf-1) may be useful in treating A-Raf-mediated, B-Raf-mediated or c-Raf-1-mediated diseases or conditions selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, brain, bladder, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, chronic myelomonocytic leukemia, childhood, acute lymphoblastic leukemia, plasma cell leukemia, multiple myeloma, tumor angiogenesis, gastrointestinal stromal tumors, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, *Hepatitis* and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 7-position of the pyrrolo [2,3-d]pyrimidine ring, the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative Reactions:

Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive Reactions:

Reductive reactions are exemplified without limitation by reactions such as reduction of carbonyl functionalitites, reduction of alcohol functionalities and carbon-carbon double bonds, reduction of nitrogen-containing functional groups, and other reduction reactions.

Reactions without Change in the Oxidation State:

Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, 1 *Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4 aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences,* 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitiates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

Formulations and Administration

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present invention provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

In addition to the disclosures herein, the following non-limiting embodiments are contemplated herein:

1. A compound having the chemical structure of Formula I,

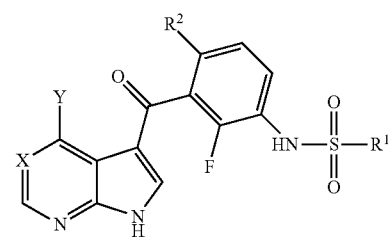

Formula I or a pharmaceutically acceptable salt, hydrate or solvate thereof,
wherein:
X is —N= or —C($R^5$)=;
Y is selected from the group consisting of fluoro, chloro, bromo, iodo, lower alkyl, lower alkoxy, haloalkyl, CN, —OH, cycloalkyl, —$OR^8$, and —N($R^3$)($R^4$); wherein:
$R^3$ is hydrogen and $R^4$ is selected from the group consisting of (i) hydrogen, —$OR^8$ and lower alkyl optionally substituted with one or more $R^{11}$; (ii) cycloalkyl or cycloalkylalkyl, each of which is optionally substituted with one or more $R^{12}$; (iii) heterocycloalkyl or heterocycloalkylalkyl, each of which is optionally substituted with one or more $R^{13}$; (iv) aryl or arylalkyl, each of which is optionally substituted with one or more $R^{14}$, optionally, wherein the two adjacent $R^{14}$ groups on the aryl ring are taken together to form a 5 or 6-membered hetero cyclic aromatic ring having from 1-4 heteroatoms selected from O or N; and (v) heteroaryl or heteroarylalkyl, each of which is optionally substituted with one or more $R^{15}$; or $R^3$ and $R^4$ are both lower alkyl; or $R^3$ and $R^4$ combine with the nitrogen atom to which they are attached to form a 3-7 membered ring having 0-1 additional ring heteroatom selected from O, N or S, wherein the nitrogen or sulfur atom is optionally oxidized;

$R^1$ is selected from the group consisting of lower alkyl, haloalkyl, haloalkoxy, fluoro substituted lower alkyl, cycloalkyl optionally substituted with one or more $R^7$, heterocycloalkyl, mono-alkylamino, di-alkylamino, cycloalkylamino, heterocycloalkylamino, aryl optionally substituted with one or more $R^6$ and heteroaryl optionally substituted with one or more $R^7$;

$R^2$ is hydrogen, fluoro, chloro, or lower alkyl optionally substituted with one or more fluorine;

$R^5$ is selected from the group consisting of hydrogen, fluoro, chloro, —CN, lower alkyl optionally substituted with one or more $R^{16}$, and lower alkoxy optionally substituted with one or more $R^{17}$;

each $R^6$, when present, is independently selected from the group consisting of fluoro, chloro, —CN, —NO$_2$, lower alkyl, fluoro substituted lower alkyl, lower alkoxy, fluoro substituted lower alkoxy, —C(O)—O—$R^{15}$, —N(H)—C(O)—$R^{16}$, and heteroaryl optionally substituted with one or more lower alkyl; or two $R^5$ on adjacent carbons combine to form a fused heterocycloalkyl optionally substituted with one or more lower alkyl;

each $R^7$, when present, is independently selected from the group consisting of lower alkyl, fluoro substituted lower alkyl, lower alkoxy, —C(O)—O—$R^{20}$, and heteroaryl optionally substituted with one or more lower alkyl;

$R^8$ is hydrogen, lower alkyl optionally substituted with one or more fluorine, or, when $R^8$ is a $C_{2-6}$ alkyl, said alkyl may optionally be substituted with one or more $R^{21}$; cycloalkyl optionally substituted with one or more $R^{21}$, or heterocycloalkyl optionally substituted with one or more $R^{21}$;

each $R^{11}$, when present, is independently selected from the group consisting of fluoro, —OH, lower alkoxy, fluoro substituted lower alkoxy, —NH$_2$, mono-alkylamino, di-alkylamino, cycloalkylamino, heterocycloalkylamino, cycloalkyl optionally substituted with one or more $R^{12}$, heterocycloalkyl optionally substituted with one or more $R^{13}$, aryl optionally substituted with one or more $R^{14}$, and heteroaryl optionally substituted with one or more $R^{15}$;

each $R^{12}$, when present, is independently selected from the group consisting of fluoro, lower alkyl, fluoro substituted lower alkyl, —OH, lower alkoxy, fluoro substituted lower alkoxy, —NH$_2$, mono-alkylamino, di-alkylamino, cycloalkylamino, heterocycloalkylamino, —N(H)—C(O)—$R^{22}$, —N(H)—S(O)$_2$—$R^{23}$, C(O)—$R^{24}$, and S(O)$_2$—$R^{25}$;

each $R^{13}$, when present, is independently selected from the group consisting of fluoro, —OH, lower alkoxy, fluoro substituted lower alkoxy, —NH$_2$, mono-alkylamino, di-alkylamino, cycloalkylamino, heterocycloalkylamino, —N(H)—C(O)—$R^{26}$, —N(H)—S(O)$_2$—$R^{27}$, C(O)—$R^{28}$, S(O)$_2$—$R^{29}$, and lower alkyl optionally substituted with one or more $R^{30}$;

each $R^{14}$ and $R^{15}$, when present, are independently selected from the group consisting of fluoro, chloro, —OH, —NH$_2$, —CN, —NO$_2$, —N(H)—C(O)—$R^{31}$, —N(H)—S(O)$_2$—$R^{32}$, C(O)—$R^{33}$, S(O)$_2$—$R^{34}$, lower alkyl, fluoro substituted lower alkyl, lower alkoxy, fluoro substituted lower alkoxy, mono-alkylamino, di-alkylamino, cycloalkylamino, heterocycloalkylamino, aryl optionally substituted with one or more $R^{35}$, and heteroaryl optionally substituted with one or more $R^{36}$;

each $R^{16}$, when present, is independently fluoro, —OH, lower alkoxy, —NH$_2$, mono-alkylamino, di-alkylamino, cycloalkylamino, or heterocycloalkylamino;

each $R^{17}$, when present, is independently fluoro, —OH, lower alkoxy, —NH$_2$, mono-alkylamino, di-alkylamino, cycloalkylamino, or heterocycloalkylamino;

each $R^{18}$ and $R^{20}$, when present, are independently hydrogen, lower alkyl or fluoro substituted lower alkyl;

each $R^{19}$, $R^{22}$, $R^{23}$, $R^{26}$, $R^{27}$, $R^{31}$ and $R^{32}$, when present, are independently lower alkyl or fluoro substituted lower alkyl;

each $R^{21}$, when present, is fluoro, —OH, lower alkoxy, —NH$_2$, mono-alkylamino, di-alkylamino, cycloalkylamino, or heterocycloalkylamino;

each $R^{24}$, $R^{25}$, $R^{28}$, $R^{29}$, $R^{33}$, and $R^{34}$, when present, are independently lower alkyl, fluoro substituted lower alkyl, —OH, lower alkoxy, fluor substituted lower alkoxy, —NH$_2$, mono-alkylamino, di-alkylamino, cycloalkylamino, or heterocycloalkylamino;

each $R^{30}$, when present, is independently fluoro, aryl optionally substituted with one or more $R^{35}$ or heteroaryl optionally substituted with one or more $R^{36}$; and each $R^{35}$ and $R^{36}$, when present, are independently selected from the group consisting of fluoro, chloro, —OH, —NH$_2$, —CN, —NO$_2$, lower alkyl, fluoro substituted lower alkyl, lower alkoxy, fluoro substituted lower alkoxy, mono-alkylamino, di-alkylamino, cycloalkylamino, and heterocycloalkylamino 2. The compound of embodiment 1, wherein:

X is —N= or —C($R^5$)=, wherein $R^5$ is selected from the group consisting of hydrogen, fluoro, chloro, —CN, lower alkyl and lower alkoxy, wherein the lower alkyl or lower alkoxy is optionally substituted with from one or three groups selected from fluoro, —OH, lower alkoxy, —NH$_2$, mono-alkylamino, di-alkylamino, cycloalkylamino, or heterocycloalkylamino;

Y is selected from the group consisting of fluoro, chloro, bromo, iodo, lower alkyl, lower alkoxy, haloalkyl, CN, —OH, cycloalkyl, —O$R^8$, and —N($R^3$)($R^4$); wherein:

$R^3$ is hydrogen and $R^4$ is selected from the group consisting of (i) hydrogen, —O$R^8$ and lower alkyl optionally substituted with from one to three $R^{11}$; (ii) cycloalkyl or cycloalkylalkyl, each of which is optionally substituted with from one to three $R^{12}$; (iii) heterocycloalkyl or heterocycloalkylalkyl, each of which is optionally substituted with from one to three $R^{13}$; (iv) aryl or arylalkyl, each of which is optionally substituted with from one to three $R^{14}$ optionally, wherein the two adjacent $R^{14}$ groups on the aryl ring are taken together to form a 5 or 6-membered heterocyclic aromatic ring having from 1-4 heteroatoms selected from O or N; and (v) heteroaryl or heteroarylalkyl, each of which is optionally substituted with from one to three $R^{15}$; or $R^3$ and $R^4$ are both lower alkyl; or $R^3$ and $R^4$ are combined with the nitrogen atom to which they are attached to form a three to seven membered ring having 0-1 additional ring heteroatom selected from O, N or S, wherein the nitrogen or sulfur atom is optionally oxidized;

$R^1$ is selected from the group consisting of lower alkyl, haloalkyl, haloalkoxy, fluoro substituted lower alkyl, cycloalkyl optionally substituted with from one to three $R^7$, heterocycloalkyl, mono-alkylamino, di-alkylamino, cycloalkylamino, heterocycloalkylamino, aryl optionally substituted with from one to three $R^6$ and heteroaryl optionally substituted with one to three $R^7$;

$R^2$ is hydrogen, fluoro, chloro, or lower alkyl optionally substituted with from one to five fluorine atoms;

each $R^6$, when present, is independently selected from the group consisting of fluoro, chloro, —CN, —NO$_2$, lower alkyl, fluoro substituted lower alkyl, lower alkoxy, fluoro substituted lower alkoxy, —C(O)—O—$R^{15}$, —N(H)—C(O)—$R^{16}$, and heteroaryl optionally substituted with one or more lower alkyl; or two $R^5$ on adjacent carbons combine to form a fused heterocycloalkyl optionally substituted with one or more lower alkyl;

each $R^7$, when present, is independently selected from the group consisting of lower alkyl, fluoro substituted lower alkyl, lower alkoxy, —C(O)—O—$R^{20}$, and heteroaryl optionally substituted with one or more lower alkyl;

$R^8$ is hydrogen, lower alkyl optionally substituted with one or more fluorine, or, when $R^8$ is a $C_{2-6}$ alkyl, said alkyl may optionally be substituted with one or more $R^{21}$; cycloalkyl optionally substituted with one or more $R^{21}$, or heterocycloalkyl optionally substituted with one or more $R^{21}$;

each $R^{11}$, when present, is independently selected from the group consisting of fluoro, —OH, lower alkoxy, fluoro substituted lower alkoxy, —NH$_2$, mono-alkylamino, di-alkylamino, cycloalkylamino, heterocycloalkylamino, cycloalkyl optionally substituted with one or more $R^{12}$, heterocycloalkyl optionally substituted with one or more $R^{13}$, aryl optionally substituted with one or more $R^{14}$, and heteroaryl optionally substituted with one or more $R^{15}$;

each $R^{12}$, when present, is independently selected from the group consisting of fluoro, lower alkyl, fluoro substituted lower alkyl, —OH, lower alkoxy, fluoro substituted lower alkoxy, —NH$_2$, mono-alkylamino, di-alkylamino, cycloalkylamino, heterocycloalkylamino, —N(H)—C(O)—$R^{22}$, —N(H)—S(O)$_2$—$R^{23}$, C(O)—$R^{24}$, and S(O)$_2$—$R^{25}$;

each $R^{13}$, when present, is independently selected from the group consisting of fluoro, —OH, lower alkoxy, fluoro substituted lower alkoxy, —NH$_2$, mono-alkylamino, di-alkylamino, cycloalkylamino, heterocycloalkylamino, —N(H)—C(O)—$R^{26}$, —N(H)—S(O)$_2$—$R^{27}$, C(O)—$R^{28}$, S(O)$_2$—$R^{29}$, and lower alkyl optionally substituted with one or more $R^{30}$;

each $R^{14}$ and $R^{15}$, when present, are independently selected from the group consisting of fluoro, chloro, —OH, —NH$_2$, —CN, —NO$_2$, —N(H)—C(O)—$R^{31}$, —N(H)—S(O)$_2$—$R^{32}$, C(O)—$R^{33}$, S(O)$_2$—$R^{34}$, lower alkyl, fluoro substituted lower alkyl, lower alkoxy, fluoro substituted lower alkoxy, mono-alkylamino, di-alkylamino, cycloalkylamino, heterocycloalkylamino, aryl optionally substituted with one to three $R^{35}$, and heteroaryl optionally substituted with one to three $R^{36}$;

each $R^{18}$ and $R^{20}$, when present, are independently hydrogen, lower alkyl or fluoro substituted lower alkyl;

each $R^{19}$, $R^{22}$, $R^{23}$, $R^{26}$, $R^{27}$, $R^{31}$ and $R^{32}$, when present, are independently lower alkyl or fluoro substituted lower alkyl;

each $R^{21}$, when present, is fluoro, —OH, lower alkoxy, —NH$_2$, mono-alkylamino, di-alkylamino, cycloalkylamino, or heterocycloalkylamino;

each $R^{24}$, $R^{25}$, $R^{28}$, $R^{29}$, $R^{33}$, and $R^{34}$, when present, are independently lower alkyl, fluoro substituted lower alkyl, —OH, lower alkoxy, fluor substituted lower alkoxy, —NH$_2$, mono-alkylamino, di-alkylamino, cycloalkylamino, or heterocycloalkylamino;

each $R^{30}$, when present, is independently fluoro, aryl optionally substituted with one or more $R^{35}$ or heteroaryl optionally substituted with one to three $R^{36}$; and each $R^{35}$ and $R^{36}$, when present, are independently selected from the group consisting of fluoro, chloro, —OH, —NH$_2$, —CN, —NO$_2$, lower alkyl, fluoro substituted lower alkyl, lower alkoxy, fluoro substituted lower alkoxy, mono-alkylamino, di-alkylamino, cycloalkylamino, and heterocycloalkylamino 3. The compound of embodiment 1 or 2, having Formula II:

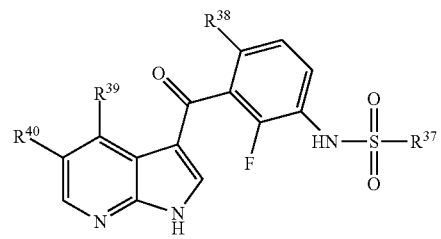

wherein:

$R^{37}$ is selected from the group consisting of lower alkyl, fluoro substituted lower alkyl, cycloalkyl, mono-alkylamino, di-alkylamino, cycloalkylamino, heterocycloalkylamino, phenyl optionally substituted with one or more $R^{41}$ and heteroaryl optionally substituted with one or more $R^{42}$;

$R^{38}$ is hydrogen, fluoro, chloro, or lower alkyl optionally substituted with one or more fluorine;

$R^{39}$ and $R^{40}$ are each independently selected from the group consisting of fluoro, chloro, —CN, —OH, —NH$_2$, lower alkoxy, lower alkyl optionally substituted with one or more $R^{43}$, lower alkenyl optionally substituted with C(O)—O—$R^{44}$, lower alkynyl optionally substituted with lower alkyl optionally substituted with one or more fluorine, or, on a non-alkynyl carbon thereof, $R^{45}$, lower alkoxy optionally substituted with $R^{46}$, mono-alkylamino, di-alkylamino, cycloalkylamino, cycloalkylalkyl-NH—, heterocycloalkylamino and heterocycloalkylalkyl-NH—;

each $R^{41}$, when present, is independently selected from the group consisting of halogen, —CN, —NO$_2$, lower alkyl, fluoro substituted lower alkyl, lower alkoxy, fluoro substituted lower alkoxy, —C(O)—O—$R^{47}$, —N(H)—C(O)—$R^{48}$, and heteroaryl optionally substituted with one or more lower alkyl; or two $R^{41}$ on adjacent carbons combine to form a fused heterocycloalkyl optionally substituted with one or more lower alkyl;

each $R^{42}$, when present, is independently selected from the group consisting of lower alkyl, fluoro substituted lower alkyl, lower alkoxy, fluoro substituted lower alkoxy, —C(O)—O—R$^{49}$, and heteroaryl optionally substituted with one or more lower alkyl;

each R$^{43}$, when present, is independently selected from the group consisting of fluoro, —OH, lower alkoxy, mono-alkylamino, di-alkylamino, cycloalkylamino, and heterocycloalkylamino;

each R$^{44}$, when present, is independently hydrogen or lower alkyl optionally substituted with one or more fluorine;

each R$^{45}$, when present, is independently selected from the group consisting of —OH, lower alkoxy, mono-alkylamino, di-alkylamino, cycloalkylamino, and heterocycloalkylamino;

each R$^{46}$, when present, is independently selected from the group consisting of —OH, lower alkoxy, mono-alkylamino, di-alkylamino, cycloalkylamino, and heterocycloalkylamino;

each R$^{47}$, when present, is independently hydrogen or lower alkyl optionally substituted with one or more fluorine;

each R$^{48}$, when present, is independently lower alkyl optionally substituted with one or more fluorine; and each R$^{49}$, when present, is independently hydrogen or lower alkyl optionally substituted with one or more fluorine.

4. The compound of embodiment 3, wherein R$^{37}$ is lower alkyl, fluoro substituted lower alkyl or phenyl, optionally substituted with from 1-3R$^{41}$ groups.

5. The compound of embodiment 4, wherein R$^{37}$ is lower alkyl, fluoro substituted lower alkyl or phenyl substituted with from 1-3 groups selected from fluoro, chloro, —CN, —NO$_2$, lower alkyl, fluoro substituted lower alkyl, lower alkoxy, fluoro substituted lower alkoxy, —C(O)—O—R$^{47}$ or —N(H)—C(O)—R$^{48}$.

6. The compound of embodiment 5, wherein R$^{37}$ is lower alkyl or phenyl substituted with from 1-2 groups selected from fluoro, chloro, —CN, —NO$_2$, lower alkyl, fluoro substituted lower alkyl, lower alkoxy or fluoro substituted lower alkoxy.

7. The compound of embodiment 3, wherein R$^{38}$ is H, —F or fluoro substituted lower alkyl.

8. The compound of embodiment 3, wherein R$^{39}$ is fluoro, chloro, —CN, —OH, —NH$_2$, lower alkoxy, lower alkyl optionally substituted with one or more R$^{43}$, cycloalkylamino, cycloalkylalkyl-NH—, heterocycloalkylamino and heterocycloalkylalkyl-NH—.

9. The compound of embodiment 3, wherein R$^{40}$ is H, lower alkyl optionally substituted with one or more R$^{43}$, halogen, lower alkoxy or CN.

10. The compound of any of embodiments 3-9, wherein R$^{37}$ is lower alkyl or phenyl optionally substituted with 1-2 members selected from CF$_3$ or halogen.

11. The compound of embodiment 10, wherein R$^{37}$ is propyl, 2-trifluoromethylphenyl, 3-trifluoromethylphenyl, 4-trifluoromethylphenyl, 2-fluorophenyl, 3-fluorophenyl, 4-fluorophenyl or 2,5-difluoro-substituted phenyl.

12. The compound of embodiment 11, wherein R$^{37}$ is propyl, 4-trifluoromethylphenyl, 2-fluorophenyl, 3-fluorophenyl or 2,5-difluoro-substituted phenyl.

13. The compound of any of embodiments 3-9, wherein R$^{38}$ is H, F or CF$_3$.

14. The compound of any of embodiments 3-9, wherein R$^{38}$ is F.

15. The compound of any of embodiments 3-9, wherein R$^{39}$ is fluoro, chloro, —CN, —OH, —NH$_2$, lower alkyl optionally substituted with fluoro, lower alkoxy, cycloalkylamino, cycloalkylalkyl-NH—, heterocycloalkylamino and heterocycloalkylalkyl-NH—.

16. The compound of embodiment 15, wherein R$^{39}$ is fluoro, chloro, —CN, —OH, —NH$_2$, CH$_3$, CH$_3$O—, CF$_3$, cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopentylamino, cyclohexylamino, cyclopropylmethylamino, cyclobutylmethylamino, cyclopentylmethylamino, cyclohexylmethylamino, 2-tetrahydrofuranylamino, 3-tetrahydrofuranylamino or 4-tetrahydropyranylamino.

17. The compound of embodiment 1 or 2, having Formula III:

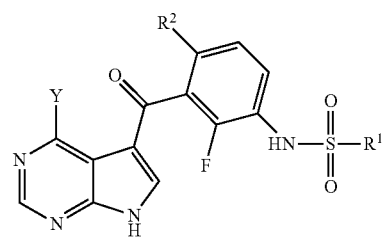

18. The compound of any of embodiments 1, 2 or 17, wherein X is selected from the group consisting of —N═, —CH═, —C(CH$_3$)═, —C(OCH$_3$)═, —C(F)═, —C(CN)═, —C(CH$_2$OH)═ and —C(Cl)═.

19. The compound of any of embodiments 1, 2 or 17, wherein X is —N═, —CH═, —C(CH$_3$)═, —C(F)═ or —C(CN)═.

20. The compound of any of embodiments 1, 2 or 17, wherein X is —N═.

21. The compound of any of embodiments 1, 2 or 17, wherein Y is fluoro, chloro, bromo, iodo, lower alkyl, lower alkoxy, haloalkyl, CN, —OH, cycloalkyl, —OR$^{8}$ or —NH(R$^{4}$).

22. The compound of any of embodiments 1, 2 or 17, wherein Y is CH$_3$, ethyl, methoxy, ethyoxy, isobutyl, CN, OH, F, Cl, Br, I, NH$_2$, butyoxy, 2-methylpropoxy, 4-tetrahydropyranyloxy, 2-tetrahyrofuranyloxy, 3-tetrahyrofuranyloxy, alkoxyamino or HO—NH—.

23. The compound of embodiments 1 or 2, having Formula IIIa:

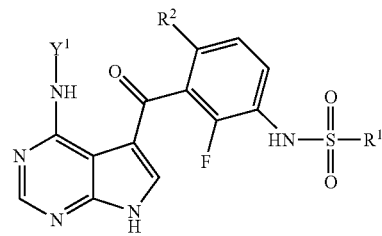

wherein Y$^{1}$ is lower alkyl optionally substituted with from one to three R$^{11}$, cycloalkyl, cycloalkylalkyl, aryl, arylalkyl, heterocycloalkyl, heterocycloalkylalkyl, heteroaryl or heteroarylalkyl, wherein:

(i) the cycloalkyl and cycloalkylalkyl are each optionally substituted with from one to three R$^{12}$;

(ii) the heterocycloalkyl and heterocycloalkylalkyl are each optionally substituted with from one to three $R^{13}$;

(iii) the aryl and arylalkyl are each optionally substituted with from one to three $R^{14}$ optionally, wherein the two adjacent $R^{14}$ groups on the aryl ring are taken together to form a 5 or 6-membered hetero aromatic ring having from 1-4 heteroatoms selected from O or N; and (iv) the heteroaryl and heteroarylalkyl are each optionally substituted with from one to three $R^{15}$.

24. The compound of embodiment 23, wherein $Y^1$ is selected from lower alkyl, halogen substituted lower alkyl, 2-hydroxyethyl, cyclopropylamino, cyclobutyl, cyclopropylmethyl, cyclobutylmethyl, cyclopentyl, cyclopentylmethyl, cyclohexylmethyl, cyclohexyl, 2-oxetanyl, 2-oxetanylmethyl, 3-oxetanyl, 3-oxetanylmethyl, 2-tetrahydrofuranyl, 3-tetrahydrofuranyl, 2-tetrahydropyranyl, 3-tetrahydropyranyl, 4-tetrahydropyranyl, 2-tetrahydrofuranylmethyl, 3-tetrahydrofuranylmethyl, 2-tetrahydropyranylmethyl, 3-tetrahydropyranylmethyl, 4-tetrahydropyranylmethyl, 1-methyl-2-aziridinyl, 1-methyl-2-aziridinylmethyl, 1-methyl-2-azetidinyl, 1-methyl-2-azetidinylmethyl, 1-methyl-3-azetidinyl, 1-methyl-3-azetidinylmethyl, 1-methyl-2-pyrrolidinyl, 1-methyl-2-pyrrolidinylmethyl, 1-methyl-3-pyrrolidinyl, 1-methyl-3-pyrrolidinylmethyl, 1-methyl-2-piperidinyl, 1-methyl-2-piperidinylmethyl, 1-methyl-3-piperidinyl, 1-methyl-3-piperidinylmethyl, 1-methyl-4-piperidinyl, 1-methyl-4-piperidinylmethyl, 1-methylsulfonyl-2-piperidinyl, 1-methylsulfonyl-2-piperidinylmethyl, 1-methylsulfonyl-3-piperidinyl, 1-methylsulfonyl-3-piperidinylmethyl, 1-methylsulfonyl-4-piperidinyl, 1-methylsulfonyl-4-piperidinylmethyl, 1,1-dioxo-4-thianyl, 1,1-dioxo-4-thianylmethyl, phenyl, 2-fluorophenyl, 3-fluorophenyl, 4-fluorophenyl, 2-benzyl, 2-fluorobenzyl, 3 fluorobenzyl, 4-fluorobenzyl, 2-pyridyl, 2-pyridylmethyl, 3-pyridyl, 3-pyridylmethyl, 4-pyridyl, 4-pyridylmethyl, 2-chlorophenyl, 3-chlorophenyl, 4-chlorophenyl, 2-dimethylaminophenyl, 3-dimethylaminophenyl, 4-dimethylaminophenyl, 2-dimethylaminobenzyl, 2-dimethylaminobenzyl, 3-dimethylaminobenzyl, 4-dimethylaminobenzyl, 2-hydroxyphenyl, 3-hydroxyphenyl, 4-hydroxyphenyl, 2-hydroxybenzyl, 3-hydroxybenzyl, 4-hydroxybenzyl, 2-carboxyphenyl, 3-carboxyphenyl, 4-carboxyphenyl, 2-carboxybenzyl, 3-carboxybenzyl, 4-carboxybenzyl, 2-methoxycarbonylphenyl, 3-methoxycarbonylphenyl, 4-methoxycarbonylphenyl, 2-methoxycarbonylbenzyl, 3-methoxycarbonylbenzyl, 4-methoxycarbonylbenzyl, 1-alkyl-4-pyrazolyl, 1-alkyl-4-pyrazolylmethyl, 3-pyridazinyl, pyridazinylmethyl, 4-pyridazinyl, 4-pyridazinylmethyl, triazolyl, triazolymethyl, tetrazolyl, tetrazolymethyl, 2,1,3-benzoxadiazolyl, 2,1,3-benzoxadiazol-5-yl, 2,1,3-benzoxadiazolyl-methyl, 2,1,3-benzoxadiazol-5-ylmethyl, 2,1,3-benzothiadiazolyl, 2,1,3-benzothiadiazol-5-yl, 2,1,3-benzothiadiazolyl-methyl, 2,1,3-benzothiadiazol-5-ylmethyl, 1H-1,2,4-triazol-5-yl, 1H-1,2,4-triazol-5-methyl, 2-oxobenzimidazol-4-yl, 2-oxobenzimidazol-4-methyl, 2-oxobenzimidazol-5-yl, 2-oxobenzimidazol-5-methyl, 1,1-dioxo-thiolan-3-yl, 1,1-dioxothiolan-3-methyl, 3-(2-methyl-1,2,3,4-tetrazol-5-yl)phenyl, 3-(2-methyl-1,2,3,4-tetrazol-5-yl)benzyl, 3-(5-methyl-1,2,3,4-tetrazol-1-yl)phenyl, 3-(1,2,4-triazol-5-yl)phenyl, 3-(1,24-triazol-5-yl)benzyl, 3-3-methyl-4H-1,2,4-triazol-5-methyl or 2-(3-methyl-4H-1,2,4-triazol-5-yl)ethyl.

25. The compound of any of embodiments 17-23 or 24, wherein $R^2$ is H or F.

26. The compound of any of embodiments 17-23 or 24, wherein $R^1$ is lower alkyl, cycloalkyl optionally substituted with 1-2 groups selected from halogen or lower alkyl, heterocycloalkyl, heteroaryl optionally substituted with lower alkyl or lower alkoxy, phenyl optionally substituted with 1-2 substitutents selected from lower alkyl, halogen, lower alkoxy, haloalkyl, haloalkoxy or CN.

27. The compound of embodiment 26, wherein $R^1$ is methyl, propyl, isobutyl, 2-methylpropyl, $CF_3$, $CF_3CH_2$—, $CHF_2CH_2$—, 4-trifluorophenyl, 2-trifluorophenyl, 3-trifluorophenyl, 3,5-dimethylphenyl, 4-propylphenyl, 3-fluoro-4-methoxyphenyl, 2-cyanophenyl, 3-cyanophenyl, 4-cyanophenyl, 4-fluoro-3-methoxyphenyl, 2,5-difluorophenyl, 2,6-difluorophenyl, 2,4-difluorophenyl, 2-pyridyl, 3-pyridyl, 5-methoxy-2-pyridyl, 3-methoxy-2-pyridyl, 4-methoxy-2-pyridyl, 6-methyl-2-pyridyl, 5-methyl-2-pyridyl, 4-methyl-2-pyridyl, 3-methyl-2-pyridyl, dialkylamino, 1-pyrrolidinyl, 1-piperidinyl, 4-morpholinyl, cycloprpyl, cyclobutyl, cyclopentyl, cyclohexyl, 4,4-difluorocyclohexyl, 1-methyl-4-pyrazolyl, 1-ethyl-4-pyrazolyl, 1-methyl-3-pyrazolyl, 1-ethyl-3-pyrazolyl, 6-methyl-3-pyridyl, 5-methyl-3-pyridyl, 4-methyl-3-pyridyl or 2-methyl-3-pyridyl.

28. The compound of embodiment 27, wherein $R^1$ is 2-fluorophenyl, 3-fluorophenyl, 2,5-difluorophenyl or 4-lower alkyl-substituted phenyl, wherein lower alkyl is optionally substituted with one or more fluorine.

29. The compound of any of embodiments 17-22, wherein Y is —$NR^3R^4$, wherein $R^3$ and $R^4$ are combined with the nitrogen atom to which they are attached to form a three to seven membered ring having 0-1 additional heteroatom selected from O, N or S, wherein the nitrogen and sulfur atoms are optionally oxidized.

30. The compound of embodiment 29, wherein Y is 1-aziridinyl, 1-azetidinyl, 1-pyrrolidinyl, 1-piperidinyl, 1-morpholinyl or 1-azepanyl.

31. A compound selected from the group consisting of:
N-[2,4-Difluoro-3-(4-methyl-7H-pyrrolo[2,3-d]pyrimidine-5-carbonyl)-phenyl]-4-trifluoromethyl-benzenesulfonamide (P-1001),
Propane-1-sulfonic acid [3-(4-ethoxy-7H-pyrrolo[2,3-d]pyrimidine-5-carbonyl)-2,4-difluoro-phenyl]-amide (P-1002),
2-Methyl-propane-1-sulfonic acid [2,4-difluoro-3-(4-methyl-7H-pyrrolo[2,3-d]pyrimidine-5-carbonyl)-phenyl]-amide (P-1003),
2-Methyl-propane-1-sulfonic acid [2,4-difluoro-3-(4-methoxy-7H-pyrrolo[2,3-d]pyrimidine-5-carbonyl)-phenyl]-amide (P-1004),
N-[2,4-Difluoro-3-(4-methoxy-7H-pyrrolo[2,3-d]pyrimidine-5-carbonyl)-phenyl]-4-propyl-benzenesulfonamide (P-1005),
N-[3-(4-Ethoxy-7H-pyrrolo[2,3-d]pyrimidine-5-carbonyl)-2,4-difluoro-phenyl]-4-trifluoromethyl-benzenesulfonamide (P-1006),
N-[2,4-Difluoro-3-(4-methyl-7H-pyrrolo[2,3-d]pyrimidine-5-carbonyl)-phenyl]-4-propyl-benzenesulfonamide (P-1007),
N-[2,4-Difluoro-3-(4-methoxy-7H-pyrrolo[2,3-d]pyrimidine-5-carbonyl)-phenyl]-4-ethyl-benzenesulfonamide (P-1008),
N-[2,4-Difluoro-3-(4-methyl-7H-pyrrolo[2,3-d]pyrimidine-5-carbonyl)-phenyl]-4-isopropyl-benzenesulfonamide (P-1009),
N-[2,4-Difluoro-3-(4-methoxy-7H-pyrrolo[2,3-d]pyrimidine-5-carbonyl)-phenyl]-4-isopropyl-benzenesulfonamide (P-1010),
N-[2,4-Difluoro-3-(4-hydroxy-7H-pyrrolo[2,3-d]pyrimidine-5-carbonyl)-phenyl]-4-trifluoromethyl-benzenesulfonamide (P-1012), Propane-1-sulfonic acid [2,4-difluoro-3-(4-isobutyl-7H-pyrrolo[2,3-d]pyrimidine-5-carbonyl)-phenyl]-amide (P-1014), N-[2,4-Difluoro-3-(4-isobutyl-7H-pyrrolo[2,3-d]pyrimidine-5-carbonyl)-phenyl]-4-trifluoromethyl-benzenesulfonamide (P-1015), N-[3-(4-Chloro-7H-pyrrolo[2,3-d]pyrimidine-5-carbonyl)-2,4-difluoro-phenyl]-4-trifluoromethyl-benzenesulfonamide (P-1016), 6-Methoxy-pyridine-3-sulfonic acid [2,4-difluoro-3-(4-methoxy-7H-pyrrolo[2,3-d]pyrimidine-5-carbonyl)-phenyl]-amide (P-1018), N-[2,4-Difluoro-3-(4-methyl-7H-pyrrolo[2,3-d]pyrimidine-5-carbonyl)-phenyl]-4-ethyl-benzenesulfonamide (P-1019), N-{2,4-Difluoro-3-[4-(tetrahydro-pyran-4-yloxy)-7H-pyrrolo[2,3-d]pyrimidine-5-carbonyl]-phenyl}-4-trifluoromethyl-benzenesulfonamide (P-1021), Propane-1-sulfonic acid [2,4-difluoro-3-(4-hydroxy-7H-pyrrolo[2,3-d]pyrimidine-5-carbonyl)-phenyl]-amide (P-1022), N-[3-(4-Cyano-7H-pyrrolo[2,3-d]pyrimidine-5-carbonyl)-2,4-difluoro-phenyl]-4-trifluoromethyl-benzenesulfonamide (P-1023), N-[2,4-Difluoro-3-(4-methoxy-7H-pyrrolo[2,3-d]pyrimidine-5-carbonyl)-phenyl]-3,5-dimethyl-benzenesulfonamide (P-1025), N-[2,4-Difluoro-3-(4-methyl-7H-pyrrolo[2,3-d]pyrimidine-5-carbonyl)-phenyl]-3,5-dimethyl-benzenesulfonamide (P-1027), N-[2,4-Difluoro-3-(4-isobutoxy-7H-pyrrolo[2,3-d]pyrimidine-5-carbonyl)-phenyl]-4-trifluoromethyl-benzenesulfonamide (P-1028), N-[2,4-Difluoro-3-(4-isopropyl-7H-pyrrolo[2,3-d]pyrimidine-5-carbonyl)-phenyl]-4-trifluoromethyl-benzenesulfonamide (P-1029), N-[2,4-Difluoro-3-(4-hydroxy-7H-pyrrolo[2,3-d]pyrimidine-5-carbonyl)-phenyl]-4-propyl-benzenesulfonamide (P-1030), Propane-1-sulfonic acid [3-(4-chloro-7H-pyrrolo[2,3-d]pyrimidine-5-carbonyl)-2,4-difluoro-phenyl]-amide (P-1033), N-[3-(4-Chloro-7H-pyrrolo[2,3-d]pyrimidine-5-carbonyl)-2,4-difluoro-phenyl]-4-propyl-benzenesulfonamide (P-1034), N-[2,4-Difluoro-3-(4-methyl-7H-pyrrolo[2,3-d]pyrimidine-5-carbonyl)-phenyl]-3-fluoro-4-methoxy-benzenesulfonamide (P-1036), N-[3-(4-Ethoxy-7H-pyrrolo[2,3-d]pyrimidine-5-carbonyl)-2,4-difluoro-phenyl]-4-propyl-benzenesulfonamide (P-1038), N-[3-(4-Cyclopropylmethoxy-7H-pyrrolo[2,3-d]pyrimidine-5-carbonyl)-2,4-difluoro-phenyl]-4-trifluoromethyl-benzenesulfonamide (P-1053), N-[2,4-Difluoro-3-(4-hydroxy-7H-pyrrolo[2,3-d]pyrimidine-5-carbonyl)-phenyl]-2-fluoro-benzenesulfonamide (P-1070), N-[3-(4-Chloro-7H-pyrrolo[2,3-d]pyrimidine-5-carbonyl)-2,4-difluoro-phenyl]-2-fluoro-benzenesulfonamide (P-1071), N-[3-(4-Cyclopropyl-7H-pyrrolo[2,3-d]pyrimidine-5-carbonyl)-2,4-difluoro-phenyl]-2,5-difluoro-benzenesulfonamide (P-1107), N-[3-(4-Cyclopropylmethoxy-7H-pyrrolo[2,3-d]pyrimidine-5-carbonyl)-2,4-difluoro-phenyl]-2,5-difluoro-benzenesulfonamide (P-1181), N-[2,4-Difluoro-3-(4-isopropyl-7H-pyrrolo[2,3-d]pyrimidine-5-carbonyl)-phenyl]-2,5-difluoro-benzenesulfonamide (P-1182), N-[2,4-Difluoro-3-(4-hydroxy-7H-pyrrolo[2,3-d]pyrimidine-5-carbonyl)-phenyl]-2,5-difluoro-benzenesulfonamide (P-1183), N-[3-(4-Chloro-7H-pyrrolo[2,3-d]pyrimidine-5-carbonyl)-2,4-difluoro-phenyl]-2,5-difluoro-benzenesulfonamide (P-1184), Propane-1-sulfonic acid [2,4-difluoro-3-(4-trifluoromethyl-1H-pyrrolo[2,3-b]pyridine-3-carbonyl)-phenyl]-amide (P-2015), N-[2,4-Difluoro-3-(4-trifluoromethyl-1H-pyrrolo[2,3-b]pyridine-3-carbonyl)-phenyl]-4-trifluoromethyl-benzenesulfonamide (P-2016), N-[2,4-Difluoro-3-(4-trifluoromethyl-1H-pyrrolo[2,3-b]pyridine-3-carbonyl)-phenyl]-benzenesulfonamide (P-2017), and any pharmaceutically acceptable salt thereof.

32. A composition comprising a compound of any of embodiments 1-31 and a pharmaceutically acceptable excipient or carrier.

33. A pharmaceutical composition comprising a compound of any of embodiments 1-31 and another drug.

34. A kit comprising a compound according to any of embodiments 1-31 or a composition according to Embodiment 32 or 33.

35. A method for treating a Raf protein kinase mediated disease or condition in a subject in need thereof, said method comprising administering to said subject an effective amount of a compound according to any one of embodiments 1-31 or a composition of embodiments 32 or 33.

36. A method for treating a Raf protein kinase mediated disease or condition in a subject in need thereof, said method comprising administering to said subject an effective amount of a compound according to any one of embodiments 1-31 and another drug or a pharmaceutically acceptable salt thereof.

37. The method of embodiment 35 or 36, wherein the disease or condition is selected from the group consisting of multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to Helicobacter pylori, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

38. The method of embodiment 37 wherein the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma.

39. A method for preparing a compound of Formula I according to embodiment 1

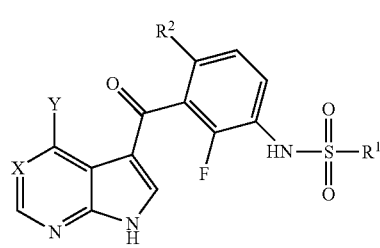

said method comprising:
contacting a compound of Formula IVc:

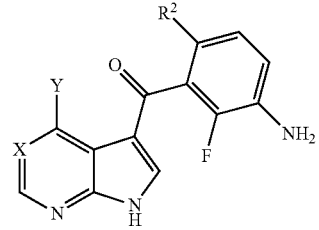

with a compound of Formula V:

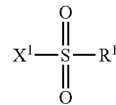

under conditions sufficient to form the compound of Formula I, wherein:
$X^1$ is a halogen.

40. The method of embodiment 39, wherein X is —N═, —CH═, —C(CH$_3$)═, —C(OCH$_3$)═, —C(F)═, —C(CN)═, —C(CH$_2$OH)═ or —C(Cl)═.

41. Use of a compound according to any one of Embodiments 1-31 or a composition according to any one of Embodiments 32 or 33 for the preparation of a medicament for treating any Raf protein kinase mediated disease or condition in a subject in need thereof.

42. A compound according to any one of Embodiments 1-31 or a composition according to any one of Embodiments 32 or 33 for use in treating of a Raf protein kinase mediated disease or condition in a subject in need thereof.

43. A method for treating one or more indications selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma in a subject in need thereof, said method comprising administering to said subject an effective amount of a compound according to any one of Embodiments 1-31, a compound listed on Table I or Table II, or an effective amount of a composition according to any one of Embodiments 32 or 33.

44. Use of a compound according to any one of Embodiments 1-31, a compound listed on Table I or Table II, or a composition according to any one of Embodiments 32 or 33 for the preparation of a medicament for treating one or more indications selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma in a subject in need thereof.

45. A compound according to any one of Embodiments 1-31, a compound listed on Table I or Table II, or a composition according to any one of Embodiments 32 or 33 for the treatment of one or more indications selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma in a subject in need thereof.

46. A method for treating melanoma in a subject in need thereof, said method comprising administering to said subject an effective amount of a compound according to any one of Embodiments 1-31, a compound listed on Table I or Table II, or an effective amount of a composition according to any one of Embodiments 32 or 33.

47. Use of a compound according to any one of Embodiments 1-31, a compound listed on Table I or Table II, or a composition according to any one of Embodiments 32 or 33 for the preparation of a medicament for treating melanoma in a subject in need thereof.

48. A compound according to any one of Embodiments 1-31, a compound listed on Table I or Table II, or a composition according to any one of Embodiments 32 or 33 for the treatment melanoma in a subject in need thereof.

49. A method for treating glioma in a subject in need thereof, said method comprising administering to said subject an effective amount of a compound according to any one of Embodiments 1-31, a compound listed on Table I or Table II, or an effective amount of a composition according to any one of Embodiments 32 or 33.

50. Use of a compound according to any one of Embodiments 1-31, a compound listed on Table I or Table II, or a composition according to any one of Embodiments 32 or 33 for the preparation of a medicament for treating glioma in a subject in need thereof.

51. A compound according to any one of Embodiments 1-31, a compound listed on Table I or Table II, or a composition according to any one of Embodiments 32 or 33 for glioma in a subject in need thereof.

52. A method for treating glioblastoma multiforme in a subject in need thereof, said method comprising administering to said subject an effective amount of a compound according to any one of Embodiments 1-31, a compound listed on Table I or Table II, or an effective amount of a composition according to any one of Embodiments 32 or 33.

53. Use of a compound according to any one of 1-31, a compound listed on Table I or Table II, or a composition according to any one of Embodiments 32 or 33 for the preparation of a medicament for treating glioblastoma multiforme in a subject in need thereof.

54. A compound according to any one of Embodiments 1-31, a compound listed on Table I or Table II, or a composition according to any one of Embodiments 32 or 33 for the treatment of glioblastoma multiforme in a subject in need thereof.

55. A method for treating pilocytic astrocytoma, said method comprising administering to said subject an effective amount of a compound according to any one of Embodiments 1-31, a compound listed on Table I or Table II, or an effective amount of a composition according to any one of Embodiments 32 or 33.

56. Use of a compound according to any one of Embodiments 1-31, a compound listed on Table I or Table II, or a composition according to any one of Embodiments 32 or 33 for the preparation of a medicament for treating pilocytic astrocytoma in a subject in need thereof.

57. A compound according to any one of Embodiments 11-31, a compound listed on Table I or Table II, or a composition according to any one of Embodiments 32 or 33 for the treatment of pilocytic astrocytoma in a subject in need thereof.

58. A method for treating colorectal cancer comprising administering to said subject an effective amount of a compound according to any one of Embodiments 1-31, a compound listed on Table I or Table II, or an effective amount of a composition according to any one of Embodiments 32 or 33.

59. Use of a compound according to any one of Embodiments 1-31, a compound listed on Table I or Table II, or a composition according to any one of Embodiments 32 or 33 for the preparation of a medicament for treating colorectal cancer in a subject in need thereof.

60. A compound according to any one of Embodiments 1-31, a compound listed on Table I or Table II, or a composition according to any one of Embodiments 32 or 33 for the treatment of colorectal cancer in a subject in need thereof.

61. A method for treating thyroid cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

62. Use of a compound according to any one of Embodiments 1-31, a compound listed on Table I or Table II, or a composition according to any one of Embodiments 32 or 33 for the preparation of a medicament for treating thyroid cancer in a subject in need thereof.

63. A compound according to any one of Embodiments 1-31, a compound listed on Table I or Table II, or a composition according to any one of Embodiments 32 or 33 for the treatment of thyroid cancer in a subject in need thereof.

64. A method for treating, lung cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

65. Use of a compound according to any one of Embodiments 1-31, a compound listed on Table I or Table II, or a composition according to any one of Embodiments 32 or 33 for the preparation of a medicament for treating lung cancer in a subject in need thereof.

66. A compound according to any one of Embodiments 1-31, a compound listed on Table I or Table II, or a composition according to any one of Embodiments 32 or 33 for the treatment of lung cancer in a subject in need thereof.

67. A method for treating ovarian cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

68. Use of a compound according to any one of Embodiments 1-31, a compound listed on Table I or Table II, or a composition according to any one of Embodiments 32 or 33 for the preparation of a medicament for treating ovarian cancer in a subject in need thereof.

69. A compound according to any one of Embodiments 1-31, a compound listed on Table I or Table II, or a composition according to any one of Embodiments 32 or 33 for the treatment of ovarian cancer in a subject in need thereof.

70. A method for treating prostate cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

71. Use of a compound according to any one of Embodiments 1-31, a compound listed on Table I or Table II, or a composition according to any one of Embodiments 32 or 33 for the preparation of a medicament for treating prostate cancer in a subject in need thereof.

72. A compound according to any one of Embodiments 1-31, a compound listed on Table I or Table II, or a composition according to any one of Embodiments 32 or 33 for the treatment of prostate cancer in a subject in need thereof.

73. A method for treating liver cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

74. Use of a compound according to any one of Embodiments 1-31, a compound listed on Table I or Table II, or a composition according to any one of Embodiments 32 or 33 for the preparation of a medicament for treating liver cancer in a subject in need thereof.

75. A compound according to any one of Embodiments 1-31, a compound listed on Table I or Table II, or a composition according to any one of Embodiments 32 or 33 for the treatment of liver cancer in a subject in need thereof.

76. A method for treating gallbladder cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

77. Use of a compound according to any one of Embodiments 1-31, a compound listed on Table I or Table II, or a composition according to any one of Embodiments 32 or 33 for the preparation of a medicament for treating gallbladder cancer in a subject in need thereof.

78. A compound according to any one of Embodiments 1-31, a compound listed on Table I or Table II, or a composition according to any one of Embodiments 32 or 33 for the treatment of gallbladder cancer in a subject in need thereof.

79. A method for treating gastrointestinal stromal tumors in a subject in need thereof, said method comprising administering to said subject an effective amount of a compound according to any one of Embodiments 1-31, a compound listed on Table I or Table II, or an effective amount of a composition according to any one of Embodiments 32 or 33.

80. Use of a compound according to any one of Embodiments 1-31, a compound listed on Table I or Table II, or a composition according to any one of Embodiments 32 or 33 for the preparation of a medicament for treating gastrointestinal stromal tumors in a subject in need thereof.

81. A compound according to any one of Embodiments 1-31, a compound listed on Table I or Table II, or a composition according to any one of Embodiments 32 or 33 for the treatment of gastrointestinal stromal tumors in a subject in need thereof.

82. A method for treating biliary tract cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

83. Use of a compound according to any one of Embodiments 1-31, a compound listed on Table I or Table II, or a composition according to any one of Embodiments 32 or 33 for the preparation of a medicament for treating biliary tract cancer in a subject in need thereof.

84. A compound according to any one of Embodiments 1-31, a compound listed on Table I or Table II, or a composition according to any one of Embodiments 32 or 33 for the treatment of biliary tract cancer in a subject in need thereof.

85. A method for treating cholangiocarcinoma in a subject in need thereof, said method comprising administering to said subject an effective amount of a compound according to any one of Embodiments 1-31, a compound listed on Table I or Table II, or an effective amount of a composition according to any one of Embodiments 32 or 33.

86. Use of a compound according to any one of Embodiments 1-31, a compound listed on Table I or Table II, or a composition according to any one of Embodiments 32 or 33 for the preparation of a medicament for treating cholangiocarcinoma in a subject in need thereof.

87. A compound according to any one of Embodiments 1-31, a compound listed on Table I or Table II, or a composition according to any one of Embodiments 32 or 33 for the treatment of cholangiocarcinoma in a subject in need thereof.

88. A method for treating one or more indications selected from the group consisting of acute pain, chronic pain, and polycystic kidney disease in a subject in need thereof, said method comprising administering to said subject an effective amount of a compound according to any one of Embodiments 1-31, a compound listed on Table I or Table II, or an effective amount of a composition according to any one of Embodiments 32 or 33.

89. Use of a compound according to any one of Embodiments 1-31, a compound listed on Table I or Table II, or a composition according to any one of Embodiments 32 or 33 for the preparation of a medicament for treating one or more indications selected from the group consisting of acute pain, chronic pain, and polycystic kidney disease in a subject in need thereof.

90. A compound according to any one of Embodiments 1-31, a compound listed on Table I or Table II, or a composition according to any one of Embodiments 32 or 33 for the treatment of one or more indications selected from the group consisting of acute pain, chronic pain, and polycystic kidney disease in a subject in need thereof.

91. A method for treating acute pain in a subject in need thereof, said method comprising administering to said subject an effective amount of a compound according to any one of Embodiments 1-31, a compound listed on Table I or Table II, or an effective amount of a composition according to any one of Embodiments 32 or 33.

92. Use of a compound according to any one of Embodiments 1-31, a compound listed on Table I or Table II, or a composition according to any one of Embodiments 32 or 33 for the preparation of a medicament for treating acute pain in a subject in need thereof.

93. A compound according to any one of Embodiments 1-31, a compound listed on Table I or Table II, or a composition according to any one of Embodiments 32 or 33 for the treatment of acute pain in a subject in need thereof.

94. A method for treating chronic pain in a subject in need thereof, said method comprising administering to said subject an effective amount of a compound according to any one of Embodiments 1-31, a compound listed on Table I or Table II, or an effective amount of a composition according to any one of Embodiments 32 or 33.

95. Use of a compound according to any one of Embodiments 1-31, a compound listed on Table I or Table II, or a composition according to any one of Embodiments 32 or 33 for the preparation of a medicament for treating chronic pain in a subject in need thereof.

96. A compound according to any one of Embodiments 1-31, a compound listed on Table I or Table II, or a composition according to any one of Embodiments 32 or 33 for the treatment of chronic pain in a subject in need thereof.

97. A method for treating polycystic kidney disease in a subject in need thereof, said method comprising administering to said subject an effective amount of a compound according to any one of Embodiments 1-31, a compound listed on Table I or Table II, or an effective amount of a composition according to any one of Embodiments 32 or 33.

98. Use of a compound according to any one of Embodiments 1-31, a compound listed on Table I or Table II, or a composition according to any one of Embodiments 32 or 33 for the preparation of a medicament for treating polycystic kidney disease in a subject in need thereof.

99. A compound according to any one of Embodiments 1-31, a compound listed on Table I or Table II, or a composition according to any one of Embodiments 32 or 33 for the treatment of polycystic kidney disease in a subject in need thereof.

100. A method for treating one or more indications selected from the group consisting of multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, *Hepatitis* and *Influenza* viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency) in a subject in need thereof, said method comprising administering to said subject an effective amount of a compound according to any one of Embodiments 1-31, a compound listed on Table I or Table II, or an effective amount of a composition according to any one of Embodiments 32 or 33.

101. Use of a compound according to any one of Embodiments 1-31, a compound listed on Table I or Table II, or a composition according to any one of Embodiments 32 or 33 for the preparation of a medicament for treating one or more indications selected from the group consisting of multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori, Hepatitis* and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency) in a subject in need thereof.

102. A compound according to any one of Embodiments 1-31, a compound listed on Table I or Table II, or a composition according to any one of Embodiments 32 or 33 for the treatment of one or more indications selected from the group consisting of multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori, Hepatitis* and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency) in a subject in need thereof.

103. A method for treating testicular cancer in a subject in need thereof, said method comprising administering to said subject an effective amount of a compound according to any one of Embodiments 1-31, a compound listed on Table I or Table II, or an effective amount of a composition according to any one of Embodiments 32 or 33.

104. Use of a compound according to any one of Embodiments 1-31, a compound listed on Table I or Table II, or a composition according to any one of Embodiments 32 or 33 for the preparation of a medicament for treating testicular cancer in a subject in need thereof.

105. A compound according to any one of Embodiments 11-31, a compound listed on Table I or Table II, or a composition according to any one of Embodiments 32 or 33 for the treatment of testicular cancer in a subject in need thereof.

106. A method for treating Noonan's syndrome in a subject in need thereof, said method comprising administering to said subject an effective amount of a compound according to any one of Embodiments 1-31, a compound listed on Table I or Table II, or an effective amount of a composition according to any one of Embodiments 32 or 33.

107. Use of a compound according to any one of Embodiments 1-31, a compound listed on Table I or Table II, or a composition according to any one of Embodiments 32 or 33 for the preparation of a medicament for treating Noonan's syndrome in a subject in need thereof.

108. A compound according to any one of Embodiments 1-31, a compound listed on Table I or Table II, or a composition according to any one of Embodiments 32 or 33 for the treatment of Noonan's syndrome in a subject in need thereof.

109. A method for treating cardio-faciocutaneous syndrome (CFC) in a subject in need thereof, said method comprising administering to said subject an effective amount of a compound according to any one of Embodiments 1-31, a compound listed on Table I or Table II, or an effective amount of a composition according to any one of Embodiments 32 or 33.

110. Use of a compound according to any one of Embodiments 1-31, a compound listed on Table I or Table II, or a composition according to any one of Embodiments 32 or 33 for the preparation of a medicament for treating cardio-faciocutaneous syndrome (CFC) in a subject in need thereof.

111. A compound according to any one of Embodiments 1-31, a compound listed on Table I or Table II, or a composition according to any one of Embodiments 32 or 33 for the treatment of cardio-faciocutaneous syndrome (CFC) in a subject in need thereof.

112. A compound according to any one of Embodiments 1-31, a compound listed on Table I or Table II, or a composition according to any one of Embodiments 32 or 33 wherein said compound is a pan Raf inhibitor.

113. A compound according to any one of Embodiments 1-31, a compound listed on Table I or Table II, or a composition according to any one of Embodiments 32 or 33 wherein said compound is a Ras activity inhibitor.

114. A compound according to any one of Embodiments 1-31, a compound listed on Table I or Table II, or a composition according to any one of Embodiments 32 or 33 wherein said compound is a pan Raf inhibitor and a Ras activity inhibitor.

115. A compound or composition according to any one of the preceeding embodiments, wherein said compound inhibits proliferation of a mutant Ras cell line with an $IC_{50}$ of less than 1 µM.

116. A compound or composition according to any one of the preceeding embodiments, wherein said compound inhibits proliferation of a mutant Ras cell line with an $IC_{50}$ of less than 100 nM.

117. A compound or composition according to any one of the preceeding embodiments, wherein said compound inhibits proliferation of a mutant Ras cell line with an $IC_{50}$ of less than 20 nM.

118. A compound or composition according to any one of the preceeding embodiments, wherein said compound inhibits proliferation of a mutant Ras cell line with an $IC_{50}$ of less than 1 nM.

119. A compound or composition according to any one of the preceeding embodiments, wherein said compound inhibits proliferation of a mutant Ras cell line with an $IC_{50}$ of less than 1 µM and wherein said compound is a pan Raf inhibitor having an $IC_{50}$ of less than 500 nM in activity assays for each of B-Raf, c-Raf-1 and B-Raf V600E protein kinases.

120. A compound or composition according to any one of the preceeding embodiments, wherein said compound inhibits proliferation of a mutant Ras cell line with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

121. A compound or composition according to any one of the preceeding embodiments, wherein said compound inhibits proliferation of a mutant Ras cell line with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

122. A compound or composition according to any one of the preceeding embodiments, wherein said compound inhibits proliferation of a mutant Ras cell line with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

123. A compound or composition according to any one of the preceeding embodiments, wherein said compound inhibits proliferation of a N-Ras mutant cell line with an $IC_{50}$ of less than 1 µM.

124. A compound or composition according to any one of the preceeding embodiments, wherein said compound inhibits proliferation of a N-Ras mutant cell line with an $IC_{50}$ of less than 100 nM.

125. A compound or composition according to any one of the preceeding embodiments, wherein said compound inhibits proliferation of a N-Ras mutant cell line with an $IC_{50}$ of less than 20 nM.

126. A compound or composition according to any one of the preceeding embodiments, wherein said compound inhibits proliferation of a N-Ras mutant cell line with an $IC_{50}$ of less than 1 nM.

127. A compound or composition according to any one of the preceeding embodiments, wherein said compound inhibits proliferation of a N-Ras mutant cell line with an $IC_{50}$ of less than 1 µM and wherein said compound is a pan Raf inhibitor having an $IC_{50}$ of less than 500 nM in activity assays for each of B-Raf, c-Raf-1 and B-Raf V600E protein kinases.

128. A compound or composition according to any one of the preceeding embodiments, wherein said compound inhibits proliferation of a N-Ras mutant cell line with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

129. A compound or composition according to any one of the preceeding embodiments, wherein said compound inhibits proliferation of a N-Ras mutant cell line with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

120. A compound or composition according to any one of the preceeding embodiments, wherein said compound inhibits proliferation of a N-Ras mutant cell line with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

121. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 1 µM.

122. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 100 nM.

123. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 20 nM.

124. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 1 nM.

125. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 1 µM and wherein said compound is a pan Raf inhibitor having an $IC_{50}$ of less than 500 nM in activity assays for each of B-Raf, c-Raf-1 and B-Raf V600E protein kinases.

126. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

127. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

128. A compound or composition according to any one of the preceeding embodiments, wherein said compound inhibits proliferation of a mutant Ras cell line selected from the group consisting of M244, M202, M207, SK-MEL-2, SK-MEL-173, and IPC298 with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

129. A compound or composition according to any one of the preceeding embodiments, wherein said compound inhibits proliferation of IPC298 cells with an $IC_{50}$ of less than 1 µM.

130. A compound or composition according to any one of the preceeding embodiments, wherein said compound inhibits proliferation of IPC298 cells with an $IC_{50}$ of less than 100 nM.

131. A compound or composition according to any one of the preceeding embodiments, wherein said compound inhibits proliferation of IPC298 cells with an $IC_{50}$ of less than 20 nM.

132. A compound or composition according to any one of the preceeding embodiments, wherein said compound inhibits proliferation of IPC298 cells with an $IC_{50}$ of less than 1 nM.

133. A compound or composition according to any one of the preceeding embodiments, wherein said compound inhibits proliferation of IPC298 cells with an $IC_{50}$ of less than 1 µM and wherein said compound is a pan Raf inhibitor having an $IC_{50}$ of less than 500 nM in activity assays for each of B-Raf, c-Raf-1 and B-Raf V600E protein kinases.

134. A compound or composition according to any one of the preceeding embodiments, wherein said compound inhibits proliferation of IPC298 cells with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

135. A compound or composition according to any one of the preceeding embodiments, wherein said compound inhibits proliferation of IPC298 cells with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

136. A compound or composition according to any one of the preceeding embodiments, wherein said compound inhibits proliferation of IPC298 cells with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

EXAMPLES

Examples related to the present invention are described below. In most cases, alternative techniques can be used. The examples are intended to be illustrative and are not limiting or restrictive to the scope of the invention. For example, where additional compounds are prepared following a protocol of a Scheme for a particular compound, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Ring numbering for the 1H-pyrrolo[2,3-b]pyridine in the following Examples is as follows:

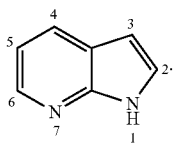

Ring numbering for the 7H-pyrrolo[2,3-d]pyrimidine in the following Examples is as follows:

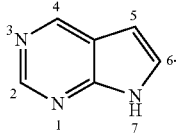

Example 1

Synthesis of 7H-pyrrolo[2,3-d]pyrimidine compounds 4-methoxy-7H-pyrrolo[2,3-d]pyrimidine 2 is prepared in one step from 4-chloro-7H-pyrrolo[2,3-d]pyrimidine 1 as shown in Scheme 1.

Scheme 1

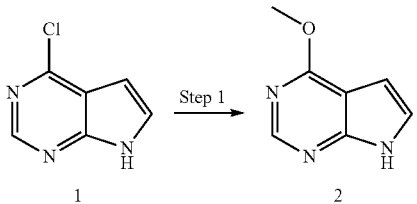

Step 1—Preparation of 4-methoxy-7H-pyrrolo[2,3-c]pyrimidine (2)

To 4-chloro-7H-pyrrolo[2,3-d]pyrimidine (1, 3.5 g, 23.0 mmol) in 70 mL of methanol, potassium hydroxide (2.3 g, 41.0 mmol) is added and the reaction stirred at 60° C. overnight, then poured into water and extracted with ethyl acetate. The organic layer is separated and dried over sodium sulfate, filtered and the filtrate concentrated under vacuum to provide the desired compound (2, 3.20 g).

4-ethoxy-7H-pyrrolo[2,3-d]pyrimidine 3, 4-cyclopropyl-methoxy-7H-pyrrolo[2,3-d]pyrimidine 4, 4-isobutoxy-7H-pyrrolo[2,3-d]pyrimidine 5, and 4-(tetrahydro-pyran-4-yloxy)-7H-pyrrolo[2,3-d]pyrimidine 6,

3

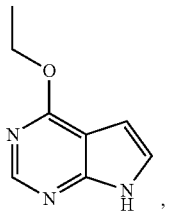

-continued

4

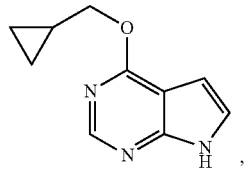

5

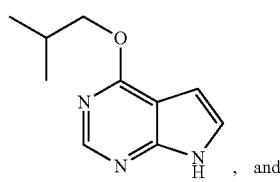
, and

6

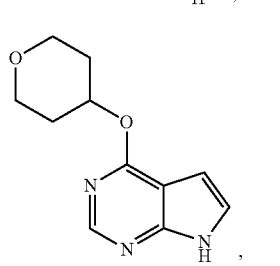
, are prepared following the protocol of Scheme 1, replacing methanol with ethanol, cyclopropyl-methanol, isobutyl alcohol, and tetrahydro-pyran-4-ol, respectively. MS (ESI) $[M+H^+]^+$=164.9 (3); 190.1 (4); 192.1 (5); and 220.1 (6).

4-Methyl-7H-pyrrolo[2,3-d]pyrimidine 7 is synthesized in one step from 4-chloro-7H-pyrrolo[2,3-d]pyrimidine 1 as shown in Scheme 1a.

Scheme 1a

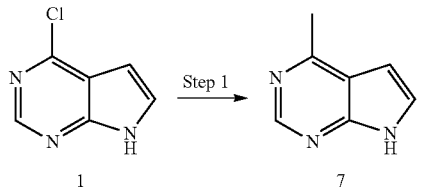

Step 1—Preparation of 4-methyl-7H-pyrrolo[2,3-c]pyrimidine (7)

Into a round bottom flask the catalyst [1,1'-bis(diphenyl-phosphino)ferrocene]dichloropalladium(II), 1:1 complex with dichloromethane (70.0 mg, 0.09 mmol), is placed under nitrogen with 15 mL of toluene along with a stir bar. A suspension of 4-chloro-7H-pyrrolo[2,3-d]pyrimidine (1, 1.47 g, 9.57 mmol) in 15 mL of toluene is added at room temperature. After stirring for 10 minutes, methylmagnesium bromide (17.00 mL, 3.00 M in ether, 51.00 mmol) is added dropwise. The solution is slowly heated to 60° C. and stirred for 3 hrs at 60° C., then overnight at room temperature. The resulting dark orange reaction mixture is quenched with 1 N hydrochloric acid and adjusted to pH 5, then extracted with ethyl acetate and water saturated with sodium chloride. The organic layer is washed with water and brine, dried over magnesium sulfate, filtered and the filtrate concentrated under vacuum. The resulting material is purified by silica gel column chromatography eluting with ethyl acetate and hexane. Appropriate fractions are combined and concentrated under vacuum to provide the desired compound as a yellow solid (8, 202 mg). $^1$H-NMR (dmso-$d_6$) is consistent with the desired compound. MS (ESI) [M+H$^+$]$^+$=134.3.

4-Isopropyl-7H-pyrrolo[2,3-d]pyrimidine 8, 4-isobutyl-7H-pyrrolo[2,3-d]pyrimidine 9, and 4-cyclopropyl-1H-pyrrolo[2,3-b]pyridine 10,

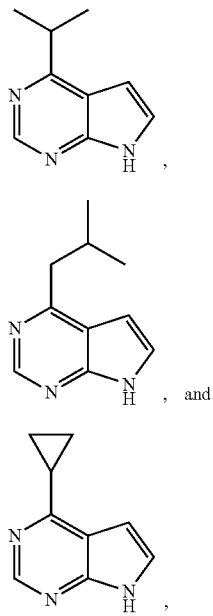

are prepared following the protocol of Scheme 1a, replacing methylmagnesium bromide with isopropylmagnesium bromide, isobutylmagnesium bromide, and cyclopropylmagnesium bromide, respectively. MS (ESI) [M+H$^+$]$^+$=162.1 (8); and 176.1 (9).

Isopropyl-(7H-pyrrolo[2,3-d]pyrimidin-4-yl)-amine 12 is synthesized in one step from 4-chloro-7H-pyrrolo[2,3-d]pyrimidine 1 as shown in Scheme 1b.

Scheme 1b

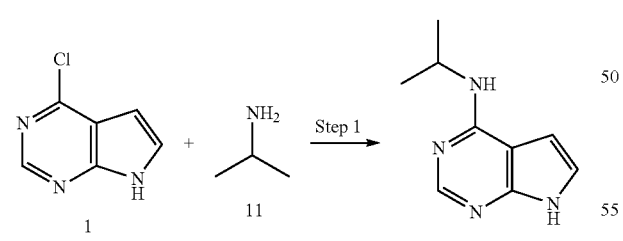

Step 1—Preparation of isopropyl-(7H-pyrrolo[2,3-c]pyrimidin-4-yl)-amine (12)

To 4-chloro-7H-pyrrolo[2,3-d]pyrimidine (1, 168 mg, 1.09 mmol), 2.00 mL of isopropyl alcohol is added, followed by 2-propanamine (11, 0.280 mL, 3.28 mmol). The reaction is heated by microwave at 120° C. for 20 minutes, then an additional 40 minutes. Another 0.250 mL of 2-propanamine is added and heated at 120° C. for 60 minutes. The reaction is poured into water and extracted with ethyl acetate. The organic layer is concentrated under vacuum and purified by silica gel column chromatography, eluting with a gradient of 1-5% methanol in dichloromethane. Appropriate fractions are combined and concentrated under vacuum to provide the desired compound (12, 172 mg). MS (ESI) [M+H$^+$]$^+$=176.85.

Additional compounds are prepared following the protocol of Scheme 1b. In some instances, without limitation, 4-chloro-7H-pyrrolo[2,3-d]pyrimidine 1 is reacted directly in the liquid amine compound without additional solvent (e.g. isopropyl alcohol). Compounds are prepared substituting 2-propanamine 11 with a suitable amine. The following compounds are made using this procedure:

Isobutyl-(7H-pyrrolo[2,3-d]pyrimidin-4-yl)-amine (13),
(7H-Pyrrolo[2,3-d]pyrimidin-4-yl)-(tetrahydro-pyran-4-yl)-amine (14),
Cyclopentyl-(7H-pyrrolo[2,3-d]pyrimidin-4-yl)-amine (15),
Cyclopropyl-(7H-pyrrolo[2,3-d]pyrimidin-4-yl)-amine (16)
4-Morpholin-4-yl-7H-pyrrolo[2,3-d]pyrimidine (17), and
4-Pyrrolidin-1-yl-7H-pyrrolo[2,3-d]pyrimidine (18).

The following table indicates the amine compound (column 2) used to afford the desired compound (column 3). The compound number is provided in column 1, and the observed mass is in column 4

| Compound number | Amine | Compound Structure | MS (ESI) [M + H$^+$]$^+$ |
|---|---|---|---|
| 13 | | 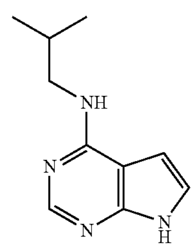 | 191.1 |
| 14 | | 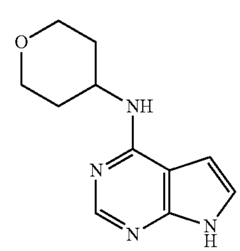 [SMILES: c1nc(NC2CCOCC2)c2cc[nH]c2n1] | 219.1 |
| 15 | | 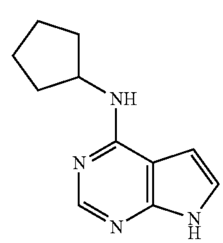 [SMILES: c1nc(NC2CCCC2)c2cc[nH]c2n1] | 203.0 |

-continued

| Compound number | Amine | Compound Structure | MS (ESI) [M + H⁺]⁺ |
|---|---|---|---|
| 16 | cyclopropylamine | N-cyclopropyl-7H-pyrrolo[2,3-d]pyrimidin-4-amine | 175.1 |
| 17 | morpholine | 4-morpholino-7H-pyrrolo[2,3-d]pyrimidine | 205.0 |
| 18 | pyrrolidine | 4-pyrrolidin-1-yl-7H-pyrrolo[2,3-d]pyrimidine | 189.0 |
| 19 | cyclopropylmethylamine | N-(cyclopropylmethyl)-7H-pyrrolo[2,3-d]pyrimidin-4-amine | 189.0 |

1H-Pyrrolo[2,3-b]pyridine compounds similarly substituted at the 4-position, (1H-pyrrolo[2,3-b]pyridin-4-yl)-(tetrahydro-pyran-4-yl)-amine 20, cyclopentyl-(1H-pyrrolo[2,3-b]pyridin-4-yl)-amine 21, and cyclopropylmethyl-(1H-pyrrolo[2,3-b]pyridin-4-yl)-amine 21-A,

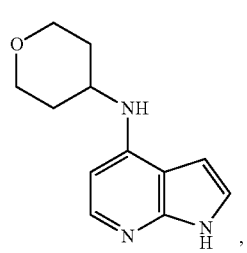

20

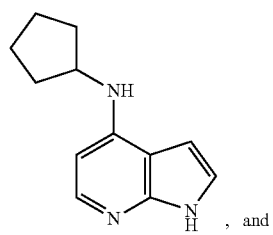

21

, and

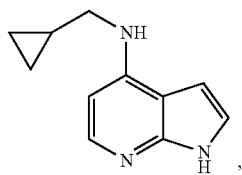

21-A are also prepared following the protocol of Scheme 1b, substituting 2-propanamine 11 with tetrahydro-pyran-4-ylamine, cyclopentylamine, and c-cyclopropyl-methylamine, respectively, and using 4-chloro-1H-pyrrolo[2,3-b]pyridine in place of 4-chloro-7H-pyrrolo[2,3-d]pyrimidine 1. These reactions are carried out using toluene as solvent, and include Pd(OR)(OAc) and potassium tert-butoxide in the reaction. Pd(OR)(OAc) is a palladium catalyst wherein R is 2-(di-tert-butylphosphino)biphenyl, prepared by combining palladium(II) acetate (225 mg, 1 mmol) with 2-(di-tert-butylphosphino)biphenyl (299 mg, 1 mmol) in 15 mL of toluene. The solution is shaken overnight at room temperature for use in the above reaction. MS (ESI) [M+H⁺]⁺=218.1 (20), 202.4 (21), and 187.8 (21-A).

(5-Chloro-1H-pyrrolo[2,3-b]pyridin-4-yl)-cyclopropylmethyl-amine 24 is synthesized in one step from 5-chloro-1H-pyrrolo[2,3-b]pyridin-4-ylamine 22 as shown in Scheme 1c.

Scheme 1c

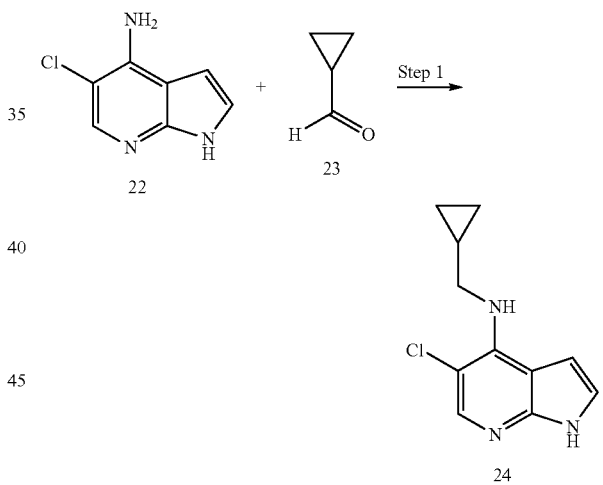

Step 1—Preparation of (5-chloro-1H-pyrrolo[2,3-b]pyridin-4-yl)-cyclopropylmethyl-amine (24)

In a round bottom flask, 5-chloro-1H-pyrrolo[2,3-b]pyridin-4-ylamine (22, 0.21 g, 1.25 mmol) is combined with 3.5 mL of ethanol, acetic acid (0.38 g, 6.25 mmol), silica bound sodium cyanoborohydride (1.1 g, 1.02 mmol), and cyclopropanecarbaldehyde (23, 0.26 g, 4 mmol). The reaction mixture was stirred over night at room temperature, heated up to 145° C. until the reaction was complete, filtered, concentrated, and purified by flash chromatography to provide compound as a solid (24, 0.191 g; yield=69%).

4-Trifluoromethyl-1H-pyrrolo[2,3-b]pyridine 26 is synthesized in one step from 1-tert-butyl-4-trifluoromethyl-1H-pyrrolo[2,3-b]pyridine-3-carbonitrile 25 as shown in Scheme 1d.

Scheme 1d

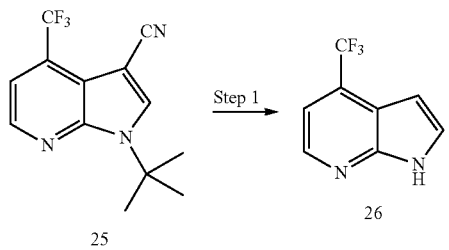

Step 1—Preparation of 4-trifluoromethyl-1H-pyrrolo[2, 3-b]pyridine (26)

1-tert-Butyl-4-trifluoromethyl-1H-pyrrolo[2,3-b]pyridine-3-carbonitrile (25, 1.071 g, 4.007 mmol) is dissolved in 10 mL of aqueous 60% sulfuric acid and stirred at 120° C. for 20 hours. The reaction is adjusted to pH 7 with sodium hydroxide and aqueous saturated sodium bicarbonate, then extracted with ethyl acetate. The organic layer is washed with water, then brine and dried with magnesium sulfate, filtered and the filtrate concentrated under vacuum. The resulting material is purified by silica gel column chromatography, eluting with ethyl acetate and hexane. Appropriate fractions are combined and concentrated under vacuum to provide the desired compound (26, 373 mg). MS (ESI) [M+H$^+$]$^+$=187.1.

4-chloro-5-iodo-7-(toluene-4-sulfonyl)-7H-pyrrolo[2,3-d]pyrimidine 29 is synthesized in two steps from 4-chloro-7H-pyrrolo[2,3-d]pyrimidine 1 as shown in Scheme 1e.

Scheme 1e

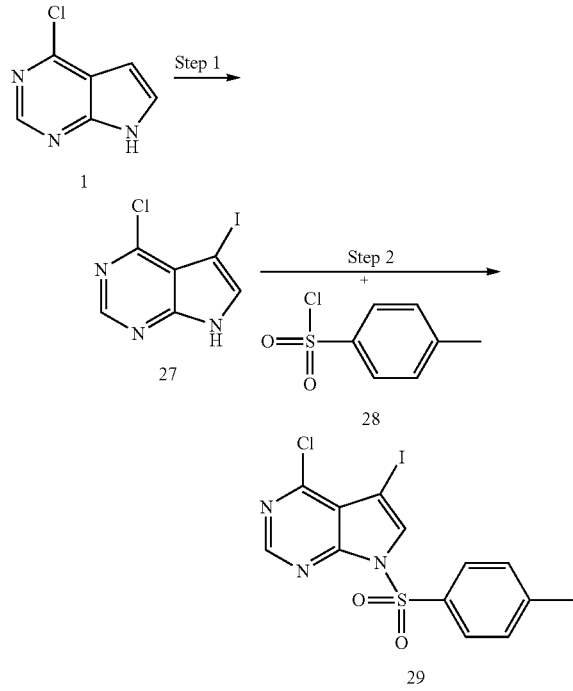

Step 1—Preparation of 4-chloro-5-iodo-7H-pyrrolo[2,3-c]pyrimidine (27)

To 4-chloro-7H-pyrrolo[2,3-d]pyrimidine (1, 1.21 g, 7.88 mmol) dissolved in 50 mL of dichloromethane, N-iodosuccinimide (1.95 g, 8.67 mmol) is added and the reaction is stirred at room temperature overnight. The reaction is quenched with 50% aqueous sodium thiosulfate and the mixture is filtered through celite. The aqueous layer is extracted with ethyl acetate. The organic layers are combined and washed with water, then brine, and dried with sodium sulfate, filtered and the filtrate concentrated under vacuum. The resulting material is purified by silica gel column chromatography, eluting with ethyl acetate and dichloromethane. Appropriate fractions are combined and concentrated under vacuum to provide the desired compound (27, 1.383 g). MS (ESI) [M+H$^{30}$]$^+$=279.8, 281.8.

Step 2—Preparation of 4-chloro-5-iodo-7-(toluene-4-sulfonyl)-7H-pyrrolo[2,3-d]pyrimidine (29)

To 4-chloro-5-iodo-7H-pyrrolo[2,3-d]pyrimidine (27, 2.45 g, 8.77 mmol) in 68 mL of tetrahydrofuran, sodium hydride (0.4208 g, 10.52 mmol) is added and the reaction is stirred at room temperature for 30 minutes. 4-Methyl-benzenesulfonyl chloride (28, 1.838 g, 9.643 mmol) is added and the reaction stirred at room temperature overnight. Water is added and the reaction is extracted with ethyl acetate, resulting in some precipitate that is removed by filtration. The aqueous layer is separated and extracted with ethyl acetate. The organic layers are combined, washed with water, then brine and dried with magnesium sulfate, filtered and the filtrate concentrated under vacuum. The residue is suspended in ethyl acetate, sonicated for 30 minutes, and the solid collected by filtration to provide the desired compound (29, 3.325 g). MS (ESI) [M+H$^+$]$^+$=433.8.

(3-Amino-2,6-difluoro-phenyl)-(4-methoxy-7H-pyrrolo[2,3-d]pyrimidin-5-yl)-methanone 36 is synthesized in five steps from 2,4-difluoroaniline 30 as shown in Scheme 1f.

Scheme 1f

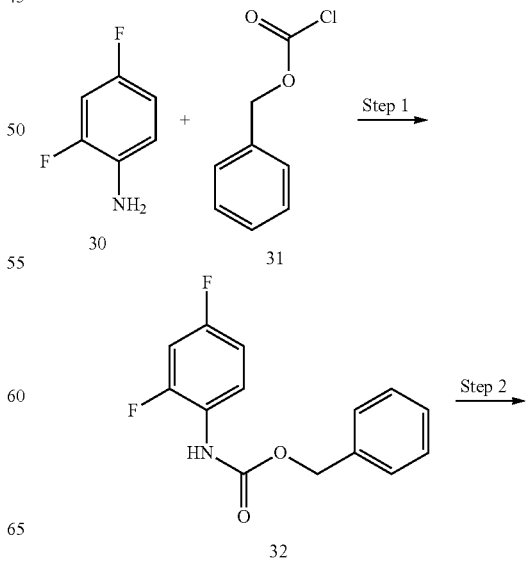

-continued

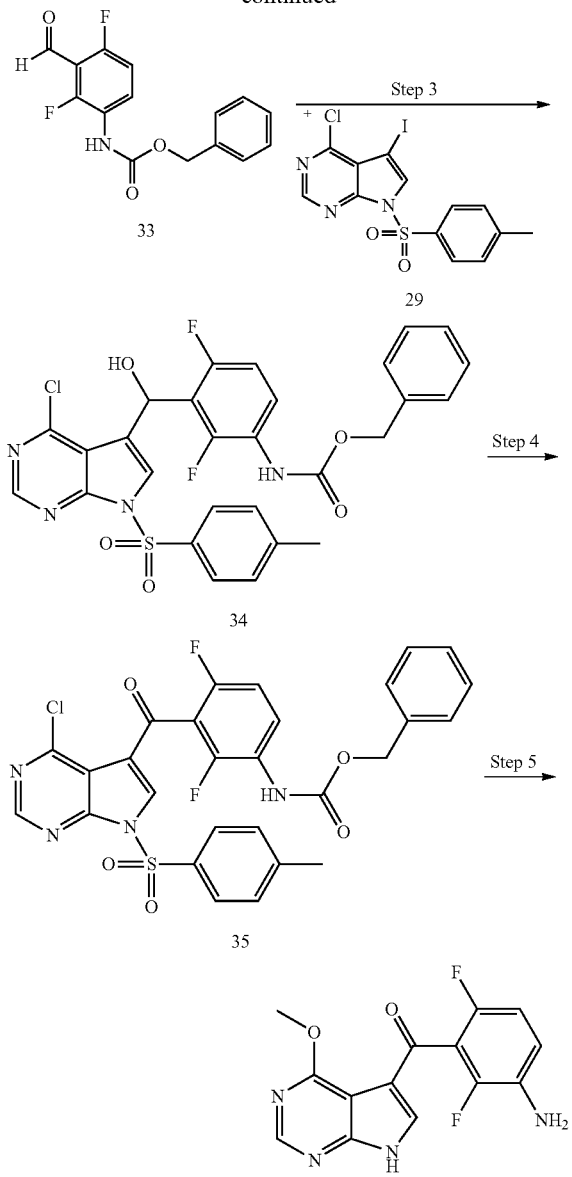

Step 1—Preparation of (2,4-difluoro-phenyl)-carbamic acid benzyl ester (32)

To 2,4-difluoro-phenylamine (30, 7.0 mL, 70.0 mmol) in 100 mL of dichloromethane, pyridine (11 mL, 0.14 mol) and benzyl chloroformate (31, 11.9 mL, 83.4 mmol) are added. The reaction mixture is stirred at ambient temperature for 1.5 hours. The reaction mixture is concentrated under vacuum and the residue is partitioned between ethyl acetate and potassium bisulfate solution. The organic layer is dried with magnesium sulfate, filtered, and the filtrate concentrated under vacuum. The resulting material is crystallized from hexanes to provide the desired compound (32, 15.6 g, 85%).

Step 2—Preparation of (2,4-difluoro-3-formyl-phenyl)-carbamic acid benzyl ester (33)

In a round bottom flask (2,4-difluoro-phenyl)-carbamic acid benzyl ester (30, 3.83 g, 14.5 mmol) is combined with 148 mL of tetrahydrofuran. The solution is chilled to −78° C. and n-butyllithium (19.1 mL, 1.60 M in hexane, 30.0 mmol) is added over 30 minutes, followed by the addition of N,N-dimethylformamide (1.12 mL, 14.5 mol). The reaction mixture is allowed to warm to ambient temperature and is stirred overnight, then poured into water and extracted with ethyl acetate. The organic layer is washed with brine, dried over sodium sulfate, filtered and the filtrate concentrated under vacuum. The resulting material is crystallized from ether to provide the desired compound (33, 3.0 g, 71%).

Step 3—Preparation of (3-{[4-chloro-7-(toluene-4-sulfonyl)-7H-pyrrolo[2,3-d]pyrimidin-5-yl]hydroxy-methyl}-2,4-difluoro-phenyl)-carbamic acid benzyl ester (34)

In a round bottom flask, 4-chloro-5-iodo-7-(toluene-4-sulfonyl)-7H-pyrrolo[2,3-d]pyrimidine (29, 1.549 g, 3.572 mmol) is combined with 25.0 mL of tetrahydrofuran and the solution is cooled to −50° C. under nitrogen. Isopropylmagnesium chloride (2.76 mL, 2.0 M in tetrahydrofuran, 5.00 mmol) is added slowly and the reaction is allowed to warm to 5° C. over 70 minutes, then cooled to −45° C. In a separate vessel, (2,4-difluoro-3-formyl-phenyl)-carbamic acid benzyl ester (33, 805 mg, 2.76 mmol) in 5 mL of tetrahydrofuran is cooled to −5° C. and o-tolylmagnesium chloride (2.76 mL, 1 M in tetrahydrofuran, 2.76 mmol) is added dropwise slowly, maintaining the temperature at −5° C. for 1 hour. This is then cooled to −30° C. and added to the above 4-chloro-5-iodo-7-(toluene-4-sulfonyl)-7H-pyrrolo[2,3-d]pyrimidine reaction mixture. The resulting reaction mixture is warmed to room temperature over 2-3 hours, then quenched with the addition of 1 M aqueous citric acid and extracted with ethyl acetate. The organic layer is washed with water, brine and dried over magnesium sulfate, then filtered and the filtrate is concentrated under vacuum. The resulting material is purified by silica gel column chromatography eluting with ethyl acetate and hexane. Appropriate fractions are combined and concentrated under vacuum to provide the desired compound (34, 445 mg). MS (ESI) [M+H$^+$]$^+$=598.8.

Step 4—Preparation of {3-[4-chloro-7-(toluene-4-sulfonyl)-7H-pyrrolo[2,3-d]pyrimidine-5-carbonyl]-2,4-difluoro-phenyl}-carbamic acid benzyl ester (35)

In a round bottom flask, (3-{[4-chloro-7-(toluene-4-sulfonyl)-7H-pyrrolo[2,3-d]pyrimidin-5-yl]-hydroxy-methyl}-2,4-difluoro-phenyl)-carbamic acid benzyl ester (34, 311 mg, 0.519 mmol) is dissolved in 35 mL of tetrahydrofuran and Dess-Martin periodinane (242 mg, 0.571 mmol) is added. The resulting mixture is stirred at room temperature, and additional Dess-Martin periodinane is added. After 60 minutes, the reaction is quenched with water and extracted with ethyl acetate. The organic layer is washed with aqueous sodium bicarbonate, then brine, and dried with magnesium sulfate, filtered and the filtrate is concentrated under vacuum. The resulting material is purified by silica gel chromatography eluting with ethyl acetate and hexane.

Appropriate fractions are combined and concentrated under vacuum to provide the desired compound (35, 152 mg). MS (ESI) [M+H$^+$]$^+$=596.8.

Step 5—Preparation of (3-amino-2,6-difluoro-phenyl)-(4-methoxy-7H-pyrrolo[2,3-d]pyrimidin-5-yl)-methanone (36)

{3-[4-Chloro-7-(toluene-4-sulfonyl)-7H-pyrrolo[2,3-d]pyrimidine-5-carbonyl]-2,4-difluoro-phenyl}-carbamic acid benzyl ester (35, 152 mg, 0.255 mmol) is combined with 15 mL of methanol and potassium hydroxide (1.06 g, 18.9 mmol) is added. The mixture is heated at 70° C. for 36 hours, then 6 N aqueous hydrochloric acid is added and the mixture is extracted with ethyl acetate. The organic layer is washed with brine, then dried with magnesium sulfate, filtered and the filtrate concentrated under vacuum. The resulting material is purified by silica gel column chromatography, eluting with ethyl acetate and hexane. Appropriate fractions are combined and concentrated under vacuum to provide the desired compound (36, 0.03 mg). MS (ESI) [M+H]$^+$=305.1.

(3-Amino-2,6-difluoro-phenyl)-(4-hydroxy-7H-pyrrolo[2,3-d]pyrimidin-5-yl)-methanone 39 is synthesized in two steps from 7H-pyrrolo[2,3-d]pyrimidin-4-ol 37 and (2,4-difluoro-3-formyl-phenyl)-carbamic acid benzyl ester 33 as shown in Scheme 1g.

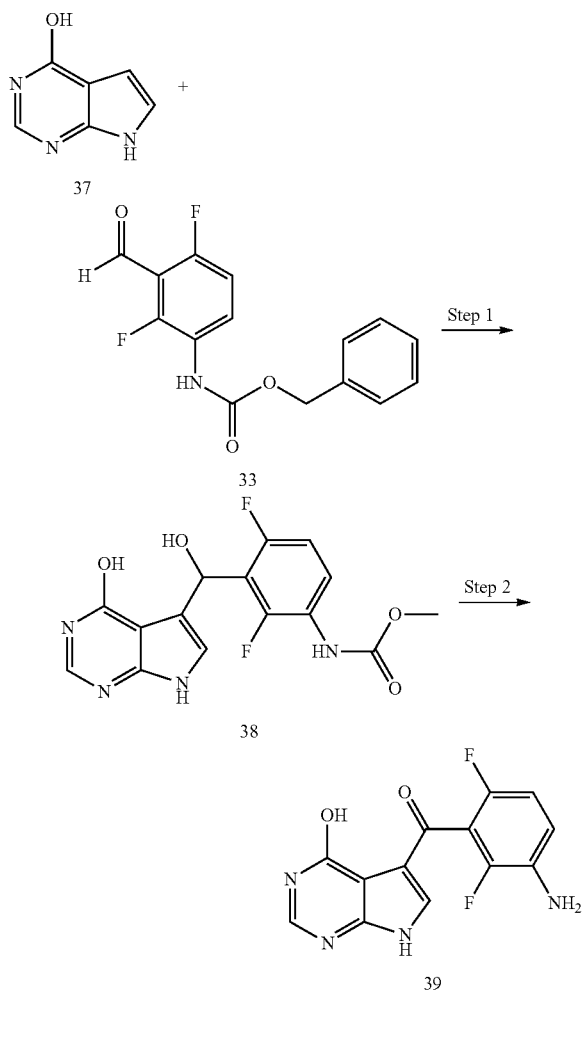

Scheme 1g

Step 1—Preparation of {2,4-difluoro-3-[hydroxy-(4-hydroxy-7H-pyrrolo[2,3-d]pyrimidin-5-yl)-methyl]-phenyl}-carbamic acid methyl ester (38)

In a reaction vessel, 7H-pyrrolo[2,3-d]pyrimidin-4-ol (37, 855 mg, 6.33 mmol) is combined with (2,4-difluoro-3-formyl-phenyl)-carbamic acid benzyl ester (33, 2.03 g, 6.96 mmol) and potassium hydroxide (1.06 g, 19.0 mmol) and 5 mL of methanol is added. The resulting solution is stirred at 50° C. for 2 days. The reaction is diluted with 1N hydrochloric acid and extracted with ethyl acetate, and the resulting solids collected by filtration and dried under vacuum. The organic layer is separated from the filtrate and the aqueous layer extracted twice more with ethyl acetate. The organic layers are combined and washed with water, brine, dried with magnesium sulfate and filtered. The filtrate is concentrated under vacuum and the resulting material is suspended in acetonitrile and sonicated for 1 hour. The solid is collected by filtration and dried under vacuum, then combined with the first solid collected to provide the desired compound (38, 2.05 g). MS (ESI) [M−H$^+$]$^-$=349.0.

Step 2—Preparation of (3-amino-2,6-difluoro-phenyl)-(4-hydroxy-7H-pyrrolo[2,3-d]pyrimidin-5-yl)-methanone (39)

In a reaction vessel, {2,4-difluoro-3-[hydroxy-(4-hydroxy-7H-pyrrolo[2,3-d]pyrimidin-5-yl)-methyl]-phenyl}-carbamic acid methyl ester (38, 690 mg, 1.97 mmol) is dissolved in 200 mL of tetrahydrofuran and Dess-Martin periodinane (877.3 mg, 2.068 mmol) is added. The resulting mixture is stirred at room temperature for 3 hours, then 20 mL of saturated aqueous sodium bicarbonate, 5 mL of saturated aqueous sodium thiosulfate, and 100 mL of ethyl acetate are added for extraction. The organic layer is isolated and the aqueous layer extracted with 50 mL of ethyl acetate. The organic fractions are combined and washed with water, then brine, dried with magnesium sulfate, filtered and the filtrate is concentrated under vacuum. The resulting material is suspended in acetonitrile, sonicated for 1 hour, then filtered to collect the solid material, which is then washed with acetonitrile. The resulting material is suspended in 15 mL of dioxane, and combined with 15 mL of 10N aqueous sodium hydroxide, and heated to reflux for 5 hours. The reaction mixture is adjusted to approximately pH 6 with 6N hydrochloric acid and extracted with ethyl acetate. The organic layer is concentrated under vacuum and the resulting material purified by silica gel chromatography eluting with methanol and dichloromethane. Appropriate fractions are combined and concentrated under vacuum to provide the desired compound (39, 287 mg). MS (ESI) [M−H$^+$]$^-$=289.1.

Additional compounds are prepared following the protocol of Scheme 1f or 1g, reacting a suitable 7H-pyrrolo[2,3-d]pyrimidine or 1H-pyrrolo[2,3-b]pyridine with aldehyde 33 (or alternatively with (2,4-difluoro-3-formyl-phenyl)-carbamic acid methyl ester). The following compounds are made using this procedure:

(3-Amino-2,6-difluoro-phenyl)-(4-methyl-7H-pyrrolo[2,3-d]pyrimidin-5-yl)-methanone (40),
(3-amino-2,6-difluoro-phenyl)-(4-isopropylamino-7H-pyrrolo[2,3-d]pyrimidin-5-yl)-methanone (41),
(3-Amino-2,6-difluoro-phenyl)-(4-cyclopropylamino-7H-pyrrolo[2,3-d]pyrimidin-5-yl)-methanone (42),
(3-Amino-2,6-difluoro-phenyl)-(4-cyclopropyl-7H-pyrrolo[2,3-d]pyrimidin-5-yl)-methanone (43), (3-Amino-2,6-difluoro-phenyl)-[4-(cyclopropylmethyl-amino)-7H-pyrrolo[2,3-d]pyrimidin-5-yl]-methanone (44), and
(3-Amino-2,6-difluoro-phenyl)-[5-chloro-4-(cyclopropylmethyl-amino)-1H-pyrrolo[2,3-b]pyridin-3-yl]-methanone (45).

The following table indicates the 7H-pyrrolo[2,3-d]pyrimidine or 1H-pyrrolo[2,3-b]pyridine compound (column 2) used to afford the desired compound (column 3). The compound number is provided in column 1, and the observed mass is in column 4

| Compound number | 7H-pyrrolo[2,3-d]pyrimidine or 1H-pyrrolo[2,3-b]pyridine | Compound structure | MS (ESI) [M + H⁺]⁺ |
|---|---|---|---|
| 40 | | 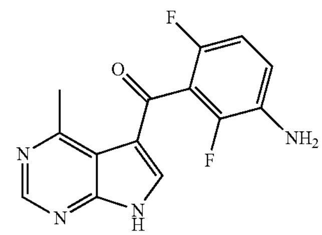 [SMILES: Cc1ncnc2[nH]cc(C(=O)c3c(F)ccc(N)c3F)c12] | |
| 41 | | 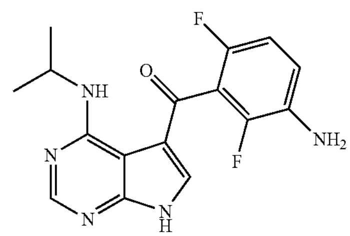 [SMILES: CC(C)Nc1ncnc2[nH]cc(C(=O)c3c(F)ccc(N)c3F)c12] | 331.9 |
| 42 | | 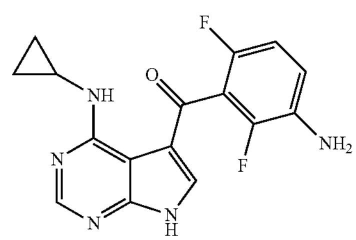 [SMILES: Nc1ccc(F)c(C(=O)c2c[nH]c3ncnc(NC4CC4)c23)c1F] | 329.9 |
| 43 | | 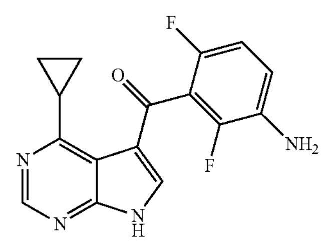 [SMILES: Nc1ccc(F)c(C(=O)c2c[nH]c3ncnc(C4CC4)c23)c1F] | 314.9 |
| 44 | | 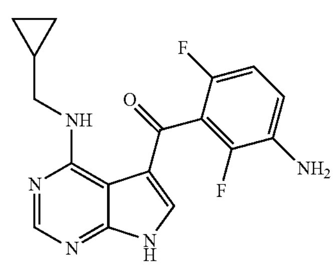 [SMILES: Nc1ccc(F)c(C(=O)c2c[nH]c3ncnc(NCC4CC4)c23)c1F] | 343.9 |

| Compound number | 7H-pyrrolo[2,3-d]pyrimidine or 1H-pyrrolo[2,3-b]pyridine | Compound structure | MS (ESI) [M + H⁺]⁺ |
|---|---|---|---|
| 45 | 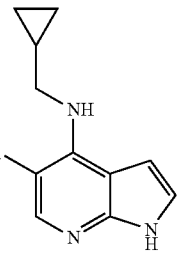 | 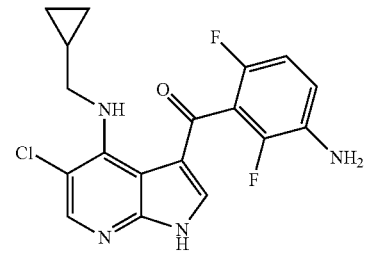 [SMILES: Nc1ccc(F)c(C(=O)c2c[nH]c3ncc(Cl)c(NCC4CC4)c23)c1F] | |

3-(3-Amino-2,6-difluoro-benzoyl)-4-chloro-1H-pyrrolo[2,3-b]pyridine-5-carbonitrile 52 is synthesized in five steps from 2,4-difluoro-1-nitro-benzene 46 and benzyl chloroformate 31 as shown in Scheme 1h.

Scheme 1h

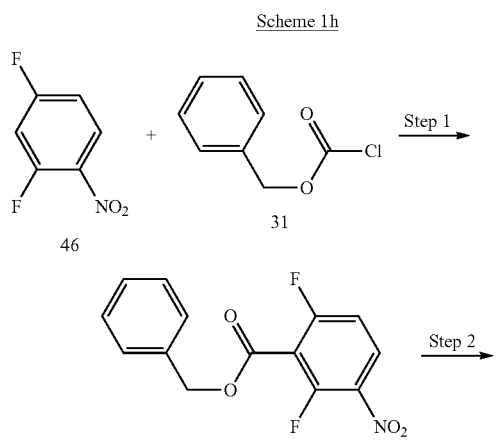

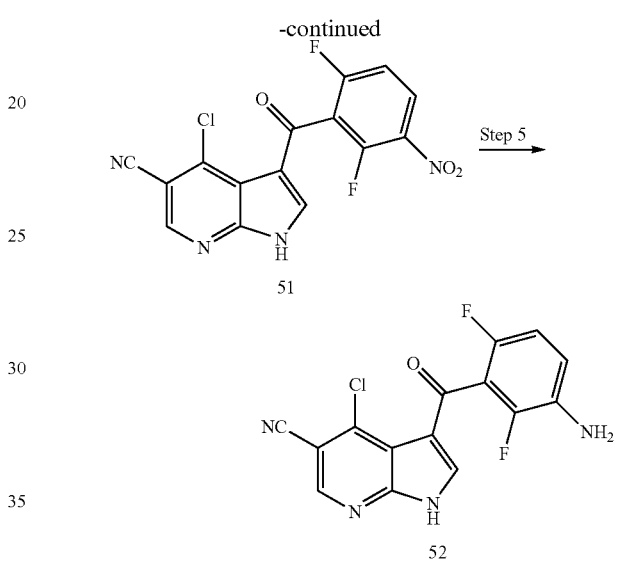

Step 1—Preparation of 2,6-difluoro-3-nitro-benzoic acid benzyl ester (47)

2,4-Difluoro-1-nitro-benzene (46, 1.4 mL, 13.0 mmol) and benzyl chloroformate (31, 10.42 g, 61.1 mmol) in 20 mL of tetrahydrofuran is cooled to −78° C. and stirred for 1 hour. Lithium diisopropylamine (1.5 g, 14.0 mmol) is added dropwise and the reaction is stirred at −78° C. for 1 hour, then warmed to room temperature over 2 hours. The reaction was purified by silica gel chromatography, eluting with hexane:ethyl acetate 90:10. Appropriate fractions are combined and concentrated under vacuum, then washed with methanol and the solid collected by filtration to provide the desired compound (47, 110 mg).

Step 2—Preparation of 2,6-difluoro-3-nitro-benzoic acid (48)

To 2,6-difluoro-3-nitro-benzoic acid benzyl ester (47, 750 mg, 2.6 mmol) in 4 mL of tetrahydrofuran and 2 mL of water, sodium hydroxide (0.2 g, 5.0 mmol) is added and the reaction is stirred for 2 hours. The reaction is acidified with dilute hydrochloric acid and extracted with ethyl acetate. The organic layer is concentrated under vacuum to provide the desired compound (48, 300 mg).

Step 3—Preparation of 2,6-difluoro-3-nitro-benzoyl chloride (49)

To 2,6-difluoro-3-nitro-benzoic acid (48, 5.50 g, 27.1 mmol), thionyl chloride (20 mL, 300 mmol) is added, followed by N,N-dimethylformamide (0.1 mL, 2.0 mmol) and the reaction is heated in an oil bath at 80° C. After overnight reaction, the reaction mixture is concentrated under vacuum, azeotroped with toluene (2×) to provide the desired compound (49, 5.95 g).

Step 4—Preparation of 4-chloro-3-(2,6-difluoro-3-nitro-benzoyl)-1H-pyrrolo[2,3-b]pyridine-5-carbonitrile (51)

In a vial, 4-chloro-1H-pyrrolo[2,3-b]pyridine-5-carbonitrile (50, 500 mg, 2.82 mmol) is cooled in an ice water bath, and trifluoromethanesulfonic acid (2.49 mL, 28.15 mmol) is added. The solution is stirred at 0-5° C. for 5 minutes, then 2,6-difluoro-3-nitro-benzoyl chloride (49, 748.5 mg, 3.38 mmol) is added. The reaction is stirred at 0-5° C. for 1 hour, then warmed to room temperature and stirred for 4 days. The reaction is quenched with 5 mL of methanol, and stirred at room temperature for 1 hour. The reaction is poured into saturated aqueous sodium bicarbonate and extracted with ethyl acetate. The organic layer is washed with water, brine, dried with magnesium sulfate, filtered and the filtrate is concentrated under vacuum. The resulting material is purified by silica gel column chromatography, eluting with 0-100% ethyl acetate in hexane. Appropriate fractions are combined and concentrated under vacuum to provide the desired compound (51, 134 mg).

Step 5—Preparation of 3-(3-amino-2,6-difluoro-benzoyl)-4-chloro-1H-pyrrolo[2,3-b]pyridine-5-carbonitrile (52)

In a round bottom flask, 4-chloro-3-(2,6-difluoro-3-nitro-benzoyl)-1H-pyrrolo[2,3-b]pyridine-5-carbonitrile (51, 0.15 g, 0.42 mmol) in 10 mL of ethanol and 10 mL of tetrahydrofuran, tin(II) chloride (0.1 mL, 2.1 mmol) is added. An additional 10 mL of tetrahydrofuran is added to give a clear solution, and the reaction is heated at 60° C. for 24 hours. The reaction is combined with 10 mL of water and 10 mL of saturated aqueous sodium bicarbonate and 20 mL of ethyl acetate is added. Celite is added with mixing, and then filtered. Brine is added to the filtrate and the layers are separated. The organic layer is washed with water, brine, dried with magnesium sulfate, filtered and the filtrate is concentrated under vacuum. The resulting material is purified by silica gel column chromatography, eluting with 0-80% ethyl acetate in hexane. Appropriate fractions are combined and concentrated under vacuum to provide the desired compound (52, 123 mg). MS (ESI) $[M+H^+]^+$=332.8 and 334.8.

Additional substituted (3-amino-2,6-difluoro-phenyl)-(1H-pyrrolo[2,3-b]pyridin-3-yl)-methanone compounds are prepared following the protocol of Scheme 1h. Compounds are prepared substituting 4-chloro-1H-pyrrolo[2,3-b]pyridine-5-carbonitrile 50 with a suitable substituted 1H-pyrrolo[2,3-b]pyridine in step 4. The following compounds are made using this procedure:
(3-Amino-2,6-difluoro-phenyl)-(4-chloro-1H-pyrrolo[2,3-b]pyridin-3-yl)-methanone (53),
(3-Amino-2,6-difluoro-phenyl)-(5-fluoro-4-iodo-1H-pyrrolo[2,3-b]pyridin-3-yl)-methanone (54),
(3-Amino-2,6-difluoro-phenyl)-(5-chloro-4-iodo-1H-pyrrolo[2,3-b]pyridin-3-yl)-methanone (55),
(3-Amino-2,6-difluoro-phenyl)-(4-chloro-5-methyl-1H-pyrrolo[2,3-b]pyridin-3-yl)-methanone (56),
(3-Amino-2,6-difluoro-phenyl)-(4-chloro-5-hydroxymethyl-1H-pyrrolo[2,3-b]pyridin-3-yl)-methanone (57), and
(3-Amino-2,6-difluoro-phenyl)-(4-iodo-5-methoxy-1H-pyrrolo[2,3-b]pyridin-3-yl)-methanone (58).

The following table indicates the 1H-pyrrolo[2,3-b]pyridine compound (column 2) used in step 4 to afford the desired compound (column 3). The compound number is provided in column 1, and the observed mass is in column 4

| Compound number | 1H-pyrrolo[2,3-b]pyridine | Compound structure | MS (ESI) $[M - H^+]^-$ |
|---|---|---|---|
| 53 | (Cl-substituted 1H-pyrrolo[2,3-b]pyridine) | (4-chloro-1H-pyrrolo[2,3-b]pyridin-3-yl methanone with 3-amino-2,6-difluorophenyl) | 308.3 |
| 54 | (5-fluoro-4-iodo-1H-pyrrolo[2,3-b]pyridine) | (5-fluoro-4-iodo-1H-pyrrolo[2,3-b]pyridin-3-yl methanone with 3-amino-2,6-difluorophenyl) | 418.0 |

-continued
| Compound number | 1H-pyrrolo[2,3-b]pyridine | Compound structure | MS (ESI) [M − H⁺]⁻ |
|---|---|---|---|
| 55 | | 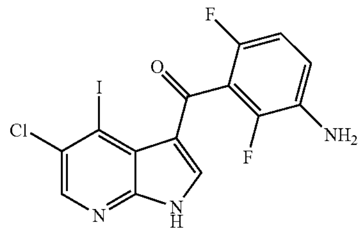 [SMILES: Nc1ccc(F)c(C(=O)c2c[nH]c3ncc(Cl)c(I)c23)c1F] | |
| 56 | | 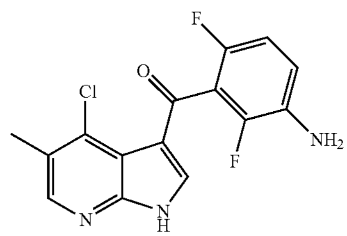 [SMILES: Cc1cnc2[nH]cc(C(=O)c3c(F)ccc(N)c3F)c2c1Cl] | |
| 57 | | 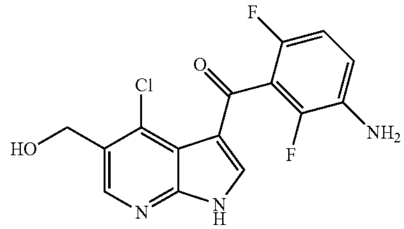 [SMILES: Nc1ccc(F)c(C(=O)c2c[nH]c3ncc(CO)c(Cl)c23)c1F] | |
| 58 | | 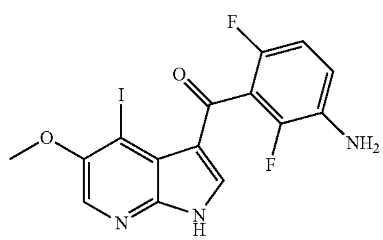 [SMILES: COc1cnc2[nH]cc(C(=O)c3c(F)ccc(N)c3F)c2c1I] | |
Example 2
Synthesis of N-(2,4-difluoro-3-formyl-phenyl)-4-ethyl-benzenesulfonamide 61
N-(2,4-Difluoro-3-formyl-phenyl)-4-ethyl-benzenesulfonamide 61 is synthesized in two steps from 2,4-difluorophenylamine 30 and 4-ethyl-benzenesulfonyl chloride 59 as shown in Scheme 2.
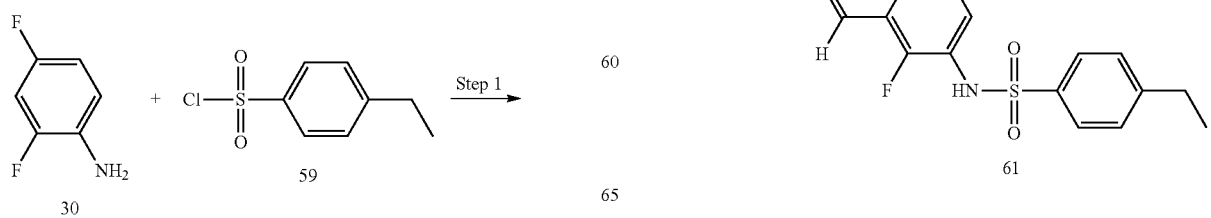

Step 1—Preparation of N-(2,4-difluoro-phenyl)-4-ethyl-benzenesulfonamide (60)

To 2,4-difluoro-phenylamine (30, 2.0 g, 15.5 mmol) in 20 mL of dichloromethane, pyridine (1.326 mL, 16.4 mmol) and dimethylaminopyridine (0.076 g, 0.62 mmol) are added followed by the dropwise addition of 4-ethyl-benzenesulfonyl chloride (59, 3.357 g, 16.4 mmol) and the reaction is heated to reflux overnight. The reaction is concentrated under vacuum to dryness, then brought up in ethyl acetate and water for extraction. The organic layer is isolated and concentrated under vacuum. The resulting material is purified by silica gel column chromatography eluting with a gradient of 10-20% ethyl acetate in hexane. Appropriate fractions are combined and concentrated under vacuum to provide the desired compound (60, 4.344 g).

Step 2—Preparation of N-(2,4-difluoro-3-formyl-phenyl)-4-ethyl-benzenesulfonamide (61)

To N,N-diisopropylamine (4.50 mL, 32.1 mmol) in 130 mL of tetrahydrofuran, n-butyllithium (12.8 mL, 2.50 M in hexane, 32.1 mmol) is added at −78° C. under nitrogen. After 15 minutes, N-(2,4-difluoro-phenyl)-4-ethyl-benzenesulfonamide (60, 4.344 g, 14.61 mmol) in 20 mL of tetrahydrofuran is added at −78° C. under nitrogen. After 30 minutes, N,N-dimethylformamide (2.83 mL, 36.5 mmol) is added and the reaction continued at −78° C. under nitrogen for 1 hour, then warmed to room temperature over 60 minutes. The reaction is quenched with 6 mL of 6 N aqueous hydrochloric acid. The aqueous layer is extracted with ethyl acetate. The organic layers are combined and washed with brine, dried over magnesium sulfate, filtered and the filtrate concentrated under vacuum. The resulting material is purified by silica gel column chromatography eluting with a gradient of 5-35% ethyl acetate in hexane. Appropriate fractions are combined and concentrated under vacuum to provide the desired compound (61, 2.634 g). MS (ESI) $[M-H^+]^-=324.2$.

Additional aldehyde compounds are prepared following the protocol of Scheme 2. Compounds are prepared substituting 4-ethyl-benzenesulfonyl chloride 59 with a suitable sulfonyl chloride in step 1.

The following compounds are made using this procedure:
2-Methyl-propane-1-sulfonic acid (2,4-difluoro-3-formyl-phenyl)-amide (62),
N-(2,4-Difluoro-3-formyl-phenyl)-4-trifluoromethyl-benzenesulfonamide (63),
N-(2,4-Difluoro-3-formyl-phenyl)-4-propyl-benzenesulfonamide (64),
N-(2,4-Difluoro-3-formyl-phenyl)-4-isopropyl-benzenesulfonamide (65), Propane-1-sulfonic acid (2,4-difluoro-3-formyl-phenyl)-amide (66),
N-(2,4-Difluoro-3-formyl-phenyl)-3,5-dimethyl-benzenesulfonamide (67),
N-(2,4-Difluoro-3-formyl-phenyl)-benzenesulfonamide (68), and
N-(2,4-Difluoro-3-formyl-phenyl)-2,5-difluoro-benzenesulfonamide (69).

The following table indicates the sulfonyl chloride compound (column 2) used in step 1 to afford the desired aldehyde compound (column 3). The compound number is provided in column 1, and the observed mass is in column 4

| Compound number | Sulfonyl chloride | Aldehyde structure | MS (ESI) $[M-H^+]^-$ |
|---|---|---|---|
| 62 | [structure: Cl-S(=O)₂-CH₂-CH(CH₃)₂] | [structure: 2,4-difluoro-3-formylphenyl with isobutylsulfonamide] | 276.1 |
| 63 | [structure: Cl-S(=O)₂-C₆H₄-CF₃] | [structure: 2,4-difluoro-3-formylphenyl with 4-trifluoromethylbenzenesulfonamide] | 364.1 |
| 64 | [structure: Cl-S(=O)₂-C₆H₄-CH₂CH₃ (propyl)] | [structure: 2,4-difluoro-3-formylphenyl with 4-propylbenzenesulfonamide] | 338.18 |

-continued

| Compound number | Sulfonyl chloride | Aldehyde structure | MS (ESI) [M − H⁺]⁻ |
|---|---|---|---|
| 65 | 4-isopropylbenzenesulfonyl chloride | N-(3-formyl-2,4-difluorophenyl)-4-isopropylbenzenesulfonamide | 338.2 |
| 66 | propane-1-sulfonyl chloride | N-(3-formyl-2,4-difluorophenyl)propane-1-sulfonamide | 262 |
| 67 | 3,5-dimethylbenzenesulfonyl chloride | N-(3-formyl-2,4-difluorophenyl)-3,5-dimethylbenzenesulfonamide | 323.9 |
| 68 | benzenesulfonyl chloride | N-(3-formyl-2,4-difluorophenyl)benzenesulfonamide | |
| 69 | 2,5-difluorobenzenesulfonyl chloride | N-(3-formyl-2,4-difluorophenyl)-2,5-difluorobenzenesulfonamide | 331.9 |

Example 3

Synthesis of 2,5-difluoro-N-(2-fluoro-3-formyl-phenyl)-benzenesulfonamide 76

2,5-Difluoro-N-(2-fluoro-3-formyl-phenyl)-benzenesulfonamide 76 is prepared in five steps from 2-fluoro-3-nitro-benzoic acid 70 as shown in Scheme 3.

Scheme 3

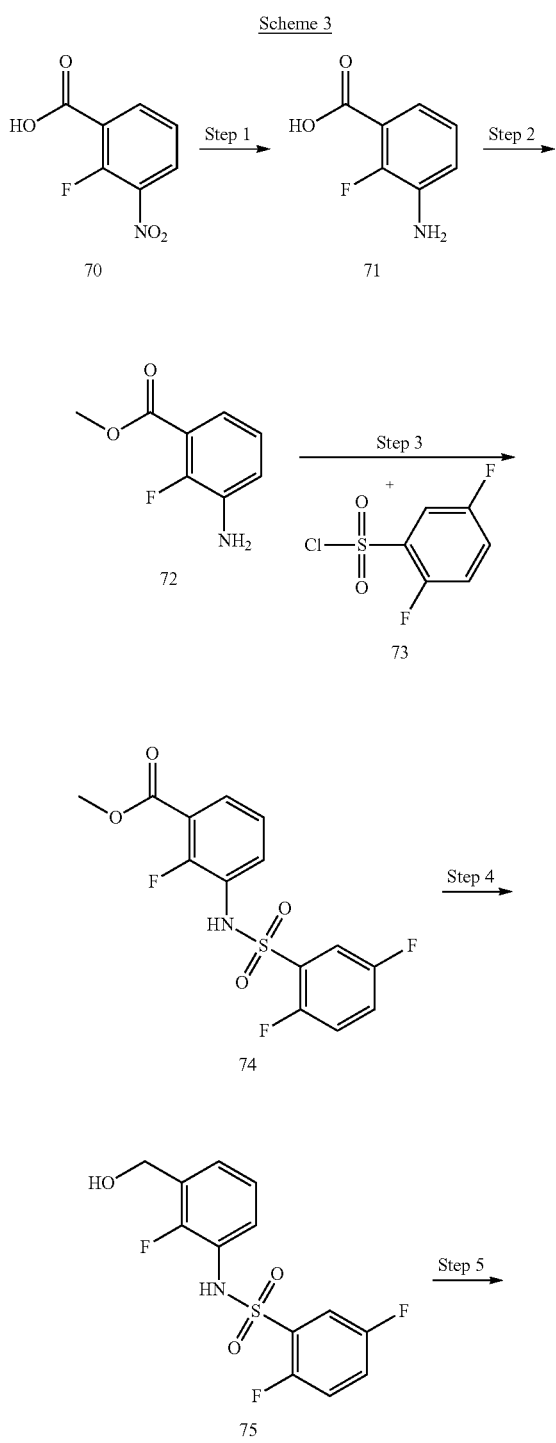

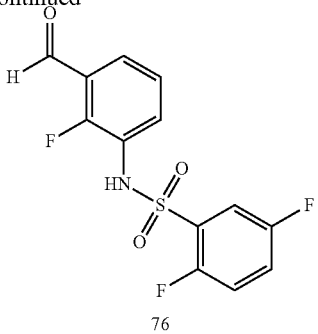

Step 1—Preparation of 3-amino-2-fluoro-benzoic acid (71)

To 2-fluoro-3-nitro-benzoic acid (70, 6.77 g, 36.6 mmol) in 150 mL of methanol, Palladium on carbon (5:95 Palladium:Carbon, 0.338 g, 0.159 mmol) is added under a balloon of hydrogen. The reaction is stirred at room temperature for 40 hours, then a new balloon of hydrogen is attached, and the reaction continued for 5 hours. The reaction is filtered and the filtrate is concentrated under vacuum to provide the desired compound (71, 5.62 g). MS (ESI) $[M-H^+]^-=154.1$.

Step 2—Preparation of 3-amino-2-fluoro-benzoic acid methyl ester (72)

In a round bottom flask, 3-amino-2-fluoro-benzoic acid (71, 2.51 g, 16.2 mmol) is dissolved in 100 mL of methanol and 1 mL of concentrated sulfuric acid is added. The reaction is heated to reflux for 24 hours and an additional 1 mL of concentrated sulfuric acid is added. The reaction is heated to reflux another 20 hours, then extracted with ethyl acetate and saturated aqueous sodium chloride. The organic layer is isolated and washed with water, sodium bicarbonate, and brine, then dried with magnesium sulfate, and filtered. The filtrate is concentrated under vacuum to provide the desired compound (72, 2.688 g).

Step 3—Preparation of 3-(2,5-difluoro-benzenesulfonylamino)-2-fluoro-benzoic acid methyl ester (74)

To 3-amino-2-fluoro-benzoic acid methyl ester (72, 1.08 g, 6.4 mmol) in 40.64 mL of dichloromethane, pyridine (1.29 mL, 16 mmol) is added, followed by 2,5-difluorobenzenesulfonyl chloride (73, 3.391 g, 16 mmol). The reaction is stirred at room temperature overnight, then quenched with 1M aqueous hydrochloric acid. The organic layer is removed and the aqueous layer is extracted with dichloromethane. The organic layers are combined and washed with brine, then dried over sodium sulfate, filtered and the filtrate is concentrated under vacuum. The resulting material is purified by silica gel column chromatography, eluting with ethyl acetate and hexane. Appropriate fractions are combined and concentrated under vacuum to provide the desired compound (74, 0.956 g). MS (ESI) $[M-H^+]^-=344$.

Step 4—Preparation of 2,5-difluoro-N-(2-fluoro-3-hydroxymethyl-phenyl)-benzenesulfonamide (75)

To 3-(2,5-difluoro-benzenesulfonylamino)-2-fluoro-benzoic acid methyl ester (74, 0.955 g, 2.8 mmol) in 22 mL of tetrahydrofuran, lithium tetrahydroaluminate (6 mL, 1M in tetrahydrofuran, 6 mmol) is added at −40° C. under nitrogen.

The reaction is allowed to warm to room temperature and stirred overnight. The reaction is poured into 1M aqueous sodium hydroxide, then neutralized with 1M aqueous hydrochloric acid. The solids are filtered through a bed of celite, and the celite bed is washed with ethyl acetate and tetrahydrofuran. The filtrate layers are separated and the aqueous layer is extracted with ethyl acetate. The organic layers are combined and washed with brine, dried over sodium sulfate, filtered and the filtrate is concentrated under vacuum. The resulting material is purified by silica gel column chromatography, eluting with ethyl acetate and dichloromethane. Appropriate fractions are combined and concentrated under vacuum to provide the desired compound (75, 0.875 g). MS (ESI) [M−H$^+$]$^−$=316.

Step 5—Preparation of 2,5-difluoro-N-(2-fluoro-3-formyl-phenyl)-benzenesulfonamide (76)

2,5-Difluoro-N-(2-fluoro-3-hydroxymethyl-phenyl)-benzenesulfonamide (75, 950 mg, 2.99 mmol) and stabilized 2-iodoxybenzoic acid (2.608 g, 45%, 4.2 mmol) are dissolved in 150 mL of tetrahydrofuran and the reaction is stirred at room temperature for 16 hours. The reaction is poured into water and extracted with ethyl acetate. The organic layer is washed with brine, dried over sodium sulfate, filtered and the filtrate is concentrated under vacuum. The resulting material is purified by silica gel column chromatography, eluting with ethyl acetate and dichloromethane. Appropriate fractions are combined and concentrated under vacuum to provide the desired compound (76, 0.944 g). MS (ESI) [M−H$^+$]$^−$=314.

Example 4

Synthesis of N-[2,4-difluoro-3-(4-methoxy-7H-pyrrolo[2,3-d]pyrimidine-5-carbonyl)-phenyl]-4-ethyl-benzenesulfonamide P-1008

N-[2,4-Difluoro-3-(4-methoxy-7H-pyrrolo[2,3-d]pyrimidine-5-carbonyl)-phenyl]-4-ethyl-benzenesulfonamide P-1008 is prepared in one step from (3-amino-2,6-difluoro-phenyl)-(4-methoxy-7H-pyrrolo[2,3-d]pyrimidin-5-yl)-methanone 36 and 4-ethyl-benzenesulfonyl chloride 59 as shown in Scheme 4.

Scheme 4

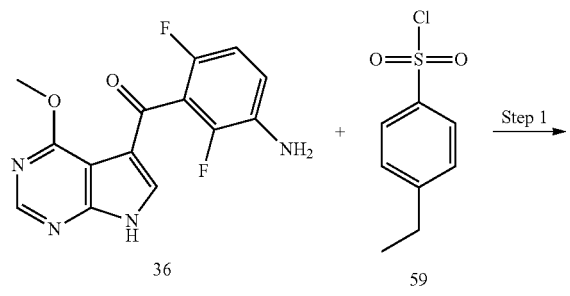

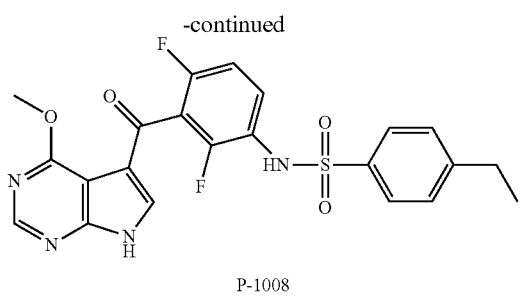

P-1008

Step 1—Preparation of N-[2,4-difluoro-3-(4-methoxy-7H-pyrrolo[2,3-c]pyrimidine-5-carbonyl)-phenyl]-4-ethyl-benzenesulfonamide (P-1008)

To (3-amino-2,6-difluoro-phenyl)-(4-methoxy-7H-pyrrolo[2,3-d]pyrimidin-5-yl)-methanone (36, 30.0 mg, 0.0986 mmol) 1.0 mL of tetrahydrofuran and pyridine (23.9 μL, 0.296 mmol) are added, followed by 4-ethyl-benzenesulfonyl chloride (59, 40.4 mg, 0.197 mmol). The reaction vial is stirred at room temperature for 5 days, then extracted by adding aqueous saturated sodium chloride and ethyl acetate. The organic layer is washed with water, then sodium bicarbonate, then brine, and dried over magnesium sulfate, filtered and the filtrate concentrated under vacuum. The resulting material is purified by silica gel column chromatography eluting with ethyl acetate and hexane. Appropriate fractions are combined and concentrated under vacuum to provide the desired compound (P-1008, 27 mg). MS (ESI) [M+H$^+$]$^+$=473.0.

Additional compounds are prepared following the protocol of Scheme 4, optionally replacing (3-amino-2,6-difluoro-phenyl)-(4-methoxy-7H-pyrrolo[2,3-d]pyrimidin-5-yl)-methanone 36 with an appropriately 4-substituted (3-amino-2,6-difluoro-phenyl)-(7H-pyrrolo[2,3-d]pyrimidin-5-yl)-methanone or suitably substituted (3-amino-2,6-difluoro-phenyl)-(1H-pyrrolo[2,3-b]pyridin-3-yl)-methanone and optionally replacing 4-ethyl-benzenesulfonyl chloride 59 with an appropriate sulfonyl chloride. The following compounds are made using this procedure:

N-[3-(4-Chloro-1H-pyrrolo[2,3-b]pyridine-3-carbonyl)-2,4-difluoro-phenyl]-2,5-difluoro-benzenesulfonamide (77), 6-Methoxy-pyridine-3-sulfonic acid [2,4-difluoro-3-(4-methoxy-7H-pyrrolo[2,3-d]pyrimidine-5-carbonyl)-phenyl]-amide (P-1018), N-[2,4-Difluoro-3-(4-methyl-7H-pyrrolo[2,3-d]pyrimidine-5-carbonyl)-phenyl]-3-fluoro-4-methoxy-benzenesulfonamide (P-1036), N-[2,4-Difluoro-3-(4-hydroxy-7H-pyrrolo[2,3-d]pyrimidine-5-carbonyl)-phenyl]-2-fluoro-benzenesulfonamide (P-1070), N-[2,4-Difluoro-3-(4-isopropylamino-7H-pyrrolo[2,3-d]pyrimidine-5-carbonyl)-phenyl]-2-fluoro-benzenesulfonamide (P-1073), N-[3-(4-Cyclopropylamino-7H-pyrrolo[2,3-d]pyrimidine-5-carbonyl)-2,4-difluoro-phenyl]-2,5-difluoro-benzenesulfonamide (P-1104), N-[3-(4-Cyclopropyl-7H-pyrrolo[2,3-d]pyrimidine-5-carbonyl)-2,4-difluoro-phenyl]-2,5-difluoro-benzenesulfonamide (P-1107), 4-Cyano-N-[2,4-difluoro-3-(4-isopropylamino-7H-pyrrolo[2,3-d]pyrimidine-5-carbonyl)-phenyl]-benzenesulfonamide (P-1108), 2,2,2-Trifluoro-ethanesulfonic acid [2,4-difluoro-3-(4-isopropylamino-7H-pyrrolo[2,3-d]pyrimidine-5-carbonyl)-phenyl]-amide (P-1109), N-[2,4-Difluoro-3-(4-isopropylamino-7H-pyrrolo[2,3-d]pyrimidine-5-carbonyl)-phenyl]-4-difluoromethoxy-benzenesulfonamide (P-1110), N-[2,4-Difluoro-3-(4-isopropylamino-7H-pyrrolo[2,3-d]pyrimidine-5-carbonyl)-phenyl]-2,5-difluoro-benzenesulfonamide (P-1111), N-[2,4-Difluoro-3-(4-isopropylamino-7H-pyrrolo[2,3-d]pyrimidine-5-carbonyl)-phenyl]-2,6-difluoro-benzenesulfonamide (P-1112), N-[2,4-Difluoro-3-(4-isopropylamino-7H-pyrrolo[2,3-d]pyrimidine-5-carbonyl)-phenyl]-2,4-difluoro-benzenesulfonamide (P-1113), Propane-2-sulfonic acid [2,4-difluoro-3-(4-isopropylamino-7H-pyrrolo[2,3-d]pyrimidine-5-carbonyl)-phenyl]-amide (P-1114), N-[2,4-Difluoro-3-(4-isopropylamino-7H-pyrrolo[2,3-d]pyrimidine-5-carbonyl)-phenyl]-3-fluoro-benzenesulfonamide (P-1115), 3-Cyano-N-[2,4-difluoro-3-(4-isopropylamino-7H-pyrrolo[2,3-d]pyrimidine-5-carbonyl)-phenyl]-benzenesulfonamide (P-1116), N-[2,4-Difluoro-3-(4-isopropylamino-7H-pyrrolo[2,3-d]pyrimidine-5-carbonyl)-phenyl]-3-fluoro-4-methoxy-benzenesulfonamide (P-1117), 3,3,3-Trifluoro-propane-1-sulfonic acid [2,4-difluoro-3-(4-isopropylamino-7H-pyrrolo[2,3-d]pyrimidine-5-carbonyl)-phenyl]-amide (P-1118), N-[2,4-Difluoro-3-(4-isopropylamino-7H-pyrrolo[2,3-d]pyrimidine-5-carbonyl)-phenyl]-3-difluoromethoxy-benzenesulfonamide (P-1119), 1-Ethyl-1H-pyrazole-4-sulfonic acid [2,4-difluoro-3-(4-isopropylamino-7H-pyrrolo[2,3-d]pyrimidine-5-carbonyl)-phenyl]-amide (P-1120), 1-Methyl-1H-pyrazole-4-sulfonic acid [2,4-difluoro-3-(4-isopropylamino-7H-pyrrolo[2,3-d]pyrimidine-5-carbonyl)-phenyl]-amide (P-1121), Piperidine-1-sulfonic acid [2,4-difluoro-3-(4-isopropylamino-7H-pyrrolo[2,3-d]pyrimidine-5-carbonyl)-phenyl]-amide (P-1122), Cyclohexanesulfonic acid [2,4-difluoro-3-(4-isopropylamino-7H-pyrrolo[2,3-d]pyrimidine-5-carbonyl)-phenyl]-amide (P-1123), Cyclopentanesulfonic acid [2,4-difluoro-3-(4-isopropylamino-7H-pyrrolo[2,3-d]pyrimidine-5-carbonyl)-phenyl]-amide (P-1124), Pyrrolidine-1-sulfonic acid [2,4-difluoro-3-(4-isopropylamino-7H-pyrrolo[2,3-d]pyrimidine-5-carbonyl)-phenyl]-amide (P-1125), 2-Methyl-propane-1-sulfonic acid [2,4-difluoro-3-(4-isopropylamino-7H-pyrrolo[2,3-d]pyrimidine-5-carbonyl)-phenyl]-amide (P-1126), Diethylamine-1-sulfonic acid [2,4-difluoro-3-(4-isopropylamino-7H-pyrrolo[2,3-d]pyrimidine-5-carbonyl)-phenyl]-amide (P-1127), Cyclobutanesulfonic acid [2,4-difluoro-3-(4-isopropylamino-7H-pyrrolo[2,3-d]pyrimidine-5-carbonyl)-phenyl]-amide (P-1128), Morpholine-4-sulfonic acid [2,4-difluoro-3-(4-isopropylamino-7H-pyrrolo[2,3-d]pyrimidine-5-carbonyl)-phenyl]-amide (P-1129), 6-Methoxy-pyridine-3-sulfonic acid [2,4-difluoro-3-(4-isopropylamino-7H-pyrrolo[2,3-d]pyrimidine-5-carbonyl)-phenyl]-amide (P-1130), 6-Methyl-pyridine-2-sulfonic acid [2,4-difluoro-3-(4-isopropylamino-7H-pyrrolo[2,3-d]pyrimidine-5-carbonyl)-phenyl]-amide (P-1131), Pyridine-3-sulfonic acid [2,4-difluoro-3-(4-isopropylamino-7H-pyrrolo[2,3-d]pyrimidine-5-carbonyl)-phenyl]-amide (P-1132), Pyridine-2-sulfonic acid [2,4-difluoro-3-(4-isopropylamino-7H-pyrrolo[2,3-d]pyrimidine-5-carbonyl)-phenyl]-amide (P-1133), N-[2,4-Difluoro-3-(4-isopropylamino-7H-pyrrolo[2,3-d]pyrimidine-5-carbonyl)-phenyl]-benzenesulfonamide (P-1155), Dimethylamine-1-sulfonic acid [2,4-difluoro-3-(4-isopropylamino-7H-pyrrolo[2,3-d]pyrimidine-5-carbonyl)-phenyl]-amide (P-1156), N-[2,4-Difluoro-3-(4-hydroxy-7H-pyrrolo[2,3-d]pyrimidine-5-carbonyl)-phenyl]-2,5-difluoro-benzenesulfonamide (P-1183), N-{3-[4-(Cyclopropylmethyl-amino)-7H-pyrrolo[2,3-d]pyrimidine-5-carbonyl]-2,4-difluoro-phenyl}-2,4-difluoro-benzenesulfonamide (P-1186), N-{3-[4-(Cyclopropylmethyl-amino)-7H-pyrrolo[2,3-d]pyrimidine-5-carbonyl]-2,4-difluoro-phenyl}-3-fluoro-benzenesulfonamide (P-1187), N-{3-[4-(Cyclopropylmethyl-amino)-7H-pyrrolo[2,3-d]pyrimidine-5-carbonyl]-2,4-difluoro-phenyl}-3-fluoro-4-methoxy-benzenesulfonamide (P-1188), N-{3-[4-(Cyclopropylmethyl-amino)-7H-pyrrolo[2,3-d]pyrimidine-5-carbonyl]-2,4-difluoro-phenyl}-4-fluoro-benzenesulfonamide (P-1189), N-{3-[4-(Cyclopropylmethyl-amino)-7H-pyrrolo[2,3-d]pyrimidine-5-carbonyl]-2,4-difluoro-phenyl}-3-fluoro-4-methyl-benzenesulfonamide (P-1190), N-{3-[4-(Cyclopropylmethyl-amino)-7H-pyrrolo[2,3-d]pyrimidine-5-carbonyl]-2,4-difluoro-phenyl}-3,5-difluoro-benzenesulfonamide (P-1191), N-{3-[4-(Cyclopropylmethyl-amino)-7H-pyrrolo[2,3-d]pyrimidine-5-carbonyl]-2,4-difluoro-phenyl}-4-fluoro-2-methyl-benzenesulfonamide (P-1192), N-{3-[4-(Cyclopropylmethyl-amino)-7H-pyrrolo[2,3-d]pyrimidine-5-carbonyl]-2,4-difluoro-phenyl}-2-fluoro-5-methyl-benzenesulfonamide (P-1193), N-{3-[4-(Cyclopropylmethyl-amino)-7H-pyrrolo[2,3-d]pyrimidine-5-carbonyl]-2,4-difluoro-phenyl}-2-fluoro-5-trifluoromethyl-benzenesulfonamide (P-1194), N-{3-[4-(Cyclopropylmethyl-amino)-7H-pyrrolo[2,3-d]pyrimidine-5-carbonyl]-2,4-difluoro-phenyl}-2-fluoro-4-methyl-benzenesulfonamide (P-1195), N-{3-[4-(Cyclopropylmethyl-amino)-7H-pyrrolo[2,3-d]pyrimidine-5-carbonyl]-2,4-difluoro-phenyl}-2-fluoro-4-methoxy-benzenesulfonamide (P-1196), 5-Chloro-N-{3-[4-(cyclopropylmethyl-amino)-7H-pyrrolo[2,3-d]pyrimidine-5-carbonyl]-2,4-difluoro-phenyl}-2-fluoro-benzenesulfonamide (P-1197), 3-Chloro-N-{3-[4-(cyclopropylmethyl-amino)-7H-pyrrolo[2,3-d]pyrimidine-5-carbonyl]-2,4-difluoro-phenyl}-2-fluoro-benzenesulfonamide (P-1198), N-{3-[4-(Cyclopropylmethyl-amino)-7H-pyrrolo[2,3-d]pyrimidine-5-carbonyl]-2,4-difluoro-phenyl}-3,4-difluoro-benzene sulfonamide (P-1199), N-{3-[4-(Cyclopropylmethyl-amino)-7H-pyrrolo[2,3-d]pyrimidine-5-carbonyl]-2,4-difluoro-phenyl}-3-fluoro-5-trifluoromethyl-benzenesulfonamide (P-1200), N-{3-[4-(Cyclopropylmethyl-amino)-7H-pyrrolo[2,3-d]pyrimidine-5-carbonyl]-2,4-difluoro-phenyl}-3-fluoro-2-methyl-benzenesulfonamide (P-1201), 4-Chloro-N-{3-[4-(cyclopropylmethyl-amino)-7H-pyrrolo[2,3-d]pyrimidine-5-carbonyl]-2,4-difluoro-phenyl}-3-fluoro-benzenesulfonamide (P-1202), N-{3-[4-(Cyclopropylmethyl-amino)-7H-pyrrolo[2,3-d]pyrimidine-5-carbonyl]-2,4-difluoro-phenyl}-5-fluoro-2-methyl-benzenesulfonamide (P-1203), N-{3-[4-(Cyclopropylmethyl-amino)-7H-pyrrolo[2,3-d]pyrimidine-5-carbonyl]-2,4-difluoro-phenyl}-5-fluoro-2-methoxy-benzenesulfonamide (P-1204), N-{3-[4-(Cyclopropylmethyl-amino)-7H-pyrrolo[2,3-d]pyrimidine-5-carbonyl]-2,4-difluoro-phenyl}-3-trifluoromethyl-benzenesulfonamide (P-1205), N-{3-[4-(Cyclopropylmethyl-amino)-7H-pyrrolo[2,3-d]pyrimidine-5-carbonyl]-2,4-difluoro-phenyl}-2,6-difluoro-benzenesulfonamide (P-1206), N-{3-[4-(Cyclopropylmethyl-amino)-7H-pyrrolo[2,3-d]pyrimidine-5-carbonyl]-2,4-difluoro-phenyl}-benzenesulfonamide (P-1207), Pyridine-2-sulfonic acid {3-[4-(cyclopropylmethyl-amino)-7H-pyrrolo[2,3-d]pyrimidine-5-carbonyl]-2,4-difluoro-phenyl}-amide (P-1208), 4-Methyl-pyridine-2-sulfonic acid {3-[4-(cyclopropylmethyl-amino)-7H-pyrrolo[2,3-d]pyrimidine-5-carbonyl]-2,4-difluoro-phenyl}-amide (P-1209), 6-Fluoro-pyridine-2-sulfonic acid {3-[4-(cyclopropylmethyl-amino)-7H-pyrrolo[2,3-d]pyrimidine-5-carbonyl]-2,4-difluoro-phenyl}-amide (P-1210), Pyridine-3-sulfonic acid {3-[4-(cyclopropylmethyl-amino)-7H-pyrrolo[2,3-d]pyrimidine-5-carbonyl]-2,4-difluoro-phenyl}-amide (P-1211), 4-Chloro-pyridine-3-sulfonic acid {3-[4-(cyclopropylmethyl-amino)-7H-pyrrolo[2,3-d]pyrimidine-5-carbonyl]-2,4-difluoro-phenyl}-amide (P-1212), 2-Chloro-pyridine-3-sulfonic acid {3-[4-(cyclopropylmethyl-amino)-7H-pyrrolo[2,3-d]pyrimidine-5-carbonyl]-2,4-difluoro-phenyl}-amide (P-1213), 1-Methyl-1H-pyrazole-4-sulfonic acid {3-[4-(cyclopropylmethyl-amino)-7H-pyrrolo[2,3-d]pyrimidine-5-carbonyl]-2,4-difluoro-phenyl}-amide (P-1214), N,N-Dimethylamino-sulfonic acid {3-[4-(cyclopropylmethyl-amino)-7H-pyrrolo[2,3-d]pyrimidine-5-carbonyl]-2,4-difluoro-phenyl}-amide (P-1215), N,N-Diethylamino-sulfonic acid {3-[4-(cyclopropylmethyl-amino)-7H-pyrrolo[2,3-d]pyrimidine-5-carbonyl]-2,4-difluoro-phenyl}-amide (P-1216), Pyrrolidine-1-sulfonic acid {3-[4-(cyclopropylmethyl-amino)-7H-pyrrolo[2,3-d]pyrimidine-5-carbonyl]-2,4-difluoro-phenyl}-amide (P-1217), Morpholine-4-sulfonic acid {3-[4-(cyclopropylmethyl-amino)-7H-pyrrolo[2,3-d]pyrimidine-5-carbonyl]-2,4-difluoro-phenyl}-amide (P-1218), Tetrahydro-pyran-4-sulfonic acid {3-[4-(cyclopropylmethyl-amino)-7H-pyrrolo[2,3-d]pyrimidine-5-carbonyl]-2,4-difluoro-phenyl}-amide (P-1219), Ethanesulfonic acid {3-[4-(cyclopropylmethyl-amino)-7H-pyrrolo[2,3-d]pyrimidine-5-carbonyl]-2,4-difluoro-phenyl}-amide (P-1220), Propane-2-sulfonic acid {3-[4-(cyclopropylmethyl-amino)-7H-pyrrolo[2,3-d]pyrimidine-5-carbonyl]-2,4-difluoro-phenyl}-amide (P-1221), Butane-2-sulfonic acid {3-[4-(cyclopropylmethyl-amino)-7H-pyrrolo[2,3-d]pyrimidine-5-carbonyl]-2,4-difluoro-phenyl}-amide (P-1222), 2-Methyl-propane-1-sulfonic acid {3-[4-(cyclopropylmethyl-amino)-7H-pyrrolo[2,3-d]pyrimidine-5-carbonyl]-2,4-difluoro-phenyl}-amide (P-1223), Butane-1-sulfonic acid {3-[4-(cyclopropylmethyl-amino)-7H-pyrrolo[2,3-d]pyrimidine-5-carbonyl]-2,4-difluoro-phenyl}-amide (P-1224), Pentane-2-sulfonic acid {3-[4-(cyclopropylmethyl-amino)-7H-pyrrolo[2,3-d]pyrimidine-5-carbonyl]-2,4-difluoro-phenyl}-amide (P-1225), N-{3-[4-(Cyclopropylmethyl-amino)-7H-pyrrolo[2,3-d]pyrimidine-5-carbonyl]-2,4-difluoro-phenyl}-C,C,C-trifluoro-methanesulfonamide (P-1226), 2,2,2-Trifluoro-ethanesulfonic acid {3-[4-(cyclopropylmethyl-amino)-7H-pyrrolo[2,3-d]pyrimidine-5-carbonyl]-2,4-difluoro-phenyl}-amide (P-1227), 3,3,3-Trifluoro-propane-1-sulfonic acid {3-[4-(cyclopropylmethyl-amino)-7H-pyrrolo[2,3-d]pyrimidine-5-carbonyl]-2,4-difluoro-phenyl}-amide (P-1228), Cyclohexanesulfonic acid {3-[4-(cyclopropylmethyl-amino)-7H-pyrrolo[2,3-d]pyrimidine-5-carbonyl]-2,4-difluoro-phenyl}-amide (P-1229), Cyclopentanesulfonic acid {3-[4-(cyclopropylmethyl-amino)-7H-pyrrolo[2,3-d]pyrimidine-5-carbonyl]-2,4-difluoro-phenyl}-amide (P-1230), Cyclobutanesulfonic acid {3-[4-(cyclopropylmethyl-amino)-7H-pyrrolo[2,3-d]pyrimidine-5-carbonyl]-2,4-difluoro-phenyl}-amide (P-1231), Cyclopropanesulfonic acid {3-[4-(cyclopropylmethyl-amino)-7H-pyrrolo[2,3-d]pyrimidine-5-carbonyl]-2,4-difluoro-phenyl}-amide (P-1232), 4,4-Difluoro-cyclohexanesulfonic acid {3-[4-(cyclopropylmethyl-amino)-7H-pyrrolo[2,3-d]pyrimidine-5-carbonyl]-2,4-difluoro-phenyl}-amide (P-1233), 3,3-Difluoro-cyclopentanesulfonic acid {3-[4-(cyclopropylmethyl-amino)-7H-pyrrolo[2,3-d]pyrimidine-5-carbonyl]-2,4-difluoro-phenyl}-amide (P-1234), 3-Fluoro-cyclopentanesulfonic acid {3-[4-(cyclopropylmethyl-amino)-7H-pyrrolo[2,3-d]pyrimidine-5-carbonyl]-2,4-difluoro-phenyl}-amide (P-1235), N-{3-[5-Chloro-4-(cyclopropylmethyl-amino)-1H-pyrrolo[2,3-b]pyridine-3-carbonyl]-2,4-difluoro-phenyl}-2,5-difluoro-benzenesulfonamide (P-2021), N-[2,4-Difluoro-3-(5-fluoro-4-iodo-1H-pyrrolo[2,3-b]pyridine-3-carbonyl)-phenyl]-2,5-difluoro-benzenesulfonamide (P-2025), N-[3-(4-Chloro-5-cyano-1H-pyrrolo[2,3-b]pyridine-3-carbonyl)-2,4-difluoro-phenyl]-2,5-difluoro-benzenesulfonamide (P-2026), N-[3-(5-Chloro-4-iodo-1H-pyrrolo[2,3-b]pyridine-3-carbonyl)-2,4-difluoro-phenyl]-2,5-difluoro-benzenesulfonamide (P-2027), N-[3-(4-Chloro-5-methyl-1H-pyrrolo[2,3-b]pyridine-3-carbonyl)-2,4-difluoro-phenyl]-2,5-difluoro-benzenesulfonamide (P-2028), N-[3-(4-Chloro-5-hydroxymethyl-1H-pyrrolo[2,3-b]pyridine-3-carbonyl)-2,4-difluoro-phenyl]-2,5-difluoro-benzenesulfonamide (P-2029), and N-[2,4-Difluoro-3-(4-iodo-5-methoxy-1H-pyrrolo[2,3-b]pyridine-3-carbonyl)-phenyl]-2,5-difluoro-benzenesulfonamide (P-2030).

The following table indicates the 7H-pyrrolo[2,3-d]pyrimidine or 1H-pyrrolo[2,3-b]pyridine (column 2) and sulfonyl chloride compound (column 3) used to afford the desired compound (column 4). The compound number is provided in column 1, and the observed mass is in column 5

| Comp. number | 7H-pyrrolo[2,3-d]pyrimidine | Sulfonyl chloride | Compound structure | MS (ESI) [M + H⁺]⁺ |
|---|---|---|---|---|
| 77 | | | 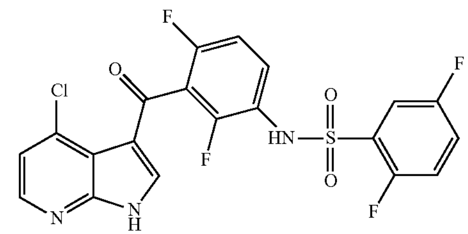 [SMILES: O=C(c1c(F)ccc(NS(=O)(=O)c2cc(F)ccc2F)c1F)c1c[nH]c2nccc(Cl)c12] | |
| P-1018 | | | 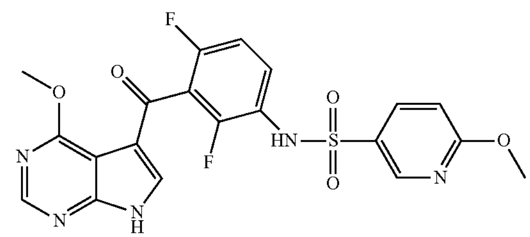 [SMILES: COc1ccc(S(=O)(=O)Nc2ccc(F)c(C(=O)c3c[nH]c4ncnc(OC)c34)c2F)cn1] | 476.0 |
| P-1036 | | | 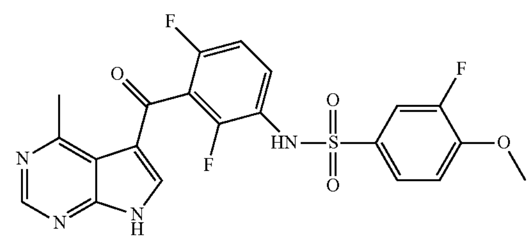 | 477.0 |

| Comp. number | 7H-pyrrolo[2,3-d]pyrimidine | Sulfonyl chloride | Compound structure | MS (ESI) [M + H+]+ |
|---|---|---|---|---|
| P-1070 | | | 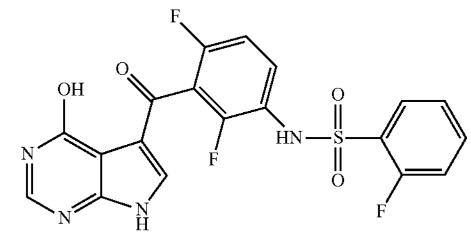 | 448.9 |
| P-1073 | | | 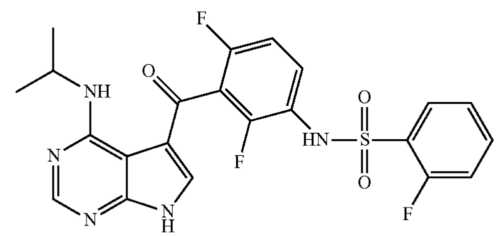 [SMILES: CC(C)Nc1ncnc2[nH]cc(C(=O)c3c(F)ccc(NS(=O)(=O)c4ccccc4F)c3F)c12] | 490.0 |
| P-1104 | | | 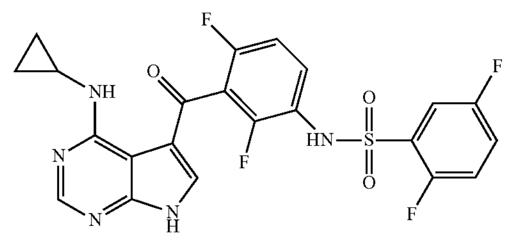 [SMILES: O=C(c1c(F)ccc(NS(=O)(=O)c2cc(F)ccc2F)c1F)c1c[nH]c2ncnc(NC3CC3)c12] | 506.0 |

-continued

| Comp. number | 7H-pyrrolo[2,3-d]pyrimidine | Sulfonyl chloride | Compound structure | MS (ESI) [M + H⁺]⁺ |
|---|---|---|---|---|
| P-1107 | | | 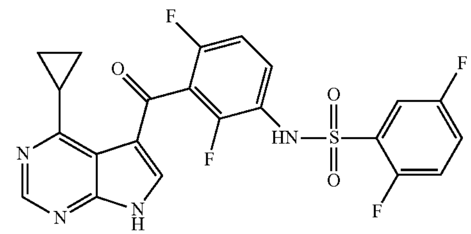 [SMILES: O=C(c1c(F)ccc(NS(=O)(=O)c2cc(F)ccc2F)c1F)c1c[nH]c2ncnc(C3CC3)c12] | 491.4 |
| P-1108 | | | 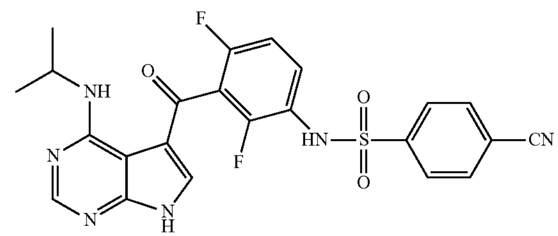 [SMILES: CC(C)Nc1ncnc2[nH]cc(C(=O)c3c(F)ccc(NS(=O)(=O)c4ccc(C#N)cc4)c3F)c12] | 497.5 |
| P-1109 | | | 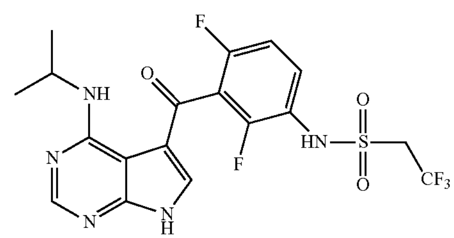 [SMILES: CC(C)Nc1ncnc2[nH]cc(C(=O)c3c(F)ccc(NS(=O)(=O)CC(F)(F)F)c3F)c12] | 478.0 |

-continued

| Comp. number | 7H-pyrrolo[2,3-d]pyrimidine | Sulfonyl chloride | Compound structure | MS (ESI) [M + H+]+ |
|---|---|---|---|---|
| P-1110 | | | 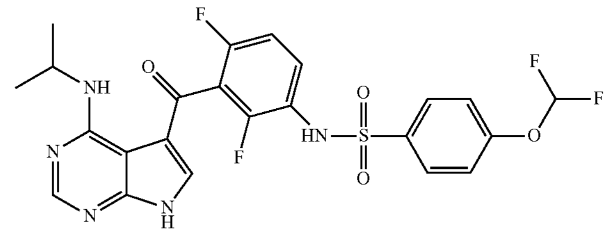 [SMILES: CC(C)Nc1ncnc2[nH]cc(C(=O)c3c(F)ccc(NS(=O)(=O)c4ccc(OC(F)F)cc4)c3F)c12] | 538.5 |
| P-1111 | | | 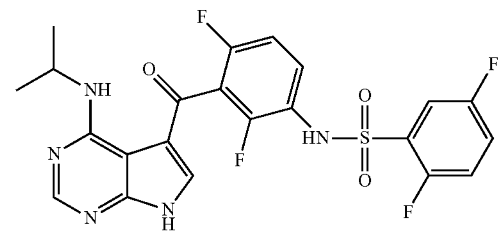 [SMILES: CC(C)Nc1ncnc2[nH]cc(C(=O)c3c(F)ccc(NS(=O)(=O)c4cc(F)ccc4F)c3F)c12] | 508.0 |
| P-1112 | | | 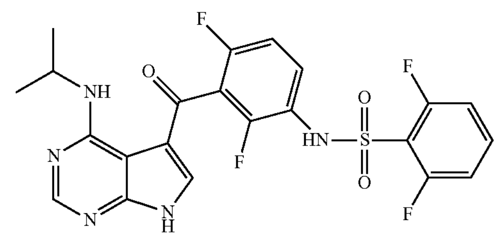 [SMILES: CC(C)Nc1ncnc2[nH]cc(C(=O)c3c(F)ccc(NS(=O)(=O)c4c(F)cccc4F)c3F)c12] | 508.0 |

-continued

| Comp. number | 7H-pyrrolo[2,3-d]pyrimidine | Sulfonyl chloride | Compound structure | MS (ESI) [M + H+]+ |
|---|---|---|---|---|
| P-1113 | | | 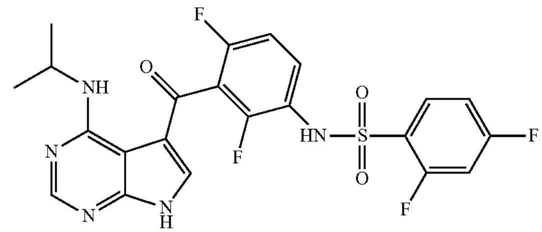 [SMILES: CC(C)Nc1ncnc2[nH]cc(C(=O)c3c(F)ccc(NS(=O)(=O)c4ccc(F)cc4F)c3F)c12] | 508.0 |
| P-1114 | | | 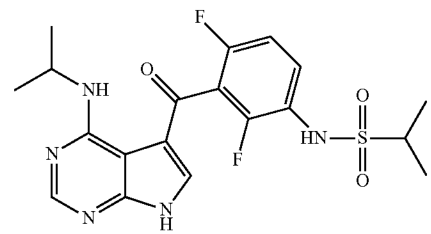 [SMILES: CC(C)Nc1ncnc2[nH]cc(C(=O)c3c(F)ccc(NS(=O)(=O)C(C)C)c3F)c12] | 438.0 |
| P-1115 | | | 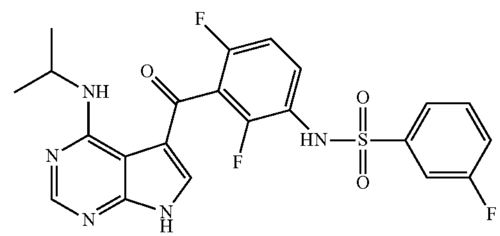 [SMILES: CC(C)Nc1ncnc2[nH]cc(C(=O)c3c(F)ccc(NS(=O)(=O)c4cccc(F)c4)c3F)c12] | 490.5 |

-continued

| Comp. number | 7H-pyrrolo[2,3-d]pyrimidine | Sulfonyl chloride | Compound structure | MS (ESI) [M + H$^+$]$^+$ |
|---|---|---|---|---|
| P-1116 | | | 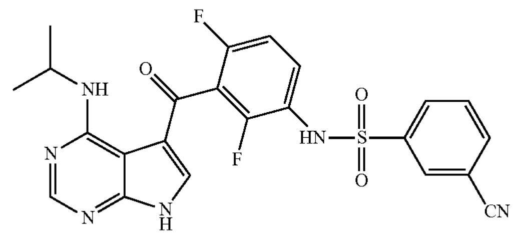 [SMILES: CC(C)Nc1ncnc2[nH]cc(C(=O)c3c(F)ccc(NS(=O)(=O)c4cccc(C#N)c4)c3F)c12] | 497.5 |
| P-1117 | | | 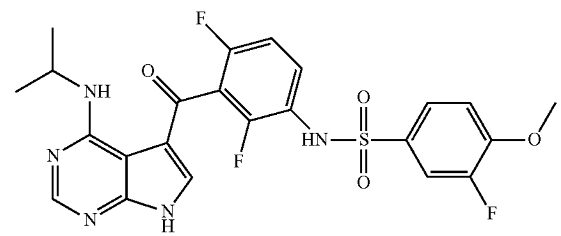 [SMILES: COc1ccc(S(=O)(=O)Nc2ccc(F)c(C(=O)c3c[nH]c4ncnc(NC(C)C)c34)c2F)cc1F] | 520.5 |
| P-1118 | | | 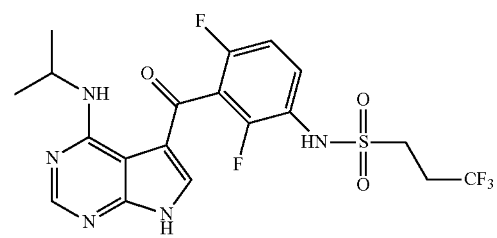 [SMILES: CC(C)Nc1ncnc2[nH]cc(C(=O)c3c(F)ccc(NS(=O)(=O)CCC(F)(F)F)c3F)c12] | 492.0 |

| Comp. number | 7H-pyrrolo[2,3-d]pyrimidine | Sulfonyl chloride | Compound structure | MS (ESI) [M + H⁺]⁺ |
|---|---|---|---|---|
| P-1119 | | | 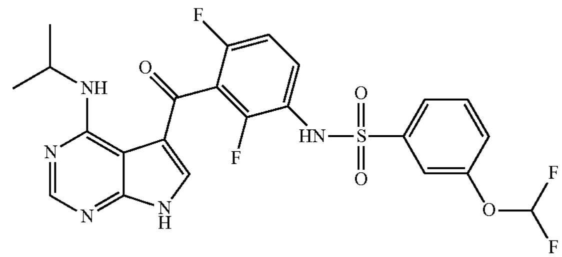 [SMILES: CC(C)Nc1ncnc2[nH]cc(C(=O)c3c(F)ccc(NS(=O)(=O)c4cccc(OC(F)F)c4)c3F)c12] | 538.5 |
| P-1120 | | | 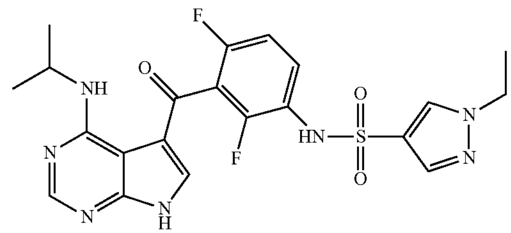 [SMILES: CCn1cc(S(=O)(=O)Nc2ccc(F)c(C(=O)c3c[nH]c4ncnc(NC(C)C)c34)c2F)cn1] | 490.5 |
| P-1121 | | | 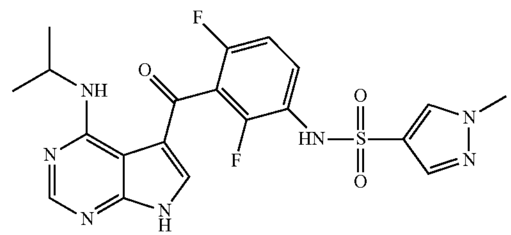 [SMILES: CC(C)Nc1ncnc2[nH]cc(C(=O)c3c(F)ccc(NS(=O)(=O)c4cnn(C)c4)c3F)c12] | 476.0 |

-continued

| Comp. number | 7H-pyrrolo[2,3-d]pyrimidine | Sulfonyl chloride | Compound structure | MS (ESI) [M + H+]+ |
|---|---|---|---|---|
| P-1122 | | | 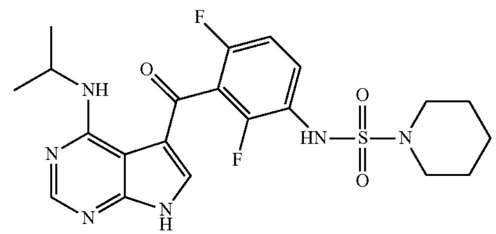 | 479.0 |
| P-1123 | | | 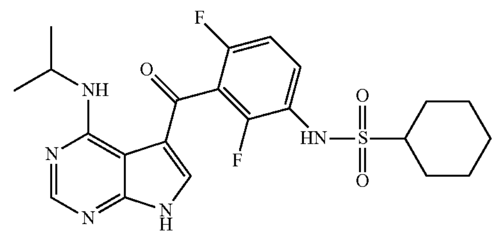 | 478.0 |
| P-1124 | | | 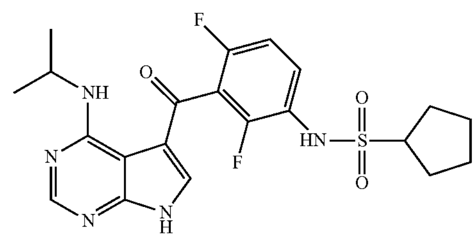 [SMILES: CC(C)Nc1ncnc2[nH]cc(C(=O)c3c(F)ccc(NS(=O)(=O)C4CCCC4)c3F)c12] | 464.0 |

| Comp. number | 7H-pyrrolo[2,3-d]pyrimidine | Sulfonyl chloride | Compound structure | MS (ESI) [M + H+]+ |
| --- | --- | --- | --- | --- |
| P-1125 | | | 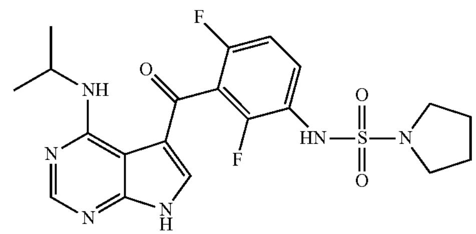 [SMILES: CC(C)Nc1ncnc2[nH]cc(C(=O)c3c(F)ccc(NS(=O)(=O)N4CCCC4)c3F)c12] | 465.0 |
| P-1126 | | | 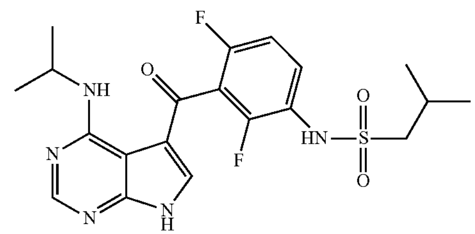 [SMILES: CC(C)CS(=O)(=O)Nc1ccc(F)c(C(=O)c2c[nH]c3ncnc(NC(C)C)c23)c1F] | 452.0 |
| P-1127 | | | 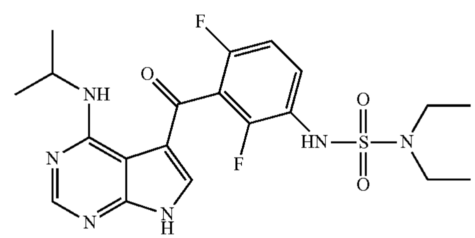 | 467.5 |

| Comp. number | 7H-pyrrolo[2,3-d]pyrimidine | Sulfonyl chloride | Compound structure | MS (ESI) [M + H⁺]⁺ |
|---|---|---|---|---|
| P-1128 | | | 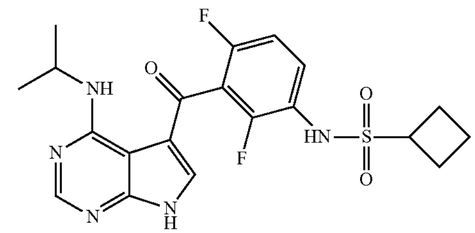 [SMILES: CC(C)Nc1ncnc2[nH]cc(C(=O)c3c(F)ccc(NS(=O)(=O)C4CCC4)c3F)c12] | 450.0 |
| P-1129 | | | 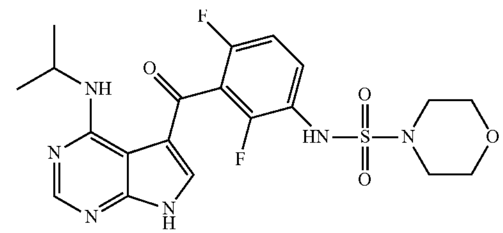 [SMILES: CC(C)Nc1ncnc2[nH]cc(C(=O)c3c(F)ccc(NS(=O)(=O)N4CCOCC4)c3F)c12] | 481.0 |
| P-1130 | | | 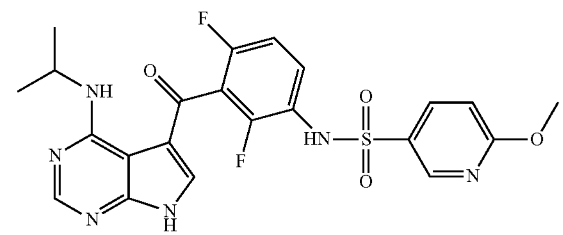 [SMILES: COc1ccc(S(=O)(=O)Nc2ccc(F)c(C(=O)c3c[nH]c4ncnc(NC(C)C)c34)c2F)cn1] | 503.0 |

| Comp. number | 7H-pyrrolo[2,3-d]pyrimidine | Sulfonyl chloride | Compound structure | MS (ESI) [M + H+]+ |
|---|---|---|---|---|
| P-1131 | | | 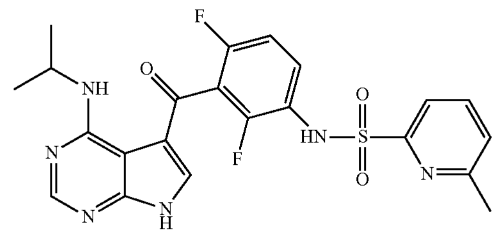 | 487.5 |
| P-1132 | | | 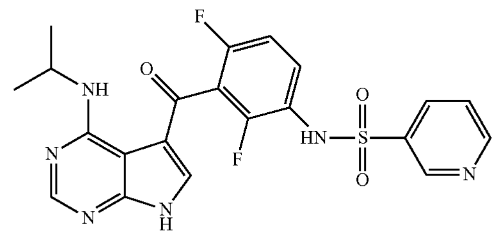 | 473.0 |
| P-1133 | | | 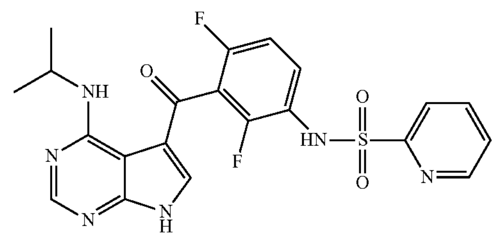 | 473.0 |

-continued

| Comp. number | 7H-pyrrolo[2,3-d]pyrimidine | Sulfonyl chloride | Compound structure | MS (ESI) [M + H$^+$]$^+$ |
|---|---|---|---|---|
| P-1155 | | | 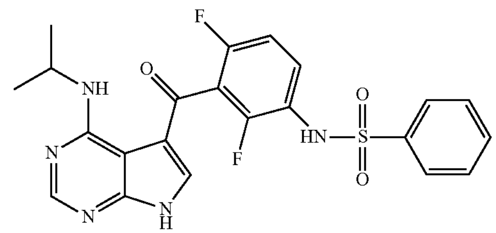 | 472.5 |
| P-1156 | | | 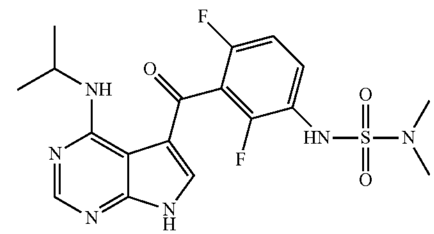 | 439.0 |
| P-1183 | | | 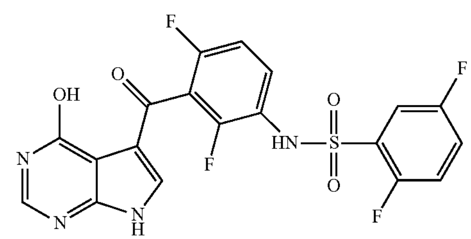 | 466.9 |

-continued

| Comp. number | 7H-pyrrolo[2,3-d]pyrimidine | Sulfonyl chloride | Compound structure | MS (ESI) [M + H⁺]⁺ |
|---|---|---|---|---|
| P-1186 | | | 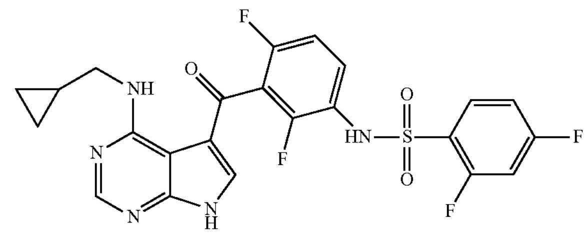 | |
| P-1187 | | | 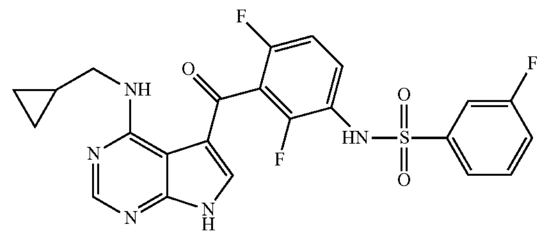 | |
| P-1188 | | | 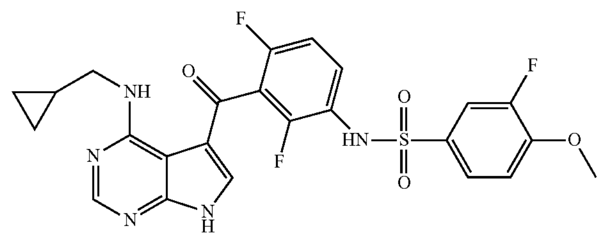 | |

-continued

| Comp. number | 7H-pyrrolo[2,3-d]pyrimidine | Sulfonyl chloride | Compound structure | MS (ESI) [M + H+]+ |
|---|---|---|---|---|
| P-1189 | | | 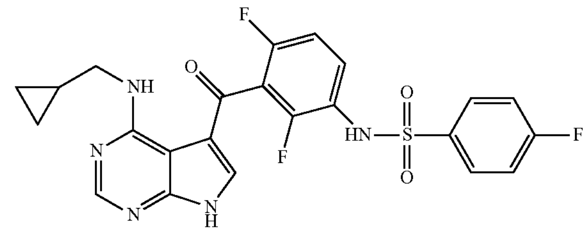 | |
| P-1190 | | | 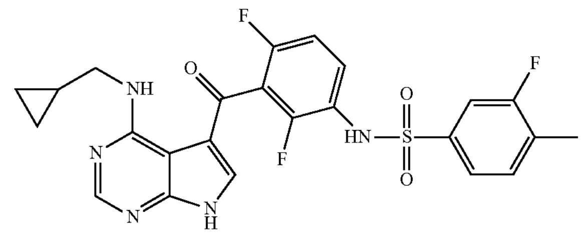 | |
| P-1191 | | | 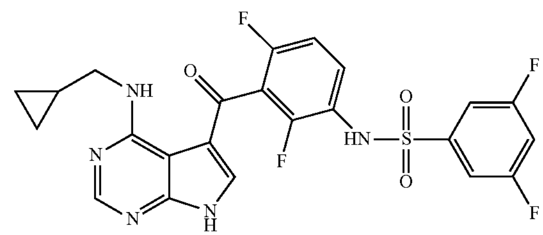 [SMILES: O=C(c1c(F)ccc(NS(=O)(=O)c2cc(F)cc(F)c2)c1F)c1c[nH]c2ncnc(NCC3CC3)c12] | |

| Comp. number | 7H-pyrrolo[2,3-d]pyrimidine | Sulfonyl chloride | Compound structure | MS (ESI) [M + H+]+ |
|---|---|---|---|---|
| P-1192 | | | 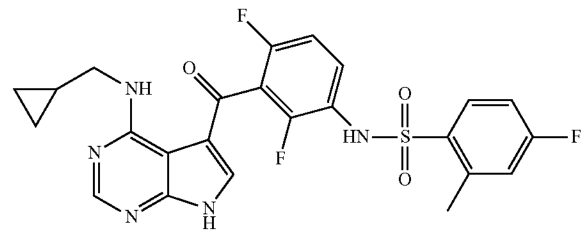 [SMILES: Cc1cc(F)ccc1S(=O)(=O)Nc1ccc(F)c(C(=O)c2c[nH]c3ncnc(NCC4CC4)c23)c1F] | |
| P-1193 | | | 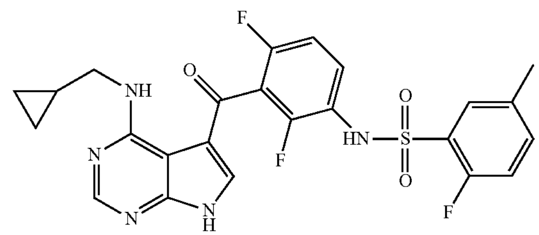 | |
| P-1194 | | | 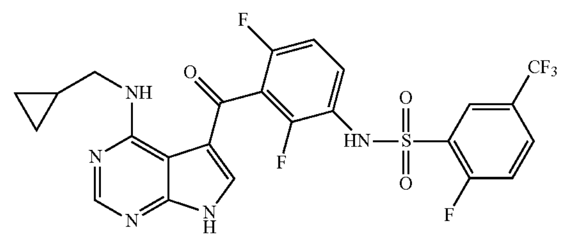 | |

-continued

| Comp. number | 7H-pyrrolo[2,3-d]pyrimidine | Sulfonyl chloride | Compound structure | MS (ESI) [M + H+]+ |
|---|---|---|---|---|
| P-1195 | | | 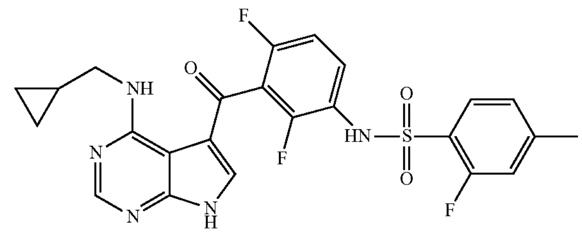 [SMILES: Cc1ccc(S(=O)(=O)Nc2ccc(F)c(C(=O)c3c[nH]c4ncnc(NCC5CC5)c34)c2F)c(F)c1] | |
| P-1196 | | | 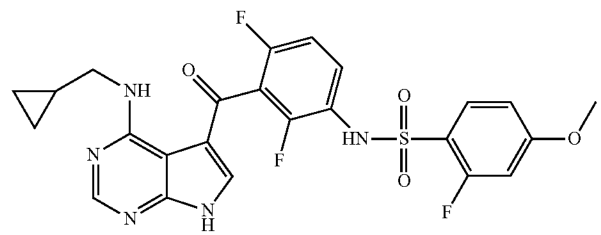 [SMILES: COc1ccc(S(=O)(=O)Nc2ccc(F)c(C(=O)c3c[nH]c4ncnc(NCC5CC5)c34)c2F)c(F)c1] | |
| P-1197 | | | 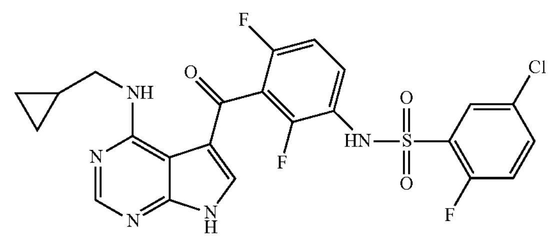 | |

| Comp. number | 7H-pyrrolo[2,3-d]pyrimidine | Sulfonyl chloride | Compound structure | MS (ESI) [M + H+]+ |
|---|---|---|---|---|
| P-1198 | | | 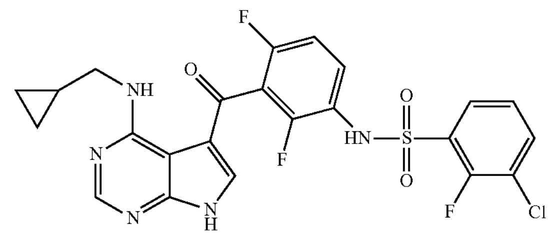 [SMILES: O=C(c1c(F)ccc(NS(=O)(=O)c2cccc(Cl)c2F)c1F)c1c[nH]c2ncnc(NCC3CC3)c12] | |
| P-1199 | | | 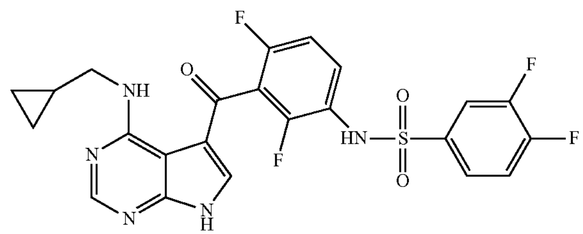 [SMILES: O=C(c1c(F)ccc(NS(=O)(=O)c2ccc(F)c(F)c2)c1F)c1c[nH]c2ncnc(NCC3CC3)c12] | |
| P-1200 | | | 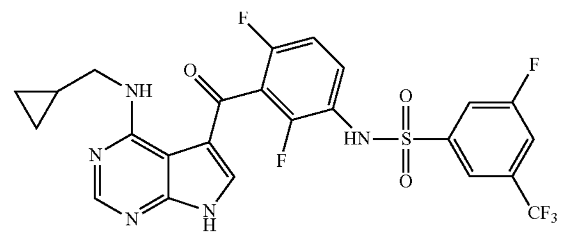 [SMILES: O=C(c1c(F)ccc(NS(=O)(=O)c2cc(F)cc(C(F)(F)F)c2)c1F)c1c[nH]c2ncnc(NCC3CC3)c12] | |

| Comp. number | 7H-pyrrolo[2,3-d]pyrimidine | Sulfonyl chloride | Compound structure | MS (ESI) [M + H⁺]⁺ |
|---|---|---|---|---|
| P-1201 | | | 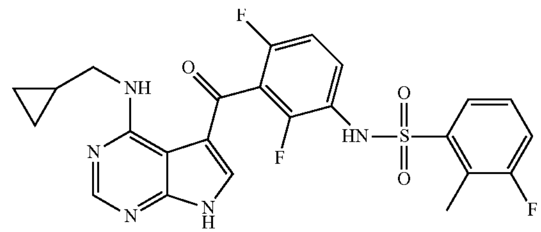 [SMILES: Cc1c(F)cccc1S(=O)(=O)Nc1ccc(F)c(C(=O)c2c[nH]c3ncnc(NCC4CC4)c23)c1F] | |
| P-1202 | | | 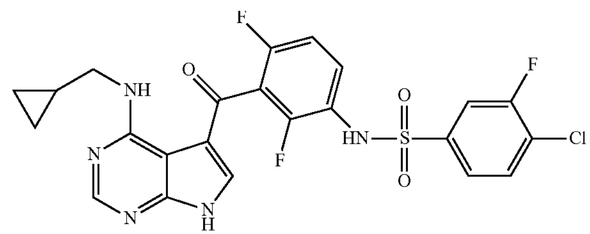 [SMILES: O=C(c1c(F)ccc(NS(=O)(=O)c2ccc(Cl)c(F)c2)c1F)c1c[nH]c2ncnc(NCC3CC3)c12] | |
| P-1203 | | | 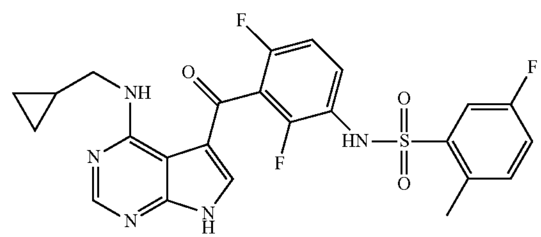 [SMILES: Cc1ccc(F)cc1S(=O)(=O)Nc1ccc(F)c(C(=O)c2c[nH]c3ncnc(NCC4CC4)c23)c1F] | |

| Comp. number | 7H-pyrrolo[2,3-d]pyrimidine | Sulfonyl chloride | Compound structure | MS (ESI) [M + H+]+ |
|---|---|---|---|---|
| P-1204 | | | 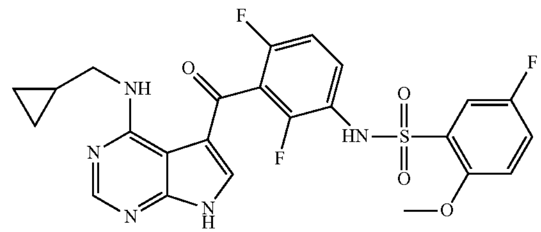 [SMILES: COc1ccc(F)cc1S(=O)(=O)Nc1ccc(F)c(C(=O)c2c[nH]c3ncnc(NCC4CC4)c23)c1F] | |
| P-1205 | | | 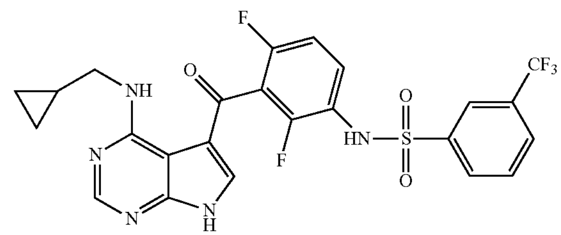 [SMILES: O=C(c1c(F)ccc(NS(=O)(=O)c2cccc(C(F)(F)F)c2)c1F)c1c[nH]c2ncnc(NCC3CC3)c12] | |
| P-1206 | | | 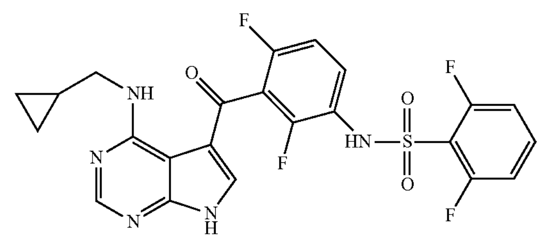 [SMILES: O=C(c1c(F)ccc(NS(=O)(=O)c2c(F)cccc2F)c1F)c1c[nH]c2ncnc(NCC3CC3)c12] | |

-continued

| Comp. number | 7H-pyrrolo[2,3-d]pyrimidine | Sulfonyl chloride | Compound structure | MS (ESI) [M + H+]+ |
|---|---|---|---|---|
| P-1207 | | | 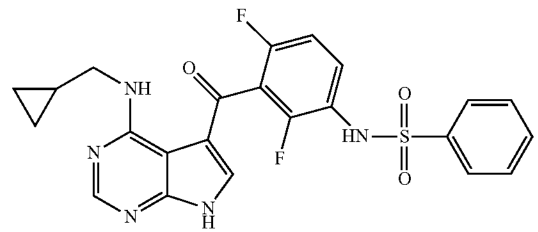 [SMILES: O=C(c1c(F)ccc(NS(=O)(=O)c2ccccc2)c1F)c1c[nH]c2ncnc(NCC3CC3)c12] | |
| P-1208 | | | 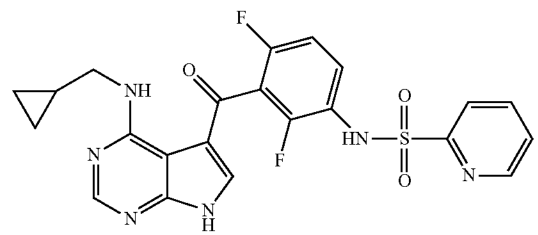 [SMILES: O=C(c1c(F)ccc(NS(=O)(=O)c2ccccn2)c1F)c1c[nH]c2ncnc(NCC3CC3)c12] | |
| P-1209 | | | 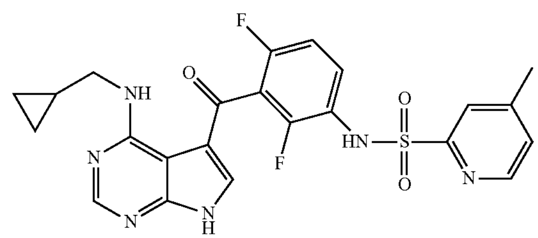 [SMILES: Cc1ccnc(S(=O)(=O)Nc2ccc(F)c(C(=O)c3c[nH]c4ncnc(NCC5CC5)c34)c2F)c1] | |

| Comp. number | 7H-pyrrolo[2,3-d]pyrimidine | Sulfonyl chloride | Compound structure | MS (ESI) [M + H+]+ |
|---|---|---|---|---|
| P-1210 | | | 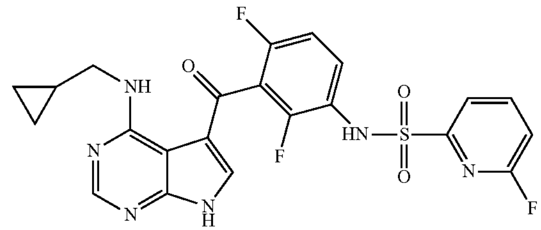 [SMILES: O=C(c1c(F)ccc(NS(=O)(=O)c2cccc(F)n2)c1F)c1c[nH]c2ncnc(NCC3CC3)c12] | |
| P-1211 | | | 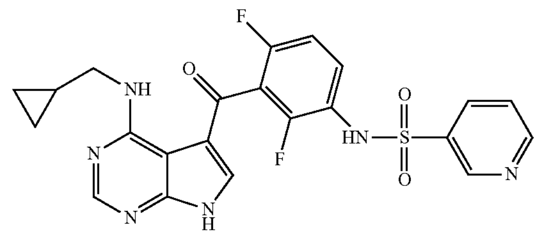 [SMILES: O=C(c1c(F)ccc(NS(=O)(=O)c2cccnc2)c1F)c1c[nH]c2ncnc(NCC3CC3)c12] | |
| P-1212 | | | 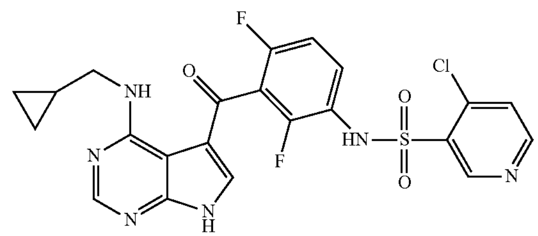 [SMILES: O=C(c1c(F)ccc(NS(=O)(=O)c2cnccc2Cl)c1F)c1c[nH]c2ncnc(NCC3CC3)c12] | |

| Comp. number | 7H-pyrrolo[2,3-d]pyrimidine | Sulfonyl chloride | Compound structure | MS (ESI) [M + H+]+ |
|---|---|---|---|---|
| P-1213 | | | 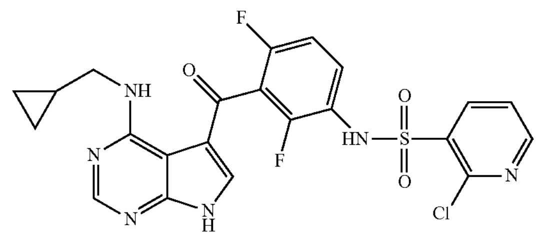 [SMILES: O=C(c1c(F)ccc(NS(=O)(=O)c2cccnc2Cl)c1F)c1c[nH]c2ncnc(NCC3CC3)c12] | |
| P-1214 | | | 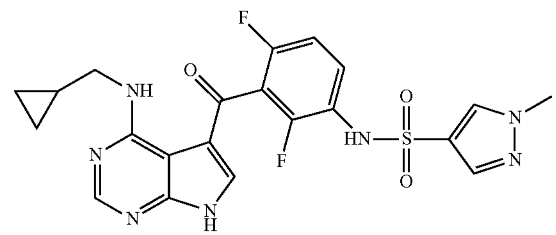 [SMILES: Cn1cc(S(=O)(=O)Nc2ccc(F)c(C(=O)c3c[nH]c4ncnc(NCC5CC5)c34)c2F)cn1] | |
| P-1215 | | | 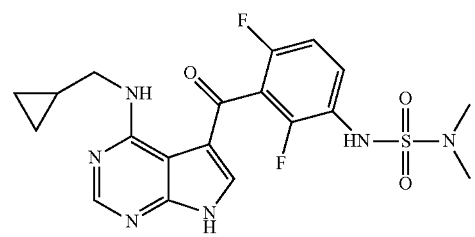 [SMILES: CN(C)S(=O)(=O)Nc1ccc(F)c(C(=O)c2c[nH]c3ncnc(NCC4CC4)c23)c1F] | |

-continued

| Comp. number | 7H-pyrrolo[2,3-d]pyrimidine | Sulfonyl chloride | Compound structure | MS (ESI) [M + H+]+ |
|---|---|---|---|---|
| P-1216 | | | 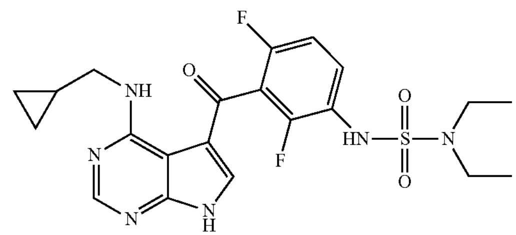 [SMILES: CCN(CC)S(=O)(=O)Nc1ccc(F)c(C(=O)c2c[nH]c3ncnc(NCC4CC4)c23)c1F] | |
| P-1217 | | | 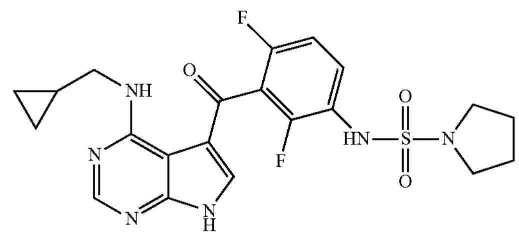 [SMILES: O=C(c1c(F)ccc(NS(=O)(=O)N2CCCC2)c1F)c1c[nH]c2ncnc(NCC3CC3)c12] | |
| P-1218 | | | 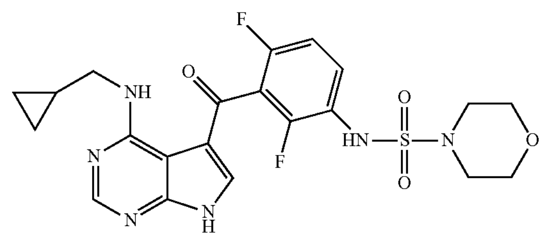 | |

| Comp. number | 7H-pyrrolo[2,3-d]pyrimidine | Sulfonyl chloride | Compound structure | MS (ESI) [M + H+]+ |
|---|---|---|---|---|
| P-1219 | | | 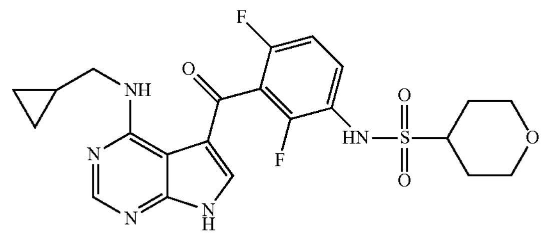 [SMILES: O=C(c1c(F)ccc(NS(=O)(=O)C2CCOCC2)c1F)c1c[nH]c2ncnc(NCC3CC3)c12] | |
| P-1220 | | | 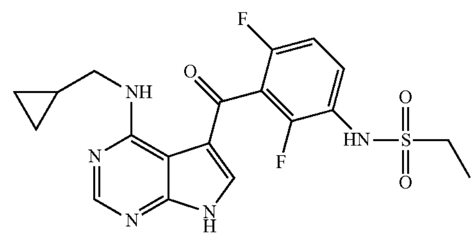 [SMILES: CCS(=O)(=O)Nc1ccc(F)c(C(=O)c2c[nH]c3ncnc(NCC4CC4)c23)c1F] | |
| P-1221 | | | 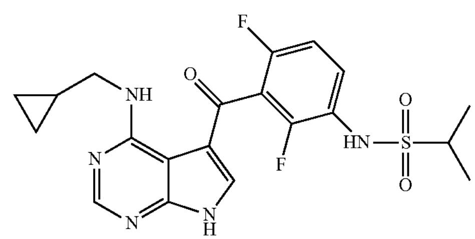 [SMILES: CC(C)S(=O)(=O)Nc1ccc(F)c(C(=O)c2c[nH]c3ncnc(NCC4CC4)c23)c1F] | |

-continued

| Comp. number | 7H-pyrrolo[2,3-d]pyrimidine | Sulfonyl chloride | Compound structure | MS (ESI) [M + H+]+ |
| --- | --- | --- | --- | --- |
| P-1222 | | | 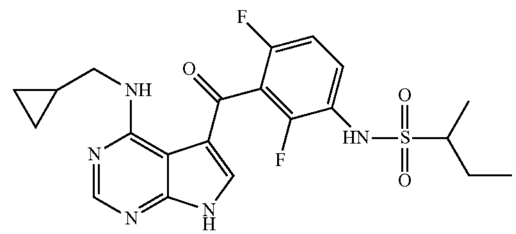 [SMILES: CCC(C)S(=O)(=O)Nc1ccc(F)c(C(=O)c2c[nH]c3ncnc(NCC4CC4)c23)c1F] | |
| P-1223 | | | 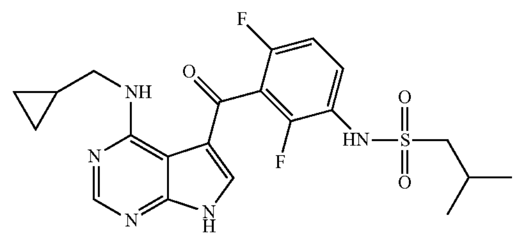 [SMILES: CC(C)CS(=O)(=O)Nc1ccc(F)c(C(=O)c2c[nH]c3ncnc(NCC4CC4)c23)c1F] | |
| P-1224 | | | 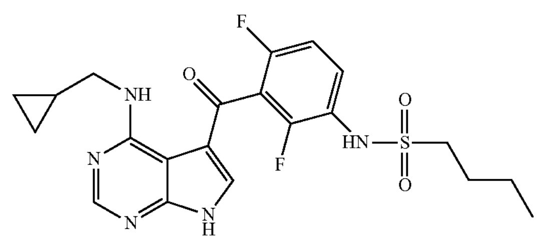 [SMILES: CCCCS(=O)(=O)Nc1ccc(F)c(C(=O)c2c[nH]c3ncnc(NCC4CC4)c23)c1F] | |

| Comp. number | 7H-pyrrolo[2,3-d]pyrimidine | Sulfonyl chloride | Compound structure | MS (ESI) [M + H+]+ |
|---|---|---|---|---|
| P-1225 | | | 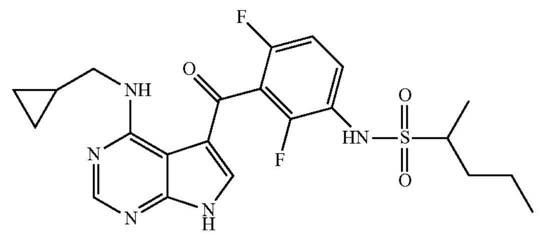 [SMILES: CCCC(C)S(=O)(=O)Nc1ccc(F)c(C(=O)c2c[nH]c3ncnc(NCC4CC4)c23)c1F] | |
| P-1226 | | | 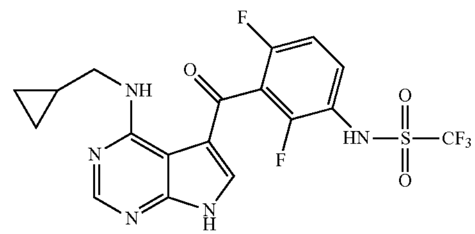 [SMILES: O=C(c1c(F)ccc(NS(=O)(=O)C(F)(F)F)c1F)c1c[nH]c2ncnc(NCC3CC3)c12] | |
| P-1227 | | | 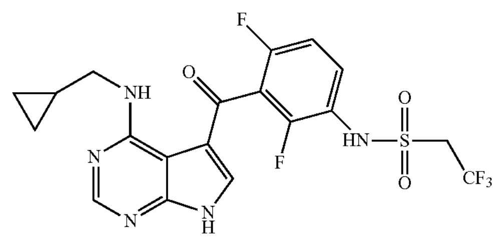 [SMILES: O=C(c1c(F)ccc(NS(=O)(=O)CC(F)(F)F)c1F)c1c[nH]c2ncnc(NCC3CC3)c12] | |

| Comp. number | 7H-pyrrolo[2,3-d]pyrimidine | Sulfonyl chloride | Compound structure | MS (ESI) [M + H+]+ |
|---|---|---|---|---|
| P-1228 | | | 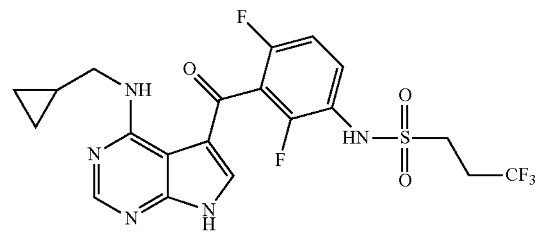 [SMILES: O=C(c1c(F)ccc(NS(=O)(=O)CCC(F)(F)F)c1F)c1c[nH]c2ncnc(NCC3CC3)c12] | |
| P-1229 | | | 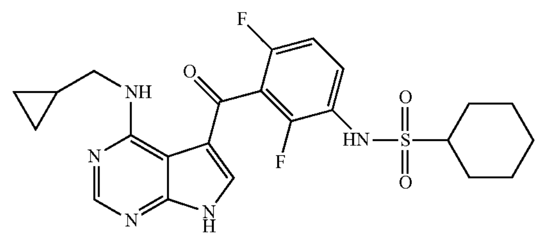 [SMILES: O=C(c1c(F)ccc(NS(=O)(=O)C2CCCCC2)c1F)c1c[nH]c2ncnc(NCC3CC3)c12] | |
| P-1230 | | | 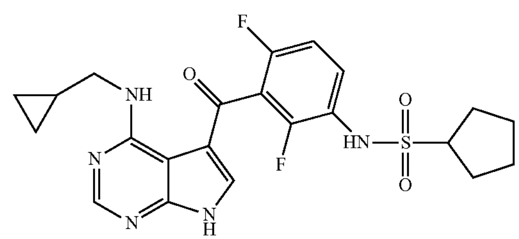 [SMILES: O=C(c1c(F)ccc(NS(=O)(=O)C2CCCC2)c1F)c1c[nH]c2ncnc(NCC3CC3)c12] | |

| Comp. number | 7H-pyrrolo[2,3-d]pyrimidine | Sulfonyl chloride | Compound structure | MS (ESI) [M + H+]+ |
|---|---|---|---|---|
| P-1231 | | | 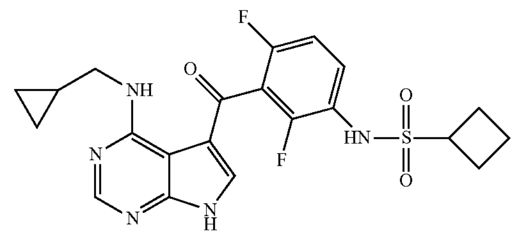 [SMILES: O=C(c1c(F)ccc(NS(=O)(=O)C2CCC2)c1F)c1c[nH]c2ncnc(NCC3CC3)c12] | |
| P-1232 | | | 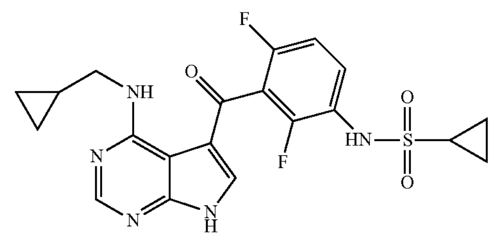 [SMILES: O=C(c1c(F)ccc(NS(=O)(=O)C2CC2)c1F)c1c[nH]c2ncnc(NCC3CC3)c12] | |
| P-1233 | | | 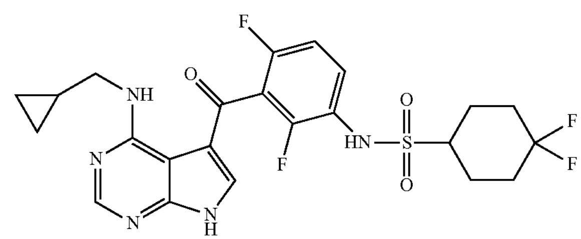 [SMILES: O=C(c1c(F)ccc(NS(=O)(=O)C2CCC(F)(F)CC2)c1F)c1c[nH]c2ncnc(NCC3CC3)c12] | |

| Comp. number | 7H-pyrrolo[2,3-d]pyrimidine | Sulfonyl chloride | Compound structure | MS (ESI) [M + H⁺]⁺ |
|---|---|---|---|---|
| P-1234 | | | 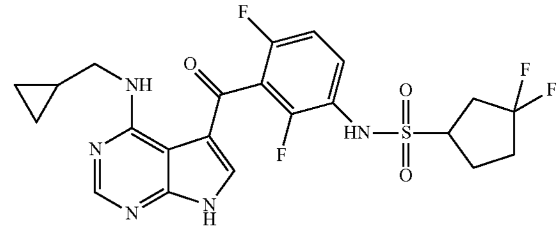 [SMILES: O=C(c1c(F)ccc(NS(=O)(=O)C2CCC(F)(F)C2)c1F)c1c[nH]c2ncnc(NCC3CC3)c12] | |
| P-1235 | | | 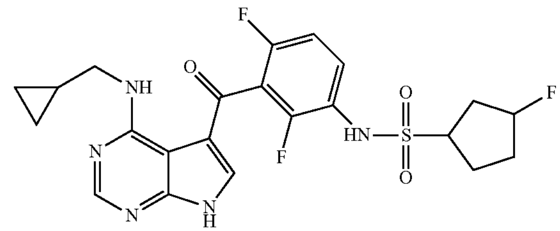 [SMILES: O=C(c1c(F)ccc(NS(=O)(=O)C2CCC(F)C2)c1F)c1c[nH]c2ncnc(NCC3CC3)c12] | |
| P-2021 | | | 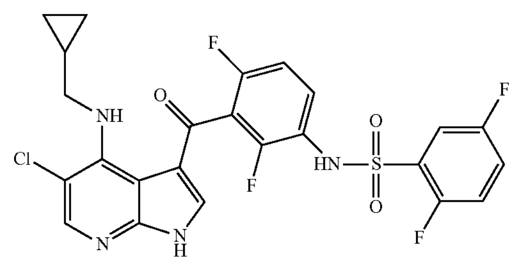 [SMILES: O=C(c1c(F)ccc(NS(=O)(=O)c2cc(F)ccc2F)c1F)c1c[nH]c2ncc(Cl)c(NCC3CC3)c12] | |

| Comp. number | 7H-pyrrolo[2,3-d]pyrimidine | Sulfonyl chloride | Compound structure | MS (ESI) [M + H⁺]⁺ |
|---|---|---|---|---|
| P-2025 | | | 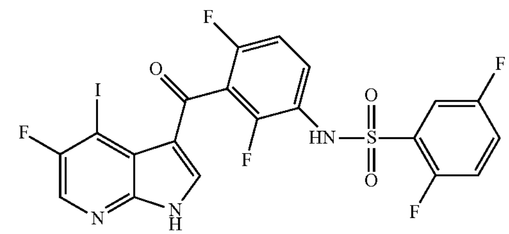 [SMILES: O=C(c1c(F)ccc(NS(=O)(=O)c2cc(F)ccc2F)c1F)c1c[nH]c2ncc(F)c(I)c12] | 593.8 |
| P-2026 | | | 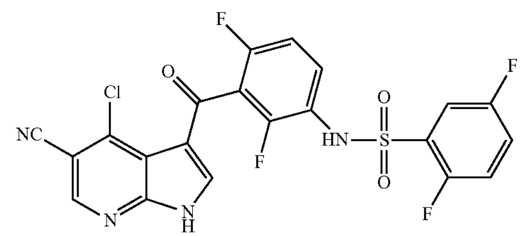 [SMILES: N#Cc1cnc2[nH]cc(C(=O)c3c(F)ccc(NS(=O)(=O)c4cc(F)ccc4F)c3F)c2c1Cl] | 508.9, 510.9 |
| P-2027 | | | 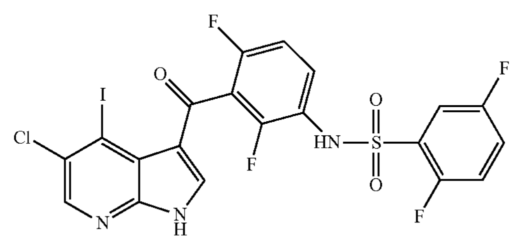 [SMILES: O=C(c1c(F)ccc(NS(=O)(=O)c2cc(F)ccc2F)c1F)c1c[nH]c2ncc(Cl)c(I)c12] | |

| Comp. number | 7H-pyrrolo[2,3-d]pyrimidine | Sulfonyl chloride | Compound structure | MS (ESI) [M + H+]+ |
|---|---|---|---|---|
| P-2028 | | | 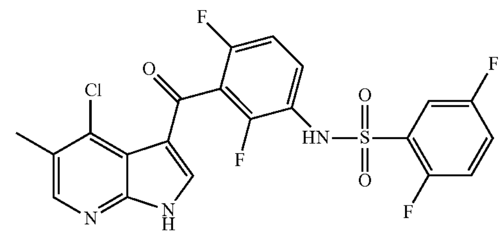 [SMILES: Cc1cnc2[nH]cc(C(=O)c3c(F)ccc(NS(=O)(=O)c4cc(F)ccc4F)c3F)c2c1Cl] | |
| P-2029 | | | 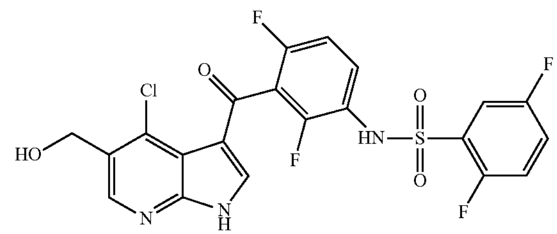 [SMILES: O=C(c1c(F)ccc(NS(=O)(=O)c2cc(F)ccc2F)c1F)c1c[nH]c2ncc(CO)c(Cl)c12] | |
| P-2030 | | | 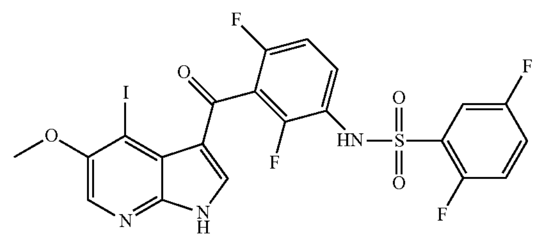 [SMILES: COc1cnc2[nH]cc(C(=O)c3c(F)ccc(NS(=O)(=O)c4cc(F)ccc4F)c3F)c2c1I] | |

Example 5

Synthesis of 2-methyl-propane-1-sulfonic acid [2,4-difluoro-3-(4-methyl-7H-pyrrolo[2,3-d]pyrimidine-5-carbonyl)-phenyl]-amide P-1003

2-Methyl-propane-1-sulfonic acid [2,4-difluoro-3-(4-methyl-7H-pyrrolo[2,3-d]pyrimidine-5-carbonyl)-phenyl]-amide P-1003 is prepared in two steps from 4-methyl-7H-pyrrolo[2,3-d]pyrimidine 7 and 2-methyl-propane-1-sulfonic acid (2,4-difluoro-3-formyl-phenyl)-amide 62 as shown in Scheme 5.

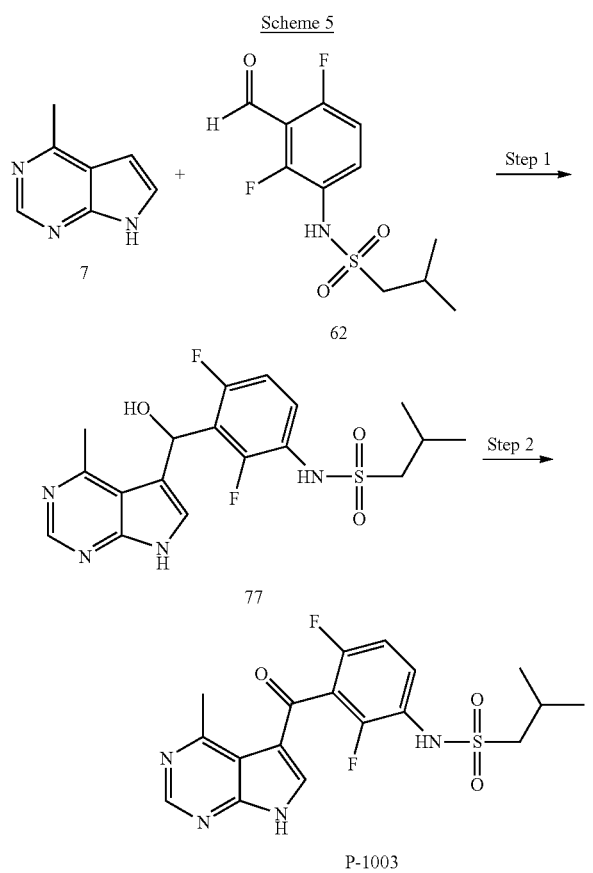

Scheme 5

Step 1—Preparation of 2-methyl-propane-1-sulfonic acid {2,4-difluoro-3-[hydroxy-(4-methyl-7H-pyrrolo[2,3-d]pyrimidin-5-yl)-methyl]-phenyl}-amide (77)

In a round bottom flask, 4-methyl-7H-pyrrolo[2,3-d]pyrimidine (7, 97.0 mg, 0.728 mmol) is combined with 2-methyl-propane-1-sulfonic acid (2,4-difluoro-3-formyl-phenyl)-amide (62, 202 mg, 0.728 mmol), potassium hydroxide (204 mg, 3.64 mmol) and 1.4 mL of methanol. The reaction is stirred at room temperature for 7 hours. The reaction is neutralized with 0.1N aqueous hydrochloric acid and extracted 3× with ethyl acetate. The combined organic layer is washed with brine, dried with sodium sulfate, filtered and the filtrate concentrated under vacuum. The resulting material is purified by silica gel column chromatography, eluting with ethyl acetate and dichloromethane. Appropriate fractions are combined and concentrated under vacuum to provide the desired compound (77, 113 mg). MS (ESI) [M−H$^+$]$^-$=409.2.

Step 2—Preparation of 2-methyl-propane-1-sulfonic acid [2,4-difluoro-3-(4-methyl-7H-pyrrolo[2,3-d]pyrimidine-5-carbonyl)-phenyl]amide (P-1003)

To 2-methyl-propane-1-sulfonic acid {2,4-difluoro-3-[hydroxy-(4-methyl-7H-pyrrolo[2,3-d]pyrimidin-5-yl)-methyl]-phenyl}-amide (77, 99 mg, 0.24 mmol) in 2 mL of tetrahydrofuran, Dess-Martin periodinane (112 mg, 0.265 mmol) is added and the reaction is stirred at room temperature for 2 hours. The reaction is poured into saturated aqueous sodium thiosulfate along with some sodium bicarbonate solid and extracted with ethyl acetate. The organic layer is washed with water, then brine, and dried with sodium sulfate, filtered and the filtrate concentrated under vacuum. The resulting material is purified by silica gel column chromatography, eluting with ethyl acetate and dichloromethane. Appropriate fractions are combined and concentrated under vacuum to provide the desired compound (P-1003, 28 mg). MS (ESI) [M+H$^+$]$^+$=409.3.

Propane-1-sulfonic acid [2-fluoro-3-(4-isopropylamino-7H-pyrrolo[2,3-d]pyrimidine-5-carbonyl)-phenyl]-amide P-1106 is prepared similarly, reacting isopropyl-(7H-pyrrolo[2,3-d]pyrimidin-4-yl)-amine 11 and propane-1-sulfonic acid (2-fluoro-3-formyl-phenyl)-amide in Step 1, and further reacting via the following Step 2a:

Step 2a—Preparation of propane-1-sulfonic acid [2-fluoro-3-(4-isopropylamino-7H-pyrrolo[2,3-d]pyrimidine-5-carbonyl)-phenyl]amide (P-1106)

To propane-1-sulfonic acid {2-fluoro-3-[hydroxy-(4-isopropylamino-7H-pyrrolo[2,3-d]pyrimidin-5-yl)-methyl]-phenyl}-amide (78, 102 mg, 0.242 mmol) in 1 mL of dimethylsulfoxide, stabilized 2-iodoxybenzoic acid (181 mg, 45%, 0.29 mmol) is added and the reaction is stirred at room temperature for 1 hour. The reaction is poured into water and stirred for 30 minutes, and the precipitate is collected by filtration. The resulting solid is dissolved in 2 mL of tetrahydrofuran and purified by silica gel column chromatography, eluting with ethyl acetate and dichloromethane. Appropriate fractions are combined and concentrated under vacuum to give the desired compound (P-1106, 34 mg). MS (ESI) [M+H$^+$]$^+$=420.0.

Additional compounds are prepared following the protocol of Scheme 5. Compounds are prepared optionally substituting 4-methyl-7H-pyrrolo[2,3-d]pyrimidine 7, with a suitable 7H-pyrrolo[2,3-d]pyrimidine and optionally substituting 2-methyl-propane-1-sulfonic acid (2,4-difluoro-3-formyl-phenyl)-amide 62 with a suitable aldehyde in step 1. The following compounds are made using this procedure:

N-[2,4-Difluoro-3-(4-methyl-7H-pyrrolo[2,3-d]pyrimidine-5-carbonyl)-phenyl]-4-trifluoromethyl-benzenesulfonamide (P-1001),
Propane-1-sulfonic acid [3-(4-ethoxy-7H-pyrrolo[2,3-d]pyrimidine-5-carbonyl)-2,4-difluoro-phenyl]-amide (P-1002),
2-Methyl-propane-1-sulfonic acid [2,4-difluoro-3-(4-methoxy-7H-pyrrolo[2,3-d]pyrimidine-5-carbonyl)-phenyl]-amide (P-1004),
N-[2,4-Difluoro-3-(4-methoxy-7H-pyrrolo[2,3-d]pyrimidine-5-carbonyl)-phenyl]-4-propyl-benzenesulfonamide (P-1005),
N-[3-(4-Ethoxy-7H-pyrrolo[2,3-d]pyrimidine-5-carbonyl)-2,4-difluoro-phenyl]-4-trifluoromethyl-benzenesulfonamide (P-1006),
N-[2,4-Difluoro-3-(4-methyl-7H-pyrrolo[2,3-d]pyrimidine-5-carbonyl)-phenyl]-4-propyl-benzenesulfonamide (P-1007),
N-[2,4-Difluoro-3-(4-methyl-7H-pyrrolo[2,3-d]pyrimidine-5-carbonyl)-phenyl]-4-isopropyl-benzenesulfonamide (P-1009),
N-[2,4-Difluoro-3-(4-methoxy-7H-pyrrolo[2,3-d]pyrimidine-5-carbonyl)-phenyl]-4-isopropyl-benzenesulfonamide (P-1010),
N-[3-(4-Cyclopropylamino-7H-pyrrolo[2,3-d]pyrimidine-5-carbonyl)-2,4-difluoro-phenyl]-4-trifluoromethyl-benzenesulfonamide (P-1011),
N-[2,4-Difluoro-3-(4-hydroxy-7H-pyrrolo[2,3-d]pyrimidine-5-carbonyl)-phenyl]-4-trifluoromethyl-benzenesulfonamide (P-1012),
N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013),
Propane-1-sulfonic acid [2,4-difluoro-3-(4-isobutyl-7H-pyrrolo[2,3-d]pyrimidine-5-carbonyl)-phenyl]-amide (P-1014),
N-[2,4-Difluoro-3-(4-isobutyl-7H-pyrrolo[2,3-d]pyrimidine-5-carbonyl)-phenyl]-4-trifluoromethyl-benzenesulfonamide (P-1015),
N-[2,4-Difluoro-3-(4-morpholin-4-yl-7H-pyrrolo[2,3-d]pyrimidine-5-carbonyl)-phenyl]-4-trifluoromethyl-benzenesulfonamide (P-1017),
N-[2,4-Difluoro-3-(4-methyl-7H-pyrrolo[2,3-d]pyrimidine-5-carbonyl)-phenyl]-4-ethyl-benzenesulfonamide (P-1019),
N-[2,4-Difluoro-3-(4-isobutylamino-7H-pyrrolo[2,3-d]pyrimidine-5-carbonyl)-phenyl]-4-trifluoromethyl-benzenesulfonamide (P-1020),
N-{2,4-Difluoro-3-[4-(tetrahydro-pyran-4-yloxy)-7H-pyrrolo[2,3-d]pyrimidine-5-carbonyl]-phenyl}-4-trifluoromethyl-benzenesulfonamide (P-1021),
Propane-1-sulfonic acid [2,4-difluoro-3-(4-hydroxy-7H-pyrrolo[2,3-d]pyrimidine-5-carbonyl)-phenyl]-amide (P-1022),
N-[2,4-Difluoro-3-(4-methoxy-7H-pyrrolo[2,3-d]pyrimidine-5-carbonyl)-phenyl]-3,5-dimethyl-benzenesulfonamide (P-1025),
N-[2,4-Difluoro-3-(4-methyl-7H-pyrrolo[2,3-d]pyrimidine-5-carbonyl)-phenyl]-3,5-dimethyl-benzenesulfonamide (P-1027),
N-[2,4-Difluoro-3-(4-isobutoxy-7H-pyrrolo[2,3-d]pyrimidine-5-carbonyl)-phenyl]-4-trifluoromethyl-benzenesulfonamide (P-1028),
N-[2,4-Difluoro-3-(4-isopropyl-7H-pyrrolo[2,3-d]pyrimidine-5-carbonyl)-phenyl]-4-trifluoromethyl-benzenesulfonamide (P-1029),
N-[2,4-Difluoro-3-(4-hydroxy-7H-pyrrolo[2,3-d]pyrimidine-5-carbonyl)-phenyl]-4-propyl-benzenesulfonamide (P-1030),
N-[3-(4-Cyclopentylamino-7H-pyrrolo[2,3-d]pyrimidine-5-carbonyl)-2,4-difluoro-phenyl]-4-trifluoromethyl-benzenesulfonamide (P-1035),
N-[3-(4-Ethoxy-7H-pyrrolo[2,3-d]pyrimidine-5-carbonyl)-2,4-difluoro-phenyl]-4-propyl-benzenesulfonamide (P-1038),
N-[2,4-Difluoro-3-(4-isopropylamino-7H-pyrrolo[2,3-d]pyrimidine-5-carbonyl)-phenyl]-4-isopropyl-benzenesulfonamide (P-1042),
N-[2,4-Difluoro-3-(4-isopropylamino-7H-pyrrolo[2,3-d]pyrimidine-5-carbonyl)-phenyl]-4-isopropyl-benzenesulfonamide (P-1044),
N-[2,4-Difluoro-3-(4-isopropylamino-7H-pyrrolo[2,3-d]pyrimidine-5-carbonyl)-phenyl]-3,5-dimethyl-benzenesulfonamide (P-1045),
N-[3-(4-Cyclopropylmethoxy-7H-pyrrolo[2,3-d]pyrimidine-5-carbonyl)-2,4-difluoro-phenyl]-4-trifluoromethyl-benzenesulfonamide (P-1053),
N-[2,4-Difluoro-3-(4-pyrrolidin-1-yl-7H-pyrrolo[2,3-d]pyrimidine-5-carbonyl)-phenyl]-4-trifluoromethyl-benzenesulfonamide (P-1061),
N-[3-(4-Cyclopropylmethoxy-7H-pyrrolo[2,3-d]pyrimidine-5-carbonyl)-2,4-difluoro-phenyl]-2,5-difluoro-benzenesulfonamide (P-1181),
N-[2,4-Difluoro-3-(4-isopropyl-7H-pyrrolo[2,3-d]pyrimidine-5-carbonyl)-phenyl]-2,5-difluoro-benzenesulfonamide (P-1182), and
N-{3-[4-(Cyclopropylmethyl-amino)-7H-pyrrolo[2,3-d]pyrimidine-5-carbonyl]-2-fluoro-phenyl}-2,5-difluoro-benzenesulfonamide (P-1185).

The following table indicates the 7H-pyrrolo[2,3-d]pyrimidine (column 2) and aldehyde compound (column 3) used in step 1 to afford the desired compound (column 4). The compound number is provided in column 1, and the observed mass is in column 5

| Comp. number | 7H-pyrrolo[2,3-d]pyrimidine | Aldehyde structure | Compound structure | MS (ESI) [M + H⁺]⁺ |
|---|---|---|---|---|
| P-1001 | | | 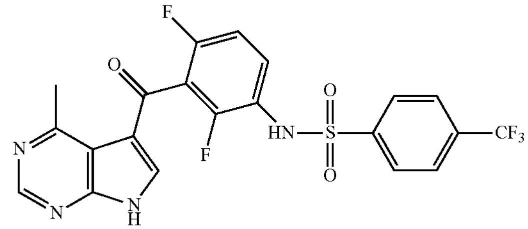 | 496.9 |
| P-1002 | | | 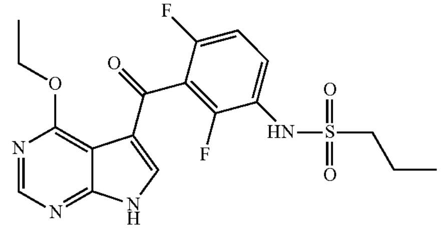 | 424.9 |
| P-1004 | | | 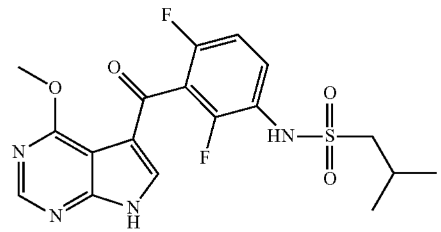 [SMILES: COc1ncnc2[nH]cc(C(=O)c3c(F)ccc(NS(=O)(=O)CC(C)C)c3F)c12] | 425.1 |
| P-1005 | | | 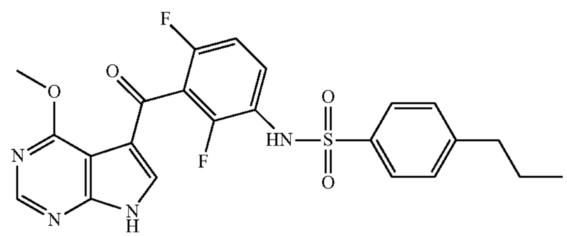 [SMILES: CCCc1ccc(S(=O)(=O)Nc2ccc(F)c(C(=O)c3c[nH]c4ncnc(OC)c34)c2F)cc1] | 486.95 |

| Comp. number | 7H-pyrrolo[2,3-d]pyrimidine | Aldehyde structure | Compound structure | MS (ESI) [M + H]+ |
|---|---|---|---|---|
| P-1006 | | | 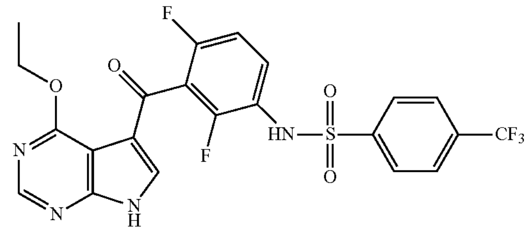 [SMILES: CCOc1ncnc2[nH]cc(C(=O)c3c(F)ccc(NS(=O)(=O)c4ccc(C(F)(F)F)cc4)c3F)c12] | 526.95 |
| P-1007 | | | 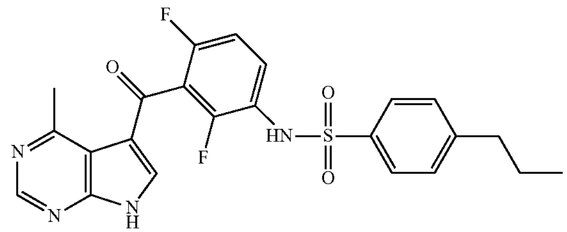 | 470.95 |
| P-1009 | | | 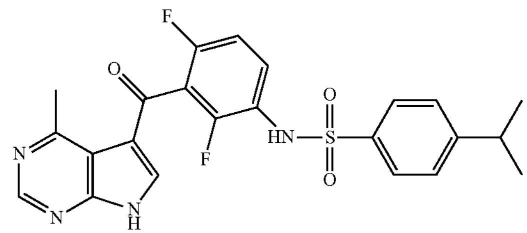 [SMILES: Cc1ncnc2[nH]cc(C(=O)c3c(F)ccc(NS(=O)(=O)c4ccc(C(C)C)cc4)c3F)c12] | 471.3 |
| P-1010 | | | 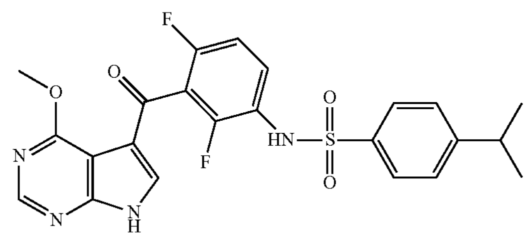 | 486.8 |

-continued

| Comp. number | 7H-pyrrolo[2,3-d]pyrimidine | Aldehyde structure | Compound structure | MS (ESI) [M + H]+ |
|---|---|---|---|---|
| P-1011 | 4-(cyclopropylamino)-7H-pyrrolo[2,3-d]pyrimidine | | 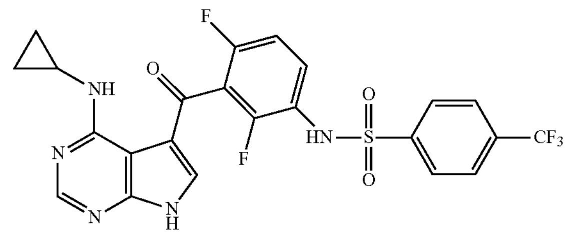 [SMILES: O=C(c1c(F)ccc(NS(=O)(=O)c2ccc(C(F)(F)F)cc2)c1F)c1c[nH]c2ncnc(NC3CC3)c12] | 537.8 |
| P-1012 | 4-hydroxy-7H-pyrrolo[2,3-d]pyrimidine | | 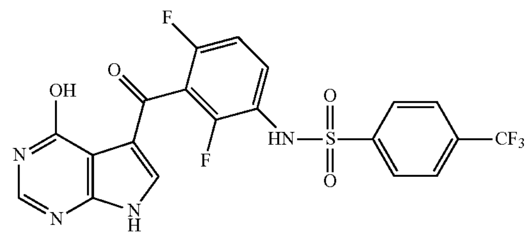 | 499.0 |
| P-1013 | 4-(tetrahydropyran-4-ylamino)-7H-pyrrolo[2,3-d]pyrimidine | | 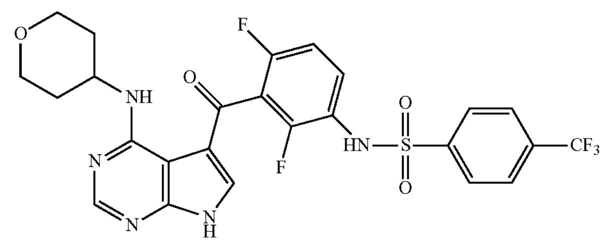 [SMILES: O=C(c1c(F)ccc(NS(=O)(=O)c2ccc(C(F)(F)F)cc2)c1F)c1c[nH]c2ncnc(NC3CCOCC3)c12] | 581.8 |
| P-1014 | 4-isobutyl-7H-pyrrolo[2,3-d]pyrimidine | | 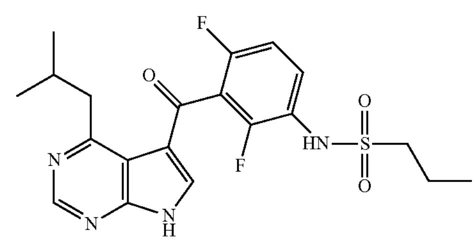 [SMILES: CCCS(=O)(=O)Nc1ccc(F)c(C(=O)c2c[nH]c3ncnc(CC(C)C)c23)c1F] | 436.7 |

-continued

| Comp. number | 7H-pyrrolo[2,3-d]pyrimidine | Aldehyde structure | Compound structure | MS (ESI) [M + H]+ |
|---|---|---|---|---|
| P-1015 | | | 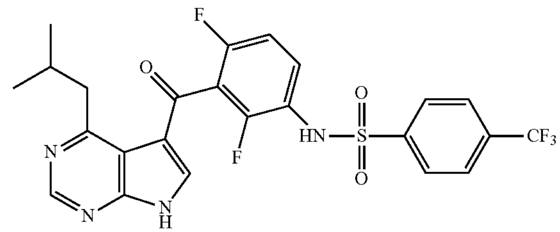 [SMILES: CC(C)Cc1ncnc2[nH]cc(C(=O)c3c(F)ccc(NS(=O)(=O)c4ccc(C(F)(F)F)cc4)c3F)c12] | 538.6 |
| P-1017 | | | 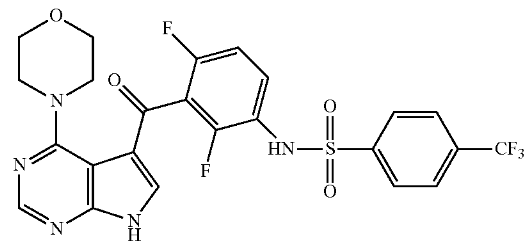 [SMILES: O=C(c1c(F)ccc(NS(=O)(=O)c2ccc(C(F)(F)F)cc2)c1F)c1c[nH]c2ncnc(N3CCOCC3)c12] | 567.8 |
| P-1019 | | | 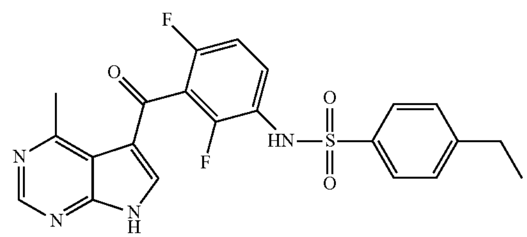 | 457.2 |
| P-1020 | | | 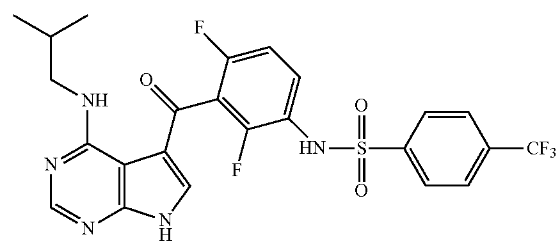 [SMILES: CC(C)CNc1ncnc2[nH]cc(C(=O)c3c(F)ccc(NS(=O)(=O)c4ccc(C(F)(F)F)cc4)c3F)c12] | 554.4 |

-continued

| Comp. number | 7H-pyrrolo[2,3-d]pyrimidine | Aldehyde structure | Compound structure | MS (ESI) [M + H⁺]⁺ |
|---|---|---|---|---|
| P-1021 | | | 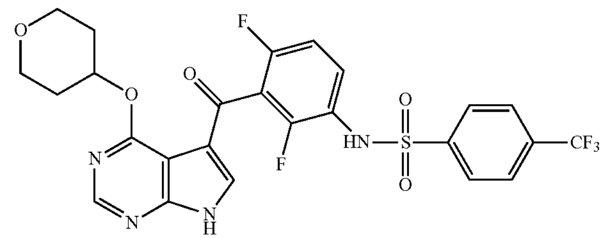 | 581.2 [M − H⁺]⁻ |
| P-1022 | | | 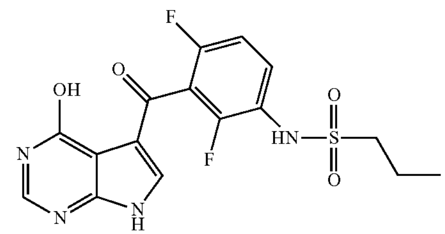 [SMILES: CCCS(=O)(=O)Nc1ccc(F)c(C(=O)c2c[nH]c3ncnc(O)c23)c1F] | 397.0 |
| P-1025 | | | 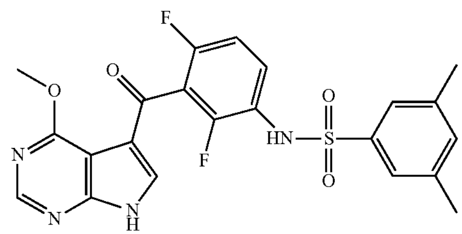 [SMILES: COc1ncnc2[nH]cc(C(=O)c3c(F)ccc(NS(=O)(=O)c4cc(C)cc(C)c4)c3F)c12] | 473.0 |
| P-1027 | | | 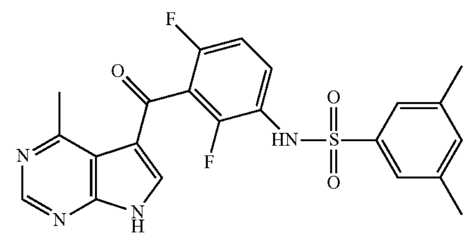 [SMILES: Cc1cc(C)cc(S(=O)(=O)Nc2ccc(F)c(C(=O)c3c[nH]c4ncnc(C)c34)c2F)c1] | 456.95 |

| Comp. number | 7H-pyrrolo[2,3-d]pyrimidine | Aldehyde structure | Compound structure | MS (ESI) [M + H⁺]⁺ |
|---|---|---|---|---|
| P-1028 | | | 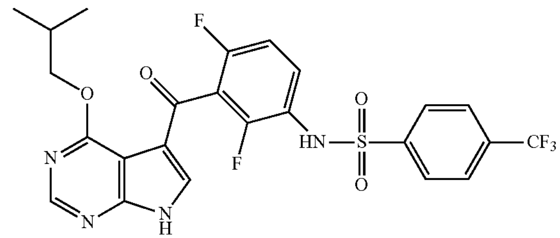 [SMILES: CC(C)COc1ncnc2[nH]cc(C(=O)c3c(F)ccc(NS(=O)(=O)c4ccc(C(F)(F)F)cc4)c3F)c12] | 553.2 [M − H⁺]⁻ |
| P-1029 | | | 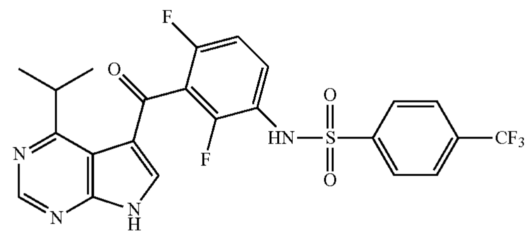 [SMILES: CC(C)c1ncnc2[nH]cc(C(=O)c3c(F)ccc(NS(=O)(=O)c4ccc(C(F)(F)F)cc4)c3F)c12] | 525.2 |
| P-1030 | | | 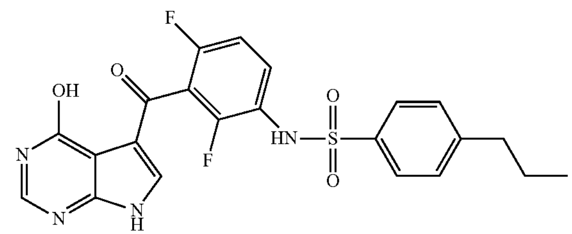 [SMILES: CCCc1ccc(S(=O)(=O)Nc2ccc(F)c(C(=O)c3c[nH]c4ncnc(O)c34)c2F)cc1] | 472.9 |
| P-1035 | | | 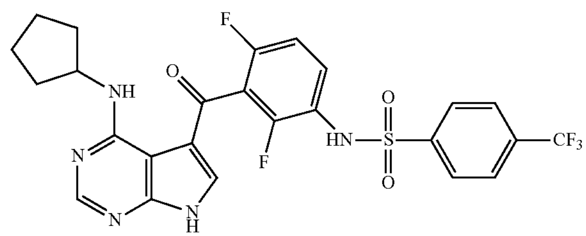 [SMILES: O=C(c1c(F)ccc(NS(=O)(=O)c2ccc(C(F)(F)F)cc2)c1F)c1c[nH]c2ncnc(NC3CCCC3)c12] | 566.3 |

| Comp. number | 7H-pyrrolo[2,3-d]pyrimidine | Aldehyde structure | Compound structure | MS (ESI) [M + H+]+ |
|---|---|---|---|---|
| P-1038 | | | 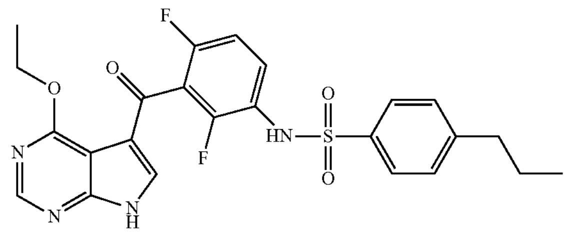 [SMILES: CCCc1ccc(S(=O)(=O)Nc2ccc(F)c(C(=O)c3c[nH]c4ncnc(OCC)c34)c2F)cc1] | 501.0 |
| P-1042 | | | 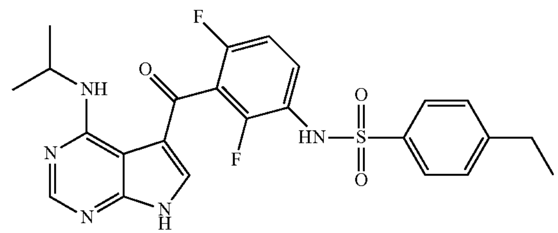 [SMILES: CCc1ccc(S(=O)(=O)Nc2ccc(F)c(C(=O)c3c[nH]c4ncnc(NC(C)C)c34)c2F)cc1] | 500.27 |
| P-1044 | | | 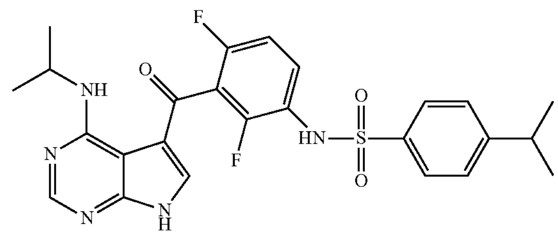 [SMILES: CC(C)Nc1ncnc2[nH]cc(C(=O)c3c(F)ccc(NS(=O)(=O)c4ccc(C(C)C)cc4)c3F)c12] | 514.0 |
| P-1045 | | | 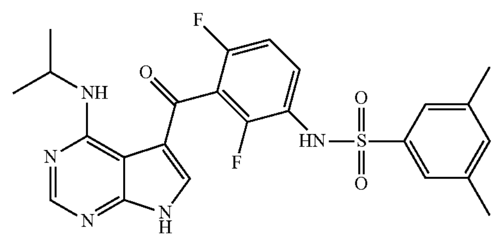 [SMILES: Cc1cc(C)cc(S(=O)(=O)Nc2ccc(F)c(C(=O)c3c[nH]c4ncnc(NC(C)C)c34)c2F)c1] | 500.05 |

| Comp. number | 7H-pyrrolo[2,3-d]pyrimidine | Aldehyde structure | Compound structure | MS (ESI) [M + H]+ |
|---|---|---|---|---|
| P-1053 | 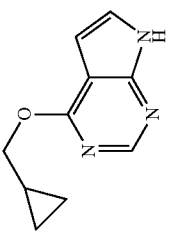 | 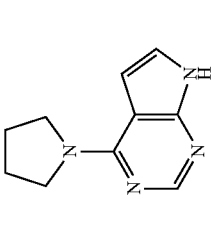 | 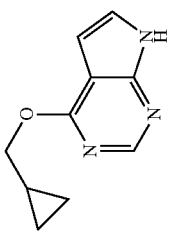 | 553.2 |
| P-1061 | 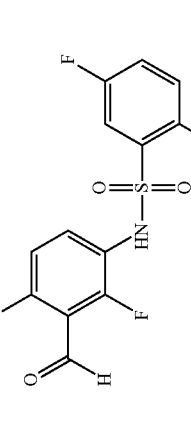 | 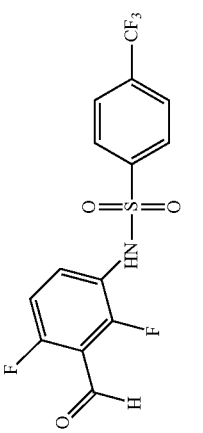 | 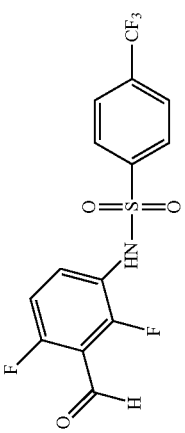 | 553.2 |
| P-1181 | 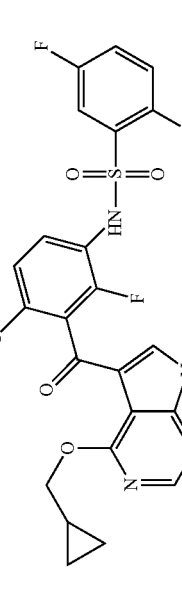 | 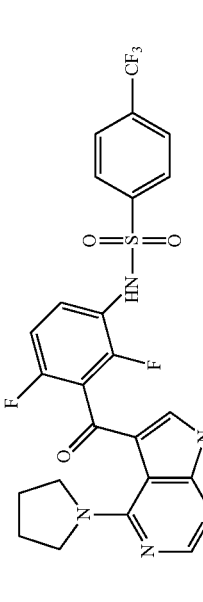 | 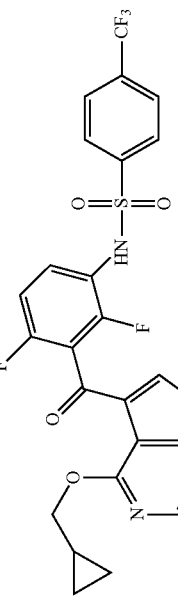 | 521.0 |

| Comp. number | 7H-pyrrolo[2,3-d]pyrimidine | Aldehyde structure | Compound structure | MS (ESI) [M + H]+ |
|---|---|---|---|---|
| P-1182 | 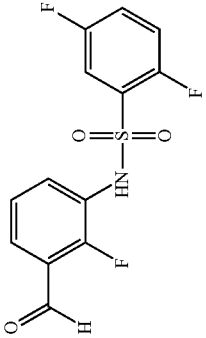 | 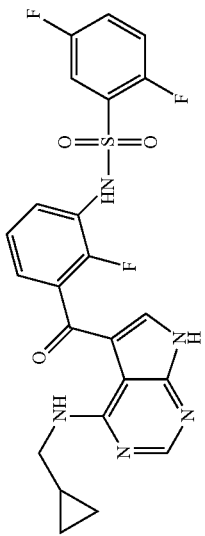 | 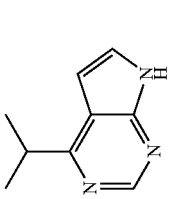 | 493.0 |
| P-1185 | 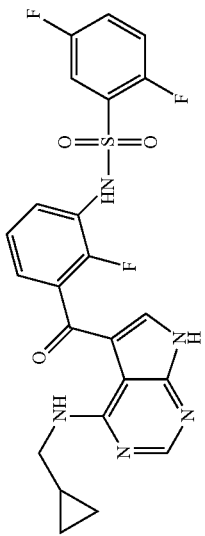 | 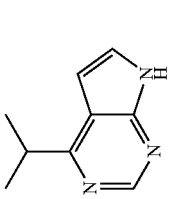 | 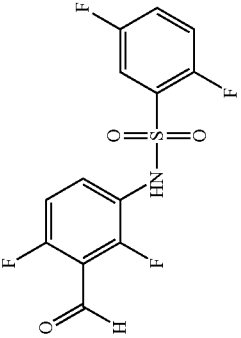 | 502.0 |

Additional compounds with a 1H-pyrrolo[2,3-b]pyridine core are prepared similarly following the protocol of Scheme 5. Compounds are prepared optionally substituting 4-methyl-7H-pyrrolo[2,3-d]pyrimidine 7, with a suitable 1H-pyrrolo[2,3-b]pyridine and optionally substituting 2-methyl-propane-1-sulfonic acid (2,4-difluoro-3-formyl-phenyl)-amide 62 with a suitable aldehyde in step 1. The following compounds are made using this procedure:

Propane-1-sulfonic acid [3-(4-chloro-5-methyl-1H-pyrrolo[2,3-b]pyridine-3-carbonyl)-2,4-difluoro-phenyl]-amide (P-2001), Propane-1-sulfonic acid [3-(4-chloro-5-methoxy-1H-pyrrolo[2,3-b]pyridine-3-carbonyl)-2,4-difluoro-phenyl]-amide (P-2002), Propane-1-sulfonic acid [3-(4-cyano-5-fluoro-1H-pyrrolo[2,3-b]pyridine-3-carbonyl)-2,4-difluoro-phenyl]-amide (P-2003), Propane-1-sulfonic acid [3-(4-chloro-5-cyano-1H-pyrrolo[2,3-b]pyridine-3-carbonyl)-2,4-difluoro-phenyl]-amide (P-2004), Propane-1-sulfonic acid [3-(5-cyano-4-methoxy-1H-pyrrolo[2,3-b]pyridine-3-carbonyl)-2,4-difluoro-phenyl]-amide (P-2005), Propane-1-sulfonic acid [3-(5-chloro-4-methoxy-1H-pyrrolo[2,3-b]pyridine-3-carbonyl)-2,4-difluoro-phenyl]-amide (P-2006), Propane-1-sulfonic acid [3-(5-chloro-4-cyano-1H-pyrrolo[2,3-b]pyridine-3-carbonyl)-2,4-difluoro-phenyl]-amide (P-2007), Propane-1-sulfonic acid [3-(5-chloro-4-methyl-1H-pyrrolo[2,3-b]pyridine-3-carbonyl)-2,4-difluoro-phenyl]-amide (P-2008), N-[3-(4-Cyano-5-fluoro-1H-pyrrolo[2,3-b]pyridine-3-carbonyl)-2,4-difluoro-phenyl]-4-trifluoromethyl-benzenesulfonamide (P-2009), N-[3-(5-Chloro-4-cyano-1H-pyrrolo[2,3-b]pyridine-3-carbonyl)-2,4-difluoro-phenyl]-4-trifluoromethyl-benzenesulfonamide (P-2010), N-[3-(5-Chloro-4-methyl-1H-pyrrolo[2,3-b]pyridine-3-carbonyl)-2,4-difluoro-phenyl]-4-trifluoromethyl-benzenesulfonamide (P-2011), Propane-1-sulfonic acid [3-(4-cyclopentylamino-1H-pyrrolo[2,3-b]pyridine-3-carbonyl)-2,4-difluoro-phenyl]-amide (P-2012), Propane-1-sulfonic acid {2,4-difluoro-3-[4-(tetrahydro-pyran-4-ylamino)-1H-pyrrolo[2,3-b]pyridine-3-carbonyl]-phenyl}-amide (P-2013), N-{2,4-Difluoro-3-[4-(tetrahydro-pyran-4-ylamino)-1H-pyrrolo[2,3-b]pyridine-3-carbonyl]-phenyl}-4-trifluoromethyl-benzenesulfonamide (P-2014), Propane-1-sulfonic acid [2,4-difluoro-3-(4-trifluoromethyl-1H-pyrrolo[2,3-b]pyridine-3-carbonyl)-phenyl]-amide (P-2015), N-[2,4-Difluoro-3-(4-trifluoromethyl-1H-pyrrolo[2,3-b]pyridine-3-carbonyl)-phenyl]-4-trifluoromethyl-benzenesulfonamide (P-2016), and N-[2,4-Difluoro-3-(4-trifluoromethyl-1H-pyrrolo[2,3-b]pyridine-3-carbonyl)-phenyl]-benzenesulfonamide (P-2017).

The following table indicates the 1H-pyrrolo[2,3-b]pyridine (column 2) and aldehyde compound (column 3) used in step 1 to afford the desired compound (column 4). The compound number is provided in column 1 and the observed mass is in column 5

| Comp. number | 1H-pyrrolo[2,3-b]pyridine | Aldehyde structure | Compound structure | MS (ESI) [M + H$^+$]$^+$ |
|---|---|---|---|---|
| P-2001 | | | 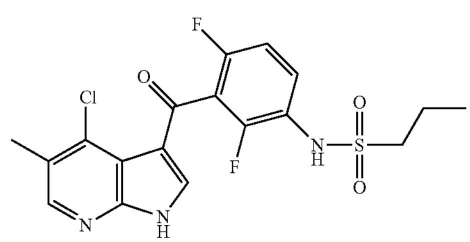 [SMILES: CCCS(=O)(=O)Nc1ccc(F)c(C(=O)c2c[nH]c3ncc(C)c(Cl)c23)c1F] | 427.9 429.9 |
| P-2002 | | | 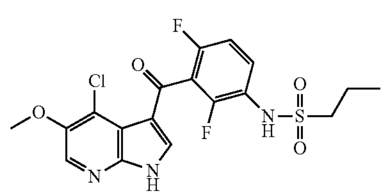 [SMILES: CCCS(=O)(=O)Nc1ccc(F)c(C(=O)c2c[nH]c3ncc(OC)c(Cl)c23)c1F] | 443.9 446.1 |

-continued

| Comp. number | 1H-pyrrolo[2,3-b]pyridine | Aldehyde structure | Compound structure | MS (ESI) [M + H⁺]⁺ |
|---|---|---|---|---|
| P-2003 | | | 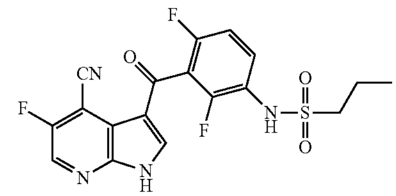 [SMILES: CCCS(=O)(=O)Nc1ccc(F)c(C(=O)c2c[nH]c3ncc(F)c(C#N)c23)c1F] | 421.4 [M − H⁺]⁻ |
| P-2004 | | | 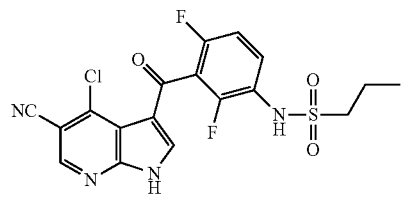 [SMILES: CCCS(=O)(=O)Nc1ccc(F)c(C(=O)c2c[nH]c3ncc(C#N)c(Cl)c23)c1F] | 439.1 |
| P-2005 | | | 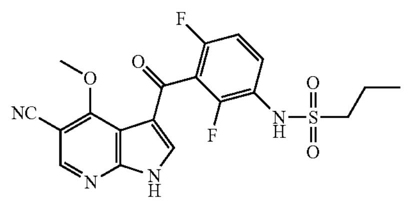 [SMILES: CCCS(=O)(=O)Nc1ccc(F)c(C(=O)c2c[nH]c3ncc(C#N)c(OC)c23)c1F] | 435.1 |
| P-2006 | | | 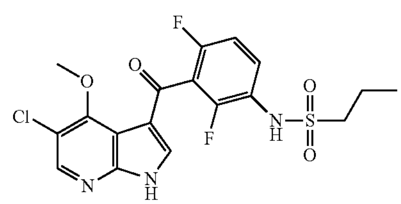 [SMILES: CCCS(=O)(=O)Nc1ccc(F)c(C(=O)c2c[nH]c3ncc(Cl)c(OC)c23)c1F] | 444.1 |
| P-2007 | | | 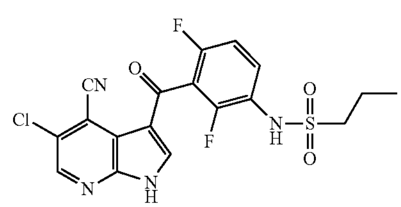 [SMILES: CCCS(=O)(=O)Nc1ccc(F)c(C(=O)c2c[nH]c3ncc(Cl)c(C#N)c23)c1F] | 437.4 439.5 |

-continued

| Comp. number | 1H-pyrrolo[2,3-b]pyridine | Aldehyde structure | Compound structure | MS (ESI) [M + H⁺]⁺ |
|---|---|---|---|---|
| P-2008 | | | 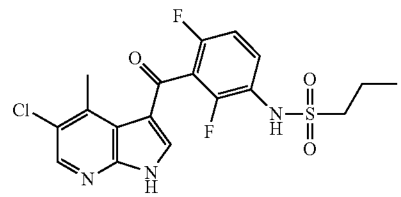 [SMILES: CCCS(=O)(=O)Nc1ccc(F)c(C(=O)c2c[nH]c3ncc(Cl)c(C)c23)c1F] | 428.1 430.1 |
| P-2009 | | | 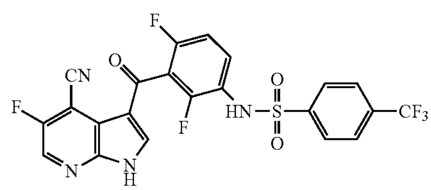 [SMILES: N#Cc1c(F)cnc2[nH]cc(C(=O)c3c(F)ccc(NS(=O)(=O)c4ccc(C(F)(F)F)cc4)c3F)c12] | 523.3 [M − H⁺]⁻ |
| P-2010 | | | 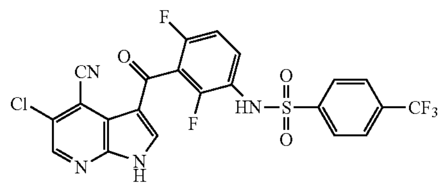 [SMILES: N#Cc1c(Cl)cnc2[nH]cc(C(=O)c3c(F)ccc(NS(=O)(=O)c4ccc(C(F)(F)F)cc4)c3F)c12] | 539.3 541.3 [M − H⁺]⁻ |
| P-2011 | | | 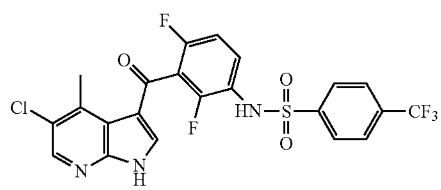 [SMILES: Cc1c(Cl)cnc2[nH]cc(C(=O)c3c(F)ccc(NS(=O)(=O)c4ccc(C(F)(F)F)cc4)c3F)c12] | 530.0 532.4 |
| P-2012 | | | 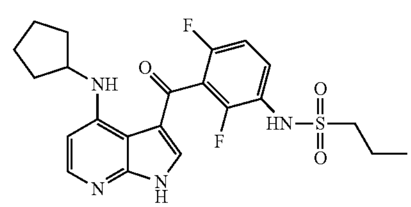 [SMILES: CCCS(=O)(=O)Nc1ccc(F)c(C(=O)c2c[nH]c3nccc(NC4CCCC4)c23)c1F] | 463.8 |

-continued

| Comp. number | 1H-pyrrolo[2,3-b]pyridine | Aldehyde structure | Compound structure | MS (ESI) [M + H+]+ |
|---|---|---|---|---|
| P-2013 | | | 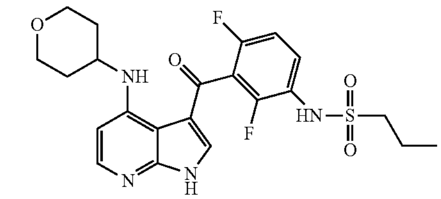 [SMILES: CCCS(=O)(=O)Nc1ccc(F)c(C(=O)c2c[nH]c3nccc(NC4CCOCC4)c23)c1F] | 479.1 |
| P-2014 | | | 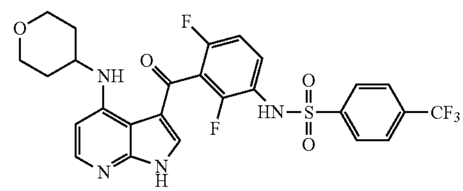 [SMILES: O=C(c1c(F)ccc(NS(=O)(=O)c2ccc(C(F)(F)F)cc2)c1F)c1c[nH]c2nccc(NC3CCOCC3)c12] | 581.4 |
| P-2015 | | | 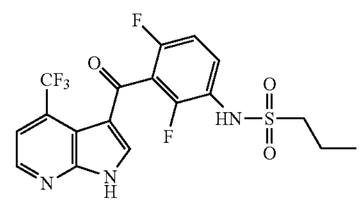 [SMILES: CCCS(=O)(=O)Nc1ccc(F)c(C(=O)c2c[nH]c3nccc(C(F)(F)F)c23)c1F] | 447.9 |
| P-2016 | | | 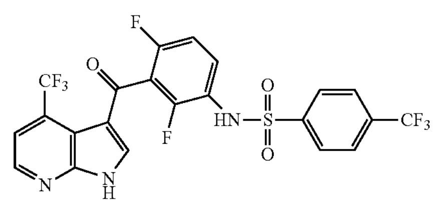 [SMILES: O=C(c1c(F)ccc(NS(=O)(=O)c2ccc(C(F)(F)F)cc2)c1F)c1c[nH]c2nccc(C(F)(F)F)c12] | 549.9 |
| P-2017 | | | 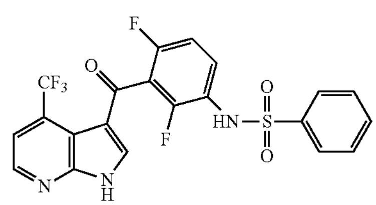 [SMILES: O=C(c1c(F)ccc(NS(=O)(=O)c2ccccc2)c1F)c1c[nH]c2nccc(C(F)(F)F)c12] | 481.9 |

*During the reaction, the 4-chloro was also displaced by methanol to form the 4-methoxy analog in step 1 in the synthesis of P-2004, which is carried through step 2 to form P-2005.

Example 6

Synthesis of N-[3-(4-chloro-7H-pyrrolo[2,3-d]pyrimidine-5-carbonyl)-2,4-difluoro-phenyl]-4-propyl-benzenesulfonamide P-1034

N-[3-(4-Chloro-7H-pyrrolo[2,3-d]pyrimidine-5-carbonyl)-2,4-difluoro-phenyl]-4-propyl-benzenesulfonamide P-1034 is synthesized in one step from N-[2,4-difluoro-3-(4-hydroxy-7H-pyrrolo[2,3-d]pyrimidine-5-carbonyl)-phenyl]-4-propyl-benzenesulfonamide P-1030 as shown in Scheme 6.

Scheme 6

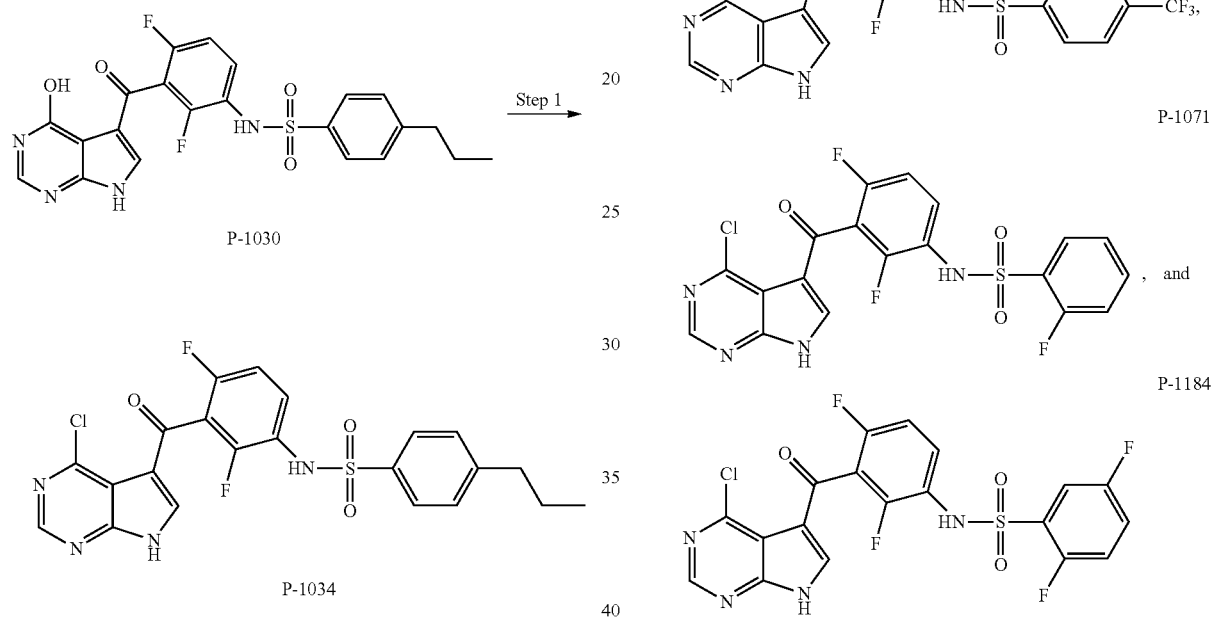

Step 1—Preparation of N-[3-(4-chloro-7H-pyrrolo[2,3-c]pyrimidine-5-carbonyl)-2,4-difluoro-phenyl]-4-propyl-benzenesulfonamide (P-1034)

To N-[2,4-difluoro-3-(4-hydroxy-7H-pyrrolo[2,3-d]pyrimidine-5-carbonyl)-phenyl]-4-propyl-benzenesulfonamide (P-1030, 239 mg, 0.506 mmol), phosphoryl chloride (4.0 mL, 43 mmol) is added and the suspension is heated in an oil bath at 100° C. for one hour. The reaction is allowed to cool, then poured onto ice. The resulting solid is collected by vacuum filtration and dried to provide the desired compound (P-1030, 218 mg). MS (ESI) [M+H$^+$]$^+$=490.9.

Propane-1-sulfonic acid [3-(4-chloro-7H-pyrrolo[2,3-d]pyrimidine-5-carbonyl)-2,4-difluoro-phenyl]-amide P-1033 and —N-[3-(4-chloro-7H-pyrrolo[2,3-d]pyrimidine-5-carbonyl)-2,4-difluoro-phenyl]-4-trifluoromethyl-benzenesulfonamide P-1016, N-[3-(4-Chloro-7H-pyrrolo[2,3-d]pyrimidine-5-carbonyl)-2,4-difluoro-phenyl]-2-fluoro-benzenesulfonamide P-1071, and —N-[3-(4-Chloro-7H-pyrrolo[2,3-d]pyrimidine-5-carbonyl)-2,4-difluoro-phenyl]-2,5-difluoro-benzenesulfonamide P-1184,

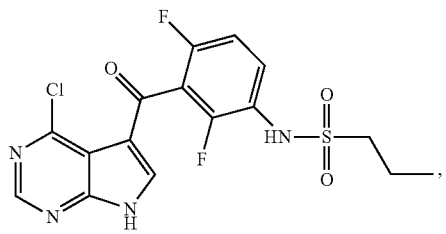

P-1033

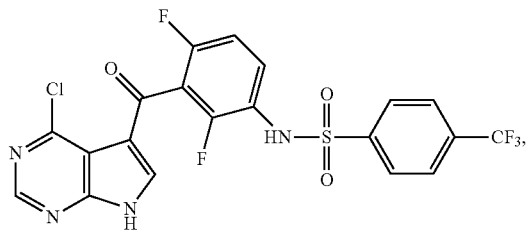

P-1016

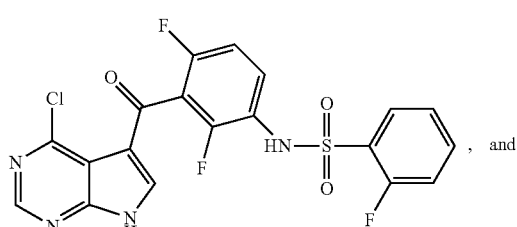

P-1071

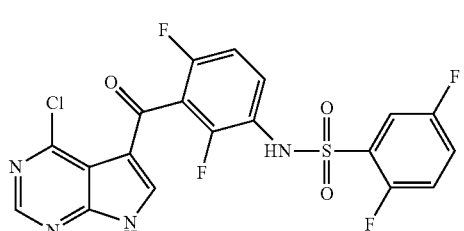

P-1184 are prepared similarly to the protocol of Scheme 6 from propane-1-sulfonic acid [2,4-difluoro-3-(4-hydroxy-7H-pyrrolo[2,3-d]pyrimidine-5-carbonyl)-phenyl]-amide P-1022, N-[2,4-difluoro-3-(4-hydroxy-7H-pyrrolo[2,3-d]pyrimidine-5-carbonyl)-phenyl]-4-trifluoromethyl-benzenesulfonamide P-1012, N-[2,4-difluoro-3-(4-hydroxy-7H-pyrrolo[2,3-d]pyrimidine-5-carbonyl)-phenyl]-2-fluoro-benzenesulfonamide P-1070, and —N-[2,4-Difluoro-3-(4-hydroxy-7H-pyrrolo[2,3-d]pyrimidine-5-carbonyl)-phenyl]-2,5-difluoro-benzene sulfonamide P-1183, respectively. MS (ESI) [M+H$^+$]$^+$=414.8 (P-1033), 516.9 (P-1016), 466.9, 468.9 (P-1071), and 484.9, 486.9 (P-1184).

Example 7

Synthesis of N-[3-(4-cyano-7H-pyrrolo[2,3-d]pyrimidine-5-carbonyl)-2,4-difluoro-phenyl]-4-trifluoromethyl-benzenesulfonamide P-1023

N-[3-(4-cyano-7H-pyrrolo[2,3-d]pyrimidine-5-carbonyl)-2,4-difluoro-phenyl]-4-trifluoromethyl-benzenesulfonamide P-1023 is synthesized in one step from N-[3-(4-chloro-7H-pyrrolo[2,3-d]pyrimidine-5-carbonyl)-2,4-difluoro-phenyl]-4-trifluoromethyl-benzenesulfonamide P-1016 as shown in Scheme 7.

Scheme 7

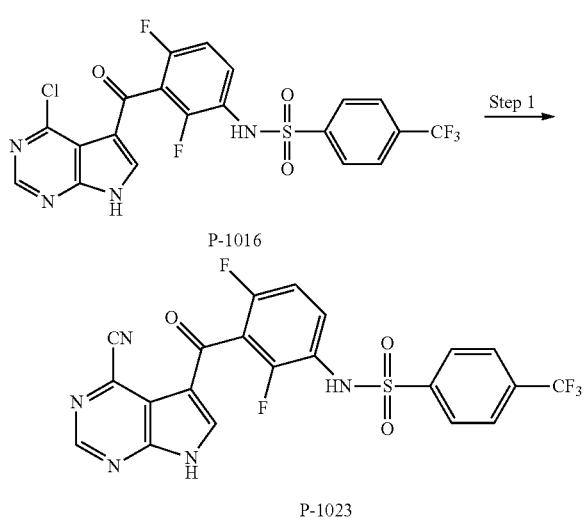

Step 1—Preparation of N-[3-(4-cyano-7H-pyrrolo [2,3-c]pyrimidine-5-carbonyl)-2,4-difluoro-phenyl]-4-trifluoromethyl-benzenesulfonamide (P-1023)

To N-[3-(4-chloro-7H-pyrrolo[2,3-d]pyrimidine-5-carbonyl)-2,4-difluoro-phenyl]-4-trifluoromethyl-benzenesulfonamide (P-1016, 62 mg, 0.12 mmol), 1.00 mL of dimethyl sulfoxide is added, followed by potassium cyanide (39.0 mg, 0.60 mmol). The reaction is heated at 150° C. in an oil bath for 4 hours, then at 150° C. overnight. The reaction is poured into water and extracted with ethyl acetate. The organic layer is concentrated under vacuum and purified by silica gel column chromatography, eluting with a gradient of 10-60% ethyl acetate in hexanes. Appropriate fractions are combined and concentrated under vacuum to provide the desired compound (P-1023, 8 mg). MS (ESI) [M+H$^+$]$^+$=508.1.

Example 8

Synthesis of N-[3-(4-cyclopropylamino-7H-pyrrolo [2,3-d]pyrimidine-5-carbonyl)-2,4-difluoro-phenyl]-4-propyl-benzenesulfonamide P-1040

N-[3-(4-Cyclopropylamino-7H-pyrrolo[2,3-d]pyrimidine-5-carbonyl)-2,4-difluoro-phenyl]-4-propyl-benzenesulfonamide P-1040 is synthesized in one step from N-[3-(4-chloro-7H-pyrrolo[2,3-d]pyrimidine-5-carbonyl)-2,4-difluoro-phenyl]-4-propyl-benzenesulfonamide P-1034 as shown in Scheme 8.

Scheme 8

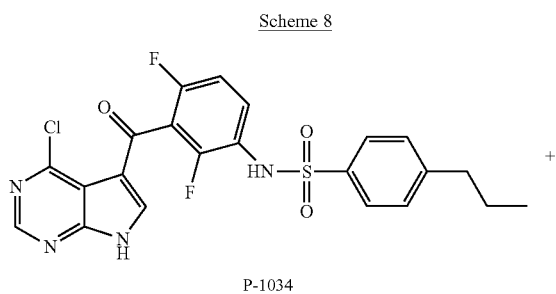

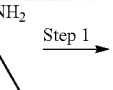

Step 1—Preparation of N-[3-(4-cyclopropylamino-7H-pyrrolo[2,3-c]pyrimidine-5-carbonyl)-2,4-difluoro-phenyl]-4-propyl-benzenesulfonamide (P-1040)

To N-[3-(4-chloro-7H-pyrrolo[2,3-d]pyrimidine-5-carbonyl)-2,4-difluoro-phenyl]-4-propyl-benzenesulfonamide (P-1034, 50 mg, 0.10 mmol), 0.702 mL of isopropyl alcohol is added, followed by cyclopropylamine (79, 0.0357 mL, 70% aqueous solution, 0.509 mmol). The reaction is heated at 80° C. in an oil bath for 17 hours, then poured into water and brine and extracted with ethyl acetate. The organic layer is dried over magnesium sulfate, filtered and the filtrate concentrated under vacuum to provide the desired compound (P-1040, 52 mg). MS (ESI) [M+H$^+$]$^+$=512.0.

Additional compounds are prepared following the protocol of Scheme 8. In some instances, without limitation, the 4-chloro-7H-pyrrolo[2,3-d]pyrimidine compound (or similar 4-halogen substituted 1H-pyrrolo[2,3-b]pyridine compound) is reacted directly in the liquid amine compound without additional solvent (e.g. isopropyl alcohol). In some instances, without limitation, the reaction mixture includes triethylamine Compounds may be further purified by standard techniques, such as silica gel chromatography or HPLC. Compounds are prepared optionally substituting N-[3-(4-chloro-7H-pyrrolo[2,3-d]pyrimidine-5-carbonyl)-2,4-difluoro-phenyl]-4-propyl-benzenesulfonamide P-1034 with a suitable 4-chloro-7H-pyrrolo[2,3-d]pyrimidine or 4-halo-1H-pyrrolo[2,3-b]pyridine compound and optionally substituting cyclopropylamine 79 with a suitable amine in step 1. The following compounds are made using this procedure:

N-{2,4-Difluoro-3-[4-(tetrahydro-pyran-4-ylamino)-7H-pyrrolo[2,3-d]pyrimidine-5-carbonyl]-phenyl}-4-trifluoromethyl-benzenesulfonamide (P-1013), N-[2,4-Difluoro-3-(4-isobutylamino-7H-pyrrolo[2,3-d]pyrimidine-5-carbonyl)-phenyl]-4-trifluoromethyl-benzenesulfonamide (P-1020), N-[3-(4-Ethylamino-7H-pyrrolo[2,3-d]pyrimidine-5-carbonyl)-2,4-difluoro-phenyl]-4-trifluoromethyl-benzenesulfonamide (P-1024), N-[2,4-Difluoro-3-(4-methylamino-7H-pyrrolo[2,3-d]pyrimidine-5-carbonyl)-phenyl]-4-trifluoromethyl-benzenesulfonamide (P-1026), N-[3-(4-Amino-7H-pyrrolo[2,3-d]pyrimidine-5-carbonyl)-2,4-difluoro-phenyl]-4-trifluoromethyl-benzenesulfonamide (P-1031), N-[2,4-Difluoro-3-(4-propylamino-7H-pyrrolo[2,3-d]pyrimidine-5-carbonyl)-phenyl]-4-trifluoromethyl-benzenesulfonamide (P-1032), N-[2,4-Difluoro-3-(4-phenylamino-7H-pyrrolo[2,3-d]pyrimidine-5-carbonyl)-phenyl]-4-trifluoromethyl-benzenesulfonamide (P-1037), N-[2,4-Difluoro-3-(4-isopropylamino-7H-pyrrolo[2,3-d]pyrimidine-5-carbonyl)-phenyl]-4-trifluoromethyl-benzenesulfonamide (P-1039), Propane-1-sulfonic acid [3-(4-cyclopropylamino-7H-pyrrolo[2,3-d]pyrimidine-5-carbonyl)-2,4-difluoro-phenyl]-amide (P-1041), N-{2,4-Difluoro-3-[4-(2-hydroxy-ethylamino)-7H-pyrrolo[2,3-d]pyrimidine-5-carbonyl]-phenyl}-4-trifluoromethyl-benzenesulfonamide (P-1043), N-{2,4-Difluoro-3-[4-(tetrahydro-pyran-4-ylamino)-7H-pyrrolo[2,3-d]pyrimidine-5-carbonyl]-phenyl}-4-propyl-benzenesulfonamide (P-1046), Propane-1-sulfonic acid {2,4-difluoro-3-[4-(tetrahydro-pyran-4-ylamino)-7H-pyrrolo[2,3-d]pyrimidine-5-carbonyl]-phenyl}-amide (P-1047), Propane-1-sulfonic acid [2,4-difluoro-3-(4-phenylamino-7H-pyrrolo[2,3-d]pyrimidine-5-carbonyl)-phenyl]-amide (P-1048), N-[3-(4-Dimethylamino-7H-pyrrolo[2,3-d]pyrimidine-5-carbonyl)-2,4-difluoro-phenyl]-4-trifluoromethyl-benzenesulfonamide (P-1049), N-{2,4-Difluoro-3-[4-(oxetan-3-ylamino)-7H-pyrrolo[2,3-d]pyrimidine-5-carbonyl]-phenyl}-4-trifluoromethyl-benzenesulfonamide (P-1050), Propane-1-sulfonic acid [2,4-difluoro-3-(4-isopropylamino-7H-pyrrolo[2,3-d]pyrimidine-5-carbonyl)-phenyl]-amide (P-1051), N-{3-[4-(Cyclopropylmethyl-amino)-7H-pyrrolo[2,3-d]pyrimidine-5-carbonyl]-2,4-difluoro-phenyl}-4-trifluoromethyl-benzenesulfonamide (P-1052), N-{2,4-Difluoro-3-[4-(tetrahydro-furan-3-ylamino)-7H-pyrrolo[2,3-d]pyrimidine-5-carbonyl]-phenyl}-4-trifluoromethyl-benzenesulfonamide (P-1054), N-[2,4-Difluoro-3-(4-isopropylamino-7H-pyrrolo[2,3-d]pyrimidine-5-carbonyl)-phenyl]-4-propyl-benzenesulfonamide (P-1055), N-{2,4-Difluoro-3-[4-(oxetan-3-ylamino)-7H-pyrrolo[2,3-d]pyrimidine-5-carbonyl]-phenyl}-4-propyl-benzenesulfonamide (P-1056), N-{2,4-Difluoro-3-[4-(1-methyl-piperidin-4-ylamino)-7H-pyrrolo[2,3-d]pyrimidine-5-carbonyl]-phenyl}-4-trifluoromethyl-benzenesulfonamide (P-1057), N-{2,4-Difluoro-3-[4-(2-methoxy-ethylamino)-7H-pyrrolo[2,3-d]pyrimidine-5-carbonyl]-phenyl}-4-trifluoromethyl-benzenesulfonamide (P-1058), N-{3-[4-(2-Dimethylamino-ethylamino)-7H-pyrrolo[2,3-d]pyrimidine-5-carbonyl]-2,4-difluoro-phenyl}-4-trifluoromethyl-benzenesulfonamide (P-1059), Propane-1-sulfonic acid {2,4-difluoro-3-[4-(oxetan-3-ylamino)-7H-pyrrolo[2,3-d]pyrimidine-5-carbonyl]-phenyl}-amide (P-1060), N-[2,4-Difluoro-3-(4-pyrrolidin-1-yl-7H-pyrrolo[2,3-d]pyrimidine-5-carbonyl)-phenyl]-4-trifluoromethyl-benzenesulfonamide (P-1061), N-{2,4-Difluoro-3-[4-(1-methyl-1H-pyrazol-4-ylamino)-7H-pyrrolo[2,3-d]pyrimidine-5-carbonyl]-phenyl}-4-trifluoromethyl-benzenesulfonamide (P-1062), N-{3-[4-(1-Ethyl-1H-pyrazol-4-ylamino)-7H-pyrrolo[2,3-d]pyrimidine-5-carbonyl]-2,4-difluoro-phenyl}-4-trifluoromethyl-benzenesulfonamide (P-1063), N-[2,4-Difluoro-3-(4-hydroxyamino-7H-pyrrolo[2,3-d]pyrimidine-5-carbonyl)-phenyl]-4-trifluoromethyl-benzenesulfonamide (P-1064), Propane-1-sulfonic acid {2,4-difluoro-3-[4-(4-fluoro-phenylamino)-7H-pyrrolo[2,3-d]pyrimidine-5-carbonyl]-phenyl}-amide (P-1065), Propane-1-sulfonic acid [2,4-difluoro-3-(4-hydrazino-7H-pyrrolo[2,3-d]pyrimidine-5-carbonyl)-phenyl]-amide (P-1066), Propane-1-sulfonic acid {2,4-difluoro-3-[4-(naphthalen-2-ylamino)-7H-pyrrolo[2,3-d]pyrimidine-5-carbonyl]-phenyl}-amide (P-1067), Propane-1-sulfonic acid (2,4-difluoro-3-{4-[(oxetan-3-ylmethyl)-amino]-7H-pyrrolo[2,3-d]pyrimidine-5-carbonyl}-phenyl)-amide (P-1068), N-{2,4-Difluoro-3-[4-(4-fluoro-phenylamino)-7H-pyrrolo[2,3-d]pyrimidine-5-carbonyl]-phenyl}-2,5-difluoro-benzenesulfonamide (P-1069), Propane-1-sulfonic acid {2,4-difluoro-3-[4-(naphthalen-1-ylamino)-7H-pyrrolo[2,3-d]pyrimidine-5-carbonyl]-phenyl}-amide (P-1072), Propane-1-sulfonic acid [3-(4-b enzylamino-7H-pyrrolo[2,3-d]pyrimidine-5-carbonyl)-2,4-difluoro-phenyl]-amide (P-1074), Propane-1-sulfonic acid [2,4-difluoro-3-(4-propylamino-7H-pyrrolo[2,3-d]pyrimidine-5-carbonyl)-phenyl]-amide (P-1075), Propane-1-sulfonic acid {2,4-difluoro-3-[4-(pyridin-4-ylamino)-7H-pyrrolo[2,3-d]pyrimidine-5-carbonyl]-phenyl}-amide (P-1076), Propane-1-sulfonic acid {2,4-difluoro-3-[4-(pyridin-2-ylamino)-7H-pyrrolo[2,3-d]pyrimidine-5-carbonyl]-phenyl}-amide (P-1077), Propane-1-sulfonic acid {2,4-difluoro-3-[4-(pyridin-3-ylamino)-7H-pyrrolo[2,3-d]pyrimidine-5-carbonyl]-phenyl}-amide (P-1078), Propane-1-sulfonic acid {3-[4-(cyclopropylmethyl-amino)-7H-pyrrolo[2,3-d]pyrimidine-5-carbonyl]-2,4-difluoro-phenyl}-amide (P-1079), Propane-1-sulfonic acid {3-[4-(1-benzyl-pyrrolidin-3-ylamino)-7H-pyrrolo[2,3-d]pyrimidine-5-carbonyl]-2,4-difluoro-phenyl}-amide (P-1080), Propane-1-sulfonic acid [3-(4-cyclopentylamino-7H-pyrrolo[2,3-d]pyrimidine-5-carbonyl)-2,4-difluoro-phenyl]-amide (P-1081), Propane-1-sulfonic acid [3-(4-ethylamino-7H-pyrrolo[2,3-d]pyrimidine-5-carbonyl)-2,4-difluoro-phenyl]-amide (P-1082), Propane-1-sulfonic acid {3-[4-(3-dimethylamino-phenylamino)-7H-pyrrolo[2,3-d]pyrimidine-5-carbonyl]-2,4-difluoro-phenyl}-amide (P-1083), Propane-1-sulfonic acid {3-[4-(3-chloro-phenylamino)-7H-pyrrolo[2,3-d]pyrimidine-5-carbonyl]-2,4-difluoro-phenyl}-amide (P-1084), Propane-1-sulfonic acid {2,4-difluoro-3-[4-(3-methoxy-phenylamino)-7H-pyrrolo[2,3-d]pyrimidine-5-carbonyl]-phenyl}-amide (P-1085), Propane-1-sulfonic acid {2,4-difluoro-3-[4-(2-methoxy-ethylamino)-7H-pyrrolo[2,3-d]pyrimidine-5-carbonyl]-phenyl}-amide (P-1086), Propane-1-sulfonic acid {3-[4-(4-chloro-phenylamino)-7H-pyrrolo[2,3-d]pyrimidine-5-carbonyl]-2,4-difluoro-phenyl}-amide (P-1087), Propane-1-sulfonic acid [2,4-difluoro-3-(4-isobutylamino-7H-pyrrolo[2,3-d]pyrimidine-5-carbonyl)-phenyl]-amide (P-1088), Propane-1-sulfonic acid {2,4-difluoro-3-[4-(4-trifluoromethyl-phenylamino)-7H-pyrrolo[2,3-d]pyrimidine-5-carbonyl]-phenyl}-amide (P-1089),
Propane-1-sulfonic acid {2,4-difluoro-3-[4-(6-methoxypyridin-3-ylamino)-7H-pyrrolo[2,3-d]pyrimidine-5-carbonyl]-phenyl}-amide (P-1090),
Propane-1-sulfonic acid {2,4-difluoro-3-[4-(3-trifluoromethyl-phenylamino)-7H-pyrrolo[2,3-d]pyrimidine-5-carbonyl]-phenyl}-amide (P-1091),
Propane-1-sulfonic acid [2,4-difluoro-3-(4-m-tolylamino-7H-pyrrolo[2,3-d]pyrimidine-5-carbonyl)-phenyl]-amide (P-1092),
Propane-1-sulfonic acid [2,4-difluoro-3-(4-p-tolylamino-7H-pyrrolo[2,3-d]pyrimidine-5-carbonyl)-phenyl]-amide (P-1093),
Propane-1-sulfonic acid {2,4-difluoro-3-[4-(3-fluoro-phenylamino)-7H-pyrrolo[2,3-d]pyrimidine-5-carbonyl]-phenyl}-amide (P-1094),
Propane-1-sulfonic acid {3-[4-(1-ethyl-piperidin-4-ylamino)-7H-pyrrolo[2,3-d]pyrimidine-5-carbonyl]-2,4-difluoro-phenyl}-amide (P-1095),
Propane-1-sulfonic acid {2,4-difluoro-3-[4-(1-methanesulfonyl-piperidin-4-ylamino)-7H-pyrrolo[2,3-d]pyrimidine-5-carbonyl]-phenyl}-amide (P-1096),
Propane-1-sulfonic acid {2,4-difluoro-3-[4-(tetrahydrofuran-3-ylamino)-7H-pyrrolo[2,3-d]pyrimidine-5-carbonyl]-phenyl}-amide (P-1097),
Propane-1-sulfonic acid [2,4-difluoro-3-(4-methylamino-7H-pyrrolo[2,3-d]pyrimidine-5-carbonyl)-phenyl]-amide (P-1098),
Propane-1-sulfonic acid {3-[4-(1-ethyl-1H-pyrazol-4-ylamino)-7H-pyrrolo[2,3-d]pyrimidine-5-carbonyl]-2,4-difluoro-phenyl}-amide (P-1099),
Propane-1-sulfonic acid {3-[4-(1,3-dimethyl-1H-pyrazol-4-ylamino)-7H-pyrrolo[2,3-d]pyrimidine-5-carbonyl]-2,4-difluoro-phenyl}-amide (P-1100),
Propane-1-sulfonic acid {2,4-difluoro-3-[4-(2-fluoro-4-methoxy-phenylamino)-7H-pyrrolo[2,3-d]pyrimidine-5-carbonyl]-phenyl}-amide (P-1101),
Propane-1-sulfonic acid {2,4-difluoro-3-[4-(1-methyl-1H-pyrazol-4-ylamino)-7H-pyrrolo[2,3-d]pyrimidine-5-carbonyl]-phenyl}-amide (P-1102),
N-[3-(4-Cyclopropylamino-7H-pyrrolo[2,3-d]pyrimidine-5-carbonyl)-2,4-difluoro-phenyl]-2-fluoro-benzenesulfonamide (P-1103),
Propane-1-sulfonic acid {2,4-difluoro-3-[4-(3-fluoro-5-methoxy-pyridin-2-ylamino)-7H-pyrrolo[2,3-d]pyrimidine-5-carbonyl]-phenyl}-amide (P-1105),
Propane-1-sulfonic acid {3-[4-(benzo[1,2,5]thiadiazol-5-ylamino)-7H-pyrrolo[2,3-d]pyrimidine-5-carbonyl]-2,4-difluoro-phenyl}-amide (P-1134),
N-[3-(4-Benzylamino-7H-pyrrolo[2,3-d]pyrimidine-5-carbonyl)-2,4-difluoro-phenyl]-2,5-difluoro-benzenesulfonamide (P-1135),
N-{2,4-Difluoro-3-[4-(pyridin-3-ylamino)-7H-pyrrolo[2,3-d]pyrimidine-5-carbonyl]-phenyl}-2,5-difluoro-benzenesulfonamide (P-1136),
N-{3-[4-(Cyclopropylmethyl-amino)-7H-pyrrolo[2,3-d]pyrimidine-5-carbonyl]-2,4-difluoro-phenyl}-2,5-difluoro-benzenesulfonamide (P-1137),
N-[3-(4-Ethylamino-7H-pyrrolo[2,3-d]pyrimidine-5-carbonyl)-2,4-difluoro-phenyl]-2,5-difluoro-benzenesulfonamide (P-1138),
N-{2,4-Difluoro-3-[4-(3-methoxy-phenylamino)-7H-pyrrolo[2,3-d]pyrimidine-5-carbonyl]-phenyl}-2,5-difluoro-benzenesulfonamide (P-1139),
N-[2,4-Difluoro-3-(4-isobutylamino-7H-pyrrolo[2,3-d]pyrimidine-5-carbonyl)-phenyl]-2,5-difluoro-benzenesulfonamide (P-1140),
N-[2,4-Difluoro-3-(4-m-tolylamino-7H-pyrrolo[2,3-d]pyrimidine-5-carbonyl)-phenyl]-2,5-difluoro-benzenesulfonamide (P-1141),
N-{3-[4-(1-Ethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1142),
N-{3-[4-(1,3-Dimethyl-1H-pyrazol-4-ylamino)-7H-pyrrolo[2,3-d]pyrimidine-5-carbonyl]-2,4-difluoro-phenyl}-2,5-difluoro-benzenesulfonamide (P-1143),
N-[3-(4-Benzylamino-7H-pyrrolo[2,3-d]pyrimidine-5-carbonyl)-2,4-difluoro-phenyl]-2-fluoro-benzenesulfonamide (P-1144),
N-{2,4-Difluoro-3-[4-(pyridin-3-ylamino)-7H-pyrrolo[2,3-d]pyrimidine-5-carbonyl]-phenyl}-2-fluoro-benzenesulfonamide (P-1145),
N-{3-[4-(Cyclopropylmethyl-amino)-7H-pyrrolo[2,3-d]pyrimidine-5-carbonyl]-2,4-difluoro-phenyl}-2-fluoro-benzenesulfonamide (P-1146),
N-[3-(4-Cyclopentylamino-7H-pyrrolo[2,3-d]pyrimidine-5-carbonyl)-2,4-difluoro-phenyl]-2-fluoro-benzenesulfonamide (P-1147),
N-[3-(4-Ethylamino-7H-pyrrolo[2,3-d]pyrimidine-5-carbonyl)-2,4-difluoro-phenyl]-2-fluoro-benzenesulfonamide (P-1148),
N-{2,4-Difluoro-3-[4-(3-methoxy-phenylamino)-7H-pyrrolo[2,3-d]pyrimidine-5-carbonyl]-phenyl}-2-fluoro-benzenesulfonamide (P-1149),
N-{2,4-Difluoro-3-[4-(2-methoxy-ethylamino)-7H-pyrrolo[2,3-d]pyrimidine-5-carbonyl]-phenyl}-2-fluoro-benzenesulfonamide (P-1150),
N-[2,4-Difluoro-3-(4-isobutylamino-7H-pyrrolo[2,3-d]pyrimidine-5-carbonyl)-phenyl]-2-fluoro-benzenesulfonamide (P-1151),
N-[2,4-Difluoro-3-(4-m-tolylamino-7H-pyrrolo[2,3-d]pyrimidine-5-carbonyl)-phenyl]-2-fluoro-benzenesulfonamide (P-1152),
N-{3-[4-(1-Ethyl-1H-pyrazol-4-ylamino)-7H-pyrrolo[2,3-d]pyrimidine-5-carbonyl]-2,4-difluoro-phenyl}-2-fluoro-benzenesulfonamide (P-1153),
N-{3-[4-(1,3-Dimethyl-1H-pyrazol-4-ylamino)-7H-pyrrolo[2,3-d]pyrimidine-5-carbonyl]-2,4-difluoro-phenyl}-2-fluoro-benzenesulfonamide (P-1154),
Propane-1-sulfonic acid {2,4-difluoro-3-[4-(1H-indazol-6-ylamino)-7H-pyrrolo[2,3-d]pyrimidine-5-carbonyl]-phenyl}-amide (P-1157),
Propane-1-sulfonic acid {2,4-difluoro-3-[4-(1H-indazol-5-ylamino)-7H-pyrrolo[2,3-d]pyrimidine-5-carbonyl]-phenyl}-amide (P-1158),
Propane-1-sulfonic acid {2,4-difluoro-3-[4-(4-hydroxy-phenylamino)-7H-pyrrolo[2,3-d]pyrimidine-5-carbonyl]-phenyl}-amide (P-1159),
Propane-1-sulfonic acid (2,4-difluoro-3-{4-[(5-methyl-1H-pyrazol-3-ylmethyl)-amino]-7H-pyrrolo[2,3-d]pyrimidine-5-carbonyl}-phenyl)-amide (P-1160),
3-({5-[2,6-Difluoro-3-(propane-1-sulfonylamino)-benzoyl]-7H-pyrrolo[2,3-d]pyrimidin-4-ylamino}-methyl)-benzoic acid (P-1161),
4-{5-[2,6-Difluoro-3-(propane-1-sulfonylamino)-benzoyl]-7H-pyrrolo[2,3-d]pyrimidin-4-ylamino}-benzoic acid methyl ester (P-1162),
Propane-1-sulfonic acid {2,4-difluoro-3-[4-(3-[1,2,4]triazol-1-yl-phenylamino)-7H-pyrrolo[2,3-d]pyrimidine-5-carbonyl]-phenyl}-amide (P-1164), Propane-1-sulfonic acid {2,4-difluoro-3-[4-(3-oxazol-5-yl-phenylamino)-7H-pyrrolo[2,3-d]pyrimidine-5-carbonyl]-phenyl}-amide (P-1165), Propane-1-sulfonic acid (2,4-difluoro-3-{4-[(pyridin-3-ylmethyl)-amino]-7H-pyrrolo[2,3-d]pyrimidine-5-carbonyl}-phenyl)-amide (P-1166), Propane-1-sulfonic acid {2,4-difluoro-3-[4-(3-[1,2,4]triazol-1-yl-propylamino)-7H-pyrrolo[2,3-d]pyrimidine-5-carbonyl]-phenyl}-amide (P-1167), Propane-1-sulfonic acid {2,4-difluoro-3-[4-(3-pyridin-3-yl-propylamino)-7H-pyrrolo[2,3-d]pyrimidine-5-carbonyl]-phenyl}-amide (P-1168), Propane-1-sulfonic acid {2,4-difluoro-3-[4-(3-hydroxy-phenylamino)-7H-pyrrolo[2,3-d]pyrimidine-5-carbonyl]-phenyl}-amide (P-1169), Propane-1-sulfonic acid (2,4-difluoro-3-{4-[3-(5-methyl-4H-[1,2,4]triazol-3-yl)-phenylamino]-7H-pyrrolo[2,3-d]pyrimidine-5-carbonyl}-phenyl)-amide (P-1170), Propane-1-sulfonic acid (2,4-difluoro-3-{4-[3-(5-methyl-tetrazol-1-yl)-phenylamino]-7H-pyrrolo[2,3-d]pyrimidine-5-carbonyl}-phenyl)-amide (P-1171), Propane-1-sulfonic acid (2,4-difluoro-3-{4-[3-(4H-[1,2,4]triazol-3-yl)-phenylamino]-7H-pyrrolo[2,3-d]pyrimidine-5-carbonyl}-phenyl)-amide (P-1172), Propane-1-sulfonic acid (3-{4-[(benzo[1,2,5]oxadiazol-5-ylmethyl)-amino]-7H-pyrrolo[2,3-d]pyrimidine-5-carbonyl}-2,4-difluoro-phenyl)-amide (P-1173), Propane-1-sulfonic acid {3-[4-(1,1-dioxo-hexahydro-1 lambda*6*-thiopyran-4-ylamino)-7H-pyrrolo[2,3-d]pyrimidine-5-carbonyl]-2,4-difluoro-phenyl}-amide (P-1174), Propane-1-sulfonic acid {3-[4-(1,1-dioxo-tetrahydro-1 lambda*6*-thiophen-3-ylamino)-7H-pyrrolo[2,3-d]pyrimidine-5-carbonyl]-2,4-difluoro-phenyl}-amide (P-1175), Propane-1-sulfonic acid (2,4-difluoro-3-{4-[2-(5-methyl-4H-[1,2,4]triazol-3-yl)-ethylamino]-7H-pyrrolo[2,3-d]pyrimidine-5-carbonyl}-phenyl)-amide (P-1176), Propane-1-sulfonic acid {2,4-difluoro-3-[4-(2-oxo-2,3-dihydro-1H-benzoimidazol-5-ylamino)-7H-pyrrolo[2,3-d]pyrimidine-5-carbonyl]-phenyl}-amide (P-1177), Propane-1-sulfonic acid (2,4-difluoro-3-{4-[3-(2-methyl-2H-tetrazol-5-yl)-phenylamino]-7H-pyrrolo[2,3-d]pyrimidine-5-carbonyl}-phenyl)-amide (P-1178), Propane-1-sulfonic acid (2,4-difluoro-3-{4-[3-(5-methyl-[1,3,4]oxadiazol-2-yl)-phenylamino]-7H-pyrrolo[2,3-d]pyrimidine-5-carbonyl}-phenyl)-amide (P-1179), Propane-1-sulfonic acid (2,4-difluoro-3-{4-[(pyridazin-4-ylmethyl)-amino]-7H-pyrrolo[2,3-d]pyrimidine-5-carbonyl}-phenyl)-amide (P-1180), N-{3-[4-(Cyclopropylmethyl-amino)-1H-pyrrolo[2,3-b]pyridine-3-carbonyl]-2,4-difluoro-phenyl}-2,5-difluoro-benzenesulfonamide (P-2018), N-{3-[4-(Cyclopropylmethyl-amino)-5-fluoro-1H-pyrrolo[2,3-b]pyridine-3-carbonyl]-2,4-difluoro-phenyl}-2,5-difluoro-benzenesulfonamide (P-2019), N-{3-[5-Cyano-4-(cyclopropylmethyl-amino)-1H-pyrrolo[2,3-b]pyridine-3-carbonyl]-2,4-difluoro-phenyl}-2,5-difluoro-benzenesulfonamide (P-2020), N-{3-[5-Chloro-4-(cyclopropylmethyl-amino)-1H-pyrrolo[2,3-b]pyridine-3-carbonyl]-2,4-difluoro-phenyl}-2,5-difluoro-benzenesulfonamide (P-2021), N-{3-[4-(Cyclopropylmethyl-amino)-5-methyl-1H-pyrrolo[2,3-b]pyridine-3-carbonyl]-2,4-difluoro-phenyl}-2,5-difluoro-benzenesulfonamide (P-2022), N-{3-[4-(Cyclopropylmethyl-amino)-5-hydroxymethyl-1H-pyrrolo[2,3-b]pyridine-3-carbonyl]-2,4-difluoro-phenyl}-2,5-difluoro-benzenesulfonamide (P-2023), N-{3-[4-(Cyclopropylmethyl-amino)-5-methoxy-1H-pyrrolo[2,3-b]pyridine-3-carbonyl]-2,4-difluoro-phenyl}-2,5-difluoro-benzenesulfonamide (P-2024).

The following table indicates the 4-chloro-7H-pyrrolo[2,3-d]pyrimidine compound or 1H-pyrrolo[2,3-b]pyridine (column 2) and amine compound (column 3) used in step 1 to afford the desired compound (column 4). The compound number is provided in column 1, and the observed mass is in column 5.

| Comp. number | 7H-pyrrolo[2,3-d]pyrimidine | Amine structure | Compound structure | MS (ESI) [M + H+]+ |
|---|---|---|---|---|
| P-1013 | | | 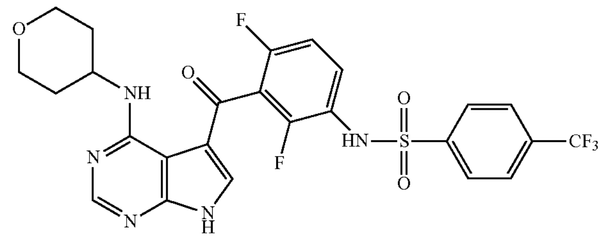 [SMILES: O=C(c1c(F)ccc(NS(=O)(=O)c2ccc(C(F)(F)F)cc2)c1F)c1c[nH]c2ncnc(NC3CCOCC3)c12] | 582.0 |
| P-1020 | | | 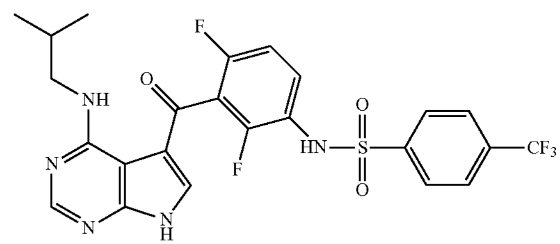 | 554.0 |
| P-1024 | | | 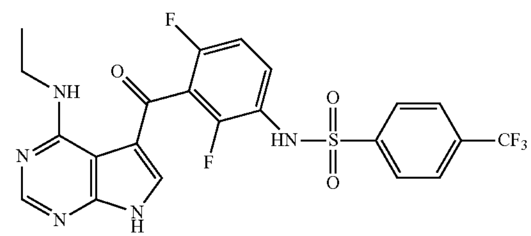 | 525.95 |
| P-1026 | | | 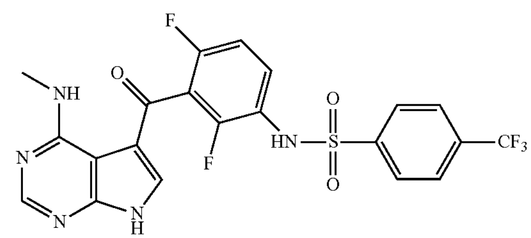 | 512.0 |

| Comp. number | 7H-pyrrolo[2,3-d]pyrimidine | Amine structure | Compound structure | MS (ESI) [M + H+]+ |
|---|---|---|---|---|
| P-1031 | | $NH_3$ | 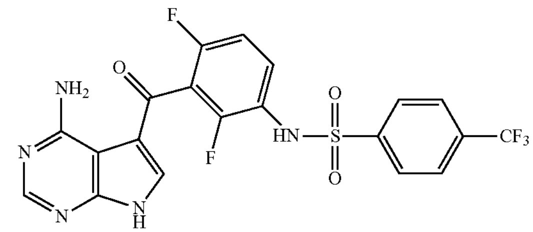 | 497.9 |
| P-1032 | | propylamine | 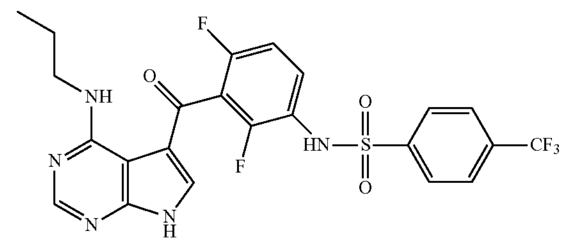 [SMILES: CCCNc1ncnc2[nH]cc(C(=O)c3c(F)ccc(NS(=O)(=O)c4ccc(C(F)(F)F)cc4)c3F)c12] | 539.95 |
| P-1037 | | aniline | 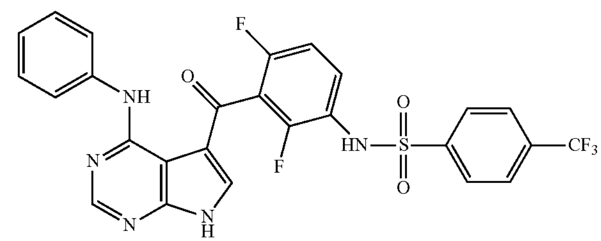 [SMILES: O=C(c1c(F)ccc(NS(=O)(=O)c2ccc(C(F)(F)F)cc2)c1F)c1c[nH]c2ncnc(Nc3ccccc3)c12] | 573.9 |
| P-1039 | | isopropylamine | 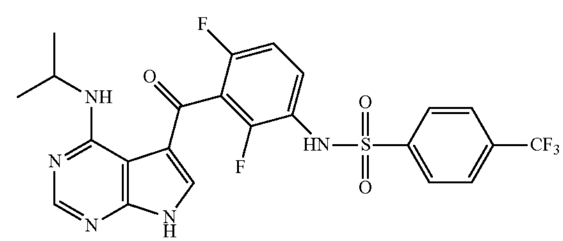 [SMILES: CC(C)Nc1ncnc2[nH]cc(C(=O)c3c(F)ccc(NS(=O)(=O)c4ccc(C(F)(F)F)cc4)c3F)c12] | 540.0 |

-continued

| Comp. number | 7H-pyrrolo[2,3-d]pyrimidine | Amine structure | Compound structure | MS (ESI) [M + H+]+ |
|---|---|---|---|---|
| P-1041 | | | 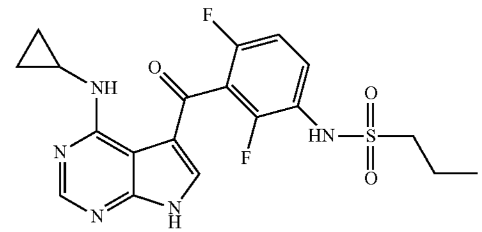 [SMILES: CCCS(=O)(=O)Nc1ccc(F)c(C(=O)c2c[nH]c3ncnc(NC4CC4)c23)c1F] | 435.95 |
| P-1043 | | | 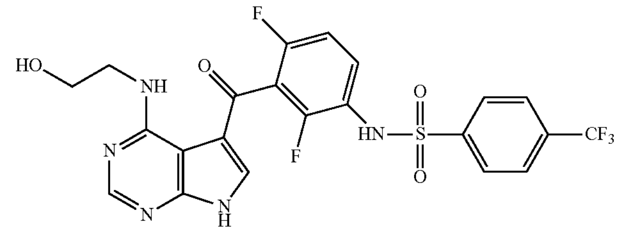 | 541.95 |
| P-1046 | | | 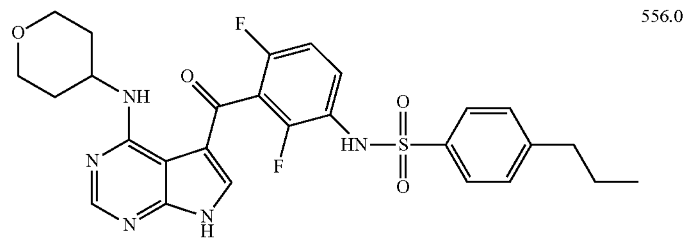 | 556.0 |
| P-1047 | | | 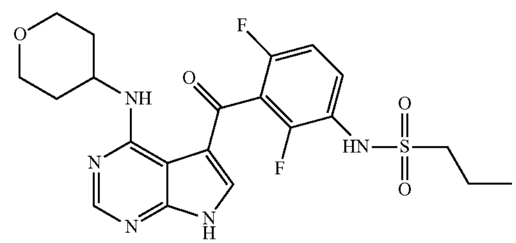 [SMILES: CCCS(=O)(=O)Nc1ccc(F)c(C(=O)c2c[nH]c3ncnc(NC4CCOCC4)c23)c1F] | 479.95 |

| Comp. number | 7H-pyrrolo[2,3-d]pyrimidine | Amine structure | Compound structure | MS (ESI) [M + H+]+ |
|---|---|---|---|---|
| P-1048 | | | 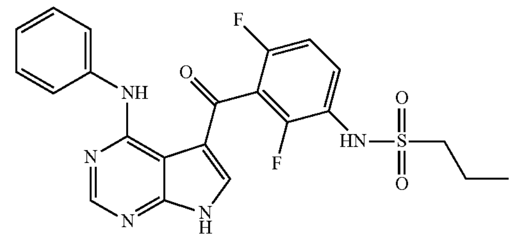 [SMILES: CCCS(=O)(=O)Nc1ccc(F)c(C(=O)c2c[nH]c3ncnc(Nc4ccccc4)c23)c1F] | 473.95 |
| P-1049 | | | 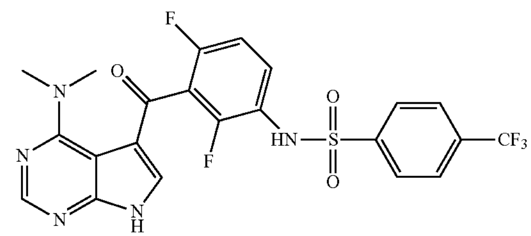 [SMILES: CN(C)c1ncnc2[nH]cc(C(=O)c3c(F)ccc(NS(=O)(=O)c4ccc(C(F)(F)F)cc4)c3F)c12] | 525.95 |
| P-1050 | | | 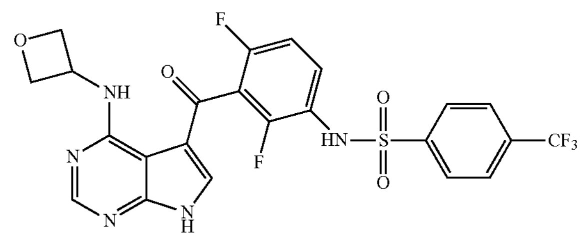 [SMILES: O=C(c1c(F)ccc(NS(=O)(=O)c2ccc(C(F)(F)F)cc2)c1F)c1c[nH]c2ncnc(NC3COC3)c12] | 554.0 |
| P-1051 | | | 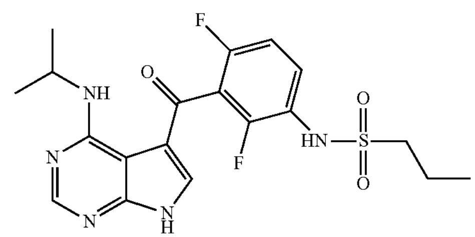 | 437.95 |

| Comp. number | 7H-pyrrolo[2,3-d]pyrimidine | Amine structure | Compound structure | MS (ESI) [M + H+]+ |
|---|---|---|---|---|
| P-1052 | | | 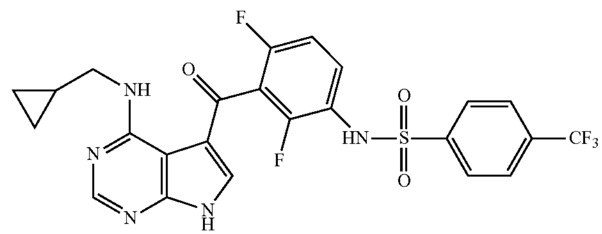 [SMILES: O=C(c1c(F)ccc(NS(=O)(=O)c2ccc(C(F)(F)F)cc2)c1F)c1c[nH]c2ncnc(NCC3CC3)c12] | 552.2 |
| P-1054 | | | 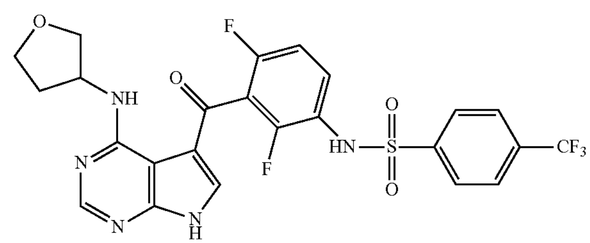 [SMILES: O=C(c1c(F)ccc(NS(=O)(=O)c2ccc(C(F)(F)F)cc2)c1F)c1c[nH]c2ncnc(NC3CCOC3)c12] | 568.0 |
| P-1055 | | | 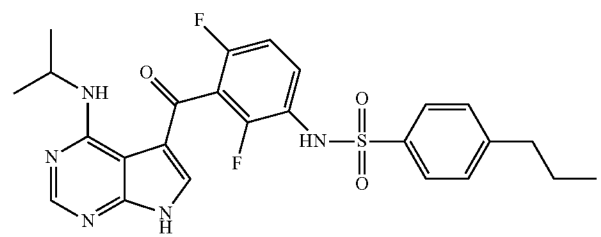 [SMILES: CCCc1ccc(S(=O)(=O)Nc2ccc(F)c(C(=O)c3c[nH]c4ncnc(NC(C)C)c34)c2F)cc1] | 514.0 |
| P-1056 | | | 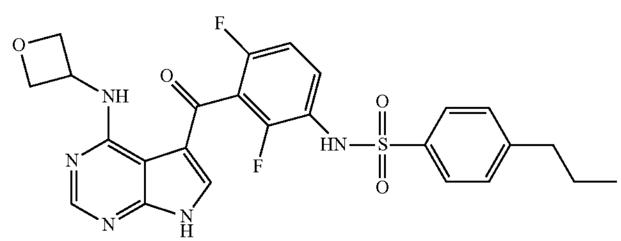 | 528.0 |

| Comp. number | 7H-pyrrolo[2,3-d]pyrimidine | Amine structure | Compound structure | MS (ESI) [M + H+]+ |
|---|---|---|---|---|
| P-1057 | | | 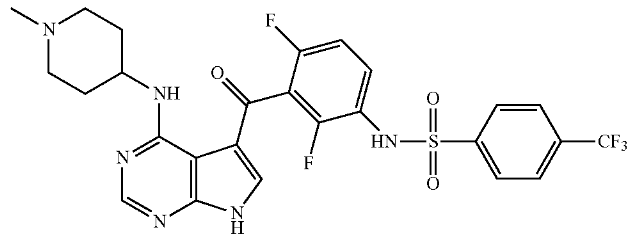 [SMILES: CN1CCC(Nc2ncnc3[nH]cc(C(=O)c4c(F)ccc(NS(=O)(=O)c5ccc(C(F)(F)F)cc5)c4F)c23)CC1] | 595.0 |
| P-1058 | | | 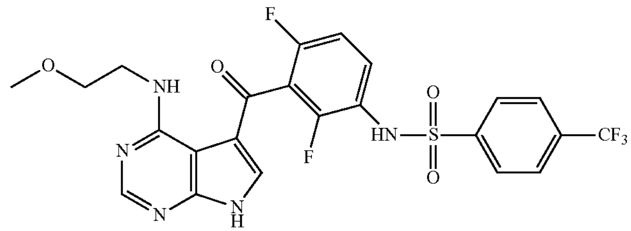 [SMILES: COCCNc1ncnc2[nH]cc(C(=O)c3c(F)ccc(NS(=O)(=O)c4ccc(C(F)(F)F)cc4)c3F)c12] | 556.3 |
| P-1059 | | | 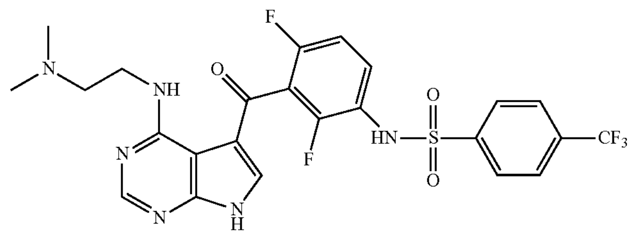 [SMILES: CN(C)CCNc1ncnc2[nH]cc(C(=O)c3c(F)ccc(NS(=O)(=O)c4ccc(C(F)(F)F)cc4)c3F)c12] | 569.5 |
| P-1060 | | | 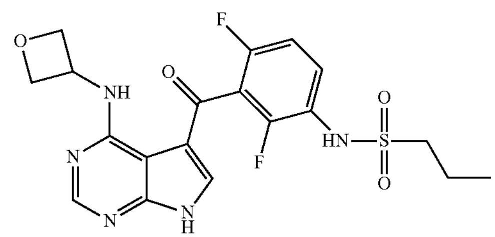 [SMILES: CCCS(=O)(=O)Nc1ccc(F)c(C(=O)c2c[nH]c3ncnc(NC4COC4)c23)c1F] | 451.95 |

| Comp. number | 7H-pyrrolo[2,3-d]pyrimidine | Amine structure | Compound structure | MS (ESI) [M + H+]+ |
|---|---|---|---|---|
| P-1061 | | | 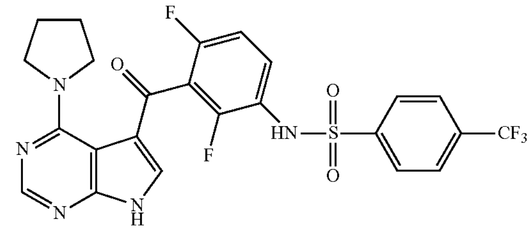 [SMILES: O=C(c1c(F)ccc(NS(=O)(=O)c2ccc(C(F)(F)F)cc2)c1F)c1c[nH]c2ncnc(N3CCCC3)c12] | 552.5 |
| P-1062 | | | 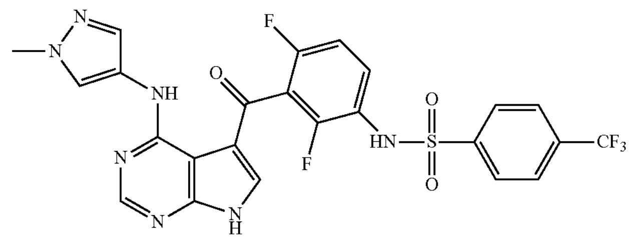 [SMILES: Cn1cc(Nc2ncnc3[nH]cc(C(=O)c4c(F)ccc(NS(=O)(=O)c5ccc(C(F)(F)F)cc5)c4F)c23)cn1] | 578.1 |
| P-1063 | | | 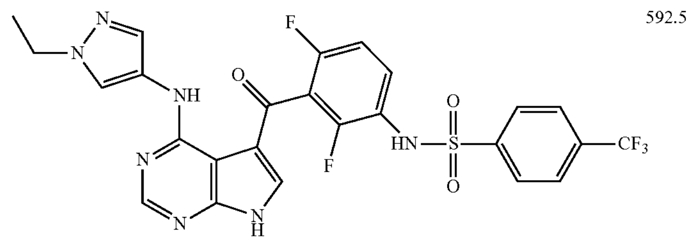 | 592.5 |
| P-1064 | | | 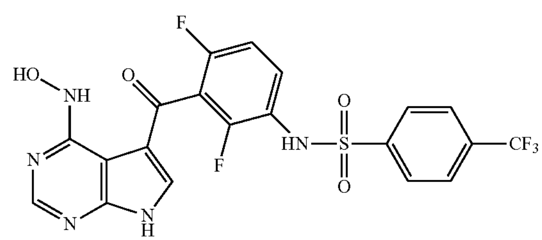 [SMILES: O=C(c1c(F)ccc(NS(=O)(=O)c2ccc(C(F)(F)F)cc2)c1F)c1c[nH]c2ncnc(NO)c12] | 513.9 |

| Comp. number | 7H-pyrrolo[2,3-d]pyrimidine | Amine structure | Compound structure | MS (ESI) [M + H⁺]⁺ |
|---|---|---|---|---|
| P-1065 | | | 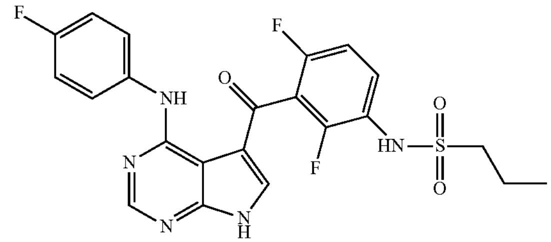 | 490.0 |
| P-1066 | | | 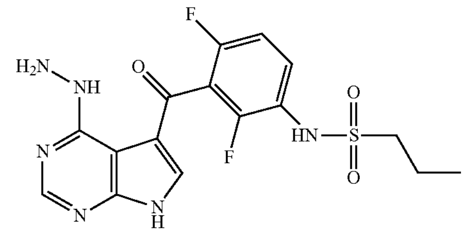 [SMILES: CCCS(=O)(=O)Nc1ccc(F)c(C(=O)c2c[nH]c3ncnc(NN)c23)c1F] | 410.85 |
| P-1067 | | | 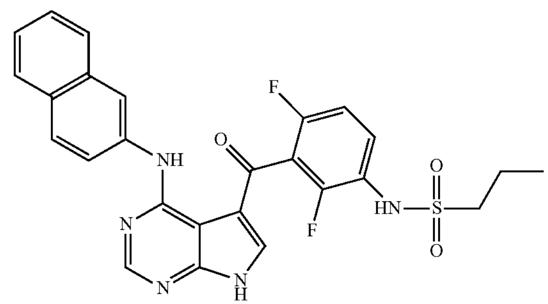 [SMILES: CCCS(=O)(=O)Nc1ccc(F)c(C(=O)c2c[nH]c3ncnc(Nc4ccc5ccccc5c4)c23)c1F] | 522.25 |
| P-1068 | | | 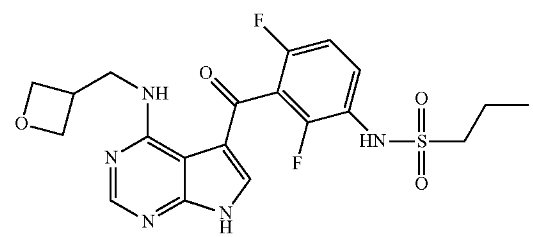 [SMILES: CCCS(=O)(=O)Nc1ccc(F)c(C(=O)c2c[nH]c3ncnc(NCC4COC4)c23)c1F] | 513.9 [M − H⁺]⁺ |

| Comp. number | 7H-pyrrolo[2,3-d]pyrimidine | Amine structure | Compound structure | MS (ESI) [M + H+]+ |
|---|---|---|---|---|
| P-1069 | | | 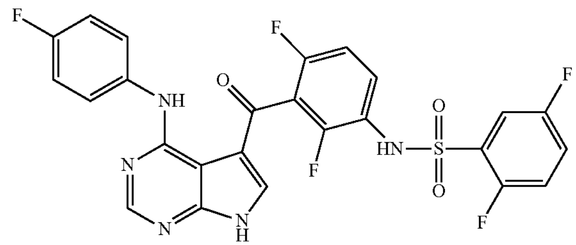 [SMILES: O=C(c1c(F)ccc(NS(=O)(=O)c2cc(F)ccc2F)c1F)c1c[nH]c2ncnc(Nc3ccc(F)cc3)c12] | 559.9 |
| P-1072 | | | 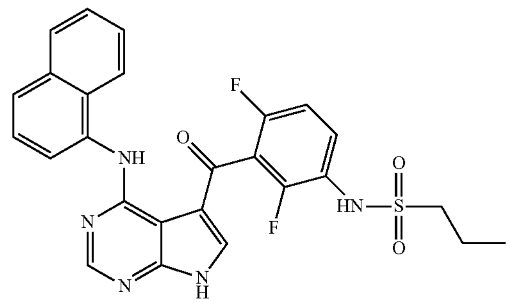 [SMILES: CCCS(=O)(=O)Nc1ccc(F)c(C(=O)c2c[nH]c3ncnc(Nc4cccc5ccccc45)c23)c1F] | 522.0 |
| P-1074 | | | 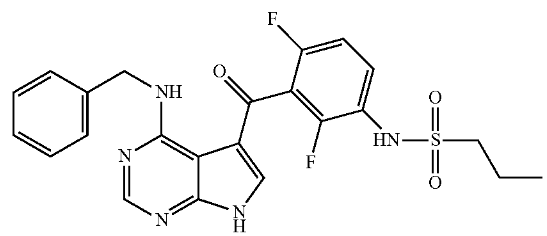 [SMILES: CCCS(=O)(=O)Nc1ccc(F)c(C(=O)c2c[nH]c3ncnc(NCc4ccccc4)c23)c1F] | 486.5 |

| Comp. number | 7H-pyrrolo[2,3-d]pyrimidine | Amine structure | Compound structure | MS (ESI) [M + H+]+ |
|---|---|---|---|---|
| P-1075 | | | 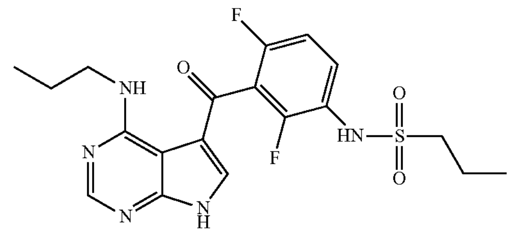 [SMILES: CCCNc1ncnc2[nH]cc(C(=O)c3c(F)ccc(NS(=O)(=O)CCC)c3F)c12] | 438.0 |
| P-1076 | | | 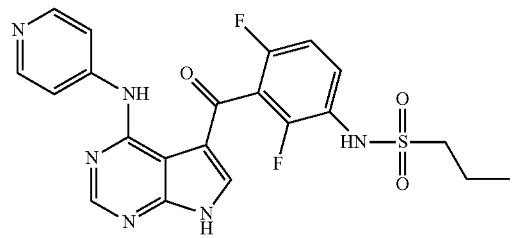 | 473.0 |
| P-1077 | | | 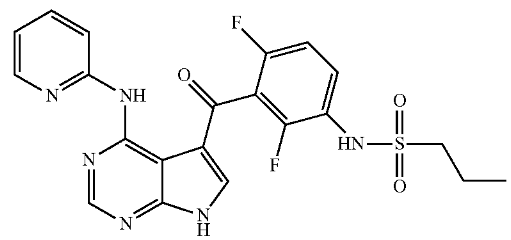 [SMILES: CCCS(=O)(=O)Nc1ccc(F)c(C(=O)c2c[nH]c3ncnc(Nc4ccccn4)c23)c1F] | 473.0 |
| P-1078 | | | 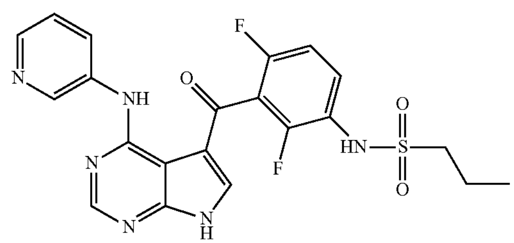 | 473.0 |

| Comp. number | 7H-pyrrolo[2,3-d]pyrimidine | Amine structure | Compound structure | MS (ESI) [M + H+]+ |
|---|---|---|---|---|
| P-1079 | | | 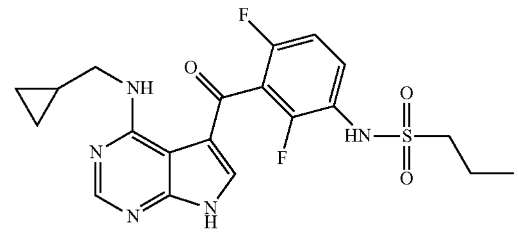 [SMILES: CCCS(=O)(=O)Nc1ccc(F)c(C(=O)c2c[nH]c3ncnc(NCC4CC4)c23)c1F] | 450.0 |
| P-1080 | | | 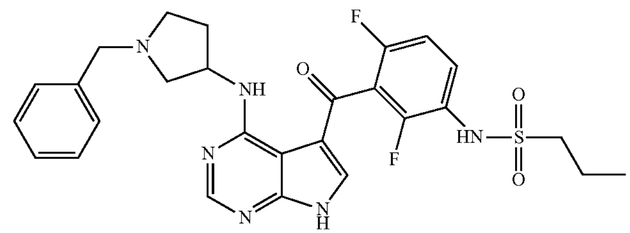 [SMILES: CCCS(=O)(=O)Nc1ccc(F)c(C(=O)c2c[nH]c3ncnc(NC4CCN(Cc5ccccc5)C4)c23)c1F] | 555.5 |
| P-1081 | | | 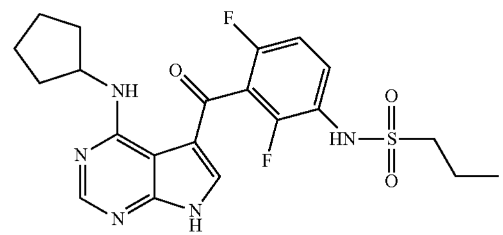 | 464.0 |
| P-1082 | | | 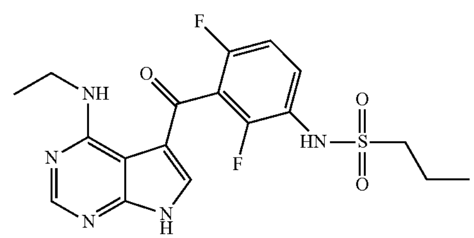 [SMILES: CCCS(=O)(=O)Nc1ccc(F)c(C(=O)c2c[nH]c3ncnc(NCC)c23)c1F] | 424.0 |

| Comp. number | 7H-pyrrolo[2,3-d]pyrimidine | Amine structure | Compound structure | MS (ESI) [M + H⁺]⁺ |
|---|---|---|---|---|
| P-1083 | | | 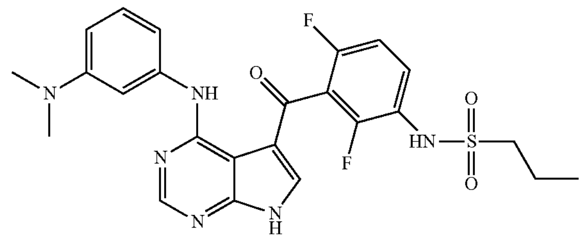 | 515.5 |
| P-1084 | | | 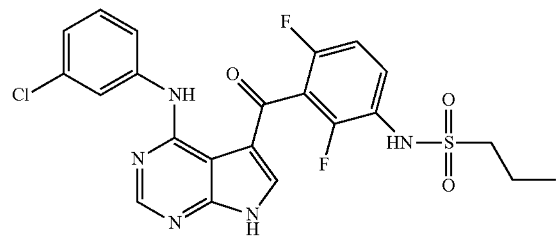 [SMILES: CCCS(=O)(=O)Nc1ccc(F)c(C(=O)c2c[nH]c3ncnc(Nc4cccc(Cl)c4)c23)c1F] | 506.0 |
| P-1085 | | | 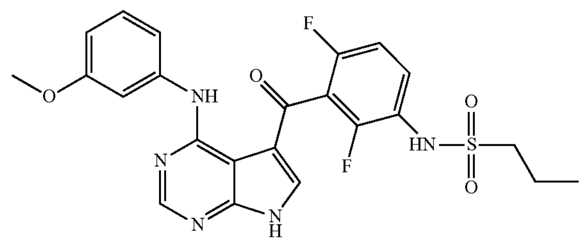 [SMILES: CCCS(=O)(=O)Nc1ccc(F)c(C(=O)c2c[nH]c3ncnc(Nc4cccc(OC)c4)c23)c1F] | 502.5 |
| P-1086 | | | 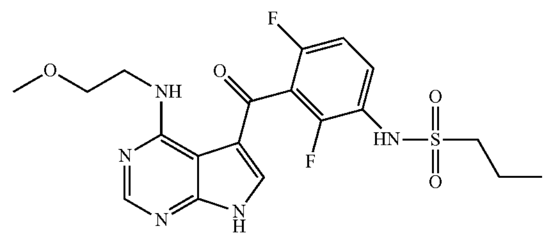 [SMILES: CCCS(=O)(=O)Nc1ccc(F)c(C(=O)c2c[nH]c3ncnc(NCCOC)c23)c1F] | 454.0 |

| Comp. number | 7H-pyrrolo[2,3-d]pyrimidine | Amine structure | Compound structure | MS (ESI) [M + H+]+ |
|---|---|---|---|---|
| P-1087 | | | 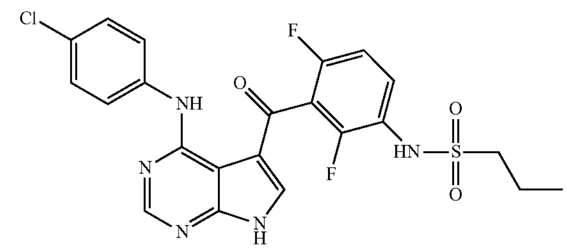 [SMILES: CCCS(=O)(=O)Nc1ccc(F)c(C(=O)c2c[nH]c3ncnc(Nc4ccc(Cl)cc4)c23)c1F] | 506.0 |
| P-1088 | | | 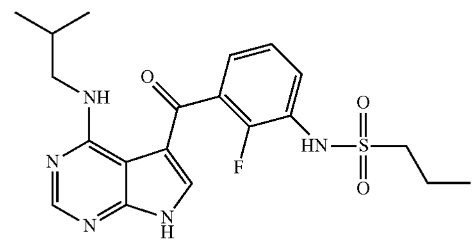 [SMILES: CCCS(=O)(=O)Nc1cccc(C(=O)c2c[nH]c3ncnc(NCC(C)C)c23)c1F] | 452.0 |
| P-1089 | | | 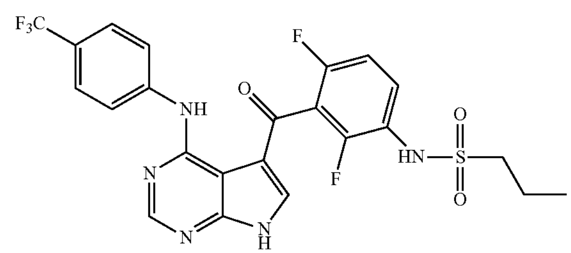 [SMILES: CCCS(=O)(=O)Nc1ccc(F)c(C(=O)c2c[nH]c3ncnc(Nc4ccc(C(F)(F)F)cc4)c23)c1F] | 540.5 |
| P-1090 | | | 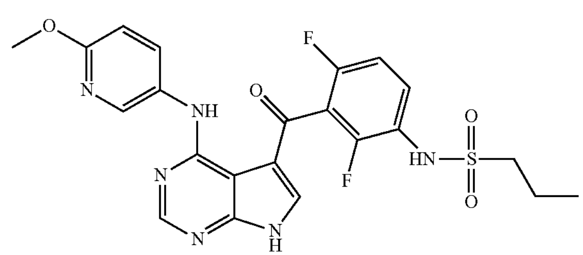 [SMILES: CCCS(=O)(=O)Nc1ccc(F)c(C(=O)c2c[nH]c3ncnc(Nc4ccc(OC)nc4)c23)c1F] | 503.0 |

| Comp. number | 7H-pyrrolo[2,3-d]pyrimidine | Amine structure | Compound structure | MS (ESI) [M + H⁺]⁺ |
|---|---|---|---|---|
| P-1091 | | | 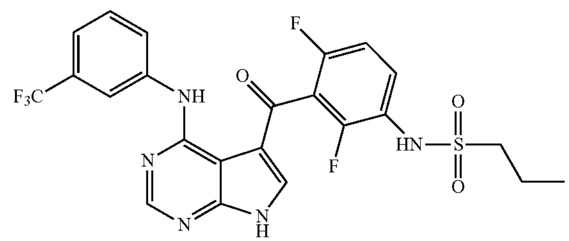 [SMILES: CCCS(=O)(=O)Nc1ccc(F)c(C(=O)c2c[nH]c3ncnc(Nc4cccc(C(F)(F)F)c4)c23)c1F] | 540.5 |
| P-1092 | | | 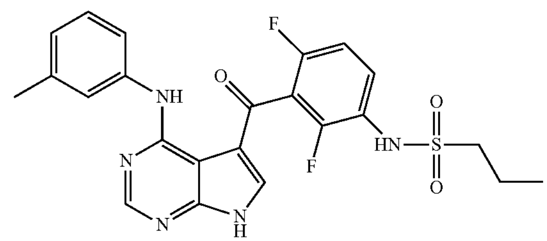 [SMILES: CCCS(=O)(=O)Nc1ccc(F)c(C(=O)c2c[nH]c3ncnc(Nc4cccc(C)c4)c23)c1F] | 486.5 |
| P-1093 | | | 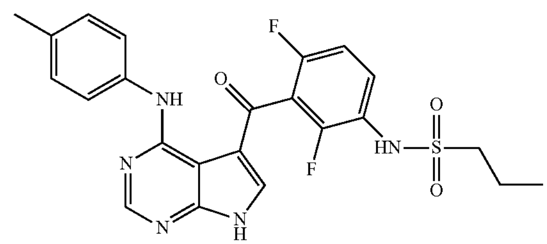 [SMILES: CCCS(=O)(=O)Nc1ccc(F)c(C(=O)c2c[nH]c3ncnc(Nc4ccc(C)cc4)c23)c1F] | 486.5 |
| P-1094 | | | 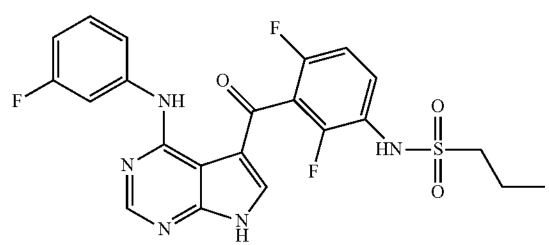 [SMILES: CCCS(=O)(=O)Nc1ccc(F)c(C(=O)c2c[nH]c3ncnc(Nc4cccc(F)c4)c23)c1F] | 490.5 |

| Comp. number | 7H-pyrrolo[2,3-d]pyrimidine | Amine structure | Compound structure | MS (ESI) [M + H⁺]⁺ |
|---|---|---|---|---|
| P-1095 | | | 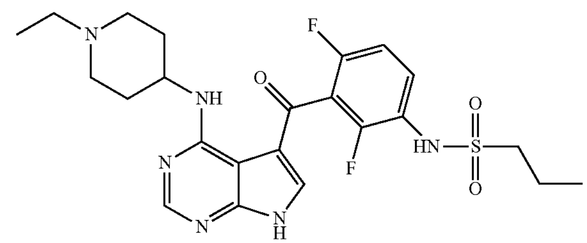 [SMILES: CCCS(=O)(=O)Nc1ccc(F)c(C(=O)c2c[nH]c3ncnc(NC4CCN(CC)CC4)c23)c1F] | 507.5 |
| P-1096 | | | 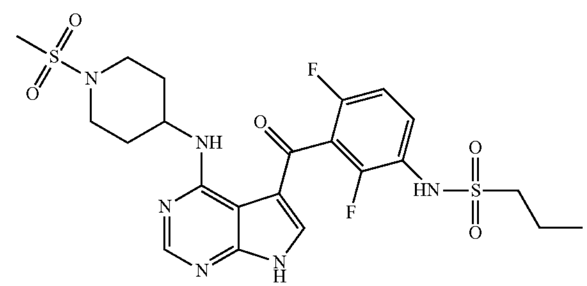 [SMILES: CCCS(=O)(=O)Nc1ccc(F)c(C(=O)c2c[nH]c3ncnc(NC4CCN(S(C)(=O)=O)CC4)c23)c1F] | 557.5 |
| P-1097 | | | 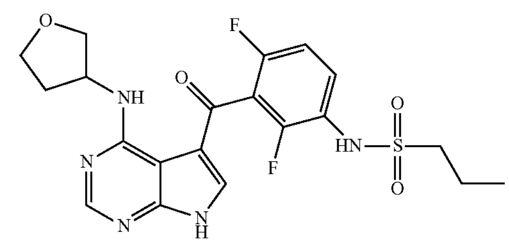 [SMILES: CCCS(=O)(=O)Nc1ccc(F)c(C(=O)c2c[nH]c3ncnc(NC4CCOC4)c23)c1F] | 466.5 |
| P-1098 | | | 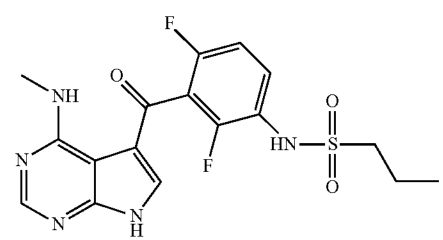 [SMILES: CCCS(=O)(=O)Nc1ccc(F)c(C(=O)c2c[nH]c3ncnc(NC)c23)c1F] | 410.0 |

-continued

| Comp. number | 7H-pyrrolo[2,3-d]pyrimidine | Amine structure | Compound structure | MS (ESI) [M + H⁺]⁺ |
|---|---|---|---|---|
| P-1099 | | | 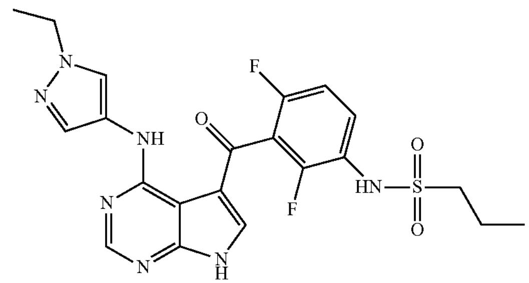 [SMILES: CCCS(=O)(=O)Nc1ccc(F)c(C(=O)c2c[nH]c3ncnc(Nc4cnn(CC)c4)c23)c1F] | 490.5 |
| P-1100 | | | 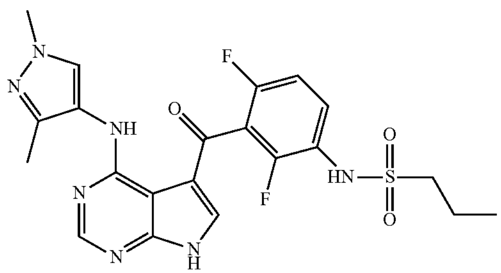 [SMILES: CCCS(=O)(=O)Nc1ccc(F)c(C(=O)c2c[nH]c3ncnc(Nc4cn(C)nc4C)c23)c1F] | 490.5 |
| P-1101 | | | 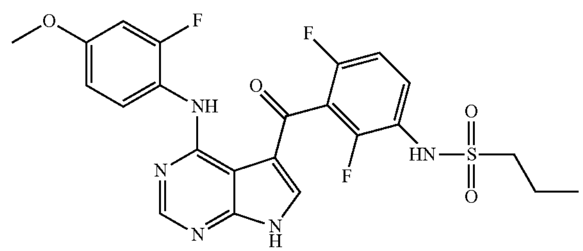 | 520.5 |

| Comp. number | 7H-pyrrolo[2,3-d]pyrimidine | Amine structure | Compound structure | MS (ESI) [M + H+]+ |
|---|---|---|---|---|
| P-1102 | | | 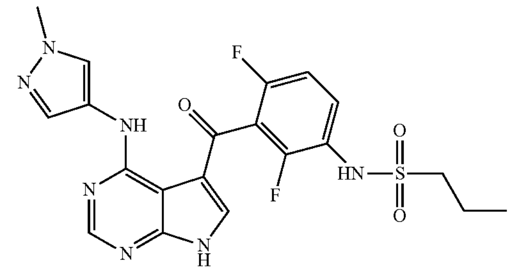 [SMILES: CCCS(=O)(=O)Nc1ccc(F)c(C(=O)c2c[nH]c3ncnc(Nc4cnn(C)c4)c23)c1F] | 476.0 |
| P-1103 | | | 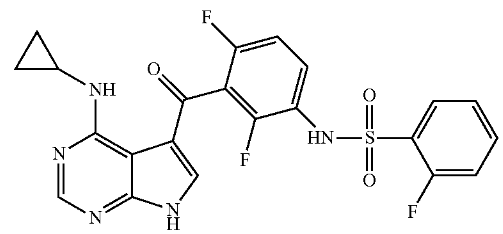 [SMILES: O=C(c1c(F)ccc(NS(=O)(=O)c2ccccc2F)c1F)c1c[nH]c2ncnc(NC3CC3)c12] | 488.0 |
| P-1105 | | | 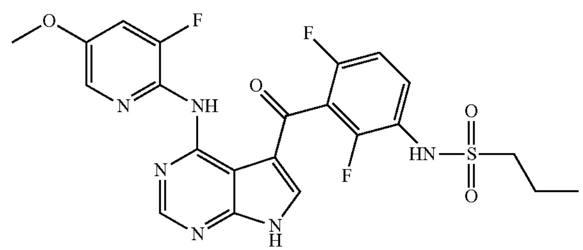 | 521.0 |
| P-1134 | | | 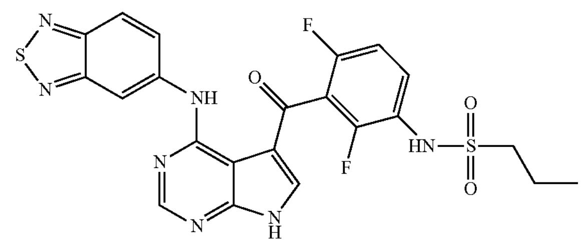 [SMILES: CCCS(=O)(=O)Nc1ccc(F)c(C(=O)c2c[nH]c3ncnc(Nc4ccc5nsnc5c4)c23)c1F] | 530.0 |

| Comp. number | 7H-pyrrolo[2,3-d]pyrimidine | Amine structure | Compound structure | MS (ESI) [M + H+]+ |
|---|---|---|---|---|
| P-1135 | | | 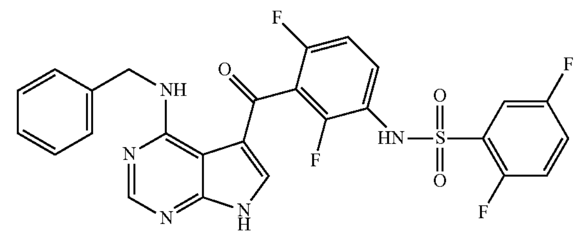 [SMILES: O=C(c1c(F)ccc(NS(=O)(=O)c2cc(F)ccc2F)c1F)c1c[nH]c2ncnc(NCc3ccccc3)c12] | 556.0 |
| P-1136 | | | 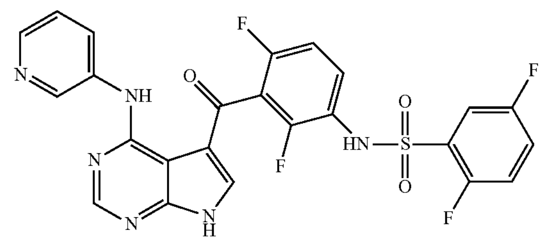 [SMILES: O=C(c1c(F)ccc(NS(=O)(=O)c2cc(F)ccc2F)c1F)c1c[nH]c2ncnc(Nc3cccnc3)c12] | 543.5 |
| P-1137 | | | 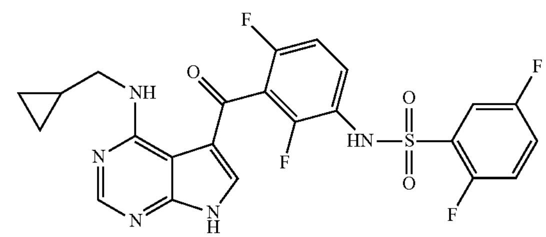 [SMILES: O=C(c1c(F)ccc(NS(=O)(=O)c2cc(F)ccc2F)c1F)c1c[nH]c2ncnc(NCC3CC3)c12] | 520.5 |
| P-1138 | | | 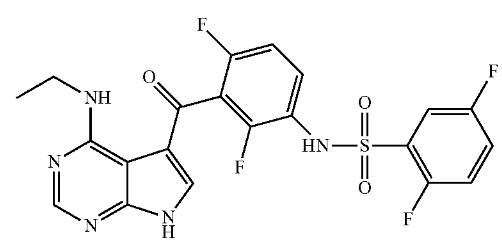 [SMILES: CCNc1ncnc2[nH]cc(C(=O)c3c(F)ccc(NS(=O)(=O)c4cc(F)ccc4F)c3F)c12] | 494.0 |

| Comp. number | 7H-pyrrolo[2,3-d]pyrimidine | Amine structure | Compound structure | MS (ESI) [M + H+]+ |
|---|---|---|---|---|
| P-1139 | | | 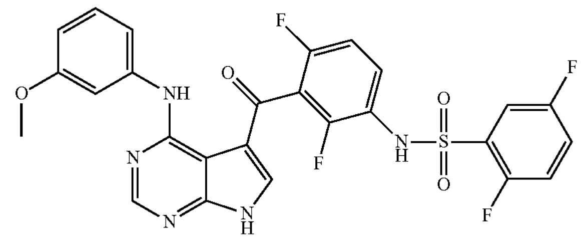 [SMILES: COc1cccc(Nc2ncnc3[nH]cc(C(=O)c4c(F)ccc(NS(=O)(=O)c5cc(F)ccc5F)c4F)c23)c1] | 572.0 |
| P-1140 | | | 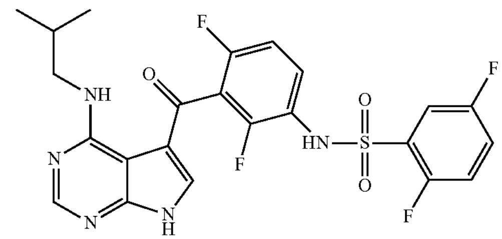 [SMILES: CC(C)CNc1ncnc2[nH]cc(C(=O)c3c(F)ccc(NS(=O)(=O)c4cc(F)ccc4F)c3F)c12] | 522.0 |
| P-1141 | | | 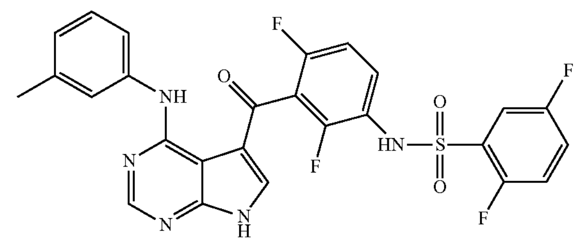 [SMILES: Cc1cccc(Nc2ncnc3[nH]cc(C(=O)c4c(F)ccc(NS(=O)(=O)c5cc(F)ccc5F)c4F)c23)c1] | 556.0 |
| P-1142 | | | 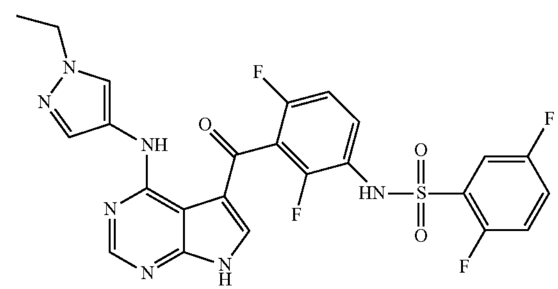 [SMILES: CCn1cc(Nc2ncnc3[nH]cc(C(=O)c4c(F)ccc(NS(=O)(=O)c5cc(F)ccc5F)c4F)c23)cn1] | 560.0 |

| Comp. number | 7H-pyrrolo[2,3-d]pyrimidine | Amine structure | Compound structure | MS (ESI) [M + H+]+ |
|---|---|---|---|---|
| P-1143 | | | 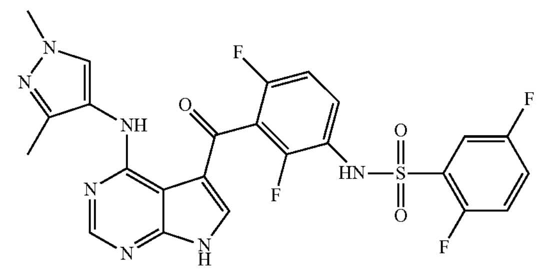 [SMILES: Cc1nn(C)cc1Nc1ncnc2[nH]cc(C(=O)c3c(F)ccc(NS(=O)(=O)c4cc(F)ccc4F)c3F)c12] | 560.0 |
| P-1144 | | | 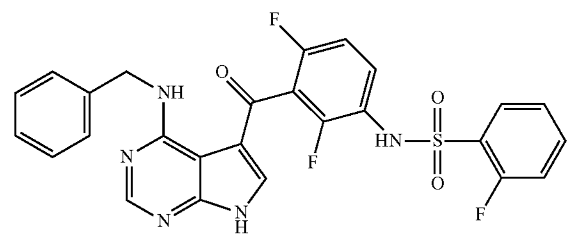 [SMILES: O=C(c1c(F)ccc(NS(=O)(=O)c2ccccc2F)c1F)c1c[nH]c2ncnc(NCc3ccccc3)c12] | 538.5 |
| P-1145 | | | 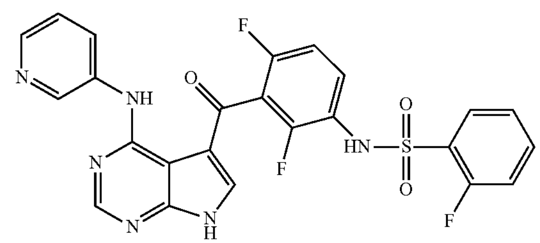 [SMILES: O=C(c1c(F)ccc(NS(=O)(=O)c2ccccc2F)c1F)c1c[nH]c2ncnc(Nc3cccnc3)c12] | 525.5 |
| P-1146 | | | 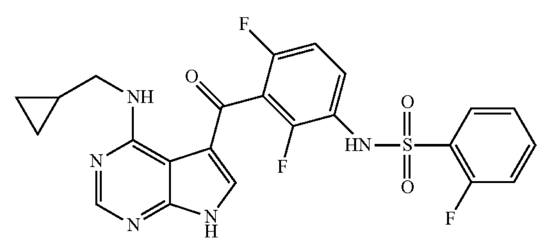 [SMILES: O=C(c1c(F)ccc(NS(=O)(=O)c2ccccc2F)c1F)c1c[nH]c2ncnc(NCC3CC3)c12] | 502.0 |

| Comp. number | 7H-pyrrolo[2,3-d]pyrimidine | Amine structure | Compound structure | MS (ESI) [M + H+]+ |
|---|---|---|---|---|
| P-1147 | | cyclopentylamine | 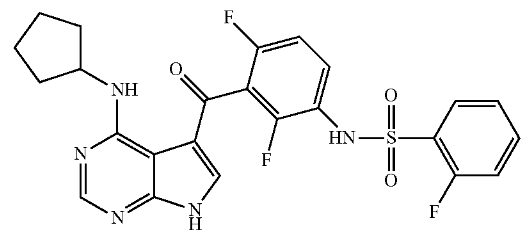 [SMILES: O=C(c1c(F)ccc(NS(=O)(=O)c2ccccc2F)c1F)c1c[nH]c2ncnc(NC3CCCC3)c12] | 516.5 |
| P-1148 | | ethylamine | 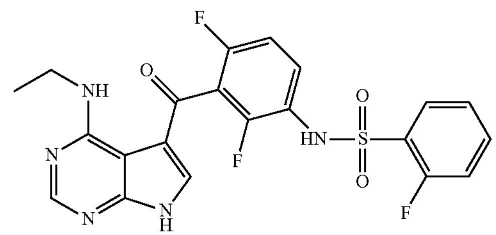 [SMILES: CCNc1ncnc2[nH]cc(C(=O)c3c(F)ccc(NS(=O)(=O)c4ccccc4F)c3F)c12] | 476.0 |
| P-1149 | | 3-methoxyaniline | 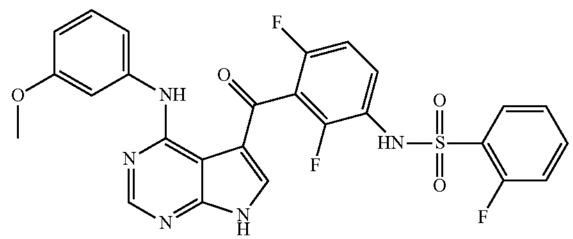 [SMILES: COc1cccc(Nc2ncnc3[nH]cc(C(=O)c4c(F)ccc(NS(=O)(=O)c5ccccc5F)c4F)c23)c1] | 554.0 |
| P-1150 | | 2-methoxyethylamine | 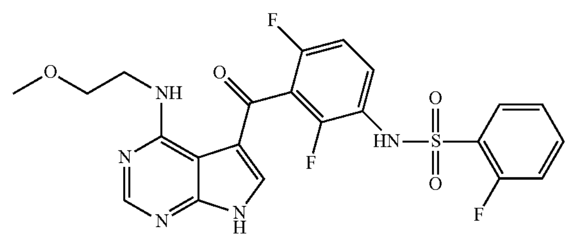 [SMILES: COCCNc1ncnc2[nH]cc(C(=O)c3c(F)ccc(NS(=O)(=O)c4ccccc4F)c3F)c12] | 506.0 |

| Comp. number | 7H-pyrrolo[2,3-d]pyrimidine | Amine structure | Compound structure | MS (ESI) [M + H+]+ |
|---|---|---|---|---|
| P-1151 | | | 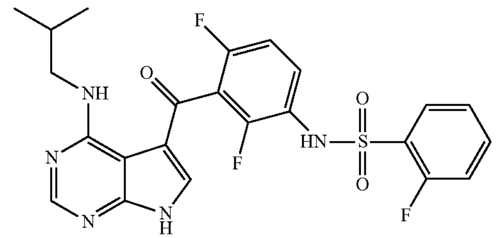 [SMILES: CC(C)CNc1ncnc2[nH]cc(C(=O)c3c(F)ccc(NS(=O)(=O)c4ccccc4F)c3F)c12] | 504.0 |
| P-1152 | | | 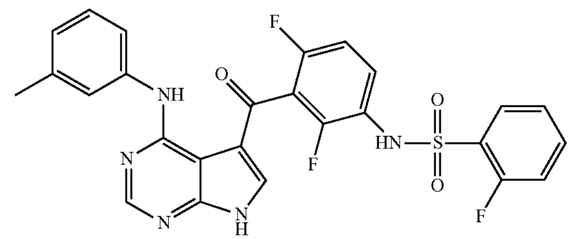 [SMILES: Cc1cccc(Nc2ncnc3[nH]cc(C(=O)c4c(F)ccc(NS(=O)(=O)c5ccccc5F)c4F)c23)c1] | 538.5 |
| P-1153 | | | 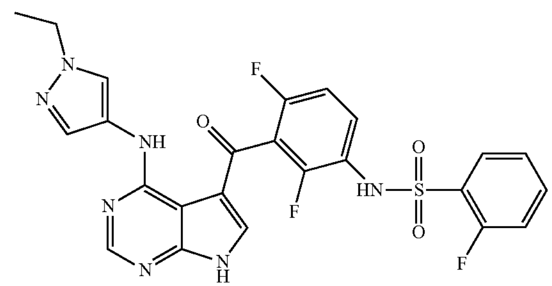 [SMILES: CCn1cc(Nc2ncnc3[nH]cc(C(=O)c4c(F)ccc(NS(=O)(=O)c5ccccc5F)c4F)c23)cn1] | 542.0 |
| P-1154 | | | 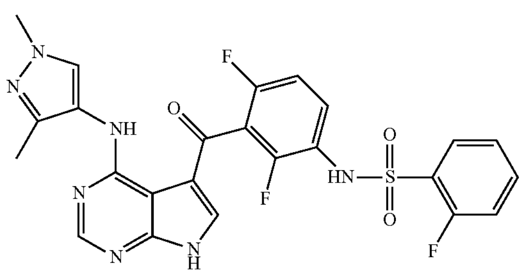 [SMILES: Cc1nn(C)cc1Nc1ncnc2[nH]cc(C(=O)c3c(F)ccc(NS(=O)(=O)c4ccccc4F)c3F)c12] | 542.0 |

| Comp. number | 7H-pyrrolo[2,3-d]pyrimidine | Amine structure | Compound structure | MS (ESI) [M + H+]+ |
|---|---|---|---|---|
| P-1157 | | | 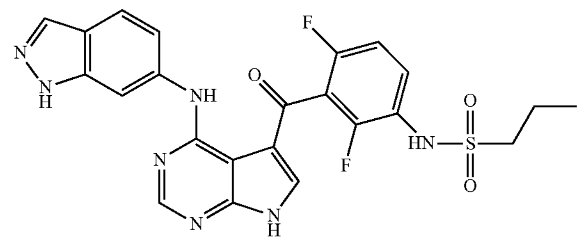 [SMILES: CCCS(=O)(=O)Nc1ccc(F)c(C(=O)c2c[nH]c3ncnc(Nc4ccc5cn[nH]c5c4)c23)c1F] | 512.0 |
| P-1158 | | | 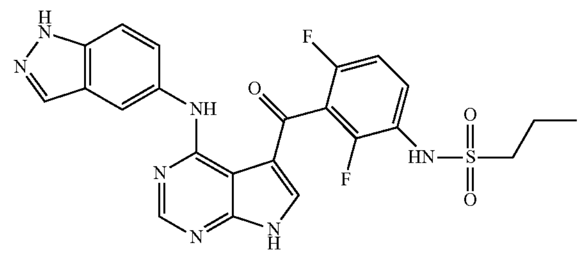 | 512.0 |
| P-1159 | | | 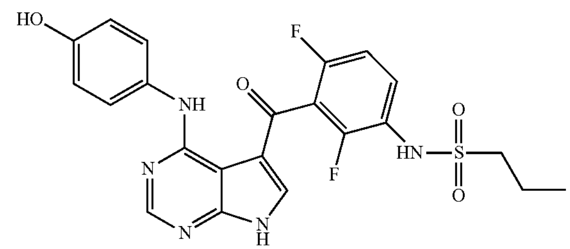 [SMILES: CCCS(=O)(=O)Nc1ccc(F)c(C(=O)c2c[nH]c3ncnc(Nc4ccc(O)cc4)c23)c1F] | 489.1 |
| P-1160 | | | 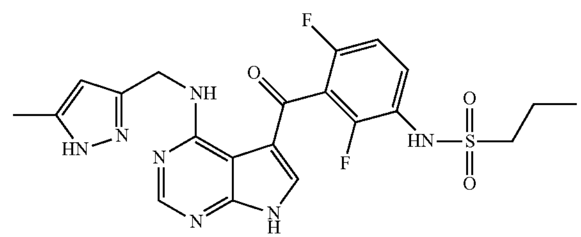 [SMILES: CCCS(=O)(=O)Nc1ccc(F)c(C(=O)c2c[nH]c3ncnc(NCc4cc(C)[nH]n4)c23)c1F] | 488.0 [M − H+]− |

| Comp. number | 7H-pyrrolo[2,3-d]pyrimidine | Amine structure | Compound structure | MS (ESI) [M + H+]+ |
|---|---|---|---|---|
| P-1161 | | | 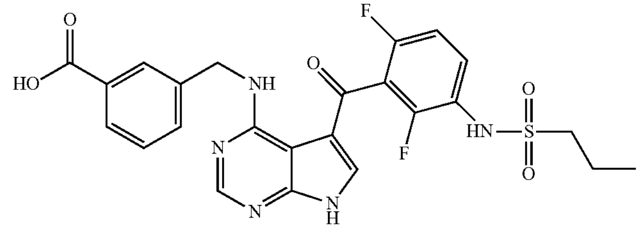 [SMILES: CCCS(=O)(=O)Nc1ccc(F)c(C(=O)c2c[nH]c3ncnc(NCc4cccc(C(=O)O)c4)c23)c1F] | 530.0 |
| P-1162 | | | 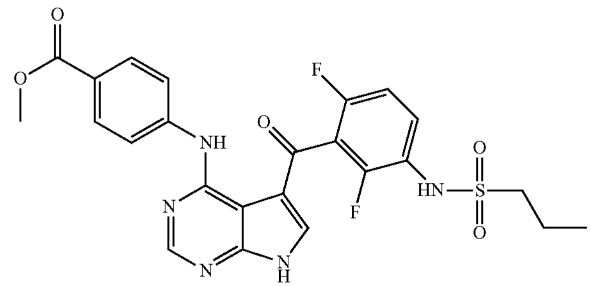 [SMILES: CCCS(=O)(=O)Nc1ccc(F)c(C(=O)c2c[nH]c3ncnc(Nc4ccc(C(=O)OC)cc4)c23)c1F] | 530.0 |
| P-1164 | | | 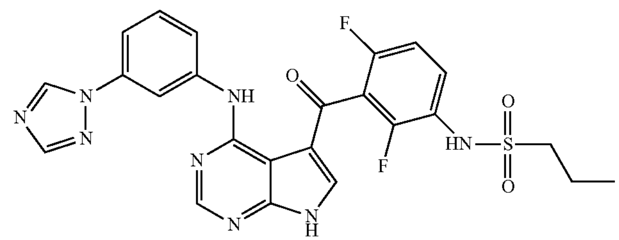 [SMILES: CCCS(=O)(=O)Nc1ccc(F)c(C(=O)c2c[nH]c3ncnc(Nc4cccc(-n5cncn5)c4)c23)c1F] | 539.5 |
| P-1165 | | | 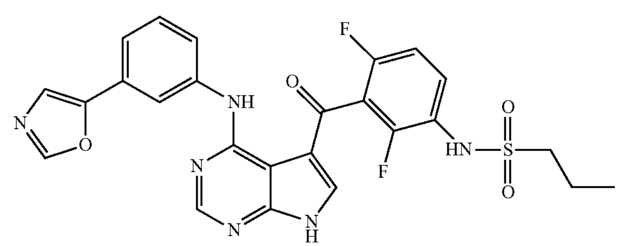 [SMILES: CCCS(=O)(=O)Nc1ccc(F)c(C(=O)c2c[nH]c3ncnc(Nc4cccc(-c5cnco5)c4)c23)c1F] | 539.5 |

-continued

| Comp. number | 7H-pyrrolo[2,3-d]pyrimidine | Amine structure | Compound structure | MS (ESI) [M + H⁺]⁺ |
|---|---|---|---|---|
| P-1166 | | | 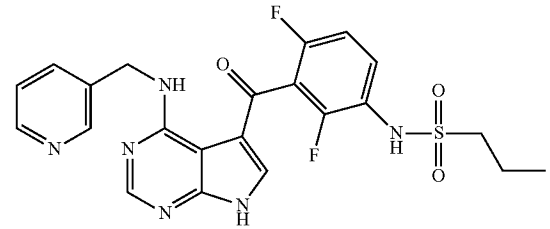 [SMILES: CCCS(=O)(=O)Nc1ccc(F)c(C(=O)c2c[nH]c3ncnc(NCc4cccnc4)c23)c1F] | 487.5 |
| P-1167 | | | 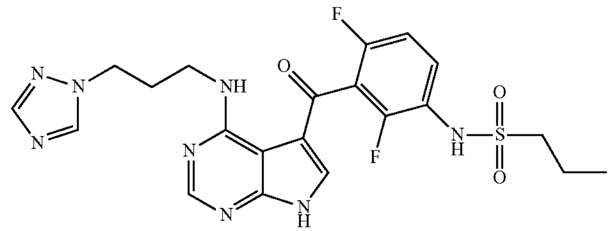 [SMILES: CCCS(=O)(=O)Nc1ccc(F)c(C(=O)c2c[nH]c3ncnc(NCCCn4cncn4)c23)c1F] | 505.0 |
| P-1168 | | | 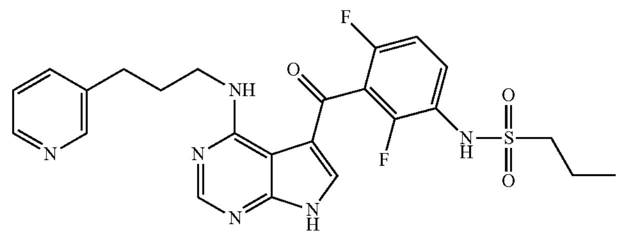 [SMILES: CCCS(=O)(=O)Nc1ccc(F)c(C(=O)c2c[nH]c3ncnc(NCCCc4cccnc4)c23)c1F] | 515.5 |
| P-1169 | | | 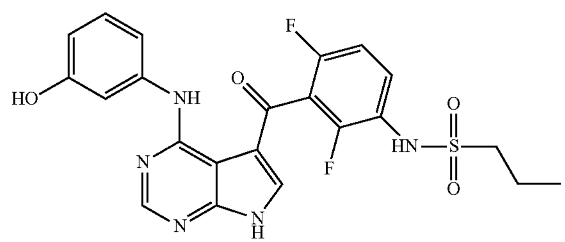 [SMILES: CCCS(=O)(=O)Nc1ccc(F)c(C(=O)c2c[nH]c3ncnc(Nc4cccc(O)c4)c23)c1F] | 488.0 |

| Comp. number | 7H-pyrrolo[2,3-d]pyrimidine | Amine structure | Compound structure | MS (ESI) [M + H+]+ |
|---|---|---|---|---|
| P-1170 | | | 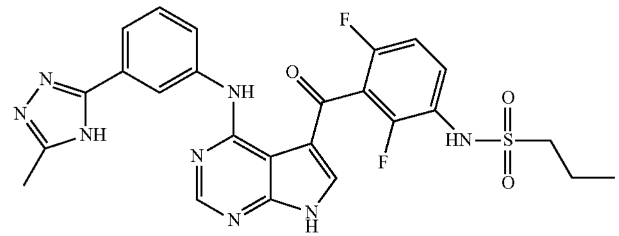 [SMILES: CCCS(=O)(=O)Nc1ccc(F)c(C(=O)c2c[nH]c3ncnc(Nc4cccc(-c5nnc(C)[nH]5)c4)c23)c1F] | 553.5 |
| P-1171 | | | 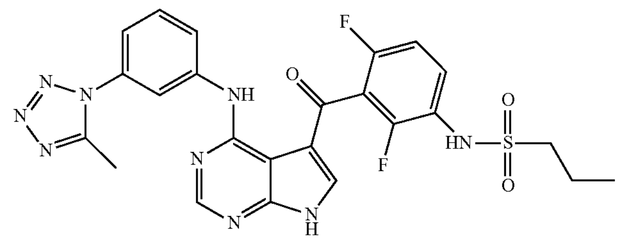 [SMILES: CCCS(=O)(=O)Nc1ccc(F)c(C(=O)c2c[nH]c3ncnc(Nc4cccc(-n5nnnc5C)c4)c23)c1F] | 554.0 |
| P-1172 | | | 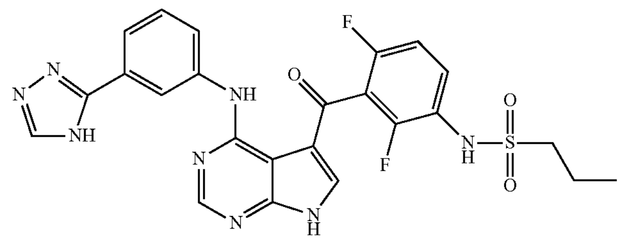 [SMILES: CCCS(=O)(=O)Nc1ccc(F)c(C(=O)c2c[nH]c3ncnc(Nc4cccc(-c5nnc[nH]5)c4)c23)c1F] | 539.5 |
| P-1173 | | | 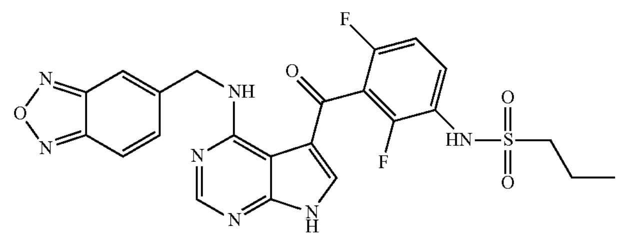 [SMILES: CCCS(=O)(=O)Nc1ccc(F)c(C(=O)c2c[nH]c3ncnc(NCc4ccc5nonc5c4)c23)c1F] | 528.0 |

| Comp. number | 7H-pyrrolo[2,3-d]pyrimidine | Amine structure | Compound structure | MS (ESI) [M + H+]+ |
|---|---|---|---|---|
| P-1174 | | | 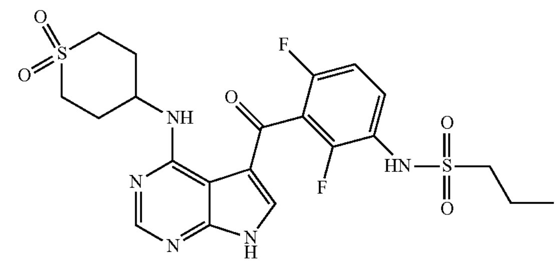 [SMILES: CCCS(=O)(=O)Nc1ccc(F)c(C(=O)c2c[nH]c3ncnc(NC4CCS(=O)(=O)CC4)c23)c1F] | 528.0 |
| P-1175 | | | 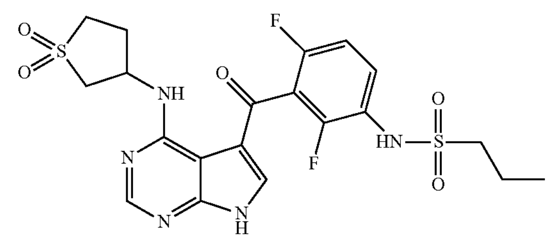 [SMILES: CCCS(=O)(=O)Nc1ccc(F)c(C(=O)c2c[nH]c3ncnc(NC4CCS(=O)(=O)C4)c23)c1F] | 514.5 |
| P-1176 | | | 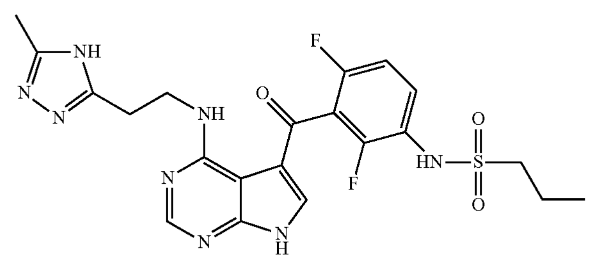 [SMILES: CCCS(=O)(=O)Nc1ccc(F)c(C(=O)c2c[nH]c3ncnc(NCCc4nnc(C)[nH]4)c23)c1F] | 505.0 |
| P-1177 | | | 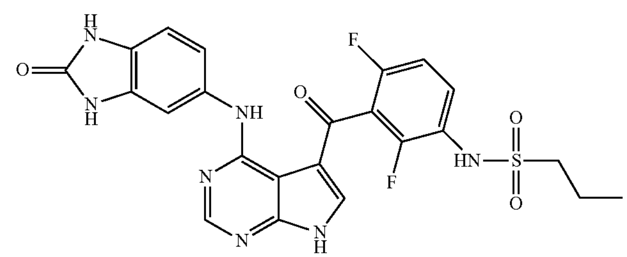 [SMILES: CCCS(=O)(=O)Nc1ccc(F)c(C(=O)c2c[nH]c3ncnc(Nc4ccc5[nH]c(=O)[nH]c5c4)c23)c1F] | 528.0 |

-continued

| Comp. number | 7H-pyrrolo[2,3-d]pyrimidine | Amine structure | Compound structure | MS (ESI) [M + H⁺]⁺ |
|---|---|---|---|---|
| P-1178 | | | 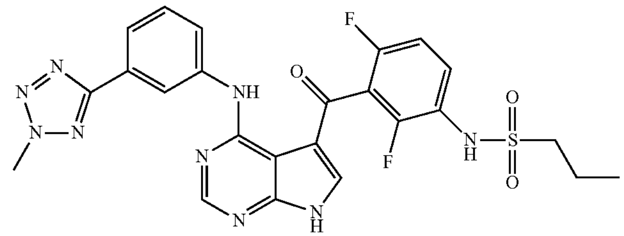 [SMILES: CCCS(=O)(=O)Nc1ccc(F)c(C(=O)c2c[nH]c3ncnc(Nc4cccc(-c5nnn(C)n5)c4)c23)c1F] | 554.0 |
| P-1179 | | | 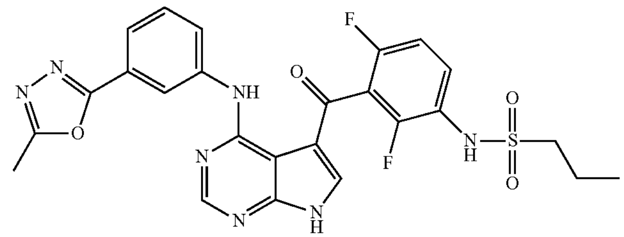 [SMILES: CCCS(=O)(=O)Nc1ccc(F)c(C(=O)c2c[nH]c3ncnc(Nc4cccc(-c5nnc(C)o5)c4)c23)c1F] | 554.0 |
| P-1180 | | | 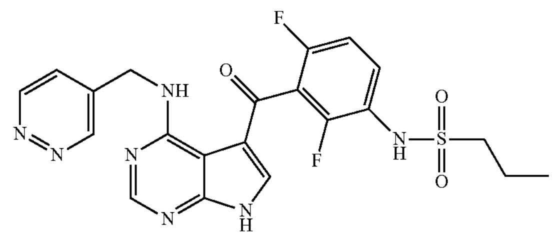 [SMILES: CCCS(=O)(=O)Nc1ccc(F)c(C(=O)c2c[nH]c3ncnc(NCc4ccnnc4)c23)c1F] | 488.0 |
| P-2018* | | | 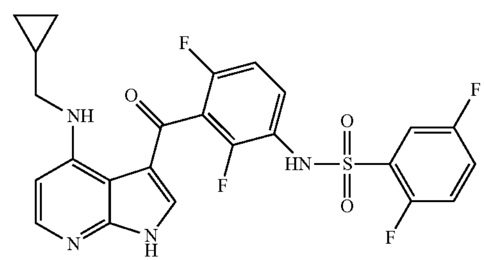 [SMILES: O=C(c1c(F)ccc(NS(=O)(=O)c2cc(F)ccc2F)c1F)c1c[nH]c2nccc(NCC3CC3)c12] | |

| Comp. number | 7H-pyrrolo[2,3-d]pyrimidine | Amine structure | Compound structure | MS (ESI) [M + H+]+ |
|---|---|---|---|---|
| P-2019 | | | 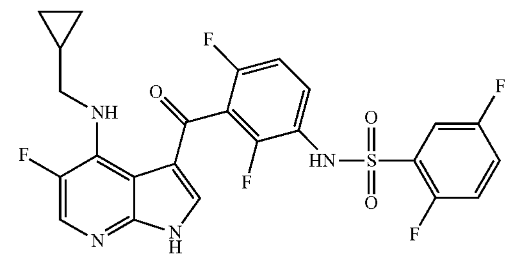 [SMILES: O=C(c1c(F)ccc(NS(=O)(=O)c2cc(F)ccc2F)c1F)c1c[nH]c2ncc(F)c(NCC3CC3)c12] | 535.1 [M − H+]− |
| P-2020 | | | 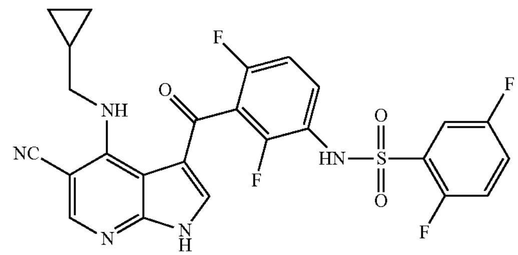 [SMILES: N#Cc1cnc2[nH]cc(C(=O)c3c(F)ccc(NS(=O)(=O)c4cc(F)ccc4F)c3F)c2c1NCC1CC1] | 544.0 [M − H+]− |
| P-2021 | | | 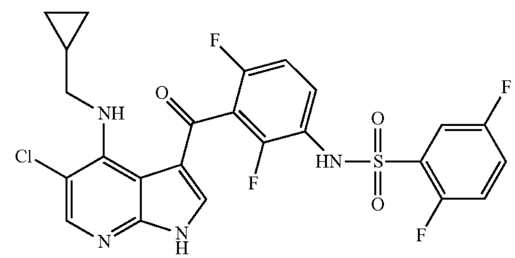 [SMILES: O=C(c1c(F)ccc(NS(=O)(=O)c2cc(F)ccc2F)c1F)c1c[nH]c2ncc(Cl)c(NCC3CC3)c12] | |
| P-2022* | | | 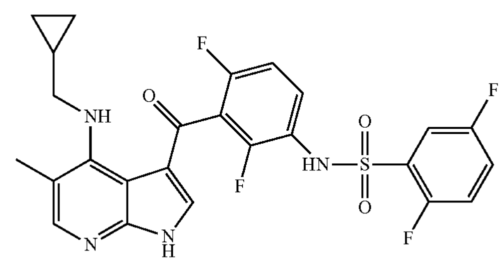 [SMILES: Cc1cnc2[nH]cc(C(=O)c3c(F)ccc(NS(=O)(=O)c4cc(F)ccc4F)c3F)c2c1NCC1CC1] | |

-continued

| Comp. number | 7H-pyrrolo[2,3-d]pyrimidine | Amine structure | Compound structure | MS (ESI) [M + H+]+ |
|---|---|---|---|---|
| P-2023* | (structure shown) | (cyclopropylmethylamine) | (structure shown) | |
| P-2024* | (structure shown) | (cyclopropylmethylamine) | (structure shown) | |

* Palladium catalyst was used to facilitated the coupling reaction.

4-{5-[2,6-Difluoro-3-(propane-1-sulfonylamino)-benzoyl]-7H-pyrrolo[2,3-d]pyrimidin-4-ylamino}-benzoic acid P-1163 is prepared from 4-{5-[2,6-Difluoro-3-(propane-1-sulfonylamino)-benzoyl]-7H-pyrrolo[2,3-d]pyrimidin-4-ylamino}-benzoic acid methyl ester P-1162 by the following Step 2.

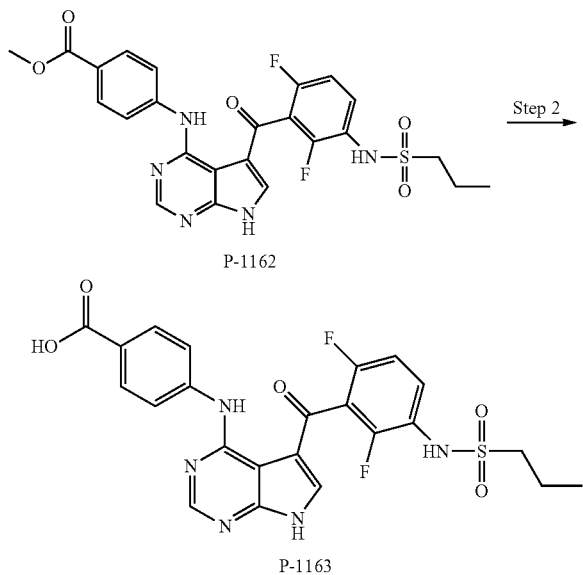

Step 2—Preparation of 4-{5-[2,6-difluoro-3-(propane-1-sulfonylamino)-benzoyl]-7H-pyrrolo[2,3-d]pyrimidin-4-ylamino}-benzoic acid (P-1163)

4-{5-[2,6-Difluoro-3-(propane-1-sulfonylamino)-benzoyl]-7H-pyrrolo[2,3-d]pyrimidin-4-ylamino}-benzoic acid methyl ester (P-1162, 26 mg, 0.05 mmol) is combined with 1 mL of methanol is added, 0.5 mL of tetrahydrofuran, and 0.5 mL of 2 M sodium hydroxide. The reaction is stirred at room temperature for 48 hours, then neutralized with 1 M hydrochloric acid and the volatile solvents are removed under vacuum. The remaining aqueous suspension is filtered to collect the solids, which are dried under vacuum to provide the desired compound (P-1163, 25 mg). MS (ESI) $[M+H^+]^+=516.0$.

Example 9

Compound Properties

While the inhibitory activity of the compounds on any Raf kinase is important to their activity in treating of disease, the compounds described herein show favorable properties that provide advantages as a pharmaceutical as well. In addition to demonstrating kinase inhibitory activity against any or all of B-Raf, c-Raf-1 and B-Raf V600E in both biochemical and cell based assays, compounds may show favorable solubility, favorable pharmacokinetic properties, and low Cyp inhibition. The compounds are assessed in the following assays or similar assays available to one skilled in the art.

Assays for biochemical and cell based activity are known in the art, for example, as described in PCT publication WO 2007/002433, the disclosure of which is hereby incorporated by reference as it relates to such assays. For example, the biochemical activity $IC_{50}$ values are determined with respect to inhibition of B-Raf kinase activity, c-Raf-1 kinase activity, or B-Raf V600E kinase activity, where inhibition of phosphorylation of a peptide substrate is measured as a function of compound concentration. Compounds to be tested are diluted in dimethyl sulfoxide to a concentration of 0.1 mM. These are serially diluted 15 μL into 30 μL of dimethyl sulfoxide seven times in 96 well plates for a total of 8 dilution points, and for each dilution point 1 μL is added to a well of an assay plate. Plates are prepared such that each well in a 384 well plate contains 1 μL of compound in 10 μL volume with 0.1 ng Raf enzyme (i.e. any of B-Raf, c-Raf-1 or B-Raf V600E, Upstate Biotechnology or prepared by methods known to one of skill in the art), 50 mM HEPES, pH 7.0, 50 mM NaCl, 2 mM $MgCl_2$, 1 mM $MnCl_2$, 0.01% Tween-20, 1 mM DTT, and 100 nM biotin-MEK1 as substrate. The reaction is started with addition of 10 μL of 200 μM ATP (i.e. final 100 μM ATP). After incubation of the kinase reaction for 45 minutes at room temperature, 5 μL/well of Stop Solution is added (25 mM Hepes pH 7.5, 100 mM EDTA, 0.01% BSA with donor beads (Streptavidin coated beads, Perkin Elmer), acceptor beads (Protein A coated, Perkin Elmer), and anti phosphor MEK1/2 antibody (CellSignal), each at final concentration 10 μg/mL). The plates are incubated for 3 hours at room temperature and read on Envision reader (Perkin Elmer). Phosphorylation of Mek1 results in binding of the anti-phosphor-MEK1/2 antibody and association of the donor and acceptor beads such that signal correlates with kinase activity. The signal vs. compound concentration is used to determine the $IC_{50}$.

Compounds are assessed in a variety of cell based assays. For example human cell lines with B-Raf V600E mutation (A375 melanoma, SKMEL3 melanoma, and COLO205 colon adenocarcinoma), as well as tumorigenic cell lines with wild-type B-RAF (SW620 colon adenocarcinoma) or with Ras mutations (SKMEL2 melanoma and IPC298 melanoma) are used in such assays. Similar assays may be used to assess additional tumorigenic cell lines with Ras mutations, including, but not limited to, M202, M207, M243, M244, M296, 5117, HCT116, HCT15, DLD1, MiaPaCa, A549, NCI-H23, NCI-H460, HOP62, MDA-MB231, Hs-578T, HL60, MOLT-4, and CCRF-CEM.

On day 1, cells are counted, then centrifuged in a conical tube for 5 minutes at 1000 rpm. The supernatant is removed and cells are re-suspended as follows:

SW620 (ATCC catalog #CCL-27): resuspend in Leibovitz's L-15 medium, 2 mM L-glutamine, 10% fetal bovine serum to $6×10^4$ cells/mL.

A375 (ATCC catalog #CRL-1619): resuspend in Dulbecco's modified Eagle's medium, 4 mM L-glutamine, 4.5 g/L D-glucose, 10% fetal bovine serum to $6×10^4$ cells/mL.

COLO205 (ATCC catalog #CCL-222): resuspend in RPMI 1640, 2 mM L-glutamine, 1.5 g/L sodium bicarbonate, 4.5 g/L D-glucose, 10 mM HEPES, 1.0 mM sodium pyruvate, 10% fetal bovine serum to $6×10^4$ cells/mL.

SKMEL2 (ATCC catalog #HTB-68): resuspend in Minimum Eagle essential medium, 2 mM L-glutamine, 1.5 g/L sodium bicarbonate, 0.1 mM non-essential amino acids, 1.0 mM sodium pyruvate, 10% fetal bovine serum to $6×10^4$ cells/mL.

SKMEL3 (ATCC catalog #HTB-69): resuspend in McCoy's 5A medium, 1.5 mM L-glutamine, 15% fetal bovine serum to $6×10^4$ cells/mL.

IPC298 (DSMZ catalog #ACC 251): resuspend in RPMI 1640, 2 mM L-glutamine, 10% fetal bovine serum to $6×10^4$ cells/mL.

The cells are plated, 50 μL in each well of a 96-well dish (Corning 3610) and incubated at 37° C. in 5% CO₂ overnight, cells plated to a final concentration of cells as follows:

SW620: 5,000 cells per well.
A375: 2,000 cells per well.
COLO205: 2,000 cells per well.
SKMEL2: 2,000 cells per well.
SKMEL3: 3,000 cells per well.
IPC298: 2,000 cells per well.

On day 2, compound at a maximum concentration of 5 mM is serially diluted 1:3 for a total of 8 point titration with DMSO as a control. A 1 μL aliquot of each dilution point and control is added to 249 μL growth media and 50 μL is added to a well containing cells, providing 10 μL compound at the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added 25 μL to each well, shake for 2 minutes, and the cells are incubated at room temperature for 10 minutes, then luminescence is read on Safire reader. The measured luminescence correlates directly with cell number, such that the reading as a function of compound concentration is used to determine the $IC_{50}$ value.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. Results for compounds that are tested and show substantially no inhibition below the highest tested concentration are represented as "-" in the tables below. In some instances, the compounds were not tested in all of the assays, or assay results were not valid, as indicated by NA in the tables below.

The following table provides data indicating the B-Raf, B-Raf V600E and c-Raf-1 biochemical inhibitory activity and corresponding activity ratios for exemplary compounds as described herein:

| Compound number | Biochemical activity ($IC_{50}$ μM) | | | Biochemical activity ratio | | |
|---|---|---|---|---|---|---|
| | B-Raf | V600E | c-Raf-1 | B/C | V600E/C | B/V600E |
| P-1001 | <0.1 | >0.1 | <0.1 | 0.1-10 | >10 | 0.1-10 |
| P-1002 | >0.1 | <0.1 | <0.1 | >10 | 0.1-10 | 0.1-10 |
| P-1003 | >0.1 | <0.1 | <0.1 | >10 | 0.1-10 | >10 |
| P-1004 | >0.1 | <0.1 | <0.1 | >10 | 0.1-10 | >10 |
| P-1005 | >0.1 | >0.1 | <0.1 | 0.1-10 | >10 | 0.1-10 |
| P-1006 | >0.1 | >0.1 | <0.1 | 0.1-10 | >10 | 0.1-10 |
| P-1007 | <0.1 | >0.1 | <0.1 | 0.1-10 | >10 | 0.1-10 |
| P-1008 | >0.1 | >0.1 | >0.1 | 0.1-10 | 0.1-10 | 0.1-10 |
| P-1009 | >0.1 | >0.1 | <0.1 | >10 | >10 | 0.1-10 |
| P-1010 | >0.1 | >0.1 | >0.1 | 0.1-10 | >10 | 0.1-10 |
| P-1011 | <0.1 | >0.1 | <0.1 | >10 | >10 | 0.1-10 |
| P-1012 | >0.1 | >0.1 | <0.1 | 0.1-10 | >10 | 0.1-10 |
| P-1013 | <0.1 | >0.1 | <0.1 | >10 | >10 | 0.1-10 |
| P-1014 | >0.1 | >0.1 | <0.1 | >10 | 0.1-10 | 0.1-10 |
| P-1015 | >0.1 | >0.1 | <0.1 | >10 | >10 | 0.1-10 |
| P-1016 | >0.1 | >0.1 | <0.1 | >10 | >10 | 0.1-10 |
| P-1017 | >0.1 | >0.1 | >0.1 | 0.1-10 | >10 | 0.1-10 |
| P-1018 | >0.1 | >0.1 | <0.1 | >10 | 0.1-10 | >10 |
| P-1019 | >0.1 | >0.1 | >0.1 | 0.1-10 | 0.1-10 | 0.1-10 |
| P-1020 | >0.1 | >0.1 | <0.1 | >10 | >10 | 0.1-10 |
| P-1021 | >0.1 | >0.1 | <0.1 | >10 | >10 | 0.1-10 |
| P-1022 | >0.1 | >0.1 | <0.1 | 0.1-10 | 0.1-10 | 0.1-10 |
| P-1023 | >0.1 | >0.1 | >0.1 | 0.1-10 | >10 | 0.1-10 |
| P-1024 | <0.1 | >0.1 | <0.1 | >10 | >10 | 0.1-10 |
| P-1025 | >0.1 | >0.1 | <0.1 | >10 | 0.1-10 | 0.1-10 |
| P-1026 | >0.1 | >0.1 | <0.1 | >10 | >10 | 0.1-10 |
| P-1027 | >0.1 | >0.1 | <0.1 | >10 | 0.1-10 | 0.1-10 |
| P-1028 | >0.1 | >0.1 | <0.1 | >10 | >10 | 0.1-10 |
| P-1029 | <0.1 | >0.1 | <0.1 | >10 | >10 | 0.1-10 |
| P-1030 | >0.1 | >0.1 | <0.1 | 0.1-10 | >10 | <0.1 |
| P-1031 | >0.1 | >0.1 | <0.1 | >10 | >10 | 0.1-10 |
| P-1032 | <0.1 | >0.1 | <0.1 | >10 | >10 | 0.1-10 |
| P-1033 | <0.1 | >0.1 | <0.1 | >10 | 0.1-10 | 0.1-10 |
| P-1034 | >0.1 | >0.1 | <0.1 | 0.1-10 | >10 | 0.1-10 |
| P-1035 | <0.1 | <0.1 | <0.1 | >10 | >10 | 0.1-10 |
| P-1036 | >0.1 | >0.1 | <0.1 | >10 | 0.1-10 | >10 |
| P-1037 | <0.1 | >0.1 | <0.1 | >10 | >10 | 0.1-10 |
| P-1038 | <0.1 | >0.1 | <0.1 | >10 | >10 | 0.1-10 |
| P-1039 | <0.1 | >0.1 | <0.1 | >10 | >10 | 0.1-10 |
| P-1040 | <0.1 | >0.1 | <0.1 | 0.1-10 | >10 | 0.1-10 |
| P-1041 | <0.1 | <0.1 | <0.1 | 0.1-10 | 0.1-10 | 0.1-10 |
| P-1042 | <0.1 | >0.1 | <0.1 | 0.1-10 | >10 | 0.1-10 |
| P-1043 | >0.1 | >0.1 | <0.1 | >10 | >10 | 0.1-10 |
| P-1044 | >0.1 | >0.1 | <0.1 | >10 | >10 | 0.1-10 |
| P-1045 | >0.1 | >0.1 | <0.1 | >10 | 0.1-10 | 0.1-10 |
| P-1046 | <0.1 | >0.1 | <0.1 | >10 | >10 | 0.1-10 |
| P-1047 | <0.1 | >0.1 | <0.1 | >10 | >10 | 0.1-10 |
| P-1048 | <0.1 | >0.1 | <0.1 | >10 | >10 | 0.1-10 |
| P-1049 | >0.1 | >0.1 | <0.1 | >10 | >10 | 0.1-10 |
| P-1050 | <0.1 | >0.1 | <0.1 | >10 | >10 | 0.1-10 |
| P-1051 | <0.1 | <0.1 | <0.1 | >10 | 0.1-10 | 0.1-10 |
| P-1052 | <0.1 | <0.1 | <0.1 | >10 | >10 | 0.1-10 |
| P-1053 | <0.1 | >0.1 | <0.1 | 0.1-10 | >10 | 0.1-10 |
| P-1054 | <0.1 | >0.1 | <0.1 | 0.1-10 | >10 | 0.1-10 |
| P-1055 | <0.1 | >0.1 | <0.1 | 0.1-10 | >10 | 0.1-10 |
| P-1056 | <0.1 | >0.1 | <0.1 | >10 | >10 | 0.1-10 |
| P-1057 | <0.1 | >0.1 | <0.1 | >10 | >10 | 0.1-10 |
| P-1058 | <0.1 | >0.1 | <0.1 | 0.1-10 | >10 | 0.1-10 |
| P-1059 | >0.1 | >0.1 | <0.1 | 0.1-10 | >10 | 0.1-10 |
| P-1060 | <0.1 | <0.1 | <0.1 | >10 | 0.1-10 | 0.1-10 |
| P-1061 | >0.1 | >0.1 | >0.1 | 0.1-10 | >10 | 0.1-10 |
| P-1062 | <0.1 | >0.1 | <0.1 | >10 | >10 | 0.1-10 |
| P-1063 | <0.1 | >0.1 | <0.1 | >10 | >10 | 0.1-10 |
| P-2001 | <0.1 | >0.1 | <0.1 | 0.1-10 | 0.1-10 | 0.1-10 |
| P-2002 | <0.1 | <0.1 | <0.1 | 0.1-10 | 0.1-10 | 0.1-10 |
| P-2003 | <0.1 | <0.1 | <0.1 | 0.1-10 | 0.1-10 | 0.1-10 |
| P-2004 | <0.1 | <0.1 | <0.1 | >10 | 0.1-10 | 0.1-10 |
| P-2005 | <0.1 | >0.1 | <0.1 | 0.1-10 | 0.1-10 | 0.1-10 |
| P-2006 | <0.1 | <0.1 | <0.1 | >10 | 0.1-10 | 0.1-10 |
| P-2007 | <0.1 | <0.1 | <0.1 | 0.1-10 | 0.1-10 | 0.1-10 |
| P-2008 | <0.1 | <0.1 | <0.1 | 0.1-10 | 0.1-10 | 0.1-10 |
| P-2009 | <0.1 | <0.1 | <0.1 | >10 | >10 | 0.1-10 |
| P-2010 | <0.1 | <0.1 | <0.1 | >10 | >10 | 0.1-10 |
| P-2011 | <0.1 | >0.1 | <0.1 | 0.1-10 | >10 | 0.1-10 |
| P-2012 | >0.1 | <0.1 | <0.1 | >10 | 0.1-10 | 0.1-10 |
| P-2013 | >0.1 | <0.1 | <0.1 | >10 | 0.1-10 | 0.1-10 |
| P-2014 | >0.1 | <0.1 | <0.1 | 0.1-10 | >10 | 0.1-10 |
| P-2015 | >0.1 | >0.1 | <0.1 | >10 | 0.1-10 | >10 |
| P-2016 | >0.1 | >0.1 | <0.1 | 0.1-10 | >10 | 0.1-10 |
| P-2017 | >0.1 | >0.1 | <0.1 | >10 | >10 | 0.1-10 |

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 μL of appropriate buffer is added to each well, and 1 μL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535, and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3 μM, moderate solubility if the threshold concentration is 31.3 μM to 250 μM, and high solubility if the threshold concentration is >250 μm.

The following table indicates the relative solubility (L=low, M=moderate, H=high) based on turbidity threshold concentration at each pH for exemplary compounds according to the invention as indicated:

| Compound number | turbidity threshold (L, M, H) | | | |
|---|---|---|---|---|
| | 1.4 | 4.5 | 6.8 | 7.4 |
| P-1001 | H | M | M | M |
| P-1002 | H | H | H | H |
| P-1003 | H | M | M | M |
| P-1004 | H | H | H | H |
| P-1005 | H | L | L | L |
| P-1006 | L | L | L | H |
| P-1007 | L | L | L | L |
| P-1008 | M | M | L | M |
| P-1009 | H | L | L | M |
| P-1010 | L | L | L | M |
| P-1011 | M | L | L | L |
| P-1012 | M | M | H | H |
| P-1013 | L | L | L | M |
| P-1014 | M | | M | M |
| P-1016 | L | | L | H |
| P-1020 | H | | | H |
| P-1024 | M | L | L | L |
| P-1025 | M | L | M | |
| P-1026 | | | M | M |
| P-1027 | | L | M | |
| P-1028 | M | L | L | M |
| P-1029 | M | | | M |
| P-1030 | | M | | M |
| P-1031 | M | M | M | M |
| P-1032 | L | L | | |
| P-1033 | H | H | H | H |
| P-1034 | M | M | M | M |
| P-1035 | L | L | L | L |
| P-1037 | L | L | L | L |
| P-1039 | M | M | M | M |
| P-1040 | M | L | L | L |
| P-1041 | H | M | M | M |
| P-1042 | M | L | L | L |
| P-1043 | H | M | M | M |
| P-1044 | M | M | M | M |
| P-1045 | M | L | L | L |
| P-1046 | M | L | L | L |
| P-1047 | M | L | L | L |
| P-1048 | M | M | M | M |
| P-1049 | M | M | M | M |
| P-1050 | H | M | M | M |
| P-1051 | H | M | M | M |
| P-1052 | L | L | L | L |
| P-1053 | L | L | L | L |
| P-1054 | M | L | L | L |
| P-1055 | L | L | L | L |
| P-1056 | M | L | L | L |
| P-1057 | H | H | M | M |
| P-1058 | M | L | L | L |
| P-1059 | H | M | M | M |
| P-1060 | H | M | H | H |
| P-1061 | H | M | M | H |
| P-1062 | L | L | L | L |
| P-1063 | L | L | L | L |
| P-1073 | M | L | L | L |
| P-1076 | H | H | H | H |
| P-1077 | H | L | L | L |
| P-1078 | M | L | L | L |
| P-1079 | M | L | L | L |
| P-1081 | H | L | L | L |
| P-1084 | M | M | M | M |
| P-1085 | L | L | L | L |
| P-1087 | M | L | M | M |
| P-1088 | M | L | L | L |
| P-1094 | L | L | M | L |
| P-1095 | H | H | H | H |
| P-1099 | M | L | M | M |
| P-1100 | M | M | L | L |
| P-1101 | L | L | L | L |
| P-1103 | M | L | L | M |
| P-1104 | H | M | M | M |
| P-1107 | M | L | M | M |
| P-1143 | L | L | L | L |
| P-1154 | L | L | L | L |
| P-2001 | M | M | M | M |
| P-2002 | M | M | M | M |
| P-2003 | M | M | M | M |
| P-2004 | L | L | L | L |
| P-2005 | M | L | L | M |
| P-2006 | M | M | M | M |
| P-2007 | M | M | M | M |
| P-2008 | L | M | L | M |
| P-2009 | L | M | M | M |
| P-2010 | L | L | L | M |
| P-2011 | L | L | L | L |
| P-2013 | H | H | H | H |
| P-2014 | L | L | L | L |
| P-2015 | M | M | M | M |
| P-2016 | L | L | L | M |
| P-2017 | L | L | L | M |

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for compounds, where inhibition of metabolism of a known substrate leads to a decrease in the fluorescence of the metabolized product. The fluorescence of the product is monitored as a function of compound concentration.

Compounds are dissolved in dimethyl sulfoxide to a concentration of 100 mM. These are diluted 1 μL into 82 μL of acetonitrile. An 11 μL aliquot of this solution is then added to 204 μL of cofactor mix (1.3% NADPH Regeneration system Solution A, 1.04% NADPH Regeneration system Solution B from BD Biosciences, 5% acetonitrile and 0.05% dimethyl sulfoxide). These are then serially diluted 1:1 (160 μL to 160 μL co-factor mix) for a total of 10 points. A 10 μL aliquot of this final mixture is dispensed into 384 well assay plates and incubated for 10 minutes at 37° C. Enzyme and substrate mix (10 μL; 0.5 pmol CYP1A2/5 μM CEC; 1.0 pmol CYP2C9/75 μM MFC; 0.5 pmol CYP2C19/25 μM CEC; 1.5 pmol CYP2D6/1.5 μM AMMC; 1.0 pmol CYP3A4/50 μM BFC; or 1.0 pmol CYP3A4/40 μM BQ) is added to these assay plates. Assay plates are incubated at 37° C. (CYP1A2-15 min; CYP2C9-45 min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 μM, more preferably $IC_{50}$ values of >10 μM.

The following table indicates the Cyp inhibition for exemplary compounds according to the invention as indicated:

| Compound number | Cyp $IC_{50}$ (μM) | | | | | |
|---|---|---|---|---|---|---|
| | 1A2 | 2C19 | 2C9 | 2D6 | 3A4(BFC) | 3A4(BQ) |
| P-1001 | >10 | >10 | >10 | >10 | <5 | >10 |
| P-1002 | >10 | >10 | >10 | >10 | >10 | >10 |
| P-1003 | >10 | >10 | 5-10 | >10 | >10 | 5-10 |
| P-1004 | >10 | >10 | 5-10 | >10 | >10 | >10 |
| P-1005 | >10 | 5-10 | >10 | >10 | 5-10 | >10 |
| P-1006 | >10 | >10 | 5-10 | >10 | <5 | >10 |
| P-1007 | >10 | >10 | >10 | >10 | 5-10 | 5-10 |
| P-1008 | >10 | >10 | 5-10 | >10 | >10 | >10 |
| P-1009 | >10 | 5-10 | <5 | >10 | <5 | >10 |
| P-1010 | >10 | 5-10 | 5-10 | >10 | >10 | >10 |
| P-1011 | >10 | 5-10 | >10 | >10 | <5 | >10 |
| P-1012 | >10 | >10 | >10 | >10 | >10 | >10 |
| P-1013 | >10 | >10 | >10 | >10 | >10 | >10 |
| P-1014 | >10 | >10 | >10 | >10 | >10 | |
| P-1015 | >10 | >10 | >10 | >10 | 5-10 | |
| P-1016 | >10 | >10 | >10 | >10 | >10 | |
| P-1020 | >10 | >10 | >10 | >10 | >10 | |
| P-1024 | >10 | 5-10 | >10 | >10 | >10 | |
| P-1025 | >10 | >10 | >10 | >10 | 5-10 | |
| P-1026 | >10 | >10 | >10 | >10 | >10 | |
| P-1027 | >10 | >10 | >10 | >10 | >10 | |
| P-1028 | >10 | >10 | 5-10 | >10 | >10 | |
| P-1029 | >10 | 5-10 | 5-10 | >10 | >10 | |
| P-1030 | >10 | >10 | >10 | >10 | >10 | |
| P-1031 | >10 | >10 | >10 | >10 | >10 | |
| P-1032 | >10 | 5-10 | >10 | >10 | >10 | |
| P-1033 | >10 | >10 | >10 | >10 | >10 | |
| P-1034 | >10 | 5-10 | >10 | >10 | 5-10 | |
| P-1035 | >10 | 5-10 | >10 | >10 | 5-10 | |
| P-1037 | >10 | <5 | >10 | >10 | >10 | |
| P-1038 | >10 | 5-10 | 5-10 | >10 | 5-10 | |
| P-1039 | >10 | >10 | >10 | >10 | 5-10 | |
| P-1040 | >10 | >10 | >10 | >10 | 5-10 | >10 |
| P-1041 | >10 | >10 | >10 | >10 | >10 | >10 |
| P-1042 | >10 | 5-10 | >10 | >10 | >10 | >10 |
| P-1043 | >10 | >10 | >10 | >10 | >10 | >10 |
| P-1044 | >10 | <5 | >10 | >10 | >10 | >10 |
| P-1045 | >10 | <5 | 5-10 | >10 | 5-10 | >10 |
| P-1046 | >10 | >10 | >10 | >10 | >10 | >10 |
| P-1047 | >10 | >10 | >10 | >10 | >10 | >10 |
| P-1048 | >10 | >10 | >10 | >10 | >10 | >10 |
| P-1049 | >10 | >10 | >10 | >10 | >10 | >10 |
| P-1050 | >10 | >10 | >10 | >10 | >10 | >10 |
| P-1051 | >10 | >10 | >10 | >10 | >10 | >10 |
| P-1052 | >10 | <5 | <5 | >10 | 5-10 | >10 |
| P-1053 | >10 | 5-10 | 5-10 | >10 | >10 | >10 |
| P-1054 | >10 | >10 | 5-10 | >10 | >10 | >10 |
| P-1055 | >10 | <5 | 5-10 | >10 | 5-10 | >10 |
| P-1056 | >10 | >10 | >10 | >10 | >10 | >10 |
| P-1057 | >10 | >10 | >10 | >10 | >10 | >10 |
| P-1058 | >10 | >10 | >10 | >10 | 5-10 | >10 |
| P-1059 | >10 | >10 | >10 | >10 | >10 | >10 |
| P-1060 | >10 | >10 | >10 | >10 | >10 | >10 |
| P-1061 | >10 | >10 | >10 | >10 | >10 | >10 |
| P-1062 | >10 | >10 | <5 | >10 | 5-10 | 5-10 |
| P-1063 | >10 | 5-10 | 5-10 | >10 | 5-10 | <5 |
| P-1073 | >10 | >10 | >10 | >10 | >10 | >10 |
| P-1074 | >10 | >10 | >10 | >10 | >10 | >10 |
| P-1077 | >10 | >10 | >10 | >10 | >10 | >10 |
| P-1078 | >10 | >10 | <5 | >10 | >10 | 5-10 |
| P-1079 | >10 | >10 | >10 | >10 | >10 | >10 |
| P-1081 | >10 | >10 | >10 | >10 | >10 | >10 |
| P-1090 | >10 | >10 | >10 | >10 | >10 | >10 |
| P-1100 | >10 | >10 | >10 | >10 | >10 | >10 |
| P-1101 | >10 | >10 | >10 | >10 | >10 | >10 |
| P-1103 | >10 | >10 | >10 | >10 | >10 | >10 |
| P-1104 | >10 | >10 | >10 | >10 | >10 | >10 |
| P-1107 | 5-10 | >10 | >10 | >10 | >10 | >10 |
| P-1111 | >10 | >10 | 5-10 | >10 | >10 | >10 |
| P-1137 | >10 | >10 | >10 | >10 | >10 | >10 |
| P-1139 | >10 | >10 | >10 | >10 | >10 | >10 |
| P-1142 | >10 | >10 | >10 | >10 | >10 | >10 |
| P-1149 | >10 | >10 | >10 | >10 | >10 | >10 |
| P-1150 | >10 | >10 | >10 | >10 | >10 | >10 |
| P-1153 | >10 | >10 | >10 | >10 | >10 | >10 |
| P-1154 | >10 | >10 | >10 | >10 | >10 | >10 |
| P-2001 | >10 | 5-10 | >10 | >10 | >10 | >10 |
| P-2002 | >10 | <5 | <5 | >10 | 5-10 | 5-10 |
| P-2003 | >10 | <5 | <5 | >10 | 5-10 | 5-10 |
| P-2004 | >10 | >10 | <5 | >10 | >10 | >10 |
| P-2005 | >10 | >10 | <5 | >10 | >10 | >10 |
| P-2006 | >10 | <5 | <5 | >10 | 5-10 | >10 |
| P-2007 | >10 | >10 | <5 | >10 | >10 | >10 |
| P-2008 | >10 | 5-10 | 5-10 | >10 | >10 | >10 |
| P-2009 | >10 | >10 | >10 | >10 | >10 | >10 |
| P-2010 | >10 | >10 | 5-10 | <5 | >10 | >10 |
| P-2011 | >10 | <5 | >10 | 5-10 | >10 | >10 |
| P-2012 | >10 | >10 | >10 | >10 | >10 | >10 |
| P-2013 | >10 | >10 | >10 | >10 | 5-10 | >10 |
| P-2015 | >10 | >10 | >10 | >10 | >10 | >10 |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, Cmax and half-life relative to previously described compounds.

Example 10

Efficacy of Compounds in Combination with Standard-of-Care Chemotherapeutic Agents in Four Human Cancer Cell Lines Compounds of the invention, such as compounds of Formula I, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Such assays are known in the art, for example, as described in U.S. patent application Ser. No. 11/473,347, the disclosure of which is hereby incorporated by reference as it relates to such assays.

Additional features of the complex can be used to demonstrate improved properties, such as comparison of the intrinsic dissolution rate of a similarly prepared substantially amorphous citrate complex or formulation thereof as compared to that of a crystalline form of the compound or similar formulation thereof in simulated gastric fluid (SGF) without enzyme and in simulated intestinal fluid (SIF). A pellet of test sample is dissolved in the appropriate fluid, and the UV absorbance as a function of time is measured at 254 nm (SGF) or 310 nm (SIF) and plotted.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:
1. A method for alleviating or ameliorating one or more symptoms of melanoma or colon adenocarcinoma in a subject in need thereof, said method comprising administering to said subject an effective amount of a compound of Formula I:

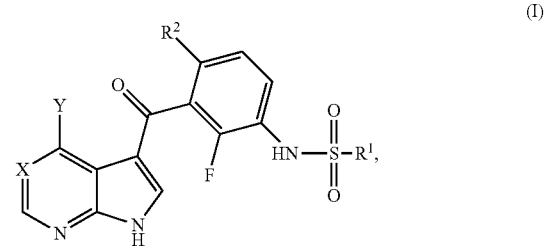

or a pharmaceutically acceptable salt, hydrate, or solvate thereof, wherein
X is —N═;
Y is —N($R^3$)($R^4$); wherein:
  $R^3$ is hydrogen and $R^4$ is selected from the group consisting of (i) hydrogen, —$OR^8$ and lower alkyl optionally substituted with one or more $R^{11}$; (ii) cycloalkyl optionally substituted with one or more $R^{12}$; (iii) heterocycloalkyl optionally substituted with one or more $R^{13}$; (iv) aryl optionally substituted with one or more $R^{14}$; and (v) heteroaryl optionally substituted with one or more $R^{15}$; or
  $R^3$ and $R^4$ are both lower alkyl; or
  $R^3$ and $R^4$ combine with the nitrogen atom to which they are attached to form cycloalkylamino;
$R^1$ is selected from the group consisting of lower alkyl, haloalkyl, haloalkoxy, fluoro substituted lower alkyl, cycloalkyl optionally substituted with one or more $R^7$, heterocycloalkyl, mono-alkylamino, di-alkylamino, cycloalkylamino, heterocycloalkylamino, aryl optionally substituted with one or more $R^6$ and heteroaryl optionally substituted with one or more $R^7$;
$R^2$ is hydrogen, fluoro, chloro, or lower alkyl optionally substituted with one or more fluorine;

each R⁶, when present, is independently selected from the group consisting of fluoro, chloro, —CN, —NO₂, lower alkyl, fluoro substituted lower alkyl, lower alkoxy, fluoro substituted lower alkoxy, —C(O)—O—R¹⁸, —N(H)—C(O)—R¹⁹, and heteroaryl optionally substituted with one or more lower alkyl;

each R⁷, when present, is independently selected from the group consisting of lower alkyl, fluoro substituted lower alkyl, lower alkoxy, —C(O)—O—R²⁰, and heteroaryl optionally substituted with one or more lower alkyl;

R⁸ is hydrogen, lower alkyl optionally substituted with one or more fluorine, or, when R⁸ is a C₂₋₆ alkyl, said alkyl may optionally be substituted with one or more R²¹; cycloalkyl optionally substituted with one or more R²¹, or heterocycloalkyl optionally substituted with one or more R²¹;

each R¹¹, when present, is independently selected from the group consisting of fluoro, —OH, lower alkoxy, fluoro substituted lower alkoxy, —NH₂, mono-alkylamino, di-alkylamino, cycloalkylamino, heterocycloalkylamino, cycloalkyl optionally substituted with one or more R¹², heterocycloalkyl optionally substituted with one or more R¹³, aryl optionally substituted with one or more R¹⁴, and heteroaryl optionally substituted with one or more R¹⁵;

each R¹², when present, is independently selected from the group consisting of fluoro, lower alkyl, fluoro substituted lower alkyl, —OH, lower alkoxy, fluoro substituted lower alkoxy, —NH₂, mono-alkylamino, di-alkylamino, cycloalkylamino, heterocycloalkylamino, —N(H)—C(O)—R²², —N(H)—S(O)₂—R²³, C(O)—R²⁴, and S(O)₂—R²⁵;

each R¹³, when present, is independently selected from the group consisting of fluoro, —OH, lower alkoxy, fluoro substituted lower alkyl, —NH₂, mono-alkylamino, di-alkylamino, cycloalkylamino, heterocycloalkylamino, —N(H)—C(O)—R²⁶, —N(H)—S(O)₂—R²⁷, C(O)—R²⁸, S(O)₂—R²⁹, and lower alkyl optionally substituted with one or more R³⁰;

each R¹⁴ and R¹⁵, when present, are independently selected from the group consisting of fluoro, chloro, —OH, —NH₂, —CN, —NO₂, —N(H)—C(O)—R³¹, —N(H)—S(O)₂—R³², C(O)—R³³, S(O)₂—R³⁴, lower alkyl, fluoro substituted lower alkyl, lower alkoxy, fluoro substituted lower alkoxy, monoalkylamino, di-alkylamino, cycloalkylamino, heterocycloalkylamino, aryl optionally substituted with one or more R³⁵, and heteroaryl optionally substituted with one or more R³⁶;

each R¹⁸ and R²⁰, when present, are independently hydrogen, lower alkyl or fluoro substituted lower alkyl;

each R¹⁹, R²², R²³, R²⁶, R²⁷, R³¹ and R³², when present, are independently lower alkyl or fluoro substituted lower alkyl;

each R²¹, when present, is fluoro, —OH, lower alkoxy, —NH₂, mono-alkylamino, di-alkylamino, cycloalkylamino, or heterocycloalkylamino;

each R²⁴, R²⁵, R²⁸, R²⁹, R³³, and R³⁴, when present, are independently lower alkyl, fluoro substituted lower alkyl, —OH, lower alkoxy, fluoro substituted lower alkoxy, —NH₂, mono-alkylamino, di-alkylamino, cycloalkylamino, or heterocycloalkylamino;

each R³⁰, when present, is independently fluoro, aryl optionally substituted with one or more R³⁵ or heteroaryl optionally substituted with one or more R³⁶;

each R³⁵ and R³⁶, when present, are independently selected from the group consisting of fluoro, chloro, —OH, —NH₂, —CN, —NO₂, lower alkyl, fluoro substituted lower alkyl, lower alkoxy, fluoro substituted lower alkoxy, mono-alkylamino, di-alkylamino, cycloalkylamino, and heterocycloalkylamino.

2. A method for alleviating or ameliorating one or more symptoms of melanoma or colon adenocarcinoma in a subject in need thereof, said method comprising administering to said subject an effective amount of a compound of Formula (I) or a pharmaceutically acceptable salt thereof as set forth in claim 1 and another drug.

3. A method for alleviating or ameliorating one or more symptoms of melanoma or colon adenocarcinoma in a subject in need thereof, said method comprising administering to said subject an effective amount of a compound selected from the group consisting of:

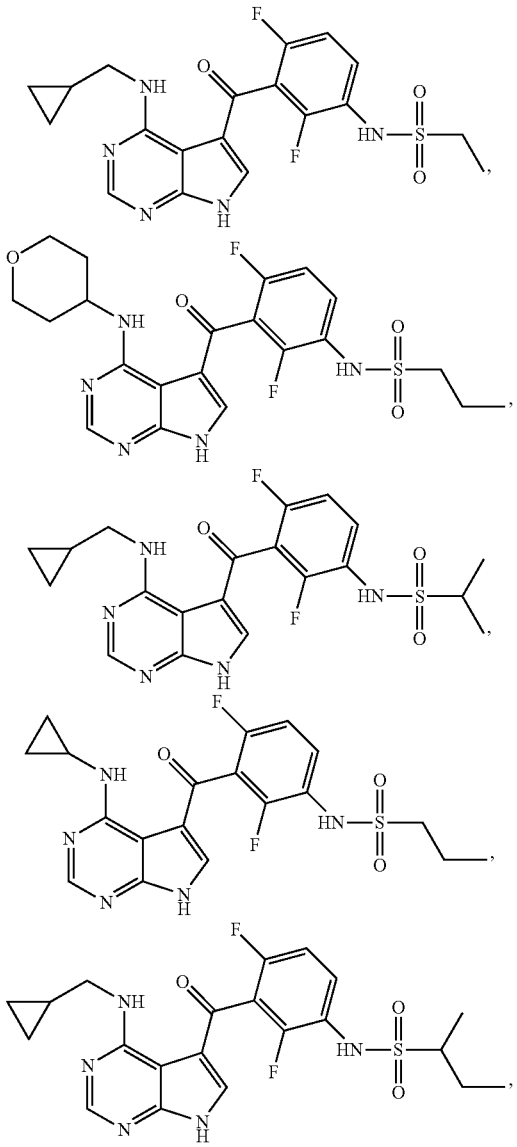

413
-continued
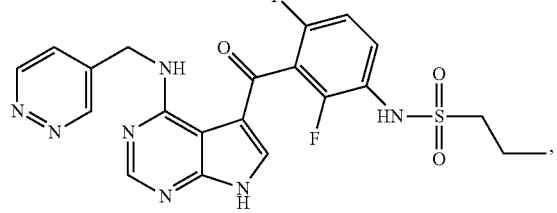
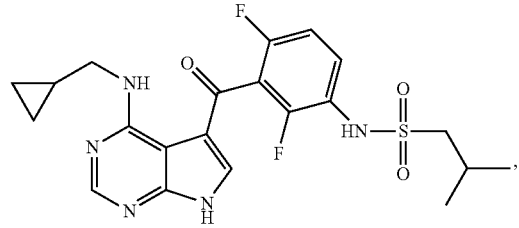
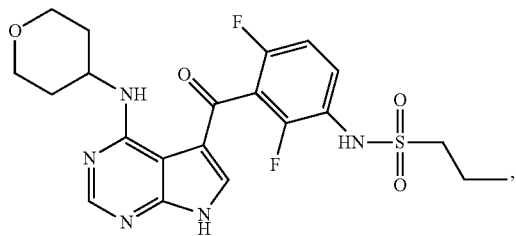
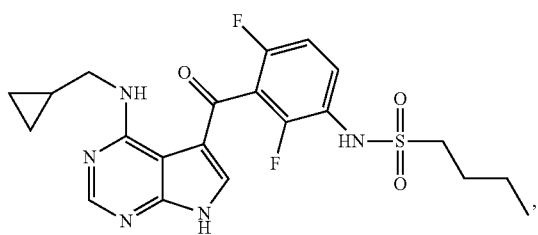
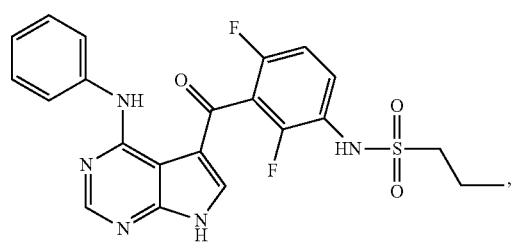
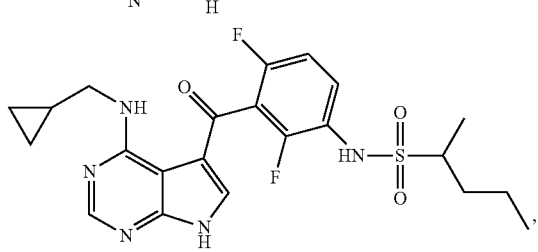
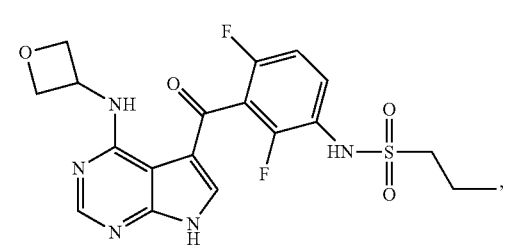
414
-continued
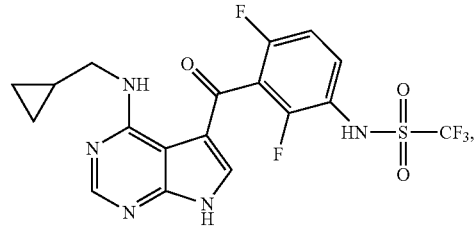
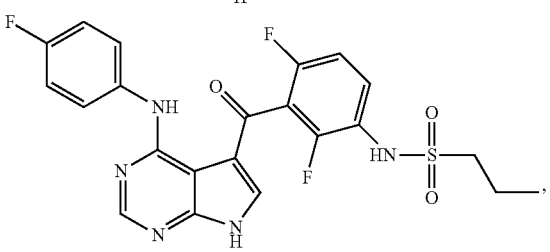
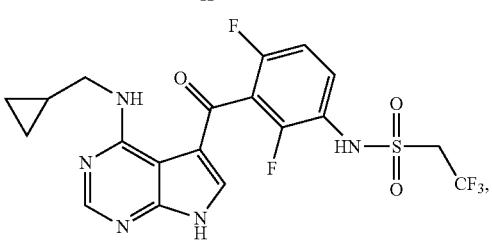
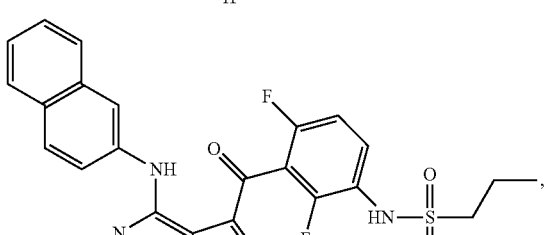
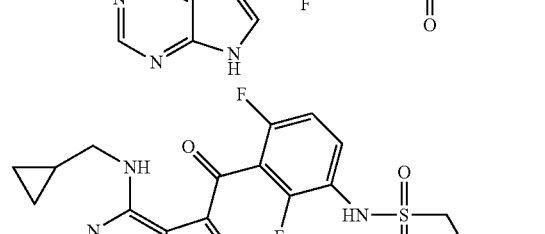
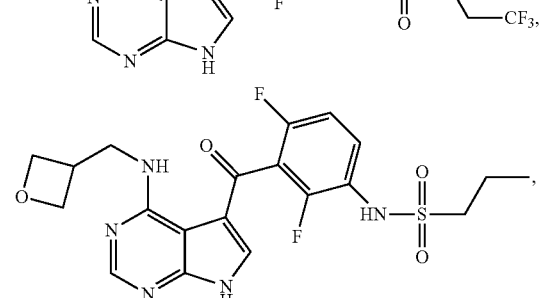
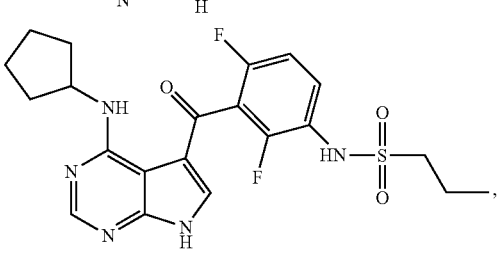

415
-continued
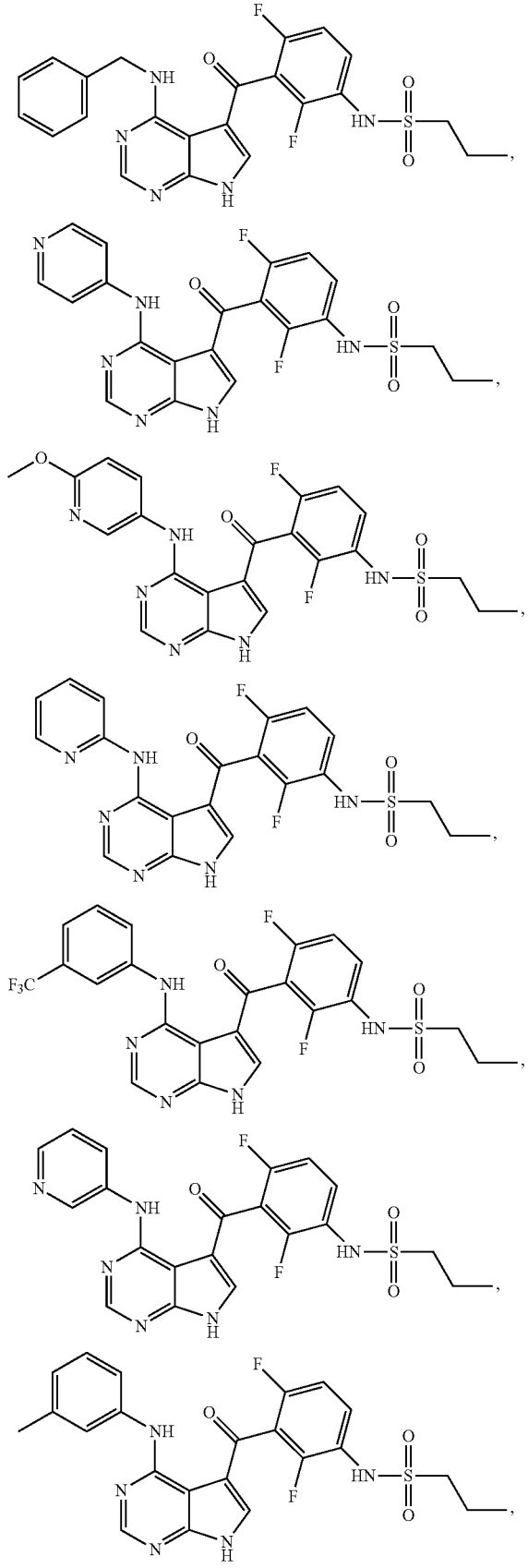
416
-continued
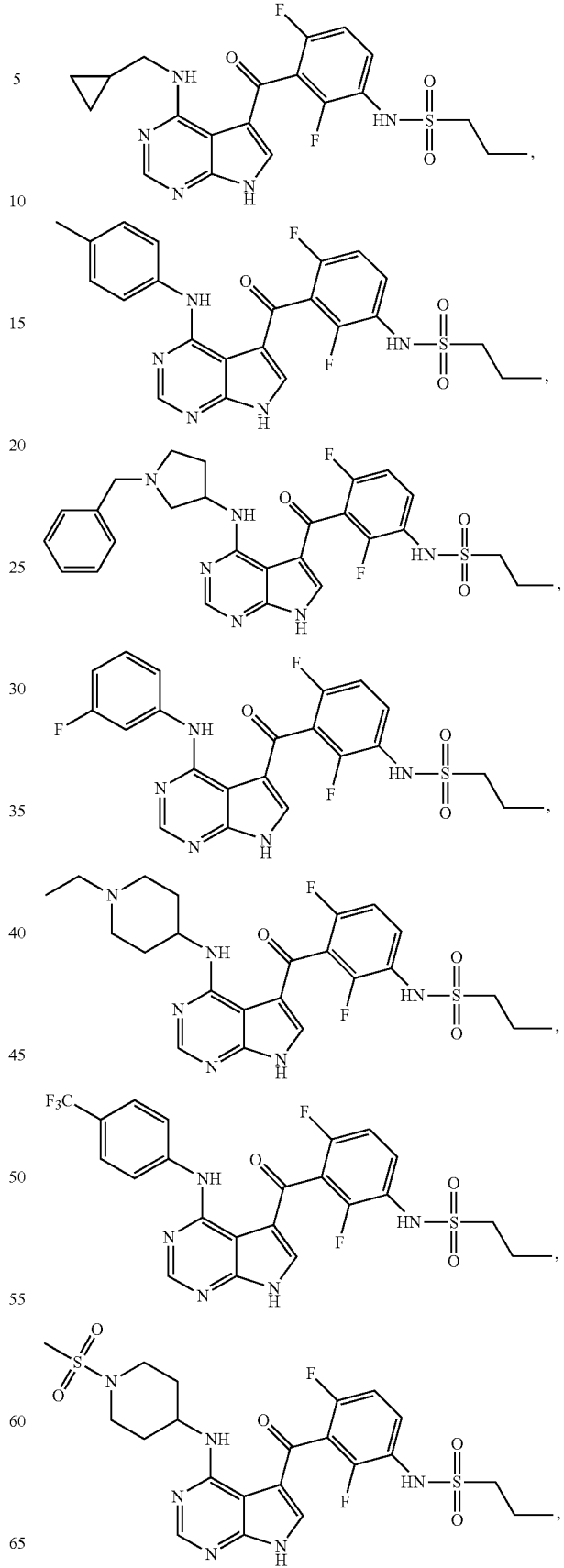

417
-continued
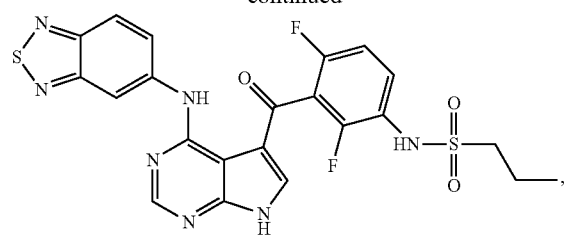
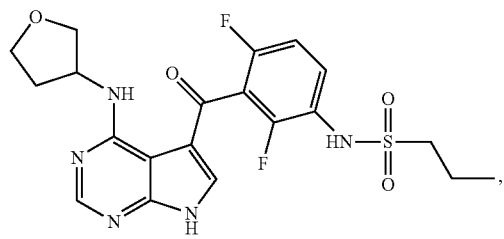
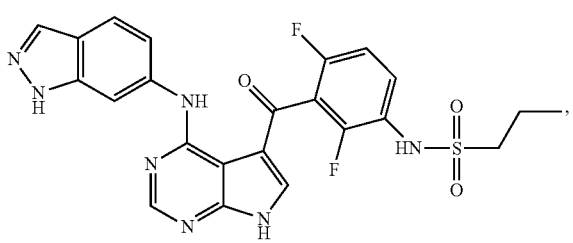
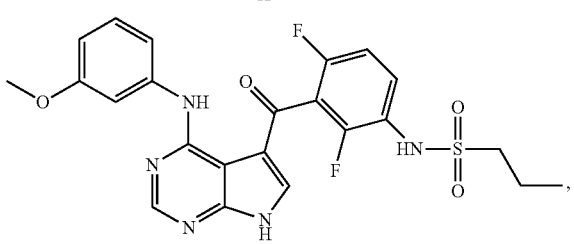
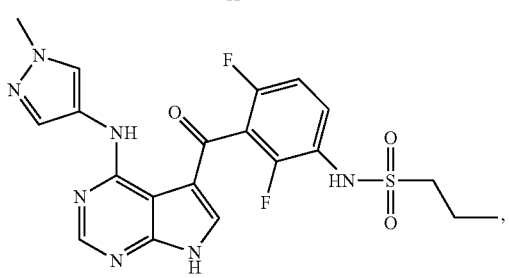
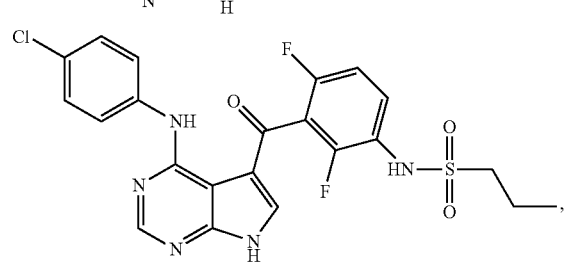
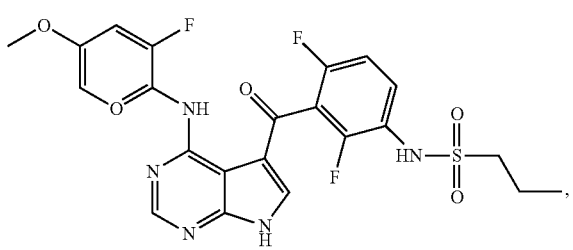
418
-continued
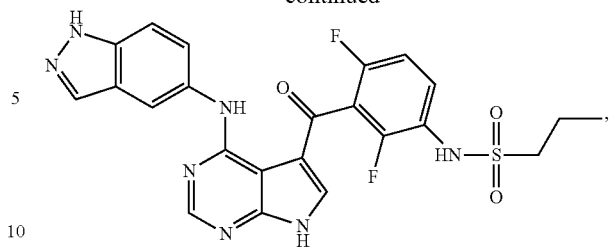
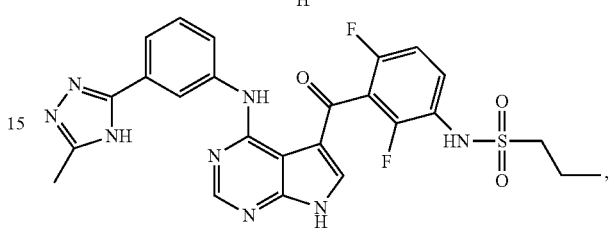
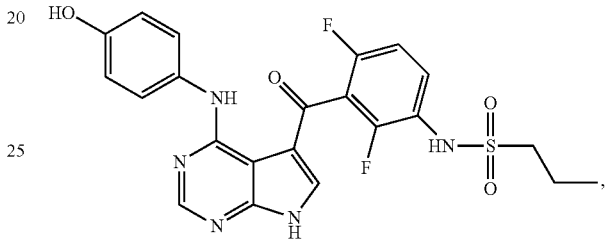
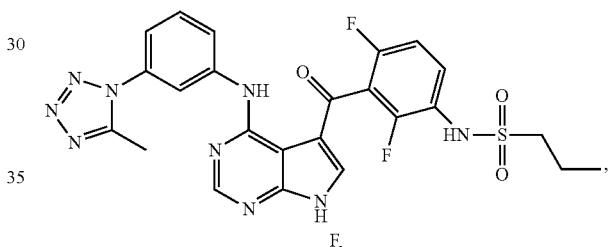
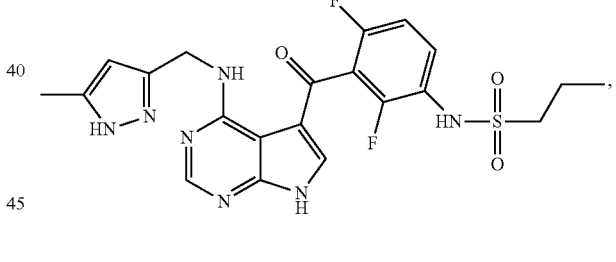
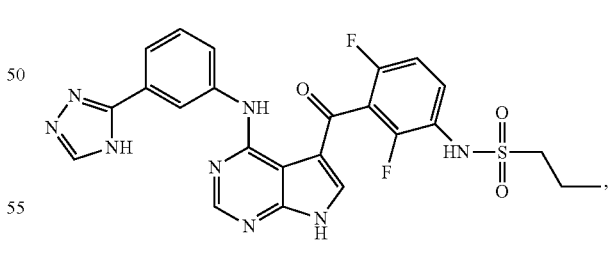
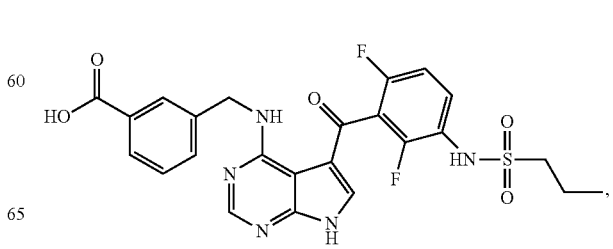

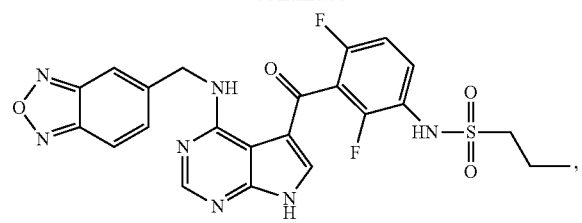
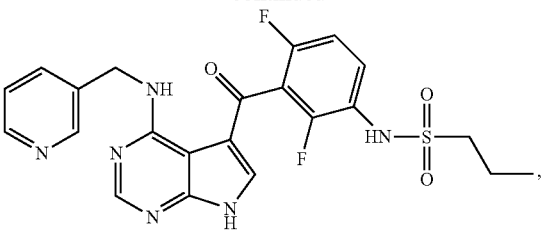
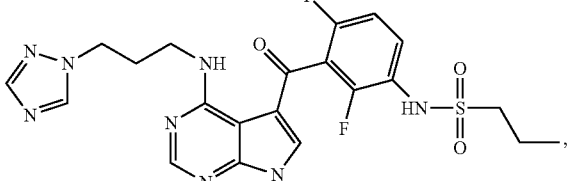
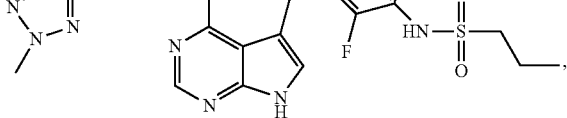
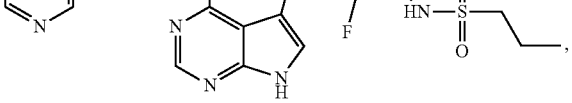
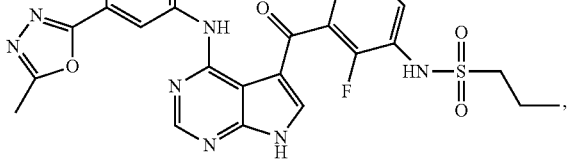
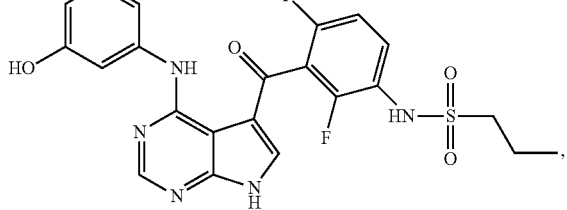

-continued

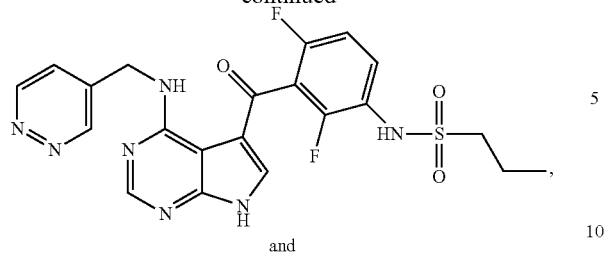

and

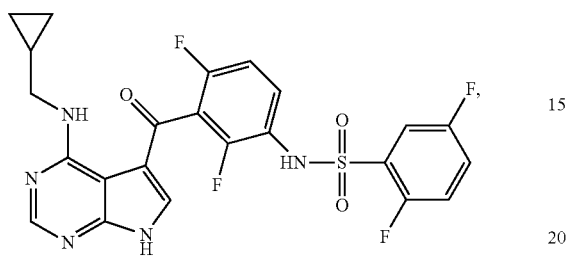

or a pharmaceutically acceptable salt thereof.

4. The method of claim 3, wherein the method further comprises administering another drug.

5. The method of claim 3, wherein the method is for alleviating or ameliorating one or more symptoms of melanoma.

6. The method of claim 3, wherein the method is for alleviating or ameliorating one or more symptoms of colon adenocarincoma.

* * * * *